United States Patent
Sommadossi et al.

(10) Patent No.: US 11,975,016 B2
(45) Date of Patent: *May 7, 2024

(54) 2'-SUBSTITUTED-N⁶-SUBSTITUTED PURINE NUCLEOTIDES FOR RNA VIRUS TREATMENT

(71) Applicant: Atea Pharmaceuticals, Inc., Boston, MA (US)

(72) Inventors: Jean-Pierre Sommadossi, Boston, MA (US); Adel Moussa, Burlington, MA (US)

(73) Assignee: Atea Pharmaceuticals, Inc., Boston, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/482,224

(22) Filed: Sep. 22, 2021

(65) Prior Publication Data

US 2023/0017958 A1 Jan. 19, 2023

Related U.S. Application Data

(63) Continuation of application No. 16/821,850, filed on Mar. 17, 2020, now abandoned, which is a continuation of application No. 16/293,423, filed on Mar. 5, 2019, now Pat. No. 10,946,033, which is a continuation of application No. PCT/US2017/050323, filed on Sep. 6, 2017.

(60) Provisional application No. 62/384,664, filed on Sep. 7, 2016.

(51) Int. Cl.
| | |
|---|---|
| *A61K 31/7076* | (2006.01) |
| *A61K 31/675* | (2006.01) |
| *A61P 1/00* | (2006.01) |
| *A61P 31/14* | (2006.01) |
| *C07H 19/16* | (2006.01) |
| *C07H 19/20* | (2006.01) |

(52) U.S. Cl.
CPC ........ *A61K 31/7076* (2013.01); *A61K 31/675* (2013.01); *A61P 1/00* (2018.01); *A61P 31/14* (2018.01); *C07H 19/16* (2013.01); *C07H 19/20* (2013.01)

(58) Field of Classification Search
None
See application file for complete search history.

(56) References Cited

U.S. PATENT DOCUMENTS

| | | |
|---|---|---|
| 5,977,061 A | 11/1999 | Holy et al. |
| 6,348,587 B1 | 2/2002 | Schinazi et al. |
| 6,602,999 B1 | 8/2003 | Kumar et al. |
| 6,660,721 B2 | 12/2003 | Devos et al. |
| 6,777,395 B2 | 8/2004 | Bhat et al. |
| 6,784,166 B2 | 8/2004 | Devos et al. |
| 6,812,219 B2 | 11/2004 | LaColla et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,949,522 B2 | 9/2005 | Otto et al. |
| 7,094,770 B2 | 8/2006 | Watanabe et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,211,570 B2 | 5/2007 | Schinazi et al. |
| 7,268,119 B2 | 9/2007 | Cook et al. |
| 7,285,658 B2 | 10/2007 | Cook et al. |
| 7,307,065 B2 | 12/2007 | Schinazi et al. |
| 7,323,449 B2 | 1/2008 | Olsen et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,388,002 B2 | 6/2008 | Babu et al. |
| 7,429,571 B2 | 9/2008 | Chand et al. |
| 7,429,572 B2 | 9/2008 | Clark |
| 7,456,155 B2 | 11/2008 | Sommadossi et al. |
| 7,495,006 B2 | 2/2009 | Liotta et al. |
| 7,514,410 B2 | 4/2009 | Babu et al. |
| 7,534,767 B2 | 5/2009 | Butora et al. |
| 7,547,704 B2 | 6/2009 | LaColla et al. |
| 7,560,434 B2 | 7/2009 | Babu et al. |

(Continued)

FOREIGN PATENT DOCUMENTS

| | | |
|---|---|---|
| CN | 103435672 A | 12/2013 |
| CN | 103980332 | 8/2014 |

(Continued)

OTHER PUBLICATIONS

Hayes, Emerging Infectious Diseases, vol. 15, No. 9, Sep. 2009. (Year: 2009).*

(Continued)

*Primary Examiner* — Layla D Berry
(74) *Attorney, Agent, or Firm* — Knowles Intellectual Property Strategies, LLC

(57) ABSTRACT

The use of described compounds or pharmaceutically acceptable salts or compositions thereof for the treatment of a host infected with an RNA virus other than HCV, or other disorder more fully described herein.

26 Claims, No Drawings

(56) References Cited

U.S. PATENT DOCUMENTS

| | | |
|---|---|---|
| 7,560,550 B2 | 7/2009 | Doring et al. |
| 7,582,618 B2 | 9/2009 | Sommadossi et al. |
| 7,601,820 B2 | 10/2009 | Wang et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,638,502 B2 | 12/2009 | Schinazi et al. |
| 7,662,798 B2 | 2/2010 | LaColla et al. |
| 7,662,938 B2 | 2/2010 | Schinazi et al. |
| 7,713,941 B2 | 5/2010 | Cook et al. |
| 7,718,790 B2 | 5/2010 | Stuyver et al. |
| 7,772,208 B2 | 8/2010 | Schinazi et al. |
| 7,824,851 B2 | 11/2010 | Sommadossi et al. |
| 7,842,672 B2 | 11/2010 | Boojamra et al. |
| RE42,015 E | 12/2010 | Watanabe et al. |
| 7,879,815 B2 | 2/2011 | MacCoss et al. |
| 7,902,202 B2 | 3/2011 | Sommadossi et al. |
| 7,919,247 B2 | 4/2011 | Stuyver et al. |
| 7,932,240 B2 | 4/2011 | Dousson et al. |
| 7,951,789 B2 | 5/2011 | Sommadossi et al. |
| 7,964,580 B2 | 6/2011 | Sofia et al. |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,567 B2 | 12/2011 | Devos et al. |
| 8,071,568 B2 | 12/2011 | Narjes et al. |
| 8,093,380 B2 | 1/2012 | Wang et al. |
| 8,114,994 B2 | 2/2012 | Liotta et al. |
| 8,114,997 B2 | 2/2012 | Otto et al. |
| 8,119,607 B2 | 2/2012 | Francom et al. |
| 8,133,870 B2 | 3/2012 | Babu et al. |
| 8,148,349 B2 | 4/2012 | Meppen et al. |
| 8,163,703 B2 | 4/2012 | Babu et al. |
| 8,168,583 B2 | 5/2012 | Schinazi et al. |
| 8,173,621 B2 | 5/2012 | Du et al. |
| 8,193,372 B2 | 6/2012 | Dousson et al. |
| 8,242,085 B2 | 8/2012 | Babu et al. |
| 8,299,038 B2 | 10/2012 | Sommadossi et al. |
| 8,318,682 B2 | 11/2012 | Butler et al. |
| 8,324,179 B2 | 12/2012 | Chen et al. |
| 8,334,270 B2 | 12/2012 | Sofia et al. |
| 8,343,937 B2 | 1/2013 | Sommadossi et al. |
| 8,362,068 B2 | 1/2013 | Dousson et al. |
| 8,399,429 B2 | 3/2013 | Jonckers et al. |
| 8,415,308 B2 | 4/2013 | Cho et al. |
| 8,415,309 B2 | 4/2013 | Francom et al. |
| 8,415,322 B2 | 4/2013 | Clark |
| 8,431,588 B2 | 4/2013 | Jonckers et al. |
| 8,440,813 B2 | 5/2013 | Babu et al. |
| 8,455,451 B2 | 6/2013 | Cho et al. |
| 8,470,834 B2 | 6/2013 | Kwong et al. |
| 8,481,510 B2 | 7/2013 | Jonckers et al. |
| 8,481,712 B2 | 7/2013 | Bhat et al. |
| 8,481,713 B2 | 7/2013 | Wang et al. |
| 8,492,539 B2 | 7/2013 | Chun et al. |
| 8,501,699 B2 | 8/2013 | Francom et al. |
| 8,507,460 B2 | 8/2013 | Surleraux et al. |
| 8,541,434 B2 | 9/2013 | Kwong et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,637,475 B1 | 1/2014 | Storer et al. |
| 8,642,756 B2 | 2/2014 | Ross et al. |
| 8,673,926 B2 | 3/2014 | Chu |
| 8,674,085 B2 | 3/2014 | Sommadossi et al. |
| 8,680,071 B2 | 3/2014 | Surleraux et al. |
| 8,691,788 B2 | 4/2014 | Sommadossi et al. |
| 8,697,694 B2 | 4/2014 | Arasappan et al. |
| 8,715,638 B2 | 5/2014 | Kwong et al. |
| 8,716,262 B2 | 5/2014 | Sofia et al. |
| 8,716,263 B2 | 5/2014 | Chun et al. |
| 8,735,345 B2 | 5/2014 | Porter et al. |
| 8,735,372 B2 | 5/2014 | Du et al. |
| 8,735,569 B2 | 5/2014 | Ross et al. |
| 8,742,101 B2 | 6/2014 | Storer et al. |
| 8,759,318 B2 | 6/2014 | Chamberlain et al. |
| 8,759,372 B2 | 6/2014 | Roberts et al. |
| 8,759,510 B2 | 6/2014 | Du et al. |
| 8,765,710 B2 | 7/2014 | Sofia et al. |
| 8,772,474 B2 | 7/2014 | Beigelman et al. |
| 8,802,840 B2 | 8/2014 | Francom et al. |
| 8,815,829 B2 | 8/2014 | Schinazi et al. |
| 8,816,074 B2 | 8/2014 | Chu et al. |
| 8,841,275 B2 | 9/2014 | Du et al. |
| 8,846,638 B2 | 9/2014 | Or et al. |
| 8,846,896 B2 | 9/2014 | Serebryany et al. |
| 8,853,171 B2 | 10/2014 | Butler et al. |
| 8,859,595 B2 | 10/2014 | Coats et al. |
| 8,871,737 B2 | 10/2014 | Smith et al. |
| 8,871,785 B2 | 10/2014 | Boojamra et al. |
| 8,877,731 B2 | 11/2014 | Beigelman et al. |
| 8,877,733 B2 | 11/2014 | Cho et al. |
| 8,889,159 B2 | 11/2014 | Cleary et al. |
| 8,889,701 B1 | 11/2014 | Ivachtchenko et al. |
| 8,895,531 B2 | 11/2014 | Shi |
| 8,895,723 B2 | 11/2014 | Serebryany et al. |
| 8,906,880 B2 | 12/2014 | Du et al. |
| 8,912,321 B2 | 12/2014 | Axt et al. |
| 8,921,384 B2 | 12/2014 | Chu |
| 8,933,052 B2 | 1/2015 | Jonckers et al. |
| 8,946,244 B2 | 2/2015 | Chu et al. |
| 8,951,985 B2 | 2/2015 | Surleraux et al. |
| 8,957,045 B2 | 2/2015 | Sofia et al. |
| 8,957,046 B2 | 2/2015 | Du et al. |
| 8,980,865 B2 | 3/2015 | Wang et al. |
| 9,012,427 B2 | 4/2015 | Blatt et al. |
| 9,012,428 B2 | 4/2015 | Jonckers et al. |
| 9,045,520 B2 | 6/2015 | Chun et al. |
| 9,061,041 B2 | 6/2015 | Girijavallabhan et al. |
| 9,085,573 B2 | 7/2015 | Du et al. |
| 9,085,599 B2 | 7/2015 | Or et al. |
| 9,090,642 B2 | 7/2015 | Cho et al. |
| 9,109,001 B2 | 8/2015 | Parsy et al. |
| 9,139,604 B2 | 9/2015 | Boojamra et al. |
| 9,156,872 B2 | 10/2015 | Girijavallabhan et al. |
| 9,173,893 B2 | 11/2015 | Cho et al. |
| 9,187,515 B2 | 11/2015 | Mayes et al. |
| 9,211,300 B2 | 12/2015 | Mayes et al. |
| 9,243,025 B2 | 1/2016 | Surleraux et al. |
| 9,603,863 B2 | 3/2017 | Blatt et al. |
| 9,603,864 B2 | 3/2017 | Blatt et al. |
| 9,822,137 B2 | 11/2017 | Dehaen et al. |
| 9,828,410 B2 | 11/2017 | Sommadossi et al. |
| 11,642,361 B2 | 5/2023 | Sofia et al. |
| 2002/0045599 A1 | 4/2002 | Arimilli et al. |
| 2004/0063658 A1 | 4/2004 | Roberts et al. |
| 2004/0229839 A1 | 11/2004 | Babu et al. |
| 2004/0259934 A1 | 12/2004 | Olsen et al. |
| 2007/0027065 A1 | 2/2007 | Lacolla et al. |
| 2008/0286230 A1 | 11/2008 | Sommadossi et al. |
| 2010/0151001 A1 | 6/2010 | Schott et al. |
| 2010/0249068 A1 | 9/2010 | Beigelman et al. |
| 2010/0279969 A1 | 11/2010 | Schinazi et al. |
| 2011/0257121 A1 | 10/2011 | Chang et al. |
| 2012/0070411 A1 | 3/2012 | Beigelman et al. |
| 2012/0071434 A1 | 3/2012 | Smith et al. |
| 2012/0135951 A1 | 5/2012 | Schinazi et al. |
| 2012/0251487 A1 | 10/2012 | Surleraux |
| 2013/0064794 A1 | 3/2013 | Surleraux et al. |
| 2013/0225636 A1 | 8/2013 | Roberts et al. |
| 2014/0038916 A1 | 2/2014 | Wang et al. |
| 2014/0066395 A1 | 3/2014 | Cho et al. |

(56) References Cited

U.S. PATENT DOCUMENTS

| | | | |
|---|---|---|---|
| 2014/0178338 A1 | 6/2014 | Mayes et al. |
| 2014/0187511 A1 | 7/2014 | Du et al. |
| 2014/0206640 A1 | 7/2014 | Girijavallabhan et al. |
| 2014/0212382 A1 | 7/2014 | Schinazi et al. |
| 2014/0235566 A1 | 8/2014 | Amblard et al. |
| 2014/0256774 A1 | 9/2014 | Roberts et al. |
| 2015/0011481 A1 | 1/2015 | Vilchez et al. |
| 2015/0011497 A1 | 1/2015 | Beigelman et al. |
| 2015/0105341 A1 | 4/2015 | Beigelman et al. |
| 2015/0150897 A1 | 6/2015 | Denning et al. |
| 2015/0366887 A1 | 12/2015 | Blatt et al. |
| 2015/0366888 A1 | 12/2015 | Blatt et al. |
| 2016/0002281 A1 | 1/2016 | Mayes et al. |
| 2016/0257706 A1 | 9/2016 | Sommadossi et al. |
| 2016/0271162 A1 | 9/2016 | Moussa et al. |
| 2019/0153017 A1 | 5/2019 | Sommadossi et al. |
| 2019/0201433 A1 | 7/2019 | Sommadossi et al. |
| 2020/0222442 A1 | 7/2020 | Sommadossi et al. |
| 2021/0015841 A1 | 1/2021 | Sommadossi et al. |

FOREIGN PATENT DOCUMENTS

| | | |
|---|---|---|
| CN | 106188192 A | 4/2015 |
| CN | 105646629 A | 6/2016 |
| CN | 106366146 | 2/2017 |
| EP | 547008 A1 | 6/1993 |
| EP | 398231 B1 | 7/1997 |
| WO | WO 1998/016184 A1 | 4/1998 |
| WO | WO 2001/009143 A2 | 2/2001 |
| WO | WO 2001/090121 A2 | 11/2001 |
| WO | WO 2001/92282 A2 | 12/2001 |
| WO | WO 2002/32920 A2 | 4/2002 |
| WO | WO 2003/033508 A1 | 4/2003 |
| WO | WO 2003/039523 A2 | 5/2003 |
| WO | WO 2003/062256 A1 | 7/2003 |
| WO | WO 2003/068244 A1 | 8/2003 |
| WO | WO 2003/093290 A2 | 11/2003 |
| WO | WO 2004/002999 A2 | 1/2004 |
| WO | WO 2004/003000 A2 | 1/2004 |
| WO | WO 2004/003138 A2 | 1/2004 |
| WO | WO 2004/014312 A2 | 2/2004 |
| WO | WO 2004/052906 A1 | 6/2004 |
| WO | WO 2004/058792 A1 | 7/2004 |
| WO | WO 2004/074350 A2 | 9/2004 |
| WO | WO 2004/091499 A2 | 10/2004 |
| WO | WO 2004/106356 A1 | 12/2004 |
| WO | WO 2005/000864 A1 | 1/2005 |
| WO | WO 2005/020884 A2 | 3/2005 |
| WO | WO 2005/021568 A2 | 3/2005 |
| WO | WO 2005/084192 A2 | 9/2005 |
| WO | WO 2005/090370 A1 | 9/2005 |
| WO | WO 2006/012078 A2 | 2/2006 |
| WO | WO 2006/063149 A1 | 6/2006 |
| WO | WO 2006/063717 A2 | 7/2006 |
| WO | WO 2006/094347 A1 | 9/2006 |
| WO | WO 2006/102533 A2 | 9/2006 |
| WO | WO 2006/121820 A1 | 11/2006 |
| WO | WO 2006/130217 A2 | 12/2006 |
| WO | WO 2007/022073 A2 | 2/2007 |
| WO | WO 2007/112028 A2 | 10/2007 |
| WO | WO 2007/130783 A1 | 11/2007 |
| WO | WO 2008/012555 A2 | 1/2008 |
| WO | WO 2008/048128 A1 | 4/2008 |
| WO | WO 2008/062206 A2 | 5/2008 |
| WO | WO 2008/095040 A2 | 10/2008 |
| WO | WO 2009/001097 A2 | 12/2008 |
| WO | WO 2009/003042 A1 | 12/2008 |
| WO | WO 2009/067409 A1 | 5/2009 |
| WO | WO 2009/086192 A1 | 7/2009 |
| WO | WO 2009/086201 A1 | 7/2009 |
| WO | WO 2009/129120 A2 | 10/2009 |
| WO | WO 2010/081082 A2 | 7/2010 |
| WO | WO 2010/091386 A2 | 8/2010 |
| WO | WO 2010/108135 A1 | 9/2010 |
| WO | WO 2010/145778 A1 | 12/2010 |
| WO | WO 2010/005595 A2 | 1/2011 |
| WO | WO 2011/005860 A2 | 1/2011 |
| WO | WO 2011/123586 A1 | 10/2011 |
| WO | WO 2012/041965 A1 | 4/2012 |
| WO | WO 2012/048013 A2 | 4/2012 |
| WO | WO 2012/092484 A2 | 7/2012 |
| WO | WO 2012/125900 A1 | 9/2012 |
| WO | WO 2012/142085 A1 | 10/2012 |
| WO | WO 2012/154321 A1 | 11/2012 |
| WO | WO 2012/158811 A2 | 11/2012 |
| WO | WO 2013/009737 A1 | 1/2013 |
| WO | WO 2013/019874 A1 | 2/2013 |
| WO | WO 2013/039855 A1 | 3/2013 |
| WO | WO 2013/039920 A1 | 3/2013 |
| WO | WO 2013/044030 A1 | 3/2013 |
| WO | WO 2013/059735 A1 | 4/2013 |
| WO | WO 2013/090420 A2 | 6/2013 |
| WO | WO 2013/096680 A1 | 6/2013 |
| WO | WO 2013/142125 A1 | 9/2013 |
| WO | WO 2013/142157 A1 | 9/2013 |
| WO | WO 2013/142159 A1 | 9/2013 |
| WO | WO 2013/151975 A1 | 10/2013 |
| WO | WO 2013/177219 A1 | 11/2013 |
| WO | WO 2013/187978 A1 | 12/2013 |
| WO | WO 2014/008236 A1 | 1/2014 |
| WO | WO 2014/047117 A1 | 3/2014 |
| WO | WO 2014/052638 A1 | 4/2014 |
| WO | WO 2014/063019 A1 | 4/2014 |
| WO | WO 2014/076490 A1 | 5/2014 |
| WO | WO 2014/082935 A1 | 6/2014 |
| WO | WO 2014/100498 A1 | 6/2014 |
| WO | WO 2014/100505 A1 | 6/2014 |
| WO | WO 2014/120981 A1 | 8/2014 |
| WO | WO 2014/124430 A1 | 8/2014 |
| WO | WO 2014/137930 A1 | 9/2014 |
| WO | WO 2014/169278 A1 | 10/2014 |
| WO | WO 2014/169280 A2 | 10/2014 |
| WO | WO 2014/209979 A1 | 12/2014 |
| WO | WO 2015/038596 A1 | 3/2015 |
| WO | WO 2015/053662 A1 | 4/2015 |
| WO | WO 2015/054465 A1 | 4/2015 |
| WO | WO 2015/061683 A1 | 4/2015 |
| WO | WO 2015/081133 A2 | 6/2015 |
| WO | WO 2015/095305 A1 | 6/2015 |
| WO | WO 2015/158913 A1 | 10/2015 |
| WO | WO 2016/041877 A1 | 3/2016 |
| WO | WO 2016/066582 A1 | 5/2016 |
| WO | WO 2016/100441 A1 | 6/2016 |
| WO | WO 2016/100569 A1 | 6/2016 |
| WO | WO 2016/145142 A1 | 9/2016 |

OTHER PUBLICATIONS

Belikov, V.G. "Pharmaceutical Chemistry", textbook, 2007, Moscow, "MEDpress-inform", pp. 27-29.
Bukrinskaya A.G. Virology.-M.: Medicine, 1986, p. 152.
Didier Musso et al. Zika Virus. Clin Microbiol. Rev., 2016, 29:487-524.
Papageorgiou, Louis et al. Mol. BioSyst., 2016, 12(7), 2080-2093.
U.S. Pat. No. 9,828,410, B2, U.S. Appl. No. 15/063,461, Sommadossi et al., May 9, 1989.
U.S. Pat. No. 10,000,523, B2, U.S. Appl. No. 15/782,628, Sommadossi et al., Jun. 19, 2018.
U.S. Pat. No. 10,005,811, B2, U.S. Appl. No. 15/782,638, Sommadossi et al., Jun. 26, 2018.
U.S. Pat. No. 10,202,412, B2, U.S. Appl. No. 15/645,701, Sommadossi et al., Feb. 12, 2019.
U.S. Pat. No. 10,239,911, B2, U.S. Appl. No. 16/001,549, Sommadossi et al., Oct. 4, 2018.
U.S. Pat. No. 10,519,186, B2, U.S. Appl. No. 15/885,630, Mousa et al., Dec. 31, 2019.
U.S. Pat. No. 10,874,687, B1, U.S. Appl. No. 17/017,443, Sommadossi et al., Dec. 29, 2020.
U.S. Pat. No. 10,815,266, B2, U.S. Appl. No. 16/278,621, Sommadossi et al., Oct. 27, 2020.
U.S. Pat. No. 10,870,672, B2, U.S. Appl. No. 16/900,397, Sommadossi et al., Dec. 22, 2020.

(56) References Cited

OTHER PUBLICATIONS

U.S. Pat. No. 10,870,673, B2, U.S. Appl. No. 16/918,898, Sommadossi et al., Dec. 22, 2020.
U.S. Pat. No. 10,875,885, B2, U.S. Appl. No. 16/918,914, Sommadossi et al., Dec. 29, 2020.
U.S. Pat. No. 10,894,804, B2, U.S. Appl. No. 16/918,918, Sommadossi et al., Jan. 19, 2021.
U.S. Pat. No. 10,906,928, B2, U.S. Appl. No. 16/687,136, Moussa et al., Feb. 2, 2021.
U.S. Pat. No. 10,946,033, B2, U.S. Appl. No. 16/293,423, Sommadossi et al., Mar. 16, 2021.
U.S. Pat. No. 10,906,928, B2, U.S. Appl. No. 16/687,136, Mousa et al., Feb. 2, 2021.
US, 2020/0179415, A1, U.S. Appl. No. 16/703,599, Sommadossi et al, Jun. 11, 2020.
US, 2021/0009628, A1, U.S. Appl. No. 17/028,724, Sommadossi et al., Jan. 14, 2021.
US, 2021/0015841, A1, U.S. Appl. No. 17/065,149, Sommadossi et al., Jan. 21, 2021.
US, 2021/0087217, A1, U.S. Appl. No. 17/118,314, Moussa et al., Mar. 25, 2021.
US, 2021/0275563, A1, U.S. Appl. No. 17/094,541, Sommadossi et al., Sep. 9, 2021.
US, 2021/0277045, A1, U.S. Appl. No. 17/306,659, Moussa et al., Sep. 9, 2021.
U.S. Appl. No. 17/184,445, filed Feb. 24, 2021, Sommadossi et al.
U.S. Appl. No. 17/306,643, filed May 3, 2021, Sommadossi et al.
U.S. Appl. No. 17/306,674, filed May 3, 2021, Sommadossi et al.
Ahmad, T. et al. "Cardiac dysfunction associated with a nucleotide polymerase inhibitor for treatment of hepatitis C" Hepatology 2015, 62, 409.
Berge, M.S. et al. "Pharmaceutical Salts" Journal of Pharmaceutical Sciences, 1977, 66, 1.
Berliba et al. Antimicrobial Agents and Chemotherapy 2019, 63, e01201-19.
Chang, W. et al. "Discovery of PSI-353661, a Novel Purine Nucleotide Prodrug for the Treatment of HCV Infection" ACS Med Chem Lett. 2011, 2, 130.
Cretton-Scott, E. et al. "In Vitro Antiviral Activity And Pharmacology Of Idx184, A Novel And Potent Inhibitor of HCV Replication" (Abstract 588) J. Hepatol. 2008, 48, Supplement 2, S220.
Freeman et al. 2-amino-9(3-azido-2,3-dideoxy-β-D-erythro-pentofuranosyl)-6-Substituted-9H-Purines: Synthesis and Anti-HIV Activity. Bioorganic and Medicinal Chemistry, 1995; 3(4): 447-448.
Fung, A. et al. "Efficiency of Incorporation and Chain Termination Determines the Inhibition Potency of 2'-Modified Nucleotide Analogs against Hepatitis C Virus Polymerase," AAC Journal, vol. 58, No. 7, Antimicrobial Agents and Chemotherapy, 58, pp. 3636-3645, Apr. 14, 2014.
Good, S. et al. "AT-337, AT-5911, and its Salt Form, AT-527: Novel Potent and Selective Pan-genotypic Purine Nucleotide Prodrug Inhibitors of HCV Polymerase" presented at the AASLD 2017 Liver Meeting; Oct. 20, 2017-Oct. 24, 2017; Washington, D.C.
Good et al., Preclinical evaluation of AT-527, a novel guanosine nucleotide prodrug with potent, pan-genotypic activity against hepatitis C virus, PLos ONE 2020, 15, e0227104.
Huang et al. "Impact of solid state properties on developability assessment of drug candidates" Advanced Drug Delivery Reviews, 2004, 56, 321.
KPCC Staff, "The biology of Zika virus: Here's what you need to know about Zika virus", internet article, https://www.scpr.org/news/2016/08/30/57263/here-s-what-you-need-to-know-about-Zika-virus/ (2016).
Low, et al., "Current Status of Dengue Therapeutics Research and Development," The Journal of Infectious Diseases, 2017:215 (Suppl 2).
Lu, Gaofei et al. "Analysis of Ribonucleotide 5'-Triphosphate Analogs as Potential Inhibitors of Zika Virus RNA-Dependent RNA Polymerase by Using Nonradioactive Polymerase Assays," Antimicrobial Agents and Chemotherapy, vol. 61, Issue Mar. 3, 2017; pp. 1-15.
McGuigan, C. et al. "Design, synthesis and evaluation of a novel double pro-drug: INX-08189. A new clinical candidate for hepatitis C virus" Bioorganic & Medicinal Chemistry Letters 2010, 20, 4850.
McGuigan, C. et al. "Dual pro-drugs of 2'-C-methyl guanosine monophosphate as potent and selective inhibitors of hepatitis C virus" Bioorganic & Medicinal Chemistry Letters 2011, 21, 6007.
Murakami, E. et al. "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem 2011, 54, 5902.
Nguyen, Lien et al., International Journal of Biomedical Science: Chiral Drugs: An Overview; Jun. 2, 2006(20; 85-100).
Poordad et al. "Daclatasvir with Sofosbuvir and Ribavirin for Hepatitis C Virus Infection with Advanced Cirrhosis or Post-Liver Transplantation Recurrence" Hepatology, 2016, 63, 1493.
Pradere, U. et al. "Synthesis of 5'-Methylene-Phosphonate Furanonucleoside Prodrugs: Application to D-2'-Deoxy-2'-α-fluoro-2'-β-C-methyl Nucleosides" Organic Letters 2012, 14, 4426.
Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters 2010, 20, 7376.
Serajuddin, A.T.M. "Salt formation to improve drug solubility" Advanced Drug Delivery Reviews, 2007, 59, 603.
Sofia, M.J. "Nucleotide Prodrugs for HCV Therapy," Antiviral Chemistry & Chemotherapy, 2011, 22, 23.
Stahl et al., "Handbook of Pharmaceutical Salts Properties, Selection, and Use," International Union of Pure and Applied Chemistry (IUPAC).
Tao, S., Zhou, L., Zhang, H., Zhou, S., Amiralaei, S., Shelton, J.R., Coats, S.J., Schinazi, R.F.: Comparison of Three 2'-C-Methyl Guanosine Prodrugs for Hepatitis C including a Novel $^2$-D-2'-C-Me-2,6-Diaminopurine Ribonucleoside Phosphoramidate (RS-1389): Interspecies Hepatocyte and Human Cardiomyocyte Metabolism Profiles. The Liver Meeting 2014, Boston, MA, USA. Nov. 6-11, 2014.
Xu, H. et al. "Evaluation of Sofosbuvir (β-D-2'deoxy-2'-α-fluoro-2'-β-C-methyluridine) as an inhibitor of Dengue virus replication" Scientific Reports, 2017, 7, 6345.
Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem 2015, 58, 3445.
Zhou, X. et al. "AT-527, a pan-genotypic purine nucleotide prodrug, exhibits potent antiviral activity in subjects with chronic hepatitis C" presented at The International Liver Congress 2018; Apr. 13, 2018; Paris, France.
Zhou, X. et al. "A Phase 1a Study of AT-527, a Novel Pan-Genotypic Purine Nucleotide Prodrug Inhibitor of Hepatitis C Virus (HCV)" presented at The Liver Meeting 2017; Oct. 23, 2017; Washington, D.C.
US, 11,738,038, A1, U.S. Appl. No. 17/306,674, Sommadossi et al., Aug. 29, 2023.
US, 2022/0347199, A1, U.S. Appl. No. 17/184,445, Sommadossi et al., Nov. 3, 2022.
US, 2023/0331751, A1, U.S. Appl. No. 18/111,316, Moussa et al., Oct. 19, 2023.
US, 2023/0049294, A1, U.S. Appl. No. 17/971,318, Moussa et al., Feb. 16, 2023.
U.S. Appl. No. 18/368,959, filed Sep. 15, 2023, Sommadossi et al.
U.S. Appl. No. 18/226,064, filed Jul. 25, 2023, Moussa et al.
U.S. Appl. No. 18/225,452, filed Jul. 24, 2023, Sommadossi et al.
U.S. Appl. No. 18/206,921, filed Jun. 7, 2023, Sommadossi et al.
U.S. Appl. No. 18/132,300, filed Apr. 7, 2023, Sommadossi et al..
U.S. Appl. No. 18/100,452, filed Jan. 23, 2023, Sommadossi et al.
U.S. Appl. No. 18/100,448, filed Jan. 23, 2023, Moussa et al.
Petition for Post Grant Review of U.S. Pat. No. 11,642,361; Filed Aug. 7, 2023 (PGR2023-00046—Paper No. 1).

(56) References Cited

OTHER PUBLICATIONS

Declaration of Alexander M. Klibanov, Ph.D.; Filed Aug. 6, 2023 (PGR2023-00046—Exhibit No. 15).

\* cited by examiner

2'-SUBSTITUTED-N⁶-SUBSTITUTED PURINE NUCLEOTIDES FOR RNA VIRUS TREATMENT

CROSS-REFERENCE TO RELATED APPLICATIONS

This application is a continuation of U.S. patent application Ser. No. 16/821,850, which is a continuation of U.S. Ser. No. 16/293,423, filed on Mar. 5, 2019, which is a continuation of International Application No. PCT/US2017/050323, filed in the United States Patent and Trademark Office Receiving Office on Sep. 6, 2017, which claims the benefit of provisional U.S. Application No. 62/384,664, filed on Sep. 7, 2016. The entirety of each of these applications is hereby incorporated by reference for all purposes.

FIELD OF THE INVENTION

The present invention is directed to nucleotide compounds, compositions and uses thereof to treat RNA viruses other than HCV.

BACKGROUND OF THE INVENTION

The Baltimore classification system sorts viruses into Groups, labeled I-VII, according to their genome. DNA viruses belong to Groups I, II, and VII, while RNA viruses belong to Groups III-VI. RNA viruses use ribonucleic acid as their genetic material. An RNA virus can have double-stranded (ds) RNA or single stranded RNA and can also be positive-stranded or negative-stranded. Group III viruses are double-stranded RNA viruses. Groups IV and V are both single-stranded RNA viruses, but Groups IV viruses are positive-sense and Groups V are negative-sense. Group VI are positive-sense single-stranded RNA viruses that replicate through a DNA intermediate.

The Group III dsRNA viruses include the following eleven families: Amalgaviridae, Birnaviridae, Chrysoviridae, Cystoviridae, Endornaviridae, Hypoviridae, Megabirnaviridae, Partitiviridae, Picobirnaviridae, Quadriviridae, Reoviridae and Totiviridae.

The Group IV positive-sense ssRNA viruses include three orders and thirty-three families. The order Nidovirales includes the following families: Arteviridae, Coronaviridae, Mesoniviridae, and Roniviridae. The order Picornavirales includes the following families: Dicistroviridae, Ifaviridae, Marnaviridae, Picornaviridae and Secoviridae. The order Tymovirales includes the following families: Alphaflexiviridae, Betaflexiviridae, Gammaflexiviridae and Tymoviridae. The following positive-sense ssRNA viruses include viruses from the following unassigned families: Alphatetraviridae, Alvernaviridae, Astroviridae, Barnaviridae, Benyviridae, Bromoviridae, Caliciviridae, Carmotetraviridae, Closteroviridae, Flaviviridae, Fusariviridae, Hepeviridae, Leviviridae, Luteoviridae, Narnaviridae, Nodaviridae, Permutotetraviridae, Potyviridae, Togaviridae, Tombusviridae and Virgaviridae.

Coronaviridae viral infections include infections with virus of the genuses Alphacoronavirus, Betacoronavirus (which includes severe acute respiratory syndrome coronavirus (SARS-CoV)), Gammacoronavirus, and Deltacoronavirus.

Flaviviridae viral infections include infections with viruses of the genera Flavivirus and Pestivirus. Flavivirus infections include Dengue fever, Kyasanur Forest disease, Powassan disease, Wesselsbron disease, West Nile fever, yellow fever, Zika virus, Rio bravo, Rocio, Negishi, and the encephalitises including: California encephalitis, central European encephalitis, Ilheus virus, Murray Valley encephalitis, St. Louis encephalitis, Japanese B encephalitis, Louping ill, and Russian spring-rodents summer encephalitis. Pestivirus infections include primarily livestock diseases, including swine fever in pigs, BVDV (bovine viral diarrhea virus) in cattle, and Border Disease virus infections.

Picornavirus infections include infections with viruses of the genuses Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Salivirus, Sapelovirus, Senecavirus, Teschovirus, and Tremovirus.

The Togaviridae family comprises four genera: Alphavirus, Arterivirus, Rubivirus and Pestivirus. The alphavirus genus contains four viruses that produce encephalitis: Eastern equine encephalitis (EEE) virus, Venezuelan equine encephalitis (VEE) virus, Western equine encephalitis (WEE) virus and the Everglades virus. In addition, the Alphavirus genus includes the Chikungunya virus, Mayaro virus, Ockelbo virus, O'nyong-nyong virus, Ross River virus, Semliki Forest virus and Sindbis virus (SINV). The Arterivirus genus contains a single member: the equine arteritis virus. The pestivirus genus contains three viruses of veterinary importance, namely the bovine viral diarrhea virus (BVDV), hog cholera virus and border disease virus. The only member of the Rubivirus genus is the rubella virus.

The Group V negative-sense ssRNA viruses include the order Mononegavirales. The Mononegavirales order includes, but is not limited to, the following families and viruses: Bornaviridae, Borna disease virus; Filoviridae, Ebola virus and Marburg virus; Paramyxoviridae, Measles virus, Mumps virus, Nipah virus, Hendra virus, respiratory syncytial virus (RSV) and Newcastle disease virus (NDV); Rhabdoviridae, Rabies virus and Nyamiviridae, Nyavirus. Unassigned families and viruses include, but are not limited to: Arenaviridae, Lassa virus; Bunyaviridae, Hantavirus, Crimean-Congo hemorrhagic fever; Ophioviridae and Orthomyxoviridae, influenza virus.

The Bunyaviridae family comprises more than two hundred named viruses and the family is divided into five genera: Hantavirus, Nairovirus, Orthobunyavirus, Phlebovirus and Tospovirus. The Hantavirus genus includes the Hantaan virus. The Nairovirus genus includes the Crimean-Congo Hemorrhagic Fever virus and Dugbe viruses. The Orthobunyavirus genus is comprised of approximately one hundred seventy viruses that have been divided into multiple serogroups. The Serogroups include Anopheles A serogroup, Anopheles B serogroup, Bakau serogroup, Bunyamwera serogroup, Bwamba serogroup, California serogroup, Capim serogroup, Gamboa serogroup, Group C serogroup, Guama serogroup, Koongol serogroup, Mapputta serogroup, Minatitlan serogroup, Nyando serogroup, Olifanstlei serogroup, Patois serogroup, Simbu serogroup, Tete serogroup, Turlock serogroup, Wyeomyia serogroup and the Unclassified group. The Anopheles A serogroup includes the Anopheles A virus, Tacaiuma virus, Virgin River virus, Trombetas complex, Arumateua virus, Caraipe virus, Trombetas virus and the Tucurui virus. The Anopheles B serogroup includes the Anopheles B virus and the Boraceia virus. The Bakau serogroup includes the Bakau virus and the Nola virus. The Bunyamwera serogroup includes the Birao virus, Bozo virus, Bunyamwera virus, Cache Valley virus, Fort Sherman virus, Germiston virus, Guaroa virus, Ilesha virus, Kairi virus, Main Drain virus, Northway virus, Playas virus, Potosi virus, Shokwe virus, Stanfield virus, Tensaw virus, Xingu virus, Batai virus, Calovo virus, Chittoor virus, Garissa virus, KV-141 virus, and Ngari virus. The Bwamba serogroup includes the Bwamba and Pongola viruses. The California serogroup includes the California encephalitis virus, Chatanga virus, Inkoo virus, Jamestown Canyon virus, Jerry Slough virus, Keystone virus, Khatanga virus, La Crosse virus, Lumbo virus, Melao virus, Morro Bay virus, San Angelo virus, Serra do Navio virus, Snowshoe hare virus, South River virus, Tahyna virus, and the Trivittatus virus. The Capim serogroup includes the Acara virus, Benevides virus and the Capim virus. The Gamboa serogroup includes the Alajuela virus, Gamboa virus, Pueblo Viejo virus and San Juan virus. The Group C serogroup includes, but is not limited to, Bruconha virus, Ossa virus, Apeu virus, Brunconha virus, Caraparu virus, Vinces virus, Madrid virus, Gumbo limbo virus, Marituba virus, Murutucu virus, Nepuyo virus, Restan virus, Itaqui virus and Oriboca virus. The Guama serogroup includes, but is not limited to, the Bertioga virus, Bimiti virus, Cananeia virus, Guama virus, Guaratuba virus, Itimirim virus and Mirim virus. The Koongol serogroup includes, but is not limited to, the Koongol virus and Wongal virus. The Mapputta serogroup includes, but is not limited to, the Buffalo Creek virus, Mapputta virus, Maprik virus, Murrumbidgee virus and Salt Ash virus. The Minatitlan serogroup includes, but is not limited to, Minatitlan virus and Palestina virus. The Nyando serogroup includes, but is not limited to, Eretmapodites virus and Nyamdo virus. The Olifanstlei serogroup includes, but is not limited to, Botambi virus and Olifanstlei virus. The Patois serogroup includes, but is not limited to, Abras virus, Babahoyo virus, Pahayokee virus, Patois virus and Shark River virus. The Simbu serogroup includes, but is not limited to, Iquitos virus, Jatobal virus, Leanyer virus, Madre de Dios virus, Oropouche virus, Oya virus, Thimiri virus, Akabane virus, Tinaroo virus, Douglas virus, Sathuperi virus, Aino virus, Shuni virus, Peaton virus, Shamonda virus, Schmallenberg virus and Simbu virus. The Tete serogroup includes, but is not limited to, Batama virus and Tete virus. The Turlock serogroup includes, but is not limited to, M'Poko virus, Turlock virus and Umbre virus. The Wyeomyia serogroup includes, but is not limited to, Anhembi virus, Cachoeira Porteira virus, Iaco virus, Macaua virus, Sororoca virus, Taiassui virus, Tucunduba virus and Wyeomyia virus. The Unclassified serogroup includes, but is not limited to, Batama virus, Belmont virus, Enseada virus, Estero Real virus, Jurona virus, Kaeng Khei virus and Kowanyama virus. The Phlebovirus genus includes, but is not limited to, the Naples and Sicilian Sandfly Fever viruses and Rift Valley Fever virus. The Tospovirus genus includes, but is not limited to, the type species Tomato spotted wilt virus and the following species: Bean necrotic mosaic virus, Capsicum chlorosis virus, Groundnut bud necrosis virus, Groundnut ringspot virus, Groundnut yellow spot virus, Impatiens necrotic spot virus, Iris yellow spot virus, Melon yellow spot virus, Peanut bud necrosis virus, Peanut yellow spot virus, Soybean vein necrosis-associated virus, Tomato chlorotic spot virus, Tomato necrotic ringspot virus, Tomato yellow ring virus, Tomato zonate spot virus, Watermelon bud necrosis virus, Watermelon silver mottle virus and Zucchini lethal chlorosis virus.

Picornavirus infections include infections with viruses of the genuses Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Salivirus, Sapelovirus, Senecavirus, Teschovirus, and Tremovirus. Coronavirus infections include infections with virus of the genuses Alphacoronavirus, Betacoronavirus (which includes severe acute respiratory syndrome coronavirus (SARS-CoV)), Gammacoronavirus, and Deltacoronavirus.

United States patents and WO applications which describe nucleoside polymerase inhibitors for the treatment of viruses include those filed by Idenix Pharmaceuticals (U.S. Pat. Nos. 6,812,219; 6,914,054; 7,105,493; 7,138,376; 7,148,206; 7,157,441; 7,163,929; 7,169,766; 7,192,936; 7,365,057; 7,384,924; 7,456,155; 7,547,704; 7,582,618; 7,608,597; 7,608,600; 7,625,875; 7,635,689; 7,662,798; 7,824,851; 7,902,202; 7,932,240; 7,951,789; 8,193,372; 8,299,038; 8,343,937; 8,362,068; 8,507,460; 8,637,475; 8,674,085; 8,680,071; 8,691,788, 8,742,101; 8,951,985; 9,109,001; 9,243,025; US2016/0002281; US2013/0064794; WO/2015/095305; WO/2015/081133; WO/2015/061683; WO/2013/177219; WO/2013/039920; WO/2014/137930; WO/2014/052638; WO/2012/154321); Merck (U.S. Pat. Nos. 6,777,395; 7,105,499; 7,125,855; 7,202,224; 7,323, 449; 7,339,054; 7,534,767; 7,632,821; 7,879,815; 8,071, 568; 8,148,349; 8,470,834; 8,481,712; 8,541,434; 8,697, 694; 8,715,638, 9,061,041; 9,156,872 and WO/2013/ 009737); Emory University (U.S. Pat. Nos. 6,348,587; 6,911,424; 7,307,065; 7,495,006; 7,662,938; 7,772,208; 8,114,994; 8,168,583; 8,609,627; US 2014/0212382; and WO2014/1244430); Gilead Sciences/Pharmasset Inc. (7,842,672; 7,973,013; 8,008,264; 8,012,941; 8,012,942; 8,318,682; 8,324,179; 8,415,308; 8,455,451; 8,551,973; 8,563,530; 8,841,275; 8,853,171; 8,871,785; 8,877,733; 8,889,159; 8,906,880; 8,912,321; 8,957,045; 8,957,046; 9,045,520; 9,085,573; 9,090,642; 9,139,604; 9,206,217; 9,284,342 and 9,394,331) and (U.S. Pat. Nos. 6,908,924; 6,949,522; 7,094,770; 7,211,570; 7,429,572; 7,601,820; 7,638,502; 7,718,790; 7,772,208; RE42,015; 7,919,247; 7,964,580; 8,093,380; 8,114,997; 8,173,621; 8,334,270; 8,415,322; 8,481,713; 8,492,539; 8,551,973; 8,580,765; 8,618,076; 8,629,263; 8,633,309; 8,642,756; 8,716,262; 8,716,263; 8,735,345; 8,735,372; 8,735,569; 8,759,510 and 8,765,710); Hoffman La-Roche (U.S. Pat. No. 6,660,721), Roche (U.S. Pat. Nos. 6,784,166; 7,608,599, 7,608,601 and 8,071,567); Alios BioPharma Inc. (U.S. Pat. Nos. 8,895,723; 8,877,731; 8,871,737, 8,846,896, 8,772,474; 8,980,865; 9,012,427; US 2015/0105341; US 2015/0011497; US 2010/ 0249068; US2012/0070411; WO 2015/054465; WO 2014/ 209979; WO 2014/100505; WO 2014/100498; WO 2013/ 142159; WO 2013/142157; WO 2013/096680; WO 2013/ 088155; WO 2010/108135), Enanta Pharmaceuticals (U.S. Pat. Nos. 8,575,119; 8,846,638; 9,085,599; WO 2013/ 044030; WO 2012/125900), Biota (U.S. Pat. Nos. 7,268, 119; 7,285,658; 7,713,941; 8,119,607; 8,415,309; 8,501,699 and 8,802,840), Biocryst Pharmaceuticals (U.S. Pat. Nos. 7,388,002; 7,429,571; 7,514,410; 7,560,434; 7,994,139; 8,133,870; 8,163,703; 8,242,085 and 8,440,813), Alla Chem, LLC (U.S. Pat. No. 8,889,701 and WO 2015/ 053662), Inhibitex (U.S. Pat. No. 8,759,318 and WO/2012/ 092484), Janssen Products (U.S. Pat. Nos. 8,399,429; 8,431, 588, 8,481,510, 8,552,021, 8,933,052; 9,006,29 and 9,012, 428) the University of Georgia Foundation (U.S. Pat. Nos. 6,348,587; 7,307,065; 7,662,938; 8,168,583; 8,673,926, 8,816,074; 8,921,384 and 8,946,244), RFS Pharma, LLC (U.S. Pat. Nos. 8,895,531; 8,859,595; 8,815,829; 8,609,627; 7,560,550; US 2014/0066395; US 2014/0235566; US 2010/ 0279969; WO/2010/091386 and WO 2012/158811) University College Cardiff Consultants Limited (WO/2014/ 076490, WO 2010/081082; WO/2008/062206), Achillion Pharmaceuticals, Inc. (WO/2014/169278 and WO 2014/ 169280), Cocrystal Pharma, Inc. (U.S. Pat. No. 9,173,893), Katholieke Universiteit Leuven (WO 2015/158913), Catabasis (WO 2013/090420), the Regents of the University of Minnesota (WO 2006/004637), and Atea Pharmaceuticals, Inc (WO 2016/144918).

Additional United States patents, United States patent applications and PCT applications that describe nucleoside compounds as virus infection inhibitors include U.S. Pat. Nos. 7,388,002; 7,560,434; 8,415,321; 9,126,971; 9,326,991; and US 2004/0229839.

There remains a strong medical need to develop anti-RNA virus therapies that are safe, effective and well-tolerated. The need is accentuated by the expectation that RNA viruses continue to spread into uninfected areas of the world and that RNA viruses mutate under drug pressure.

It is therefore an object of the present invention to provide compounds, pharmaceutical compositions, and methods and uses to treat and/or prevent infections of an RNA virus, in particular RNA viruses other than HCV.

SUMMARY OF THE INVENTION

It has been discovered that the compounds of Formula I, Formula II, Formula III, Formula IV, Formula V, and Formula VI, including 2'-substituted-$N^6$-substituted purine nucleotides, are advantageous for treatment of RNA viruses, in particular RNA viruses other than HCV, when administered in an effective amount to a host in need thereof. The host can be a human or any animal that carries the viral infection.

Disclosed nucleotides include those with advantageous activity, for example, against bovine viral diarrhea virus (BVDV), Dengue virus 2, West Nile virus (WNV), Zika and Yellow fever virus (YFV) in vitro. Disclosed nucleotides also include those with advantageous activity against subtype 5 of the Coxsackie B virus. In one embodiment, a method is presented to treat a single-stranded RNA positive stranded virus other than a hepacivirus or other than HCV. In a further embodiment, a method is provided to treat Dengue virus 2 or Yellow fever virus. In an alternative embodiment, a method is presented to treat a single-stranded RNA negative-sense virus. In an alternative embodiment, a method is presented to treat a double-stranded RNA virus.

The compounds of the present invention are anabolized to a 5-monophosphate of the $N^6$-substituted-purine without substantial $N^6$-deamination and then subsequently anabolized at the 6-position to generate active guanine triphosphate compounds in a manner that provides good activity and therapeutic index.

As an example, the metabolism of the β-D-2'-substituted-$N^6$-methyl-2,6-diaminopurine nucleoside as a phosphoramidate involves the production of a 5'-monophosphate and the subsequent anabolism of the $N^6$-methyl-2,6-diaminopurine base to generate the 2'-substituted guanine nucleoside as the 5'-monophosphate. The monophosphate is then further anabolized to the active species which is the 5'-triphosphate.

In particular, it has been discovered that a 5'-stabilized phosphate prodrug or derivative of a 2'-substituted-$N^6$-methyl-2,6-diaminopurine nucleotide, as well as a 2'-substituted-2-$N^6$-dimethyl-2,6-diaminopurine nucleotide, and other 2'-substituted-$N^6$-substituted purine nucleotides as described below are active against a range of RNA viruses. For example, a discussed in Example 14 and shown in Table 5, Compound 205 is potent against Dengue Fever ($EC_{50}$=0.8 µM) and Yellow Fever ($EC_{50}$=1.2 µM).

Thus, in one embodiment, the invention is the use of a compound of Formula I below for the treatment of an infection of an RNA virus in a host, for example, a human in need thereof. In one embodiment, a method is presented to treat a host, including a human, infected with a single-stranded RNA positive stranded virus other than a hepacivirus or other than HCV with an effective amount of a compound of Formula I. In an alternative embodiment, a method is presented to treat a host, including a human, infected with a single-stranded RNA positive stranded virus of the Flaviviridae family, including but not limited to Dengue virus 2 and Yellow Fever, with an effective amount of a compound of Formula I. In an alternative embodiment, a method is presented to treat a host, including a human, infected with a single-stranded RNA negative-sense virus with an effective amount of a compound of Formula I. In an alternative embodiment, a method is presented to treat a host, including a human, infected with a double-stranded RNA virus with an effective amount of a compound of Formula I:

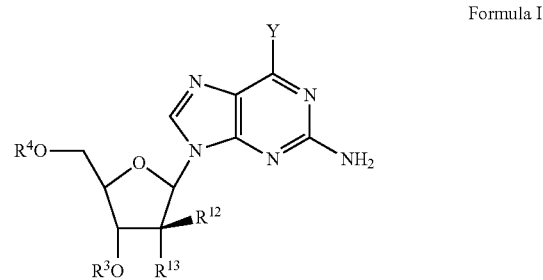

Formula I wherein:
Y is $NR^1R^2$;
$R^1$ is $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CH_2F$, $CHF_2$, $CF_3$, $CH_2CF_3$, $CF_2CH_3$ and $CF_2CF_3$), $C_2$-$C_6$ alkenyl, $C_2$-$C_6$ alkynyl, —($C_0$-$C_2$alkyl)($C_3$-$C_6$cycloalkyl), —($C_0$-$C_2$alkyl)(heterocycle), —($C_0$-$C_2$alkyl)(aryl), —($C_0$-$C_2$alkyl)(heteroaryl), —$OR^{23}$, —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$ each of which can be optionally substituted;
$R^2$ is hydrogen, $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CHF_2$, $CF_3$, $CH_2CF_3$ and $CF_2CF_3$), —($C_0$-$C_2$alkyl)($C_3$-$C_6$cycloalkyl), —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —($C_0$-$C_2$alkyl)(aryl), —($C_0$-$C_2$alkyl)heterocycle), —($C_0$-$C_2$alkyl)(heteroaryl); and wherein at least one of $R^1$ and $R^2$ is methyl, $CH_2F$, $CHF_2$ or $CF_3$;
$R^3$ is hydrogen,

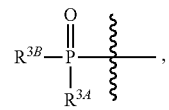

diphosphate, triphosphate, an optionally substituted carbonyl linked amino acid, or —$C(O)R^{3C}$;
$R^{3A}$ can be selected from $O^-$, OH, an —O-optionally substituted aryl, an —O-optionally substituted heteroaryl, or an optionally substituted heterocyclyl;

$R^{3B}$ can be selected from O⁻, OH, an optionally substituted N-linked amino acid or an optionally substituted N-linked amino acid ester;

$R^{3C}$ is alkyl, alkenyl, alkynyl, —(C₀-C₂)(cycloalkyl), —(C₀-C₂)(heterocyclo), —(C₀-C₂)(aryl), —(C₀-C₂)(heteroaryl), —O-alkyl, —O-alkenyl, —O-alkynyl, —O—(C₀-C₂)(cycloalkyl), —O—(C₀-C₂)(heterocyclo), —O—(C₀-C₂)(aryl), or —O—(C₀-C₂)(heteroaryl), each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug, including but not limited to, a 3',5'-cyclic phosphate prodrug;

$R^{12}$ is hydrogen, CH₃, CH₂F, CHF₂, CF₃, or ethynyl; and $R^{13}$ is hydrogen, fluoro, chloro, bromo, N₃, NH₂, CN or OR³;

wherein when $R^{12}$ is methyl, $R^{13}$ is bromo, chloro, N₃, NH₂, CN or OR³.

In an alternative embodiment, at least one of $R^1$ and $R^2$ is cyclopropyl.

In an alternative embodiment, at least one of $R^1$ and $R^2$ is cyclopentyl.

In another embodiment, the invention is the use of a compound of Formula II below for the treatment of an infection of an RNA virus in a host, for example, a human in need thereof. In one embodiment, a method is presented to treat a host, including a human, infected with a single-stranded RNA positive stranded virus other than a hepacivirus or other than HCV with an effective amount of a compound of Formula II. In an alternative embodiment, a method is presented to treat a host, including a human, infected with a single-stranded RNA positive stranded virus of the Flaviviridae family, including but not limited to Dengue virus 2 and Yellow Fever, with an effective amount of a compound of Formula II. In an alternative embodiment, a method is presented to treat a host, including a human, infected with a single-stranded RNA negative-sense virus with an effective amount of a compound of Formula II. In an alternative embodiment, a method is presented to treat a host, including a human, infected with a double-stranded RNA virus with an effective amount of a compound of Formula II:

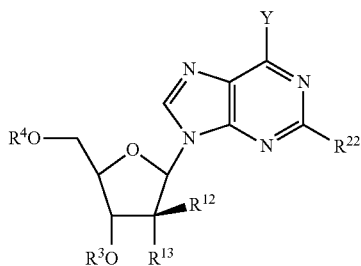

Formula II wherein:

Y is NR¹R²;

$R^1$ is C₁-C₅alkyl (including methyl, ethyl, n-propyl, iso-propyl, n-butyl, iso-butyl, sec-butyl, tert-butyl and pentyl), C₁-C₅haloalkyl (including CH₂F, CHF₂, CF₃, CH₂CF₃, CF₂CH₃ and CF₂CF₃), C₂-C₆ alkenyl, C₂-C₆ alkynyl, —(C₀-C₂alkyl)(C₃-C₆cycloalkyl), —(C₀-C₂alkyl)(heterocycle), —(C₀-C₂alkyl)(aryl), —(C₀-C₂alkyl)(heteroaryl), —OR²⁵, —C(O)R³ᶜ(including —C(O)CH₃, —C(O)CH₂CH₃—C(O)CH(CH₃)₂, —C(O)OCH₃, —C(O)OC₂H₅, —C(O)OC₃H₇, —C(O)OC₄H₉, and —C(O)OC₅H₁₁), —C(S)R³ᴰ, or —SO₂R²⁸ each of which can be optionally substituted;

$R^2$ is hydrogen, optionally substituted C₁-C₅alkyl (including methyl, ethyl, n-propyl, iso-propyl, n-butyl, iso-butyl, sec-butyl, tert-butyl and pentyl), C₁-C₅haloalkyl (including CHF₂, CHF₂, CF₃, CH₂CF₃ and CF₂CF₃), optionally substituted —(C₀-C₂alkyl)(C₃-C₆cycloalkyl), optionally substituted —(C₀-C₂alkyl)heterocycle), optionally substituted —(C₀-C₂alkyl)(aryl), optionally substituted —(C₀-C₂alkyl)(heteroaryl), —C(O)R³ᶜ (including —C(O)CH₃, —C(O)CH₂CH₃—C(O)CH(CH₃)₂, —C(O)OCH₃, —C(O)OC₂H₅, —C(O)OC₃H₇, —C(O)OC₄H₉, and —C(O)OC₅H₁₁), —C(S)R³ᴰ, or —SO₂R²⁸; and wherein at least one of $R^1$ and $R^2$ is methyl, CH₂F, CHF₂ or CF₃;

$R^3$ is hydrogen,

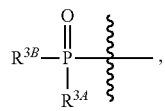

diphosphate, triphosphate, an optionally substituted carbonyl linked amino acid, or —C(O)R³ᶜ;

$R^{3A}$ can be selected from O⁻, OH, an —O-optionally substituted aryl, an —O-optionally substituted heteroaryl, or an optionally substituted heterocyclyl;

$R^{3B}$ can be selected from O⁻, OH, an optionally substituted N-linked amino acid or an optionally substituted N-linked amino acid ester;

$R^{3C}$ is alkyl, alkenyl, alkynyl, —(C₀-C₂)(cycloalkyl), —(C₀-C₂)heterocyclo, —(C₀-C₂)(aryl), —(C₀-C₂)(heteroaryl), —O-alkyl, —O-alkenyl, —O-alkynyl, —O—(C₀-C₂)(cycloalkyl), —O—(C₀-C₂)(heterocyclo), —O—(C₀-C₂)(aryl), —O—(C₀-C₂)(heteroaryl), —S-alkyl, —S-alkenyl, —S-alkynyl, —S—(C₀-C₂)(cycloalkyl), —S—(C₀-C₂)(heterocyclo), —S—(C₀-C₂)(aryl), or —S—(C₀-C₂)(heteroaryl) each of which can be optionally substituted;

$R^{3D}$ is alkyl, alkenyl, alkynyl, —(C₀-C₂)(cycloalkyl), —(C₀-C₂)heterocyclo, —(C₀-C₂)(aryl), —(C₀-C₂)(heteroaryl), —O-alkyl, —O-alkenyl, —O-alkynyl, —O—(C₀-C₂)(cycloalkyl), —O—(C₀-C₂)(heterocyclo), —O—(C₀-C₂)(aryl), or —O—(C₀-C₂)(heteroaryl), each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug, including but not limited to, a 3',5'-cyclic phosphate prodrug;

$R^5$ is C₁-C₅alkyl (including methyl, ethyl, n-propyl, iso-propyl, n-butyl, iso-butyl, sec-butyl, tert-butyl and pentyl), C₁-C₅haloalkyl (including CHF₂, CHF₂, CF₃, CH₂CF₃ and CF₂CF₃), C₂-C₆ alkenyl, C₂-C₆ alkynyl, —(C₀-C₂alkyl)(C₃-C₆cycloalkyl), —(C₀-C₂alkyl)(heterocycle), —(C₀-C₂alkyl)(aryl), —(C₀-C₂alkyl)(heteroaryl), —OR²⁵, —C(O)R³ᶜ (including —C(O)CH$_3$, —C(O)CH$_2$CH$_3$—C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$ each of which can be optionally substituted;

R$^6$ is hydrogen, optionally substituted C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CHF$_2$, CHF$_2$, CF$_3$, CH$_2$CF$_3$ and CF$_2$CF$_3$), optionally substituted —(C$_0$-C$_2$alkyl)(C$_3$-C$_6$cycloalkyl), optionally substituted —(C$_0$-C$_2$alkyl) heterocycle), optionally substituted —(C$_0$-C$_2$alkyl) (aryl), optionally substituted —(C$_0$-C$_2$alkyl) (heteroaryl), —C(O)R$^{3C}$ (including —C(O)CH$_3$, —C(O)CH$_2$CH$_3$—C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$; or R$^5$ and R$^6$ together with the nitrogen that they are bonded to can form a heterocyclic ring;

R$^{12}$ is hydrogen, CH$_3$, CH$_2$F, CHF$_2$, CF$_3$, or ethynyl;

R$^{13}$ is hydrogen, fluoro, chloro, bromo, N$_3$, NH$_2$, CN or OR$^3$;

wherein when R$^{12}$ is methyl, R$^{13}$ is bromo, chloro, N$_3$, NH$_2$, CN or OR$^3$.

R$^{22}$ is C$_1$, Br, F, CN, N$_3$, C$_1$-C$_6$ alkyl, C$_2$-C$_6$ alkenyl, C$_2$-C$_6$ alkynyl, —(C$_1$-C$_2$alkyl)(C$_3$-C$_6$cycloalkyl), —(C$_0$-C$_2$alkyl)(C$_3$-C$_6$heterocycle), —(C$_0$-C$_2$alkyl) (aryl), —(C$_0$-C$_2$alkyl)(heteroaryl); —ONHC(=O)OR$^{23}$, —NHOR$^{24}$, —OR$^{25}$, —SR$^{25}$, —NH(CH$_2$)$_{1-4}$N(R$^{26}$)$_2$, —NHNHR$^{26}$, —N=NR$^{27}$, —NHC(O)NHNHR$^{27}$, —NHC(S)NHNHR$^{27}$, —C(O)NHNHR$^{27}$, —NR$^{27}$SO$_2$R$^{28}$, —SO$_2$NR$^{27}$R$^{29}$, —C(O)NR$^{27}$R$^{29}$, —CO$_2$R$^{29}$, —SO$_2$R$^{29}$,

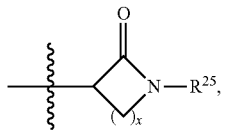

—P(O)H(OR$^{29}$), —P(O)(OR$^{29}$)(OR$^{30}$), —P(O)(OR$^{29}$)(NR$^{29}$R$^{30}$) or —NR$^5$R$^6$; for example including but not limited to the following embodiments, chloro, bromo, fluoro, cyano, azido, ethyl, n-propyl, iso-propyl, n-butyl, iso-butyl, sec-butyl, tert-butyl and n-pentyl, 1,1-dimethylpropyl, 2,2-dimethylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —(CH$_2$)-cyclopropyl, —(CH$_2$)-cyclobutyl, —(CH$_2$)-cyclopentyl, —(CH$_2$)-cyclohexyl, aziridine, oxirane, thiirane, azetidine, oxetane, thietane, pyrrolidine, tetrahydrofuran, thiolane, pyrazolidine, piperidine, oxane, thiane, —(CH$_2$)-aziridine, —(CH$_2$)-oxirane, —(CH$_2$)-thiirane, —(CH$_2$)-azetidine, —(CH$_2$)-oxetane, —(CH$_2$)-thietane, —(CH$_2$)-pyrrolidine, —(CH$_2$)-tetrahydrofuran, —(CH$_2$)-thiolane, —(CH$_2$)-pyrazolidine, —(CH$_2$)-piperidine, —(CH$_2$)-oxane, —(CH$_2$)-thiane, phenyl, pyridyl, —ONHC(=O)OCH$_3$, —ONHC(=O)OCH$_2$CH$_3$, —NHOH, NHOCH$_3$, —OCH$_3$, OC$_2$H$_5$, —OPh, OCH$_2$Ph, —SCH$_3$, —SC$_2$H$_5$, —SPh, SCH$_2$Ph, —NH(CH$_2$)$_2$NH$_2$, —NH(CH$_2$)$_2$N(CH$_3$)$_2$, —NHNH$_2$, —NHNHCH$_3$, —N=NH, —N=NCH$_3$, —N=NCH$_2$CH$_3$, —NHC(O)NHNH$_2$, —NHC(S)NHNH$_2$, —C(O)NHNH$_2$, —NHSO$_2$CH$_3$, —NHSO$_2$CH$_2$CH$_3$, —SO$_2$NHCH$_3$, —SO$_2$N(CH$_3$)$_2$, —C(O)NH$_2$, —C(O)NHCH$_3$, —C(O)N(CH$_3$)$_2$, —CO$_2$CH$_3$, —CO$_2$CH$_2$CH$_3$, —CO$_2$Ph, —CO$_2$CH$_2$Ph, —SO$_2$CH$_3$, —SO$_2$CH$_2$CH$_3$, —SO$_2$Ph, —SO$_2$CH$_2$Ph,

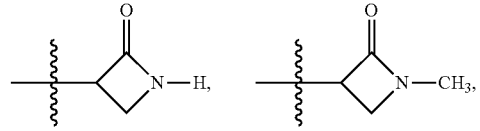

—P(O)H(OH), —P(O)H(OCH$_3$), —P(O)(OH)(OH), —P(O)(OH)(OCH$_3$), —P(O)(OCH$_3$)(OCH$_3$), —P(O)(OH)(NH$_2$), —P(O)(OH)(NHCH$_3$), —P(O)(OH)N(CH$_3$)$_2$, —NHC(O)CH$_3$, —NHC(O)CH$_2$CH$_3$, —NHC(O)CH(CH$_3$)$_2$, —NHC(O)OCH$_3$, —NHC(O)OCH$_2$CH$_3$, —NHC(O)OCH(CH$_3$)$_2$, —NHC(O)OCH$_2$CH$_2$CH$_3$, —NHC(O)OCH$_2$CH$_2$CH$_2$CH$_3$ and —NHC(O)OCH$_2$CH$_2$CH$_2$CH$_3$;

R$^{23}$ is C$_1$-C$_5$alkyl, —(C$_0$-C$_2$alkyl)(C$_3$-C$_6$cycloalkyl), —(C$_0$-C$_2$alkyl)(heterocycle), —(C$_{0-2}$alkyl)(aryl) or —(C$_0$-C$_2$alkyl)(heteroaryl) each of which can be optionally substituted;

R$^{24}$ is hydrogen, C$_1$-C$_6$ alkyl, —(C$_1$-C$_2$alkyl)(C$_3$-C$_6$cycloalkyl), —(C$_1$-C$_2$alkyl)(C$_3$-C$_6$heterocycle) —(C$_0$-C$_2$alkyl)(aryl) or —(C$_0$-C$_2$alkyl)(heteroaryl) wherein except for the hydrogen each of which can be optionally substituted;

R$^{25}$ is hydrogen, C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted;

R$^{26}$ is independently selected from hydrogen, C$_1$-C$_6$alkyl, —(C$_0$-C$_2$alkyl)(C$_3$-C$_6$cycloalkyl), —(C$_0$-C$_2$alkyl)(heterocycle), —(C$_0$-C$_2$alkyl)(aryl), or —(C$_0$-C$_2$alkyl)(heteroaryl) wherein except for the hydrogen each of which can be optionally substituted;

R$^{27}$ hydrogen or optionally substituted C$_1$-C$_6$ alkyl;

R$^{28}$ is C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) each of which can be optionally substituted;

R$^{29}$ is hydrogen, C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted; or R$^{27}$ and R$^{29}$ together with the nitrogen that they are bonded to can form a heterocyclic ring;

R$^{30}$ is hydrogen, C$_1$-C$_6$ alkyl, C$_2$-C$_6$ alkenyl, C$_2$-C$_6$ alkynyl, —(C$_0$-C$_2$alkyl)(C$_3$C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted; or R$^{29}$ and R$^{30}$ can be bonded together to form a heterocyclic ring;

x is 1, 2 or 3.

In an alternative embodiment, at least one of R$^1$ and R$^2$ is cyclopropyl.

In an alternative embodiment, at least one of R$^1$ and R$^2$ is cyclopentyl.

In an alternative embodiment, R$^{23}$ is —(C$_0$-C$_2$alkyl)(heterocycle) or —(C$_{0-2}$alkyl)(aryl).

β-D-2'-Deoxy-2'-α-fluoro-2'-β-ethynyl-N⁶-methyl-2,6-diaminopurine nucleoside phosphoramidate is first metabolized to the 5'-monophosphate and then the N⁶-methyl-2,6-diaminopurine base is anabolized to generate the β-D-2'-deoxy-2'-α-fluoro-2'-β-ethylguanine nucleoside as the 5'-monophosphate. The monophosphate is then further anabolized to the active species, the 5'-triphosphate (Scheme 1).

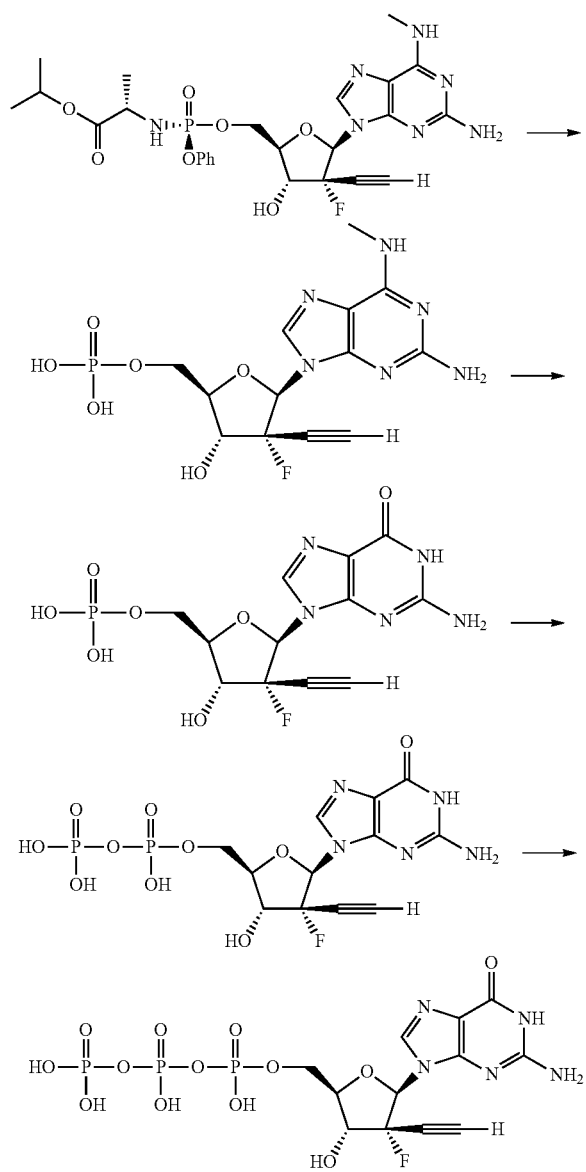

Scheme 1

2'-Substituted-N⁶-substituted-2,6-diaminopurine nucleotides can be further substituted at the N²-position by alkylation or acylated. This can modify the lipophilicity, pharmacokinetics, and/or targeting of the nucleotide to the liver. It has been discovered that 2'-substituted-N⁶-substituted-2,6-diaminopurine nucleotides modified at the 2-position of the diaminopurine can be dealkylated or deacylated by hepatic enzymes to further increase the specificity of the nucleotide derivatives both in vitro and in vivo, unless the N²-amino group is completely replaced by a different moiety, as described herein, such as fluoro. In one embodiment, N² modifications will increase cell permeability. In one embodiment, N² modifications will increase hepatic targeting.

Unless otherwise specified, the compounds described herein are provided in the β-D-configuration. Likewise, when in phosphoramidate or thiophosphoramidate form, the amino acid portion can be in the L- or D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the R⁴ stabilized phosphate prodrug, it can be provided as an R or S chiral phosphorus derivative or a mixture thereof, including a racemic mixture. All of the combinations of these stereo configurations are included in the invention described herein.

Accordingly, the present invention includes the use of a compound of Formula I, Formula II, Formula III, Formula IV, Formula V, or Formula VI or a pharmaceutically acceptable composition, salt, or prodrug thereof, as described herein in an effective amount to treat an RNA virus, for example, an RNA virus other than HCV.

In one specific embodiment, the parent nucleoside, i.e., the nucleoside wherein R⁴ is hydrogen and the 5'-position thus has a hydroxyl group, is not substantially deaminated by adenosine deaminase under conditions that mimic the in vivo environment (e.g., ambient temperature and aqueous physiological pH), for a period of 7 minutes, 10 minutes, 30 minutes, 60 minutes or 120 minutes. Unless otherwise stated, the time period is 30 minutes. In this embodiment, the term "not substantially deaminated" means that the parent compound is not converted to the corresponding guanine derivative, or 6-oxo derivative, in an amount sufficient to provide a therapeutic effect in vivo.

Compounds, methods, and compositions are provided for the treatment of a host infected with an RNA virus via administration of an effective amount of the compound or its pharmaceutically acceptable salt.

The compound or formulations that include the compounds can also be used in an effective amount prophylactically to prevent or restrict the progression of clinical illness in individuals who are RNA virus antibody- or antigen-positive.

In another embodiment, the invention is the use of an effective amount of a compound of Formula Ia below for the treatment of an infection of an RNA virus in a host, for example, a human in need thereof. In certain embodiments, a method is provided to treat a host infected with a single-stranded RNA positive stranded virus other than a hepacivirus or other than HCV. In an alternative embodiment, a method is provided that includes the administration of an effective amount of a compound of Formula Ia for the treatment of a single-stranded RNA positive stranded virus of the Flaviviridae family, including but not limited to Dengue virus 2 and Yellow Fever, in a host, including a human in need thereof. In an alternative embodiment, a method is provided that includes the administration of an effective amount of a compound of Formula Ia for the treatment of a single-stranded RNA negative-sense virus in a host, including a human in need thereof. In an alternative embodiment, a method is provided that includes the administration of an effective amount of a compound of Formula Ia for the treatment of a double-stranded RNA virus in a host, including a human in need thereof.

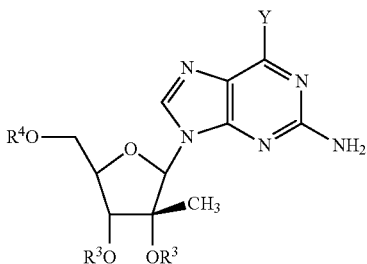

Formula Ia wherein:
Y, $R^3$, $R^{3A}$, $R^{3B}$, $R^{3C}$, $R^{3D}$, and $R^4$ are as defined above.

In one embodiment of Formula Ia, $R^3$ is hydrogen.
In one embodiment of Formula Ia, when Y is $NR^1R^2$, $R^1$ is methyl and $R^2$ is hydrogen.
In one embodiment of Formula Ia, when Y is $NR^1R^2$, both $R^1$ and $R^2$ are methyl.
In one embodiment of Formula Ia, when Y is $NR^1R^2$, $R^1$ is methyl and $R^2$ is cyclopropyl.
In one embodiment of Formula Ia, when Y is $NR^1R^2$, $R^1$ is cyclopropyl and $R^2$ is hydrogen.
In an alternative embodiment of Formula Ia, when Y is $NR^1R^2$, $R^1$ is cyclopropyl and $R^2$ is cyclopropyl.
In an alternative embodiment of Formula Ia, when Y is $NR^1R^2$, $R^1$ is cyclopentyl and $R^2$ is hydrogen.
In an alternative embodiment of Formula Ia, $R^4$ is a stabilized phosphoramidate.
In an alternative embodiment of Formula Ia, $R^3$ is independently selected from hydrogen,

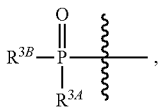

diphosphate, triphosphate, an optionally substituted carbonyl linked amino acid, and $—C(O)R^{3C}$.

In another embodiment, the invention is the use of an effective amount of a compound of Formula Ib, or a pharmaceutically acceptable salt thereof, for the treatment of an infection of an RNA virus in a host, including a human in need thereof.

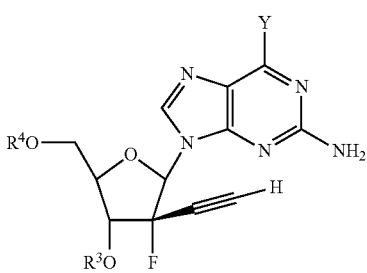

Formula Ib wherein:
Y, $R^3$ and $R^4$ are as defined above.
In one embodiment of Formula Ib, $R^3$ is hydrogen.
In one embodiment of Formula Ib, when Y is $NR^1R^2$, $R^1$ is methyl and $R^2$ is hydrogen.
In one embodiment of Formula Ib, when Y is $NR^1R^2$, both $R^1$ and $R^2$ are methyl.
In one embodiment of Formula Ib, when Y is $NR^1R^2$, $R^1$ is methyl and $R^2$ is cyclopropyl.
In one embodiment of Formula Ib, when Y is $NR^1R^2$, $R^1$ is cyclopropyl and $R^2$ is hydrogen.
In an alternative embodiment of Formula Ib, when Y is $NR^1R^2$, $R^1$ is cyclopropyl and $R^2$ is cyclopropyl.
In an alternative embodiment of Formula Ib, when Y is $NR^1R^2$, $R^1$ is cyclopentyl and $R^2$ is hydrogen.
In an alternative embodiment of Formula Ib, $R^4$ is a stabilized phosphoramidate.
In an alternative embodiment, the invention is the use of an effective amount of a compound of Formula Ib', or a pharmaceutically acceptable salt thereof, for the treatment of an infection of an RNA virus in a host, including a human in need thereof.

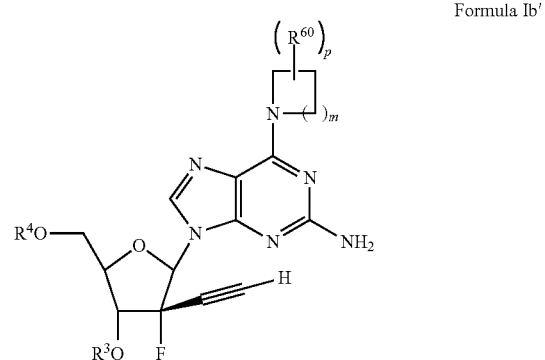

Formula Ib' wherein:
m is 1, 2, or 3;
p is 0, 1, or 2;
$R^{60}$ is independently selected from $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CHF_2$, $CF_3$, $CH_2CF_3$ and $CF_2CF_3$), $C_2$-$C_6$ alkenyl, $C_2$-$C_6$ alkynyl, $—(C_0$-$C_2$alkyl)($C_3$-$C_6$cycloalkyl), $—(C_0$-$C_2$alkyl)(heterocycle), $—(C_0$-$C_2$alkyl)(aryl), $—(C_0$-$C_2$alkyl)(heteroaryl), $—OR^{23}$, $—C(O)R^{3C}$ (including $—C(O)CH_3$, $—C(O)CH_2CH_3$—$C(O)CH(CH_3)_2$, $—C(O)OCH_3$, $—C(O)OC_2H_5$, $—C(O)OC_3H_7$, $—C(O)OC_4H_9$, and $—C(O)OC_5H_{11}$), $—C(S)R^{3D}$, and $—SO_2R^{28}$ each of which can be optionally substituted; and
$R^3$, $R^4$, $R^{3C}$, $R^{3D}$, $R^{23}$, and $R^{28}$ are as defined above.
In one embodiment of Formula Ib', m is 1 and p is 0.
In one embodiment of Formula Ib', m is 2 and p is 0.
In one embodiment of Formula Ib', m is 3 and p is 0.
In one embodiment of Formula Ib', m is 2, p is 0, and $R^3$ is hydrogen.
In one embodiment of Formula Ib', m is 2, p is 0, $R^3$ is hydrogen, and $R^4$ is a stabilized phosphoramidate.
In one embodiment of Formula Ib', m is 3, p is 0, $R^3$ is hydrogen, and $R^4$ is a stabilized phosphoramidate.
In one embodiment of Formula Ib', $R^4$ is a stabilized phosphoramidate.
In another embodiment, the invention is the use of an effective amount of a compound of Formula Ic, or a pharmaceutically acceptable salt thereof, for the treatment of an infection of an RNA virus in a host, including a human in need thereof.

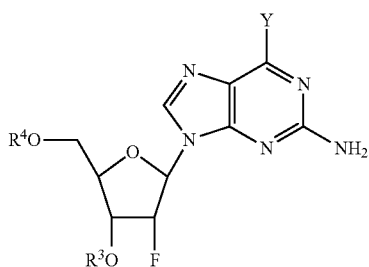

Formula Ic wherein:

Y, $R^3$ and $R^4$ are as defined above.

In one embodiment of Formula Ic, $R^3$ is hydrogen.

In one embodiment of Formula Ic, when Y is $NR^1R^2$, $R^1$ is methyl and $R^2$ is hydrogen.

In one embodiment of Formula Ic, when Y is $NR^1R^2$, both $R^1$ and $R^2$ are methyl.

In one embodiment of Formula Ic, when Y is $NR^1R^2$, $R^1$ is methyl and $R^2$ is cyclopropyl.

In one embodiment of Formula Ic, when Y is $NR^1R^2$, $R^1$ is cyclopropyl and $R^2$ is hydrogen.

In an alternative embodiment of Formula Ic, when Y is $NR^1R^2$, $R^1$ is cyclopropyl and $R^2$ is cyclopropyl.

In an alternative embodiment of Formula Ic, when Y is $NR^1R^2$, $R^1$ is cyclopentyl and $R^2$ is hydrogen.

In an alternative embodiment of Formula Ic, $R^4$ is a stabilized phosphoramidate.

In another embodiment, the invention is the use of an effective amount of a compound of Formula Id, or a pharmaceutically acceptable salt thereof, for the treatment of an infection of an RNA virus in a host, including a human in need thereof.

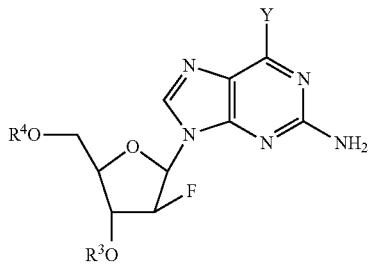

Formula Id wherein:

Y, $R^3$ and $R^4$ are as defined above.

In one embodiment of Formula Id, $R^3$ is hydrogen.

In one embodiment of Formula Id, when Y is $NR^1R^2$, $R^1$ is methyl and $R^2$ is hydrogen.

In one embodiment of Formula Id, when Y is $NR^1R^2$, both $R^1$ and $R^2$ are methyl.

In one embodiment of Formula Id, when Y is $NR^1R^2$, $R^1$ is methyl and $R^2$ is cyclopropyl.

In one embodiment of Formula Id, when Y is $NR^1R^2$, $R^1$ is cyclopropyl and $R^2$ is hydrogen.

In an alternative embodiment of Formula Id, when Y is $NR^1R^2$, $R^1$ is cyclopropyl and $R^2$ is cyclopropyl.

In an alternative embodiment of Formula Id, when Y is $NR^1R^2$, $R^1$ is cyclopentyl and $R^2$ is hydrogen.

In an alternative embodiment of Formula Id, $R^4$ is a stabilized phosphoramidate.

In another embodiment, the invention is the use of an effective amount of a compound of Formula Ie, or a pharmaceutically acceptable salt thereof, for the treatment of an infection of an RNA virus in a host, including a human in need thereof.

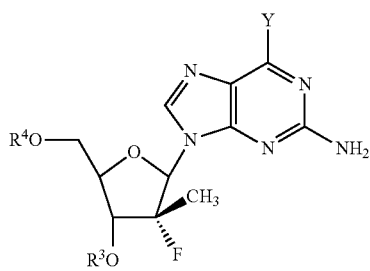

Formula Ie wherein:

Y, $R^3$ and $R^4$ are as defined above.

In one embodiment of Formula Ie, $R^3$ is hydrogen.

In one embodiment of Formula Ie, when Y is $NR^1R^2$, $R^1$ is methyl and $R^2$ is hydrogen.

In one embodiment of Formula Ie, when Y is $NR^1R^2$, $R^1$ is methyl and $R^2$ is cyclopropyl.

In an alternative embodiment of Formula Ie, when Y is $NR^1R^2$, $R^1$ is cyclopropyl and $R^2$ is cyclopropyl.

In an alternative embodiment of Formula Ie, when Y is $NR^1R^2$, $R^1$ is cyclopentyl and $R^2$ is hydrogen.

In one embodiment of Formula Ie, $R^4$ is a stabilized phosphoramidate.

In one embodiment, the invention is the use of an effective amount of a compound of Formula II, or a pharmaceutically acceptable salt thereof, for the treatment of an infection of an RNA virus in a host, including a human in need thereof.

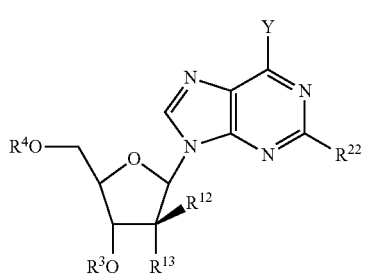

Formula II wherein:

Y, $R^3$, $R^4$, $R^{12}$, $R^{13}$ and $R^{22}$ are as defined above.

In another embodiment, the invention is the use of an effective amount of a compound of Formula IIa, or a pharmaceutically acceptable salt thereof, for the treatment of an infection of an RNA virus in a host, including a human in need thereof.

Formula IIa

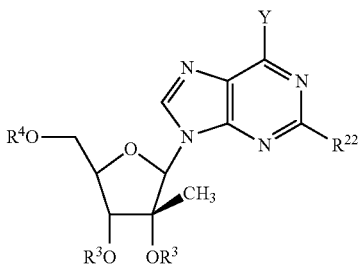

wherein:
Y, $R^3$, $R^{3A}$, $R^{3B}$, $R^{3C}$, $R^{3D}$, $R^4$ and $R^{22}$ are as defined above.

In one embodiment of Formula IIa, $R^3$ is hydrogen.
In one embodiment of Formula IIa, when Y is $NR^1R^2$, $R^1$ is methyl and $R^2$ is hydrogen.
In one embodiment of Formula IIa, when Y is $NR^1R^2$, both $R^1$ and $R^2$ are methyl.
In one embodiment of Formula IIa, when Y is $NR^1R^2$, $R^1$ is methyl and $R^2$ is cyclopropyl.
In one embodiment of Formula IIa, when Y is $NR^1R^2$, $R^1$ is cyclopropyl and $R^2$ is hydrogen.
In an alternative embodiment of Formula IIa, when Y is $NR^1R^2$, $R^1$ is cyclopropyl and $R^2$ is cyclopropyl.
In an alternative embodiment of Formula IIa, when Y is $NR^1R^2$, $R^1$ is cyclopentyl and $R^2$ is hydrogen.
In an alternative embodiment of Formula IIa, $R^4$ is a stabilized phosphoramidate.
In an alternative embodiment of Formula IIa, $R^3$ is independently selected from hydrogen,

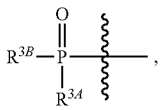

diphosphate, triphosphate, an optionally substituted carbonyl linked amino acid, and $—C(O)R^{3C}$.

In another embodiment, the invention is the use of an effective amount of a compound of Formula IIb, or a pharmaceutically acceptable salt thereof, for the treatment of an infection of an RNA virus in a host, including a human in need thereof.

Formula IIb

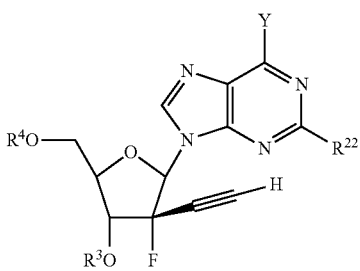

wherein:
Y, $R^3$, $R^4$, and $R^{22}$ are as defined above.
In one embodiment of Formula IIb, $R^3$ is hydrogen.
In one embodiment of Formula IIb, when Y is $NR^1R^2$, $R^1$ is methyl and $R^2$ is hydrogen.

In one embodiment of Formula IIb, when Y is $NR^1R^2$, both $R^1$ and $R^2$ are methyl.
In one embodiment of Formula IIb, when Y is $NR^1R^2$, $R^1$ is methyl and $R^2$ is cyclopropyl.
In one embodiment of Formula IIb, when Y is $NR^1R^2$, $R^1$ is cyclopropyl and $R^2$ is hydrogen.
In an alternative embodiment of Formula IIb, when Y is $NR^1R^2$, $R^1$ is cyclopropyl and $R^2$ is cyclopropyl.
In an alternative embodiment of Formula IIb, when Y is $NR^1R^2$, $R^1$ is cyclopentyl and $R^2$ is hydrogen.
In an alternative embodiment of Formula IIb, $R^4$ is a stabilized phosphoramidate.

In an alternative embodiment, the invention is the use of an effective amount of a compound of Formula IIb', or a pharmaceutically acceptable salt thereof, for the treatment of an infection of an RNA virus in a host, including a human in need thereof.

Formula IIb'

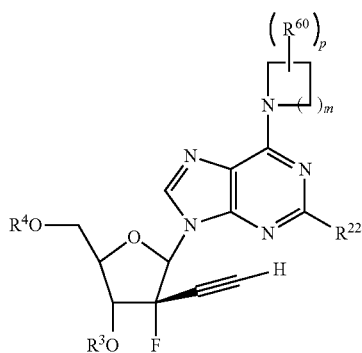

wherein:
$R^3$, $R^4$, $R^{22}$, $R^{60}$, m, and p are as defined above.
In one embodiment of Formula IIb', m is 1 and p is 0.
In one embodiment of Formula IIb', m is 2 and p is 0.
In one embodiment of Formula IIb', m is 3 and p is 0.
In one embodiment of Formula IIb', m is 2, p is 0, $R^{22}$ is $NR^5R^6$, and $R^3$ is hydrogen.
In one embodiment of Formula IIb', $R^4$ is a stabilized phosphoramidate.

In another embodiment, the invention is the use of an effective amount of a compound of Formula IIc, or a pharmaceutically acceptable salt thereof, for the treatment of an infection of an RNA virus in a host, including a human in need thereof.

Formula IIc

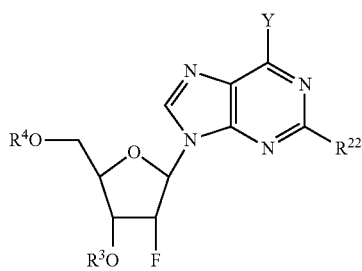

wherein:
Y, $R^3$, $R^4$, and $R^2$ are as defined above.
In one embodiment of Formula IIc, $R^3$ is hydrogen.
In one embodiment of Formula IIc, when Y is $NR^1R^2$, $R^1$ is methyl and $R^2$ is hydrogen.

In one embodiment of Formula IIc, when Y is $NR^1R^2$, both $R^1$ and $R^2$ are methyl.

In one embodiment of Formula IIc, when Y is $NR^1R^2$, $R^1$ is methyl and $R^2$ is cyclopropyl.

In one embodiment of Formula IIc, when Y is $NR^1R^2$, $R^1$ is cyclopropyl and $R^2$ is hydrogen.

In an alternative embodiment of Formula IIc, when Y is $NR^1R^2$, $R^1$ is cyclopropyl and $R^2$ is cyclopropyl.

In an alternative embodiment of Formula IIc, when Y is $NR^1R^2$, $R^1$ is cyclopentyl and $R^2$ is hydrogen.

In an alternative embodiment of Formula IIc, $R^4$ is a stabilized phosphoramidate.

In another embodiment, the invention is the use of an effective amount of a compound of Formula IId, or a pharmaceutically acceptable salt thereof, for the treatment of an infection of an RNA virus in a host, including a human in need thereof.

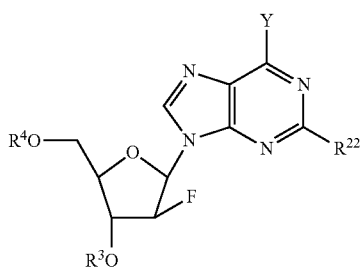

Formula IId wherein:

Y, $R^3$, $R^4$, and $R^{22}$ are as defined above.

In one embodiment of Formula IId, $R^3$ is hydrogen.

In one embodiment of Formula IId, when Y is $NR^1R^2$, $R^1$ is methyl and $R^2$ is hydrogen.

In one embodiment of Formula IId, when Y is $NR^1R^2$, both $R^1$ and $R^2$ are methyl.

In one embodiment of Formula IId, when Y is $NR^1R^2$, $R^1$ is methyl and $R^2$ is cyclopropyl.

In one embodiment of Formula IId, when Y is $NR^1R^2$, $R^1$ is cyclopropyl and $R^2$ is hydrogen.

In an alternative embodiment of Formula IId, when Y is $NR^1R^2$, $R^1$ is cyclopropyl and $R^2$ is cyclopropyl.

In an alternative embodiment of Formula IId, when Y is $NR^1R^2$, $R^1$ is cyclopentyl and $R^2$ is hydrogen.

In an alternative embodiment of Formula IId, $R^4$ is a stabilized phosphoramidate.

In another embodiment, the invention is the use of an effective amount of a compound of Formula IIe, or a pharmaceutically acceptable salt thereof, for the treatment of an infection of an RNA virus in a host, including a human in need thereof.

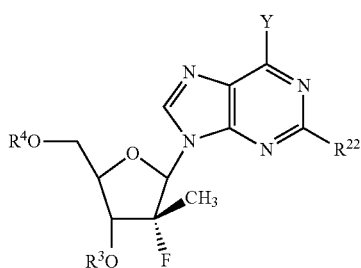

Formula IIe wherein:

Y, $R^3$, $R^4$, and $R^{22}$ are as defined above.

In one embodiment of Formula IIe, $R^3$ is hydrogen.

In one embodiment of Formula IIe, when Y is $NR^1R^2$, $R^1$ is methyl and $R^2$ is hydrogen.

In one embodiment of Formula IIe, when Y is $NR^1R^2$, $R^1$ is methyl and $R^2$ is cyclopropyl.

In an alternative embodiment of Formula IIe, when Y is $NR^1R^2$, $R^1$ is cyclopropyl and $R^2$ is cyclopropyl.

In an alternative embodiment of Formula IIe, when Y is $NR^1R^2$, $R^1$ is cyclopentyl and $R^2$ is hydrogen.

In one embodiment of Formula IIe, $R^4$ is a stabilized phosphoramidate.

In one embodiment, the invention is the use of an effective amount of a compound of Formula III, or a pharmaceutically acceptable salt thereof, for the treatment of an infection of an RNA virus in a host, including a human in need thereof.

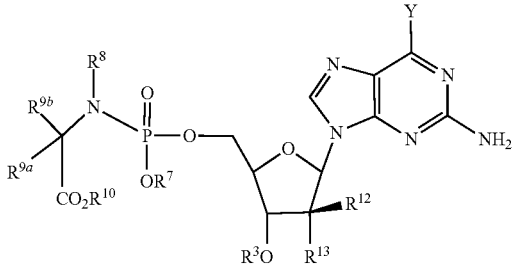

Formula III wherein $R^7$ is hydrogen, $C_{1-6}$alkyl; $C_{3-7}$cycloalkyl; heteroaryl, heterocyclic, or aryl, which includes, but is not limited to, phenyl or naphthyl, where phenyl or naphthyl are optionally substituted with $C_{1-6}$alkyl, $C_{2-6}$alkenyl, $C_{2-6}$alkynyl, $C_{1-6}$alkoxy, F, Cl, Br, I, nitro, cyano, $C_{1-6}$haloalkyl, $—N(R^{7'})_2$, $C_{1-6}$acylamino, $NHSO_2C_{1-6}$alkyl, $—SO_2N(R^{7'})_2$, $COR^{7''}$, and $—SO_2C_{1-6}$alkyl; ($R^{7'}$ is independently hydrogen or $C_{1-6}$alkyl; $R^{7''}$ is $—OR^{11}$ or $—N(R^{7'})_2$);

$R^8$ is hydrogen, $C_{1-6}$alkyl, or $R^{9a}$ or $R^{9b}$ and $R^8$ together are $(CH_2)_n$ so as to form a cyclic ring that includes the adjoining N and C atoms; where n is 2 to 4;

$R^{9a}$ and $R^{9b}$ are (i) independently selected from hydrogen, $C_{1-6}$alkyl, cycloalkyl, $—(CH_2)_c(NR^{9'})_2$, $C_{1-6}$hydroxyalkyl, $—CH_2SH$, $—(CH_2)_2S(O)(Me$, $—(CH_2)_3NHC(=NH)NH_2$, (1H-indol-3-yl)methyl, (1H-imidazol-4-yl)methyl, $—(CH_2)_cCOR^{9''}$, aryl and aryl($C_{1-3}$alkyl)-, the aryl groups can be optionally substituted with a group selected from hydroxyl, $C_{1-6}$alkyl, $C_{1-6}$alkoxy, halogen, nitro and cyano; (ii) $R^{9a}$ and $R^{9b}$ both are $C_{1-6}$alkyl; (iii) $R^{9a}$ and $R^{9b}$ together are $(CH_2)_r$ so as to form a spiro ring; (iv) $R^{9a}$ is hydrogen and $R^{9b}$ and $R^8$ together are $(CH_2)_n$ so as to form a cyclic ring that includes the adjoining N and C atoms (v) $R^{9b}$ is hydrogen and $R^{9a}$ and $R^8$ together are $(CH_2)_n$ so as to form a cyclic ring that includes the adjoining N and C atoms, where c is 1 to 6, n is 2 to 4, r is 2 to 5 and where $R^{9'}$ is independently hydrogen or $C_{1-6}$ alkyl and $R^{9''}$ is $—OR^{11}$ or $—N(R^{11'})_2$); (vi) $R^{9a}$ is hydrogen and $R^{9b}$ is hydrogen, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $—CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $—CH_2CH_2CH_2NHC(NH)$ NH$_2$, CH$_2$-imidazol-4-yl, CH$_2$OH, CH(OH)CH$_3$, CH$_2$((4'-OH)-Ph), CH$_2$SH, or lower cycloalkyl; or (vii) R$^{9a}$ is CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and R$^{9a}$ is hydrogen;

R$^{10}$ is hydrogen, C$_{1-6}$alkyl optionally substituted with an alkoxy, di(lower alkyl)-amino, or halogen; C$_{1-6}$haloalkyl, C$_{3-7}$cycloalkyl, heterocycloalkyl, aminoacyl, aryl, such as phenyl; heteroaryl, such as, pyridinyl, substituted aryl, or substituted heteroaryl;

R$^{11}$ is an optionally substituted C$_{1-6}$alkyl, an optionally substituted cycloalkyl; an optionally substituted C$_{2-6}$alkynyl, an optionally substituted C$_{2-6}$alkenyl, or optionally substituted acyl;

R$^{11'}$ is hydrogen, an optionally substituted C$_{1-6}$alkyl, an optionally substituted cycloalkyl; an optionally substituted C$_{2-6}$alkynyl, an optionally substituted C$_{2-6}$alkenyl, or optionally substituted acyl; and the variables Y, R$^3$, R$^{12}$ and R$^{13}$ are described herein.

In another embodiment, the invention is the use of an effective amount of a compound of Formula IIIa, or a pharmaceutically acceptable salt thereof, for the treatment of an infection of an RNA virus in a host, including a human in need thereof.

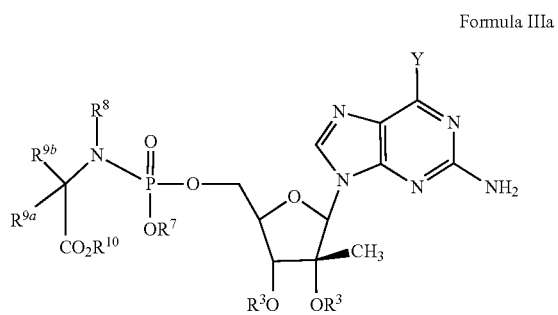

Formula IIIa wherein the variables Y, R$^3$, R$^7$, R$^8$, R$^{9a}$, R$^{9b}$ and R$^{10}$ are described herein.

In an alternative embodiment of Formula IIIa, the phosphoramidate is in the L-configuration.

In an alternative embodiment of Formula IIIa, the phosphoramidate is in the D-configuration.

In an alternative embodiment of Formula IIIa, R$^7$ is phenyl, R$^8$ is hydrogen, R$^{9a}$ is methyl, R$^{9b}$ is hydrogen, and R$^{10}$ is isopropyl and the phosphoramide is in the L-configuration.

In an alternative embodiment of Formula IIIa, R$^7$ is phenyl, R$^8$ is hydrogen, R$^{9a}$ is methyl, R$^{9b}$ is hydrogen, and R$^{10}$ is isopropyl and the phosphoramide is in the D-configuration.

In an alternative embodiment of Formula IIIa, R$^3$ is hydrogen,

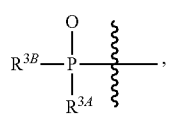

diphosphate, triphosphate, an optionally substituted carbonyl linked amino acid, or —C(O)R$^{3C}$;

In another embodiment, the invention is the use of an effective amount of a compound of Formula IIIb, or a pharmaceutically acceptable salt thereof, for the treatment of an infection of an RNA virus in a host, including a human in need thereof.

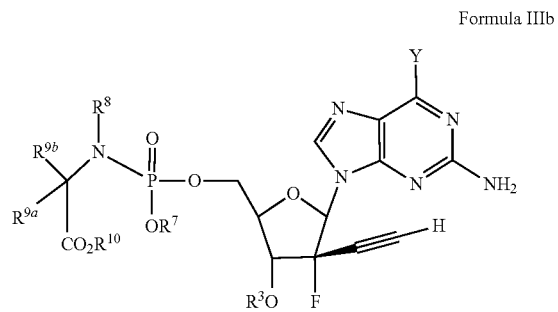

Formula IIIb wherein the variables Y, R$^3$, R$^7$, R$^8$, R$^{9a}$, R$^{9b}$ and R$^{10}$ are described herein.

In an alternative embodiment of Formula IIIb, the phosphoramidate is in the L-configuration.

In an alternative embodiment of Formula IIIb, the phosphoramidate is in the D-configuration.

In an alternative embodiment of Formula IIIb, R$^7$ is phenyl, R$^8$ is hydrogen, R$^{9a}$ is methyl, R$^{9b}$ is hydrogen, and R$^{10}$ is isopropyl and the phosphoramide is in the L-configuration.

In an alternative embodiment of Formula IIIb, R$^7$ is phenyl, R$^8$ is hydrogen, R$^{9a}$ is methyl, R$^{9b}$ is hydrogen, and R$^{10}$ is isopropyl and the phosphoramide is in the D-configuration.

In an alternative embodiment, the invention is the use of an effective amount of a compound of Formula IIIb', or a pharmaceutically acceptable salt thereof, for the treatment of an infection of an RNA virus in a host, including a human in need thereof.

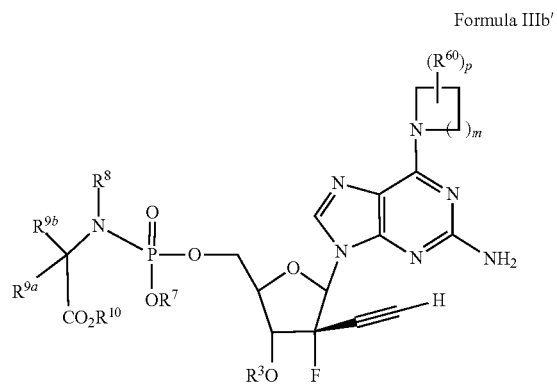

Formula IIIb' wherein the variables R$^3$, R$^7$, R$^8$, R$^{9a}$, R$^{9b}$, R$^{10}$, R$^{60}$, m, and p are described herein.

In one embodiment of Formula IIIb', m is 1 and p is 0.
In one embodiment of Formula IIIb', m is 2 and p is 0.
In one embodiment of Formula IIIb', m is 3 and p is 0.
In one embodiment of Formula IIIb', m is 2, p is 0, and R$^3$ is hydrogen.

In one embodiment of Formula IIIb', the phosphoramidate is in the L-configuration.

In one embodiment of Formula IIIb', the phosphoramidate is in the D-configuration.

In one embodiment of Formula IIIb', $R^7$ is phenyl, $R^8$ is hydrogen, $R^{9a}$ is methyl, $R^{9b}$ is hydrogen, and $R^{10}$ is isopropyl and the phosphoramide is in the L-configuration.

In one embodiment of Formula IIIb', $R^7$ is phenyl, $R^8$ is hydrogen, $R^{9a}$ is methyl, $R^{9b}$ is hydrogen, and $R^{10}$ is isopropyl and the phosphoramide is in the D-configuration.

In one embodiment of Formula IIIb', $R^3$ is hydrogen, m is 2, p is 0, $R^7$ is phenyl, $R^8$ is hydrogen, $R^{9a}$ is methyl, $R^{9b}$ is hydrogen, and $R^{10}$ is isopropyl.

In one embodiment of Formula IIIb', $R^3$ is hydrogen, m is 3, p is 0, $R^7$ is phenyl, $R^8$ is hydrogen, $R^{9a}$ is methyl, $R^{9b}$ is hydrogen, and $R^{10}$ is isopropyl.

In another embodiment, the invention is the use of an effective amount of a compound of Formula IIIc, or a pharmaceutically acceptable salt thereof, for the treatment of an infection of an RNA virus in a host, including a human in need thereof.

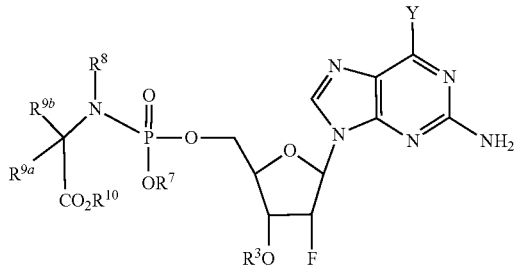

Formula IIIc wherein the variables Y, $R^3$, $R^7$, $R^8$, $R^{9a}$, $R^{9b}$ and $R^{10}$ are described herein.

In an alternative embodiment of Formula IIIc, the phosphoramidate is in the L-configuration.

In an alternative embodiment of Formula IIIc, the phosphoramidate is in the D-configuration.

In an alternative embodiment of Formula IIIc, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IIIc, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IIId or a pharmaceutically acceptable salt thereof, for the treatment of an infection of an RNA virus in a host, including a human in need thereof.

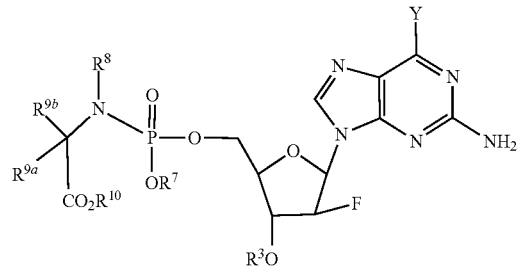

Formula IIId wherein the variables Y, $R^3$, $R^7$, $R^8$, $R^{9a}$, $R^{9b}$ and $R^{10}$ are described herein.

In an alternative embodiment of Formula IIId, the phosphoramidate is in the L-configuration.

In an alternative embodiment of Formula IIId, the phosphoramidate is in the D-configuration.

In an alternative embodiment of Formula IIId, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IIId, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IIIe, or a pharmaceutically acceptable salt thereof, for the treatment of an infection of an RNA virus in a host, including a human in need thereof.

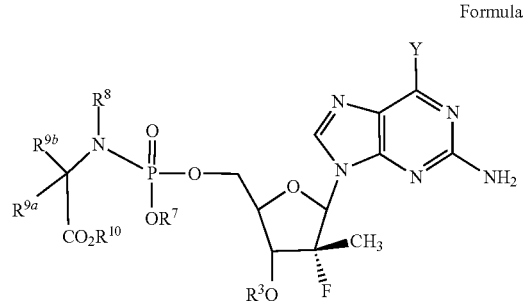

Formula IIIe wherein the variables Y, $R^3$, $R^7$, $R^8$, $R^{9a}$, $R^{9b}$ and $R^{10}$ are described herein.

In an alternative embodiment of Formula IIIe, the phosphoramidate is in the L-configuration.

In an alternative embodiment of Formula IIIe, the phosphoramidate is in the D-configuration.

In an alternative embodiment of Formula IIIe, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IIIe, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IV or a pharmaceutically acceptable salt thereof, for the treatment of an infection of an RNA virus in a host, including a human in need thereof.

Formula IV

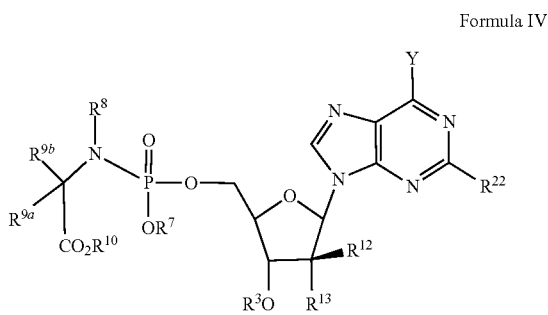

wherein the variables Y, $R^3$, $R^7$, $R^8$, $R^{9a}$, $R^{9b}$, $R^{10}$, $R^{12}$, $R^{13}$ and $R^{22}$ are described herein.

In an alternative embodiment of Formula IV, the phosphoramidate is in the L-configuration.

In an alternative embodiment of Formula IV, the phosphoramidate is in the D-configuration.

In an alternative embodiment of Formula IV, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IV, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IVa, or a pharmaceutically acceptable salt thereof, for the treatment of an infection of an RNA virus in a host, including a human in need thereof.

Formula IVa

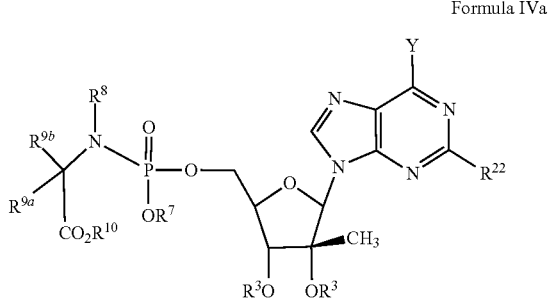

wherein the variables Y, $R^3$, $R^{3A}$, $R^{3B}$, $R^{3C}$, $R^{3D}$, $R^7$, $R^8$, $R^{9a}$, $R^{9b}$, $R^{10}$ and $R^{22}$ are described herein.

In an alternative embodiment of Formula IVa, the phosphoramidate is in the L-configuration.

In an alternative embodiment of Formula IVa, the phosphoramidate is in the D-configuration.

In an alternative embodiment of Formula IVa, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IVa, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In an alternative embodiment of Formula IVa, $R^3$ is independently selected from hydrogen,

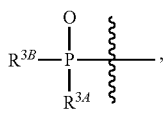

diphosphate, triphosphate, an optionally substituted carbonyl linked amino acid, or —C(O)$R^{3C}$.

In another embodiment, the invention is the use of an effective amount of a compound of Formula IVb, or a pharmaceutically acceptable salt thereof, for the treatment of an infection of an RNA virus in a host, including a human in need thereof.

Formula IVb

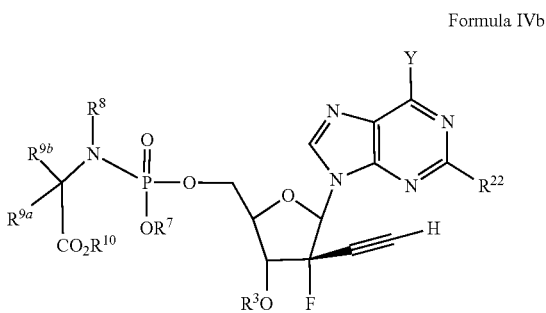

wherein the variables Y, $R^3$, $R^7$, $R^8$, $R^{9a}$, $R^{9b}$, $R^{10}$ and $R^{22}$ are described herein.

In an alternative embodiment of Formula IVb, the phosphoramidate is in the L-configuration.

In an alternative embodiment of Formula IVb, the phosphoramidate is in the D-configuration.

In an alternative embodiment of Formula IVb, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IVb, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In an alternative embodiment, the invention is the use of an effective amount of a compound of Formula IVb', or a pharmaceutically acceptable salt thereof, for the treatment of an infection of an RNA virus in a host, including a human in need thereof.

Formula IVb'

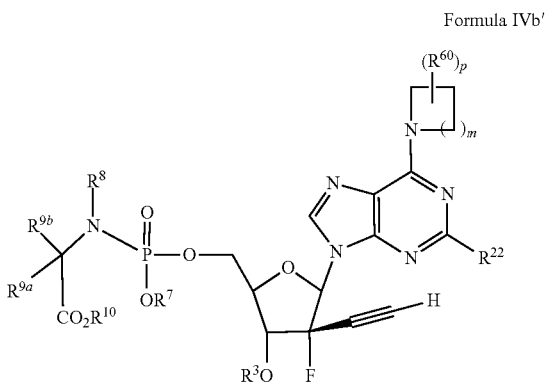

wherein the variables $R^3$, $R^7$, $R^8$, $R^{9a}$, $R^{9b}$, $R^{10}$, $R^{22}$, $R^{60}$, m, and p are described herein.

In one embodiment of Formula IVb', m is 1 and p is 0.

In one embodiment of Formula IVb', m is 2 and p is 0.

In one embodiment of Formula IVb', m is 3 and p is 0.

In one embodiment of Formula IVb', m is 2, p is 0, and $R^3$ is hydrogen.

In one embodiment of Formula IVb', m is 2, p is 0, $R^{22}$ is $NR^5R^6$, and $R^3$ is hydrogen.

In one embodiment of Formula IVb', the phosphoramidate is in the L-configuration.

In one embodiment of Formula IVb', the phosphoramidate is in the D-configuration.

In one embodiment of Formula IVb', $R^7$ is phenyl, $R^8$ is hydrogen, $R^{9a}$ is methyl, $R^{9b}$ is hydrogen, and $R^{10}$ is isopropyl and the phosphoramide is in the L-configuration.

In one embodiment of Formula IVb', $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IVc, or a pharmaceutically acceptable salt thereof, for the treatment of an infection of an RNA virus in a host, including a human in need thereof.

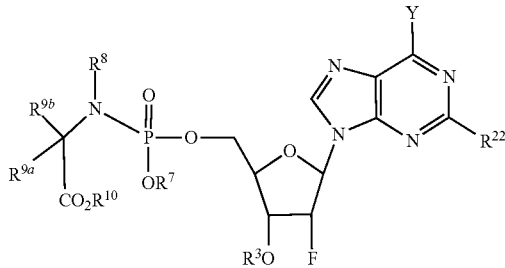

Formula IVc wherein the variables Y, $R^3$, $R^7$, $R^8$, $R^{9a}$, $R^{9b}$, $R^{10}$ and $R^{22}$ are described herein.

In an alternative embodiment of Formula IVc, the phosphoramidate is in the L-configuration.

In an alternative embodiment of Formula IVc, the phosphoramidate is in the D-configuration.

In an alternative embodiment of Formula IVc, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IVc, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IVd, or a pharmaceutically acceptable salt thereof, for the treatment of an infection of an RNA virus in a host, including a human in need thereof.

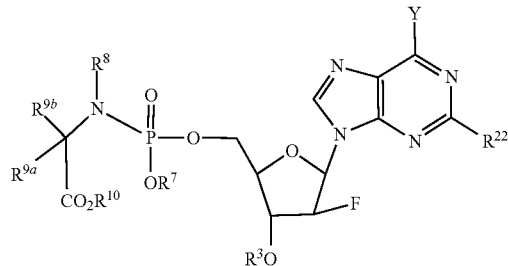

Formula IVd wherein the variables Y, $R^3$, $R^7$, $R^8$, $R^{9a}$, $R^{9b}$, $R^{10}$ and $R^{22}$ are described herein.

In an alternative embodiment of Formula IVd, the phosphoramidate is in the L-configuration.

In an alternative embodiment of Formula IVd, the phosphoramidate is in the D-configuration.

In an alternative embodiment of Formula IVd, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IVd, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In another embodiment, the invention is the use of an effective amount of a compound of Formula IVe, or a pharmaceutically acceptable salt thereof, for the treatment of an infection of an RNA virus in a host, including a human in need thereof.

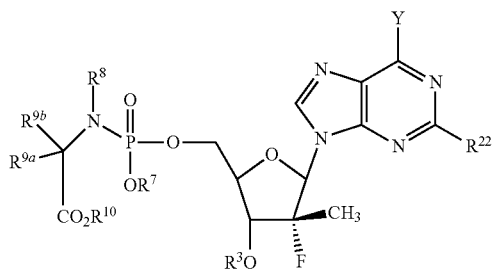

Formula IVe wherein the variables Y, $R^3$, $R^7$, $R^8$, $R^{9a}$, $R^{9b}$ and $R^{10}$ are described herein.

In an alternative embodiment of Formula IVe, the phosphoramidate is in the L-configuration.

In an alternative embodiment of Formula IVe, the phosphoramidate is in the D-configuration.

In an alternative embodiment of Formula IVe, $R^7$ is phenyl, $R^8$ is hydrogen, $R^{9a}$ is methyl, $R^{9b}$ is hydrogen, and $R^{10}$ is isopropyl and the phosphoramide is in the L-configuration.

In an alternative embodiment of Formula IVe, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In an alternative embodiment, compounds of Formula V are disclosed. In a further alternative embodiment, the invention is a method for the treatment of an infection of an RNA virus in a host, including a human in need thereof, comprising administering an effective amount of a compound of Formula V or a pharmaceutically acceptable salt thereof. In certain embodiments, the method includes administration of an effective amount of a compound of Formula V for the treatment of a single-stranded RNA positive stranded virus other than a hepacivirus or other than HCV in a host, including a human in need thereof. In an alternative embodiment, the method includes administration of an effective amount of a compound of Formula V for the treatment of a single-stranded RNA positive stranded virus of the Flaviviridae family, including but not limited to Dengue virus 2 and Yellow Fever, in a host, including a human in need thereof. In an alternative embodiment, the method includes administration of an effective amount of a compound of Formula V for the treatment of a single-stranded RNA negative-sense virus in a host, including a human in need thereof. In an alternative embodiment, the method includes administration of an effective amount of a compound of Formula V for the treatment of a double-stranded RNA virus in a host, including a human in need thereof.

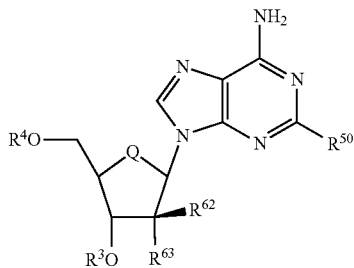

Formula V wherein:

Q is $CHR^{65}$;

$R^{50}$ is selected from hydrogen, $NH_2$, and $R^{22}$;

$R^{62}$ is hydrogen, $CH_3$, $CH_2F$, $CHF_2$, $CF_3$, or ethynyl;

$R^{63}$ is hydrogen, fluoro, chloro, bromo, $N_3$, $NH_2$, CN or $OR^3$;

$R^{65}$ is $C_1$-$C_3$alkyl (including, methyl, ethyl, isopropyl, and cyclopropyl) or $C_{1-3}$haloalkyl (including $CH_2F$, $CHF_2$, and $CF_3$); and $R^3$, $R^4$, $R^5$, and $R^{22}$ are as defined above.

In one embodiment of Formula V, $R^3$ is hydrogen.

In one embodiment of Formula V, $R^{65}$ is methyl.

In one embodiment of Formula V, $R^{50}$ is hydrogen.

In one embodiment of Formula V, $R^{50}$ is —$NH_2$.

In one embodiment of Formula V, Q is $CHR^{65}$, $R^3$ is hydrogen $R^{65}$ is methyl, and $R^{50}$ is hydrogen.

In an alternative embodiment, compounds of Formula Va are disclosed. In a further alternative embodiment, the invention is the use of an effective amount of a compound of Formula Va, or a pharmaceutically acceptable salt thereof, for the treatment of an infection of an RNA virus in a host, including a human in need thereof.

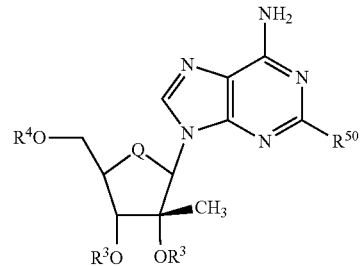

Formula Va wherein:

Q, $R^3$, $R^4$, and $R^{50}$ are defined as above.

In one embodiment of Formula Va, $R^3$ is hydrogen.

In one embodiment of Formula Va, $R^{65}$ is methyl.

In one embodiment of Formula Va, $R^{50}$ is hydrogen.

In one embodiment of Formula Va, $R^{50}$ is —$NH_2$.

In one embodiment of Formula Va, Q is $CHR^{65}$, $R^3$ is hydrogen $R^{65}$ is methyl, and $R^{50}$ is hydrogen.

In one embodiment of Formula Va, Q is $CHR^{65}$, $R^3$ is hydrogen $R^{65}$ is cyclopropyl, and $R^{50}$ is hydrogen.

In an alternative embodiment, compounds of Formula Vb are disclosed. In a further alternative embodiment, the invention is the use of an effective amount of a compound of Formula Vb, or a pharmaceutically acceptable salt thereof, for the treatment of an infection of an RNA virus in a host, including a human in need thereof.

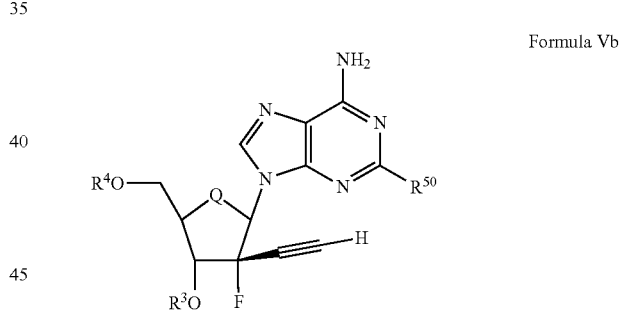

Formula Vb wherein:

Q, $R^3$, $R^4$, and $R^{50}$ are defined as above.

In one embodiment of Formula Vb, $R^3$ is hydrogen.

In one embodiment of Formula Vb, $R^{65}$ is methyl.

In one embodiment of Formula Vb, $R^{50}$ is hydrogen.

In one embodiment of Formula Vb, $R^{50}$ is —$NH_2$.

In one embodiment of Formula Vb, Q is $CHR^{65}$, $R^3$ is hydrogen $R^{65}$ is methyl, and $R^{50}$ is hydrogen.

In one embodiment of Formula Vb, Q is $CHR^{65}$, $R^3$ is hydrogen $R^{65}$ is cyclopropyl, and $R^{50}$ is hydrogen.

In an alternative embodiment, compounds of Formula Vc are disclosed. In a further alternative embodiment, the invention is the use of an effective amount of a compound of Formula Vc, or a pharmaceutically acceptable salt thereof, for the treatment of an infection of an RNA virus in a host, including a human in need thereof.

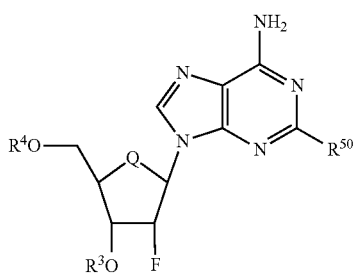

Formula Vc wherein:

Q, $R^3$, $R^4$, and $R^{50}$ are defined as above.

In one embodiment of Formula Vc, $R^3$ is hydrogen.

In one embodiment of Formula Vc, $R^{65}$ is methyl.

In one embodiment of Formula Vc, $R^{50}$ is hydrogen.

In one embodiment of Formula Vc, $R^{50}$ is —$NH_2$.

In one embodiment of Formula Vc, Q is $CHR^{65}$, $R^3$ is hydrogen $R^{65}$ is methyl, and $R^{50}$ is hydrogen.

In one embodiment of Formula Vc, Q is $CHR^{65}$, $R^3$ is hydrogen $R^{65}$ is cyclopropyl, and $R^{50}$ is hydrogen.

In an alternative embodiment, compounds of Formula Vd are disclosed. In a further alternative embodiment, the invention is the use of an effective amount of a compound of Formula Vd, or a pharmaceutically acceptable salt thereof, for the treatment of an infection of an RNA virus in a host, including a human in need thereof.

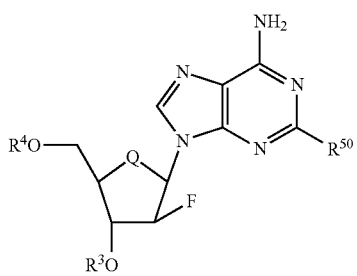

Formula Vd wherein:

Q, $R^3$, $R^4$, and $R^{50}$ are defined as above.

In one embodiment of Formula Vd, $R^3$ is hydrogen.

In one embodiment of Formula Vd, $R^{65}$ is methyl.

In one embodiment of Formula Vd, $R^{50}$ is hydrogen.

In one embodiment of Formula Vd, $R^{50}$ is —$NH_2$.

In one embodiment of Formula Vd, Q is $CHR^{65}$, $R^3$ is hydrogen $R^{65}$ is methyl, and $R^{50}$ is hydrogen.

In one embodiment of Formula Vd, Q is $CHR^{65}$, $R^3$ is hydrogen $R^{65}$ is cyclopropyl, and $R^{50}$ is hydrogen.

In an alternative embodiment, compounds of Formula Ve are disclosed. In a further alternative embodiment, the invention is the use of an effective amount of a compound of Formula Ve, or a pharmaceutically acceptable salt thereof, for the treatment of an infection of an RNA virus in a host, including a human in need thereof.

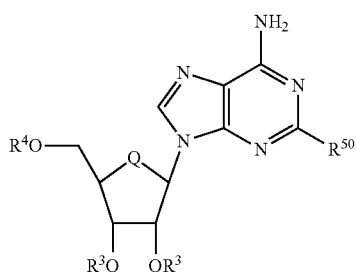

Formula Ve wherein:

Q, $R^3$, $R^4$, and $R^{50}$ are defined as above.

In one embodiment of Formula Ve, $R^3$ is hydrogen.

In one embodiment of Formula Ve, $R^{65}$ is methyl.

In one embodiment of Formula Ve, $R^{50}$ is hydrogen.

In one embodiment of Formula Ve, $R^{50}$ is —$NH_2$.

In one embodiment of Formula Ve, Q is $CHR^{65}$, $R^3$ is hydrogen $R^{65}$ is methyl, and $R^{50}$ is hydrogen.

In one embodiment of Formula Ve, Q is $CHR^{65}$, $R^3$ is hydrogen $R^{65}$ is cyclopropyl, and $R^{50}$ is hydrogen.

In an alternative embodiment, compounds of Formula Vf are disclosed. In a further alternative embodiment, the invention is the use of an effective amount of a compound of Formula Vf, or a pharmaceutically acceptable salt thereof, for the treatment of an infection of an RNA virus in a host, including a human in need thereof.

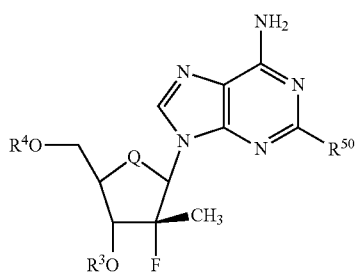

Formula Vf wherein:

Q, $R^3$, $R^4$, and $R^{50}$ are defined as above.

In one embodiment of Formula Vf, $R^3$ is hydrogen.

In one embodiment of Formula Vf, $R^{65}$ is methyl.

In one embodiment of Formula Vf, $R^{50}$ is hydrogen.

In one embodiment of Formula Vf, $R^{50}$ is —$NH_2$.

In one embodiment of Formula Vf, Q is $CHR^{65}$, $R^3$ is hydrogen $R^5$ is methyl, and $R^{50}$ is hydrogen.

In one embodiment of Formula Ve, Q is $CHR^{65}$, $R^3$ is hydrogen $R^{65}$ is cyclopropyl, and $R^{50}$ is hydrogen.

In an alternative embodiment, compounds of Formula VI are disclosed. In a further alternative embodiment, the invention is the use of an effective amount of a compound of Formula VI, or a pharmaceutically acceptable salt thereof, for the treatment of an infection of an RNA virus in a host, including a human in need thereof.

Formula VI

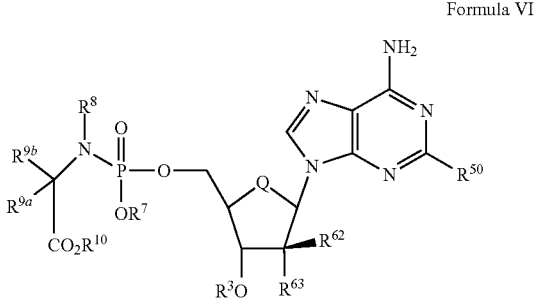

wherein:
Q, $R^3$, $R^7$, $R^8$, $R^{9a}$, $R^{9b}$, $R^{10}$, $R^{50}$, $R^{62}$, and $R^{63}$ are defined as above.

In one embodiment of Formula VI, $R^3$ is hydrogen.
In one embodiment of Formula VI, $R^{65}$ is methyl.
In one embodiment of Formula VI, $R^{50}$ is hydrogen.
In one embodiment of Formula VI, $R^{50}$ is —$NH_2$.
In one embodiment of Formula VI, Q is $CHR^{65}$, $R^3$ is hydrogen $R^{65}$ is methyl, and $R^{50}$ is hydrogen.
In one embodiment of Formula VI, the phosphoramidate is in the L-configuration.
In one embodiment, the phosphoramidate is in the D-configuration.
In one embodiment Formula VI, $R^7$ is phenyl, $R^8$ is hydrogen, $R^{9a}$ is methyl, $R^{9b}$ is hydrogen, and $R^{10}$ is isopropyl and the phosphoramide is in the L-configuration.
In one embodiment Formula VI, $R^7$ is phenyl, $R^8$ is hydrogen, $R^{9a}$ is methyl, $R^{9b}$ is hydrogen, and $R^{10}$ is isopropyl and the phosphoramide is in the D-configuration.

In an alternative embodiment, compounds of Formula VIa are disclosed. In a further alternative embodiment, the invention is the use of an effective amount of a compound of Formula VIa, or a pharmaceutically acceptable salt thereof, for the treatment of an infection of an RNA virus in a host, including a human in need thereof.

Formula VIa

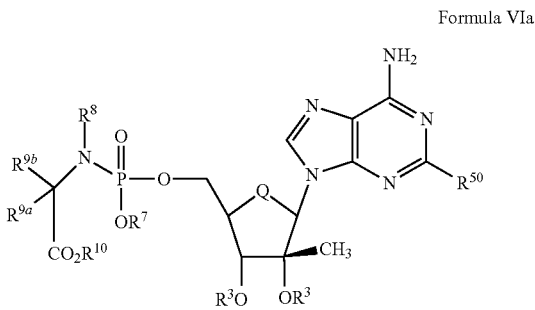

wherein:
Q, $R^3$, $R^{3A}$, $R^{3B}$, $R^{3C}$, $R^{3D}$, $R^7$, $R^8$, $R^{9a}$, $R^{9b}$, $R^{10}$, and $R^{50}$ are defined as above.

In one embodiment of Formula VIa, $R^3$ is hydrogen.
In one embodiment of Formula VIa, $R^{65}$ is methyl.
In one embodiment of Formula VIa, $R^{50}$ is hydrogen.
In one embodiment of Formula VIa, $R^{50}$ is —$NH_2$.
In one embodiment Formula VIa, Q is $CHR^{65}$, $R^3$ is hydrogen $R^{65}$ is methyl, and $R^{50}$ is hydrogen.
In one embodiment Formula VIa, the phosphoramidate is in the L-configuration.
In one embodiment Formula VIa, the phosphoramidate is in the D-configuration.

In one embodiment Formula VIa, $R^7$ is phenyl, $R^8$ is hydrogen, $R^{9a}$ is methyl, $R^{9b}$ is hydrogen, and $R^{10}$ is isopropyl and the phosphoramide is in the L-configuration.
In one embodiment Formula VIa, $R^7$ is phenyl, $R^8$ is hydrogen, $R^{9a}$ is methyl, $R^{9b}$ is hydrogen, and $R^{10}$ is isopropyl and the phosphoramide is in the D-configuration.
In one embodiment Formula VIa, Q is $CHR^{65}$, $R^3$ is hydrogen, $R^7$ is phenyl, $R^8$ is hydrogen, $R^{9a}$ is methyl, $R^{9b}$ is hydrogen, and $R^{10}$ is isopropyl.
In one embodiment Formula VIa, Q is $CHR^{65}$, $R^3$ is hydrogen, $R^{65}$ is methyl, $R^{50}$ is hydrogen, $R^7$ is phenyl, $R^8$ is hydrogen, $R^{9a}$ is methyl, $R^{9b}$ is hydrogen, and $R^{10}$ is isopropyl.
In one embodiment of Formula VIa, $R^3$ is independently selected from hydrogen,

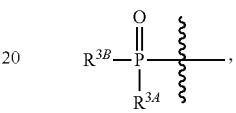

diphosphate, triphosphate, an optionally substituted carbonyl linked amino acid, or —$C(O)R^{3C}$.

In an alternative embodiment, compounds of Formula VIb are disclosed. In a further alternative embodiment, the invention is the use of an effective amount of a compound of Formula VIb, or a pharmaceutically acceptable salt thereof, for the treatment of an infection of an RNA virus in a host, including a human in need thereof.

Formula VIb

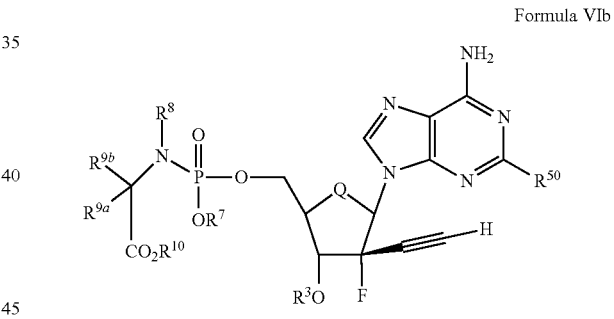

wherein:
Q, $R^3$, $R^7$, $R^8$, $R^{9a}$, $R^{9b}$, $R^{10}$, and $R^{50}$ are defined as above.
In one embodiment of Formula VIb, $R^3$ is hydrogen.
In one embodiment of Formula VIb, $R^{65}$ is methyl.
In one embodiment of Formula VIb, $R^{50}$ is hydrogen.
In one embodiment of Formula VIb, $R^{50}$ is —$NH_2$.
In one embodiment Formula VIb, Q is $CHR^{65}$, $R^3$ is hydrogen $R^{65}$ is methyl, and $R^{50}$ is hydrogen.
In one embodiment Formula VIb, the phosphoramidate is in the L-configuration.
In one embodiment Formula VIb, the phosphoramidate is in the D-configuration.
In one embodiment Formula VIb, $R^7$ is phenyl, $R^8$ is hydrogen, $R^{9a}$ is methyl, $R^{9b}$ is hydrogen, and $R^{10}$ is isopropyl and the phosphoramide is in the L-configuration.
In one embodiment Formula VIb, $R^7$ is phenyl, $R^8$ is hydrogen, $R^{9a}$ is methyl, $R^{9b}$ is hydrogen, and $R^{10}$ is isopropyl and the phosphoramide is in the D-configuration.
In one embodiment Formula VIb, Q is $CHR^{65}$, $R^3$ is hydrogen $R^7$ is phenyl, $R^8$ is hydrogen, $R^{9a}$ is methyl, $R^{9b}$ is hydrogen, and $R^{10}$ is isopropyl.

In one embodiment Formula VIb, Q is $CHR^{65}$, $R^3$ is hydrogen, $R^{65}$ is methyl, $R^{50}$ is hydrogen, $R^7$ is phenyl, $R^8$ is hydrogen, $R^{9a}$ is methyl, $R^{9b}$ is hydrogen, and $R^{10}$ is isopropyl.

In an alternative embodiment, compounds of Formula VIc are disclosed. In a further alternative embodiment, the invention is the use of an effective amount of a compound of Formula VIc, or a pharmaceutically acceptable salt thereof, for the treatment of an infection of an RNA virus in a host, including a human in need thereof.

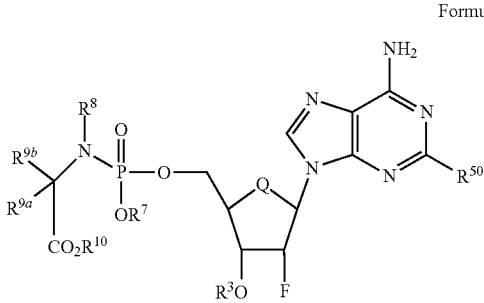

Formula VIc wherein:
Q, $R^3$, $R^7$, $R^8$, $R^{9a}$, $R^{9b}$, $R^{10}$, and $R^{50}$ are defined as above.

In one embodiment of Formula VIc, $R^3$ is hydrogen.
In one embodiment of Formula VIc, $R^{65}$ is methyl.
In one embodiment of Formula VIc, $R^{50}$ is hydrogen.
In one embodiment of Formula VIc, $R^{50}$ is —$NH_2$.
In one embodiment of Formula VIc, Q is $CHR^{65}$, $R^3$ is hydrogen $R^{65}$ is methyl, and $R^{50}$ is hydrogen.
In one embodiment Formula VIc, the phosphoramidate is in the L-configuration.
In one embodiment Formula VIc, the phosphoramidate is in the D-configuration.
In one embodiment Formula VIc, $R^7$ is phenyl, $R^8$ is hydrogen, $R^{9a}$ is methyl, $R^{9b}$ is hydrogen, and $R^{10}$ is isopropyl and the phosphoramide is in the L-configuration.
In one embodiment Formula VIc, $R^7$ is phenyl, $R^8$ is hydrogen, $R^{9a}$ is methyl, $R^{9b}$ is hydrogen, and $R^{10}$ is isopropyl and the phosphoramide is in the D-configuration.
In one embodiment Formula VIc, Q is $CHR^{65}$, $R^3$ is hydrogen, $R^7$ is phenyl, $R^8$ is hydrogen, $R^{9a}$ is methyl, $R^{9b}$ is hydrogen, and $R^{10}$ is isopropyl.
In one embodiment Formula VIc, Q is $CHR^{65}$, $R^3$ is hydrogen, $R^{65}$ is methyl, $R^{50}$ is hydrogen, $R^7$ is phenyl, $R^8$ is hydrogen, $R^{9a}$ is methyl, $R^{9b}$ is hydrogen, and $R^{10}$ is isopropyl.

In an alternative embodiment, compounds of Formula VId are disclosed. In a further alternative embodiment, the invention is the use of an effective amount of a compound of Formula VId, or a pharmaceutically acceptable salt thereof, for the treatment of an infection of an RNA virus in a host, including a human in need thereof.

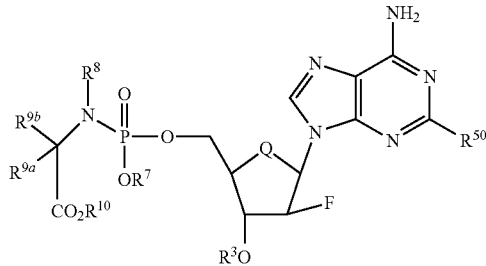

Formula VId wherein:
Q, $R^3$, $R^7$, $R^8$, $R^{9a}$, $R^{9b}$, $R^{10}$, and $R^{50}$ are defined as above.

In one embodiment of Formula VId, $R^3$ is hydrogen.
In one embodiment of Formula VId, $R^{65}$ is methyl.
In one embodiment of Formula VId, $R^{50}$ is hydrogen.
In one embodiment of Formula VId, $R^{50}$ is —$NH_2$.
In one embodiment Formula VId, the phosphoramidate is in the L-configuration.
In one embodiment Formula VId, the phosphoramidate is in the D-configuration.
In one embodiment of Formula VId, Q is $CHR^{65}$, $R^3$ is hydrogen $R^{65}$ is methyl, and $R^{50}$ is hydrogen.
In one embodiment Formula VId, $R^7$ is phenyl, $R^8$ is hydrogen, $R^{9a}$ is methyl, $R^{9b}$ is hydrogen, and $R^{10}$ is isopropyl and the phosphoramide is in the L-configuration.
In one embodiment Formula VId, $R^7$ is phenyl, $R^8$ is hydrogen, $R^{9a}$ is methyl, $R^{9b}$ is hydrogen, and $R^{10}$ is isopropyl and the phosphoramide is in the D-configuration.
In one embodiment Formula VId, Q is $CHR^{65}$, $R^3$ is hydrogen, $R^7$ is phenyl, $R^8$ is hydrogen, $R^{9a}$ is methyl, $R^{9b}$ is hydrogen, and $R^{10}$ is isopropyl.
In one embodiment Formula VId, Q is $CHR^{65}$, $R^3$ is hydrogen, $R^{65}$ is methyl, $R^{50}$ is hydrogen, $R^7$ is phenyl, $R^8$ is hydrogen, $R^{9a}$ is methyl, $R^{9b}$ is hydrogen, and $R^{10}$ is isopropyl.

In an alternative embodiment, compounds of Formula VIe are disclosed. In a further alternative embodiment, the invention is the use of an effective amount of a compound of Formula VIe, or a pharmaceutically acceptable salt thereof, for the treatment of an infection of an RNA virus in a host, including a human in need thereof.

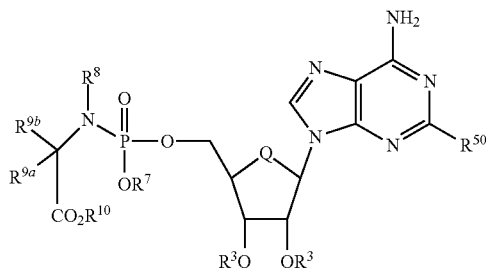

Formula VIe wherein:
Q, $R^3$, $R^7$, $R^8$, $R^{9a}$, $R^{9b}$, $R^{10}$, and $R^{50}$ are defined as above.
In one embodiment of Formula VIe, $R^3$ is hydrogen.
In one embodiment of Formula VIe, $R^{65}$ is methyl.
In one embodiment of Formula VIe, $R^{50}$ is hydrogen.
In one embodiment of Formula VIe, $R^{50}$ is —$NH_2$.

In one embodiment of Formula VIe, Q is CHR$^{65}$, R$^3$ is hydrogen R$^{65}$ is methyl, and R$^{50}$ is hydrogen.

In one embodiment Formula VIe, the phosphoramidate is in the L-configuration.

In one embodiment Formula VIe, the phosphoramidate is in the D-configuration.

In one embodiment Formula VIe, R$^7$ is phenyl, R$^8$ is hydrogen, R$^{9a}$ is methyl, R$^{9b}$ is hydrogen, and R$^{10}$ is isopropyl and the phosphoramide is in the L-configuration.

In one embodiment Formula VIe, R$^7$ is phenyl, R$^8$ is hydrogen, R$^{9a}$ is methyl, R$^{9b}$ is hydrogen, and R$^{10}$ is isopropyl and the phosphoramide is in the D-configuration.

In one embodiment Formula VIe, Q is CHR$^{65}$, R$^3$ is hydrogen, R$^7$ is phenyl, R$^8$ is hydrogen, R$^{9a}$ is methyl, R$^{9b}$ is hydrogen, and R$^{10}$ is isopropyl.

In one embodiment Formula VIe, Q is CHR$^{65}$, R$^3$ is hydrogen, R$^{65}$ is methyl, R$^{50}$ is hydrogen, R$^7$ is phenyl, R$^8$ is hydrogen, R$^{9a}$ is methyl, R$^{9b}$ is hydrogen, and R$^{10}$ is isopropyl.

In an alternative embodiment, compounds of Formula VIf are disclosed. In a further alternative embodiment, the invention is the use of an effective amount of a compound of Formula VIf, or a pharmaceutically acceptable salt thereof, for the treatment of an infection of an RNA virus in a host, including a human in need thereof.

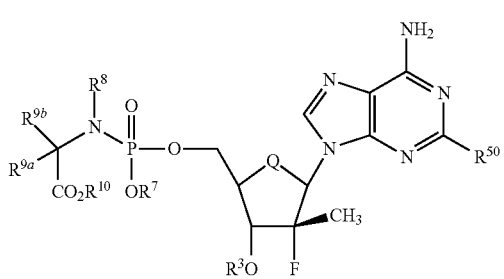

Formula VIf wherein:
Q, R$^3$, R$^7$, R$^8$, R$^{9a}$, R$^{9b}$, R$^{10}$, and Re are defined as above.

In one embodiment of Formula VIf, R$^3$ is hydrogen.
In one embodiment of Formula VIf, R$^{65}$ is methyl.
In one embodiment of Formula VIf, R$^{50}$ is hydrogen.
In one embodiment of Formula VIf, R$^{50}$ is —NH$_2$.
In one embodiment of Formula VIf, Q is CHR$^{65}$, R$^3$ is hydrogen R$^{65}$ is methyl, and R$^{50}$ is hydrogen.

In one embodiment Formula VIf, the phosphoramidate is in the L-configuration.

In one embodiment Formula VIf, the phosphoramidate is in the D-configuration.

In one embodiment Formula VIf, R$^7$ is phenyl, R$^8$ is hydrogen, R$^{9a}$ is methyl, R$^{9b}$ is hydrogen, and R$^{10}$ is isopropyl and the phosphoramide is in the L-configuration.

In one embodiment Formula VIf, R$^7$ is phenyl, R$^8$ is hydrogen, R$^{9a}$ is methyl, R$^{9b}$ is hydrogen, and R$^{10}$ is isopropyl and the phosphoramide is in the D-configuration.

In one embodiment Formula VIf, Q is CHR$^{65}$, R$^3$ is hydrogen, R$^7$ is phenyl, R$^8$ is hydrogen, R$^{9a}$ is methyl, R$^{9b}$ is hydrogen, and R$^{10}$ is isopropyl.

In one embodiment Formula VIf, Q is CHR$^{65}$, R$^3$ is hydrogen, R$^{65}$ is methyl, R$^{50}$ is hydrogen, R$^7$ is phenyl, R$^8$ is hydrogen, R$^{9a}$ is methyl, R$^{9b}$ is hydrogen, and R$^{10}$ is isopropyl.

The phosphorus in any of the Formulas above may be chiral and thus can be provided as an R or S enantiomer or mixture thereof, including a racemic mixture.

Non-limiting embodiments include:

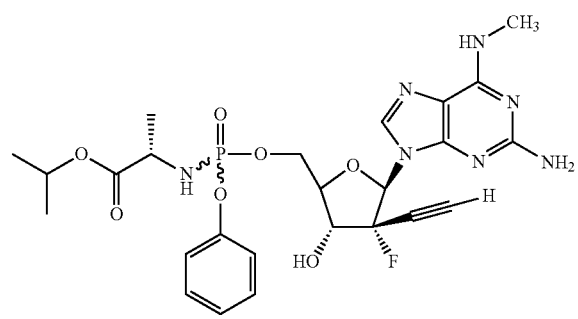

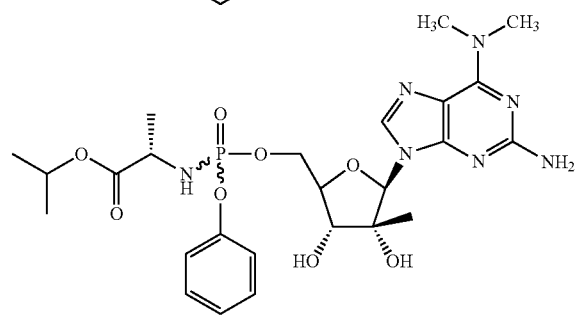

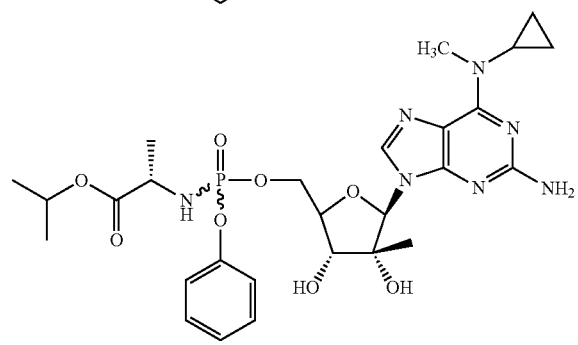

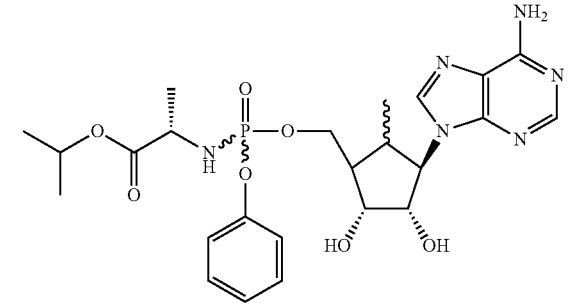

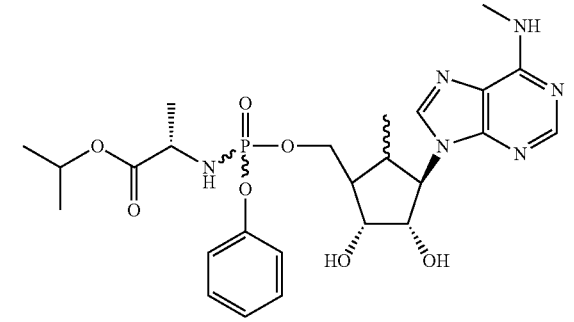

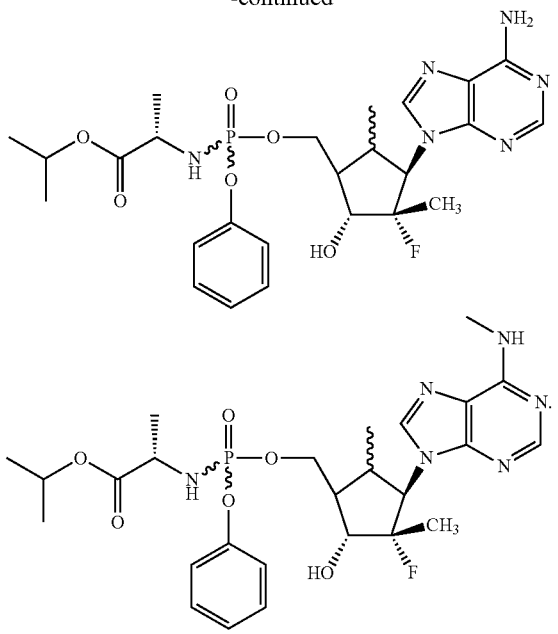

In one embodiment, compounds, methods, and compositions are provided for the treatment of a host infected with an RNA virus described herein, for example, other than a hepacivirus or HCV. For example, the compounds of the invention can be administered in an effective amount alone or in combination with another anti-RNA viral agent to treat the infected host in need thereof. In certain embodiments, it is useful to administer a combination of drugs that modulate the same or a different pathway or inhibit a different target in the virus. As the disclosed 2'-substituted-$N^6$-substituted purine nucleotides are polymerase inhibitors, it can be advantageous to administer the compound to a host in combination with a protease inhibitor or an NS5A inhibitor. The compounds of the invention can also be administered in combination with a structurally different polymerase inhibitor such as another compound described herein or otherwise known to those in the art. The compounds of the invention can also be administered in combination with ribavirin and/or interferon.

The 2'-substituted-$N^6$-substituted purine nucleotides of the invention are typically administered orally, for example in pill or tablet form, but may be administered via another route which the attending physician considers appropriate, including via intravenous, transdermal, subcutaneous, topical, parenteral, or other suitable route.

DETAILED DESCRIPTION OF THE INVENTION

The invention disclosed herein are compounds and their uses, methods, and compositions as described herein for the treatment of infections in or exposure to humans or another host animal to an RNA virus that includes the administration of an effective amount of a compound of Formula I, Formula II, Formula III, Formula IV, Formula V, or Formula VI as described herein or a pharmaceutically acceptable salt or prodrug thereof, optionally in a pharmaceutically acceptable carrier. The compounds described herein either possess anti-RNA activity, or are metabolized to a compound that exhibits such activity. In certain embodiments, the method includes the administration of a compound of Formula I, Formula II, Formula III, Formula IV, Formula V, or Formula VI or a pharmaceutically acceptable salt thereof for the treatment of an infection of a single-stranded RNA positive stranded virus other than a hepacivirus or other than HCV in a host in need thereof, including a human. In an alternative embodiment, a method is presented that includes the administration of a compound of Formula I, Formula II, Formula III, Formula IV, Formula V, or Formula VI or a pharmaceutically acceptable salt thereof for the treatment of an infection of a single-stranded RNA positive stranded virus of the Flaviviridae family, including but not limited to Dengue virus 2 and Yellow Fever, in a host in need thereof, including a human. In an alternative embodiment, a method is presented that includes the administration of a compound of Formula I, Formula II, Formula III, Formula IV, Formula V, or Formula VI or a pharmaceutically acceptable salt thereof for the treatment of an infection of a single-stranded RNA negative-sense virus in a host in need thereof, including a human. In an alternative embodiment, a method is presented that includes the administration of a compound of Formula I, Formula II, Formula III, Formula IV, Formula V, or Formula VI or a pharmaceutically acceptable salt thereof for the treatment of an infection of a double-stranded RNA virus in a host in need thereof, including a human.

The compounds and compositions can also be used to treat conditions related to or occurring as a result of an RNA viral exposure. In one embodiment, the compounds or formulations that include the compounds can also be used prophylactically to prevent or retard the progression of clinical illness in individuals who are RNA virus antibody- or RNA virus antigen-positive.

In particular, it has been discovered that a 5'-stabilized phosphate prodrug or derivative of a 2'-substituted-$N^6$-methyl-2,6-diaminopurine nucleotide, as well as a 2'-substituted-$N^6$-dimethyl-2,6-diaminopurine nucleotide, and other 2'-substituted-$N^6$-substituted purine nucleotides as described below, are highly active against an RNA virus, for example, other than hepacivirus or other than HCV.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the $R^4$ stabilized phosphate prodrug, it can be provided as an R or S chiral phosphorus derivative or a mixture thereof, including a racemic mixture. The amino acid of the phosphoramidate or thiophosphoramidate can be in the D- or L-configuration, or a mixture thereof, including a racemic mixture. All of the combinations of these stereo configurations are included in the invention described herein.

The present invention includes the following features:
(a) Formulas I-VI as described herein, and pharmaceutically acceptable salts and prodrugs thereof for use in the treatment or prophylaxis of an RNA virus infection and in one embodiment, a virus other than a hepacivirus or other than HCV;
(b) Use of Formulas I-VI, and pharmaceutically acceptable salts and prodrugs thereof in the manufacture of a medicament for treatment of an RNA virus infection a virus other than a hepacivirus or other than HCV;
(c) A method for manufacturing a medicament intended for the therapeutic use for treating an RNA virus infection, for example, a virus other than a hepacivirus or other than HCV, characterized in that a Formulas I-VI as described herein is used in the manufacture; and (d) A pharmaceutical formulation comprising an effective host-treating amount of the Formulas I-VI or a pharmaceutically acceptable salt or prodrug thereof together with a pharmaceutically acceptable carrier or diluent to treat an RNA virus other than a hepacivirus or other than HCV.

I. 2'-Deoxy-2'-Substituted-2-Modified-$N^6$-Substituted Purine Nucleotides of the Invention The active compounds of the invention are those depicted, for example, in Formula I which can be provided in a pharmaceutically acceptable composition, salt or prodrug thereof:

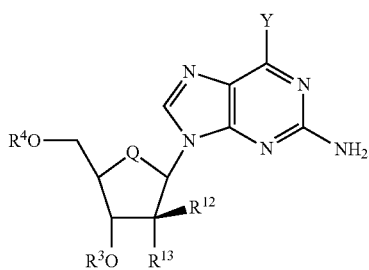

Formula I wherein:

Y is $NR^1R^2$;

$R^1$ is $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CH_2F$, $CH_2F$, $CF_3$, $CH_2CF_3$, $CF_2CH_3$ and $CF_2CF_3$), $C_2$-$C_6$ alkenyl, $C_2$-$C_6$ alkynyl, —($C_0$-$C_2$alkyl)($C_3$-$C_6$cycloalkyl), —($C_0$-$C_2$alkyl)(heterocycle), —($C_0$-$C_2$alkyl)(aryl), —($C_0$-$C_2$alkyl)(heteroaryl), —$OR^{23}$, —$C(O)R^{3C}$(including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$ each of which can be optionally substituted;

$R^2$ is hydrogen, optionally substituted $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CH_2F$, $CF_3$, $CH_2CF_3$ and $CF_2CF_3$), optionally substituted —($C_0$-$C_2$alkyl)($C_3$-$C_6$cycloalkyl), optionally substituted —($C_0$-$C_2$alkyl) heterocycle), optionally substituted —($C_0$-$C_2$alkyl) (aryl), optionally substituted —($C_0$-$C_2$alkyl) (heteroaryl), —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$; and wherein at least one of $R^1$ and $R^2$ is methyl, $CH_2F$, $CHF_2$ or $CF_3$;

$R^3$ is hydrogen,

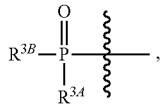

diphosphate, triphosphate, an optionally substituted carbonyl linked amino acid, or —$C(O)R^{3C}$;

$R^{3A}$ can be selected from $O^-$, OH, an —O-optionally substituted aryl, an —O-optionally substituted heteroaryl, or an optionally substituted heterocyclyl;

$R^{3B}$ can be selected from $O^-$, OH, an optionally substituted N-linked amino acid or an optionally substituted N-linked amino acid ester;

$R^{3C}$ is alkyl, alkenyl, alkynyl, —($C_0$-$C_2$)(cycloalkyl), —($C_0$-$C_2$)(heterocyclo), —($C_0$-$C_2$)(aryl), —($C_0$-$C_2$)(heteroaryl), —O-alkyl, —O-alkenyl, —O-alkynyl, —O—($C_0$-$C_2$)(cycloalkyl), —O—($C_0$-$C_2$)(heterocyclo), —O—($C_0$-$C_2$)(aryl), or —O—($C_0$-$C_2$)(heteroaryl), each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug, including but not limited to, a 3',5'-cyclic phosphate prodrug;

$R^{12}$ is hydrogen, $CH_3$, $CH_2F$, $CHF_2$, $CF_3$, or ethynyl; and $R^{13}$ is hydrogen, fluoro, chloro, bromo, $N_3$, $NH_2$, CN or $OR^3$;

wherein when $R^{12}$ is methyl, $R^{13}$ is bromo, chloro, $N_3$, $NH_2$, CN or $OR^3$.

A stabilized phosphate prodrug is any moiety that can deliver a mono, di, or triphosphate.

In an alternative embodiment, at least one of $R^1$ and $R^2$ is cyclopropyl.

In an alternative embodiment, at least one of $R^1$ and $R^2$ is cyclopently.

In another embodiment, the invention is the use of an effective amount of a compound of Formula Ia or a pharmaceutically acceptable salt thereof, for the treatment of an infection of an RNA virus in a host, including a human in need thereof.

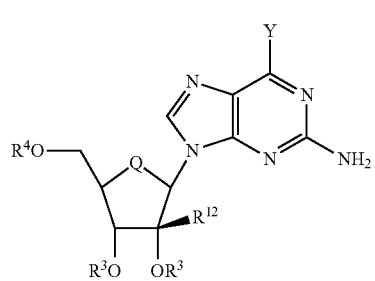

Formula Ia wherein:

Y, $R^3$ and $R^4$ are as defined above.

In another embodiment, the invention is the use of an effective amount of a compound of Formula Ib or a pharmaceutically acceptable salt thereof, for the treatment of an infection of an RNA virus in a host, including a human in need thereof.

Formula Ib

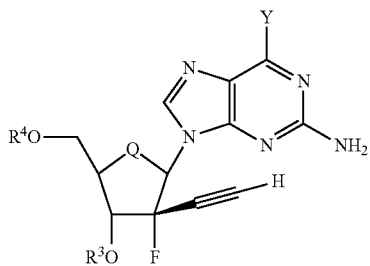

wherein:
Y, R³ and R⁴ are as defined above.

In an alternative embodiment, the invention is the use of an effective amount of a compound of Formula Ib' or a pharmaceutically acceptable salt thereof, for the treatment of an infection of an RNA virus in a host, including a human in need thereof.

Formula Ib'

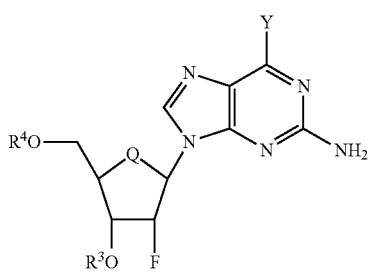

wherein:
$R^3$, $R^4$, $R^{60}$, m, and p are defined above.

In another embodiment, the invention is the use of an effective amount of a compound of Formula Ic or a pharmaceutically acceptable salt thereof, for the treatment of an infection of an RNA virus in a host, including a human in need thereof.

Formula Ic

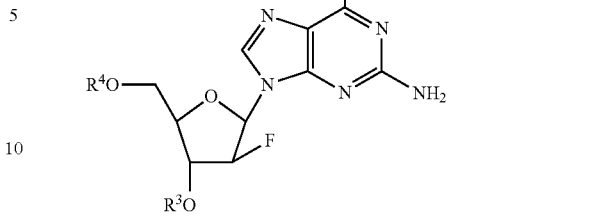

wherein:
Y, R³ and R⁴ are as defined above.

In another embodiment, the invention is the use of an effective amount of a compound of Formula Id or a pharmaceutically acceptable salt thereof, for the treatment of an infection of an RNA virus in a host, including a human in need thereof.

Formula Id

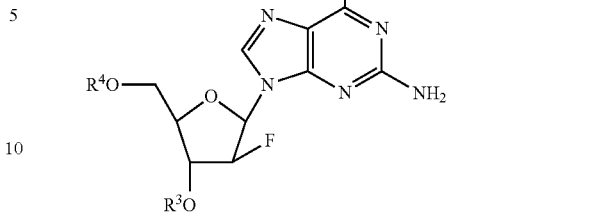

wherein:
Y, R³ and R⁴ are as defined above.

In an alternative embodiment, the invention is the use of an effective amount of a compound of Formula Ie or a pharmaceutically acceptable salt thereof, for the treatment of an infection of an RNA virus in a host, including a human in need thereof.

Formula Ie

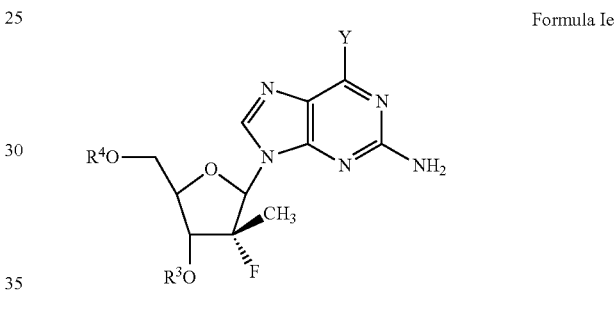

wherein:
Y, R³ and R⁴ are as defined above.

In another embodiment, the invention is the use of an effective amount of a compound of Formula II or a pharmaceutically acceptable salt thereof, for the treatment of an infection of an RNA virus in a host, including a human in need thereof.

Formula II

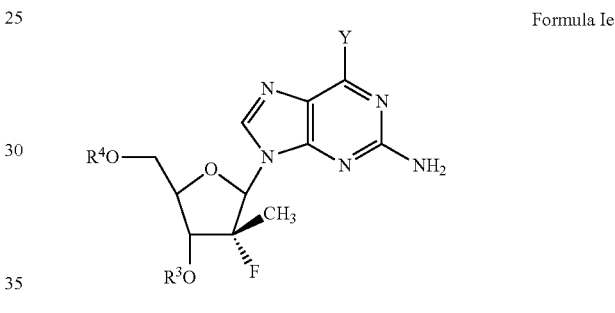

wherein:
Y, $R^3$, $R^4$, $R^{12}$, $R^{13}$ and $R^{22}$ are as defined above.

In another embodiment, the invention is the use of an effective amount of a compound of Formula IIa or a pharmaceutically acceptable salt thereof, for the treatment of an infection of an RNA virus in a host, including a human in need thereof.

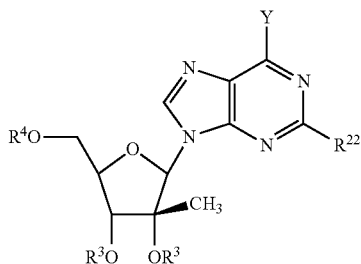

Formula IIa wherein:

Y, $R^3$, $R^4$ and $R^{22}$ are as defined above.

In another embodiment, the invention is the use of an effective amount of a compound of Formula IIb or a pharmaceutically acceptable salt thereof, for the treatment of an infection of an RNA virus in a host, including a human in need thereof.

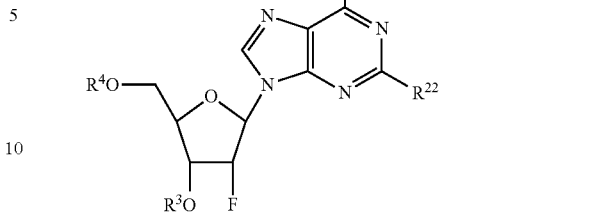

Formula IIc wherein:

Y, $R^3$, $R^4$, and $R^{22}$ are as defined above.

In another embodiment, the invention is the use of an effective amount of a compound of Formula IId or a pharmaceutically acceptable salt thereof, for the treatment of an infection of an RNA virus in a host, including a human in need thereof.

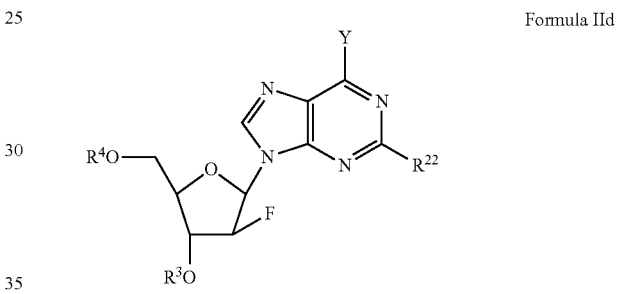

Formula IIb wherein:

Y, $R^3$, $R^4$ and $R^{22}$ are as defined above.

In an alternative embodiment, the invention is the use of an effective amount of a compound of Formula IIb' or a pharmaceutically acceptable salt thereof, for the treatment of an infection of an RNA virus in a host, including a human in need thereof.

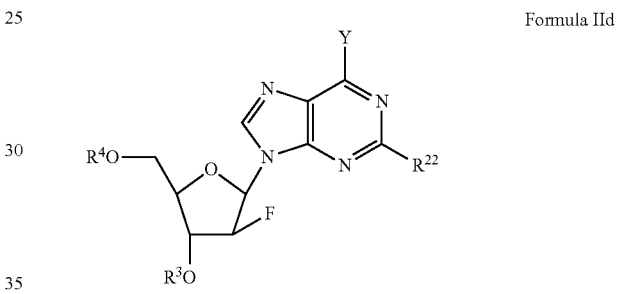

Formula IId wherein:

Y, $R^3$, $R^4$, and $R^{22}$ are as defined above.

In an alternative embodiment, the invention is the use of an effective amount of a compound of Formula IIe or a pharmaceutically acceptable salt thereof, for the treatment of an infection of an RNA virus in a host, including a human in need thereof.

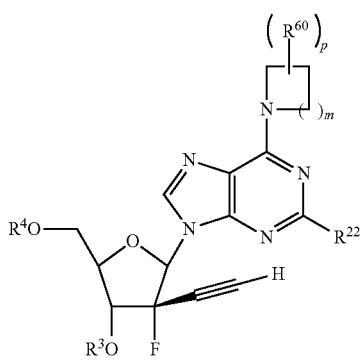

Formula IIb' wherein:

$R^3$, $R^4$, $R^{22}$, $R^{60}$, m, and p are as defined above.

In another embodiment, the invention is the use of an effective amount of a compound of Formula IIc or a pharmaceutically acceptable salt thereof, for the treatment of an infection of an RNA virus in a host, including a human in need thereof.

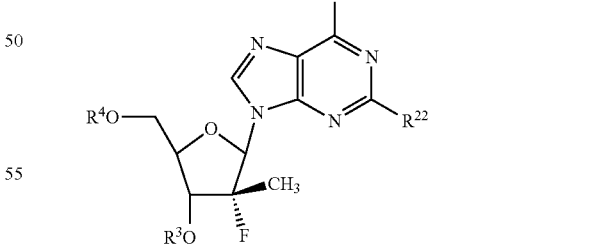

Formula IIe wherein:

Y, $R^3$, $R^4$, and $R^{22}$ are as defined above.

In another embodiment, the invention is the use of an effective amount of a compound of Formula III or a pharmaceutically acceptable salt thereof, for the treatment of an infection of an RNA virus in a host, including a human in need thereof.

Formula III

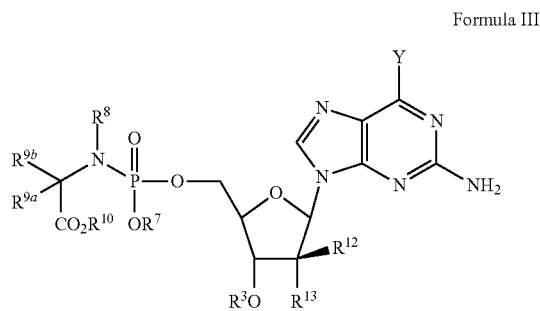

wherein the variables Y, $R^3$, $R^7$, $R^8$, $R^{9a}$, $R^{9b}$, $R^{10}$, $R^{12}$ and $R^{13}$ are described herein.

In another embodiment, the invention is the use of an effective amount of a compound of Formula IIIa or a pharmaceutically acceptable salt thereof, for the treatment of an infection of an RNA virus in a host, including a human in need thereof.

Formula IIIa

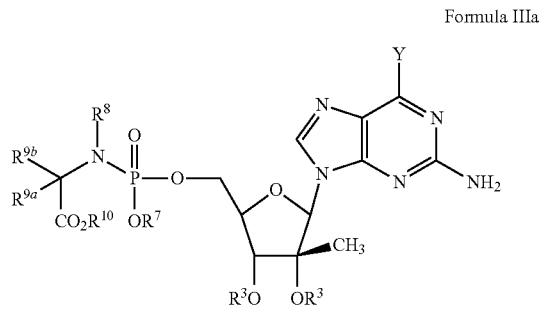

wherein the variables Y, $R^3$, $R^7$, $R^8$, $R^{9a}$, $R^{9b}$ and $R^{10}$ are described herein.

In another embodiment, the invention is the use of an effective amount of a compound of Formula IIIb or a pharmaceutically acceptable salt thereof, for the treatment of an infection of an RNA virus in a host, including a human in need thereof.

Formula IIIb

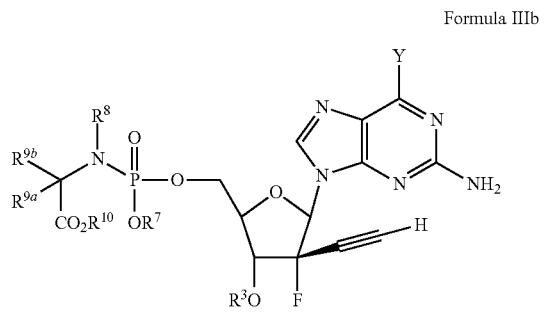

wherein the variables Y, $R^3$, $R^7$, $R^8$, $R^{9a}$, $R^{9b}$ and $R^{10}$ are described herein.

In an alternative embodiment, the invention is the use of an effective amount of a compound of Formula IIIb' or a pharmaceutically acceptable salt thereof, for the treatment of an infection of an RNA virus in a host, including a human in need thereof.

Formula IIIb'

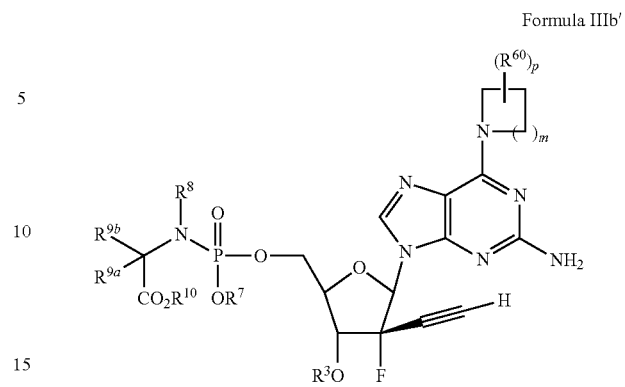

wherein the variables Y, $R^3$, $R^7$, $R^8$, $R^{9a}$, $R^{9b}$, $R^{10}$, $R^{60}$, m, and p are described herein.

In another embodiment, the invention is the use of an effective amount of a compound of Formula IIIc or a pharmaceutically acceptable salt thereof, for the treatment of an infection of an RNA virus in a host, including a human in need thereof.

Formula IIIc

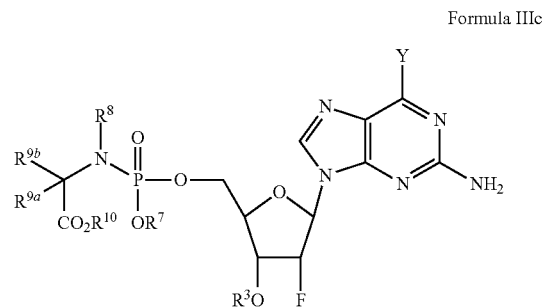

wherein the variables $R^3$, $R^7$, $R^8$, $R^{9a}$, $R^{9b}$ and $R^{10}$ are described herein.

In another embodiment, the invention is the use of an effective amount of a compound of Formula IId or a pharmaceutically acceptable salt thereof, for the treatment of an infection of an RNA virus in a host, including a human in need thereof.

Formula IIId

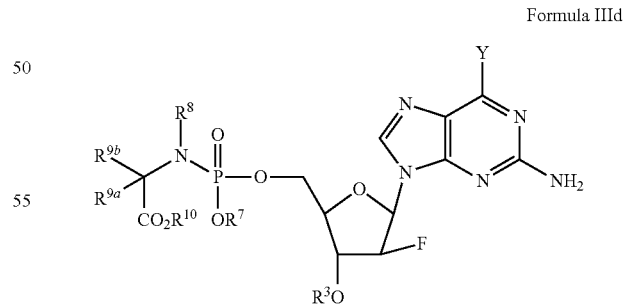

wherein the variables Y, $R^3$, $R^7$, $R^8$, $R^{9a}$, $R^{9b}$ and $R^{10}$ are described herein.

In another embodiment, the invention is the use of an effective amount of a compound of Formula IIIe or a pharmaceutically acceptable salt thereof, for the treatment of an infection of an RNA virus in a host, including a human in need thereof.

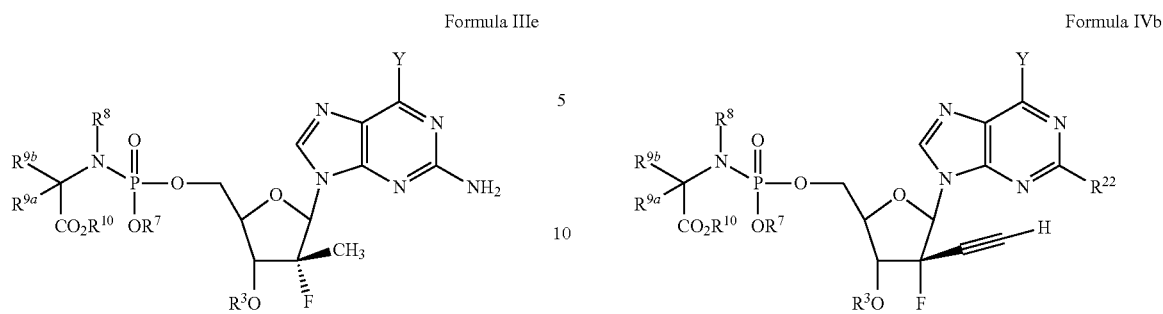

Formula IIIe wherein the variables Y, $R^3$, $R^7$, $R^8$, $R^{9a}$, $R^{9b}$ and $R^{10}$ are described herein.

In another embodiment, the invention is the use of an effective amount of a compound of Formula IV or a pharmaceutically acceptable salt thereof, for the treatment of an infection of an RNA virus in a host, including a human in need thereof.

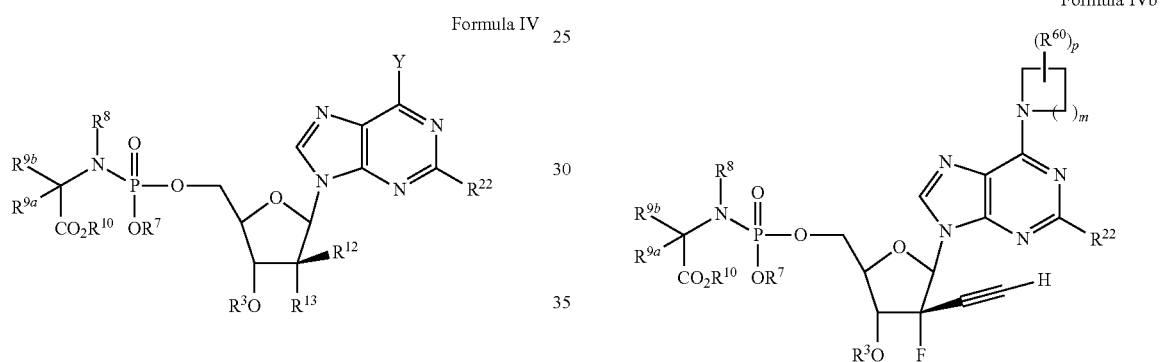

Formula IV wherein the variables Y, $R^3$, $R^7$, $R^8$, $R^{9a}$, $R^{9b}$, $R^{10}$, $R^{12}$, $R^{13}$ and $R^{22}$ are described herein.

In another embodiment, the invention is the use of an effective amount of a compound of Formula IVa or a pharmaceutically acceptable salt thereof, for the treatment of an infection of an RNA virus in a host, including a human in need thereof.

Formula IVa wherein the variables Y, $R^3$, $R^7$, $R^8$, $R^{9a}$, $R^{9b}$, $R^{10}$ and $R^{22}$ are described herein.

In another embodiment, the invention is the use of an effective amount of a compound of Formula IVb or a pharmaceutically acceptable salt thereof, for the treatment of an infection of an RNA virus in a host, including a human in need thereof.

Formula IVb wherein the variables Y, $R^3$, $R^7$, $R^8$, $R^{9a}$, $R^{9b}$, $R^{10}$ and $R^{22}$ are described herein.

In an alternative embodiment, the invention is the use of an effective amount of a compound of Formula IVb' or a pharmaceutically acceptable salt thereof, for the treatment of an infection of an RNA virus in a host, including a human in need thereof.

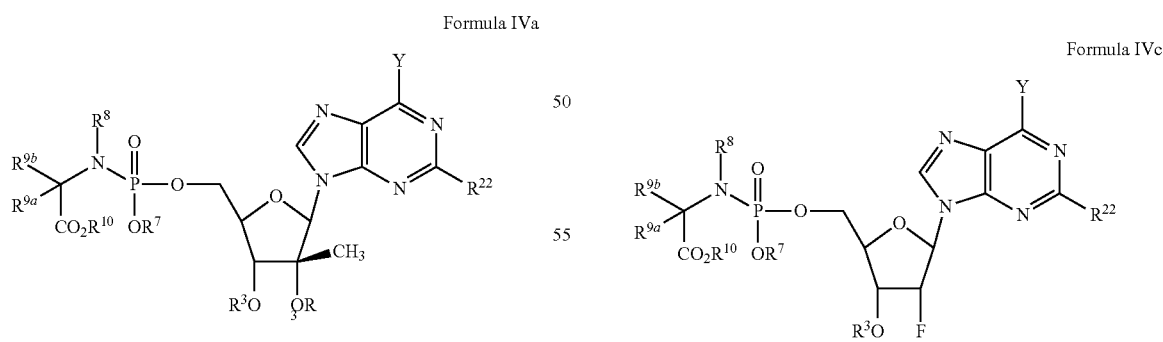

Formula IVb' wherein the variables $R^3$, $R^7$, $R^8$, $R^{9a}$, $R^{9b}$, $R^{10}$, $R^{22}$, $R^{60}$, m, and p are described herein.

In another embodiment, the invention is the use of an effective amount of a compound of Formula IVc or a pharmaceutically acceptable salt thereof, for the treatment of an infection of an RNA virus in a host, including a human in need thereof.

Formula IVc wherein the variables Y, $R^3$, $R^7$, $R^8$, $R^{9a}$, $R^{9b}$, $R^{10}$ and $R^{22}$ are described herein.

In another embodiment, the invention is the use of an effective amount of a compound of Formula IVd or a pharmaceutically acceptable salt thereof, for the treatment of an infection of an RNA virus in a host, including a human in need thereof.

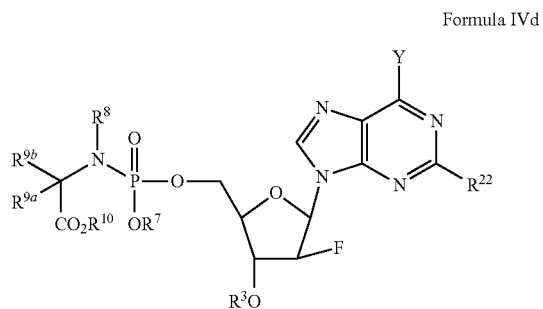

Formula IVd wherein the variables Y, $R^3$, $R^7$, $R^8$, $R^{9a}$, $R^{9b}$, $R^{10}$ and $R^{22}$ are described herein.

In another embodiment, the invention is the use of an effective amount of a compound of Formula We or a pharmaceutically acceptable salt thereof, for the treatment of an infection of an RNA virus in a host, including a human in need thereof.

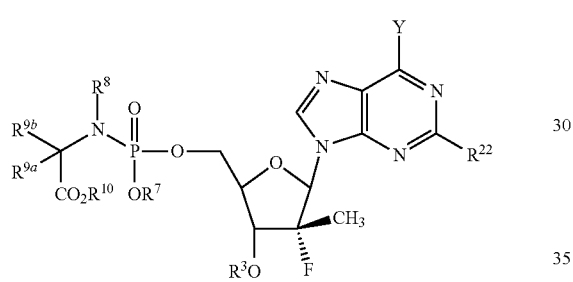

Formula IVe wherein the variables Y, $R^3$, $R^7$, $R^8$, $R^{9a}$, $R^{9b}$, $R^{10}$, and $R^{22}$ are described herein.

In another embodiment, the invention is the use of an effective amount of a compound of Formula V or a pharmaceutically acceptable salt thereof, for the treatment of an infection of an RNA virus in a host, including a human in need thereof.

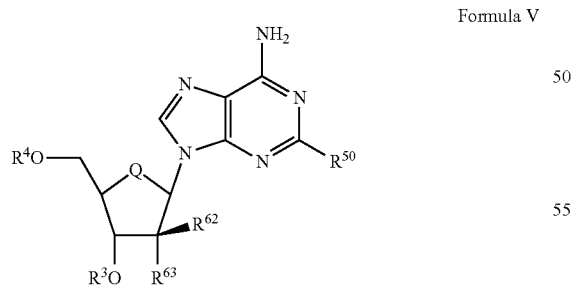

Formula V wherein:

$R^3$, $R^4$, $R^{50}$, $R^{62}$, $R^{63}$, and Q are defined above.

In an alternative embodiment, the invention is the use of an effective amount of a compound of Formula V or a pharmaceutically acceptable salt thereof, for the treatment of an infection of an RNA virus in a host, including a human in need thereof.

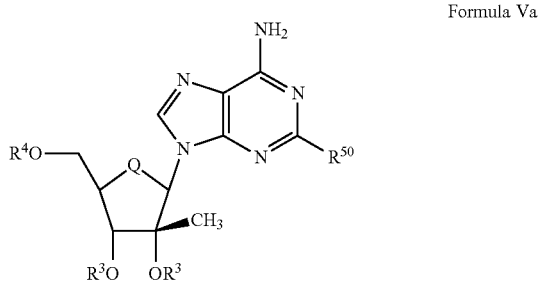

Formula Va wherein:

$R^3$, $R^4$, $R^{50}$, and Q are defined above.

In an alternative embodiment, the invention is the use of an effective amount of a compound of Formula Vb or a pharmaceutically acceptable salt thereof, for the treatment of an infection of an RNA virus in a host, including a human in need thereof.

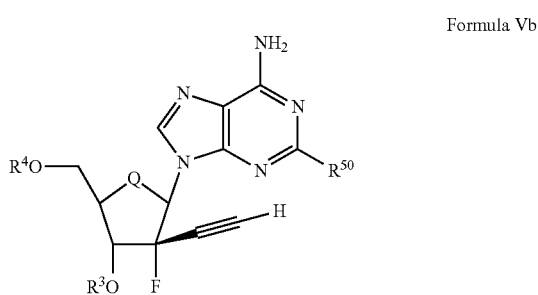

Formula Vb wherein:

$R^3$, $R^4$, $R^{50}$, and Q are defined above.

In an alternative embodiment, the invention is the use of an effective amount of a compound of Formula Vc or a pharmaceutically acceptable salt thereof, for the treatment of an infection of an RNA virus in a host, including a human in need thereof.

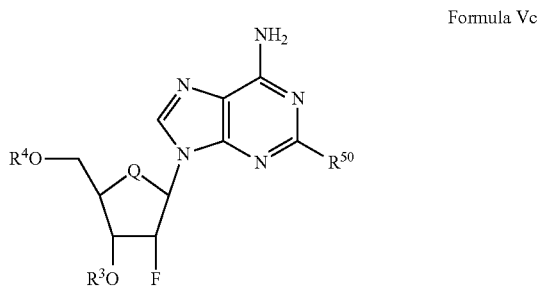

Formula Vc wherein:

$R^3$, $R^4$, $R^{50}$, and Q are defined above.

In an alternative embodiment, the invention is the use of an effective amount of a compound of Formula Vd or a pharmaceutically acceptable salt thereof, for the treatment of an infection of an RNA virus in a host, including a human in need thereof.

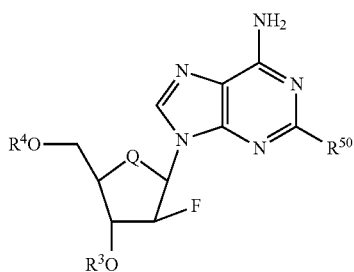

Formula Vd wherein:

$R^3$, $R^4$, $R^{50}$, and Q are defined above.

In an alternative embodiment, the invention is the use of an effective amount of a compound of Formula Ve or a pharmaceutically acceptable salt thereof, for the treatment of an infection of an RNA virus in a host, including a human in need thereof.

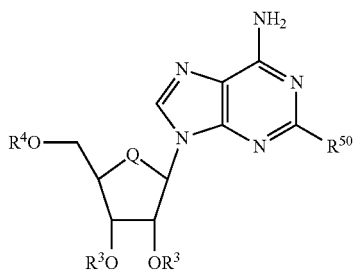

Formula Ve wherein:

$R^3$, $R^4$, $R^{50}$, and Q are defined above.

In an alternative embodiment, the invention is the use of an effective amount of a compound of Formula Vf or a pharmaceutically acceptable salt thereof, for the treatment of an infection of an RNA virus in a host, including a human in need thereof.

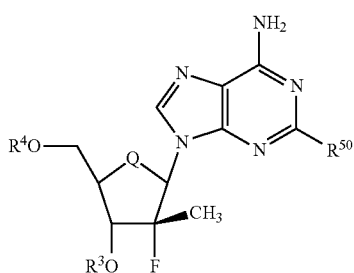

Formula Vf wherein:

$R^3$, $R^4$, $R^3$, and Q are defined above.

In an alternative embodiment, the invention is the use of an effective amount of a compound of Formula VI or a pharmaceutically acceptable salt thereof, for the treatment of an infection of an RNA virus in a host, including a human in need thereof.

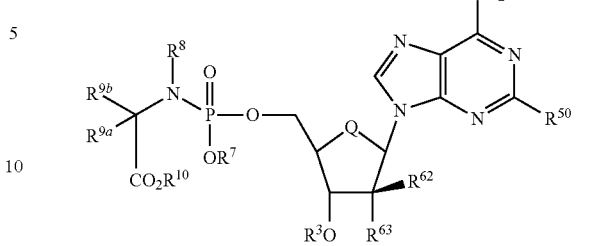

Formula VI wherein:

$R^3$, $R^7$, $R^8$, $R^{9a}$, $R^{9b}$, $R^{10}$, $R^{50}$, $R^{62}$, and $R^{63}$ and Q are defined above.

In an alternative embodiment, the invention is the use of an effective amount of a compound of Formula VIa or a pharmaceutically acceptable salt thereof, for the treatment of an infection of an RNA virus in a host, including a human in need thereof.

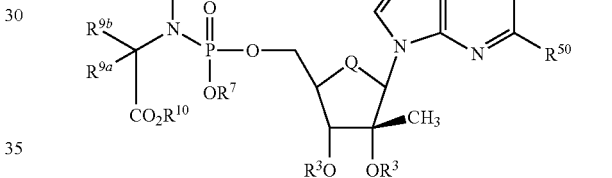

Formula VIa wherein:

$R^3$, $R^7$, $R^8$, $R^{9a}$, $R^{9b}$, $R^{10}$, $R^{50}$, and Q are defined above.

In an alternative embodiment, the invention is the use of an effective amount of a compound of Formula VIb or a pharmaceutically acceptable salt thereof, for the treatment of an infection of an RNA virus in a host, including a human in need thereof.

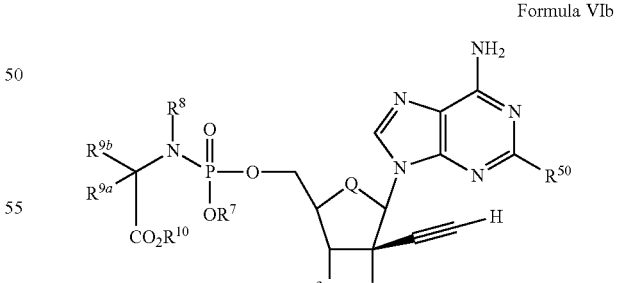

Formula VIb wherein:

$R^3$, $R^7$, $R^8$, $R^{9a}$, $R^{9b}$, $R^{10}$, $R^{50}$, and Q are defined above.

In an alternative embodiment, the invention is the use of an effective amount of a compound of Formula VIc or a pharmaceutically acceptable salt thereof, for the treatment of an infection of an RNA virus in a host, including a human in need thereof.

Formula VIc

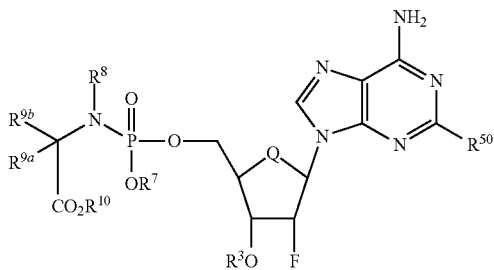

wherein:
$R^3$, $R^7$, $R^8$, $R^{9a}$, $R^{9b}$, $R^{10}$, $R^{50}$, and Q are defined above.

In an alternative embodiment, the invention is the use of an effective amount of a compound of Formula VId or a pharmaceutically acceptable salt thereof, for the treatment of an infection of an RNA virus in a host, including a human in need thereof.

Formula VId

wherein:
$R^3$, $R^7$, $R^8$, $R^{9a}$, $R^{9b}$, $R^{10}$, $R^{50}$, and Q are defined above.

In an alternative embodiment, the invention is the use of an effective amount of a compound of Formula VIe or a pharmaceutically acceptable salt thereof, for the treatment of an infection of an RNA virus in a host, including a human in need thereof.

Formula VIe

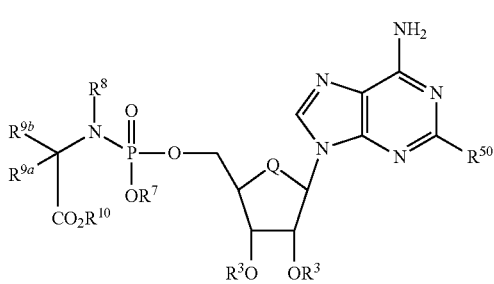

wherein:
$R^3$, $R^7$, $R^8$, $R^{9a}$, $R^{9b}$, $R^{10}$, $R^{50}$, and Q are defined above.

In an alternative embodiment, the invention is the use of an effective amount of a compound of Formula VIf or a pharmaceutically acceptable salt thereof, for the treatment of an infection of an RNA virus in a host, including a human in need thereof.

Formula VIf

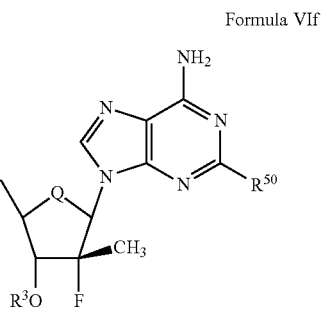

wherein:
$R^3$, $R^7$, $R^8$, $R^{9a}$, $R^{9b}$, $R^{10}$, $R^{50}$, and Q are defined above.

In a typical embodiment, the compound is a β-D isomer with reference to the corresponding nucleoside (i.e., in the naturally occurring configuration). In an alternative configuration, the compound is provided as a β-L isomer. The compound is typically at least 90% free of the opposite enantiomer, and can be at least 95%, 96%, 97%, 98%, 99% or even 100% free of the opposite enantiomer. Unless described otherwise, the compound is at least 90% free of the opposite enantiomer.

Metabolism of β-D-2'-deoxy-2'-α-fluoro-2'-β-C-substituted-N⁶-substituted-2,6-diaminopurine Nucleotides The metabolism of the β-D-2'-deoxy-2'-α-fluoro-2'-β-ethynyl-N⁶-methyl-2,6-diaminopurine nucleoside phosphoramidate involves the production of a 5'-monophosphate and the subsequent anabolism of the N⁶-methyl-2,6-diaminopurine base to generate the β-D-2'-deoxy-2'-α-fluoro-2'-β-ethylguanine nucleoside as the 5'-monophosphate. The monophosphate is then further anabolized to the active species; the 5'-triphosphate. The metabolic pathway for the β-D-2'-deoxy-2'-α-fluoro-2'-β-ethynyl-N⁶-methyl-2,6-diaminopurine nucleoside phosphoramidate is illustrated in Scheme 1.

The metabolism of the β-D-2'-deoxy-2'-α-fluoro-2'-β-ethynyl-N⁶-dimethyl-2,6-diaminopurine nucleotide involves both the formation of the β-D-2'-deoxy-2'-α-fluoro-2'-β-ethynyl-N⁶-dimethyl-2,6-diaminopurine nucleoside triphosphate as well as the generation of the corresponding guanine nucleoside triphosphate. These metabolic pathways are illustrated in Schemes 2 and 3 below.

Scheme 2

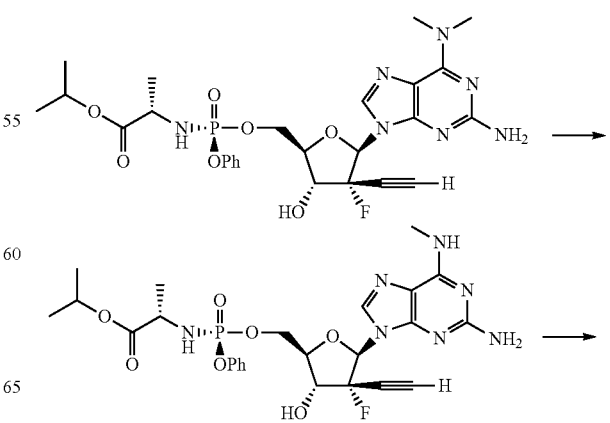

-continued
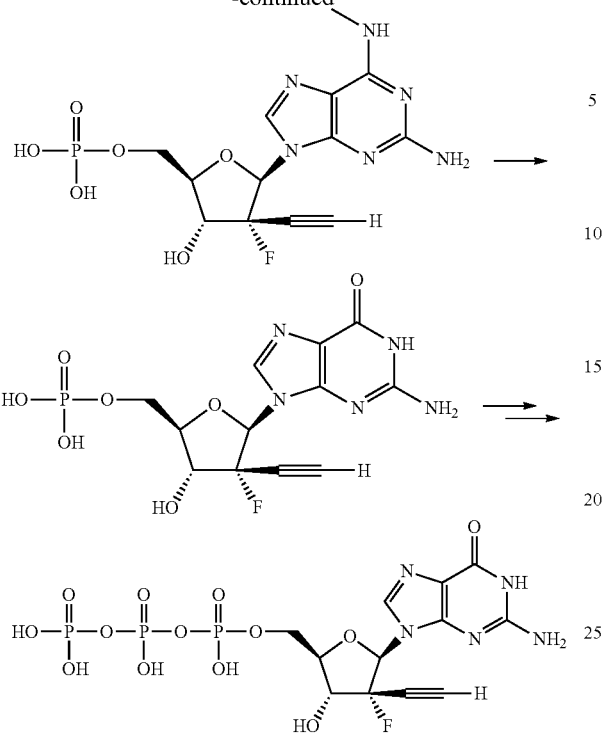
Scheme 3
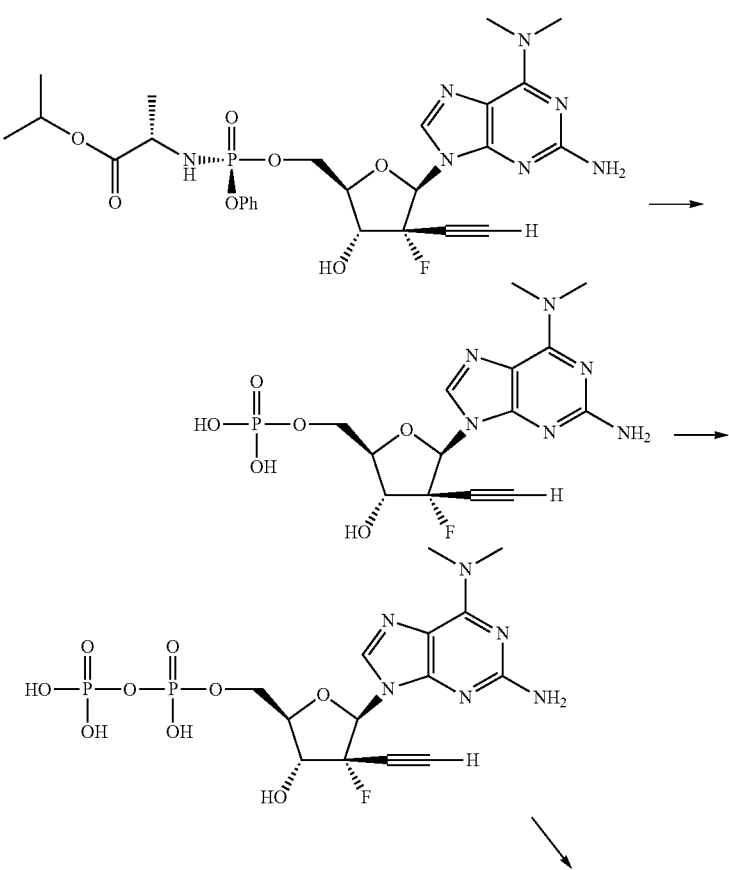

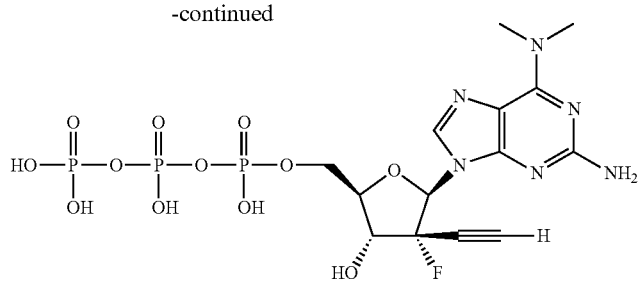

Stabilized Phosphate Prodrugs

Stabilized phosphate prodrugs are moieties that can deliver a mono, di, or triphosphate in vivo. For example, McGuigan has disclosed phosphoramidates in U.S. Pat. Nos. 8,933,053; 8,759,318; 8,658,616; 8,263,575; 8,119,779; 7,951,787 and 7,115,590. Alios has disclosed thiophosphoramidates in U.S. Pat. Nos. 8,895,723 and 8,871,737 incorporated by reference herein. Alios has also disclosed cyclic nucleotides in U.S. Pat. No. 8,772,474 incorporated by reference herein. Idenix has disclosed cyclic phosphoramidates and phosphoramidate/SATE derivatives in WO 2013/177219 incorporated by reference herein. Idenix has also disclosed substituted carbonyloxymethylphosphoramidate compounds in WO 2013/039920 incorporated by reference herein. Hostetler has disclosed lipid phosphate prodrugs, see, for example, U.S. Pat. No. 7,517,858 incorporated by reference herein. Hostetler has also disclosed lipid conjugates of phosphonate prodrugs, see, for example, U.S. Pat. Nos. 8,889,658; 8,846,643; 8,710,030; 8,309,565; 8,008,308; and 7,790,703. Emory University has disclosed nucleotide sphingoid and lipid derivatives in WO 2014/124430 incorporated by reference herein. RFS Pharma has disclosed purine nucleoside monophosphate prodrugs in WO 2010/091386. Cocrystal Pharma Inc. has also disclosed purine nucleoside monophosphate prodrugs in U.S. Pat. No. 9,173,893 incorporated by reference herein. HepDirect™ technology is disclosed in the article "Design, Synthesis, and Characterization of a Series of Cytochrome P(450) 3A-Activated Prodrugs (HepDirect Prodrugs) Useful for Targeting Phosph(on)ate-Based Drugs to the Liver," (J. Am. Chem. Soc. 126, 5154-5163 (2004). Additional phosphate prodrugs include, but are not limited to phosphate esters, 3',5'-cyclic phosphates including CycloSAL, SATE derivatives (S-acyl-2thioesters) and DTE (dithiodiethyl) prodrugs. For literature reviews that disclose non-limiting examples see: A. Ray and K. Hostetler, "Application of kinase bypass strategies to nucleoside antivirals," Antiviral Research (2011) 277-291; M. Sofia, "Nucleotide prodrugs for HCV therapy," Antiviral Chemistry and Chemotherapy 2011; 22-23-49; and S. Peyrottes et al., "SATE Pronucleotide Approaches: An Overview," Mini Reviews in Medicinal Chemistry 2004, 4, 395. In one embodiment, a 5'-prodrug described in any of these patent filings or literature can be used in the $R^4$ position of the presented compounds.

In one alternative embodiment, the stabilized phosphate prodrugs, include, but are not limited to those described in U.S. Pat. Nos. 9,173,893 and 8,609,627, incorporated by reference herein, including for processes of preparation. For example, 5'-prodrugs of Formula I, Formula II, Formula III, Formula IV, Formula V, and Formula VI can be represented by the group:

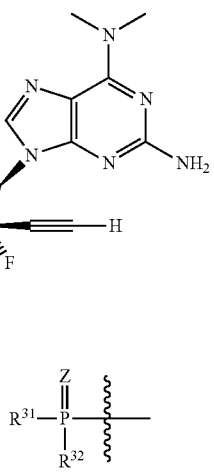

In an alternate embodiment, 3',5'-prodrugs of Formula I-VI can be represented by the group:

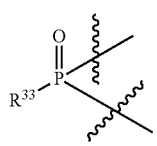

wherein:
when chirality exists at the phosphorous center it may be wholly or partially $R_p$ or $S_p$ or any mixture thereof.
Z is O or S;
$R^{33}$ is selected from $OR^{34}$,

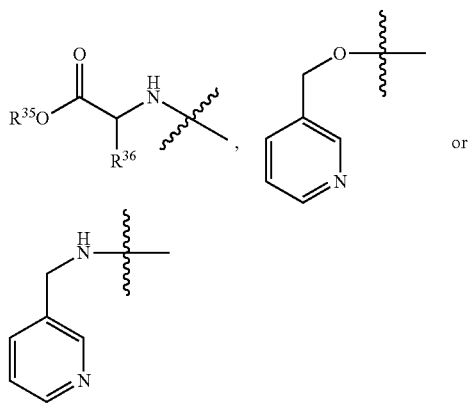

and fatty alcohol derived (for example but not limited to:

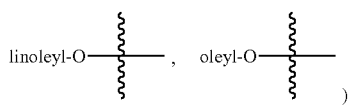

wherein $R^{34}$, $R^{35}$, and $R^{36}$ are as defined below;
$R^{31}$ and $R^{32}$, when administered in vivo, are capable of providing the nucleoside monophosphate or thiomonophosphate, which may or may not be partially or fully resistant to 6-NH$_2$ deamination in a biological system. Representative R$^{31}$ and R$^{32}$ are independently selected from:

(a) OR$^{34}$ where R$^{34}$ is selected from H, Li, Na, K, phenyl and pyridinyl; phenyl and pyridinyl are substituted with one to three substituents independently selected from the group consisting of (CH$_2$)$_{0-6}$CO$_2$R$^{37}$ and (CH$_2$)$_{0-6}$CON(R$^{37}$)$_2$;

R$^{37}$ is independently H, C$_{1-20}$ alkyl, the carbon chain derived from a fatty alcohol (such as oleyl alcohol, octacosanol, triacontanol, linoleyl alcohol, and etc) or C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;

(b)

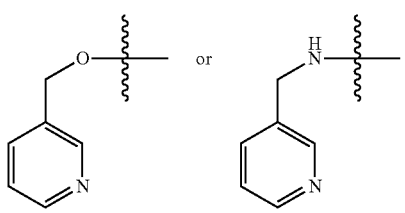

(c) the ester of a D-amino acid or L-amino acid

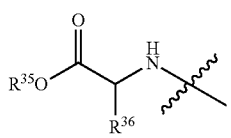

where R$^{36}$ is restricted to those sidechains occurring in natural L-amino acids, and R$^{35}$ is H, C$_{1-20}$ alkyl, the carbon chain derived from a fatty alcohol (such as oleyl alcohol, octacosanol, triacontanol, linoleyl alcohol, and etc) or C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;

(d) R$^{31}$ and R$^{32}$ can come together to form a ring

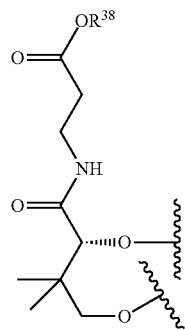

where R$^{38}$ is H, C$_{1-20}$ alkyl, C$_{1-20}$ alkenyl, the carbon chain derived from a fatty alcohol (such as oleyl alcohol, octacosanol, triacontanol, linoleyl alcohol, etc) or C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;

(e) R$^{31}$ and R$^{32}$ can come together to form a ring selected from

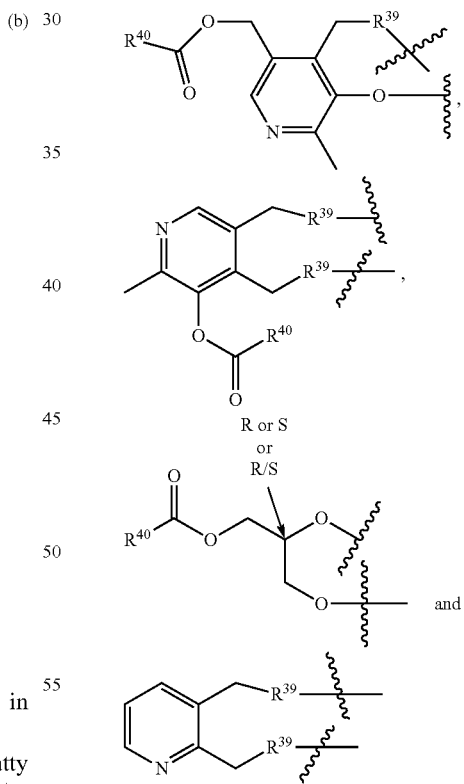

where R$^{39}$ is O or NH and

R$^{40}$ is selected from H, C$_{1-20}$ alkyl, C$_{1-20}$ alkenyl, the carbon chain derived from a fatty acid (such as oleic acid, linoleic acid, and the like), and C$_{1-20}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl.

The compounds can be prepared, for example, by preparing the 5'-OH analogs, then converting these to the monophosphate analogs.

EMBODIMENTS

In particular embodiments:
(i) in Formula Ia, Y is $NR^1R^2$, $R^1$ is methyl, $R^2$ is hydrogen, $R^3$ is hydrogen, $R^4$ is a stabilized phosphate prodrug;
(ii) in Formula Ia, Y is $NR^1R^2$, $R^1$ is methyl, $R^2$ is hydrogen, $R^3$ is hydrogen, and $R^4$ is a stabilized thiophosphate prodrug;
(iii) in Formula Ia, Y is $NR^1R^2$, $R^1$ is methyl, $R^2$ is hydrogen, $R^3$ is hydrogen, and $R^4$ is a phosphoramidate;
(iv) in Formula Ia, Y is $NR^1R^2$, $R^1$ is methyl, $R^2$ is hydrogen, $R^3$ is hydrogen, and $R^4$ is a thiophosphoramidate:
(v) in Formula Ia, Y is $NR^1R^2$, $R^1$ is methyl, $R^2$ is hydrogen, $R^3$ is hydrogen, and $R^4$ is a monophosphate;
(vi) in Formula Ia, Y is $NR^1R^2$, $R^1$ is methyl, $R^2$ is hydrogen, $R^3$ is hydrogen, and $R^4$ is a diphosphate;
(vii) in Formula Ia, Y is $NR^1R^2$, $R^1$ is methyl, $R^2$ is hydrogen, $R^3$ is hydrogen, and $R^4$ is a triphosphate;
(viii) in Formula Ia, Y is $NR^1R^2$, $R^1$ is methyl, $R^2$ is methyl, $R^3$ is hydrogen, $R^4$ is a stabilized phosphate prodrug;
(ix) in Formula Ia, Y is $NR^1R^2$, $R^1$ is methyl, $R^2$ is methyl, $R^3$ is hydrogen, and $R^4$ is a stabilized thiophosphate prodrug;
(x) in Formula Ia, Y is $NR^1R^2$, $R^1$ is methyl, $R^2$ is methyl, $R^3$ is hydrogen, and $R^4$ is a phosphoramidate;
(xi) in Formula Ia, Y is $NR^1R^2$, $R^1$ is methyl, $R^2$ is methyl, $R^3$ is hydrogen, and $R^4$ is a thiophosphoramidate:
(xii) in Formula Ia, Y is $NR^1R^2$, $R^1$ is methyl, $R^2$ is methyl, $R^3$ is hydrogen, and $R^4$ is a monophosphate;
(xiii) in Formula Ia, Y is $NR^1R^2$, $R^1$ is methyl, $R^2$ is methyl, $R^3$ is hydrogen, and $R^4$ is a diphosphate;
(xiv) in Formula Ia, Y is $NR^1R^2$, $R^1$ is methyl, $R^2$ is methyl, $R^3$ is hydrogen, and $R^4$ is a triphosphate;
(xv) in Formula Ia, Y is $NR^1R^2$, $R^1$ is methyl, $R^2$ is cyclopropyl, $R^3$ is hydrogen, $R^4$ is a stabilized phosphate prodrug;
(xvi) in Formula Ia, Y is $NR^1R^2$, $R^1$ is methyl, $R^2$ is cyclopropyl, $R^3$ is hydrogen, and $R^4$ is a stabilized thiophosphate prodrug;
(xvii) in Formula Ia, Y is $NR^1R^2$, $R^1$ is methyl, $R^2$ is cyclopropyl, $R^3$ is hydrogen, and $R^4$ is a phosphoramidate;
(xviii) in Formula Ia, Y is $NR^1R^2$, $R^1$ is methyl, $R^2$ is cyclopropyl, $R^3$ is hydrogen, and $R^4$ is a thiophosphoramidate:
(xix) in Formula Ia, Y is $NR^1R^2$, $R^1$ is methyl, $R^2$ is cyclopropyl, $R^3$ is hydrogen, and $R^4$ is a monophosphate;
(xx) in Formula Ia, Y is $NR^1R^2$, $R^1$ is methyl, $R^2$ is cyclopropyl, $R^3$ is methyl, and $R^4$ is a diphosphate;
(xxi) in Formula Ia, Y is $NR^1R^2$, $R^1$ is methyl, $R^2$ is cyclopropyl, $R^3$ is hydrogen, and $R^4$ is a triphosphate;
(xxii) in Formula Ia, Y is $NR^1R^2$, $R^1$ is methyl, $R^2$ is propyl, $R^3$ is hydrogen, and $R^4$ is a stabilized phosphate prodrug;
(xxiii) in Formula Ia, Y is $NR^1R^2$, $R^1$ is methyl, $R^2$ is propyl, $R^3$ is hydrogen, and $R^4$ is a stabilized thiophosphate prodrug;
(xxiv) in Formula Ia, Y is $NR^1R^2$, $R^1$ is methyl, $R^2$ is propyl, $R^3$ is hydrogen, and $R^4$ is a phosphoramidate;
(xxv) in Formula Ia, Y is $NR^1R^2$, $R^1$ is methyl, $R^2$ is propyl, $R^3$ is hydrogen, and $R^4$ is a thiophosphoramidate:
(xxvi) in Formula Ia, Y is $NR^1R^2$, $R^1$ is methyl, $R^2$ is propyl, $R^3$ is hydrogen, and $R^4$ is a monophosphate;
(xxvii) in Formula Ia, Y is $NR^1R^2$, $R^1$ is methyl, $R^2$ is propyl, $R^3$ is hydrogen, and $R^4$ is a diphosphate;
(xxviii) in Formula Ia, Y is $NR^1R^2$, Y is $NR^1R^2$, $R^1$ is methyl, $R^2$ is propyl, $R^3$ is hydrogen, and $R^4$ is a triphosphate;
(xxix) in Formula Ia, Y is $NR^1R^2$, $R^1$ is methyl, $R^2$ is ethyl, $R^3$ is hydrogen, $R^4$ is a stabilized phosphate prodrug;
(xxx) in Formula Ia, Y is $NR^1R^2$, $R^1$ is methyl, $R^2$ is ethyl, $R^3$ is hydrogen, and $R^4$ is a stabilized thiophosphate prodrug;
(xxxi) in Formula Ia, Y is $NR^1R^2$, $R^1$ is methyl, $R^2$ is ethyl, $R^3$ is hydrogen, and $R^4$ is a phosphoramidate;
(xxxii) in Formula Ia, Y is $NR^1R^2$, $R^1$ is methyl, $R^2$ is ethyl, $R^3$ is hydrogen, and $R^4$ is a thiophosphoramidate:
(xxxiii) in Formula Ia, Y is $NR^1R^2$, $R^1$ is methyl, $R^2$ is ethyl, $R^3$ is hydrogen, and $R^4$ is a monophosphate;
(xxxiv) in Formula Ia, Y is $NR^1R^2$, $R^1$ is methyl, $R^2$ is ethyl, $R^3$ is hydrogen, and $R^4$ is a diphosphate;
(xxxv) in Formula Ia, Y is $NR^1R^2$, $R^1$ is methyl, $R^2$ is ethyl, $R^3$ is hydrogen, and $R^4$ is a triphosphate;
(xxxvi) in Formula Ib, Y is $NR^1R^2$, $R^1$ is methyl, $R^2$ is methyl, $R^3$ is hydrogen, $R^4$ is a stabilized phosphate prodrug;
(xxxvii) in Formula Ib, Y is $NR^1R^2$, $R^1$ is methyl, $R^2$ is methyl, $R^3$ is hydrogen, and $R^4$ is a stabilized thiophosphate prodrug;
(xxxviii) in Formula Ib, Y is $NR^1R^2$, $R^1$ is methyl, $R^2$ is methyl, $R^3$ is hydrogen, and $R^4$ is a phosphoramidate;
(xxxix) in Formula Ib, Y is $NR^1R^2$, $R^1$ is methyl, $R^2$ is methyl, $R^3$ is hydrogen, and $R^4$ is a thiophosphoramidate;
(xl) in Formula Ib, Y is $NR^1R^2$, $R^1$ is methyl, $R^2$ is methyl, $R^3$ is hydrogen, and $R^4$ is a monophosphate;
(xli) in Formula Ib, Y is $NR^1R^2$, $R^1$ is methyl, $R^2$ is methyl, $R^3$ is hydrogen, and $R^4$ is a diphosphate;
(xlii) in Formula Ib, Y is $NR^1R^2$, $R^1$ is methyl, $R^2$ is methyl, $R^3$ is hydrogen, and $R^4$ is a triphosphate;
(xliii) in Formula Ib, Y is $NR^1R^2$, $R^1$ is methyl, $R^2$ is hydrogen, $R^3$ is hydrogen, $R^4$ is a stabilized phosphate prodrug;
(xliv) in Formula Ib, Y is $NR^1R^2$, $R^1$ is methyl, $R^2$ is hydrogen, $R^3$ is hydrogen, and $R^4$ is a stabilized thiophosphate prodrug;
(xlv) in Formula Ib, Y is $NR^1R^2$, $R^1$ is methyl, $R^2$ is hydrogen, $R^3$ is hydrogen, and $R^4$ is a phosphoramidate;
(xlvi) in Formula Ib, Y is $NR^1R^2$, $R^1$ is methyl, $R^2$ is hydrogen, $R^3$ is hydrogen, and $R^4$ is a thiophosphoramidate:
(xlvii) in Formula Ib, Y is $NR^1R^2$, $R^1$ is methyl, $R^2$ is hydrogen, $R^3$ is hydrogen, and $R^4$ is a monophosphate;
(xlviii) in Formula Ib, Y is $NR^1R^2$, $R^1$ is methyl, $R^2$ is hydrogen, $R^3$ is hydrogen, and $R^4$ is a diphosphate;
(xlix) in Formula Ib, Y is $NR^1R^2$, $R^1$ is methyl, $R^2$ is hydrogen, $R^3$ is hydrogen, and $R^4$ is a triphosphate;

(1) in Formula Ib, Y is NR$^1$R$^2$, R$^1$ is methyl, R$^2$ is cyclopropyl, R$^3$ is hydrogen, R$^4$ is a stabilized phosphate prodrug;
(li) in Formula Ib, Y is NR$^1$R$^2$, R$^1$ is methyl, R$^2$ is cyclopropyl, R$^3$ is hydrogen, and R$^4$ is a stabilized thiophosphate prodrug;
(lii) in Formula Ib, Y is NR$^1$R$^2$, R$^1$ is methyl, R$^2$ is cyclopropyl, R$^3$ is hydrogen, and R$^4$ is a phosphoramidate;
(liii) in Formula Ib, Y is NR$^1$R$^2$, R$^1$ is methyl, R$^2$ is cyclopropyl, R$^3$ is hydrogen, and R$^4$ is a thiophosphoramidate:
(liv) in Formula Ib, Y is NR$^1$R$^2$, R$^1$ is methyl, R$^2$ is cyclopropyl, R$^3$ is hydrogen, and R$^4$ is a monophosphate;
(lv) in Formula Ib, Y is NR$^1$R$^2$, R$^1$ is methyl, R$^2$ is cyclopropyl, R$^3$ is methyl, and R$^4$ is a diphosphate;
(lvi) in Formula Ia, Y is NR$^1$R$^2$, R$^1$ is methyl, R$^2$ is cyclopropyl, R$^3$ is hydrogen, and R$^4$ is a triphosphate.

In alternative embodiments of any of the above, the compound has an R$^{22}$ substituent. In some of these specific embodiments, the R$^{22}$ is F, amide or carbamate. In other specific aspects of the embodiments above, R$^{22}$ is chloro, bromo, cyano, azido, ethyl, n-propyl, iso-propyl, n-butyl, iso-butyl, sec-butyl, tert-butyl and n-pentyl, 1,1-dimethylpropyl, 2,2-dimethylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —(CH$_2$)-cyclopropyl, —(CH$_2$)-cyclobutyl, —(CH$_2$)-cyclopentyl, —(CH$_2$)-cyclohexyl, aziridine, oxirane, thiirane, azetidine, oxetane, thietane, pyrrolidine, tetrahydrofuran, thiolane, pyrazolidine, piperidine, oxane, thiane, —(CH$_2$)-aziridine, —(CH$_2$)-oxirane, —(CH$_2$)-thiirane, —(CH$_2$)-azetidine, —(CH$_2$)-oxetane, —(CH$_2$)-thietane, —(CH$_2$)-pyrrolidine, —(CH$_2$)-tetrahydrofuran, —(CH$_2$)-thiolane, —(CH$_2$)-pyrazolidine, —(CH$_2$)-piperidine, —(CH$_2$)-oxane, —(CH$_2$)-thiane, phenyl, pyridyl, —ONHC(=O)OCH$_3$, —ONHC(=O)OCH$_2$CH$_3$, —NHOH, NHOCH$_3$, —OCH$_3$, OC$_2$H$_5$, —OPh, OCH$_2$Ph, —SCH$_3$, —SC$_2$H$_5$, —SPh, SCH$_2$Ph, —NH(CH$_2$)$_2$NH$_2$, —NH(CH$_2$)$_2$N(CH$_3$)$_2$, —NHNH$_2$, —NHNHCH$_3$, —N=NH, —N=NCH$_3$, —N=NCH$_2$CH$_3$, —NHC(O)NHNH$_2$, —NHC(S)NHNH$_2$, —C(O)NHNH$_2$, —NHSO$_2$CH$_3$, —NHSO$_2$CH$_2$CH$_3$, —SO$_2$NHCH$_3$, —SO$_2$N(CH$_3$)$_2$, —C(O)NH$_2$, —C(O)NHCH$_3$, —C(O)N(CH$_3$)$_2$, —CO$_2$CH$_3$, —CO$_2$CH$_2$CH$_3$, —CO$_2$Ph, CO$_2$CH$_2$Ph, —SO$_2$CH$_3$, —SO$_2$CH$_2$CH$_3$, —SO$_2$Ph, —SO$_2$CH$_2$Ph,

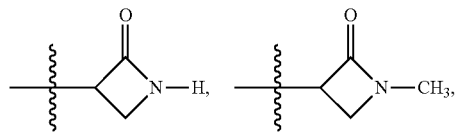

—P(O)H(OH), —P(O)H(OCH$_3$), —P(O)(OH)(OH), —P(O)(OH)(OCH$_3$), —P(O)(OCH$_3$)OCH$_3$), —P(O)(OH)(H$_2$), —P(O)OH)(NHCH$_3$), —P(O)(OH)N(CH$_3$)$_2$, —NHC(O)CH$_3$, —NHC(O)CH$_2$CH$_3$, —NHC(O)CH(CH$_3$)$_2$, —NHC(O)OCH$_3$, —NHC(O)OCH$_2$CH$_3$, —NHC(O)OCH(CH$_3$)$_2$, —NHC(O)OCH$_2$CH$_2$CH$_3$, —NHC(O)OCH$_2$CH$_2$CH$_2$CH$_3$ or —NHC(O)OCH$_2$CH$_2$CH$_2$CH$_2$CH$_3$;

In alternative embodiments of compounds (i) through (lvi), an L-nucleoside is used in Formula I-VI.

In an alternate embodiment, the Formula I R$^{12}$ variable is CH$_2$F.

In an alternate embodiment, the Formula I R$^{12}$ variable is CHF$_2$.

In an alternate embodiment, the Formula I R$^{12}$ variable is CF$_3$.

In one embodiment, the use of an effective amount of a compound of Formula I or a pharmaceutically acceptable salt thereof, for the treatment of an infection of an RNA virus in a host, including a human in need thereof is provided. Non-limiting examples of compounds of Formula I include:

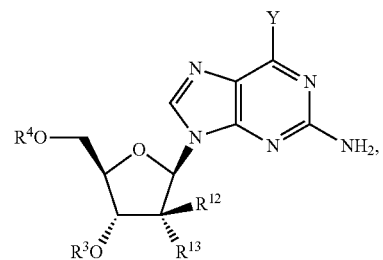

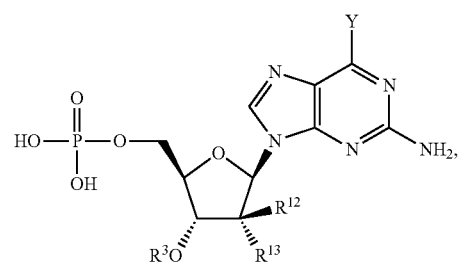

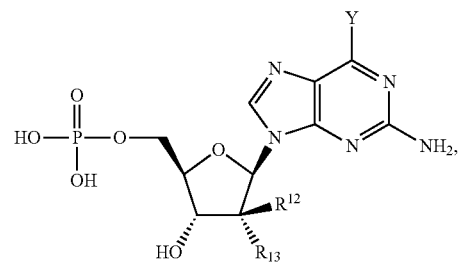

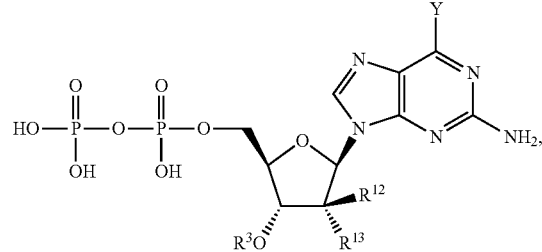

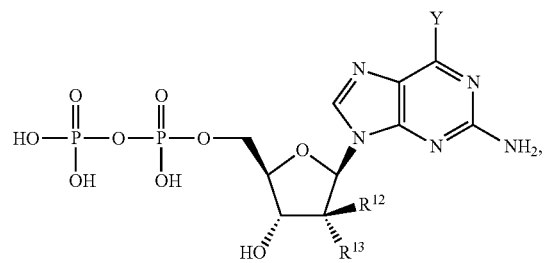

67
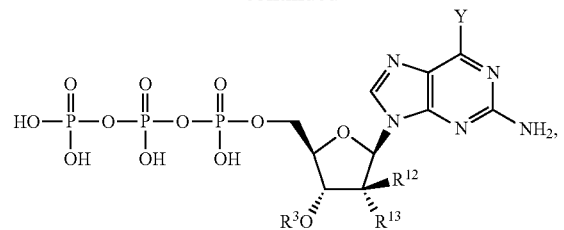
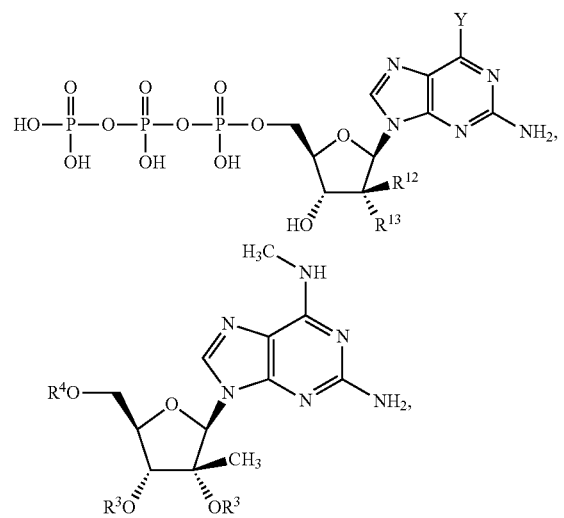
68
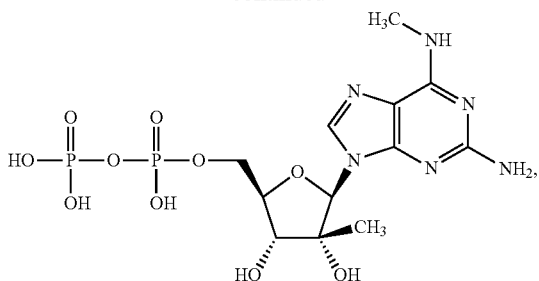

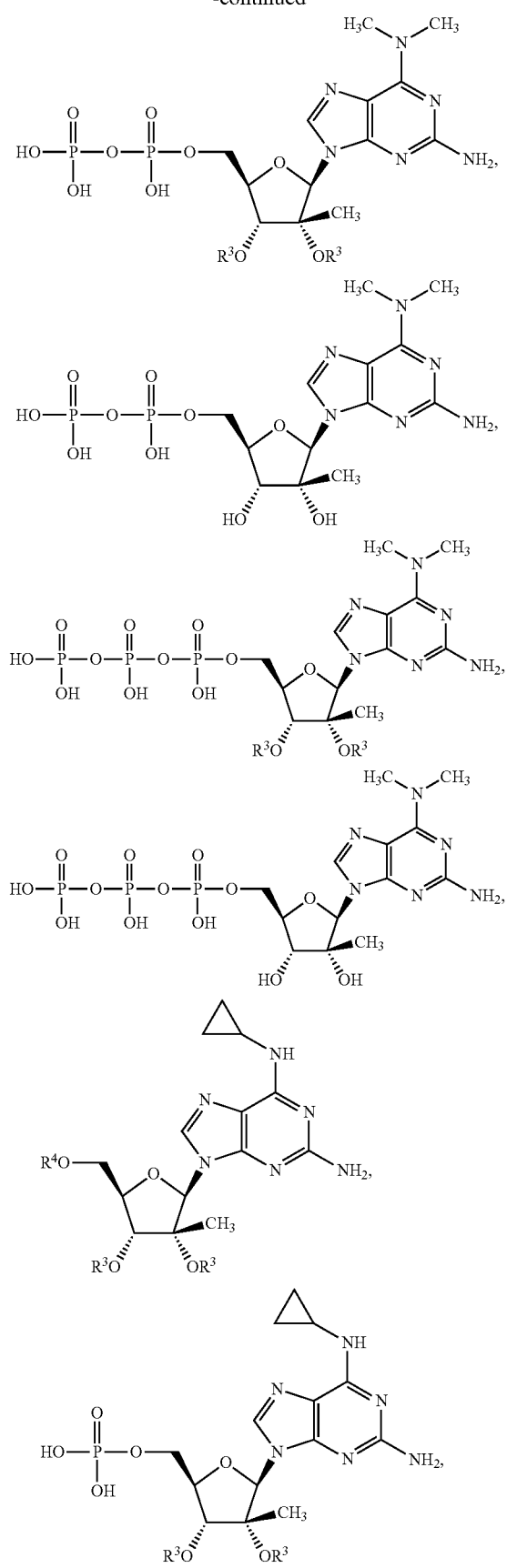
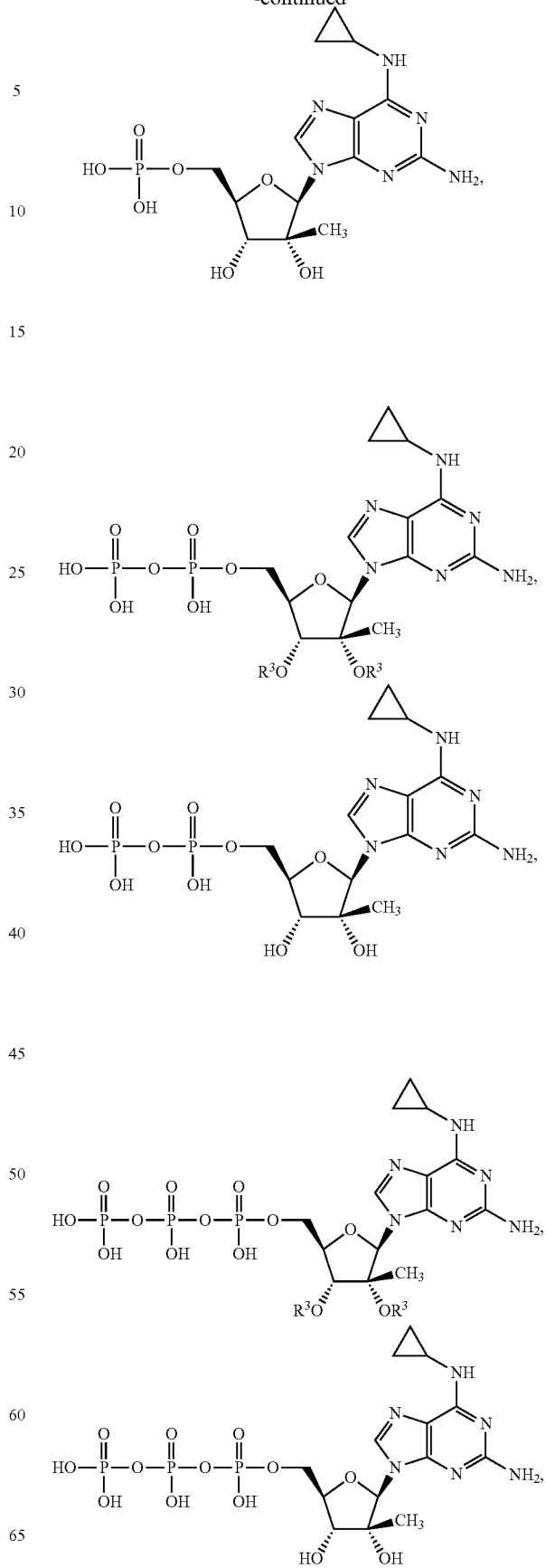

71
-continued
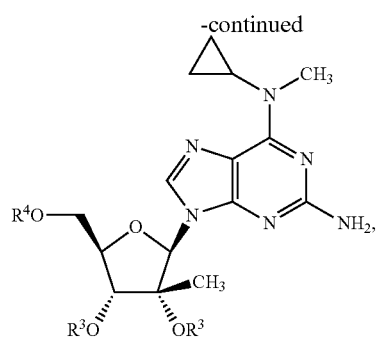
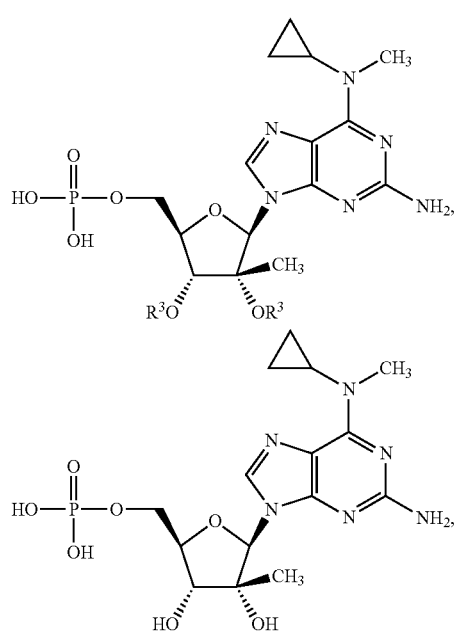
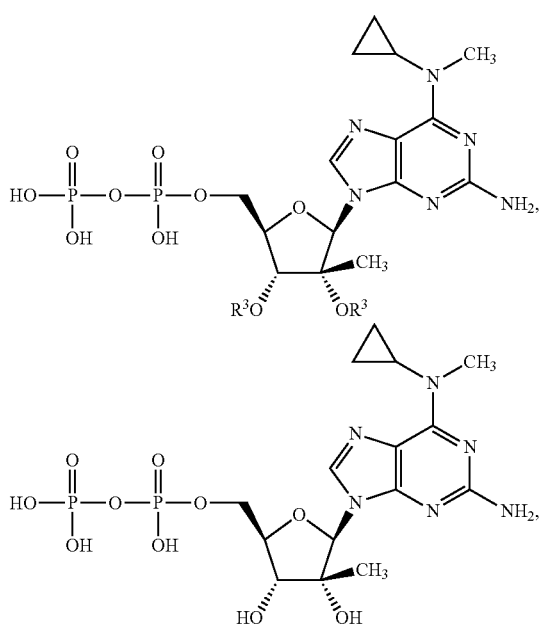
72
-continued
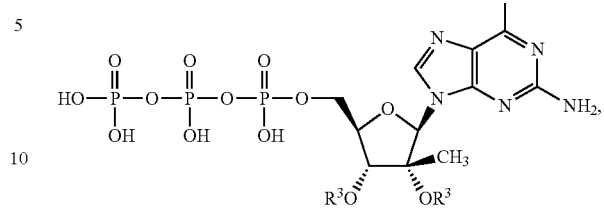

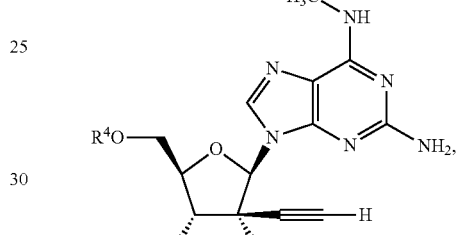
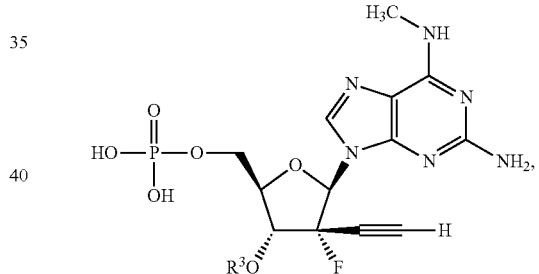
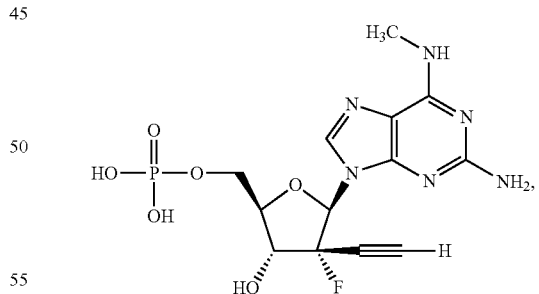
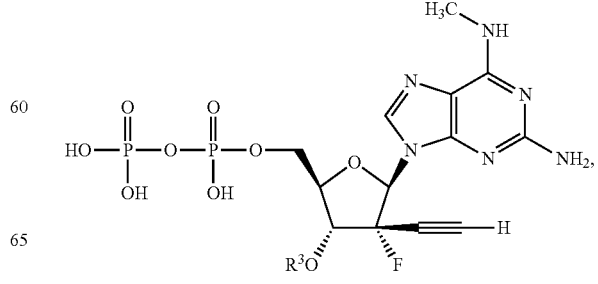

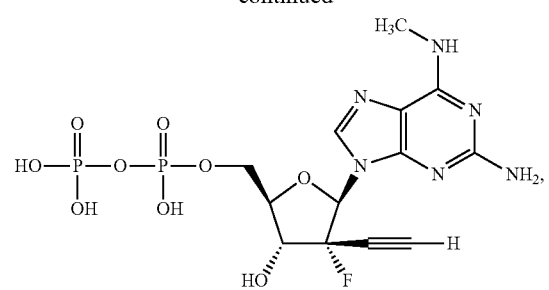
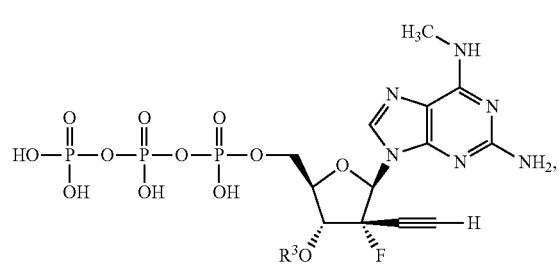
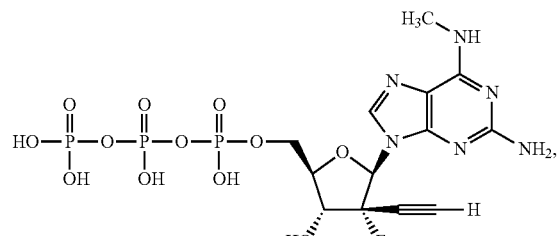
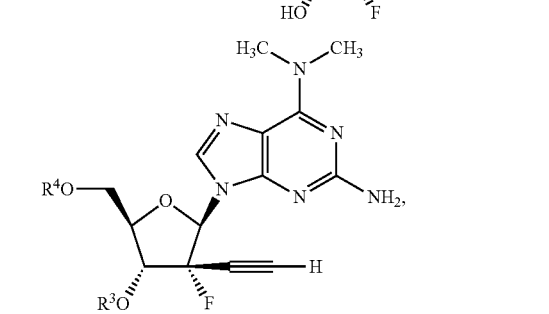
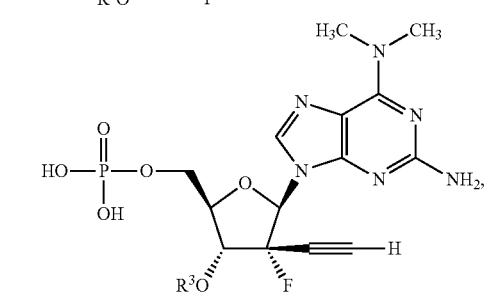
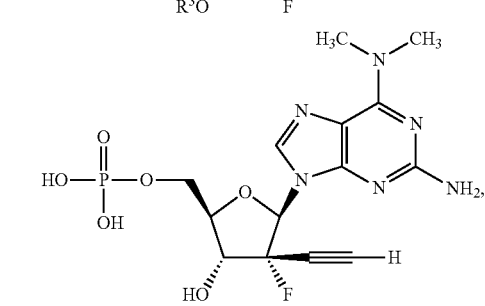
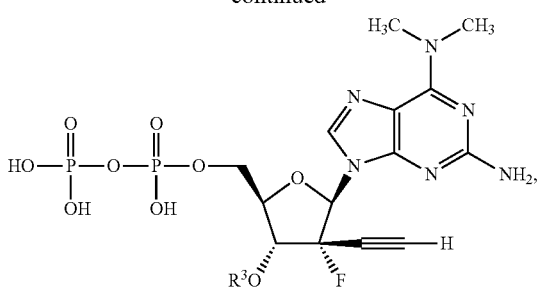
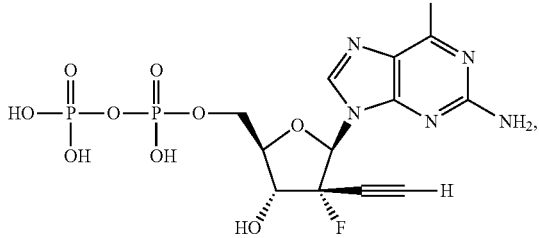
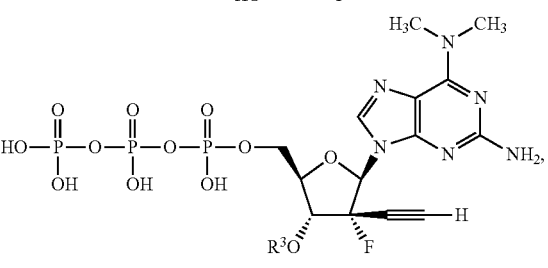
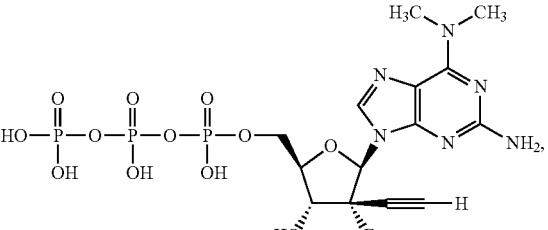
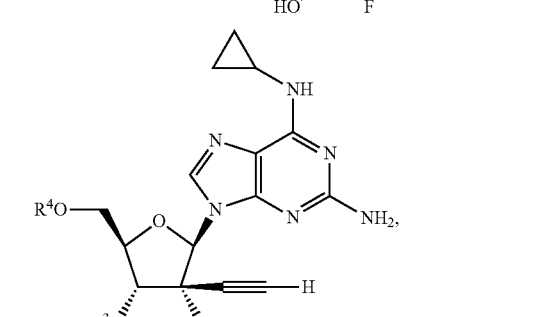
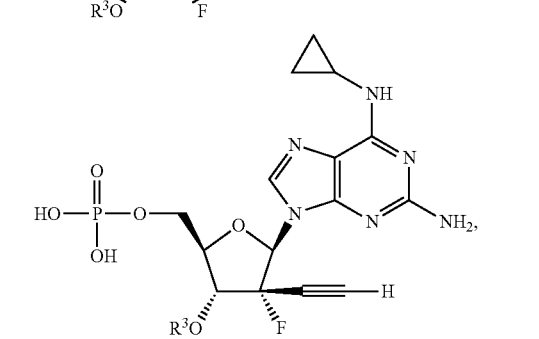

75
-continued
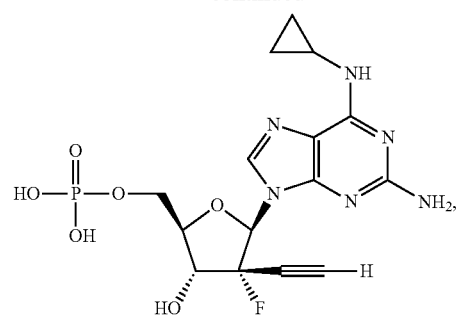
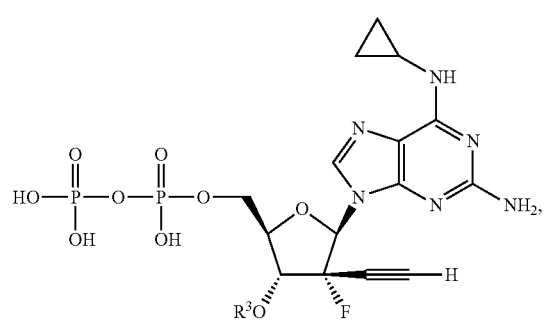
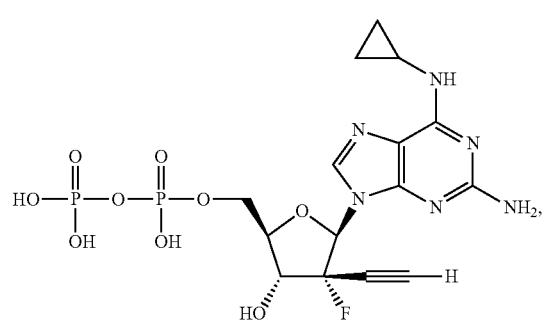
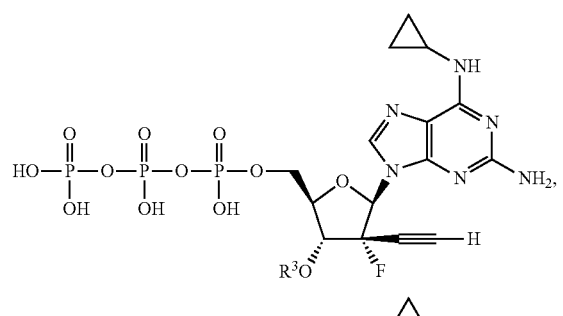
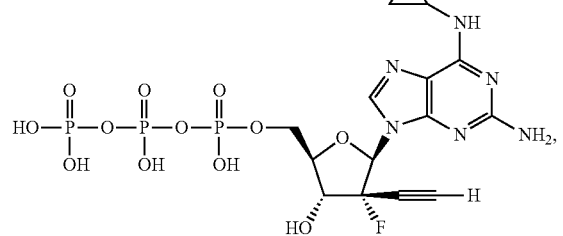
76
-continued
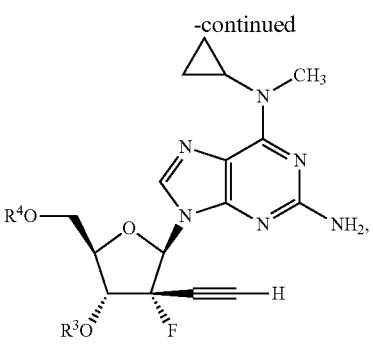
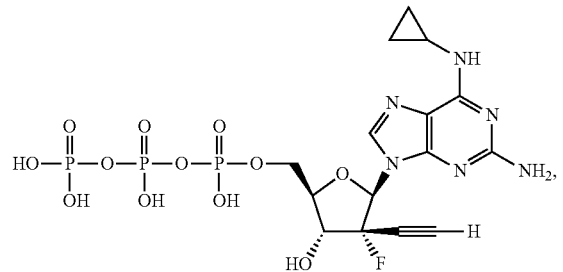
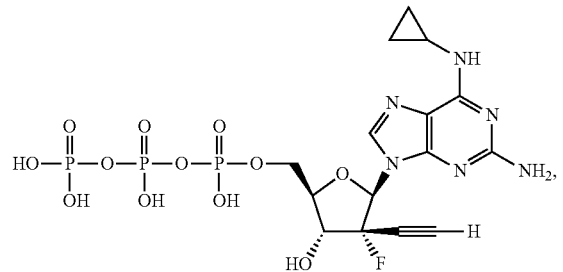
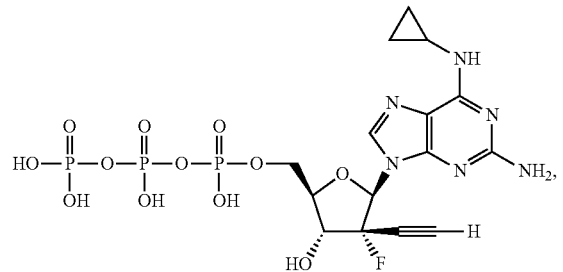
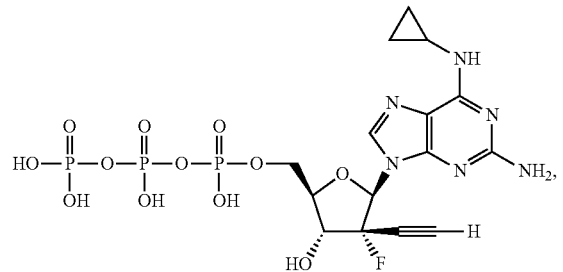

77
-continued
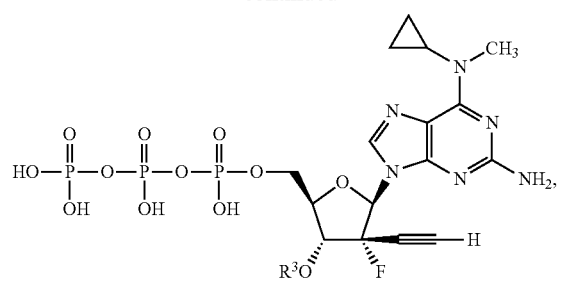
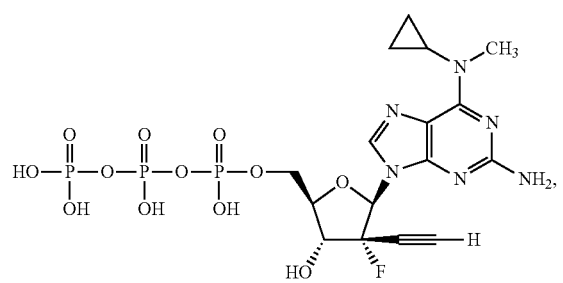
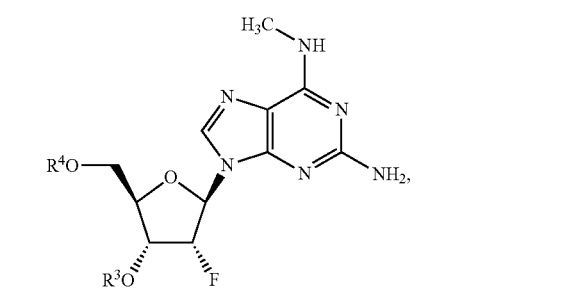
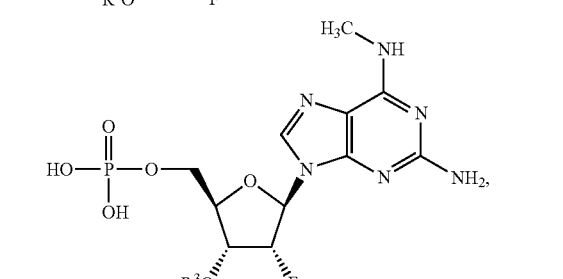
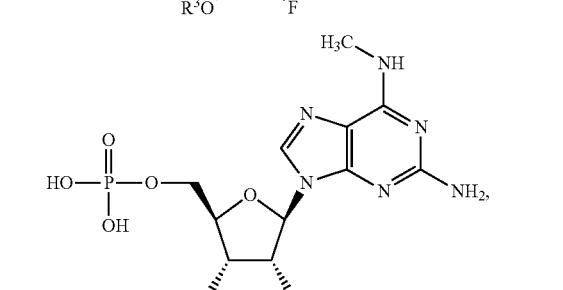
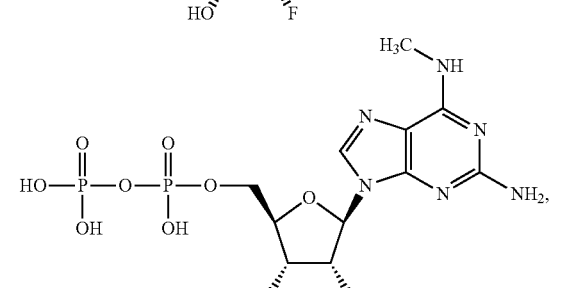
78
-continued
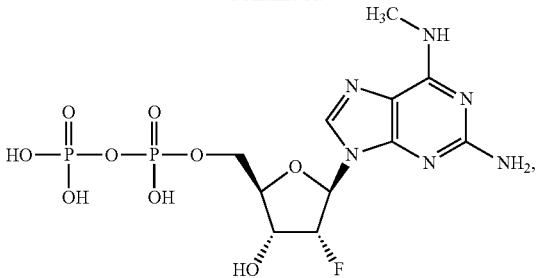
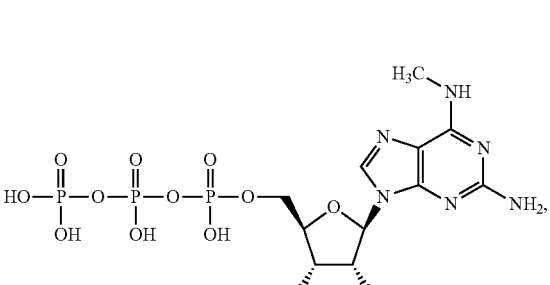
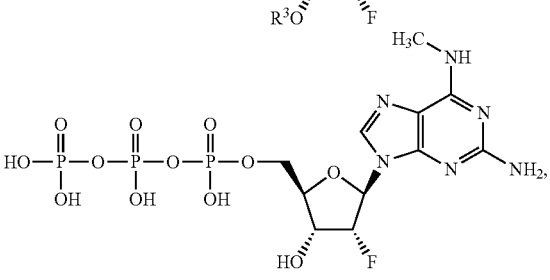
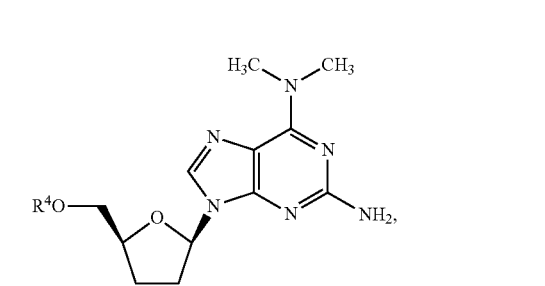
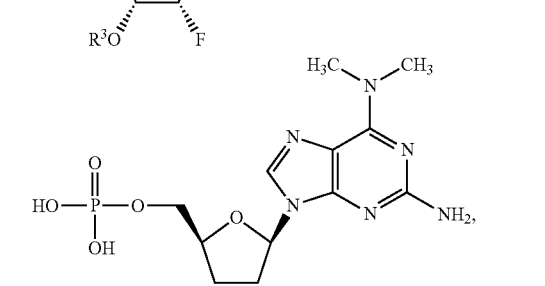
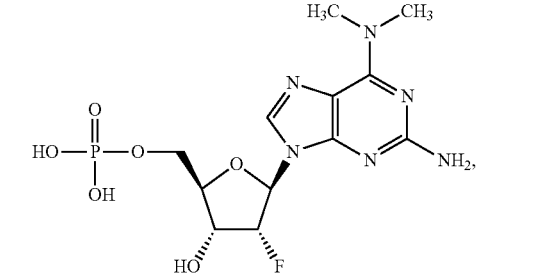

79
-continued
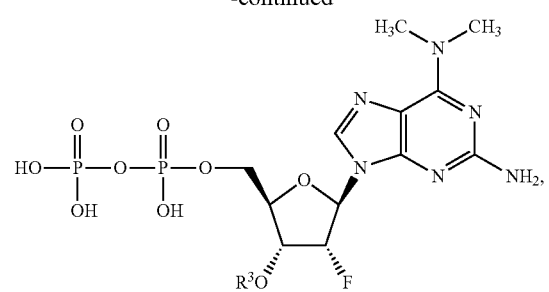
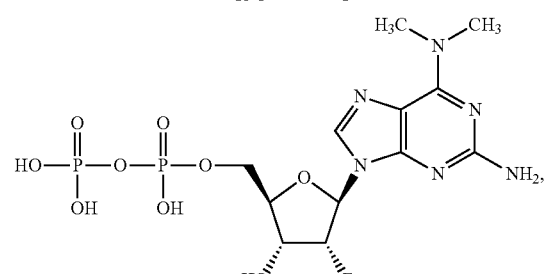
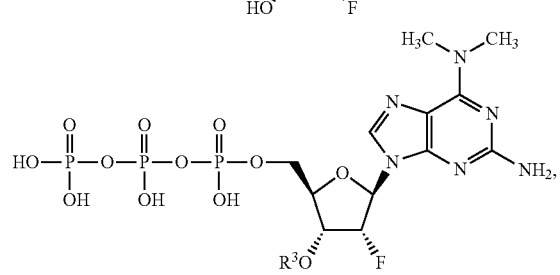
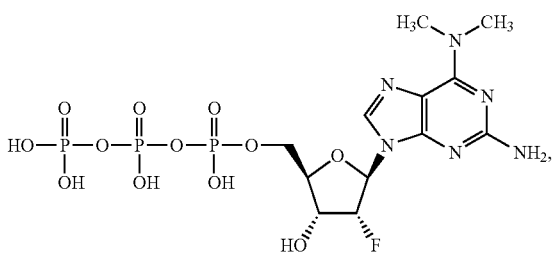
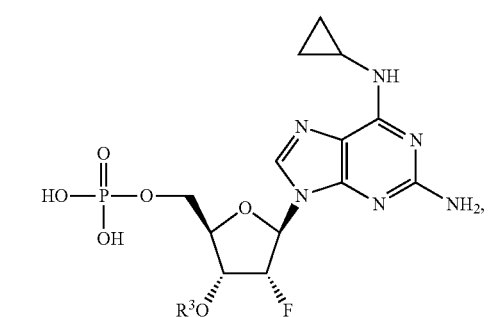
80
-continued
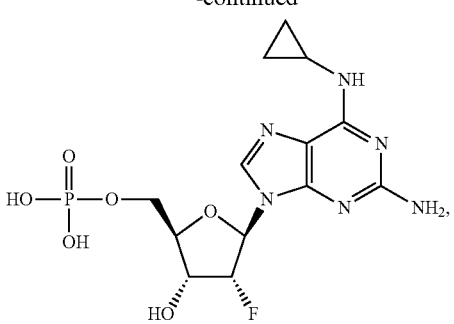
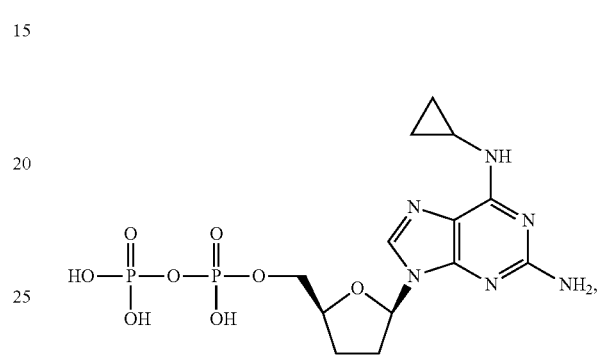
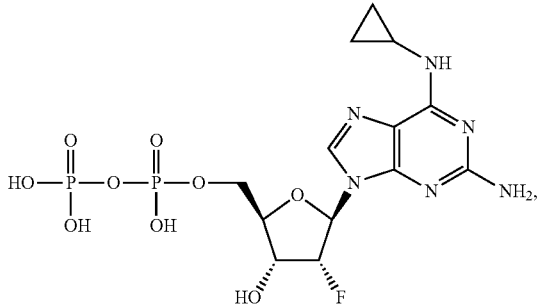
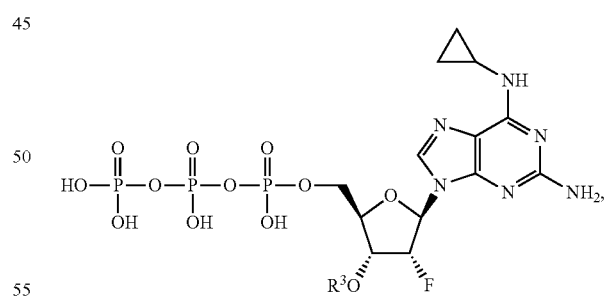
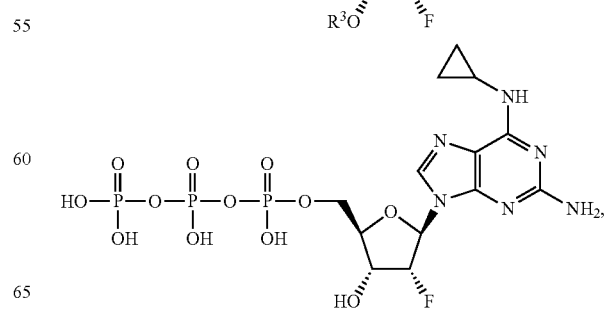

81
-continued
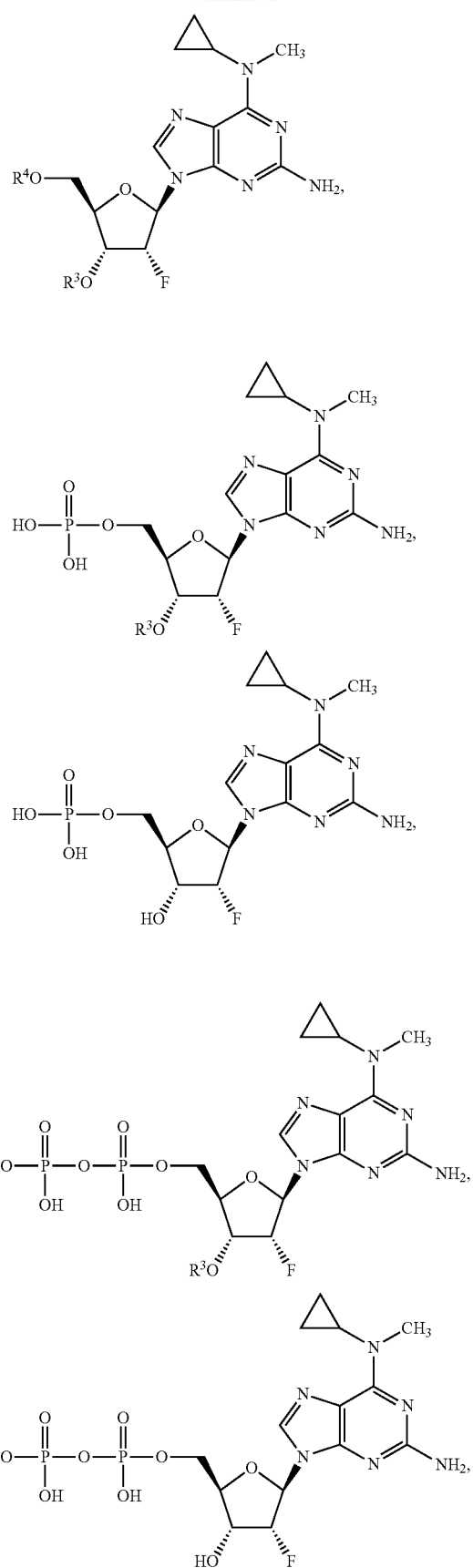
82
-continued
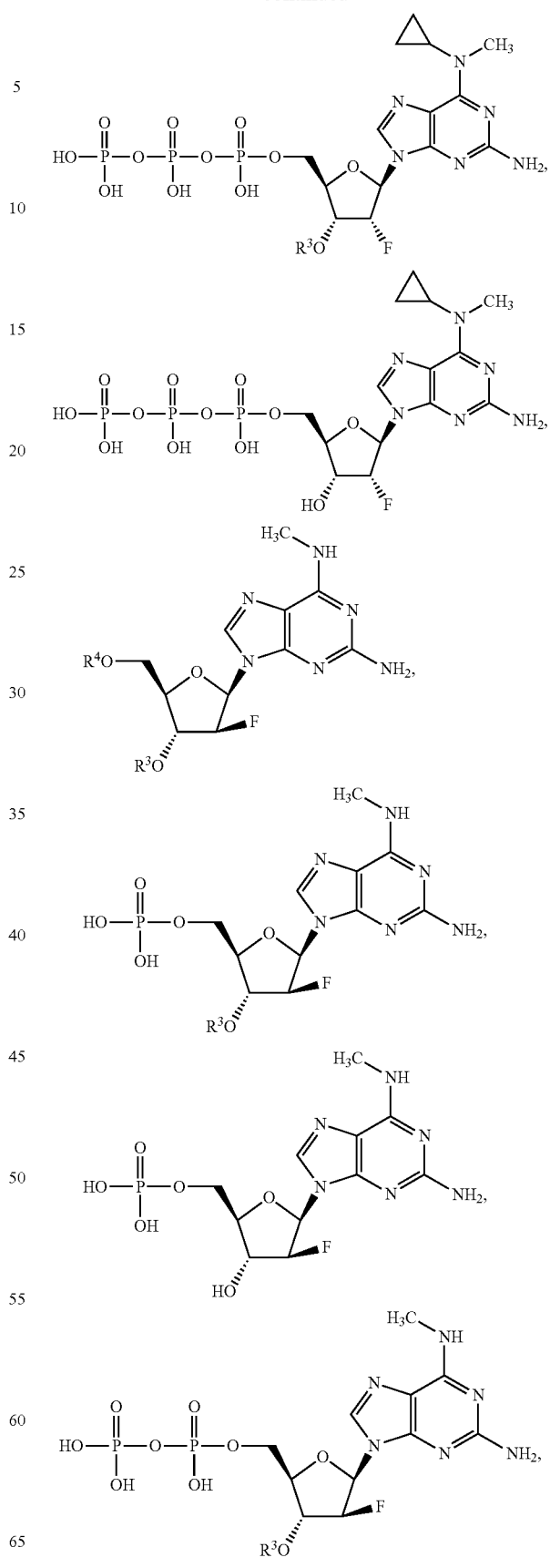

-continued
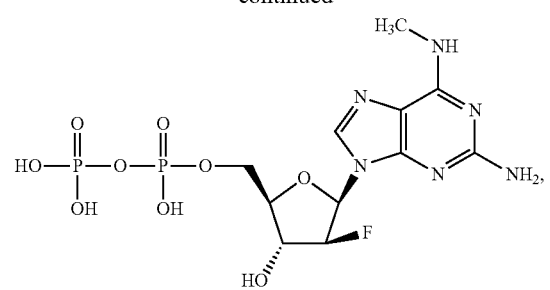
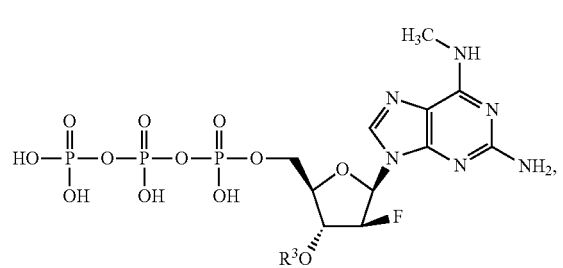
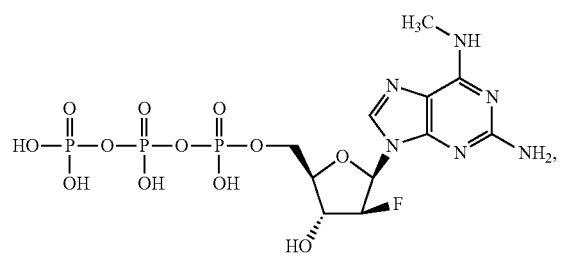
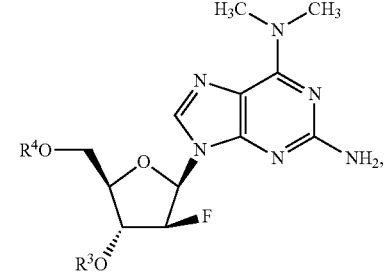
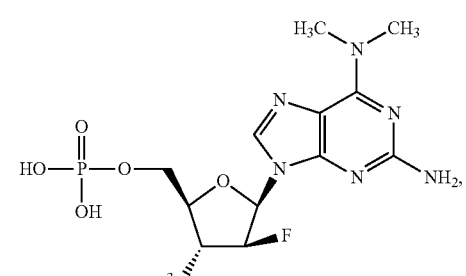
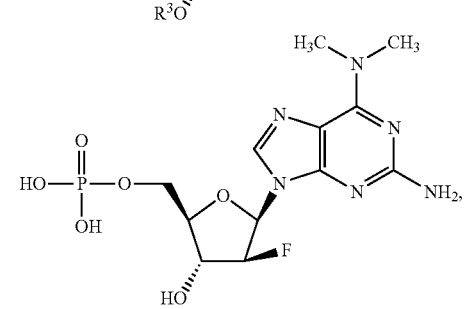
-continued
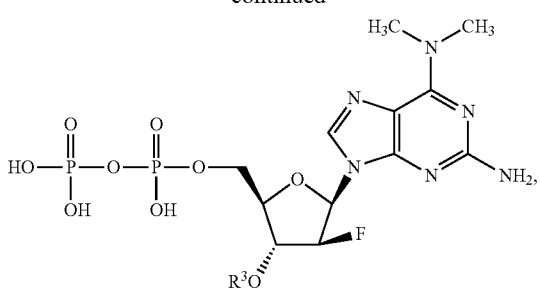
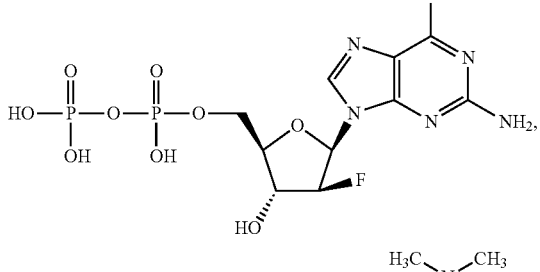
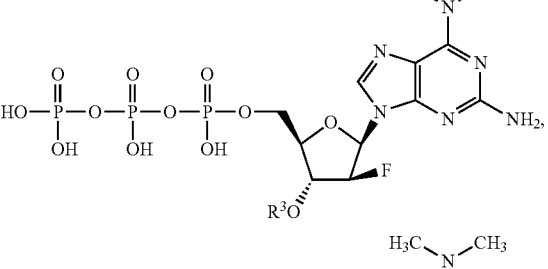
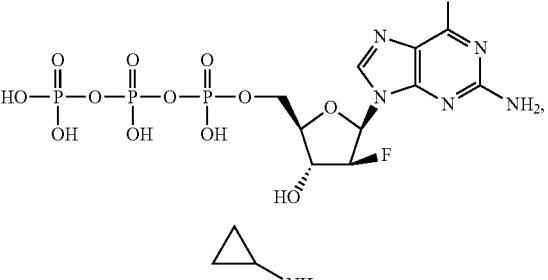
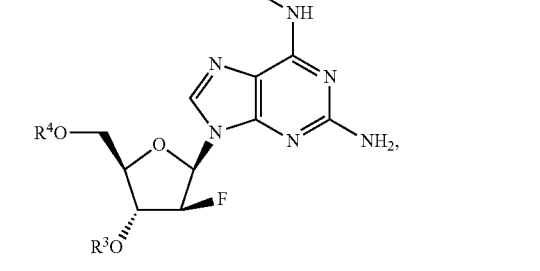
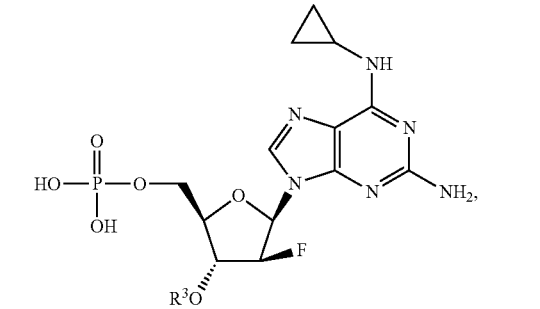

85
-continued
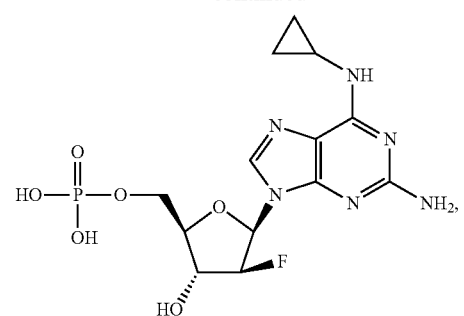
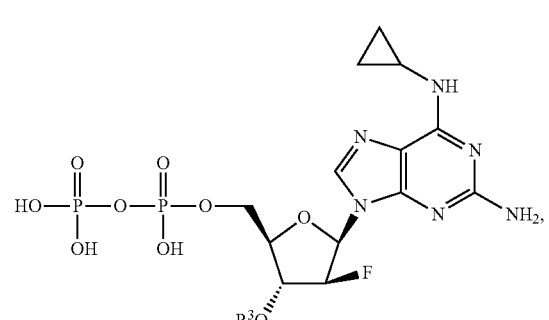
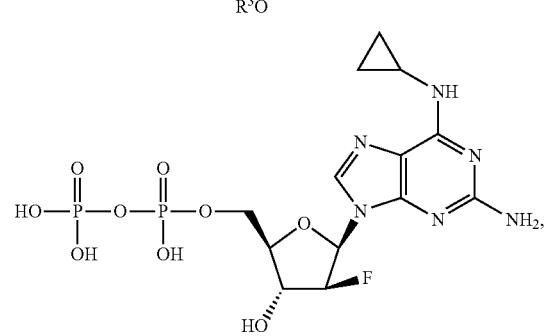
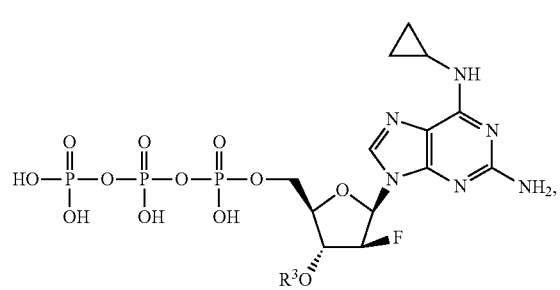
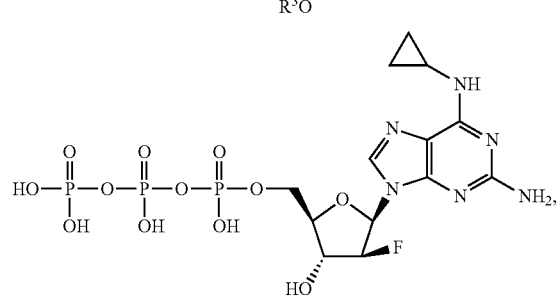
86
-continued
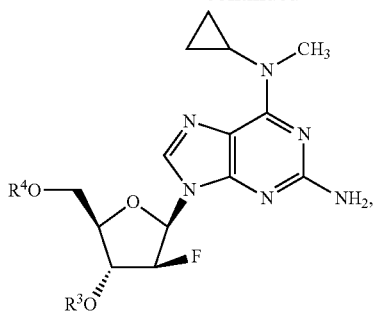
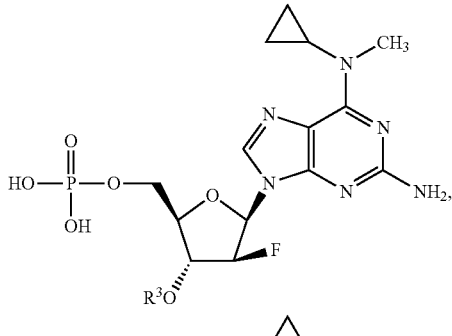
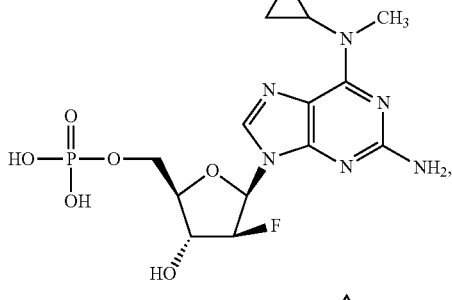
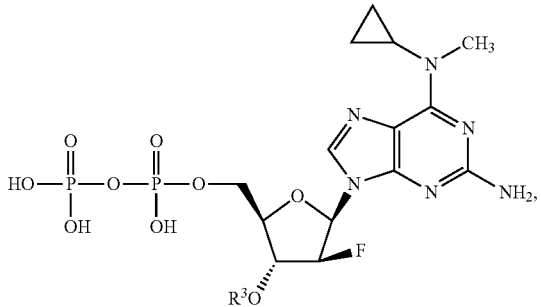
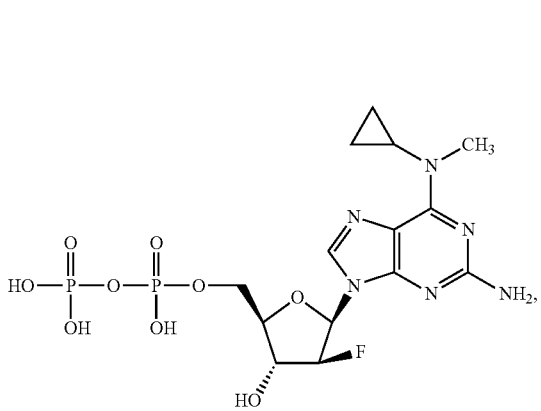

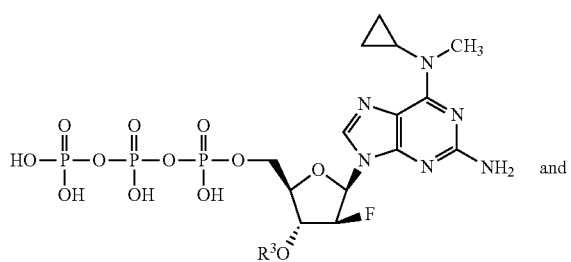
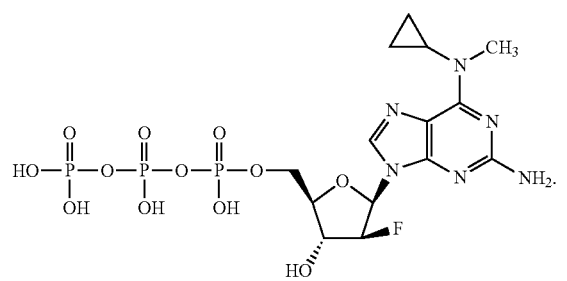
In an alternative embodiment, the use of an effective amount of a compound of Formula I or a pharmaceutically acceptable salt thereof, for the treatment of an infection of an RNA virus in a host, including a human in need thereof is provided. Additional non-limiting examples of compounds of Formula I include:
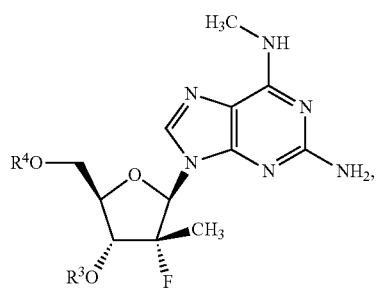
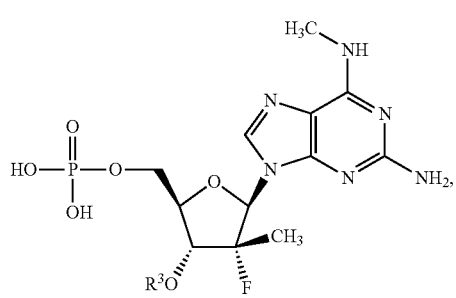
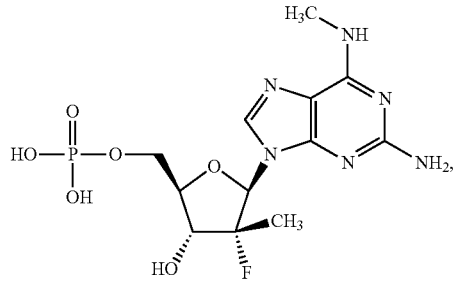
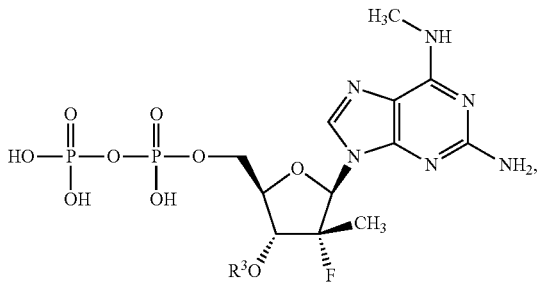
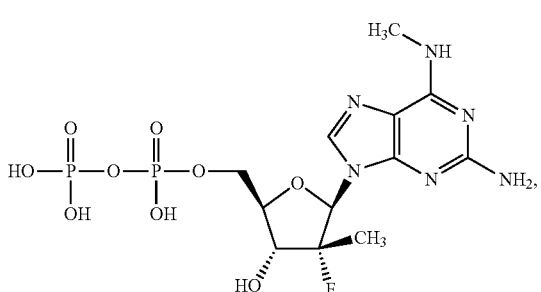
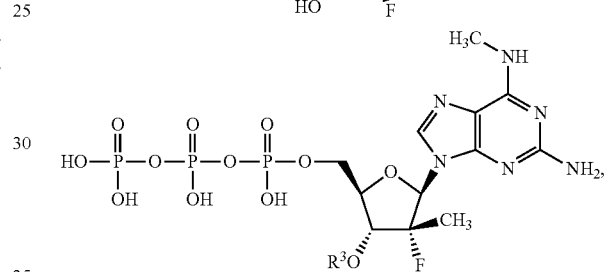
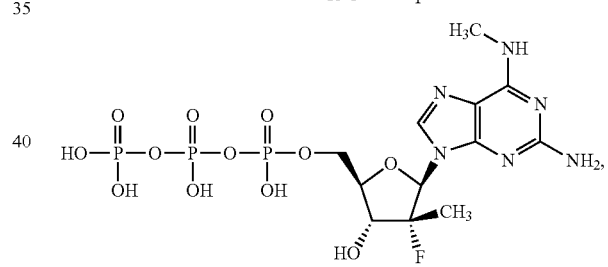
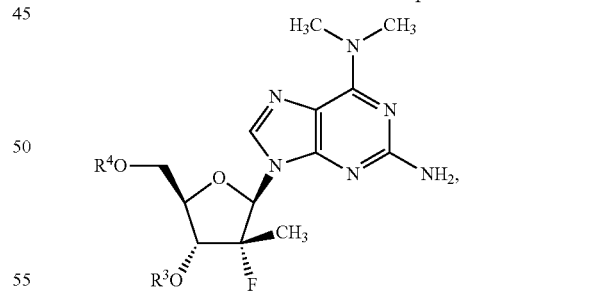
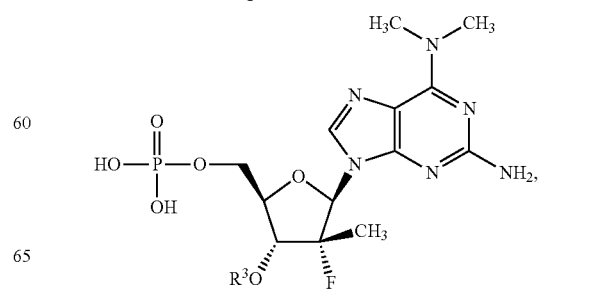

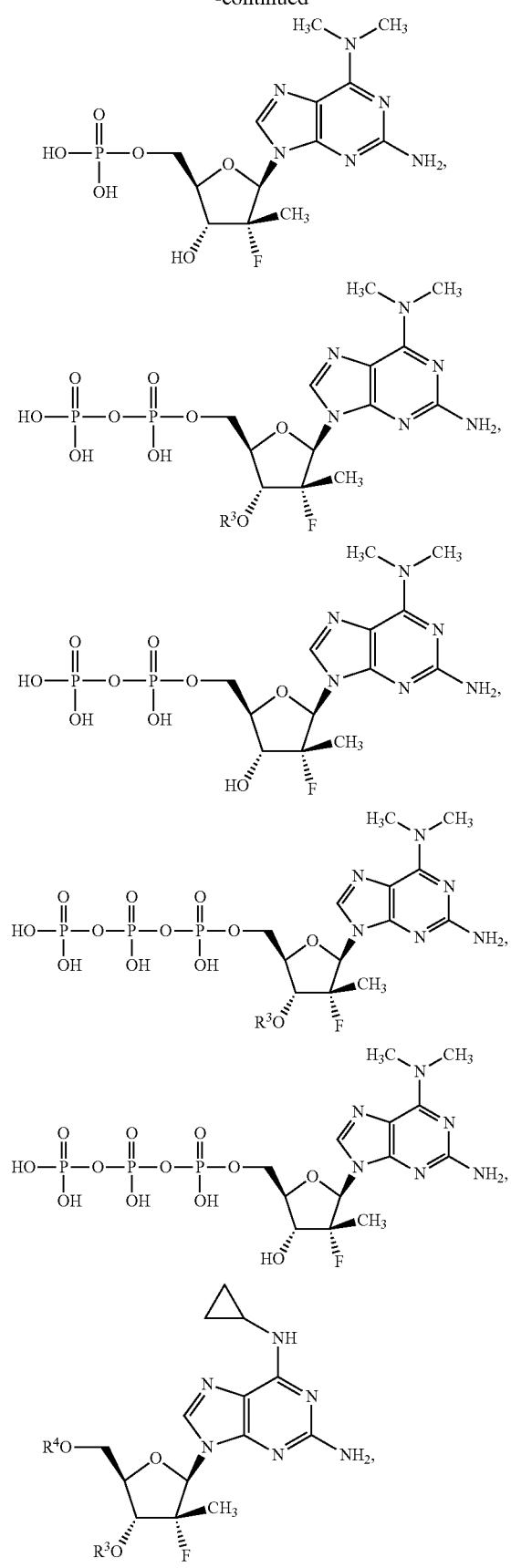
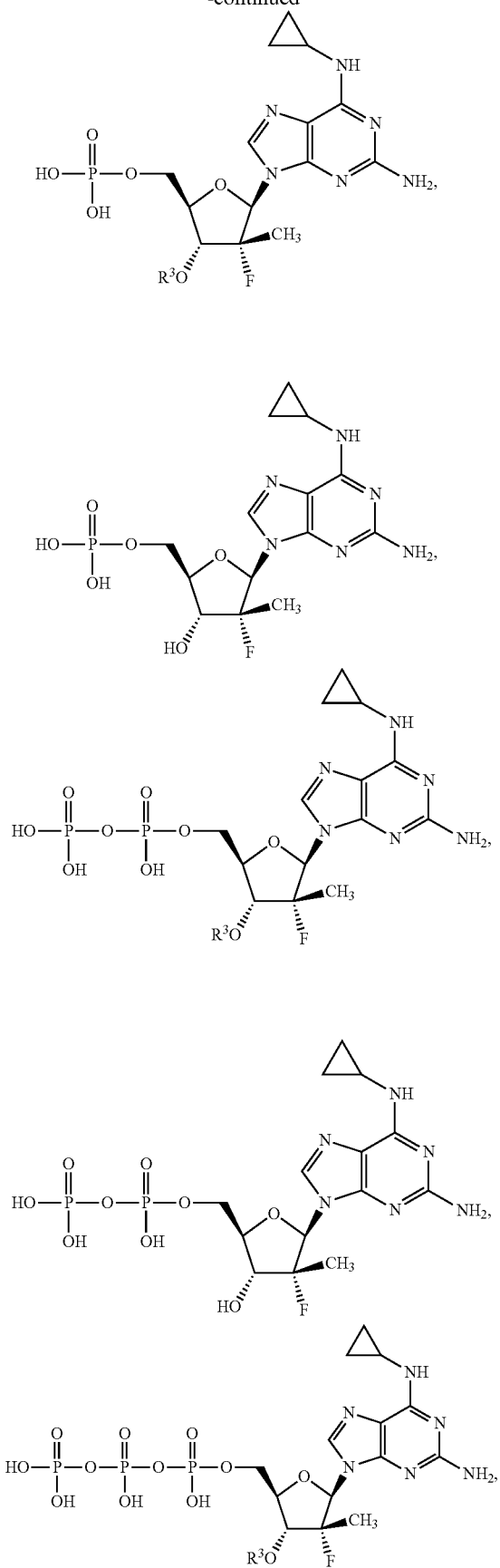

91
-continued
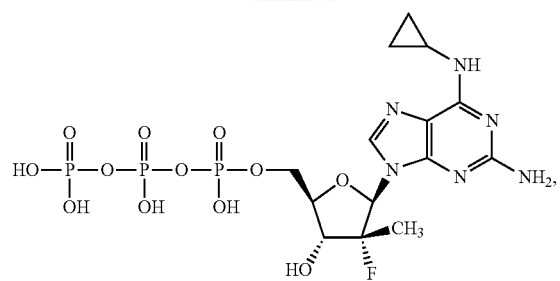
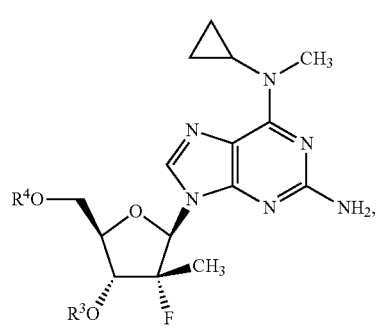
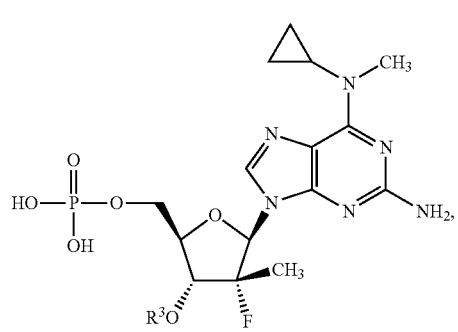
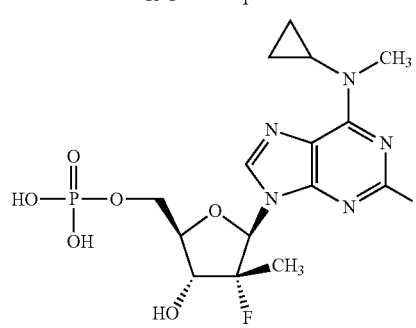
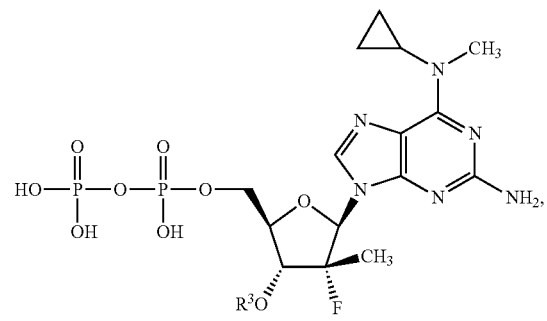
92
-continued
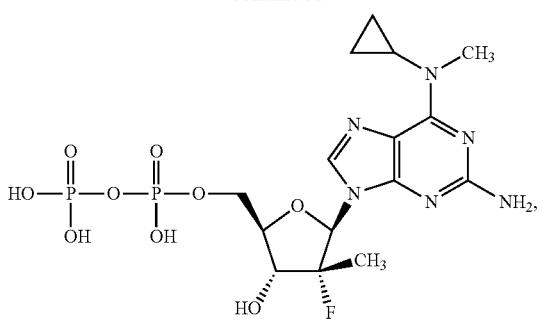
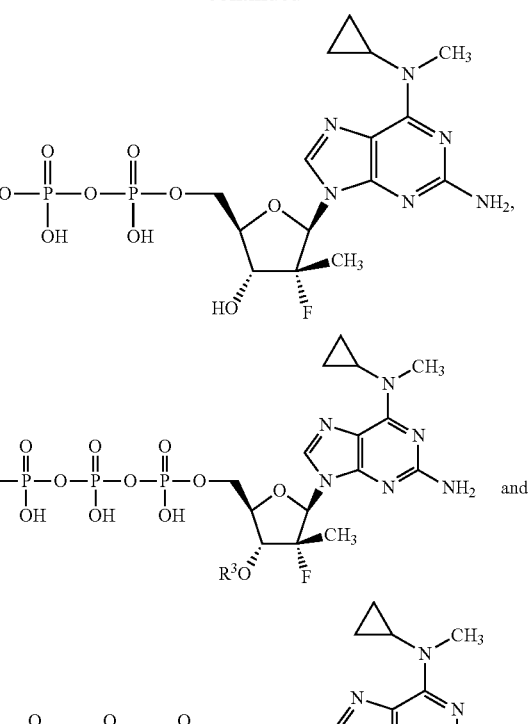
In one embodiment, the use of an effective amount of a compound of Formula III or a pharmaceutically acceptable salt thereof, for the treatment of an infection of an RNA virus in a host, including a human in need thereof is provided. Non-limiting examples of Formula III include but are not limited to:
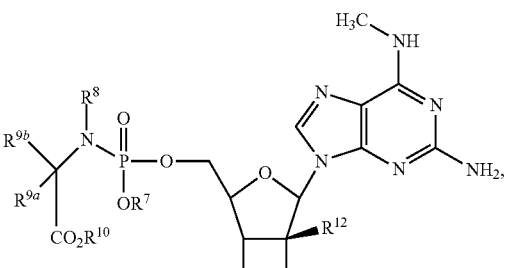
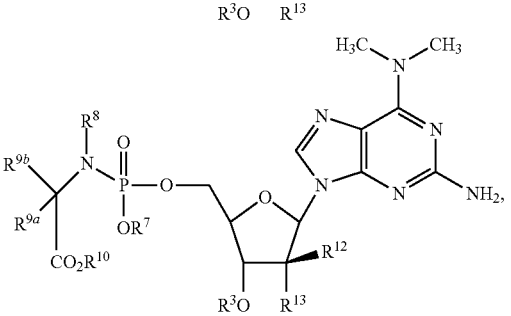

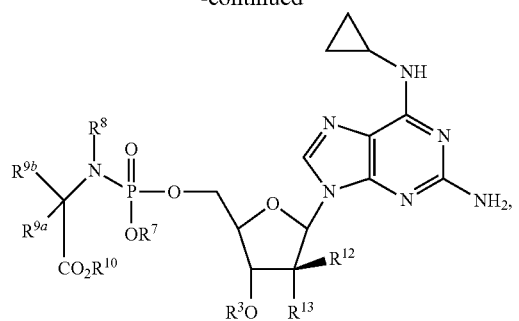
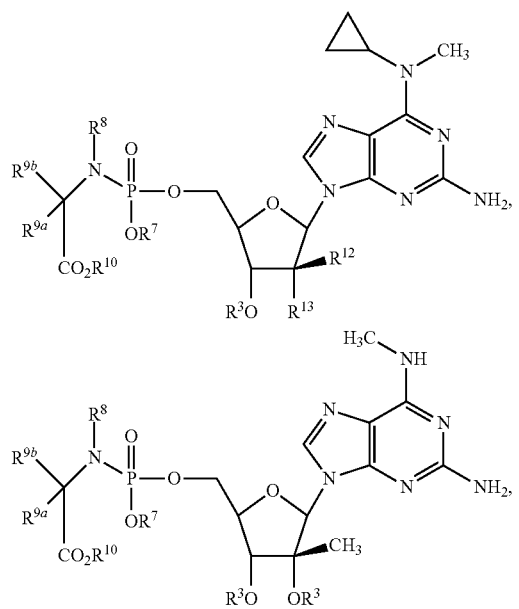
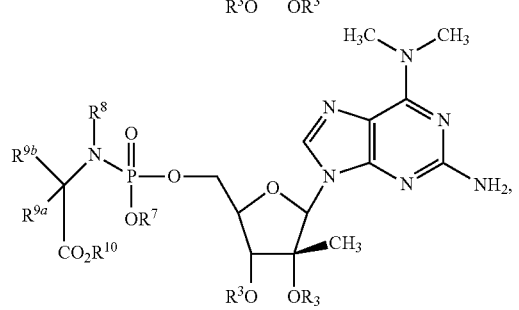
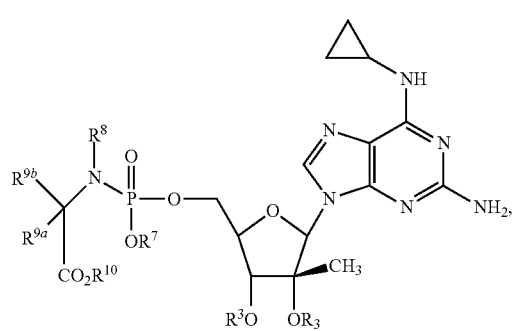
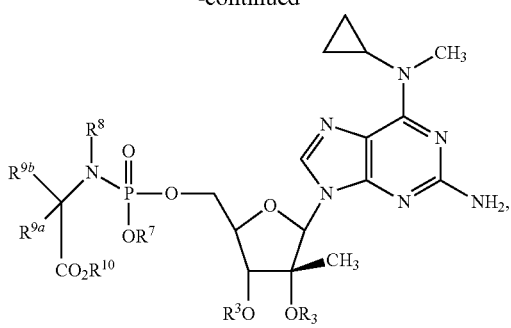
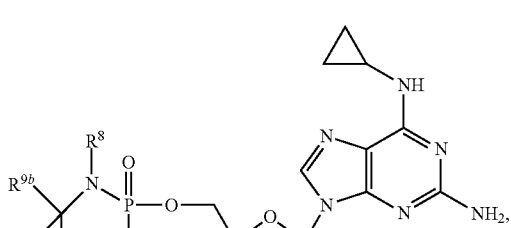
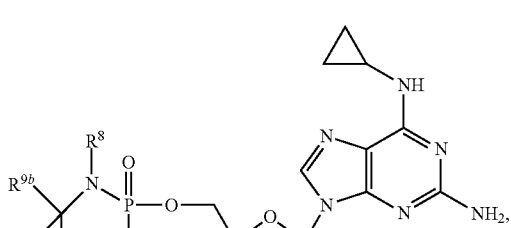
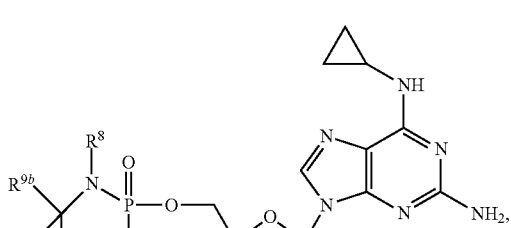

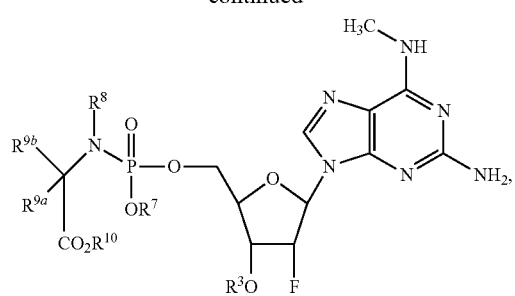
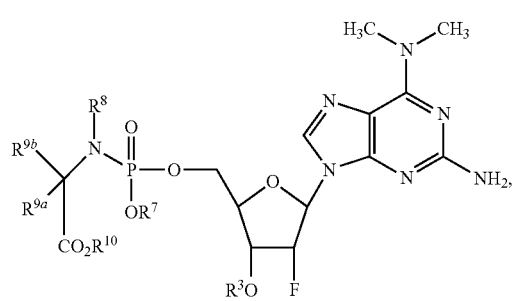
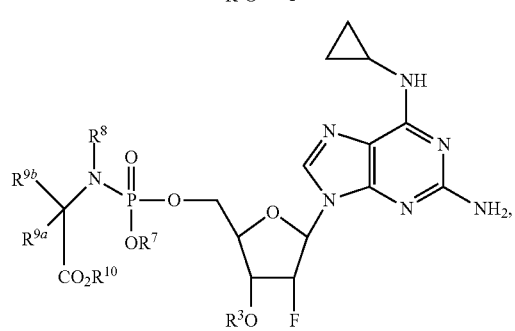
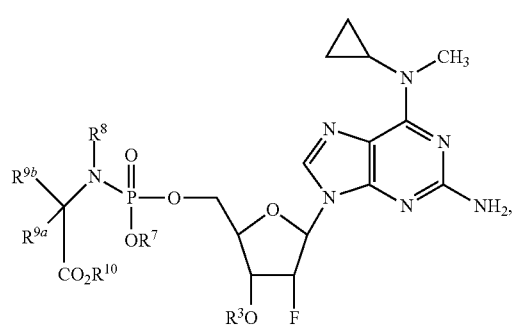
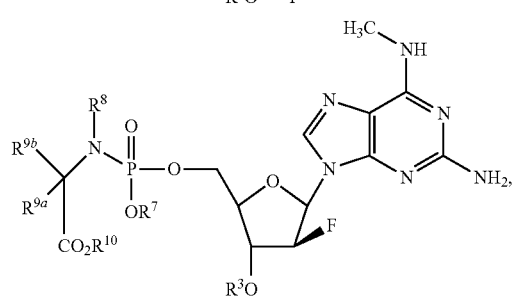
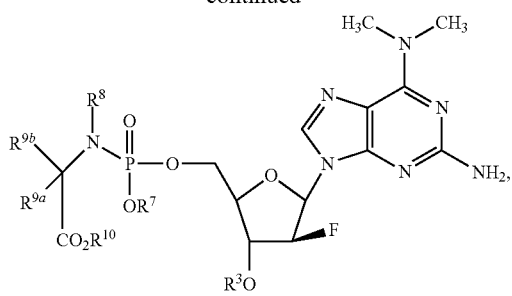
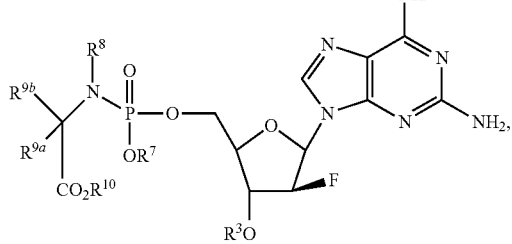
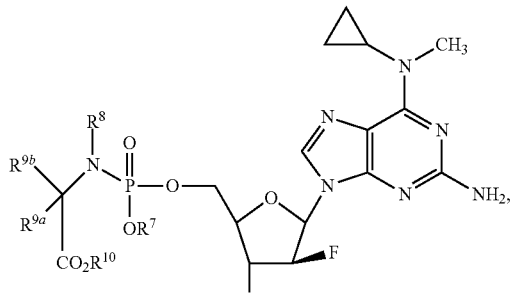
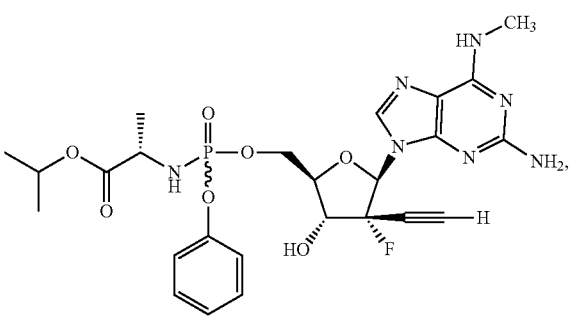
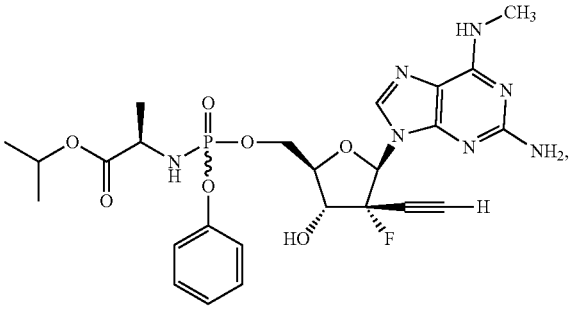

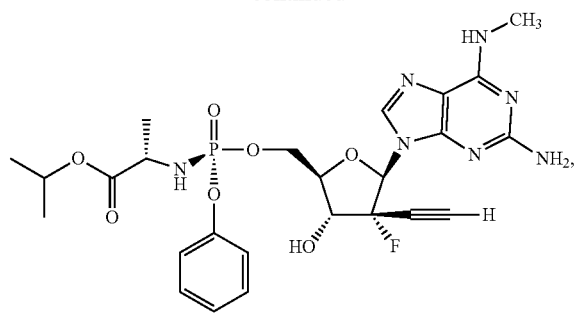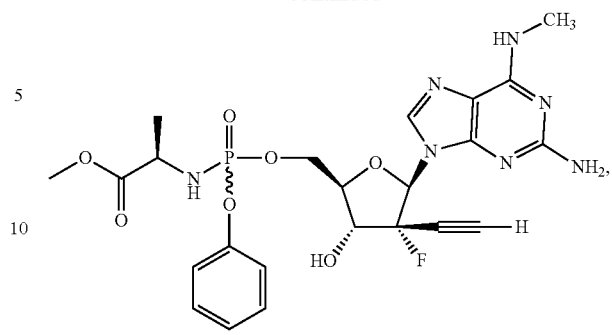

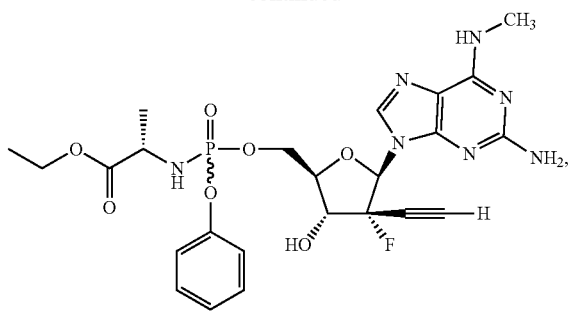
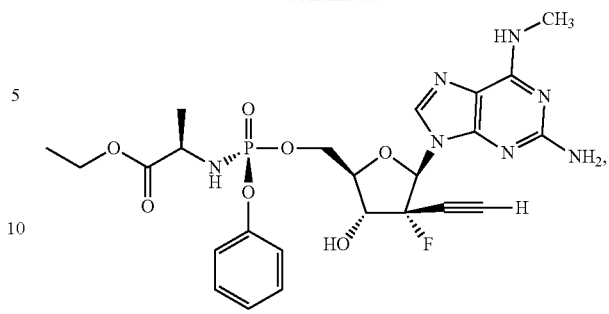
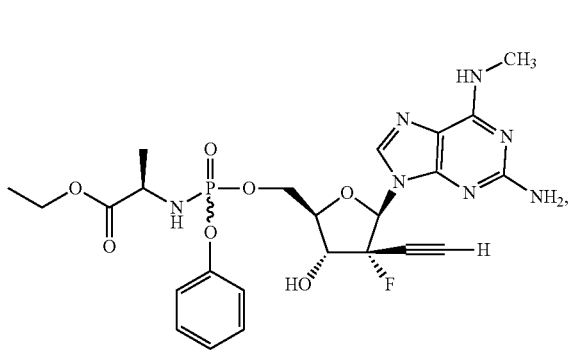
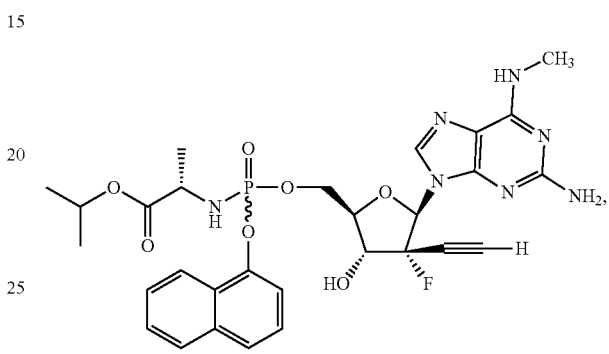
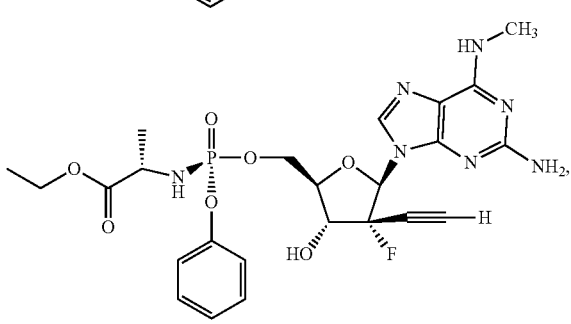
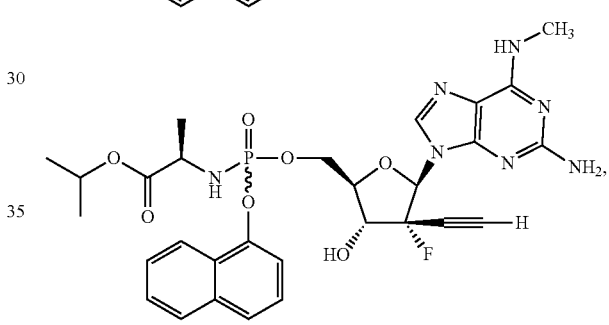
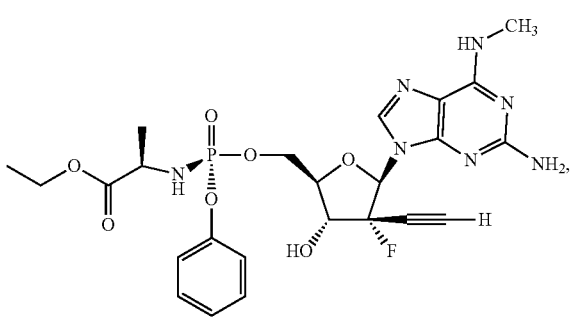
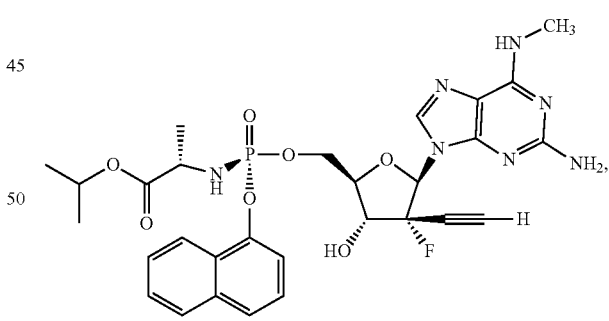
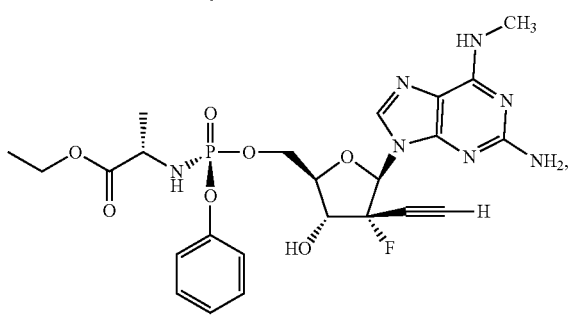
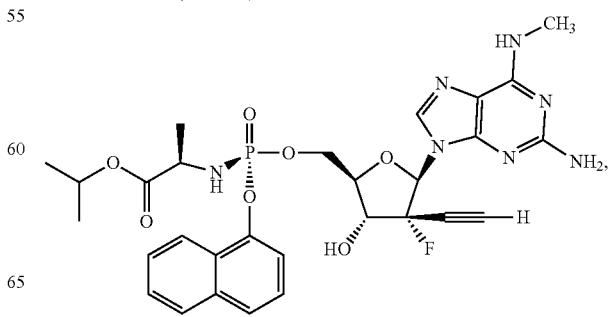

101
-continued
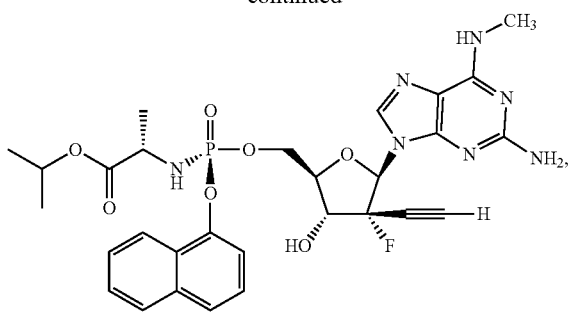
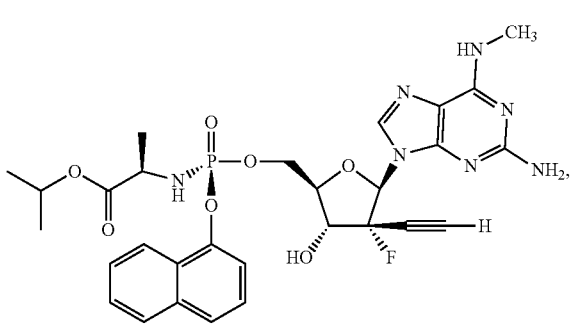
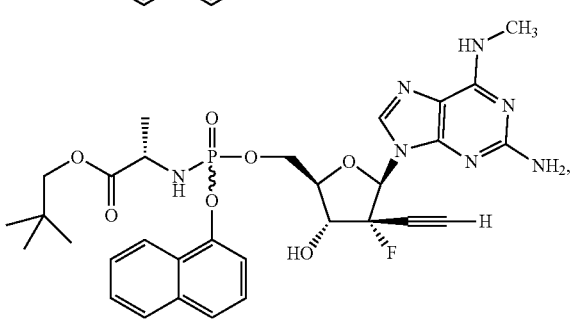
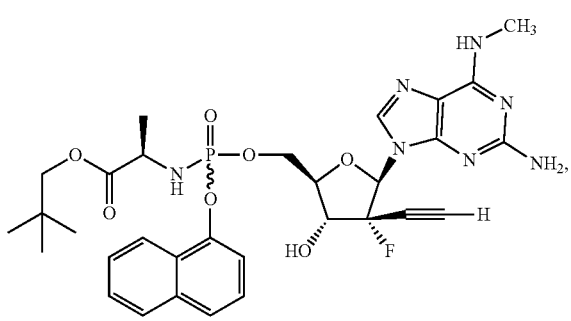
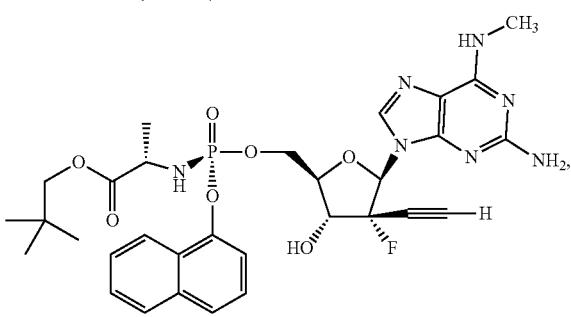
102
-continued
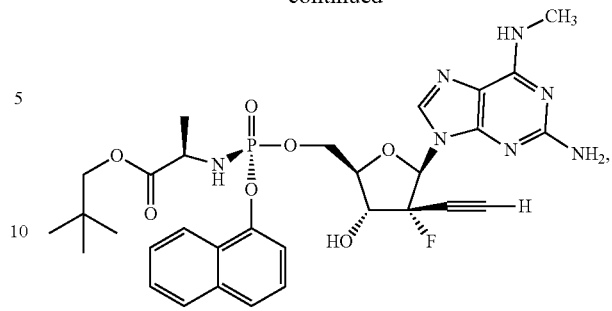
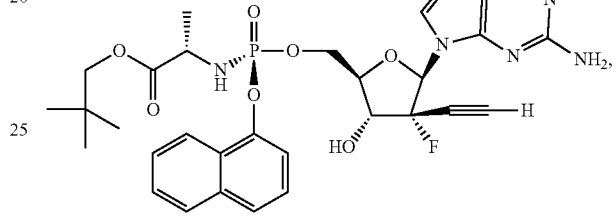
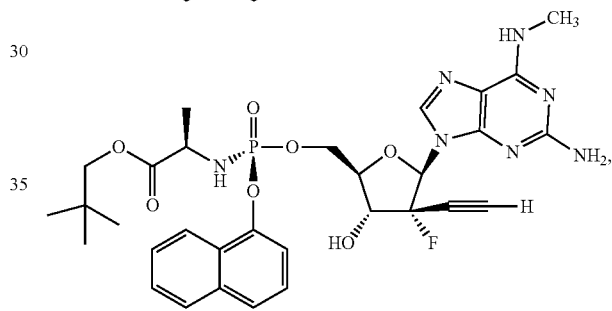
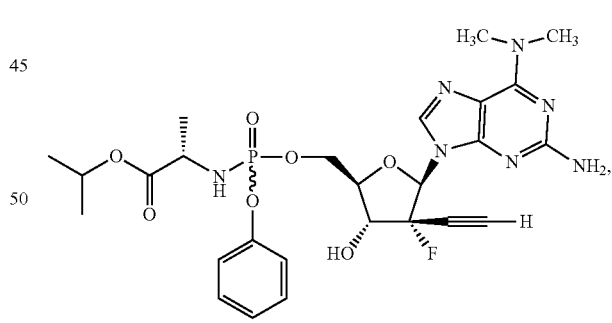
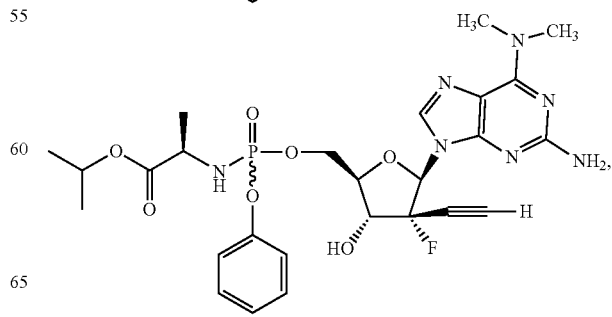

103
-continued
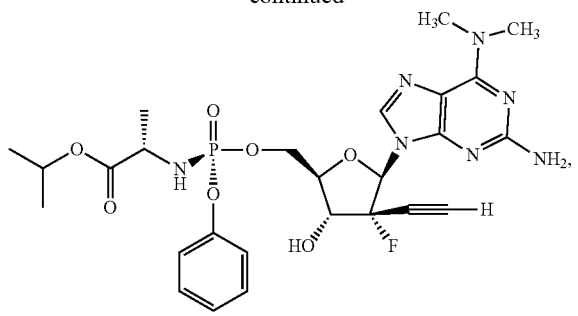
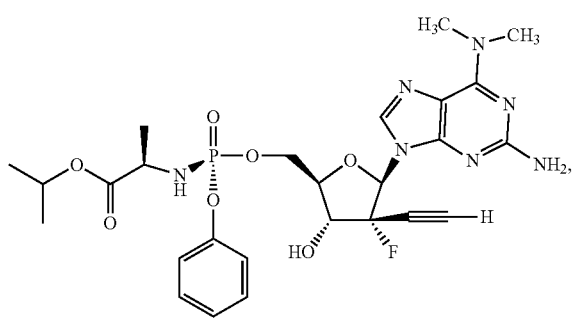
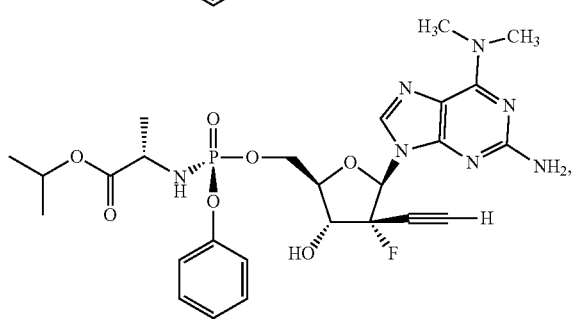
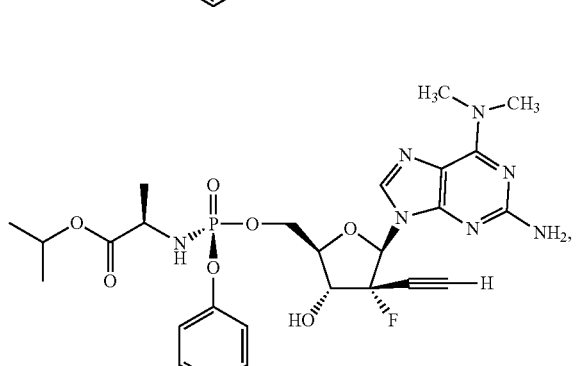
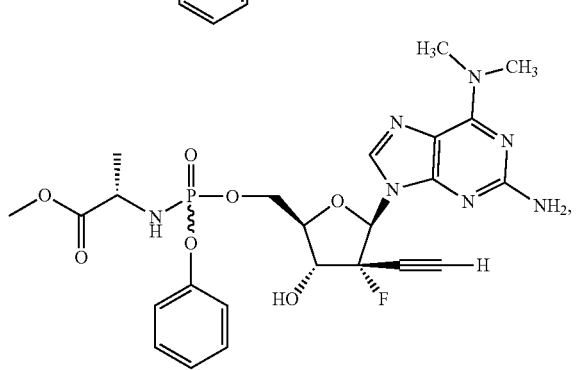
104
-continued
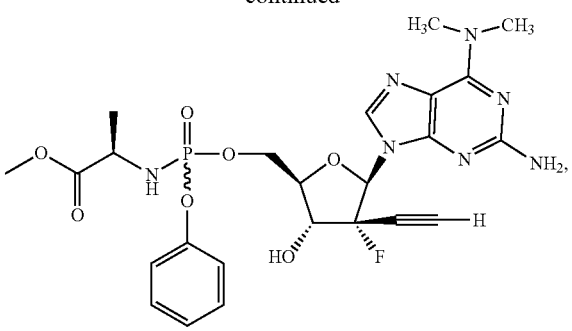
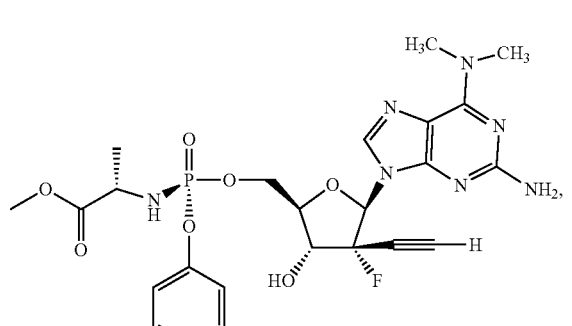
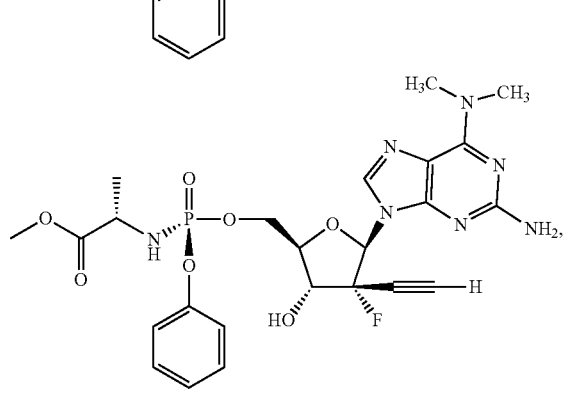
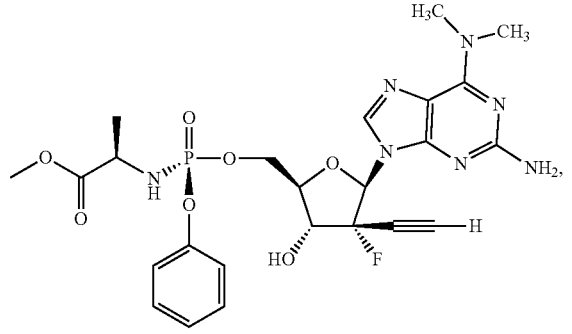

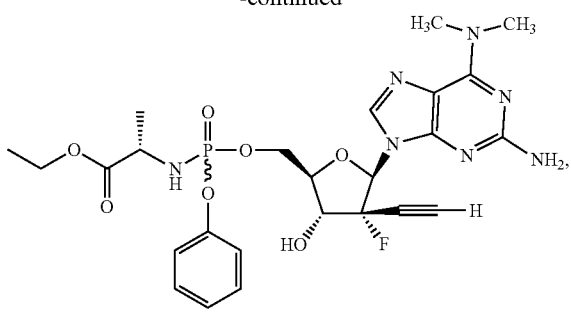
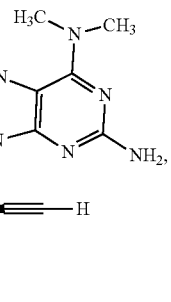
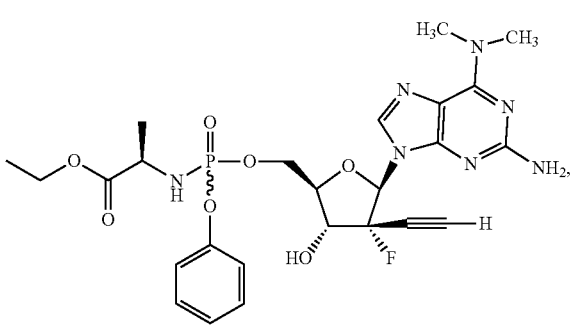
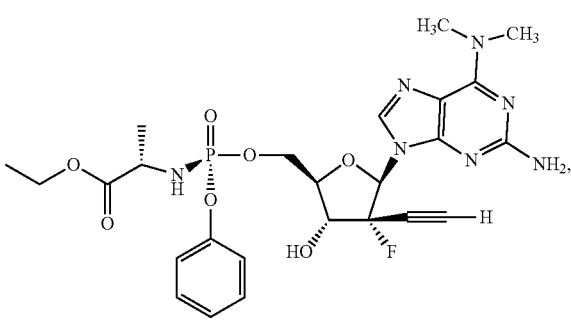
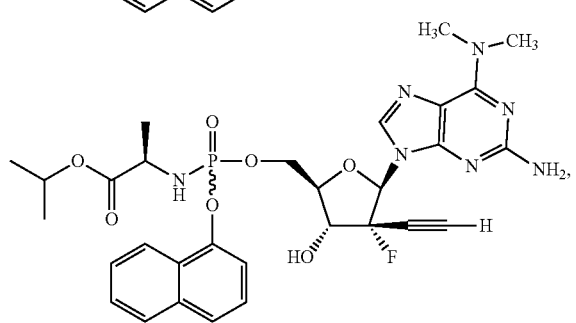
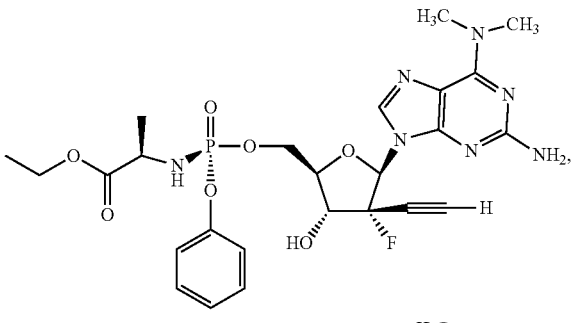
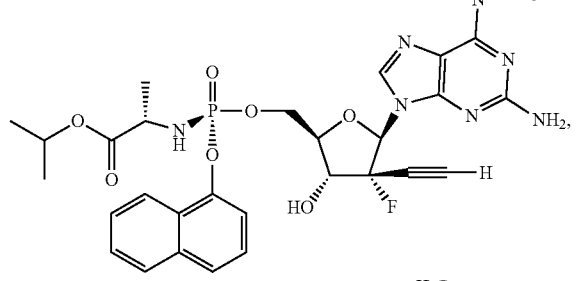
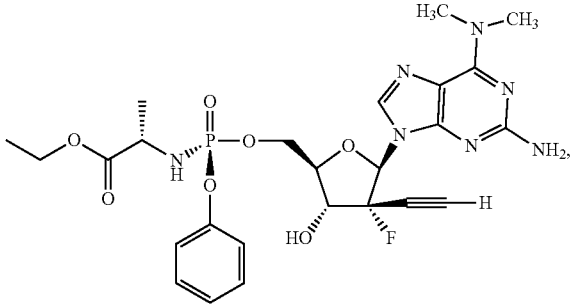
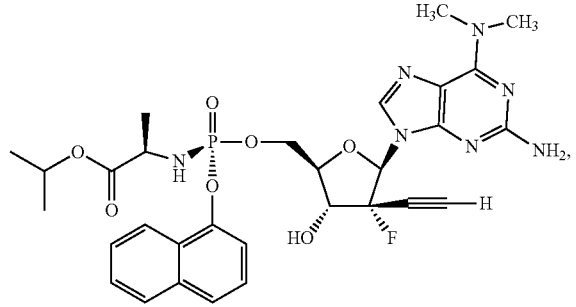

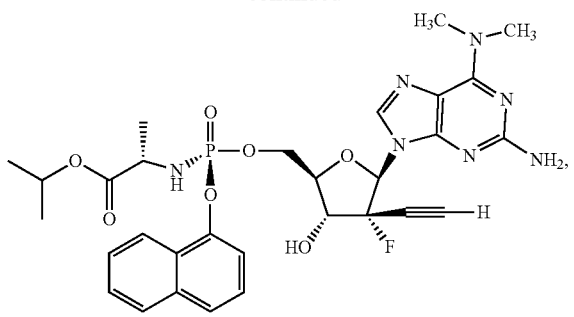
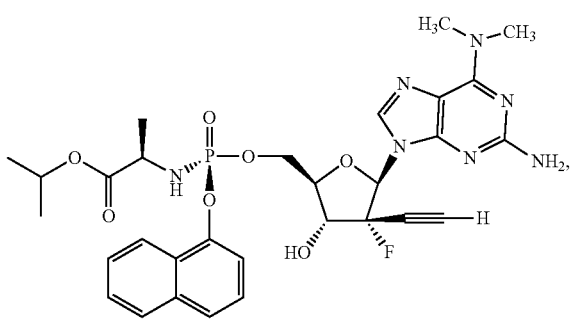
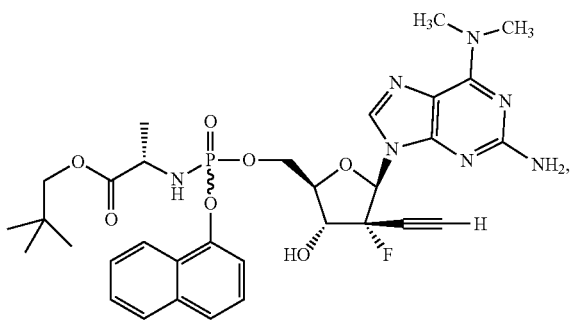
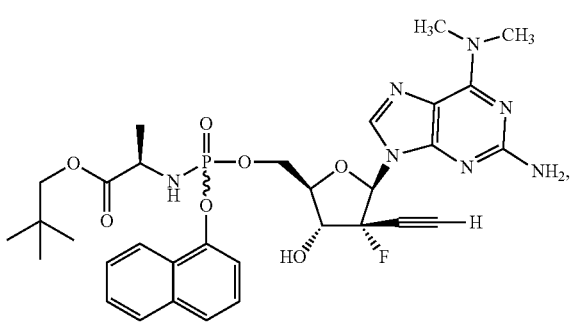
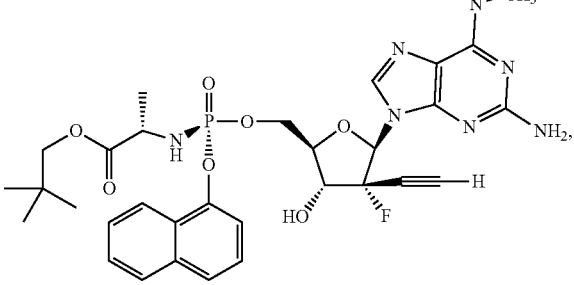
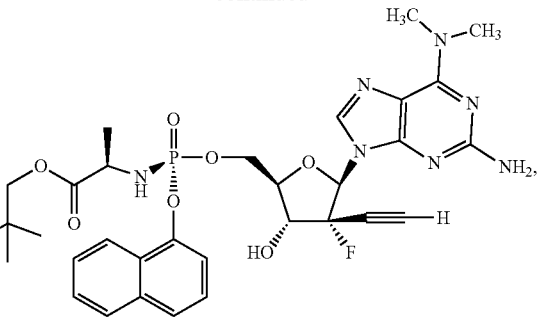
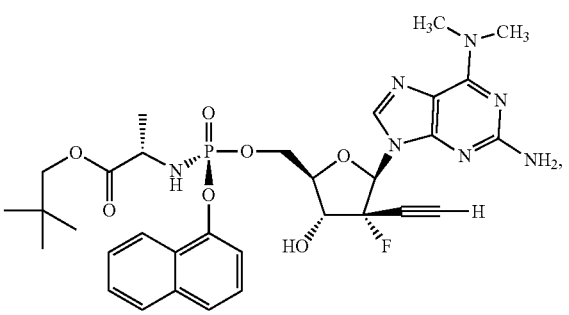
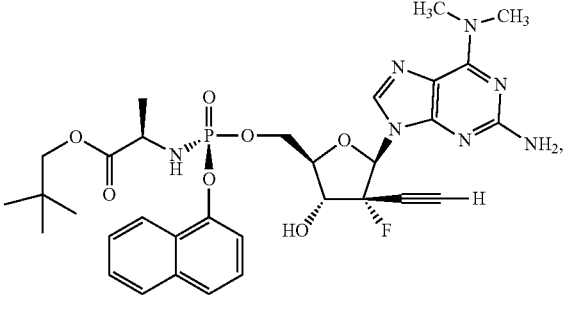
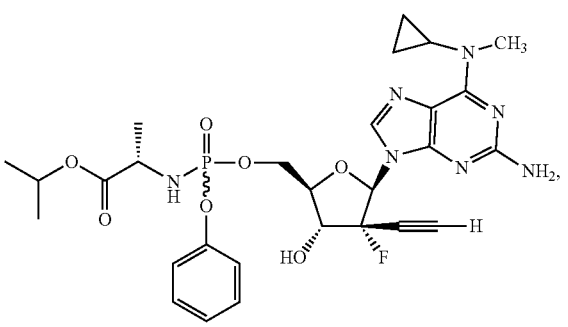
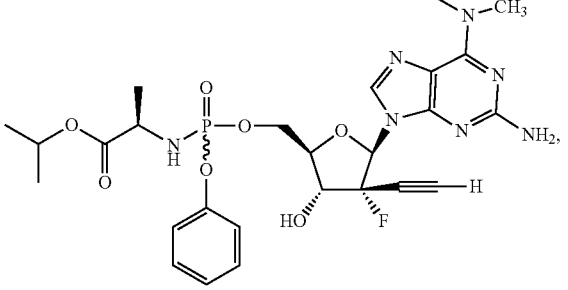

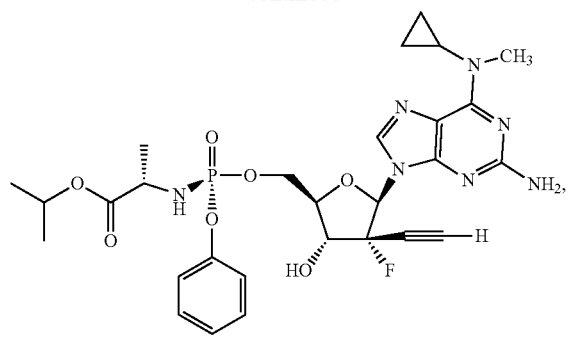
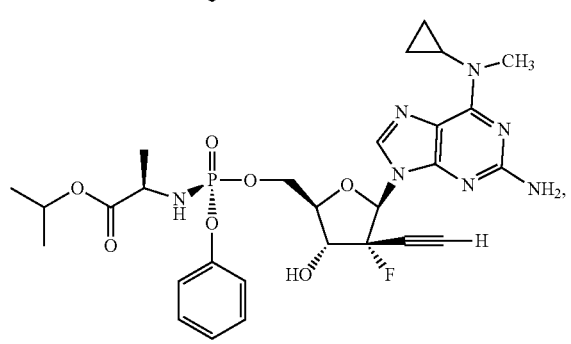
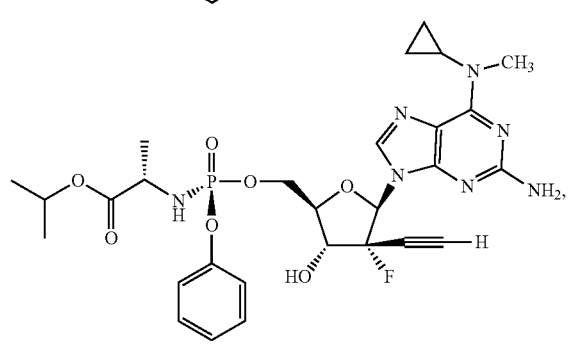
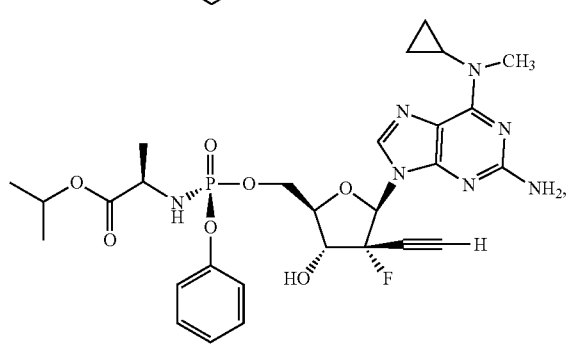
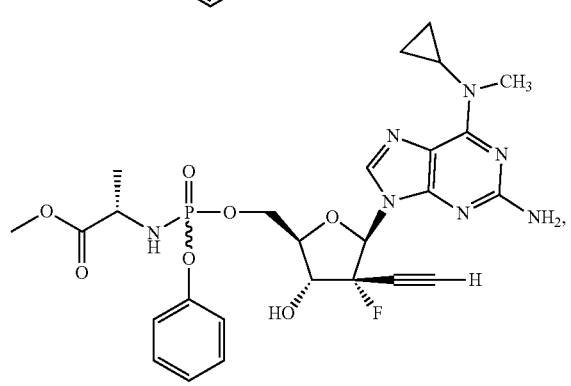
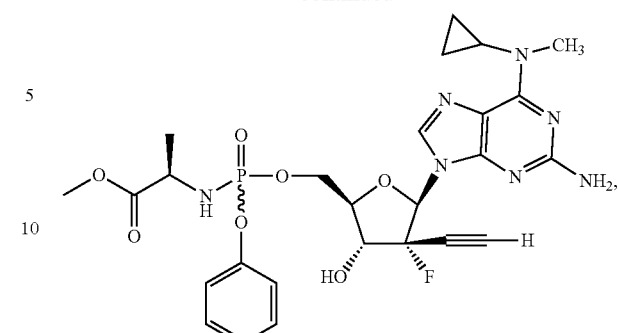
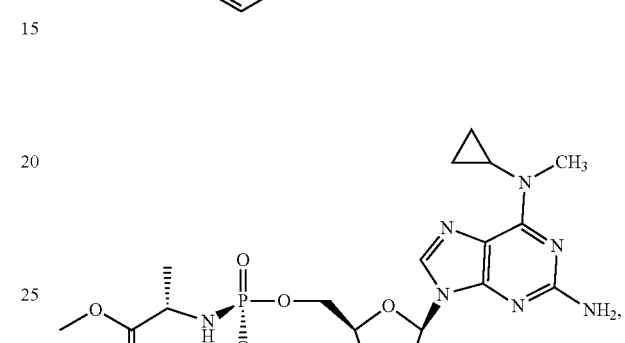

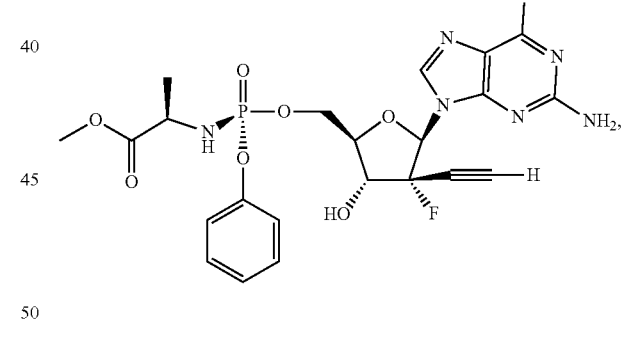
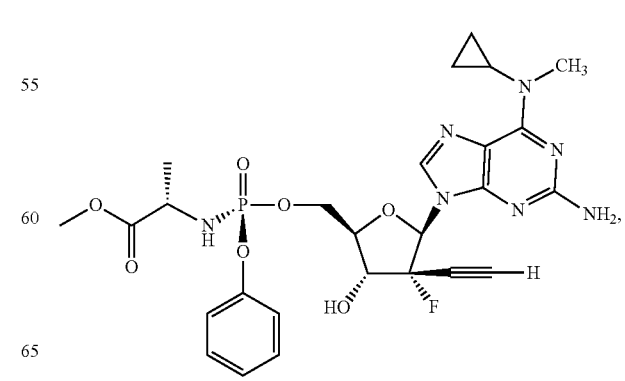

111
-continued
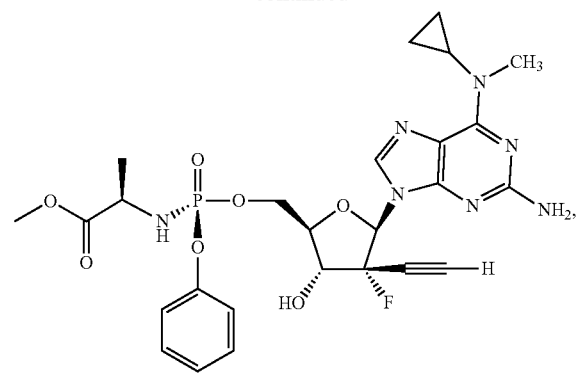
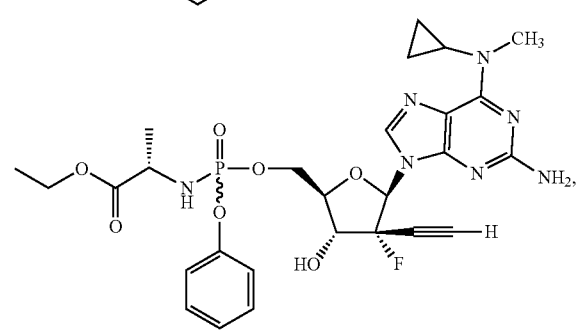
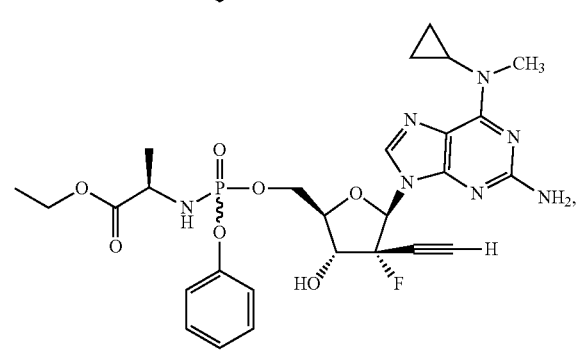
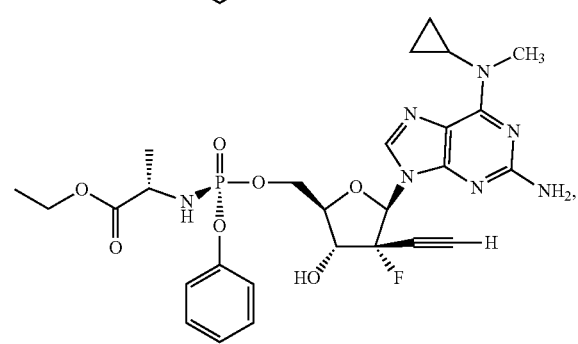
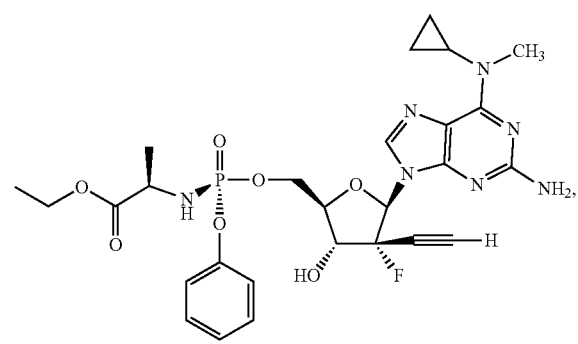
112
-continued
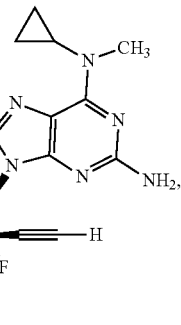
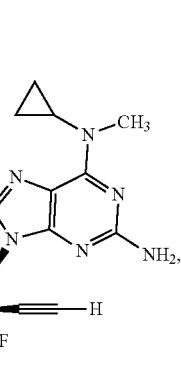
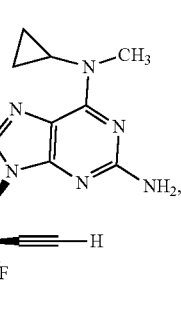
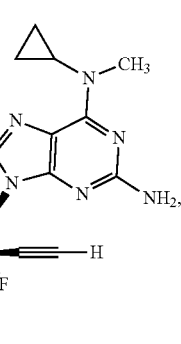
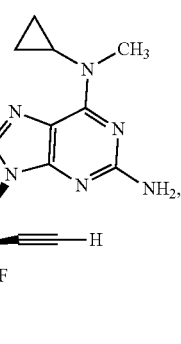

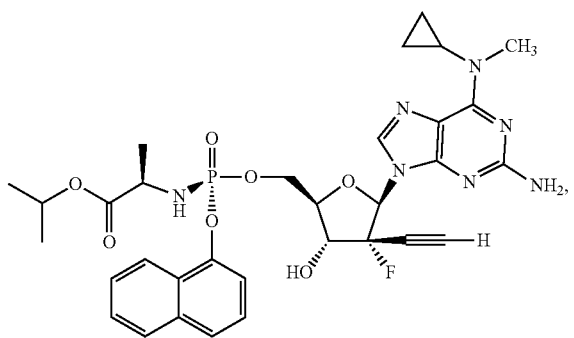
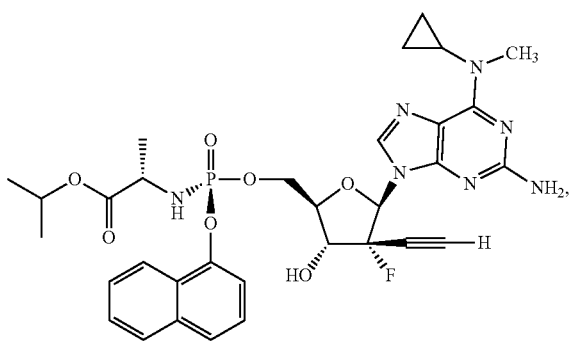
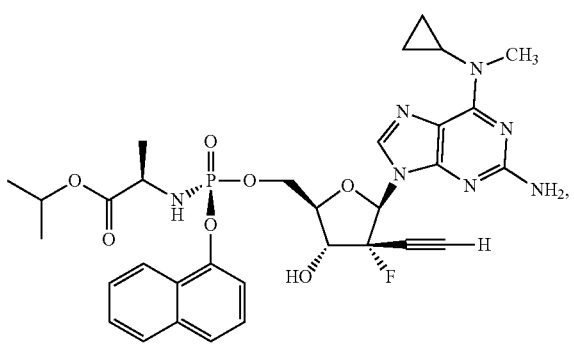
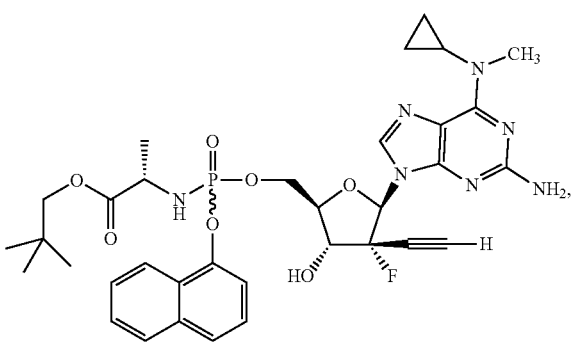
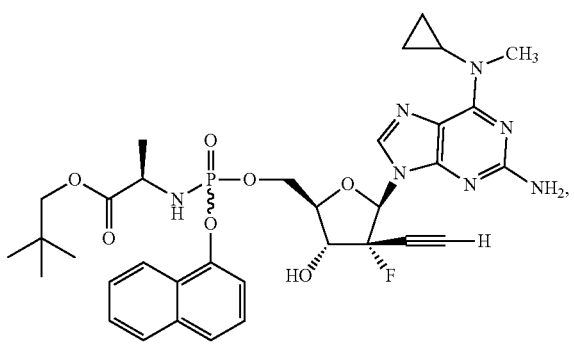
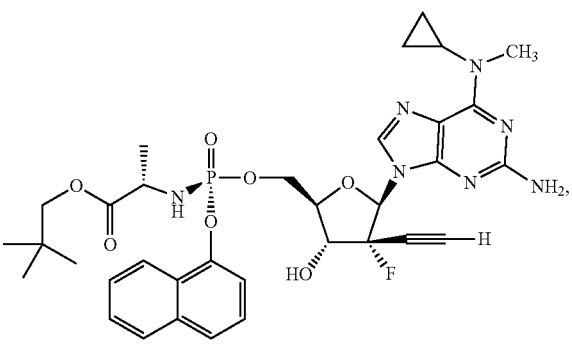
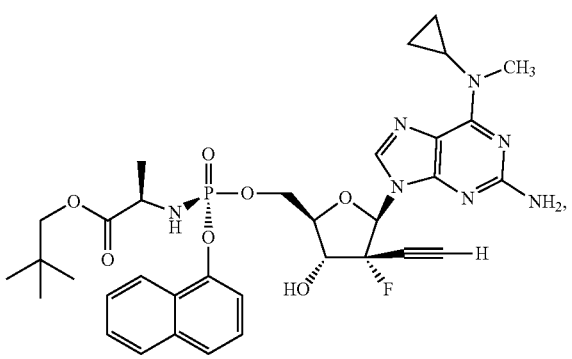
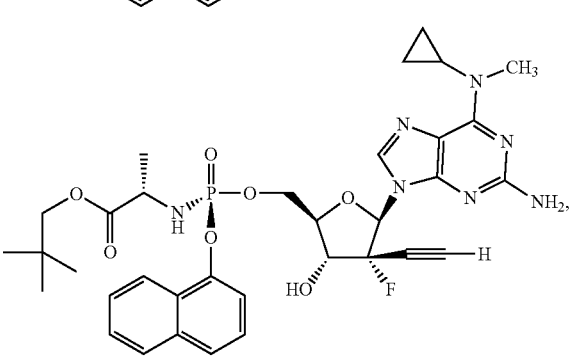
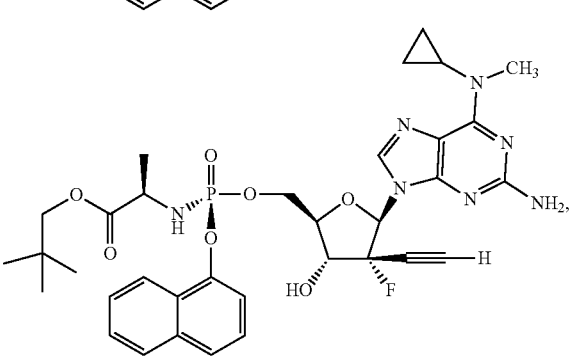
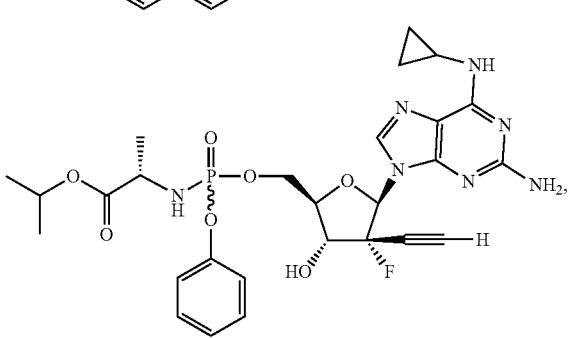

-continued
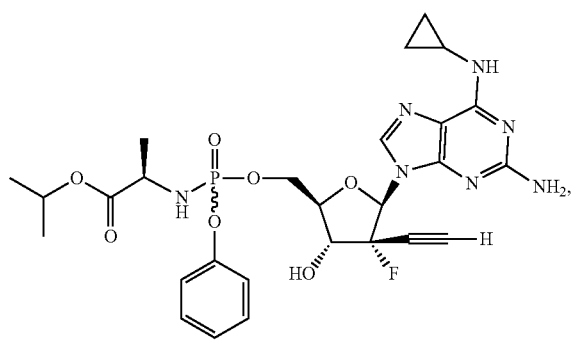
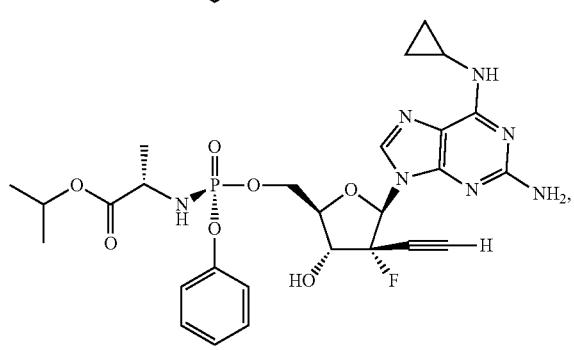
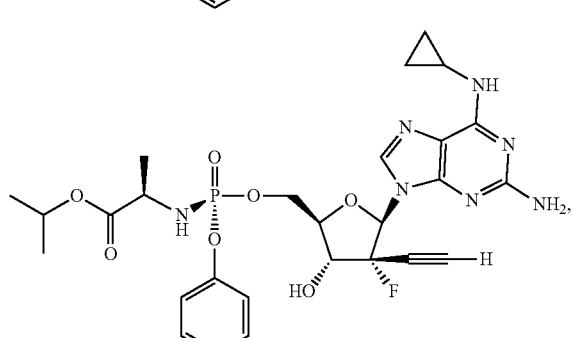
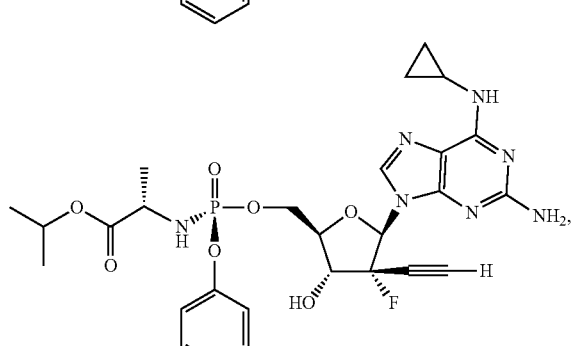
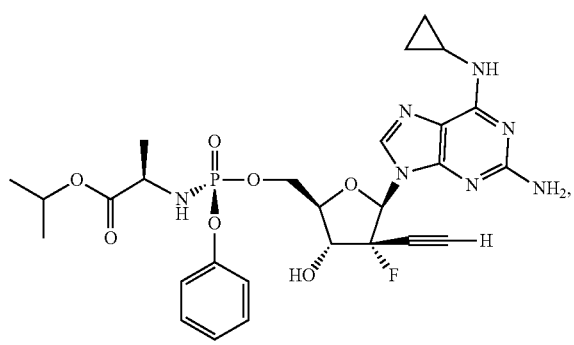
-continued
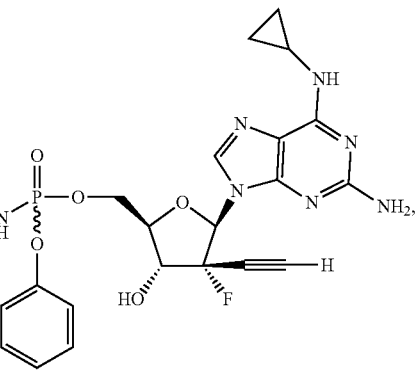
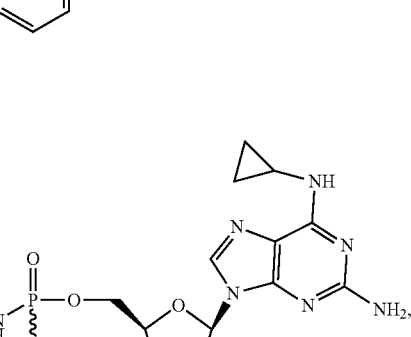
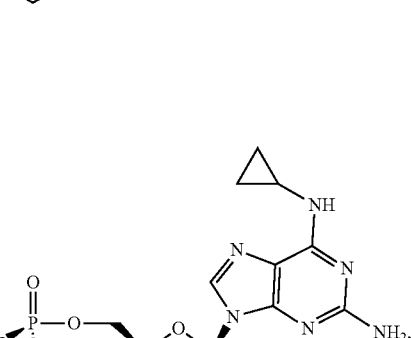
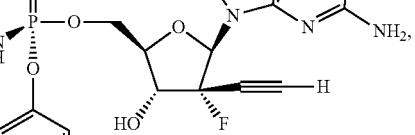

117
-continued
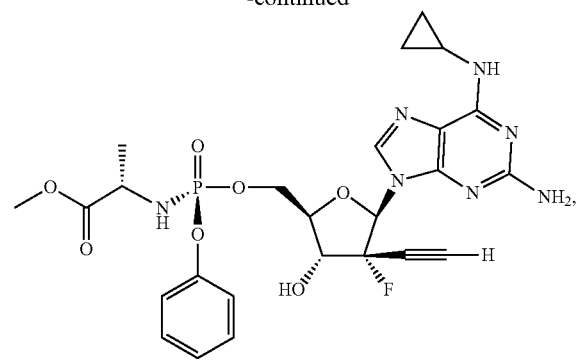
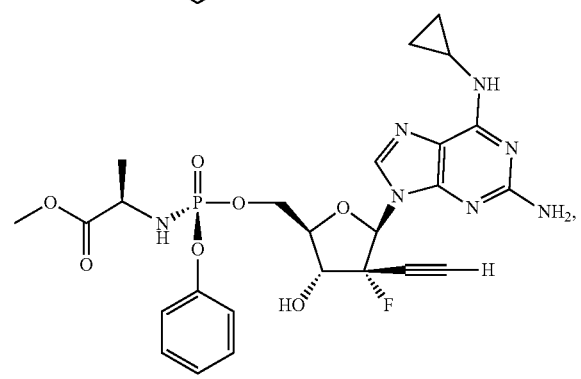
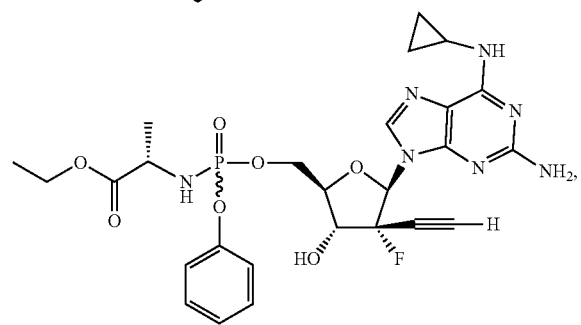
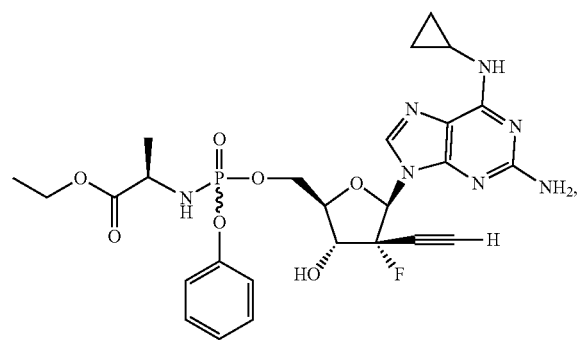
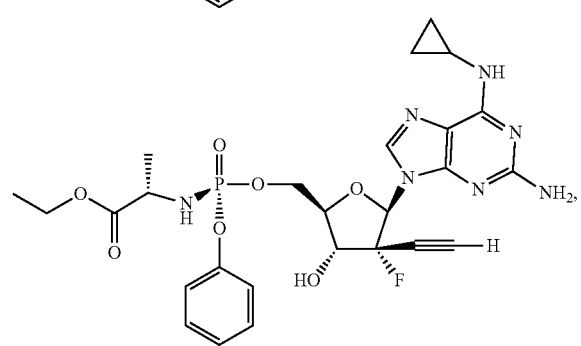
118
-continued
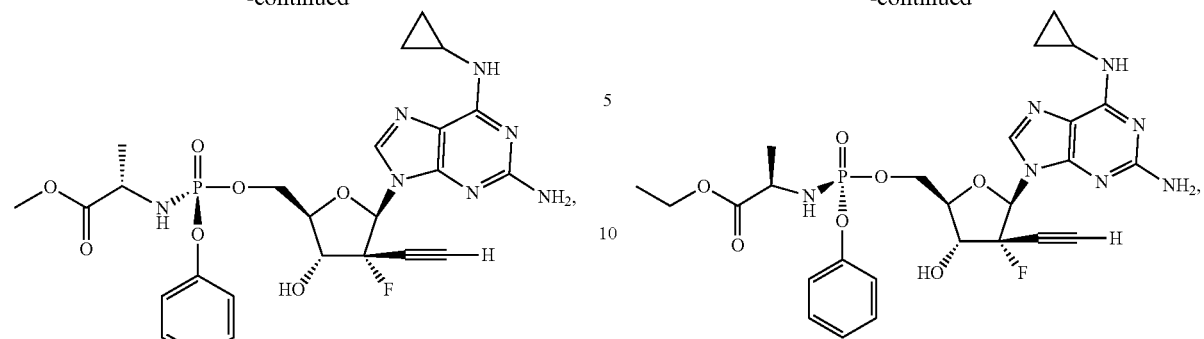
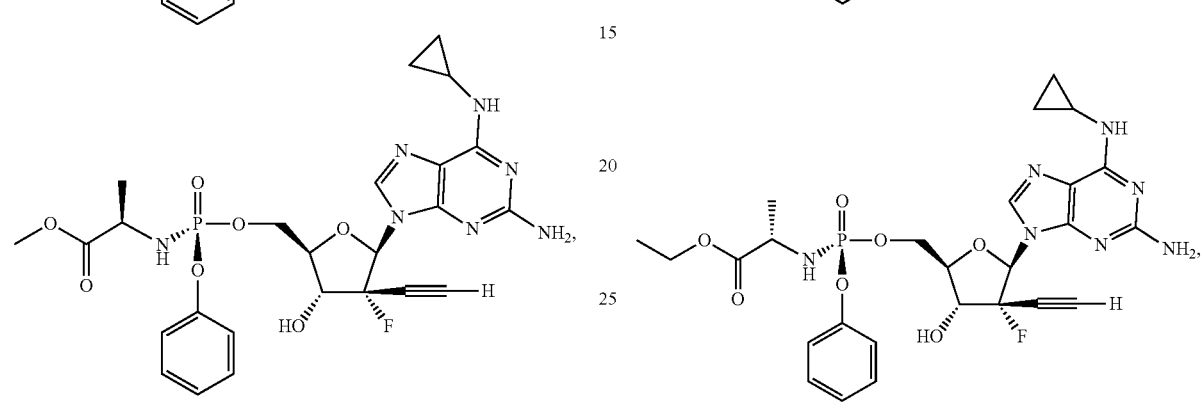
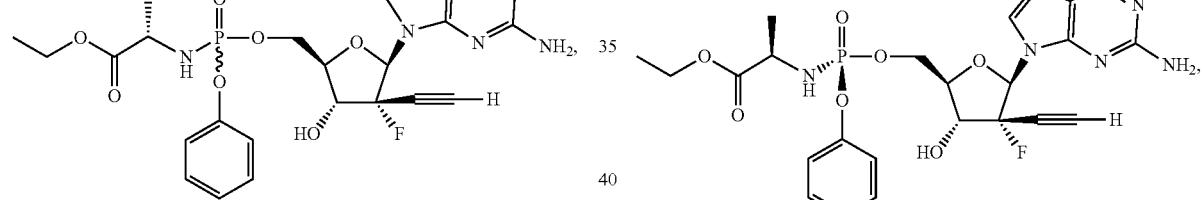

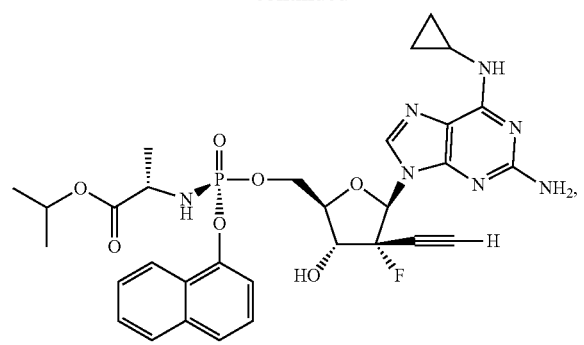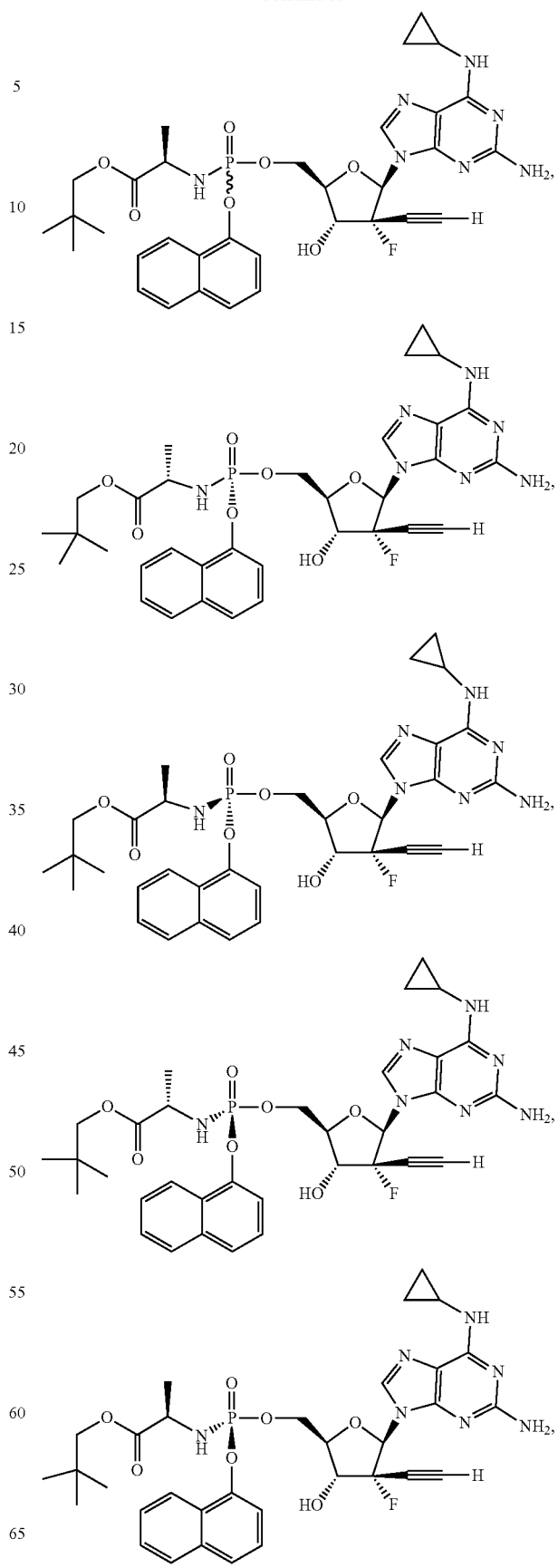

121
-continued
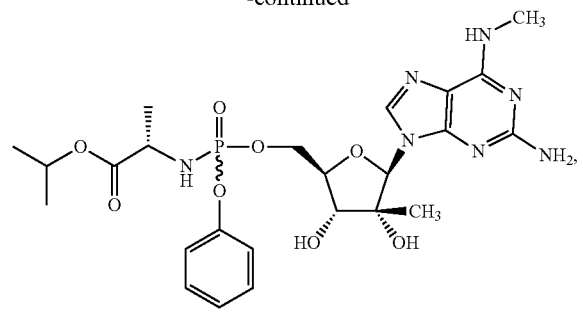
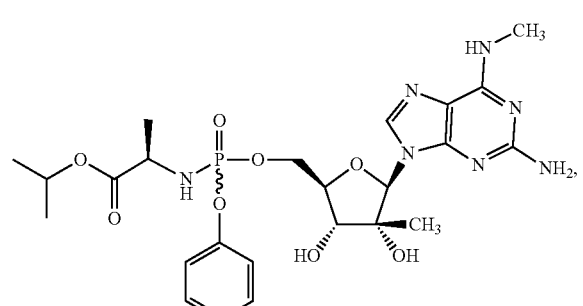
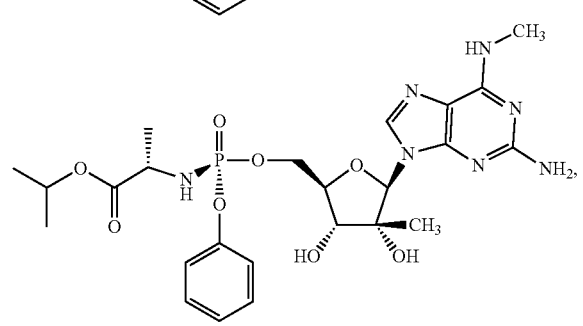
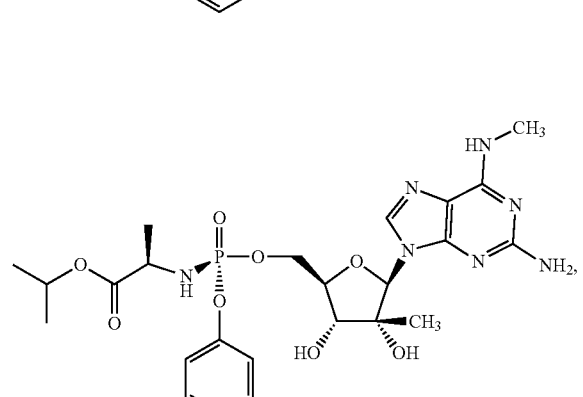
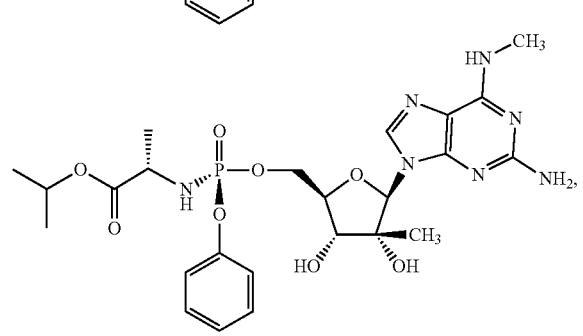
122
-continued
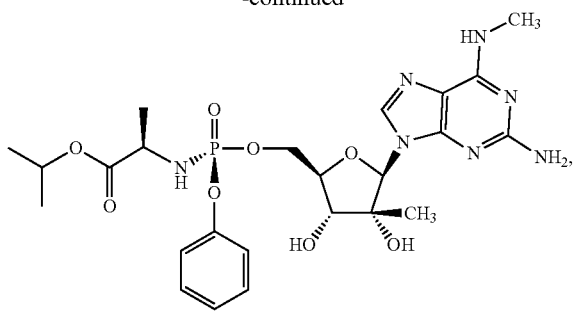
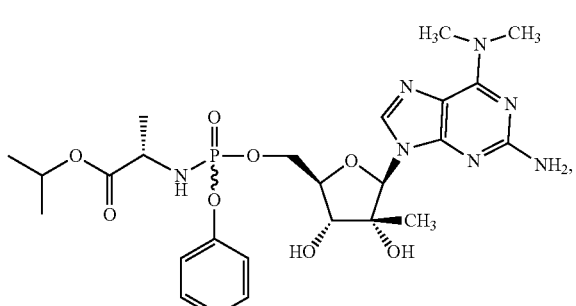
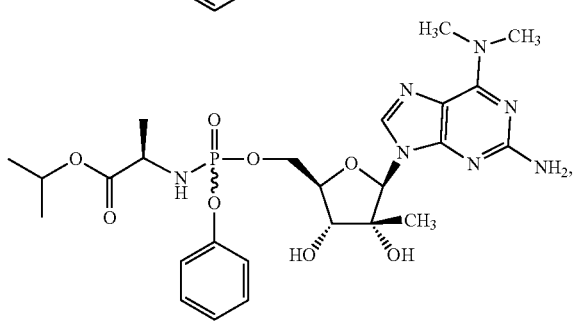
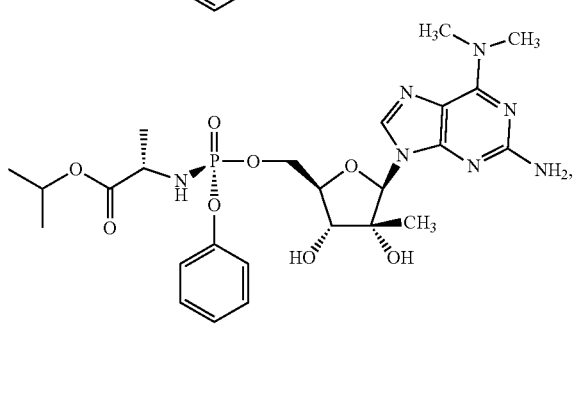
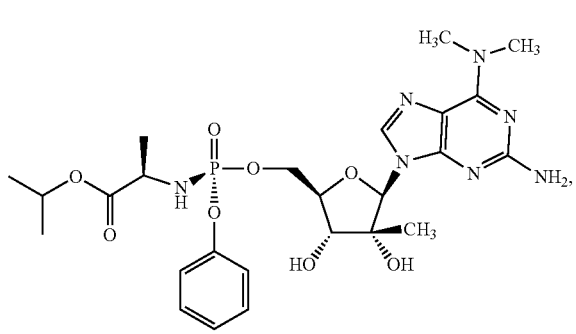

123
-continued
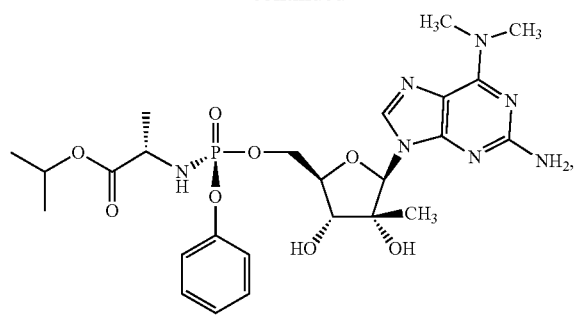
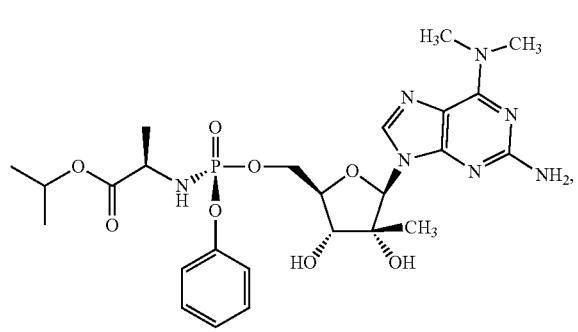
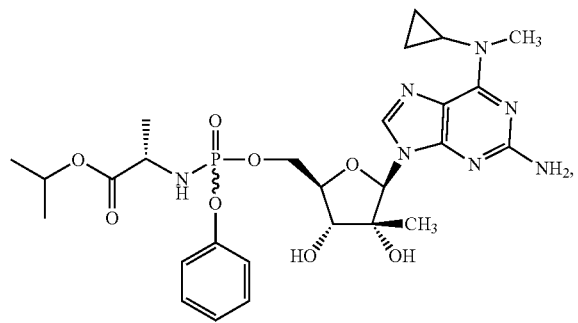
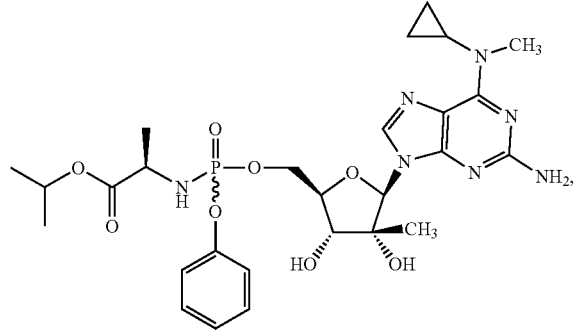
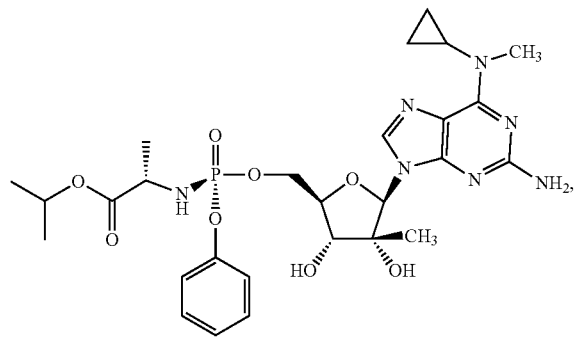
124
-continued
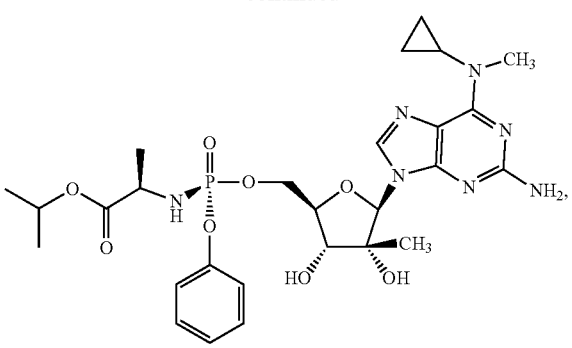
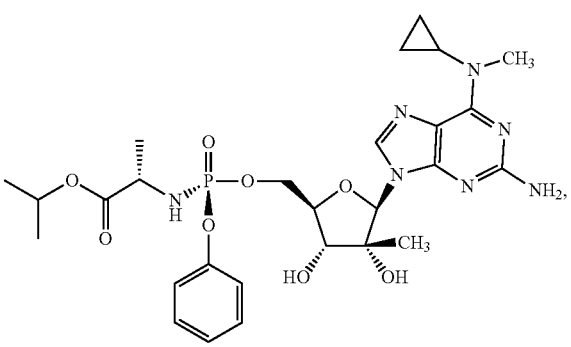
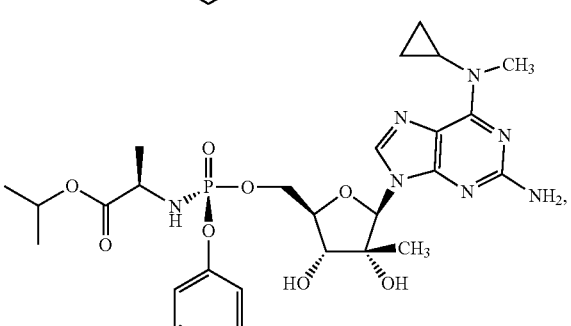
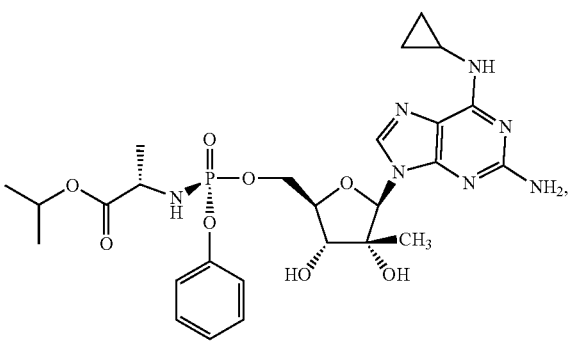
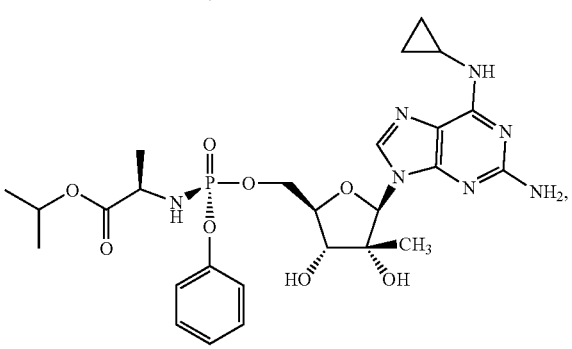

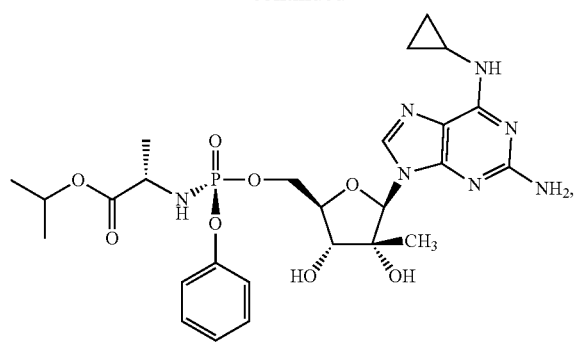
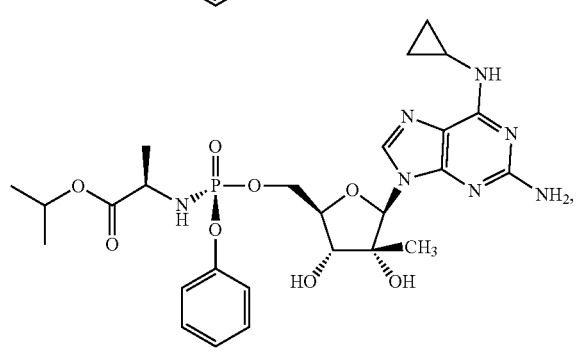
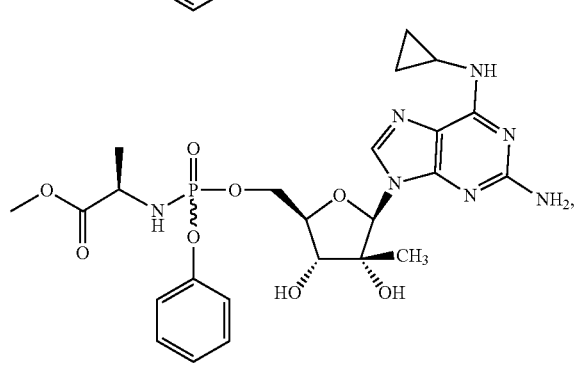
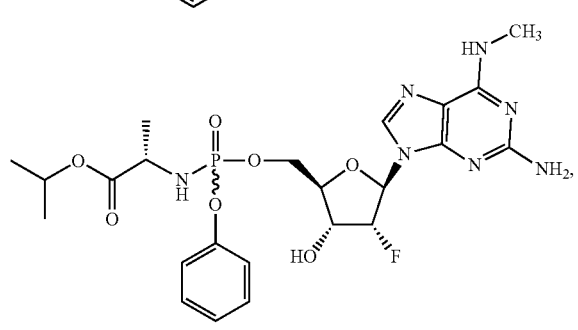
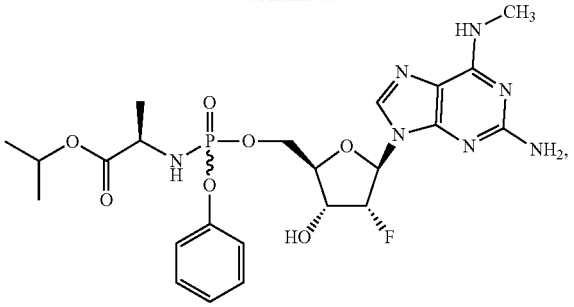
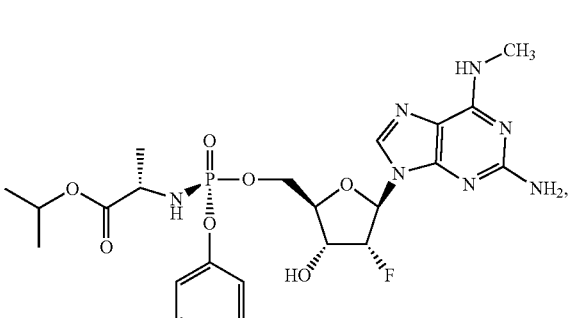
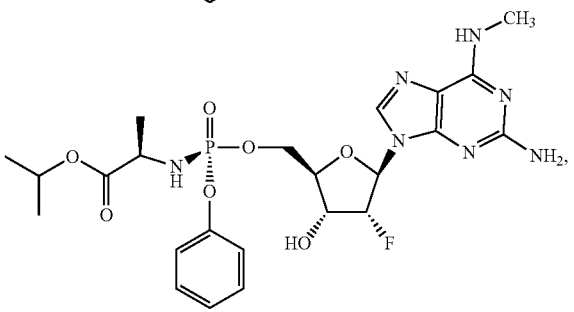
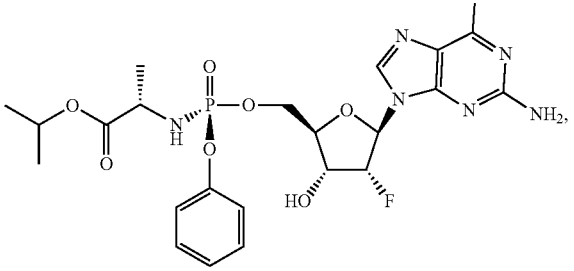
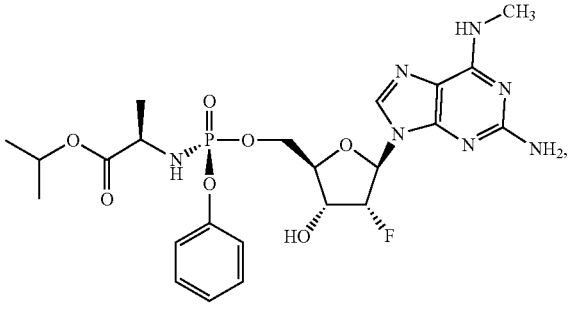

127
-continued
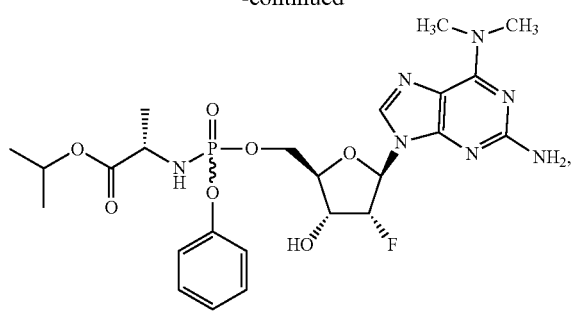
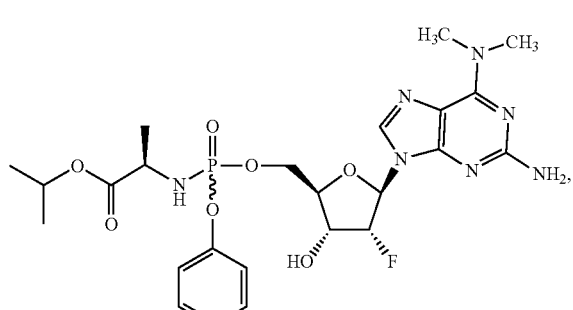
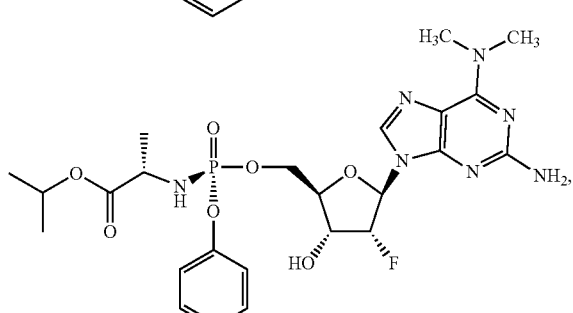
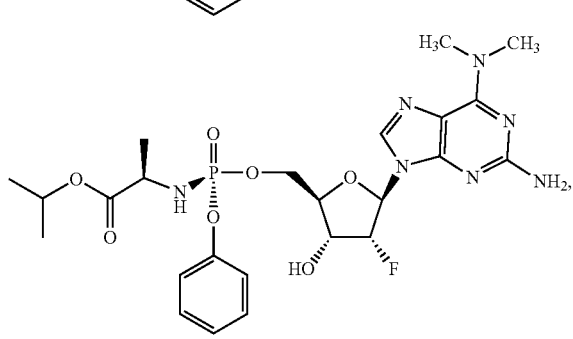
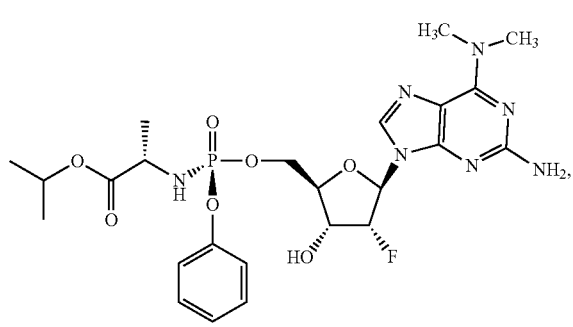
128
-continued
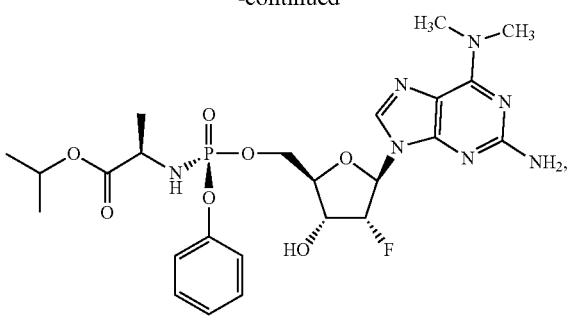
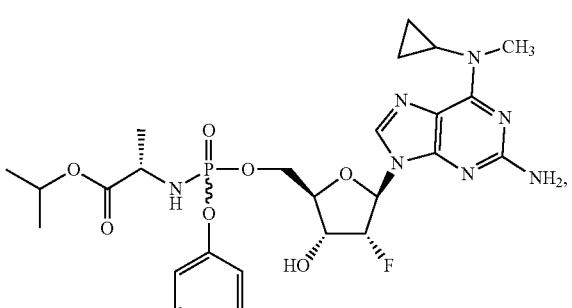
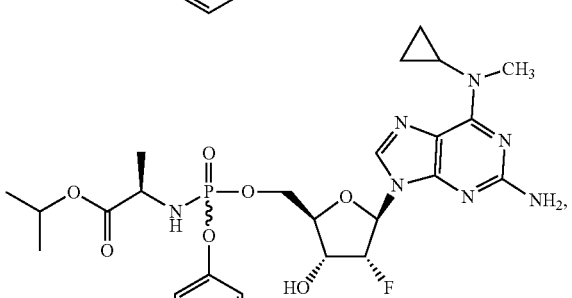
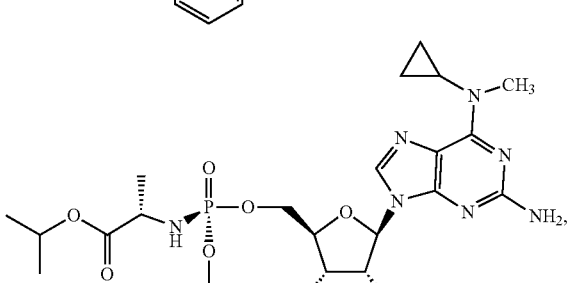
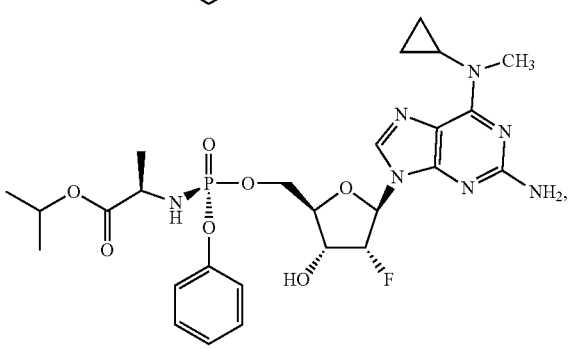

129
-continued
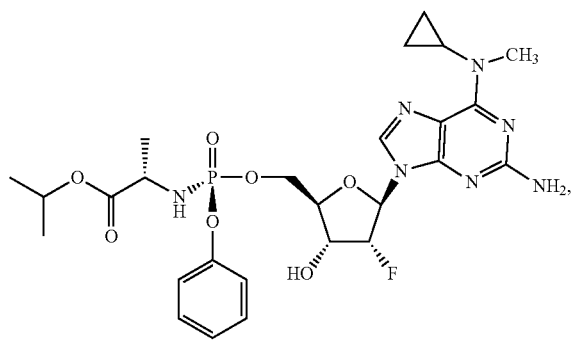
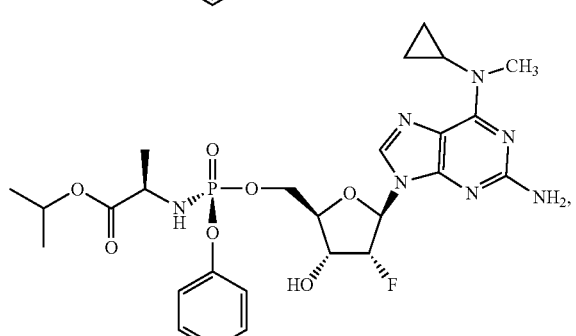
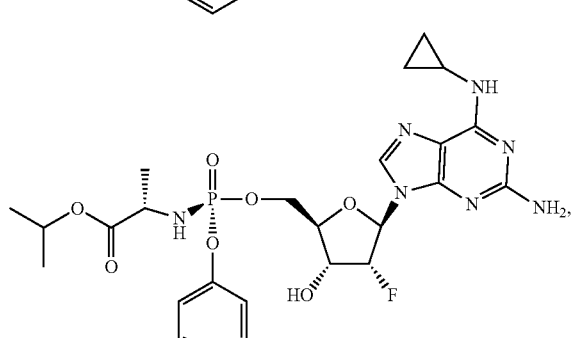
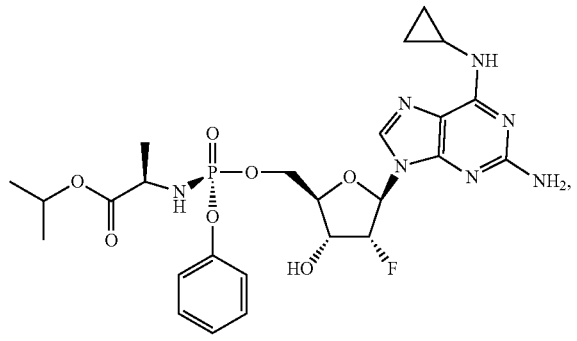
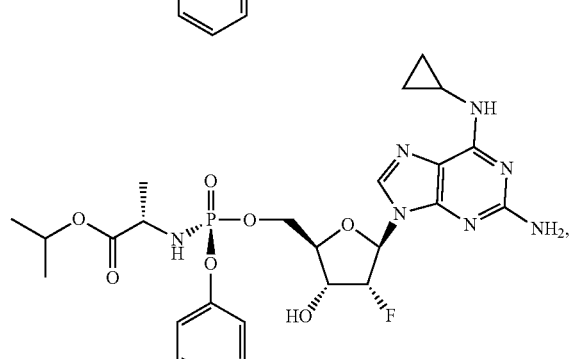
130
-continued
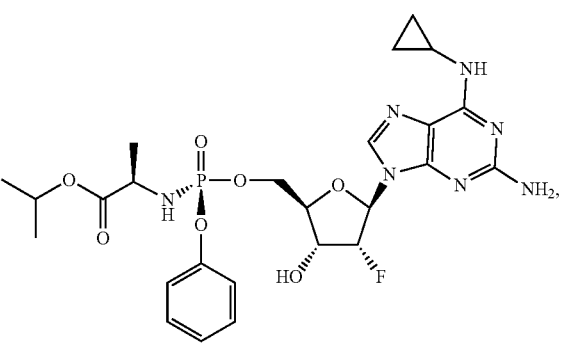
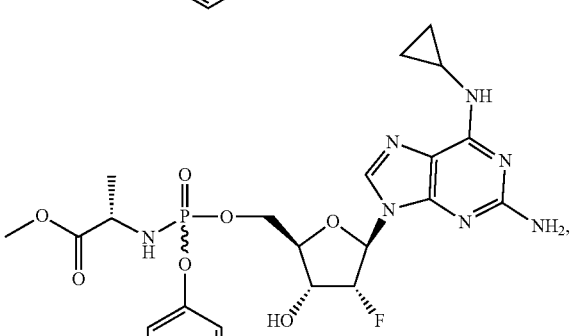
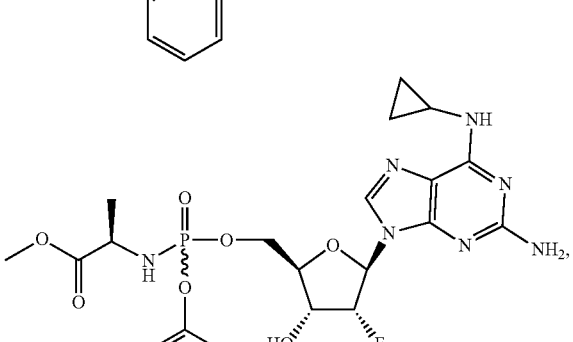
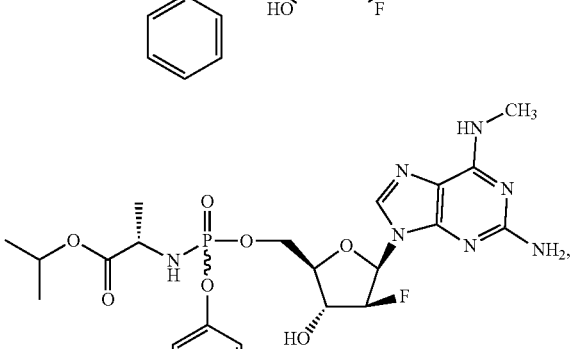
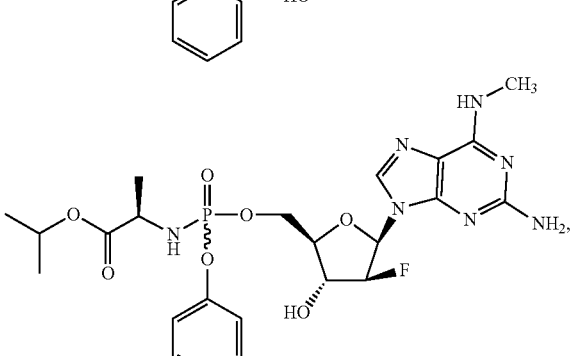

131
-continued
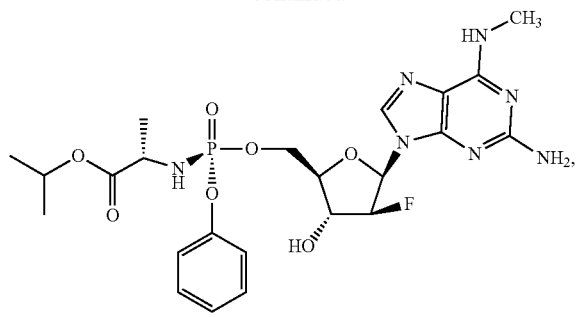
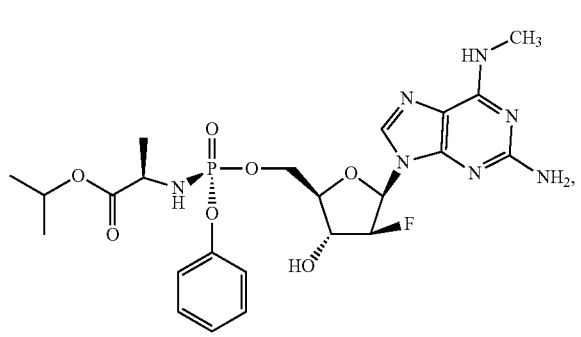
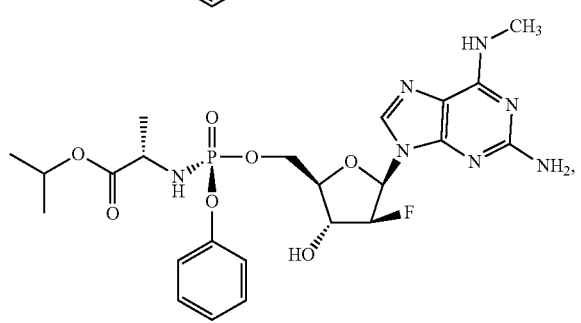
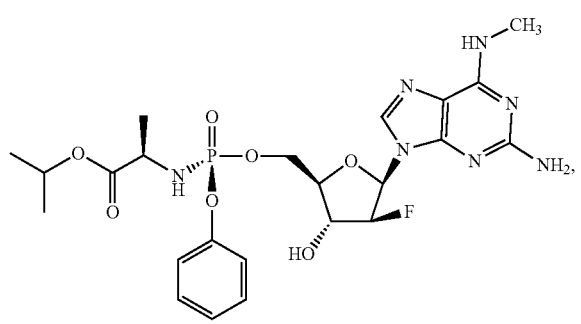
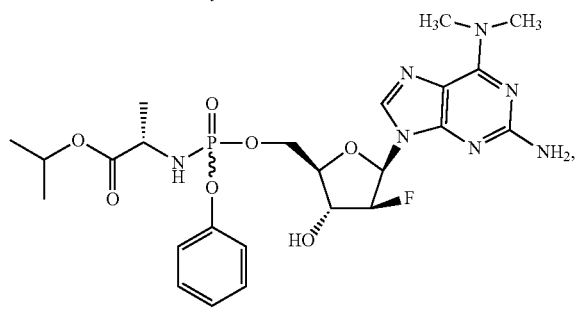
132
-continued
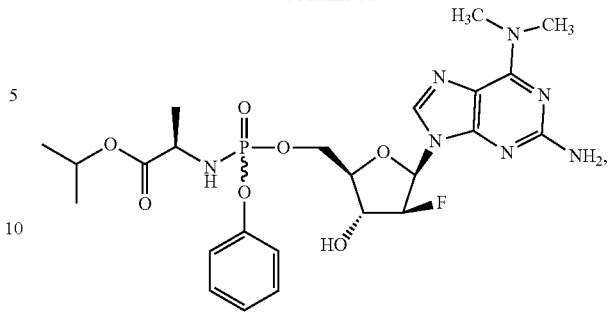
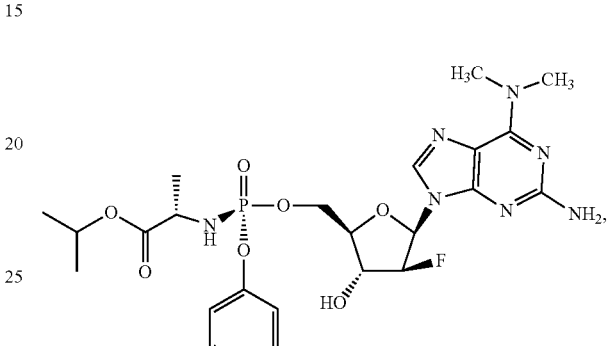
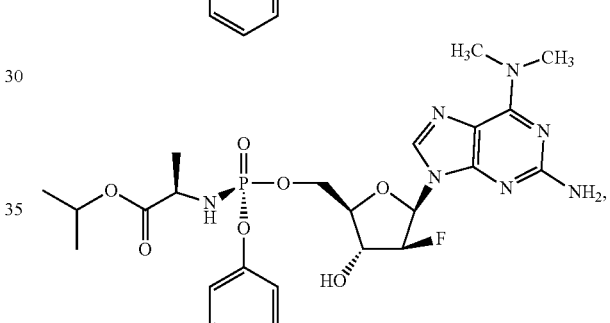
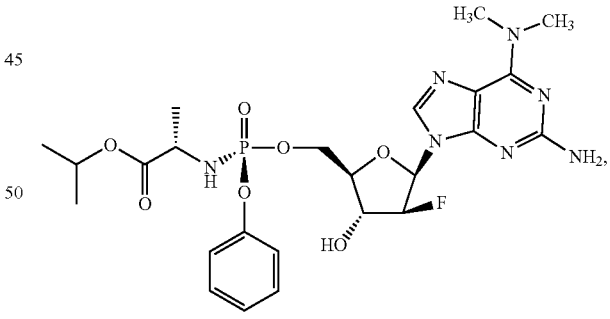
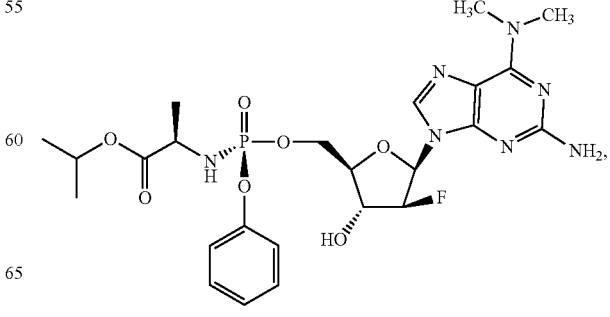

133
-continued
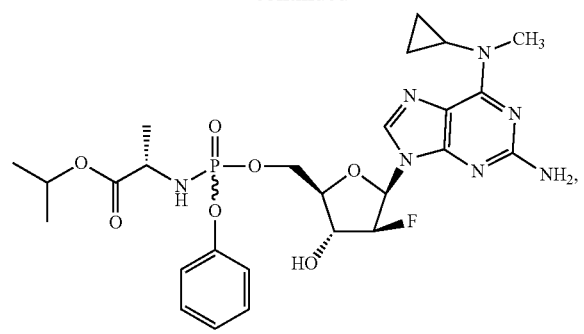
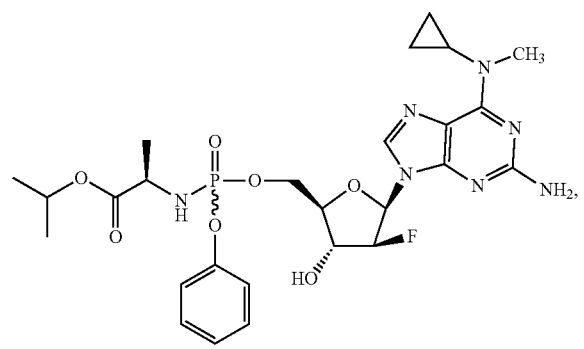
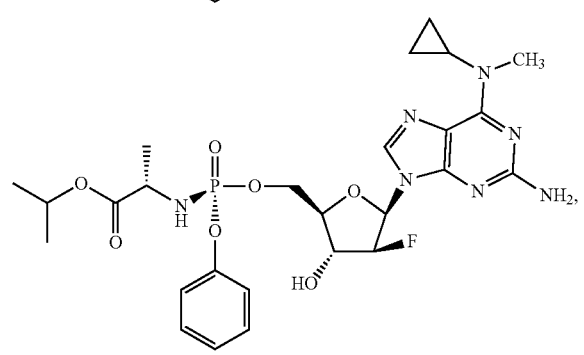
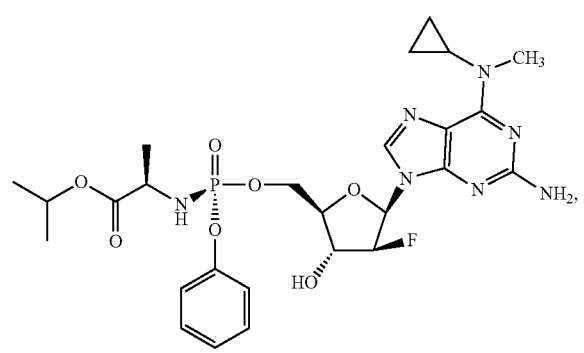
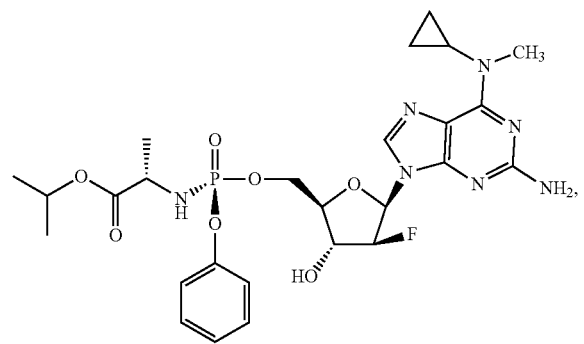
134
-continued
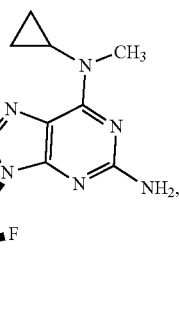
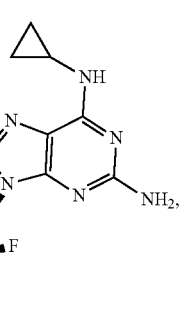
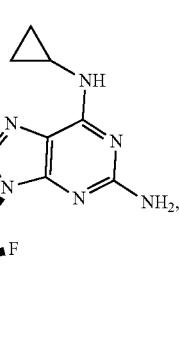
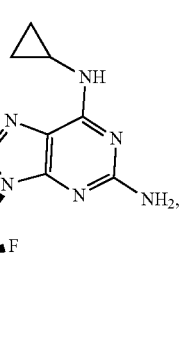
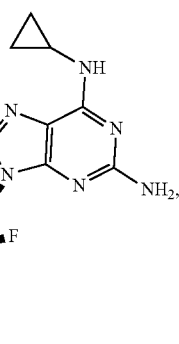

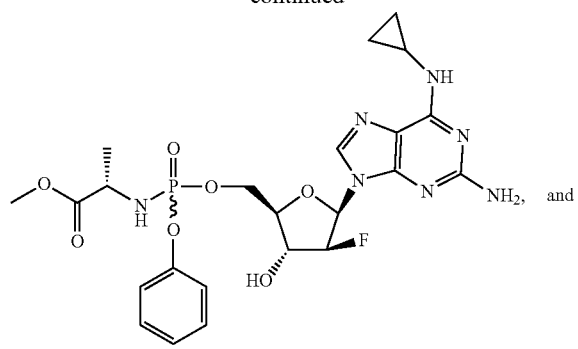
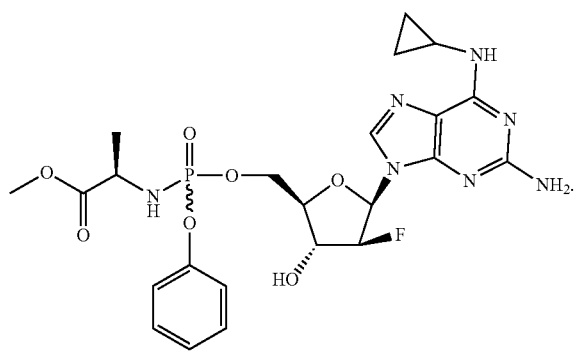
In an alternative embodiment, the use of an effective amount of a compound of Formula III or a pharmaceutically acceptable salt thereof, for the treatment of an infection of an RNA virus in a host, including a human in need thereof is provided. Additional non-limiting examples of Formula III include but are not limited to:
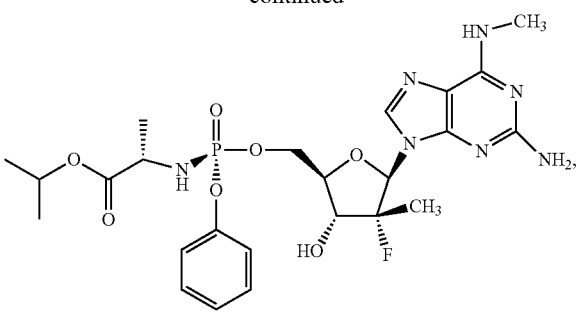
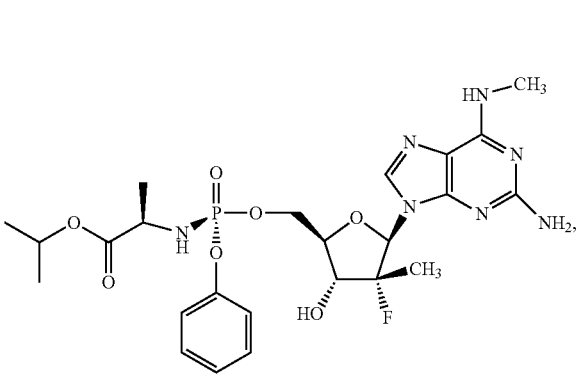
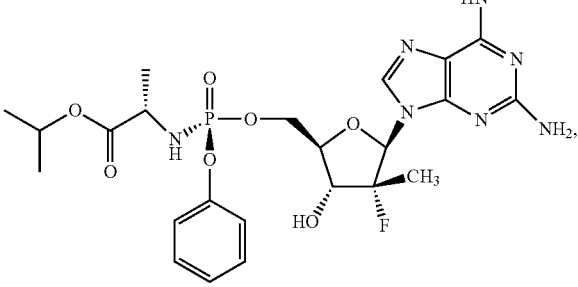
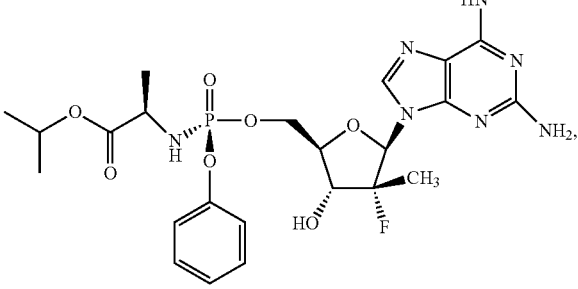
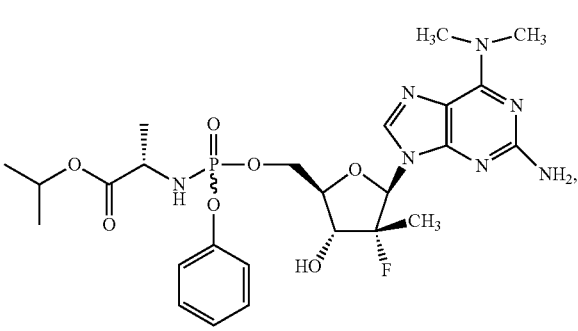

137
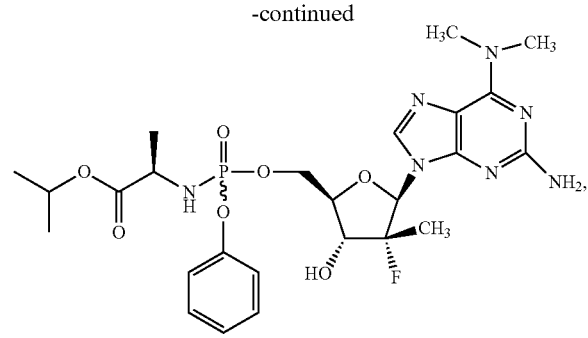
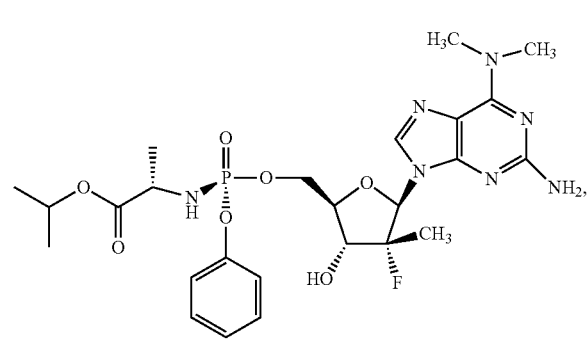
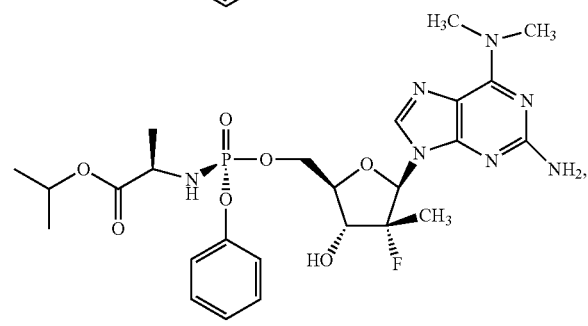
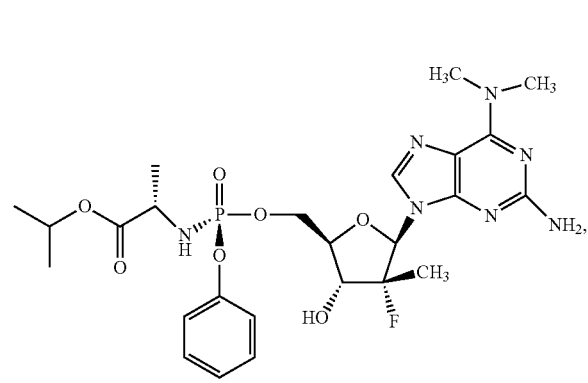
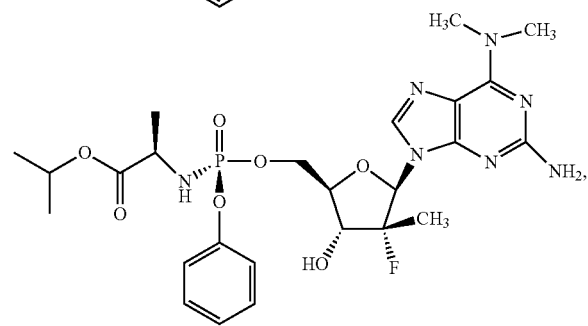
138
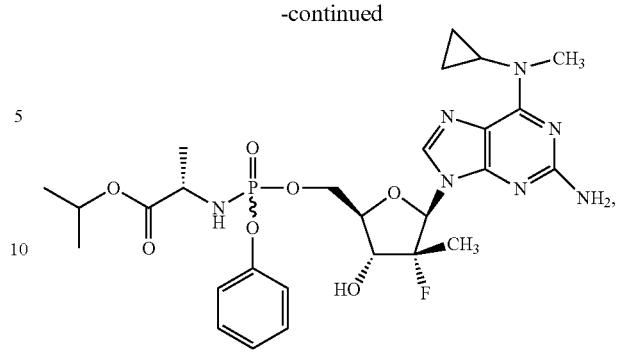
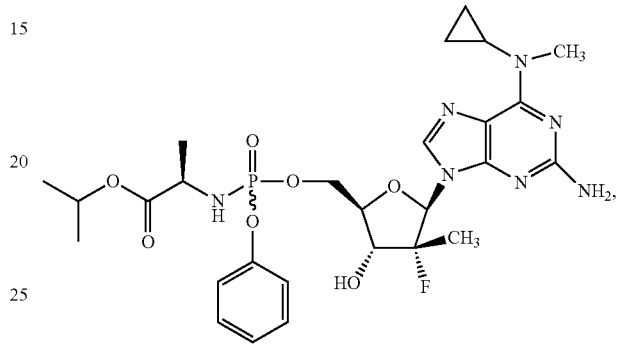
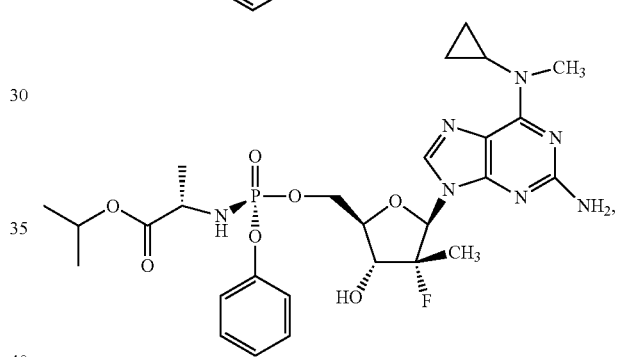
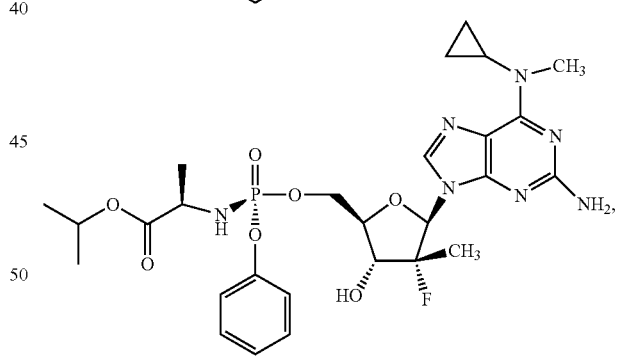
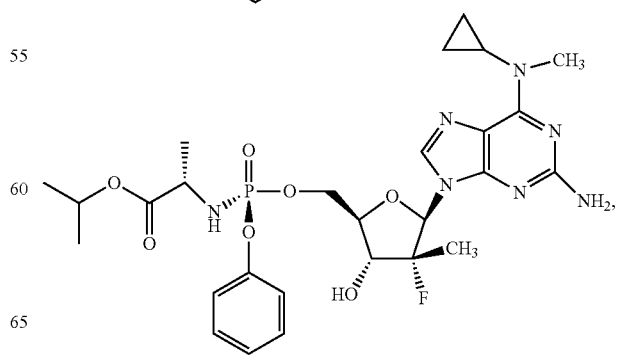

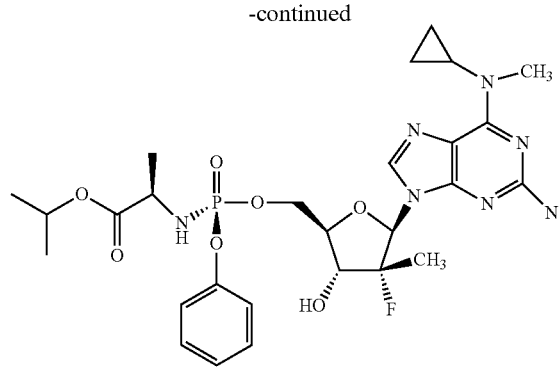
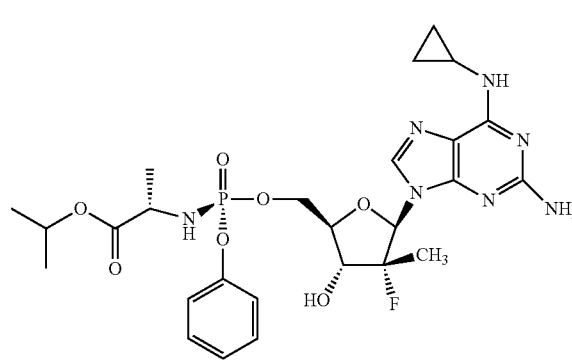
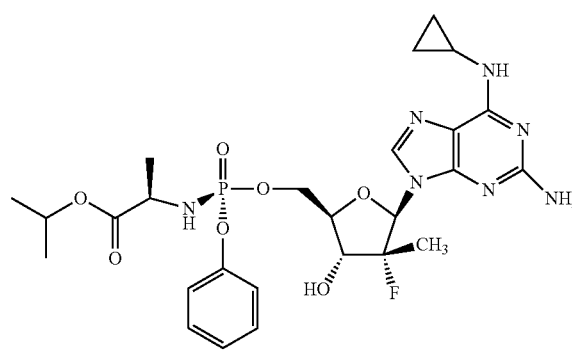
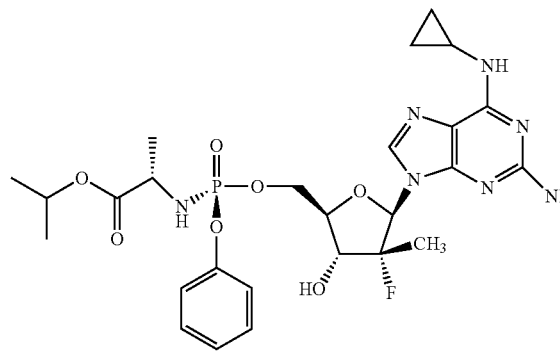
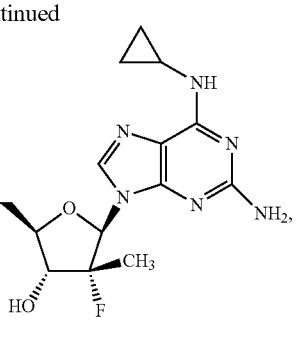
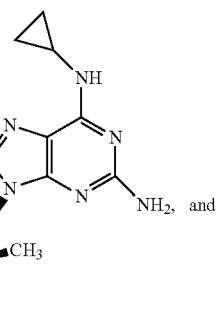
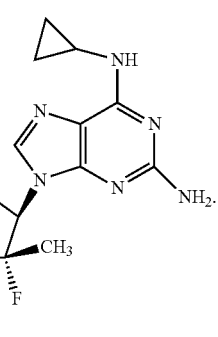
In one embodiment, the use of an effective amount of a compound of Formula III or a pharmaceutically acceptable salt thereof, for the treatment of an infection of an RNA virus in a host, including a human in need thereof is provided. Non-limiting examples of thiophosphoramidates of Formula III include, but are not limited to:
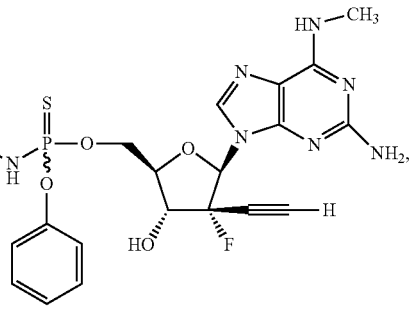

141
-continued
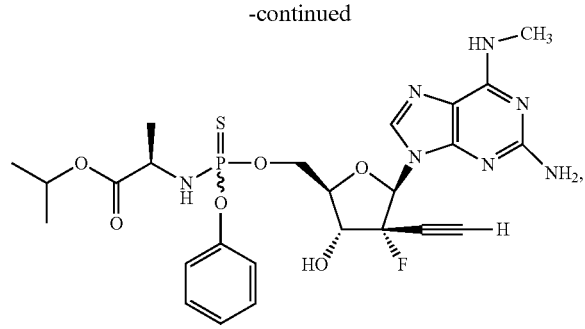
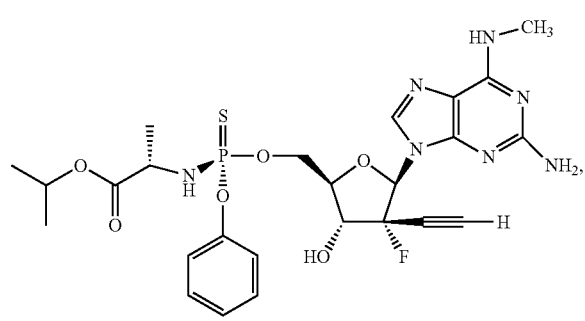
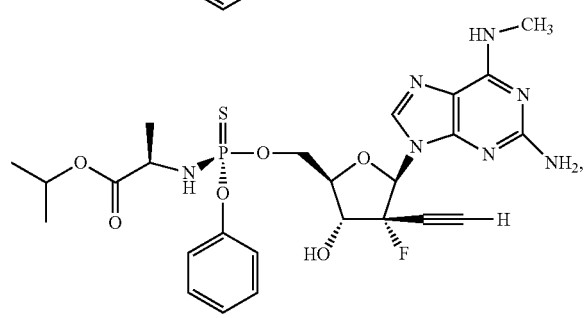
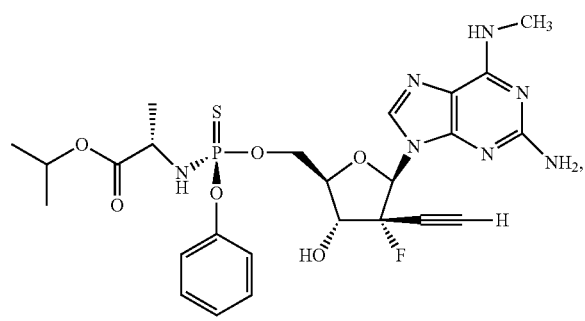
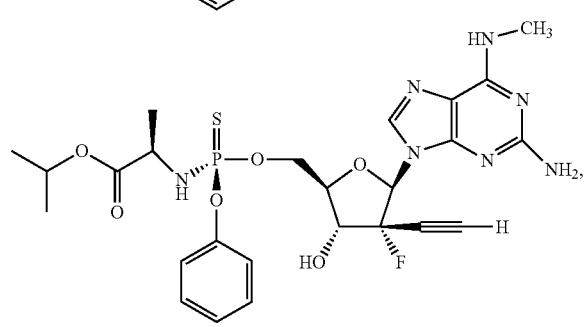
142
-continued
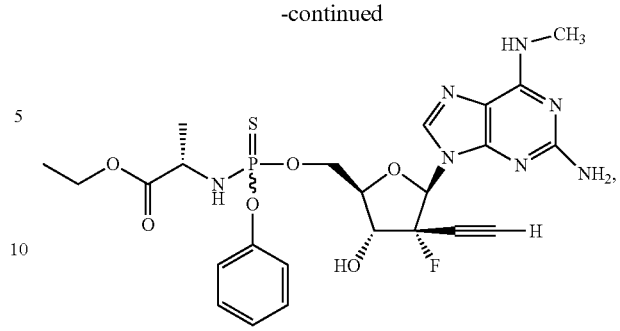
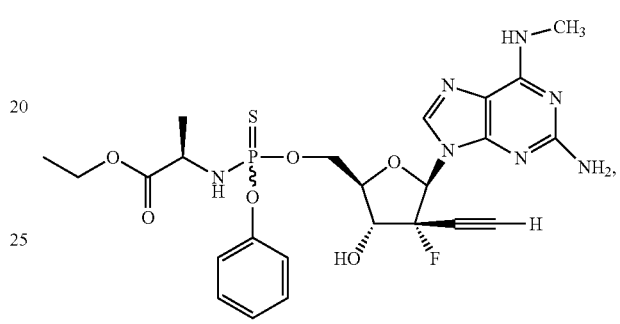
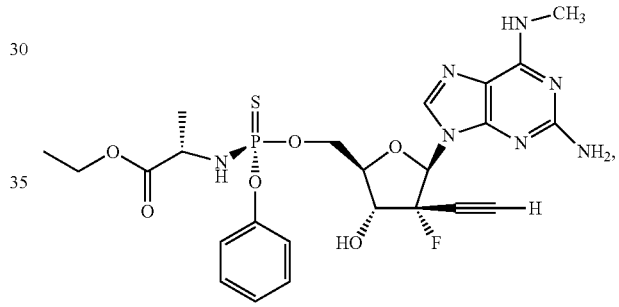
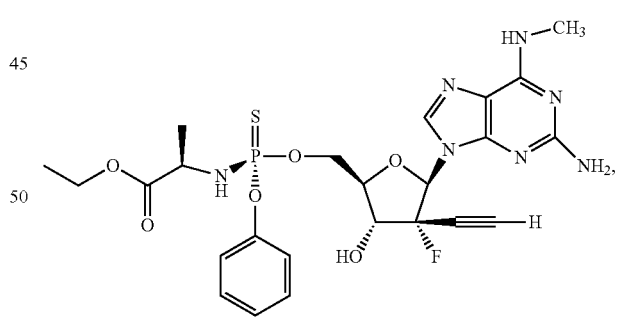
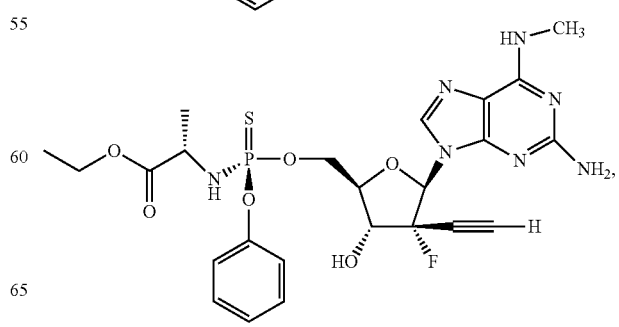

143
-continued
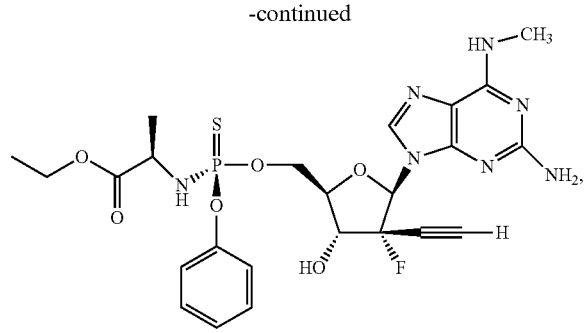
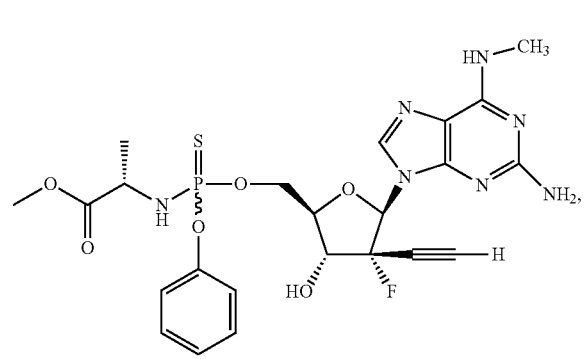
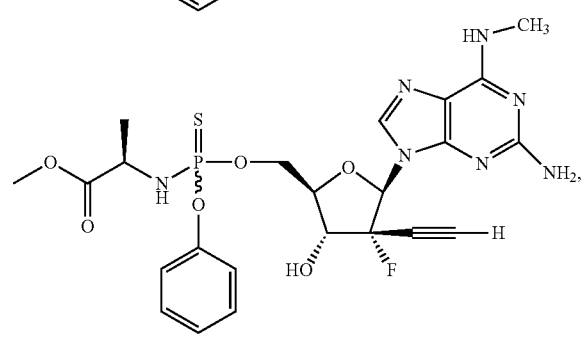
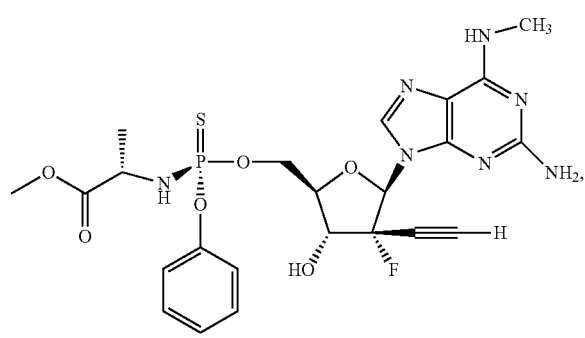
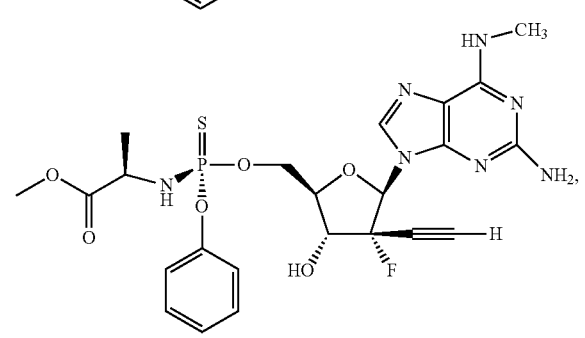
144
-continued
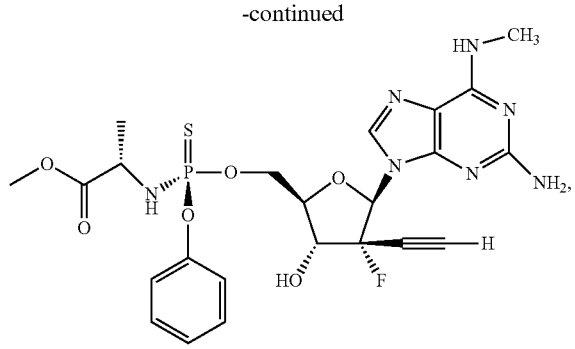
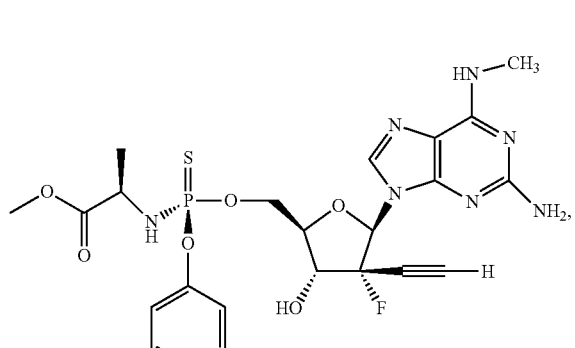
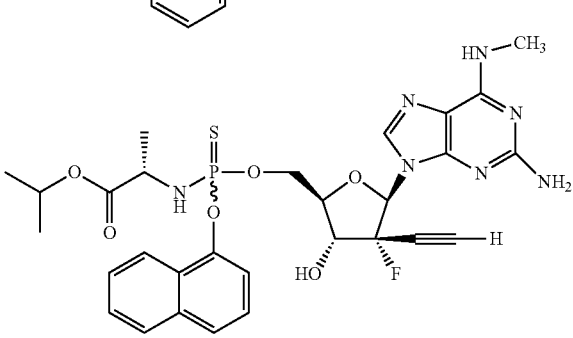
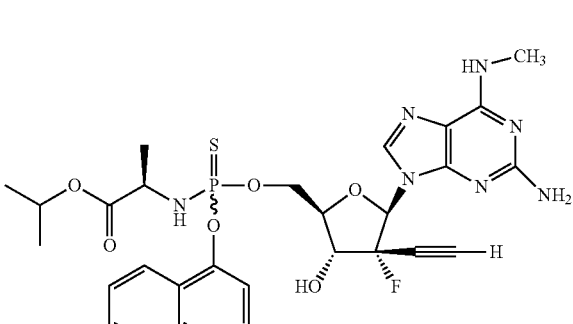
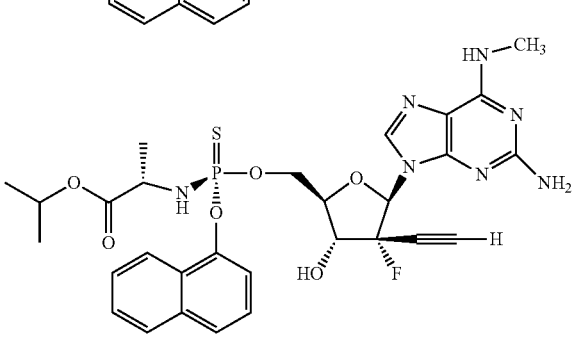

145
-continued
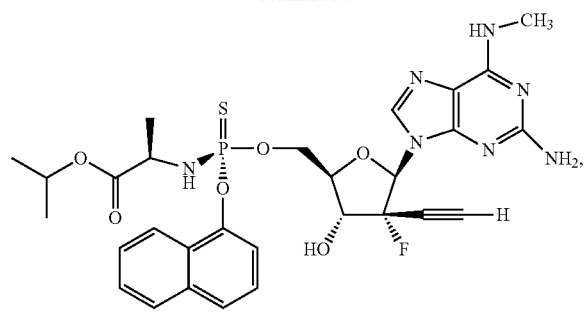
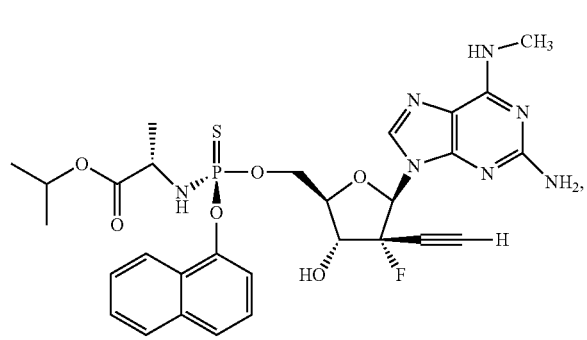
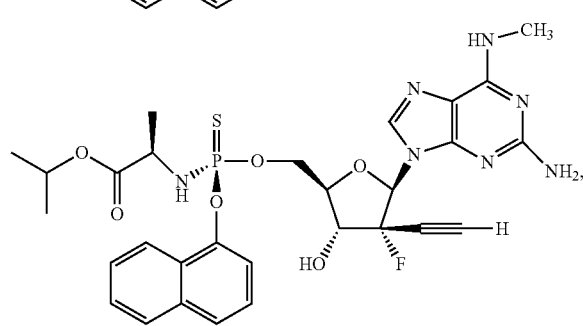
146
-continued
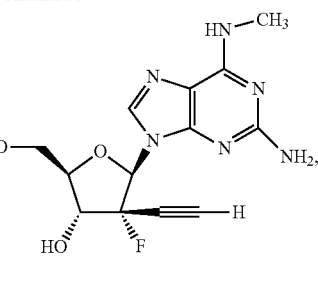
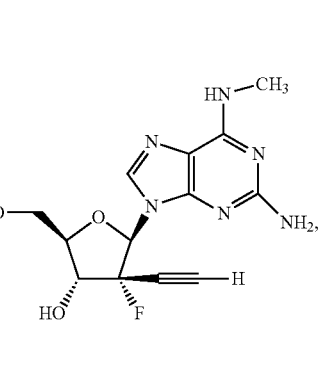
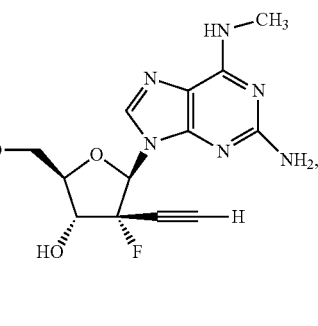
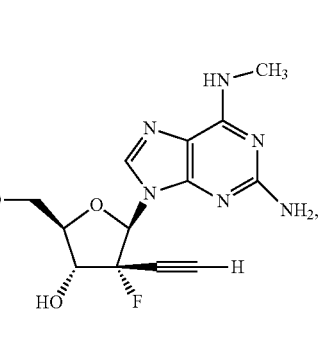
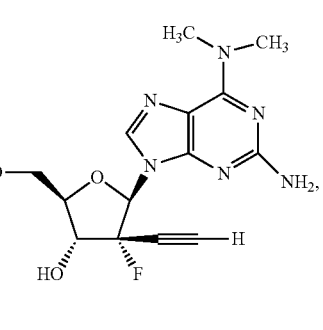

147
-continued
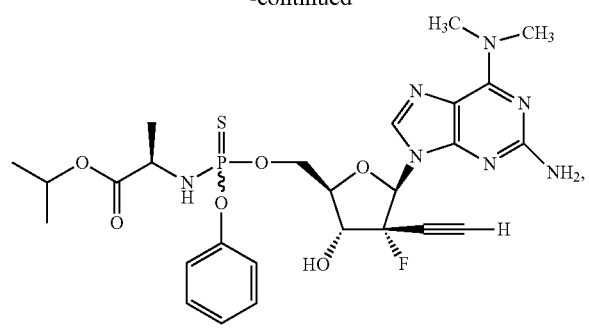
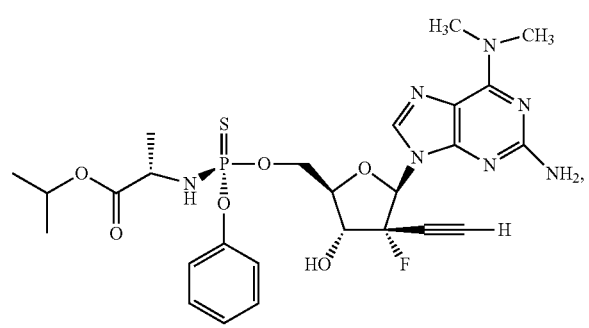
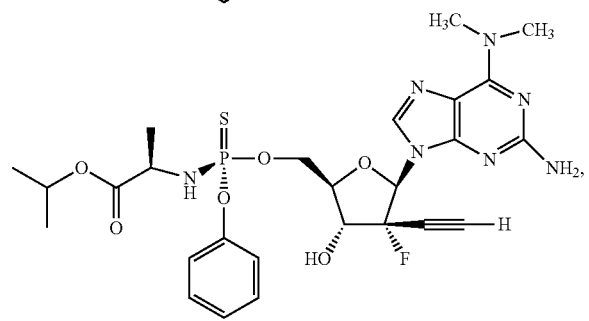
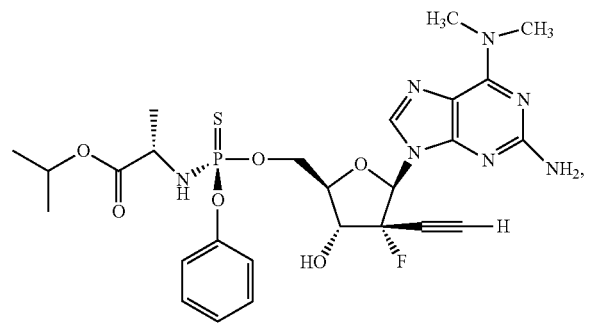
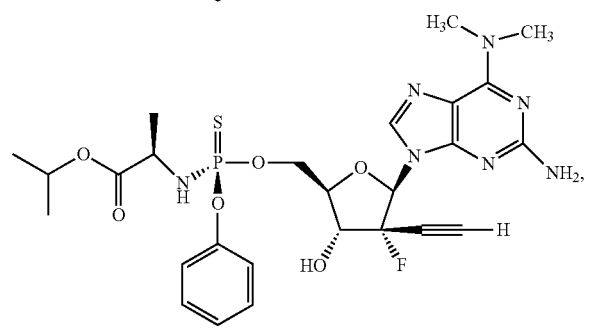
148
-continued
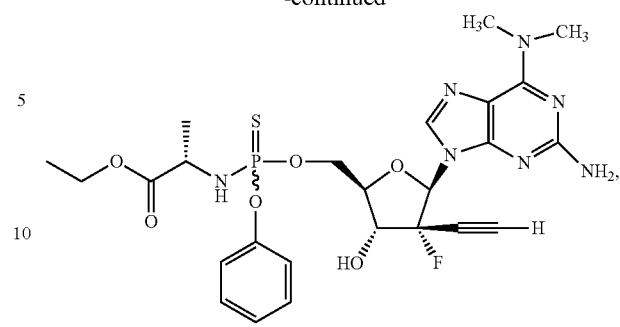
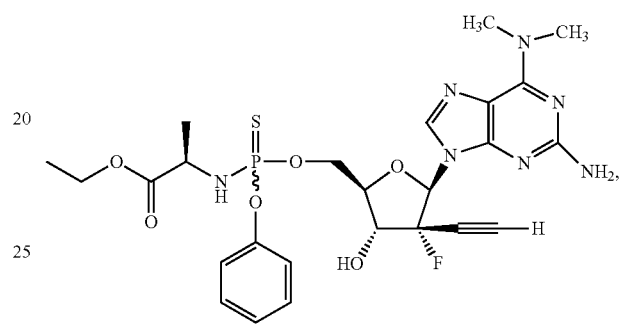
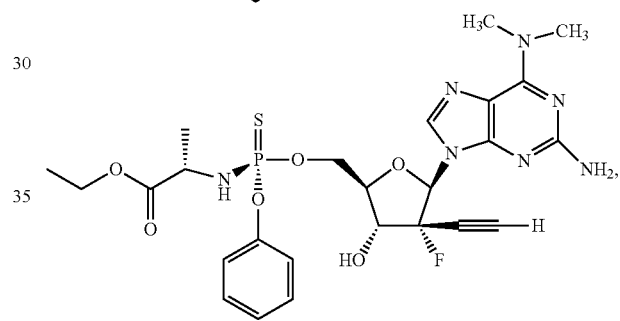
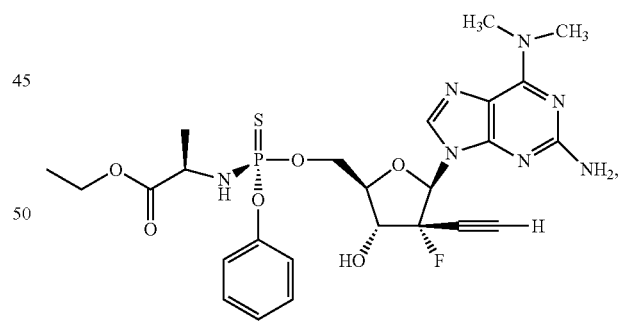
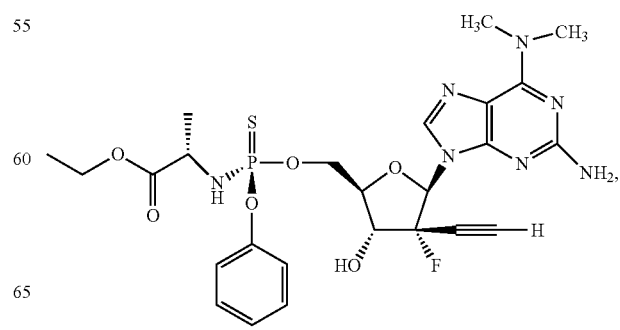

149
-continued
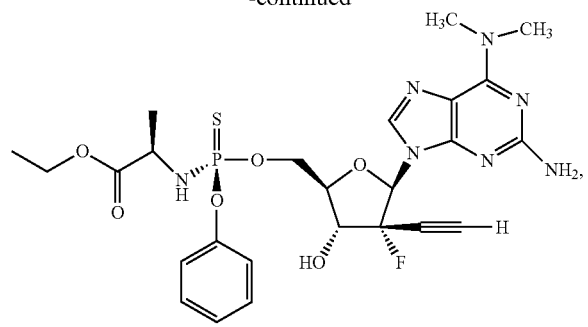
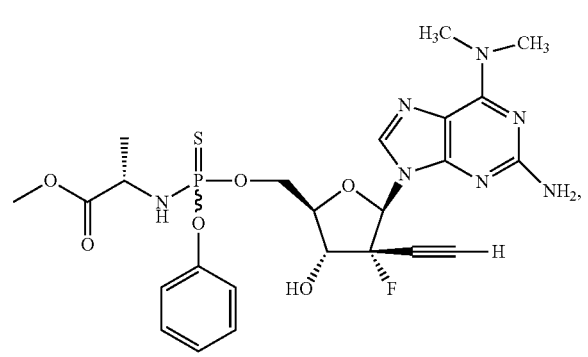
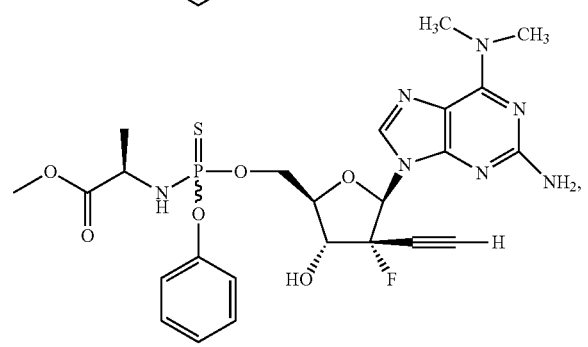
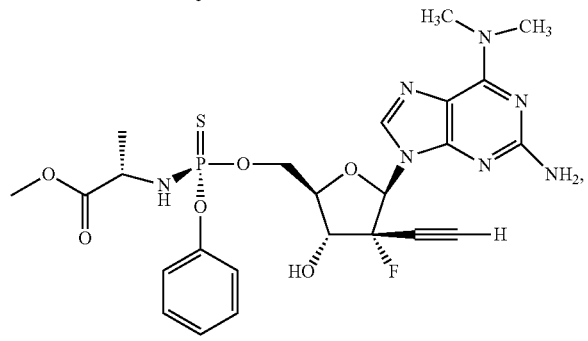
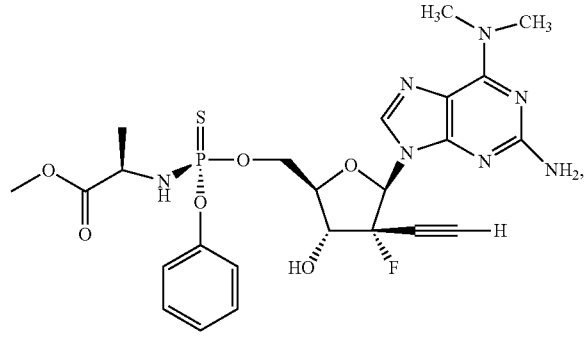
150
-continued
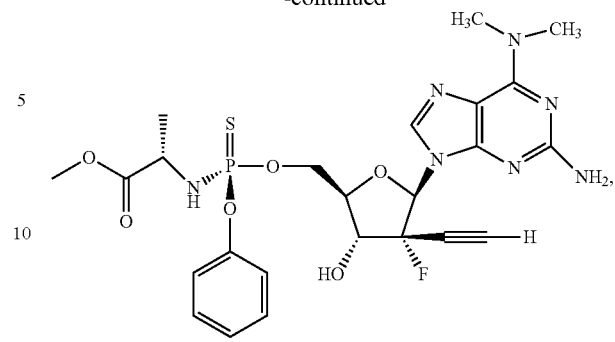
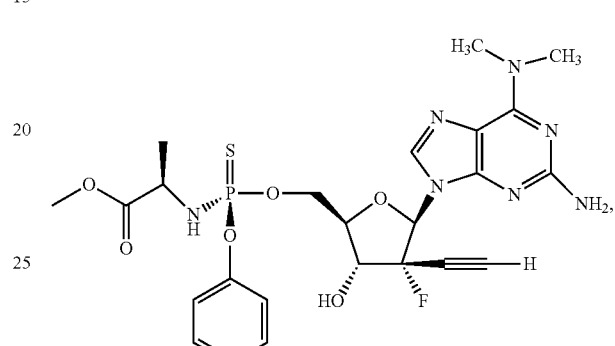
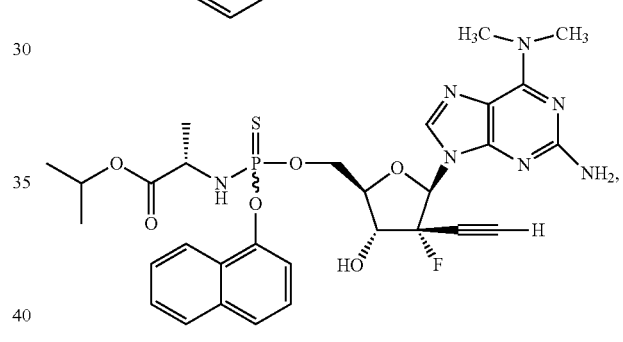
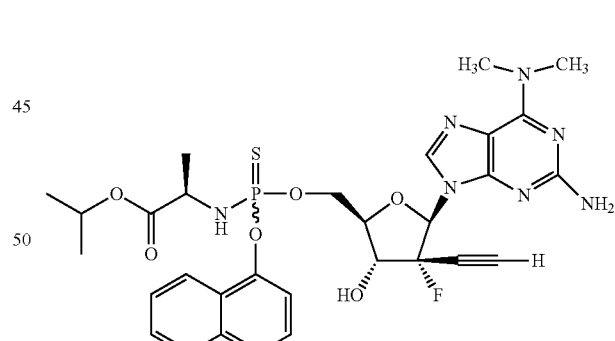
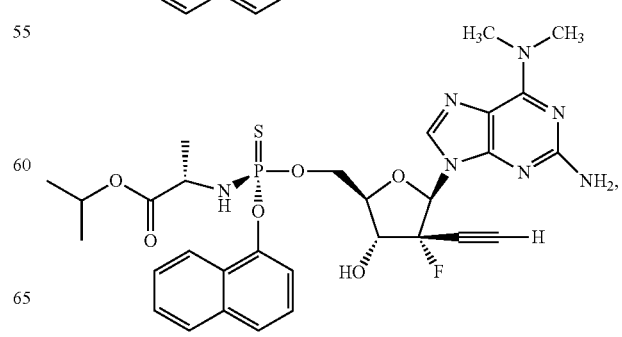

151
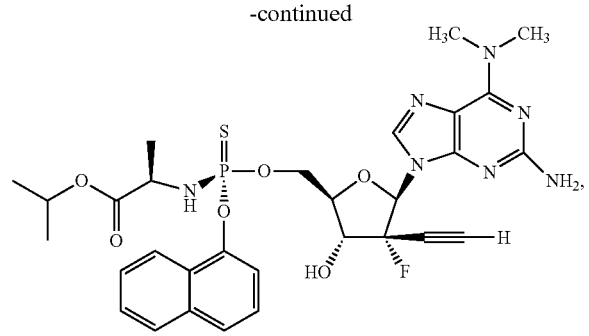
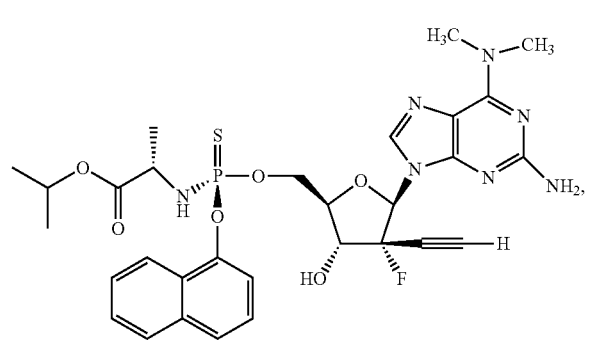
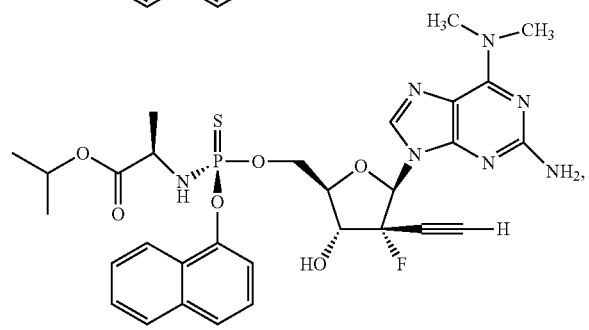
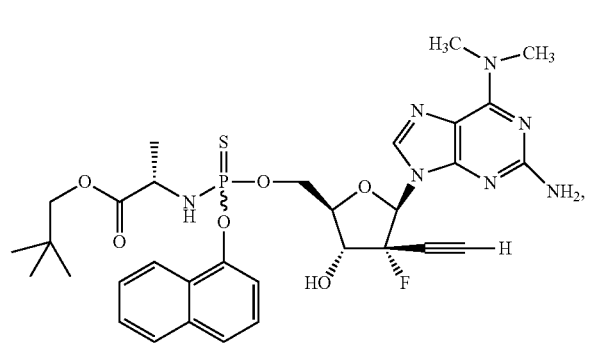
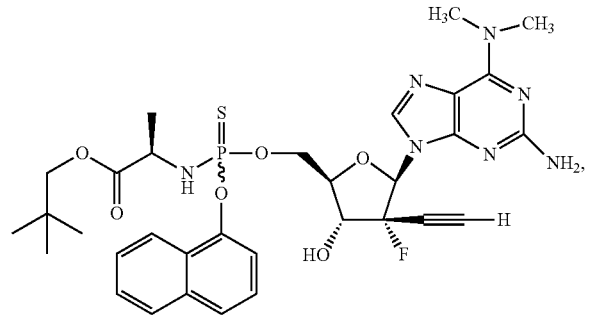
152
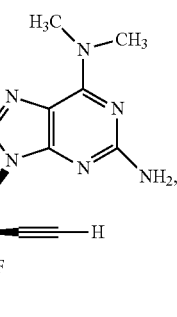
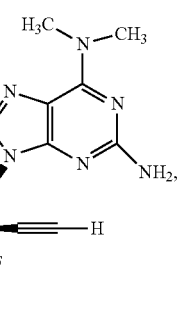
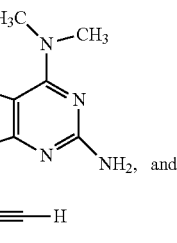
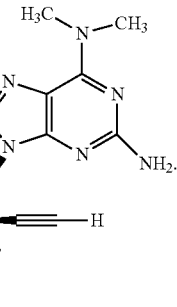
In an alternative embodiment, the use of an effective amount of a compound of Formula III or a pharmaceutically acceptable salt thereof, for the treatment of an infection of an RNA virus in a host, including a human in need thereof is provided. Additional non-limiting examples of thiophosphoramidates of Formula III include, but are not limited to:

153
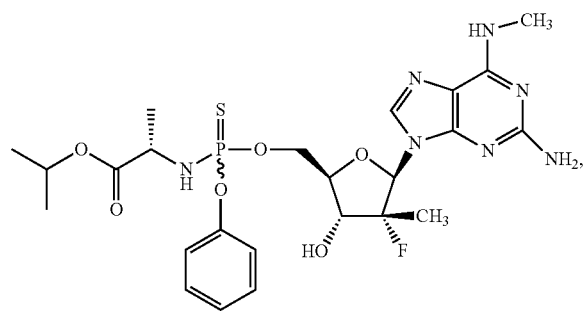
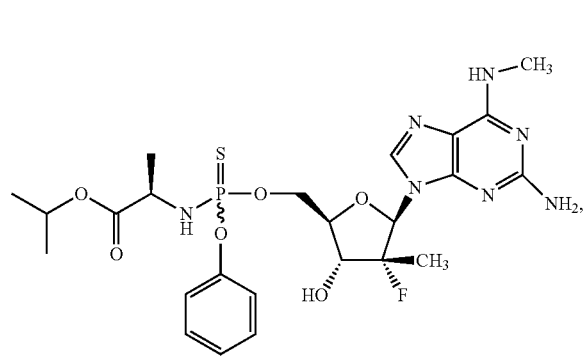
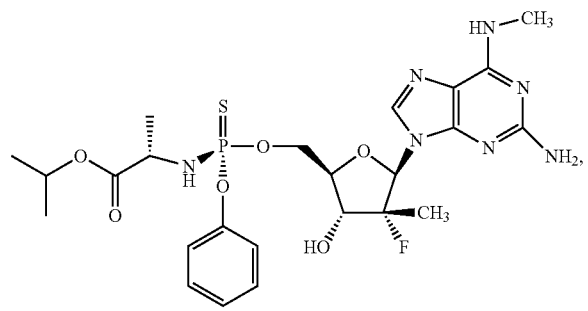
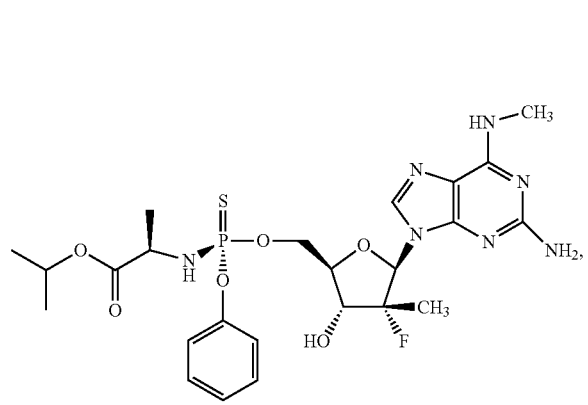
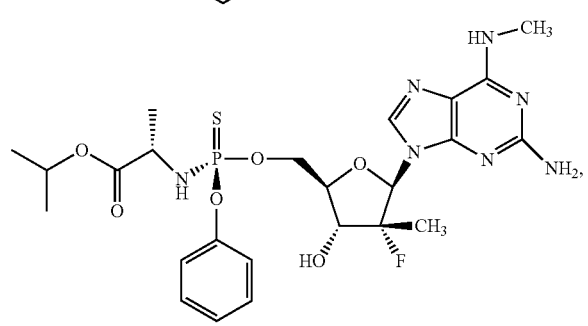
154
-continued
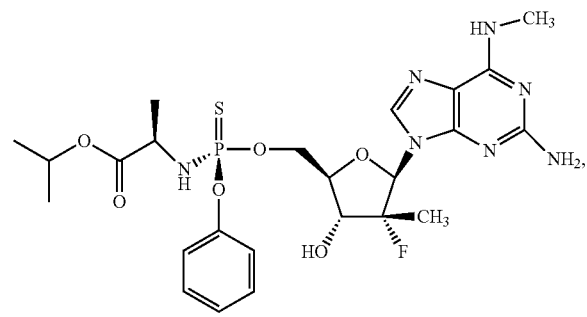
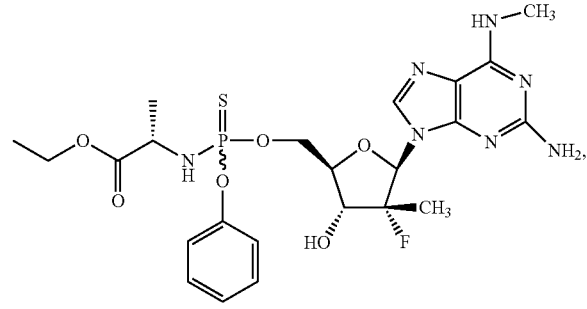
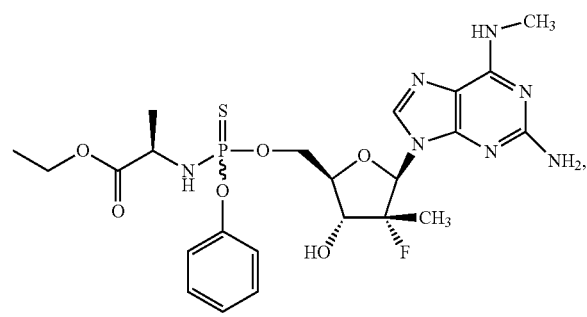
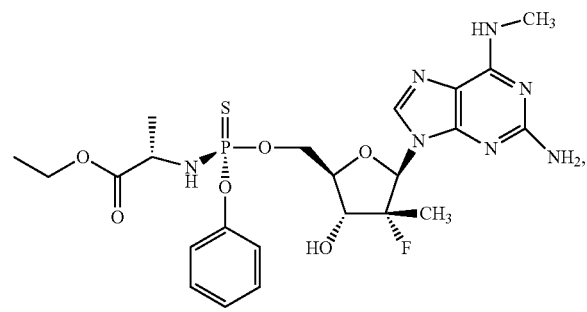
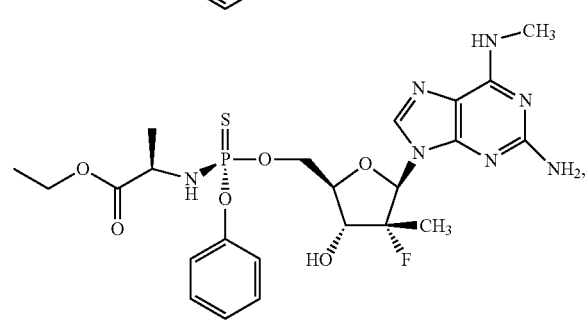

-continued
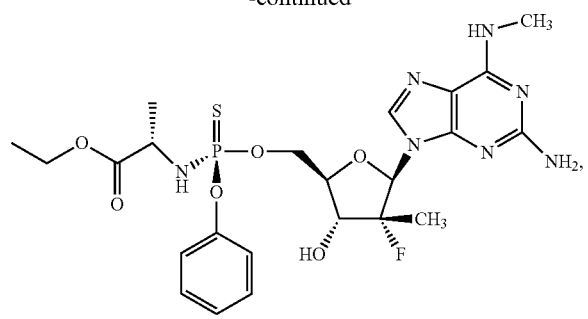
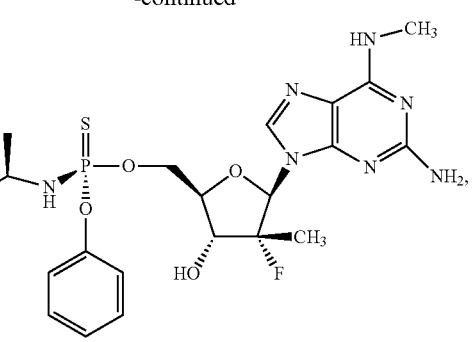
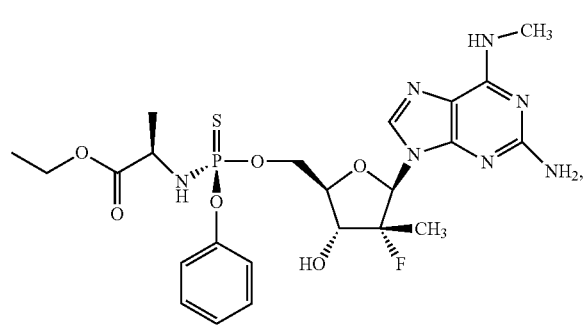
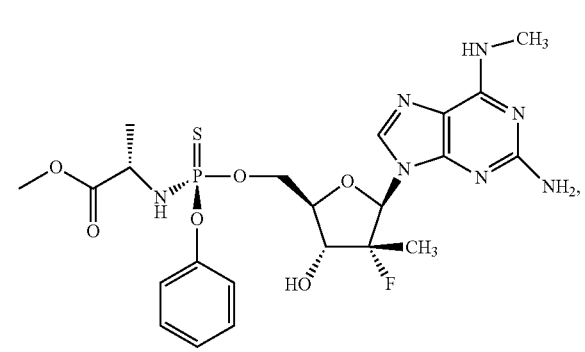
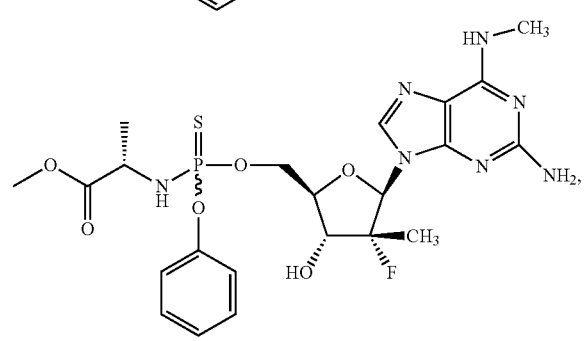
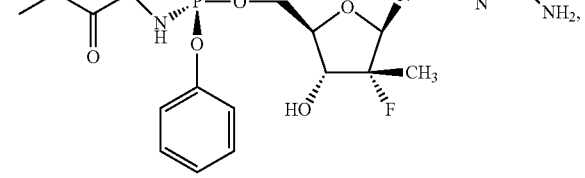
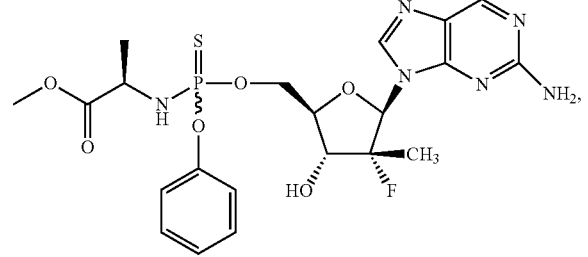
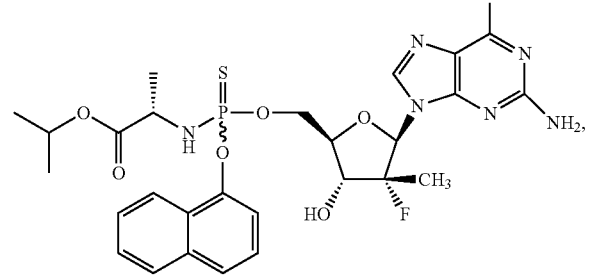
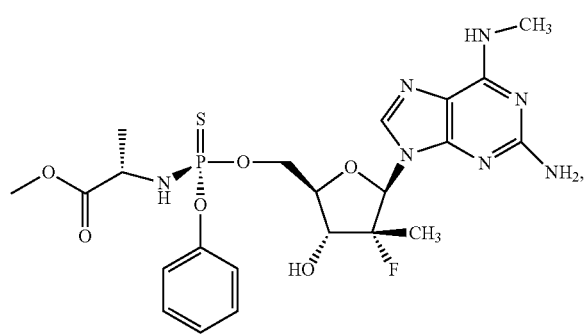
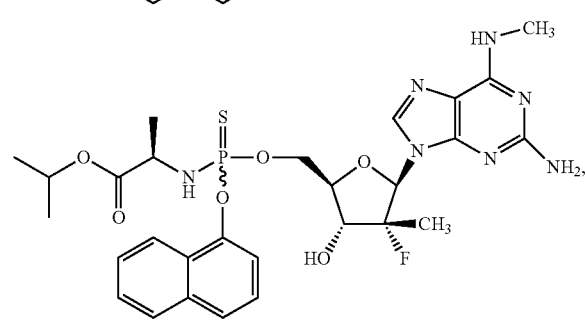

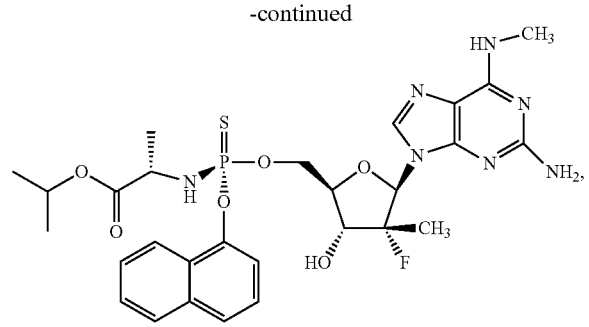
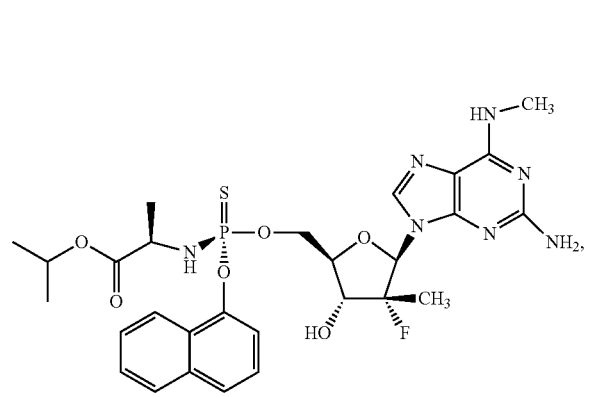
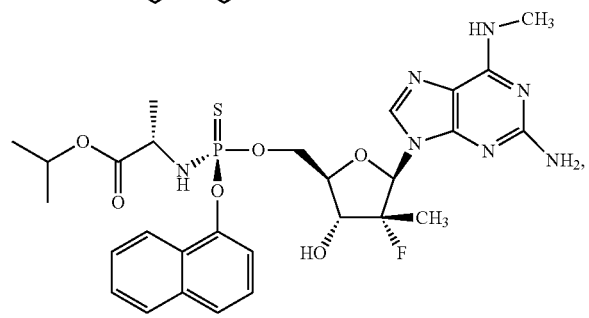
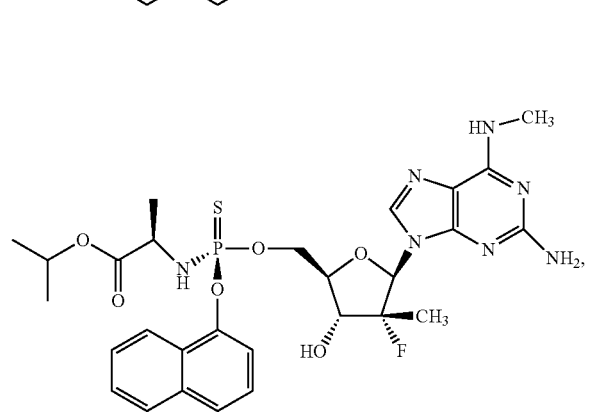
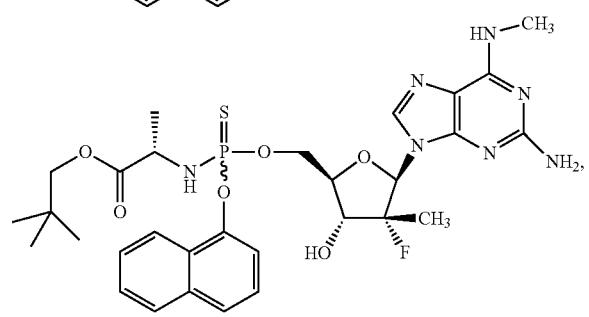
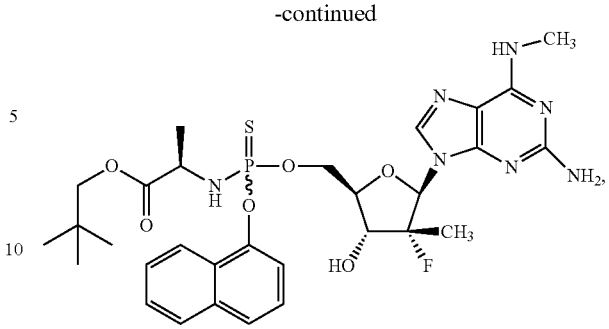
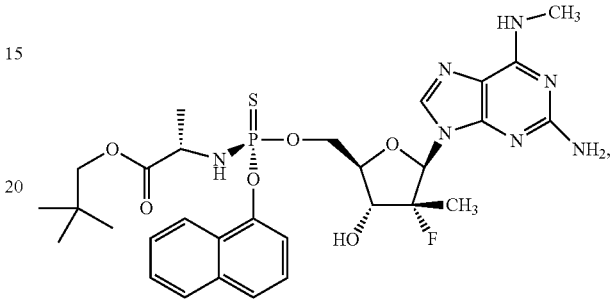
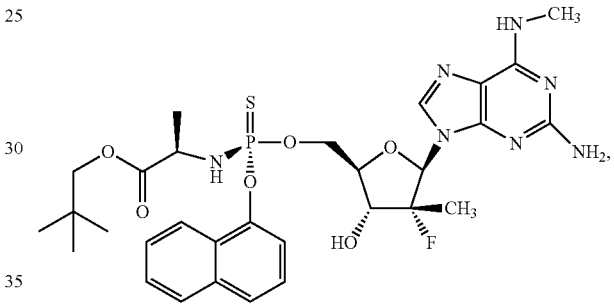
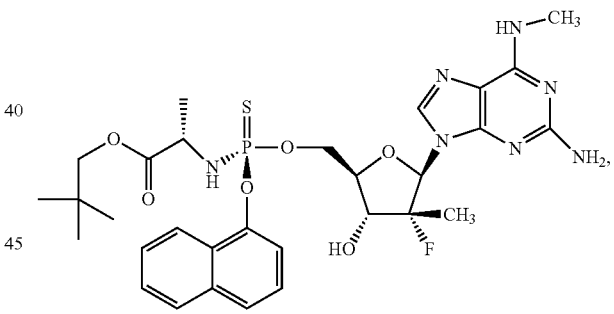
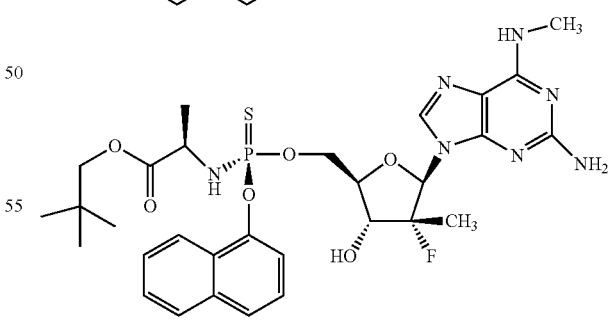
In one embodiment, the use of an effective amount of a compound of Formula I or a pharmaceutically acceptable salt thereof, for the treatment of an infection of an RNA virus in a host, including a human in need thereof is provided. Non-limiting examples of stabilized phosphate prodrugs of Formula I are illustrated below:

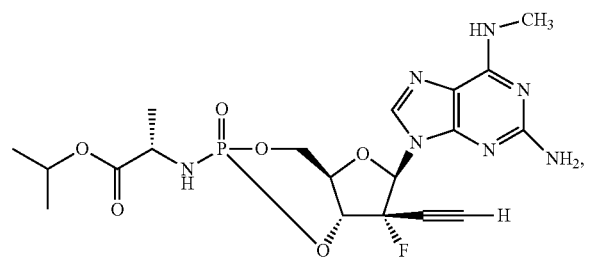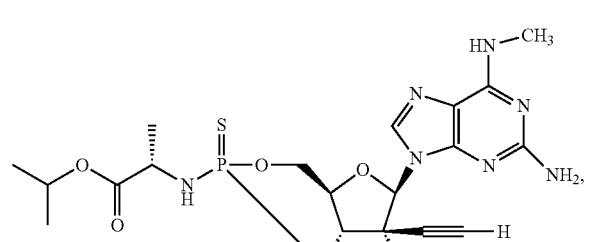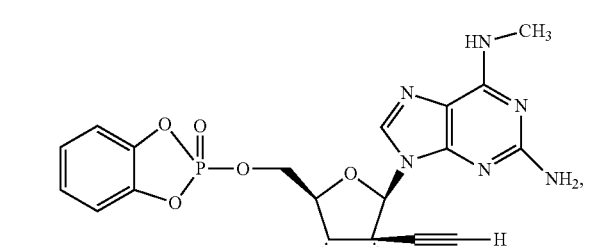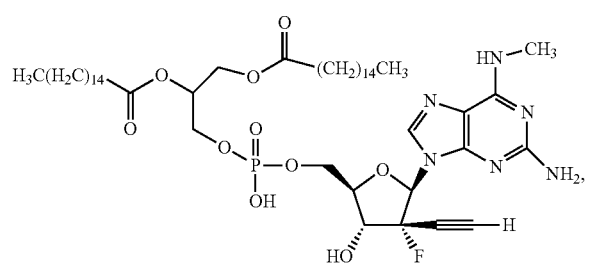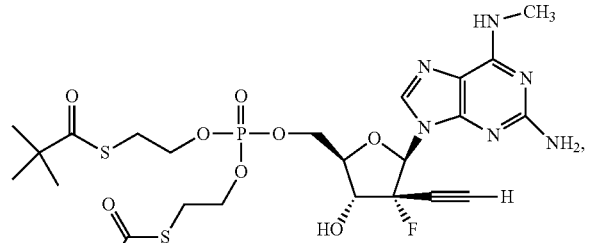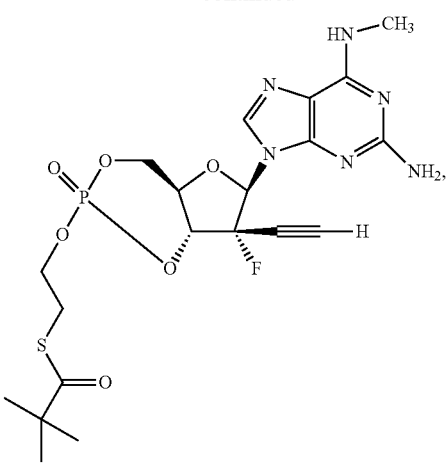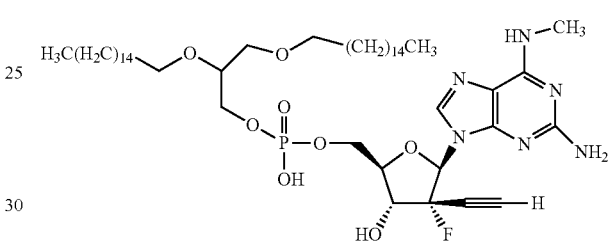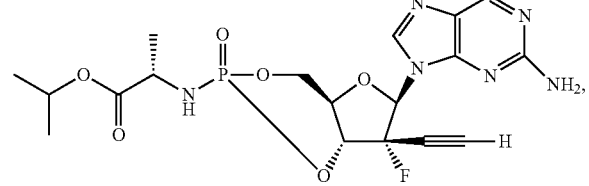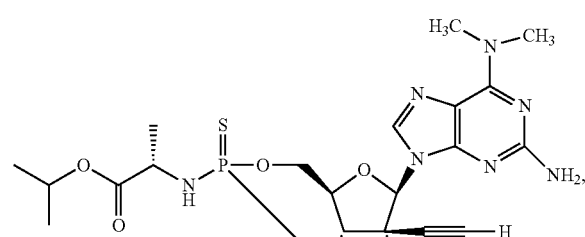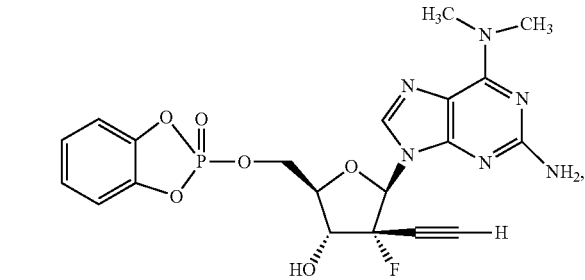

-continued
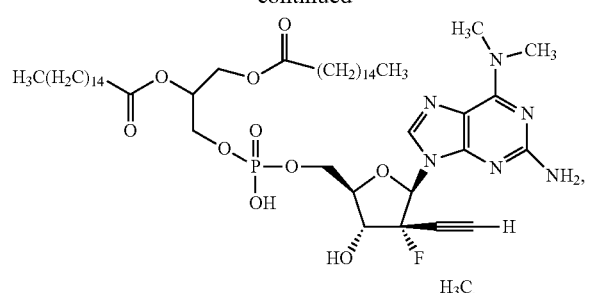
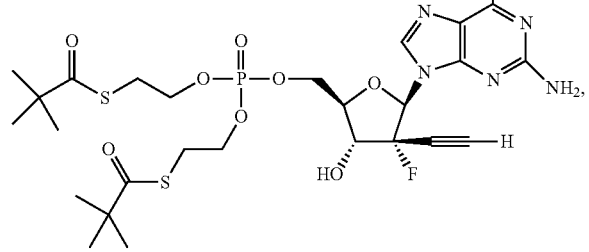
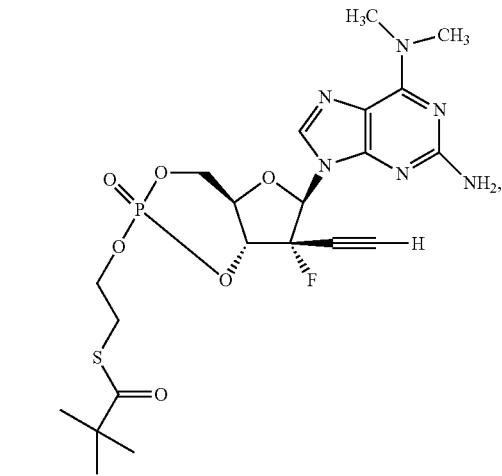
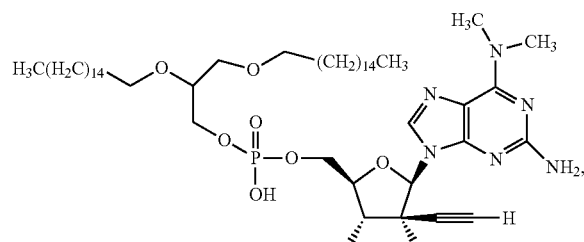
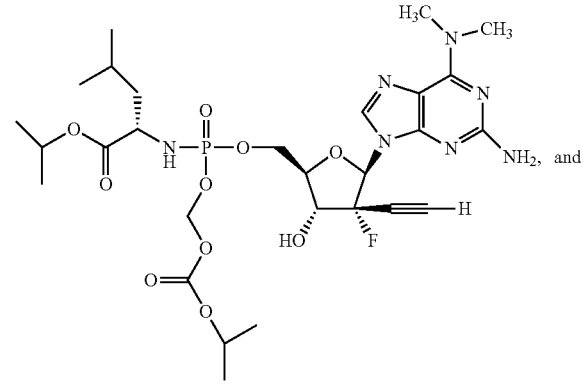
-continued
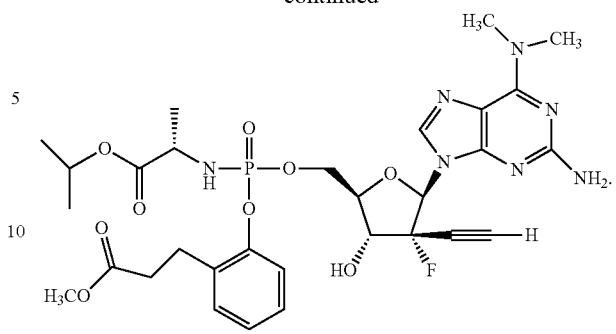
In one embodiment, the use of an effective amount of a compound of Formula II or a pharmaceutically acceptable salt thereof, for the treatment of an infection of an RNA virus in a host, including a human in need thereof is provided. Non-limiting examples of compounds of Formula II include:
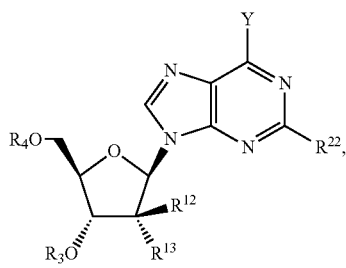
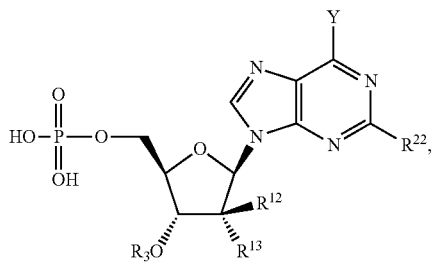
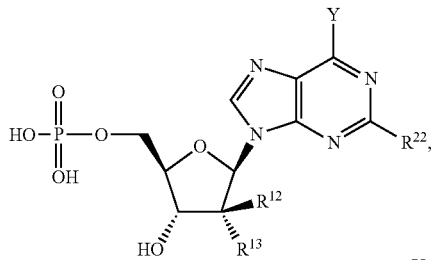
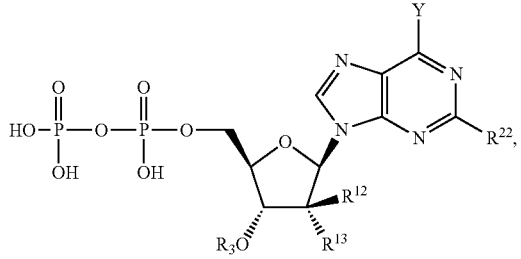

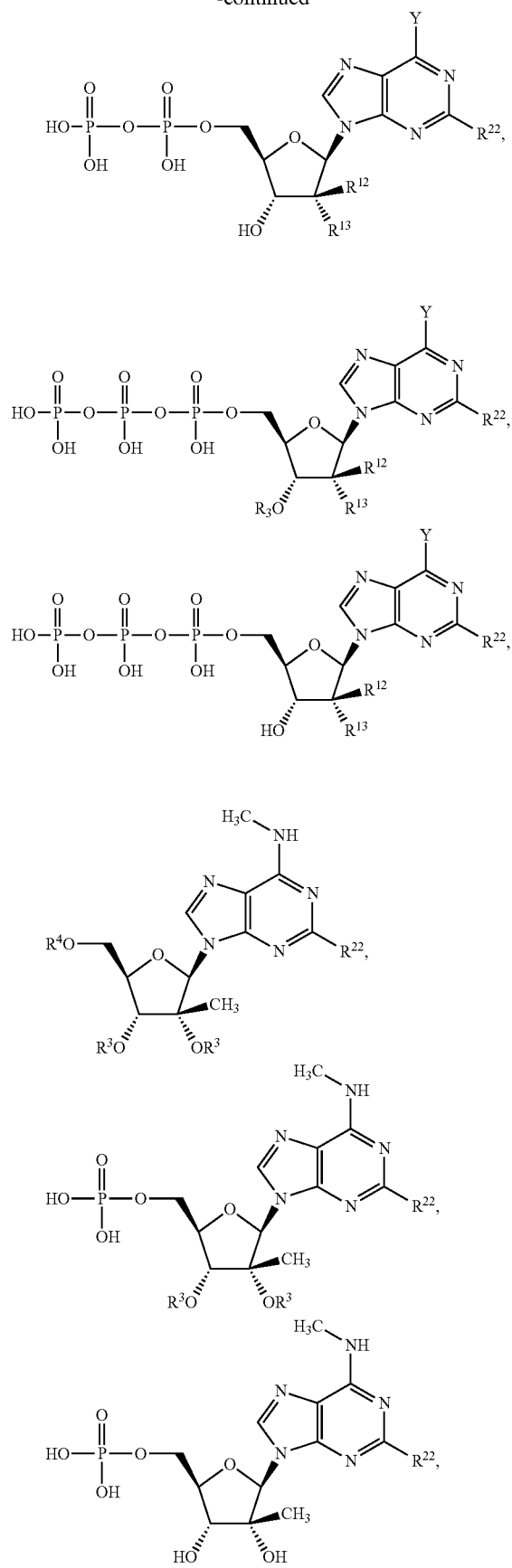
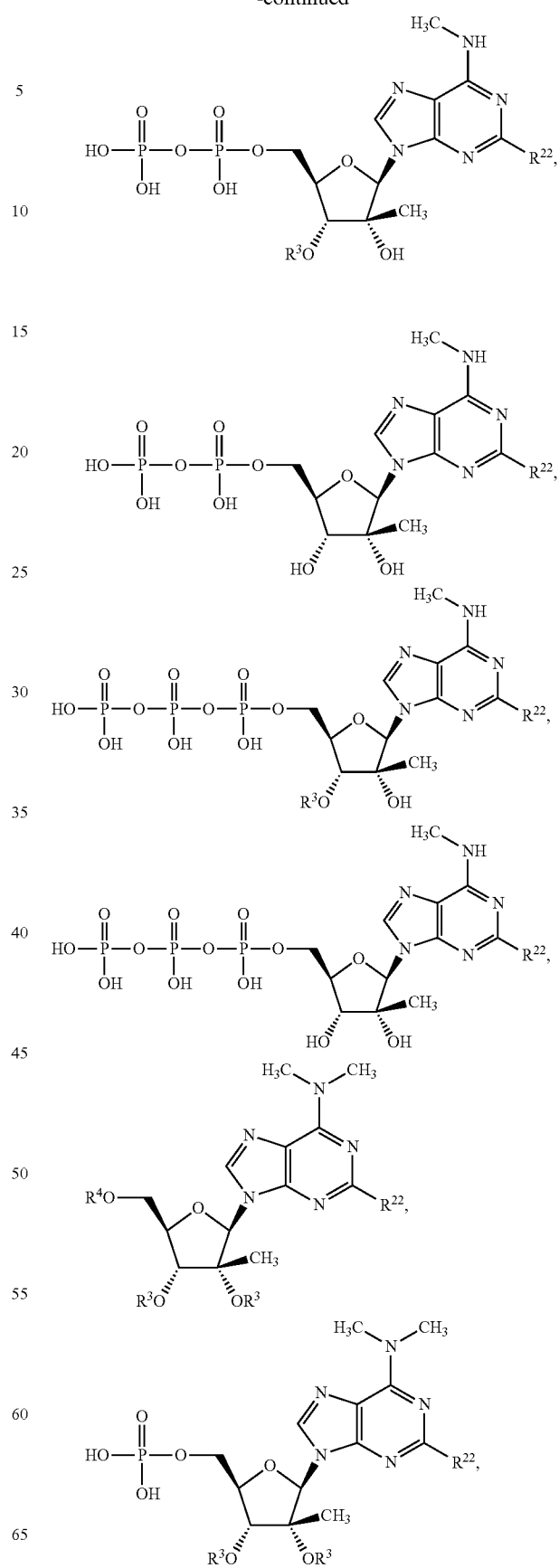

165
-continued
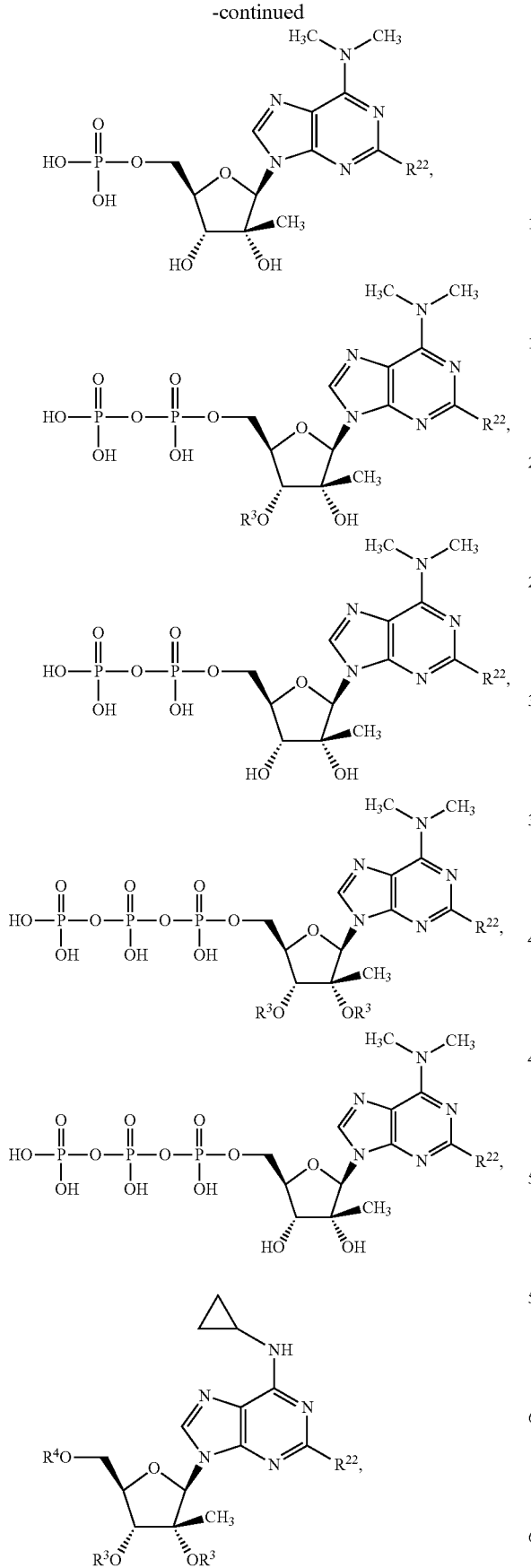
166
-continued
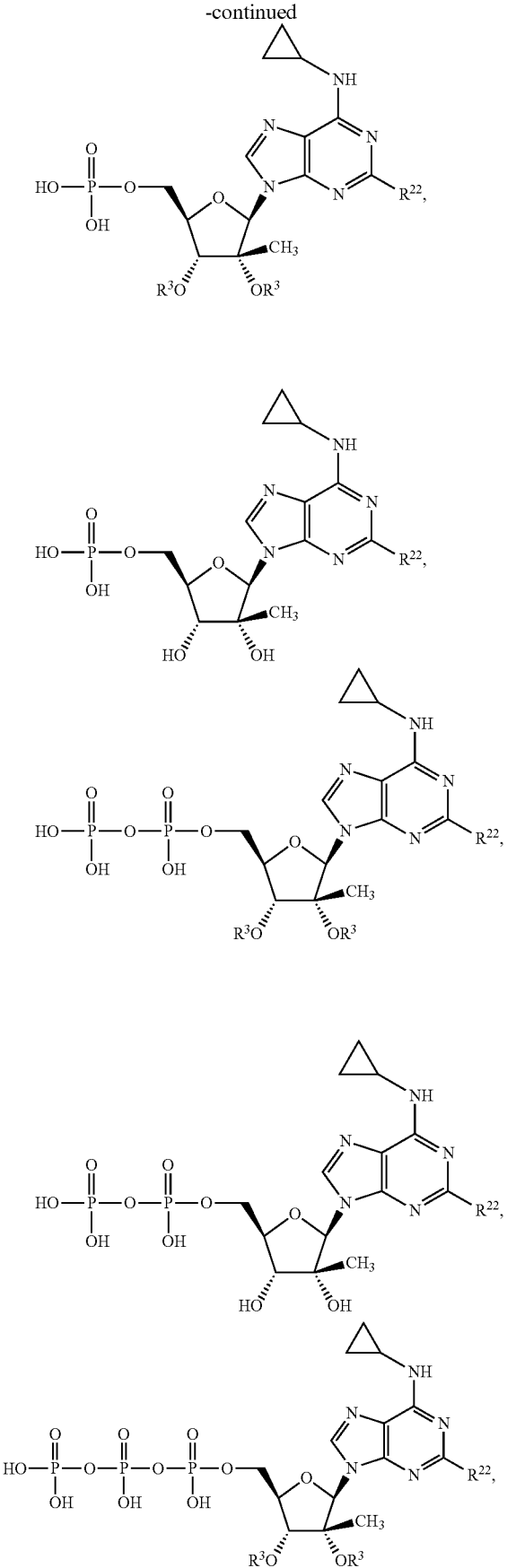

167
-continued
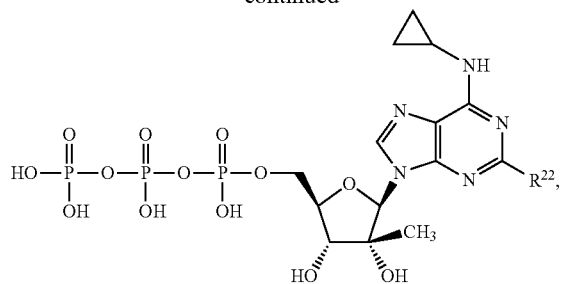
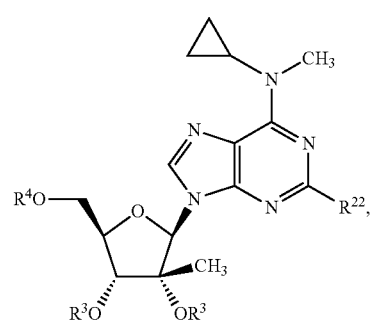
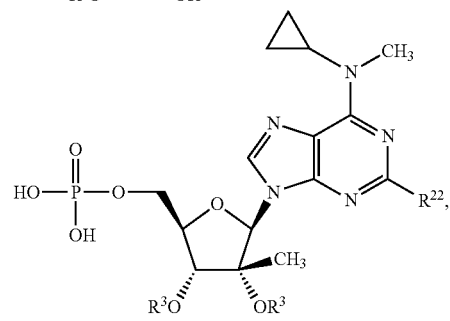
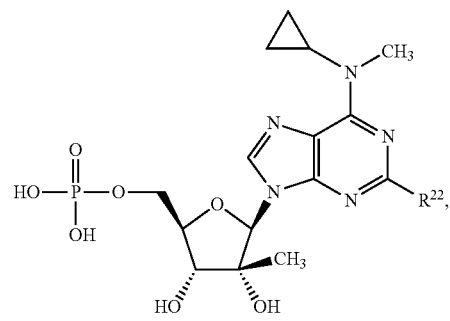
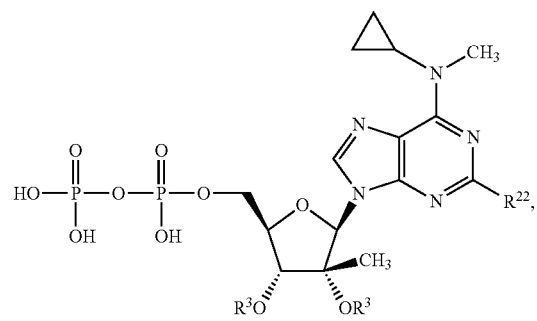
168
-continued
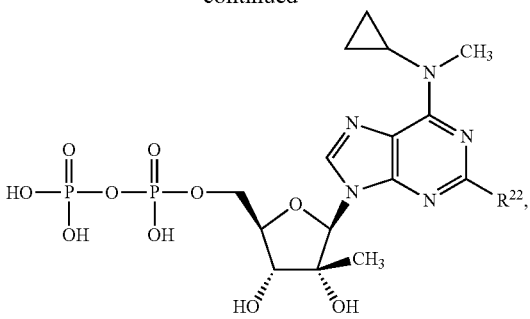
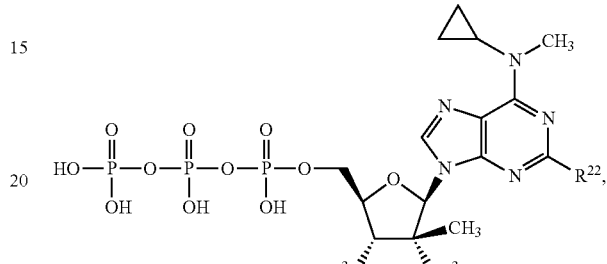
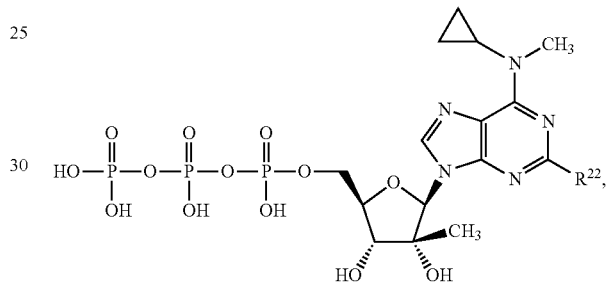
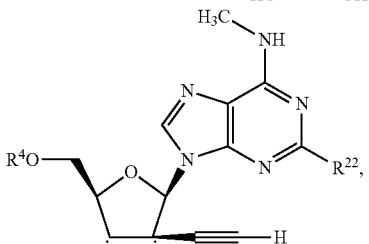
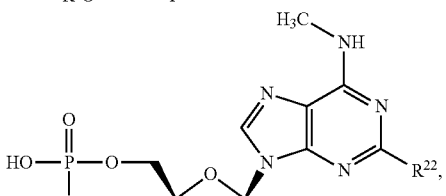
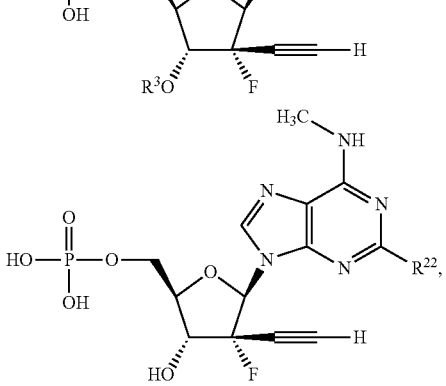

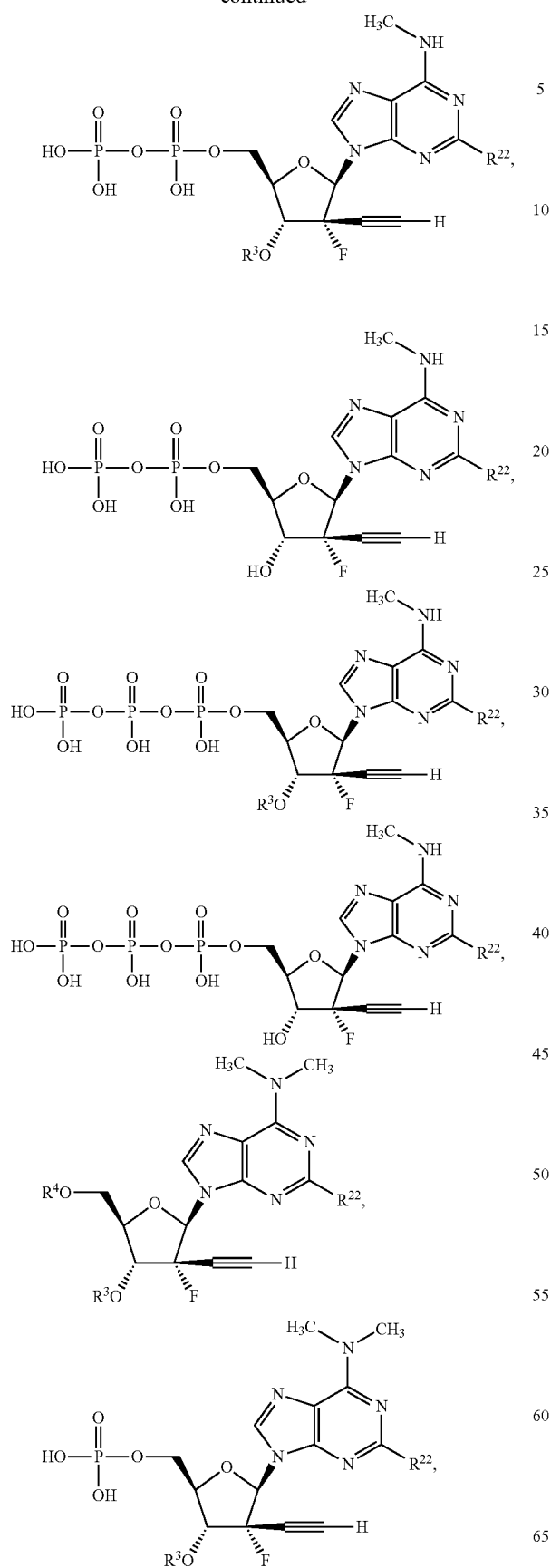

-continued
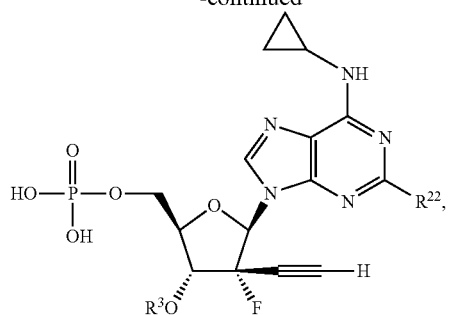
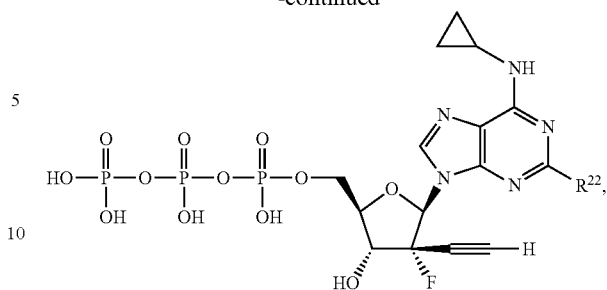
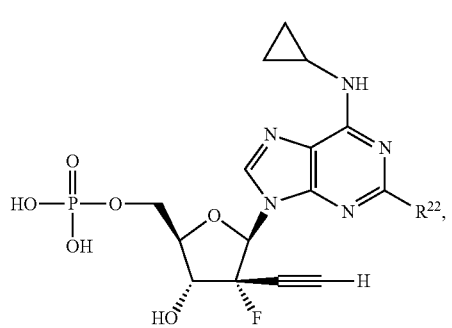
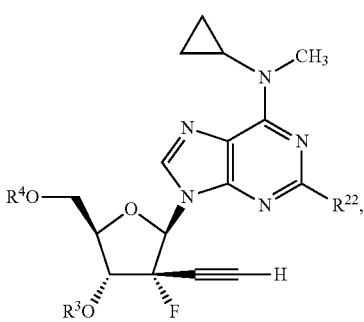
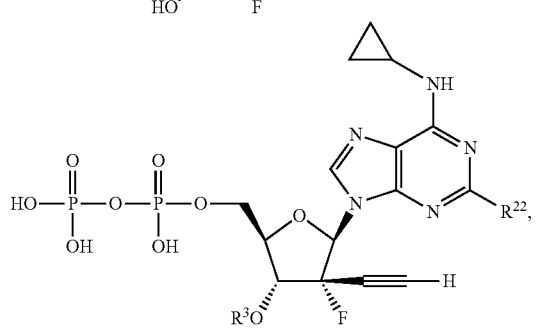
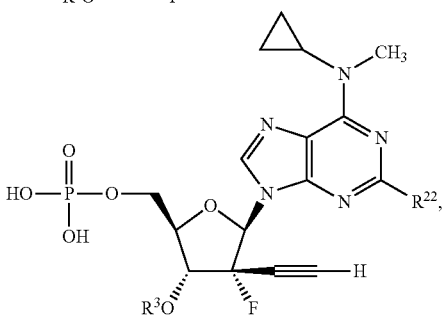
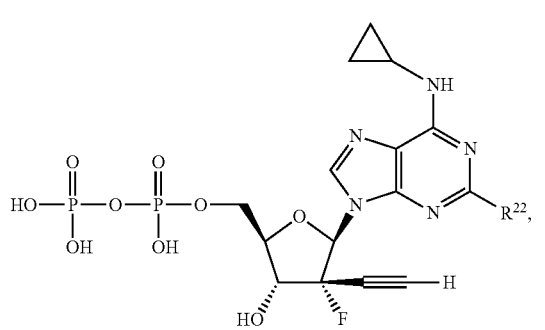
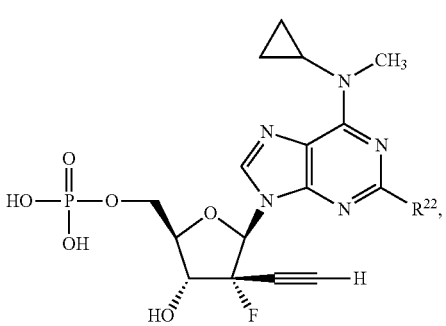
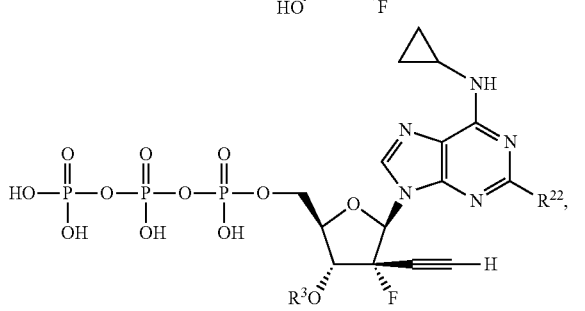
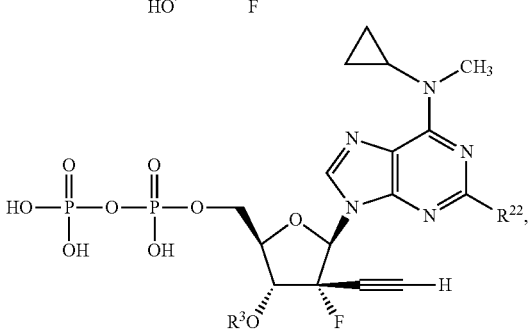

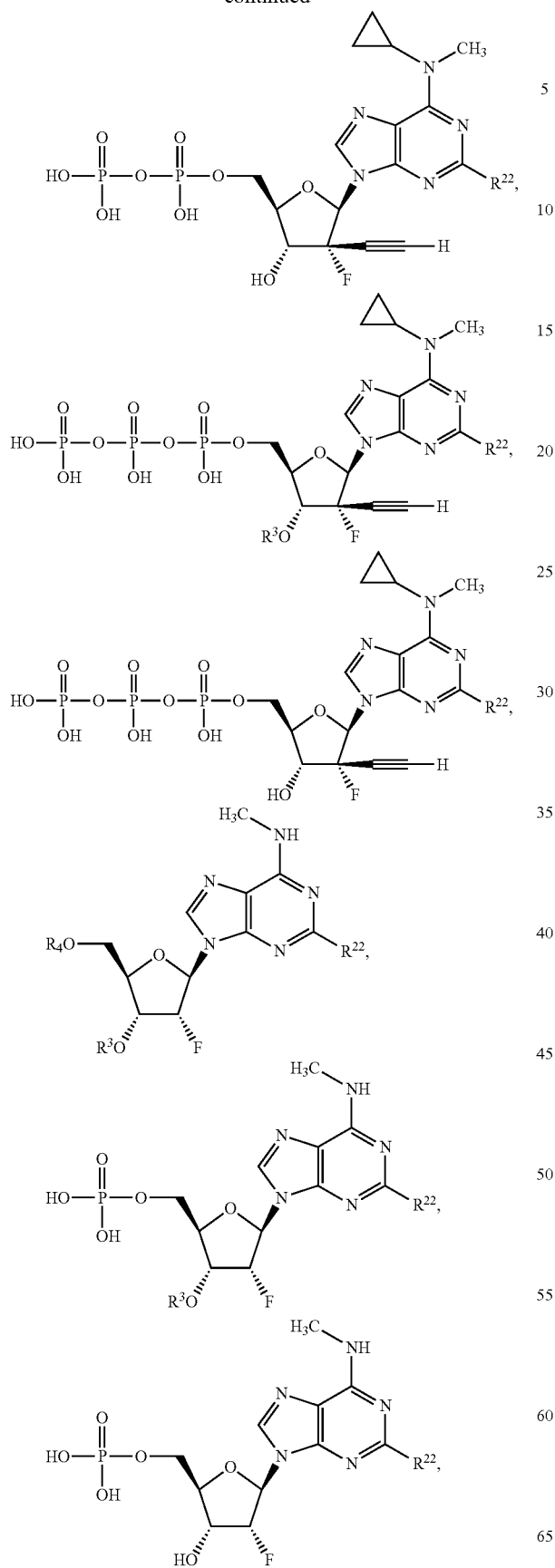
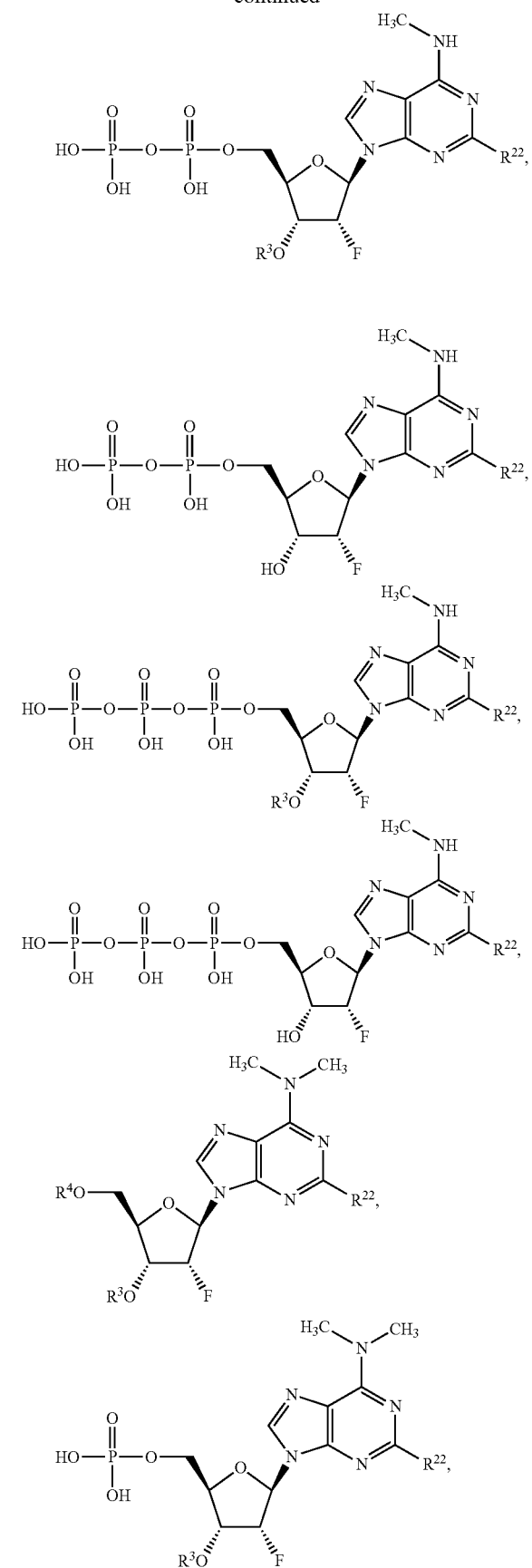

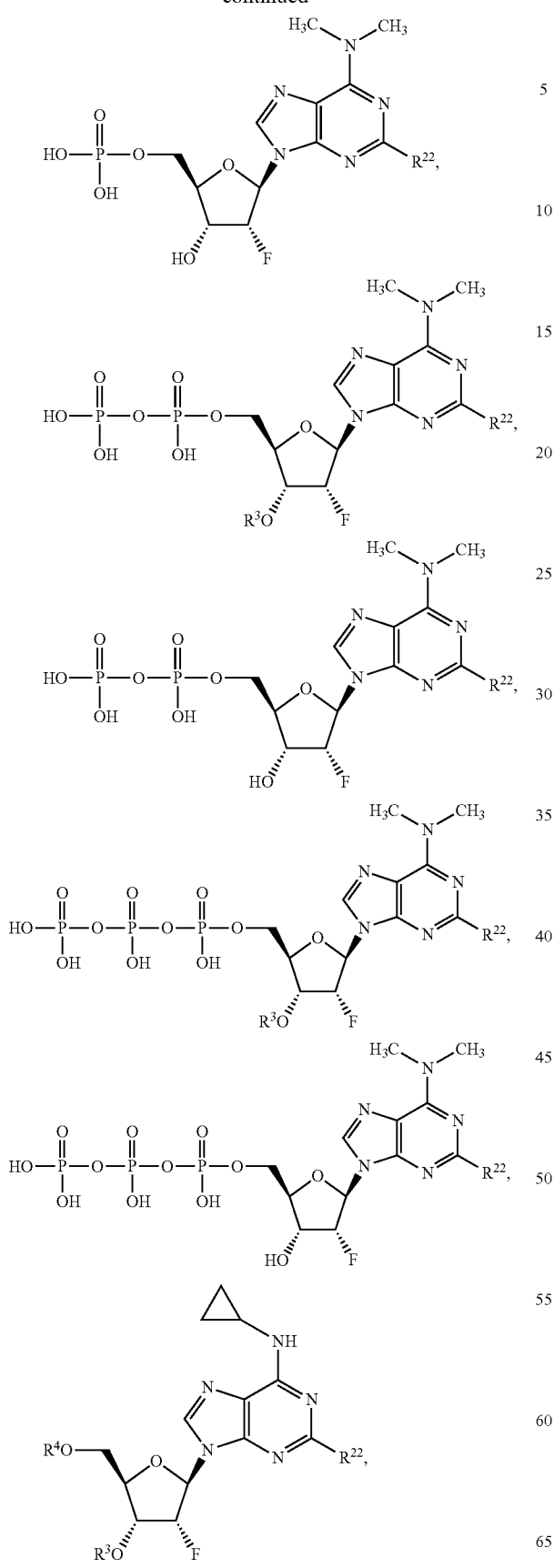
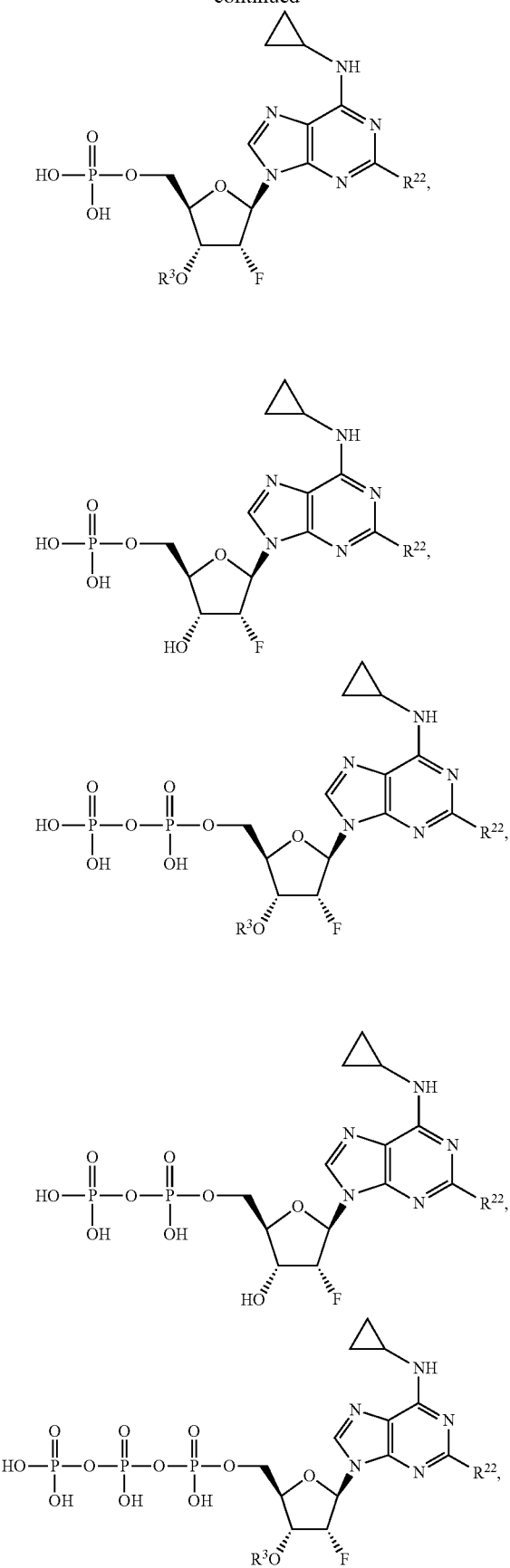

177
-continued
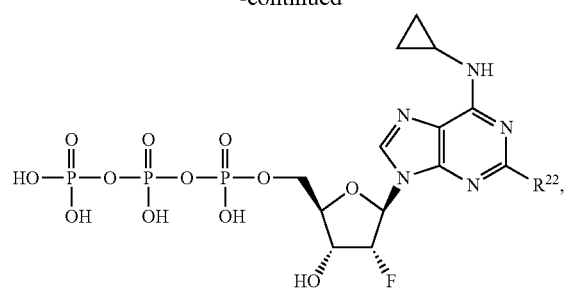
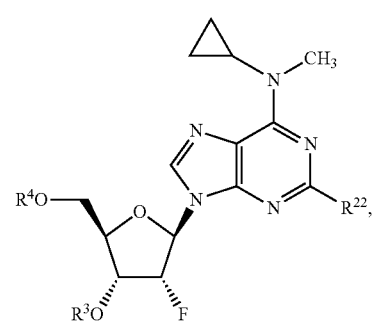
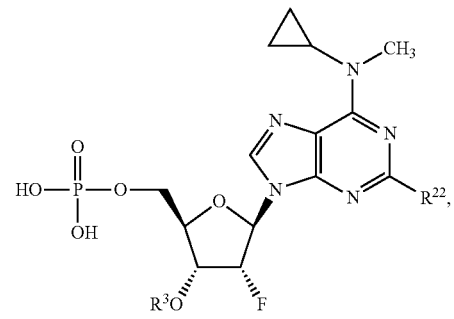
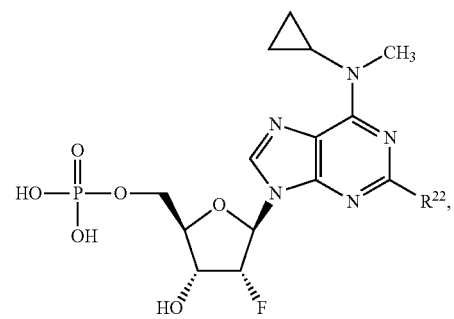
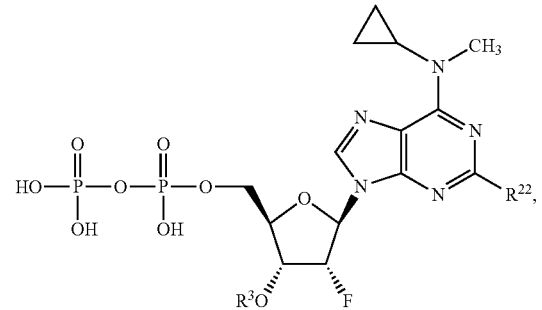
178
-continued
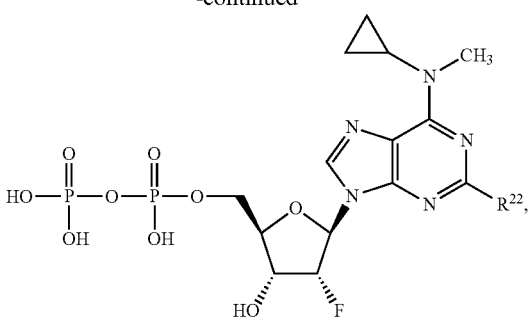
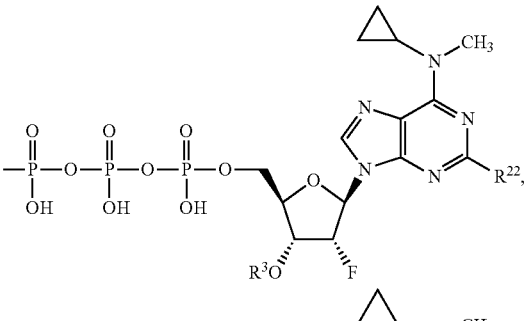
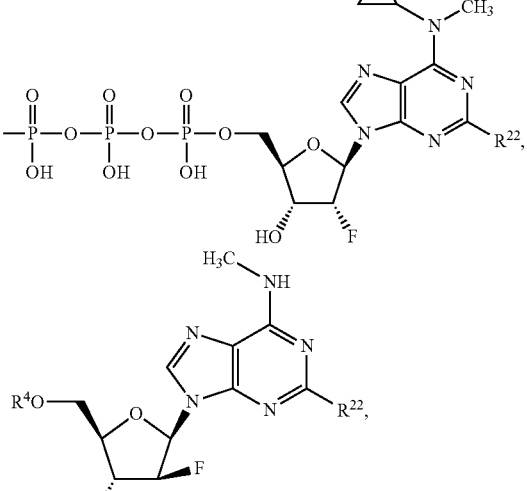
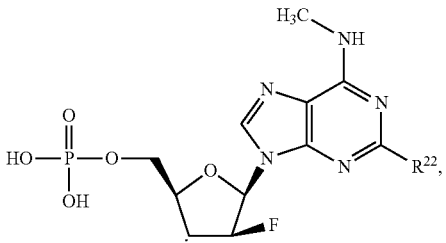
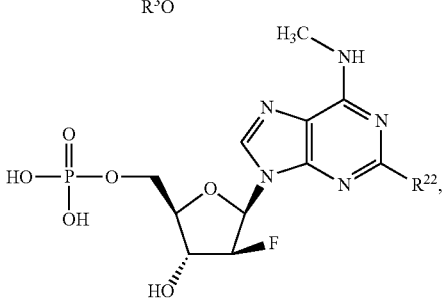

179
-continued
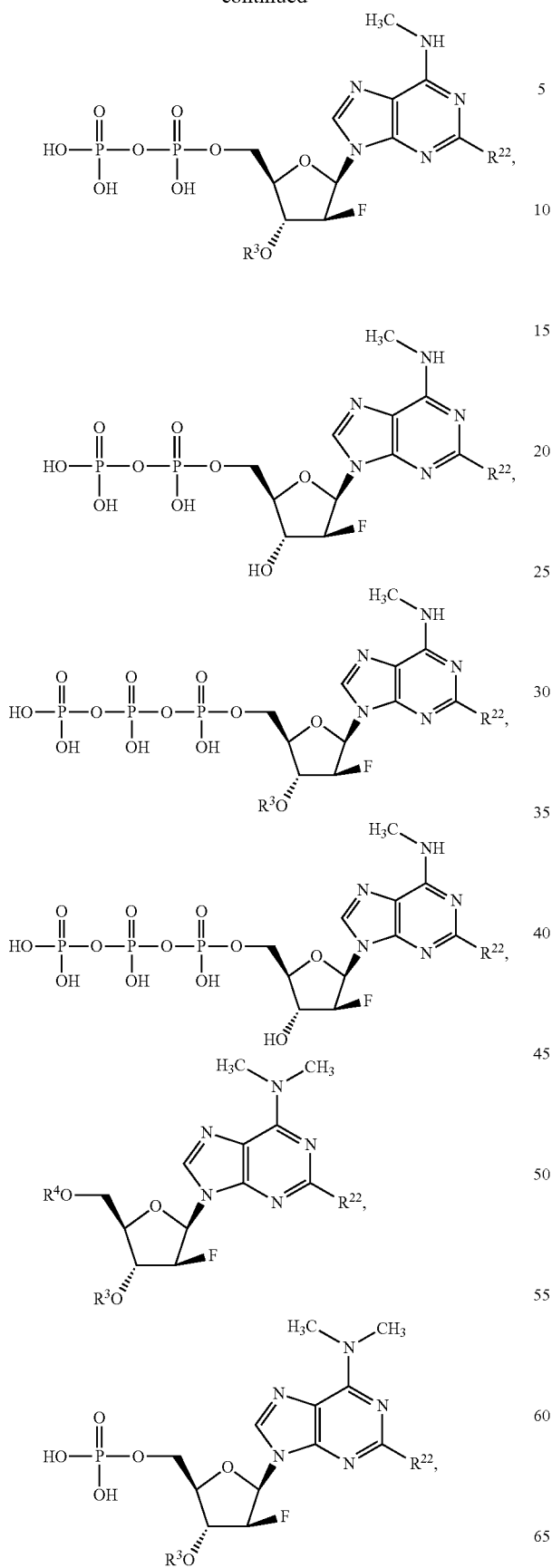
180
-continued
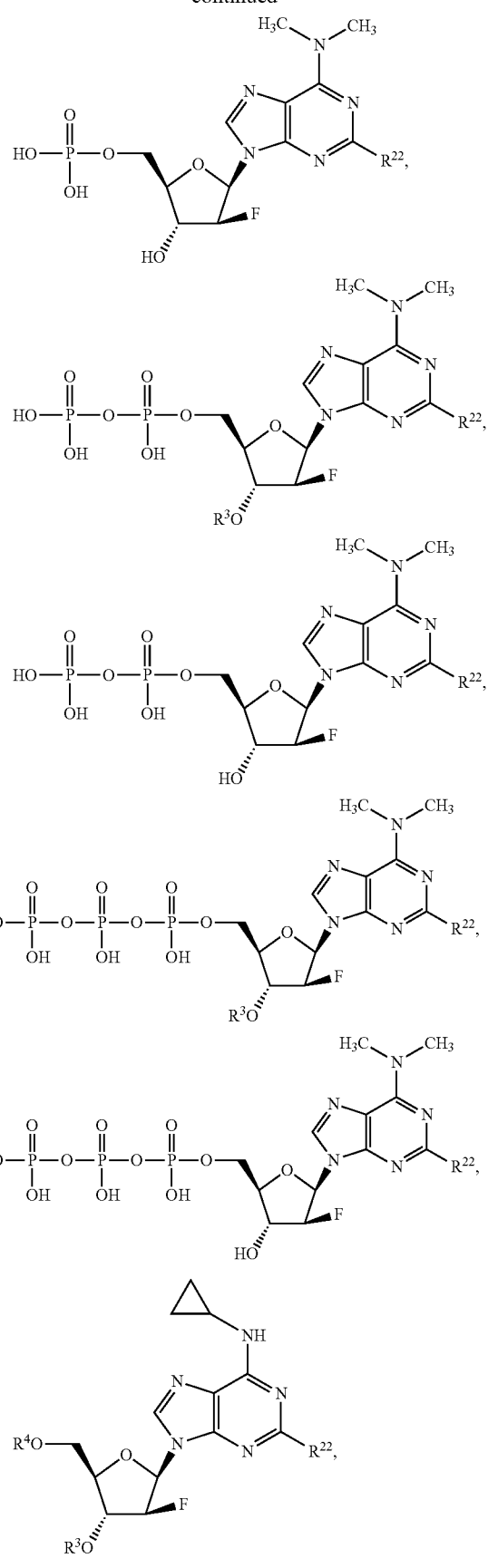

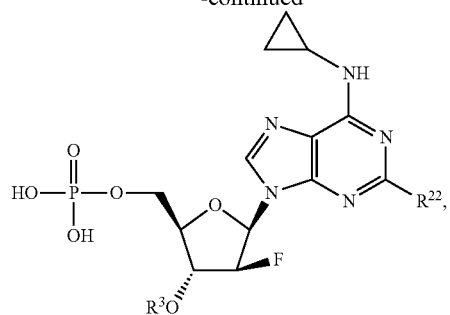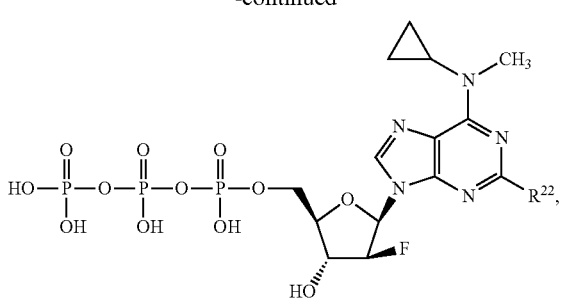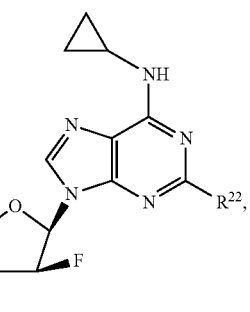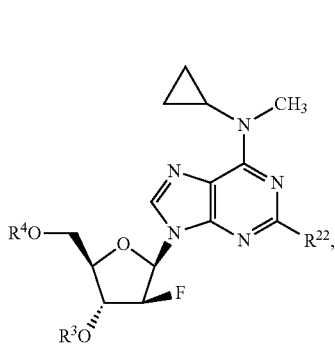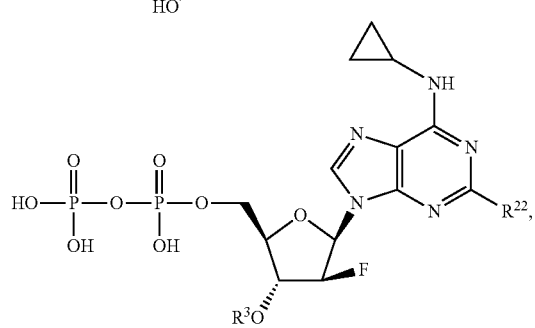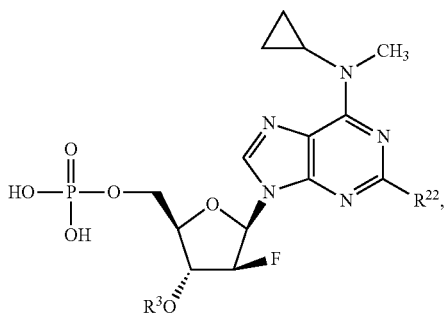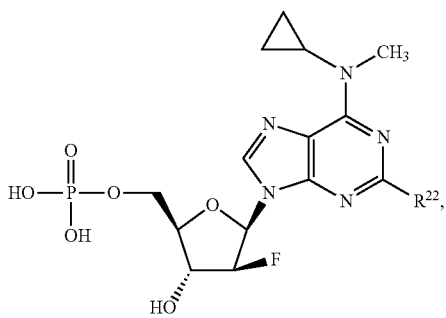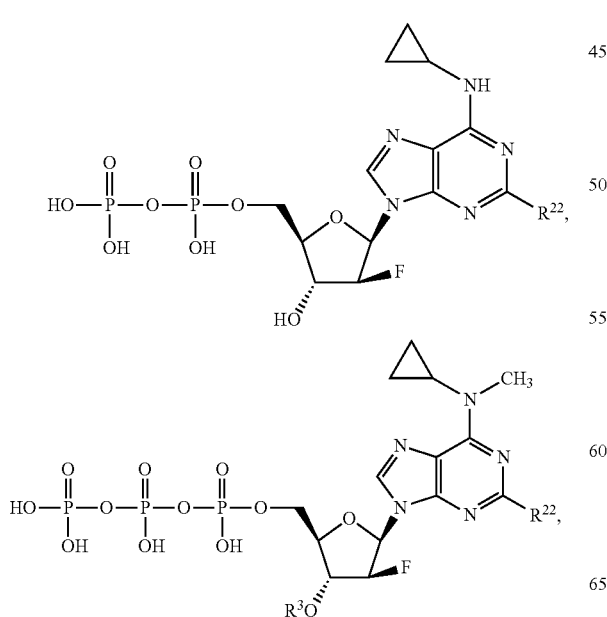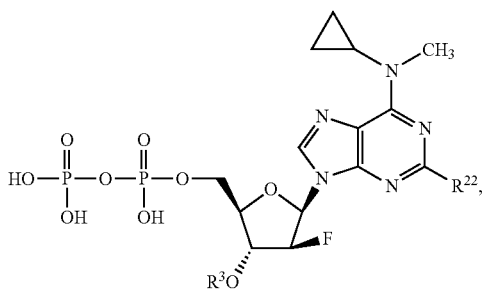

183
-continued
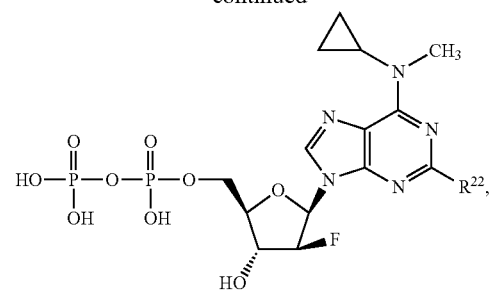
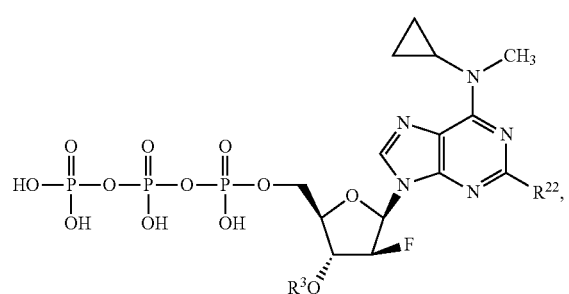
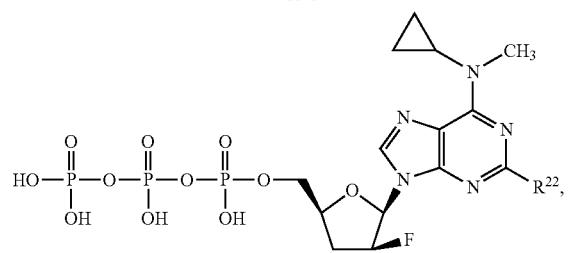
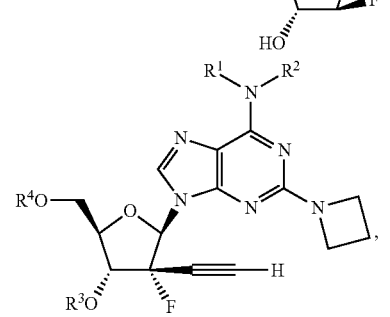
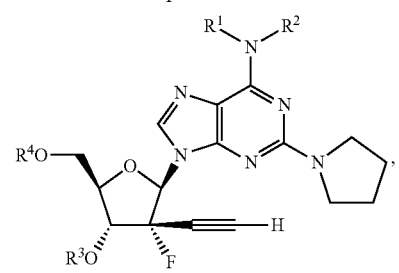
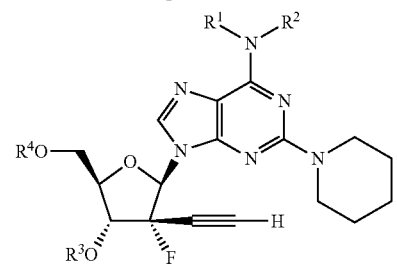
184
-continued
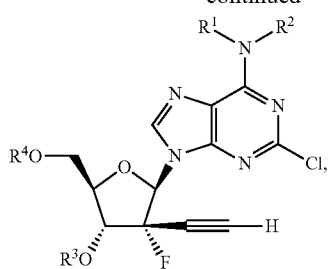
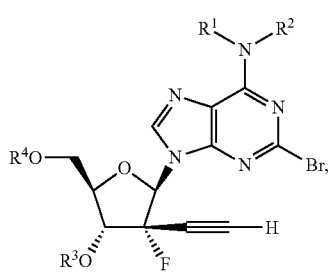
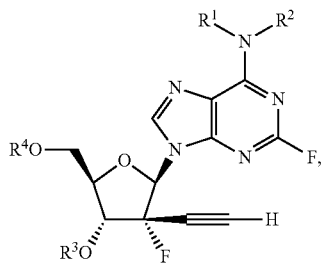
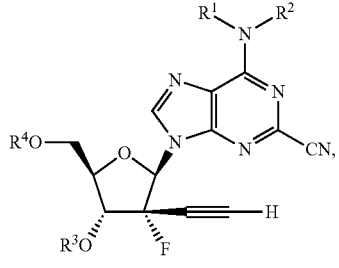
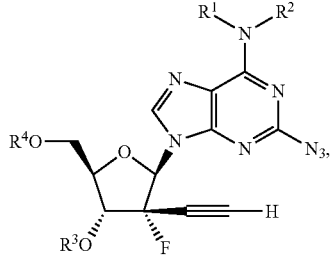
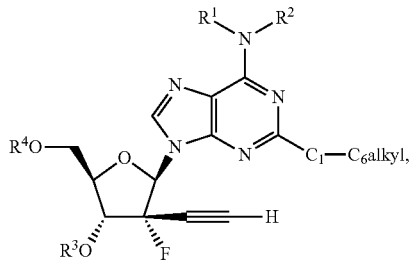

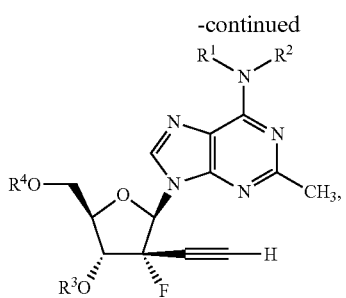
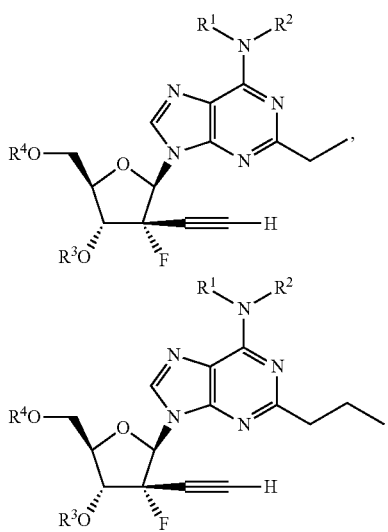
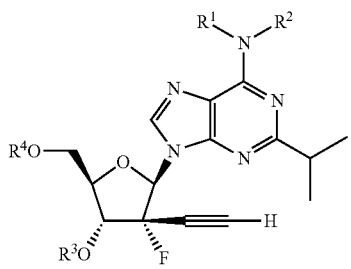
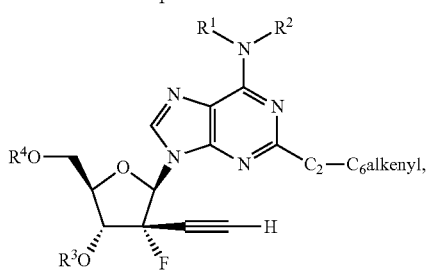
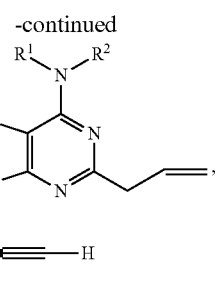
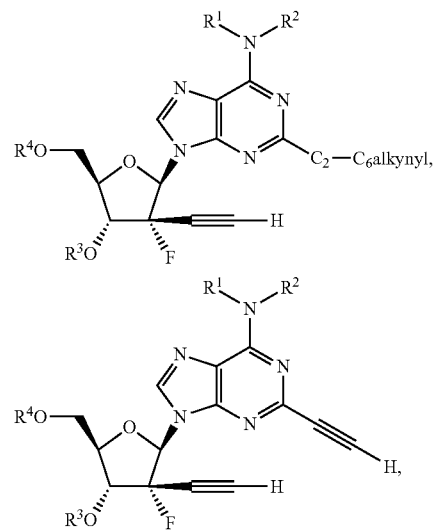
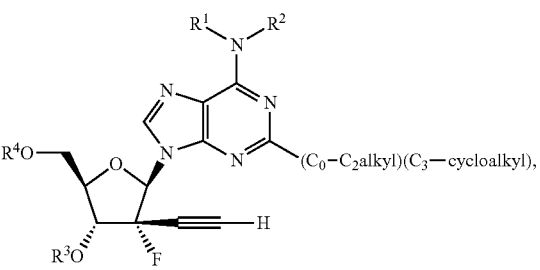
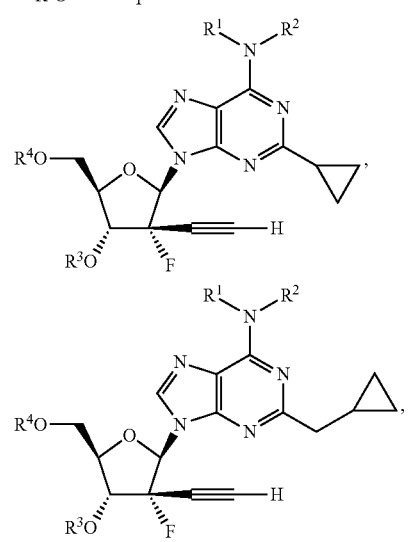

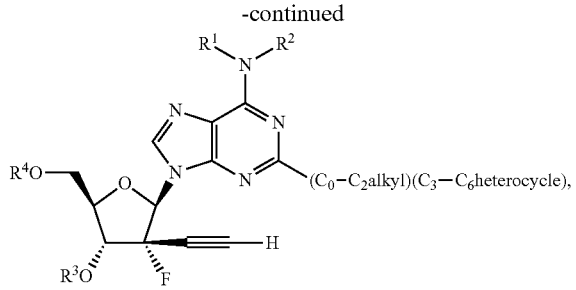
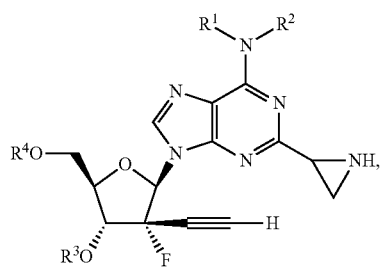
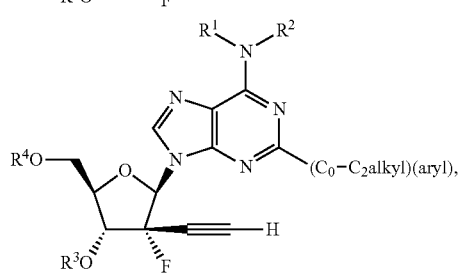
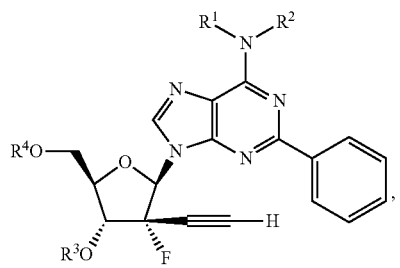
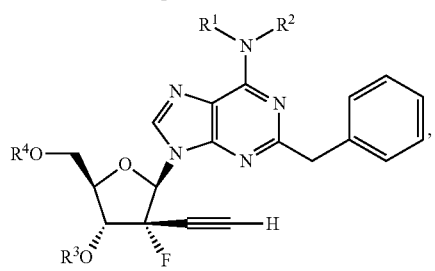
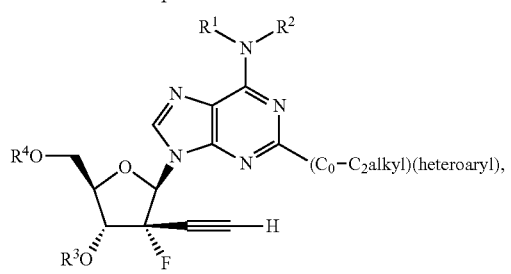
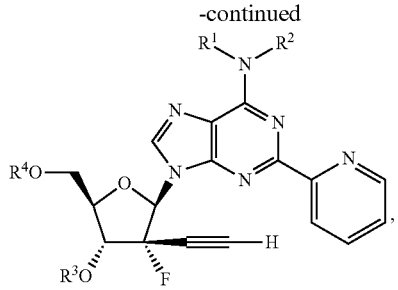
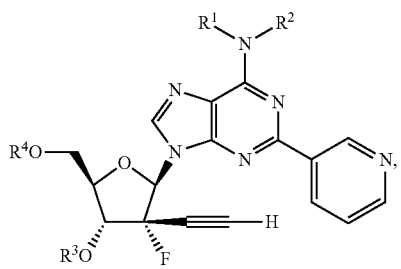
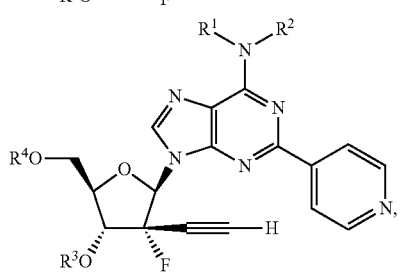
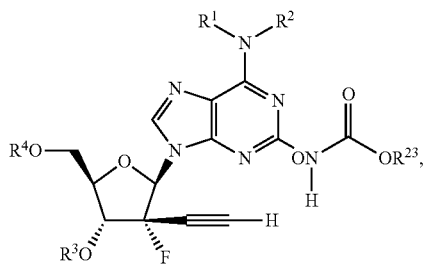
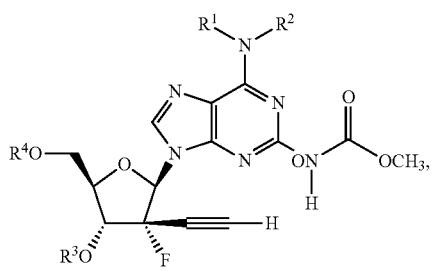
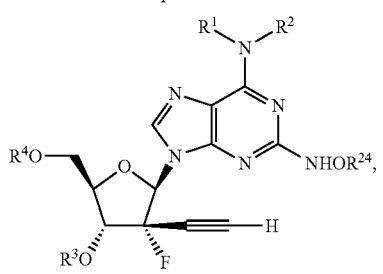

189
-continued
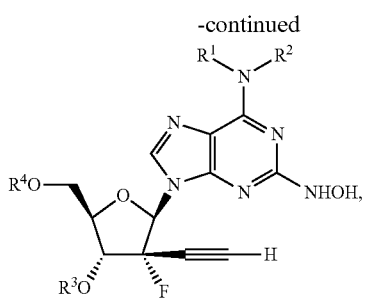
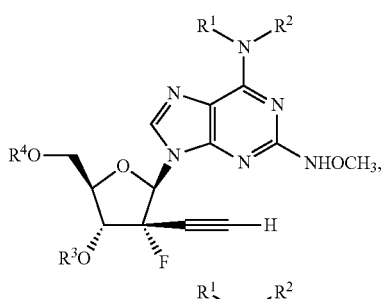
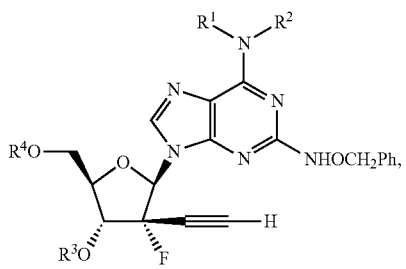
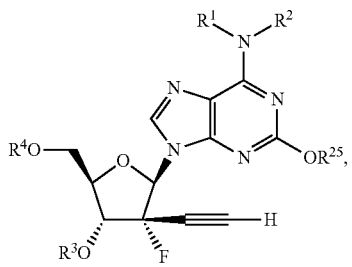
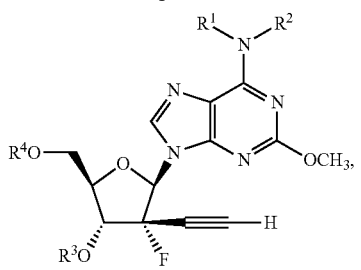
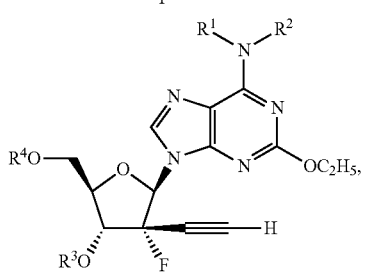
190
-continued
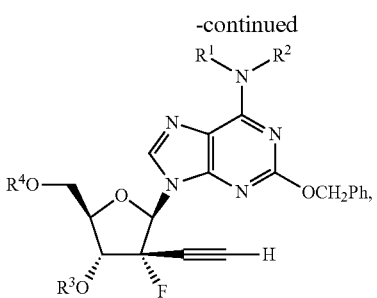
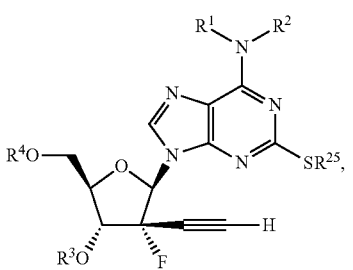
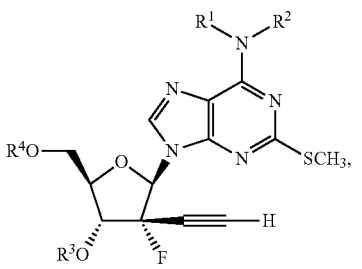
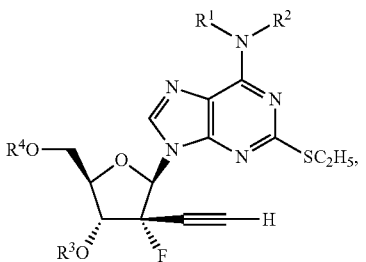
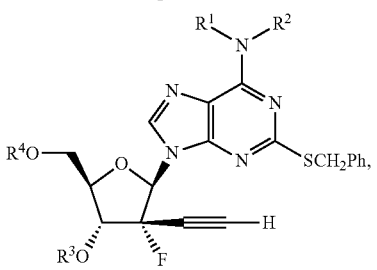
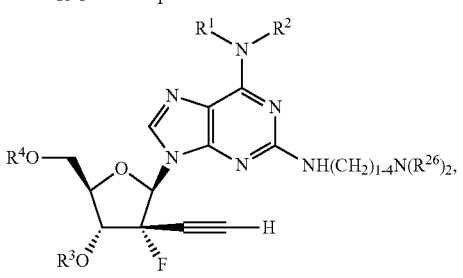

-continued
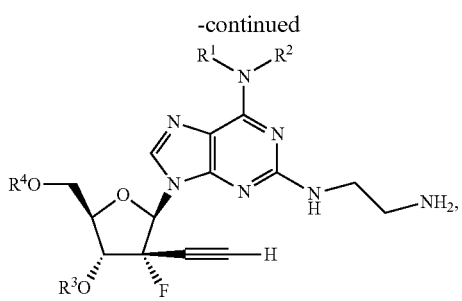
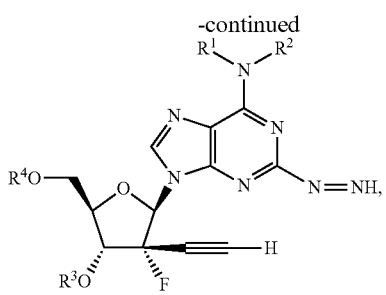
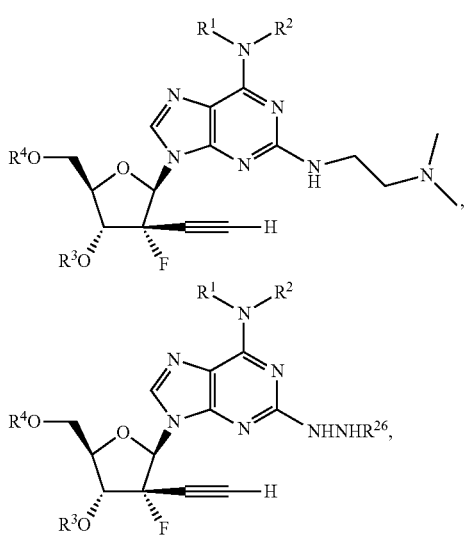
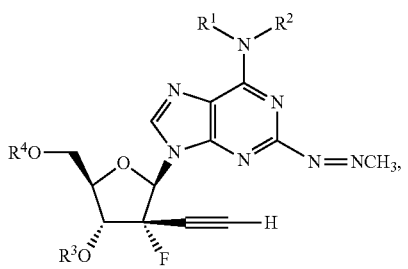
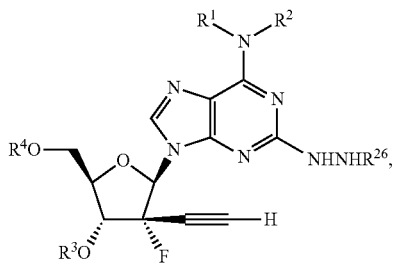
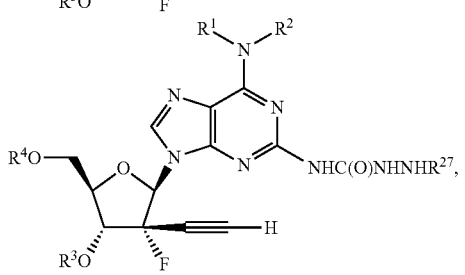
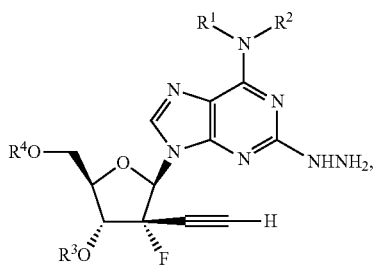
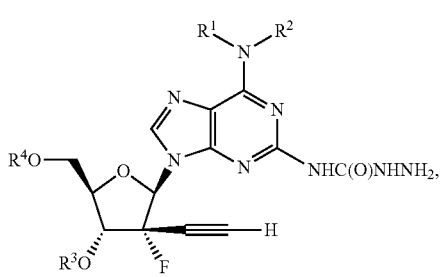
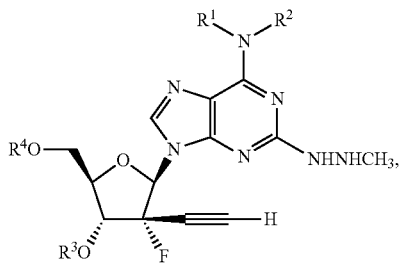
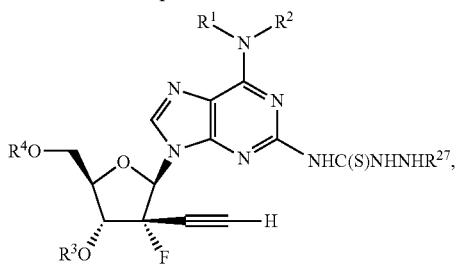
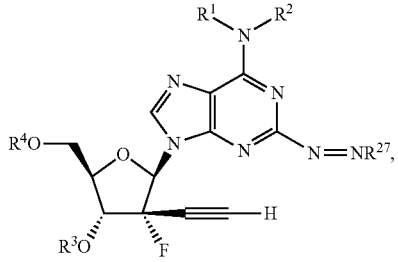
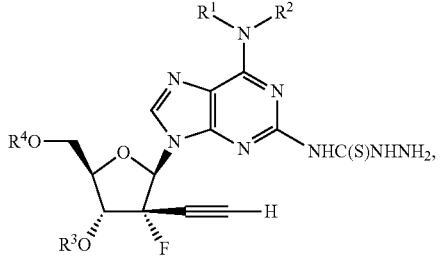

193
-continued
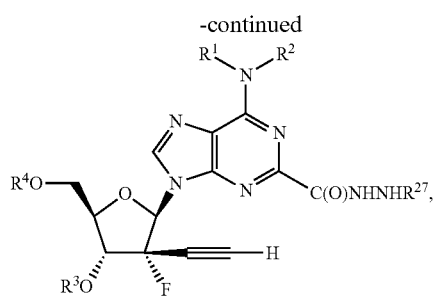
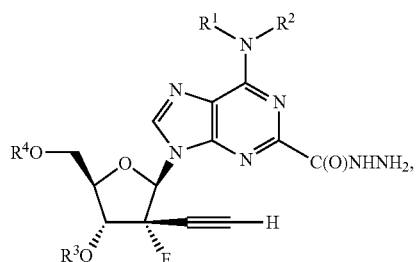
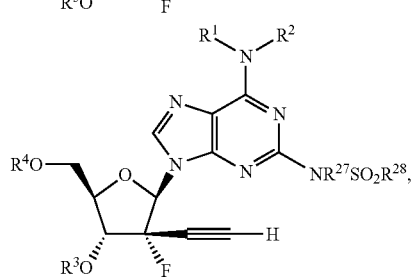
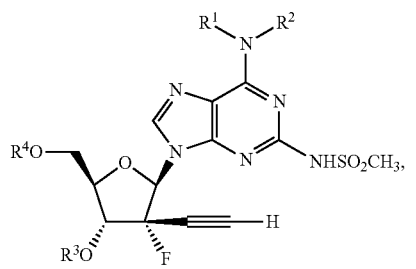
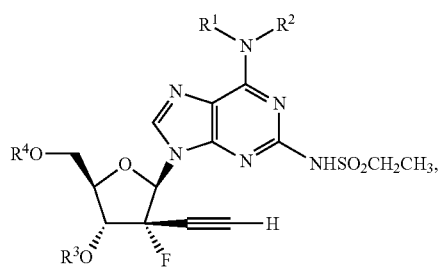
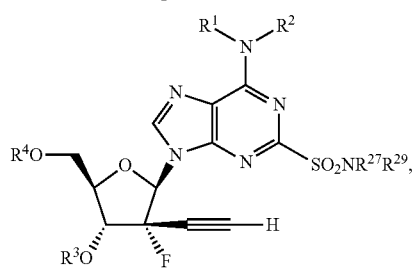
194
-continued
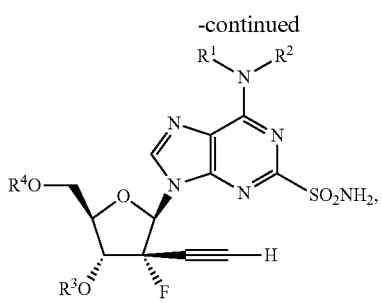
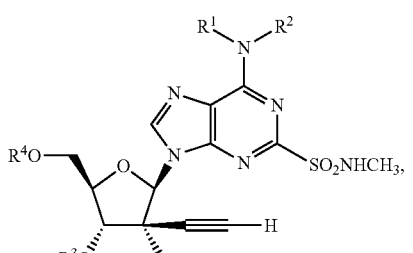
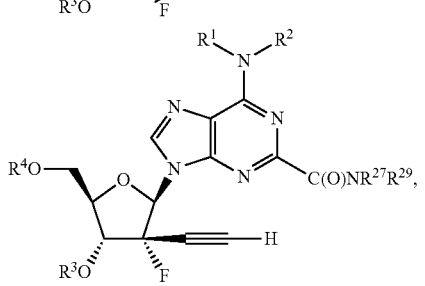
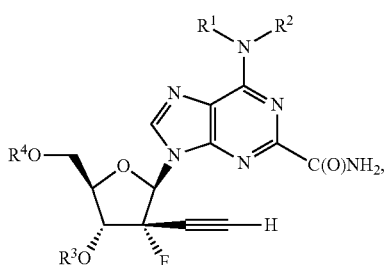
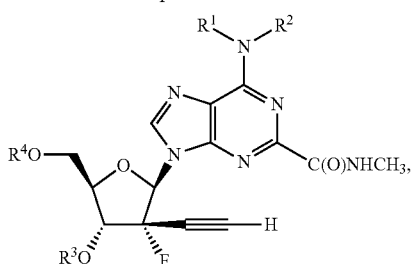
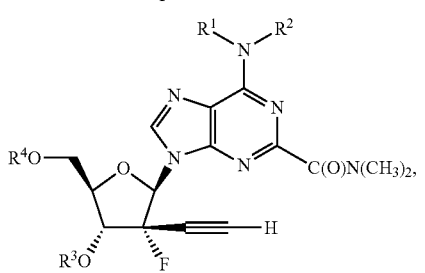

195
-continued
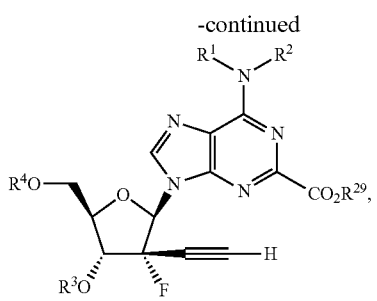
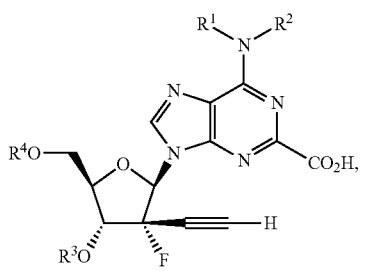
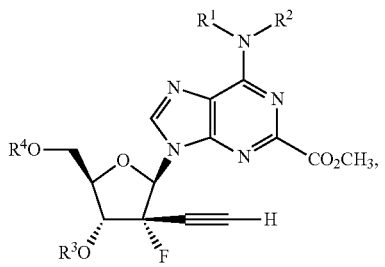
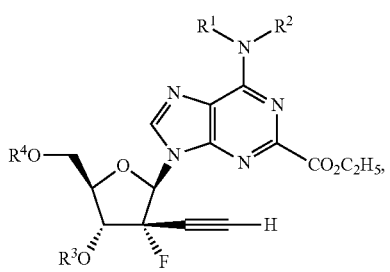
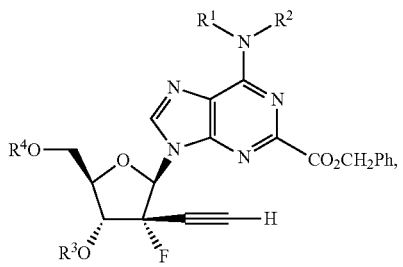
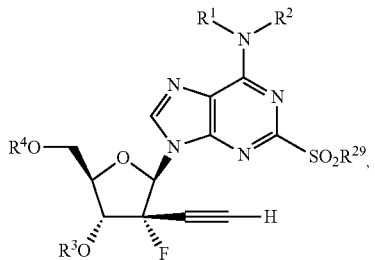
196
-continued
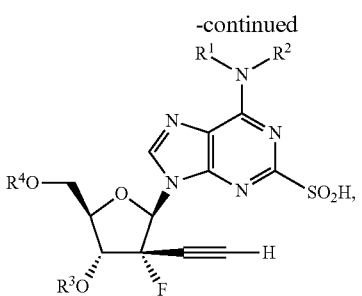
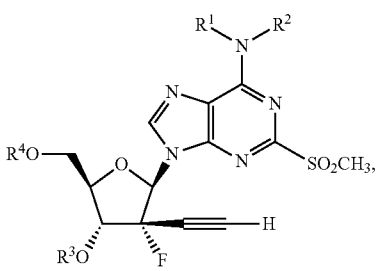
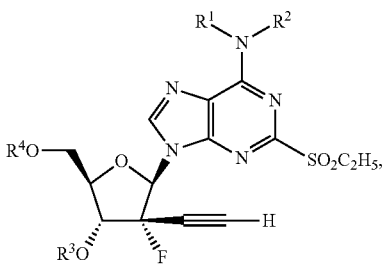
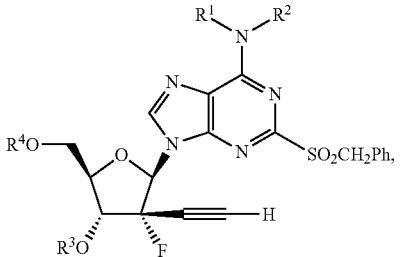
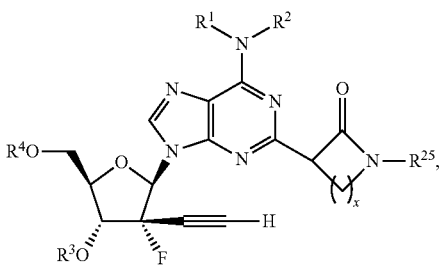
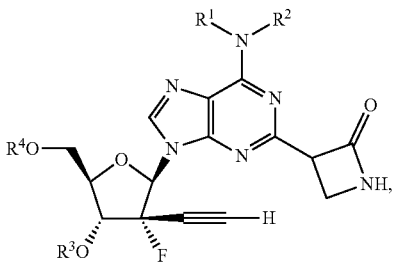

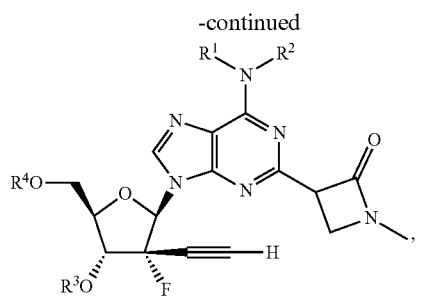
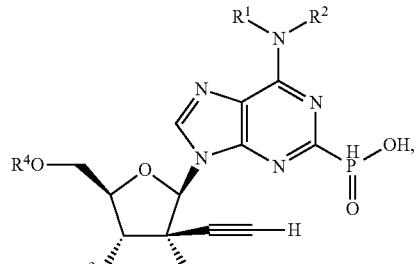
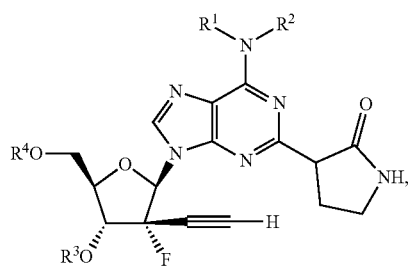
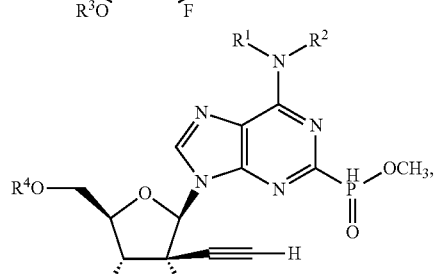
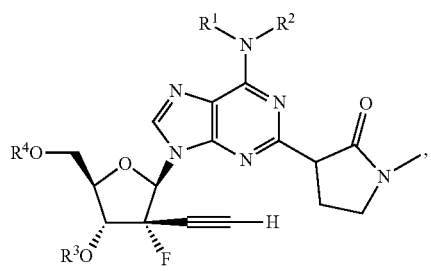
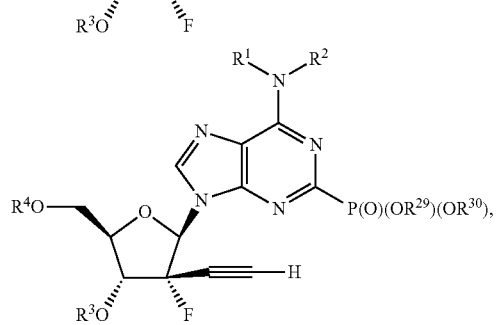
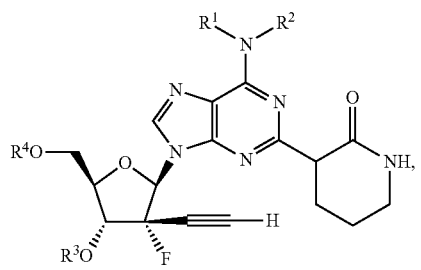
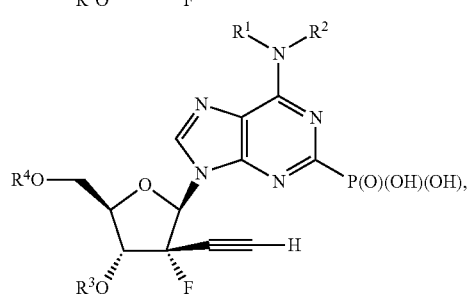
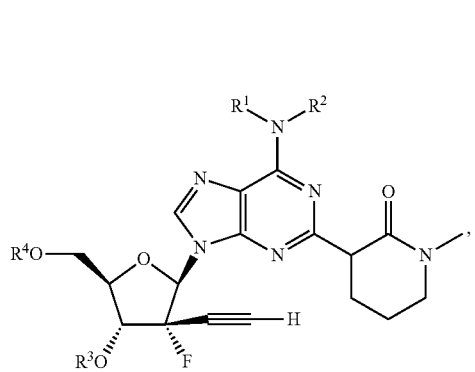
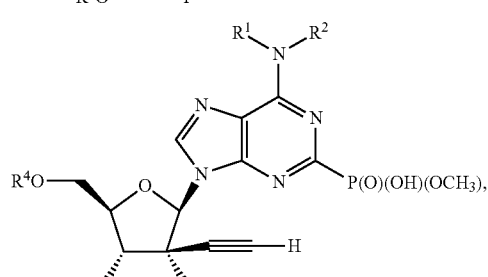
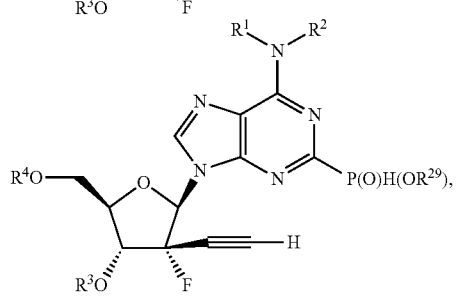
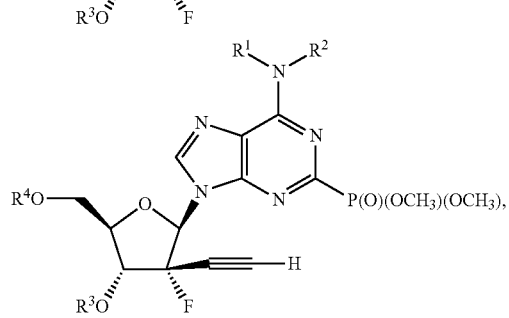

199
-continued
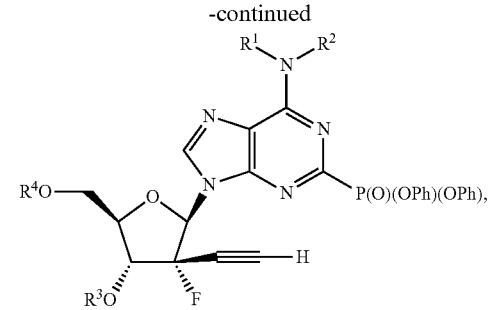
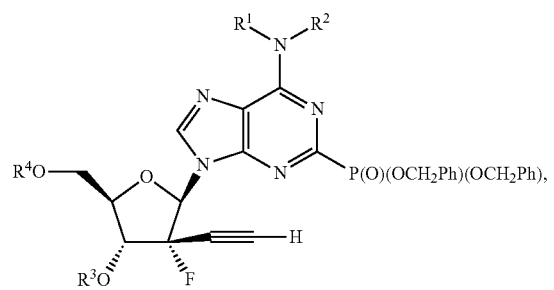
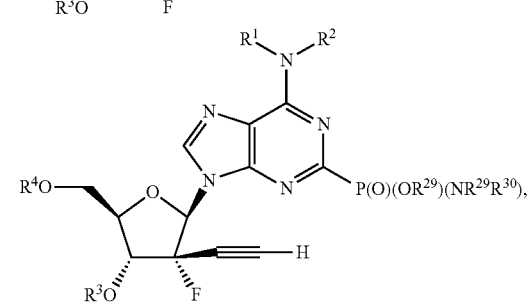
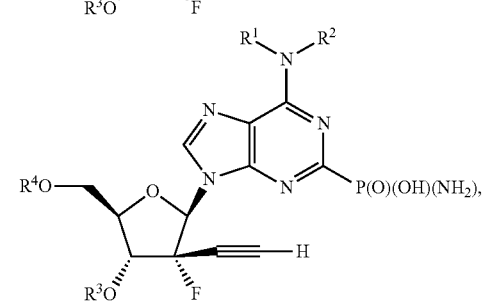
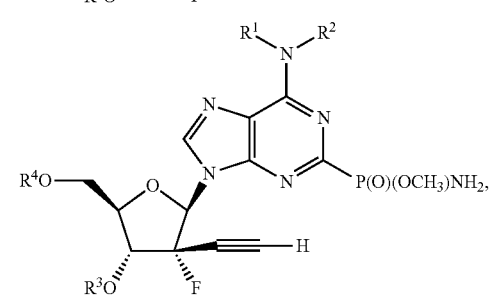
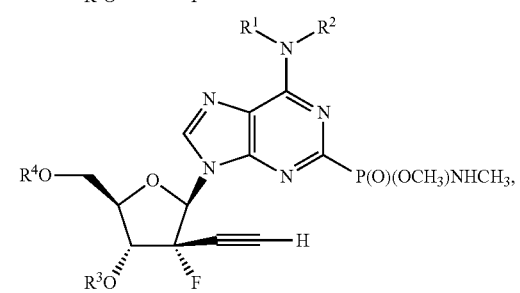
200
-continued
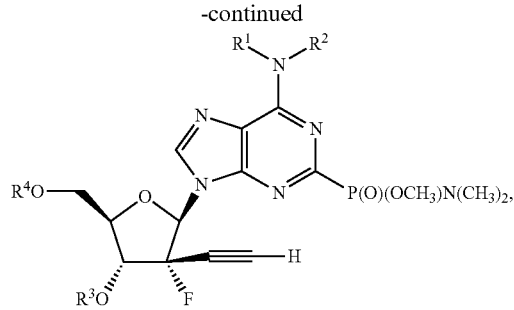
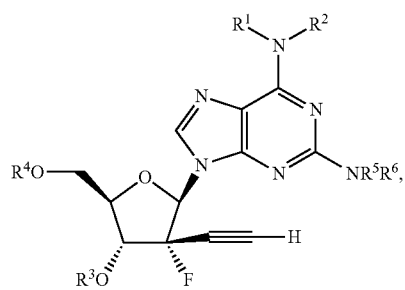
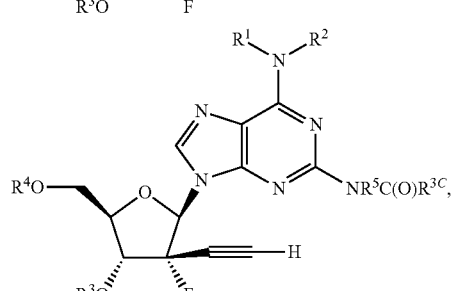
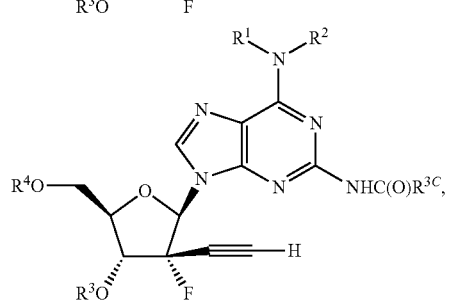
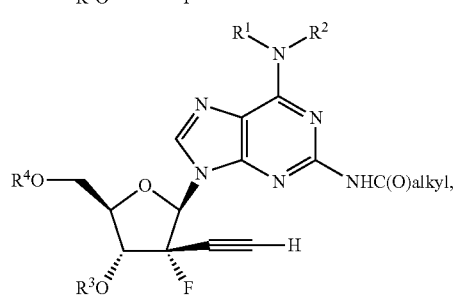
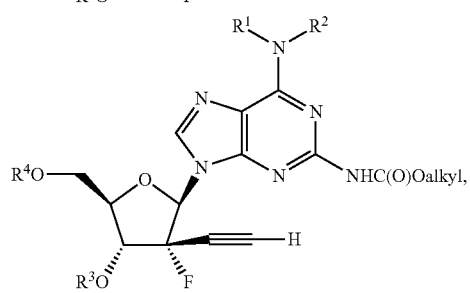

201
-continued
202
-continued
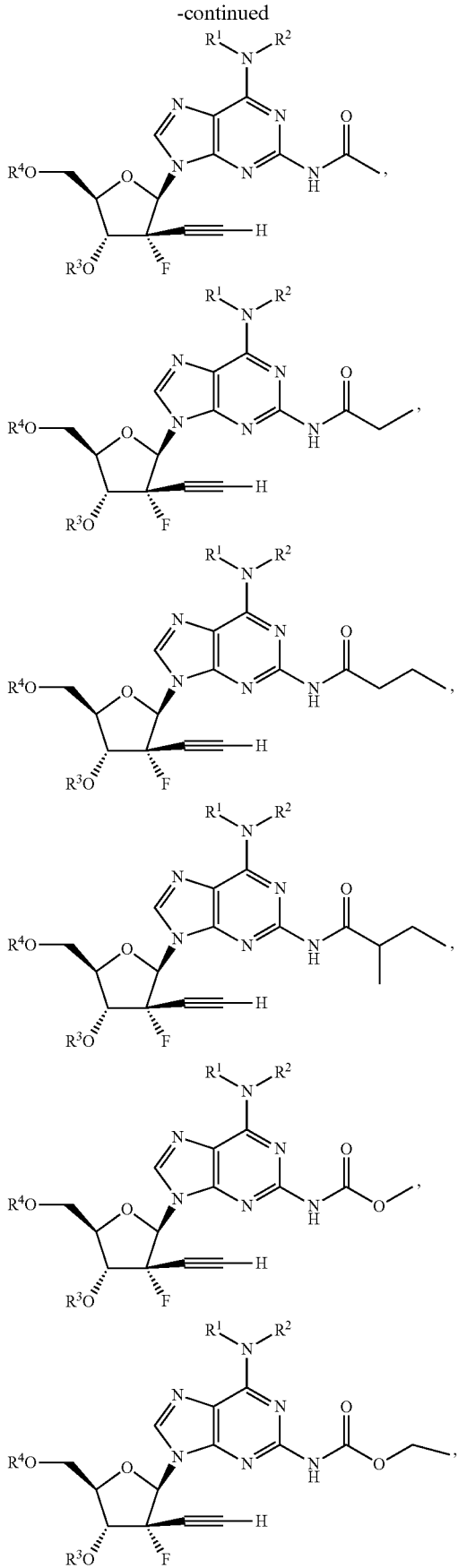
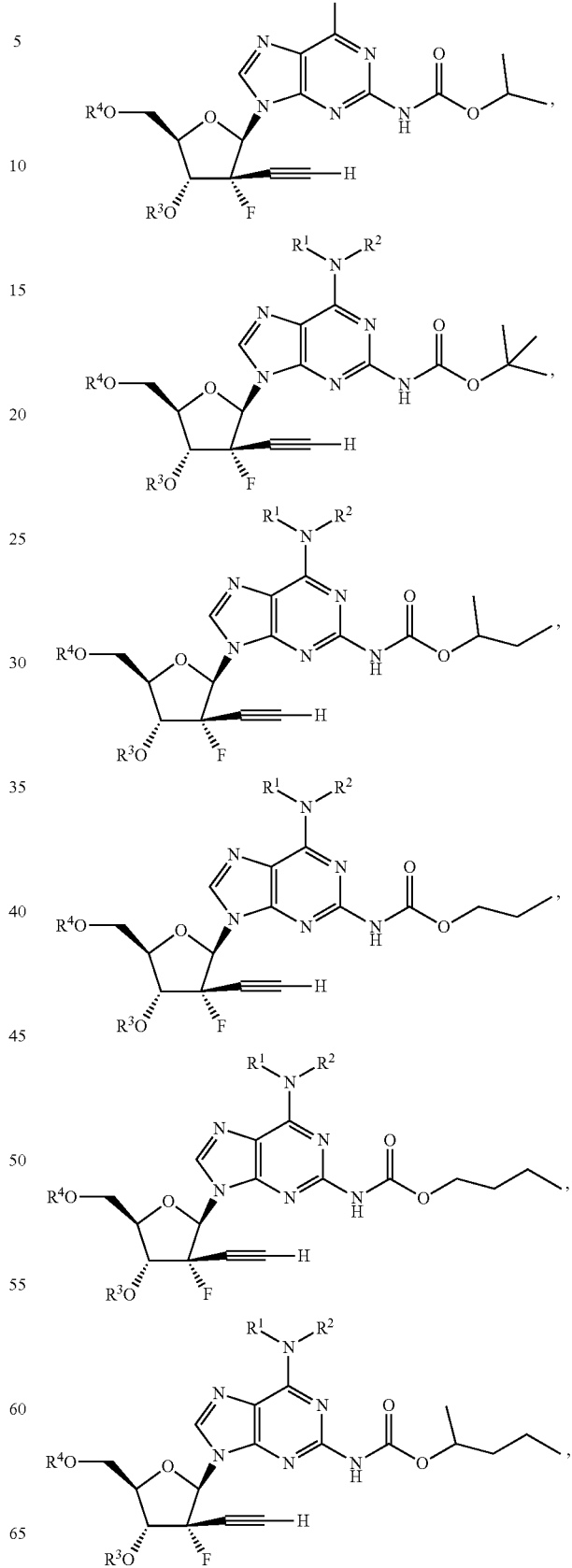

203
-continued
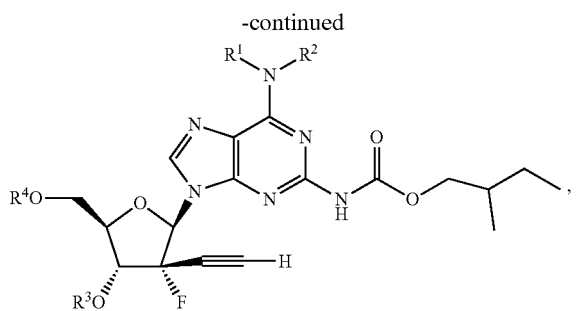
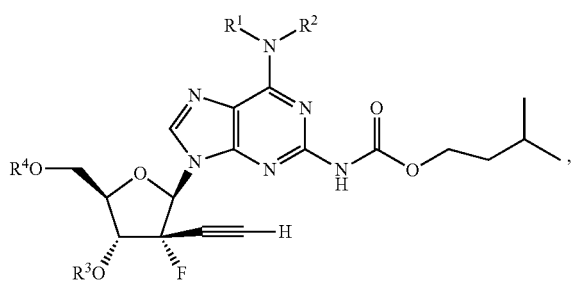
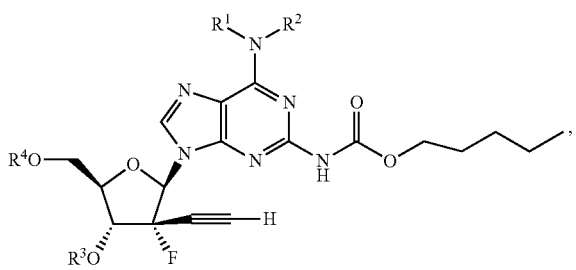
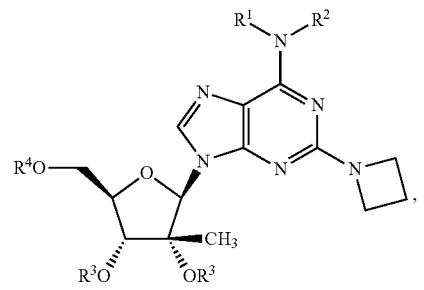
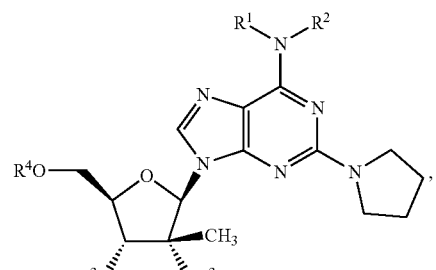
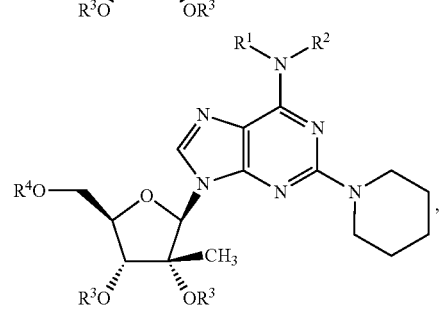
204
-continued
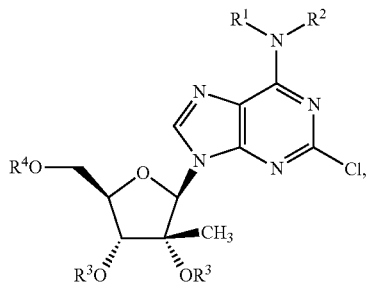
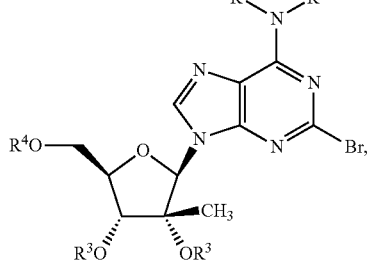
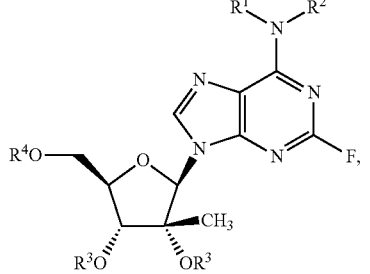
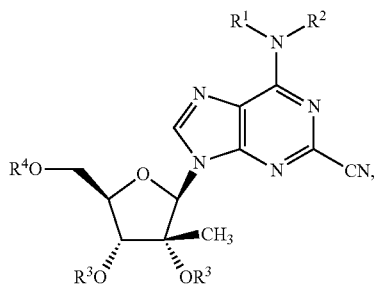
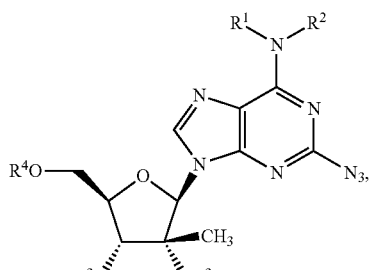
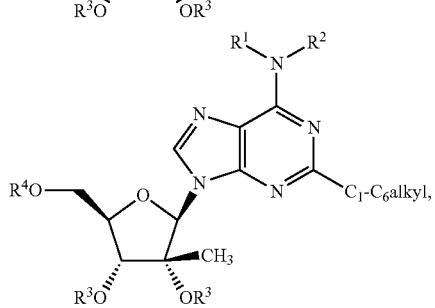

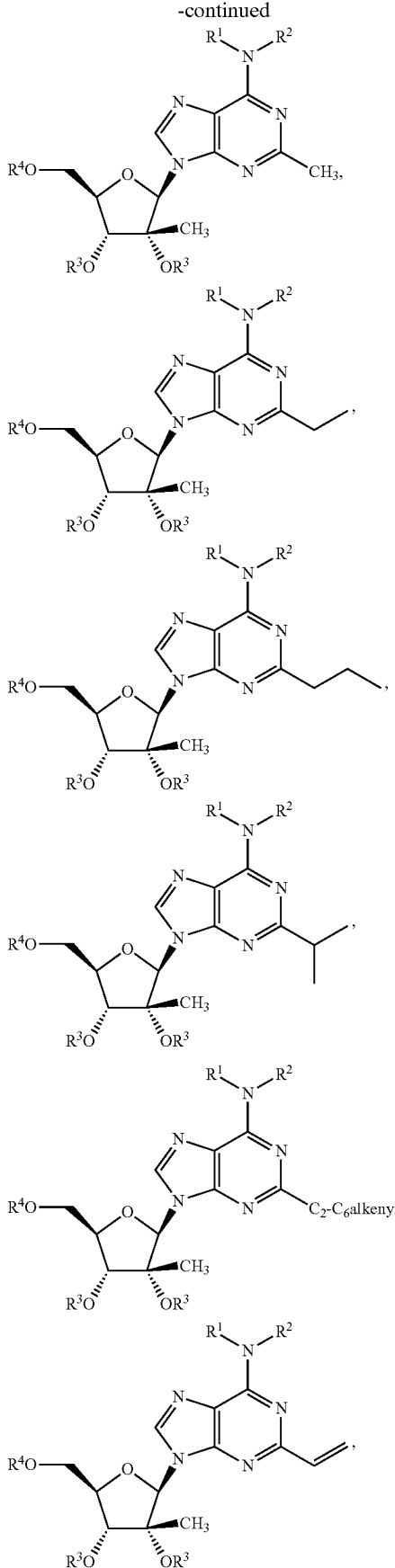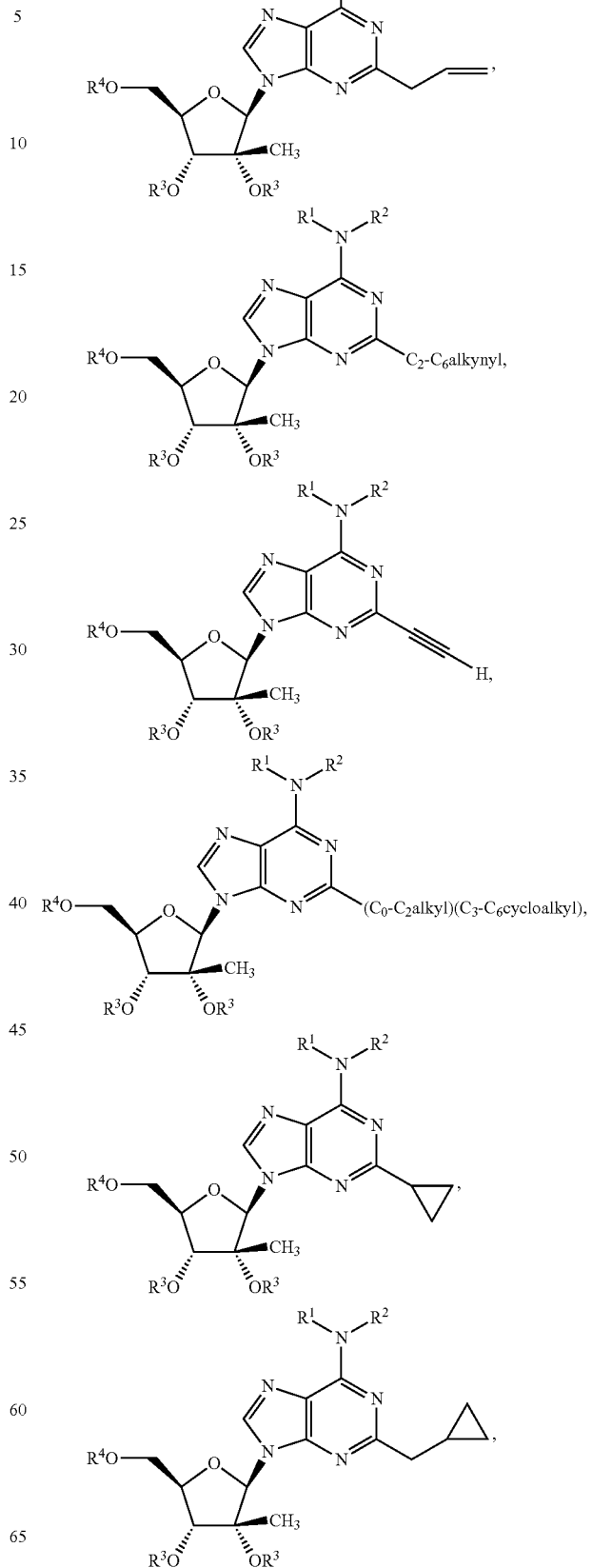

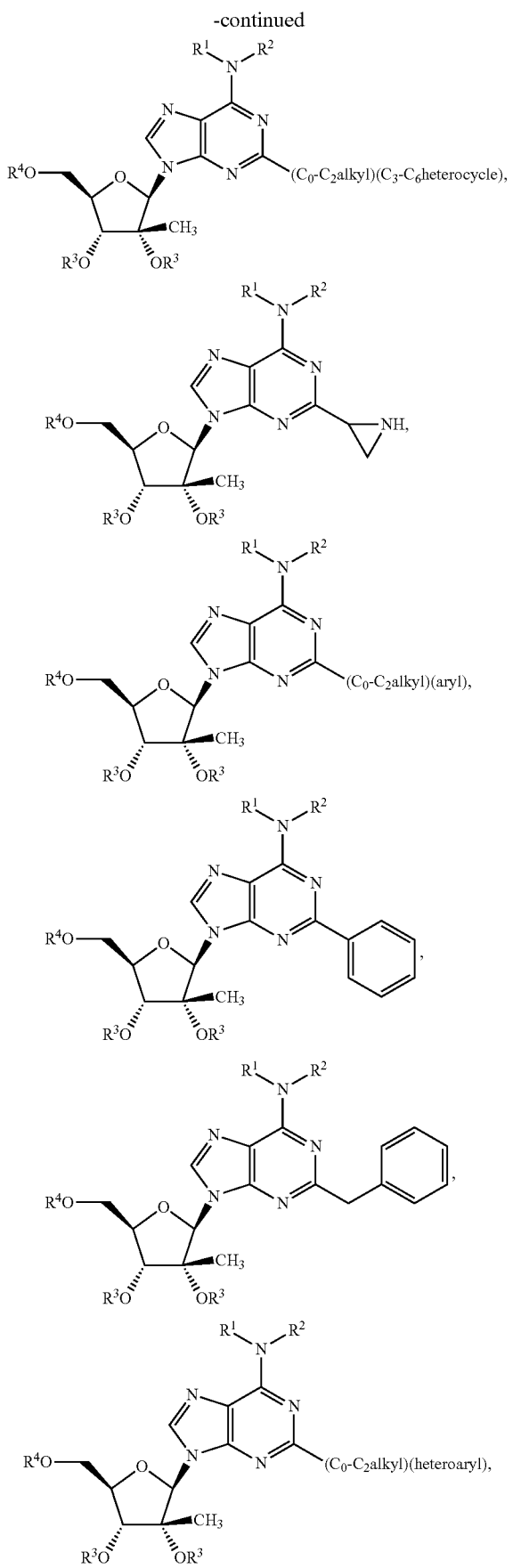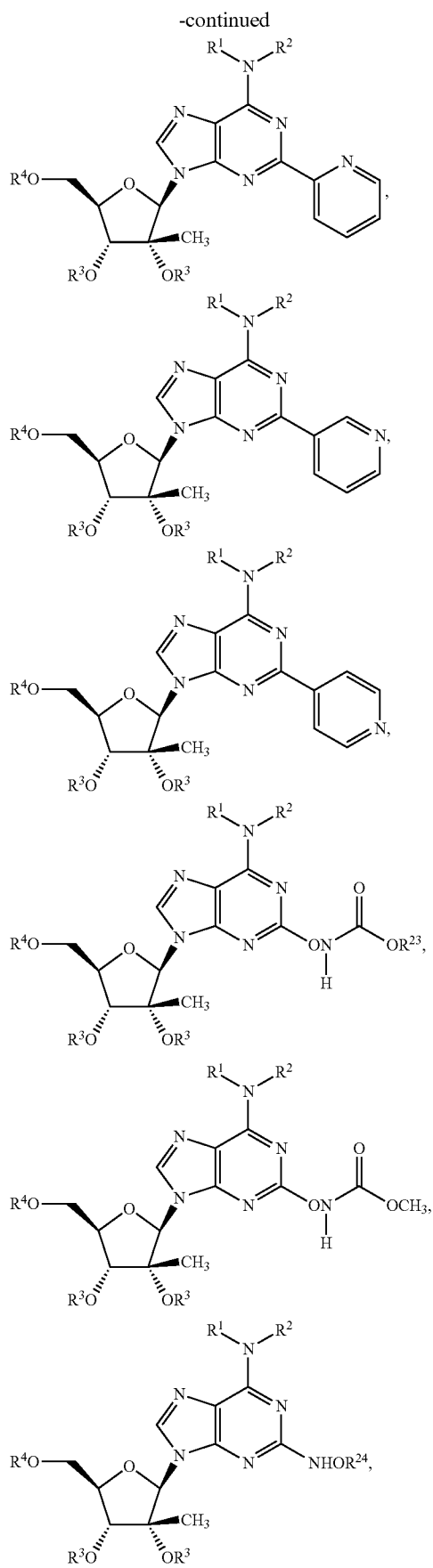

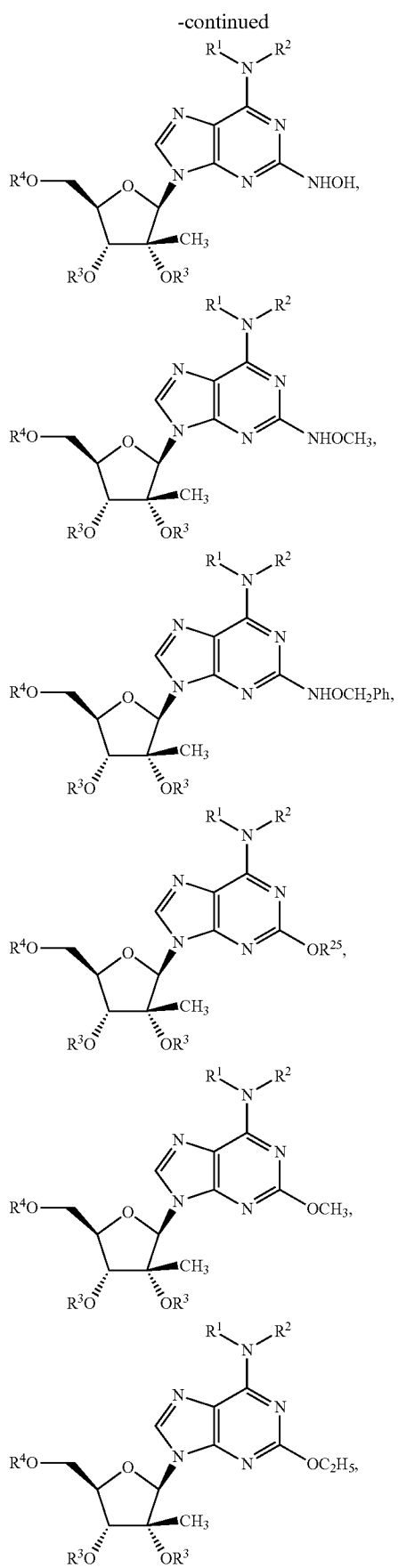
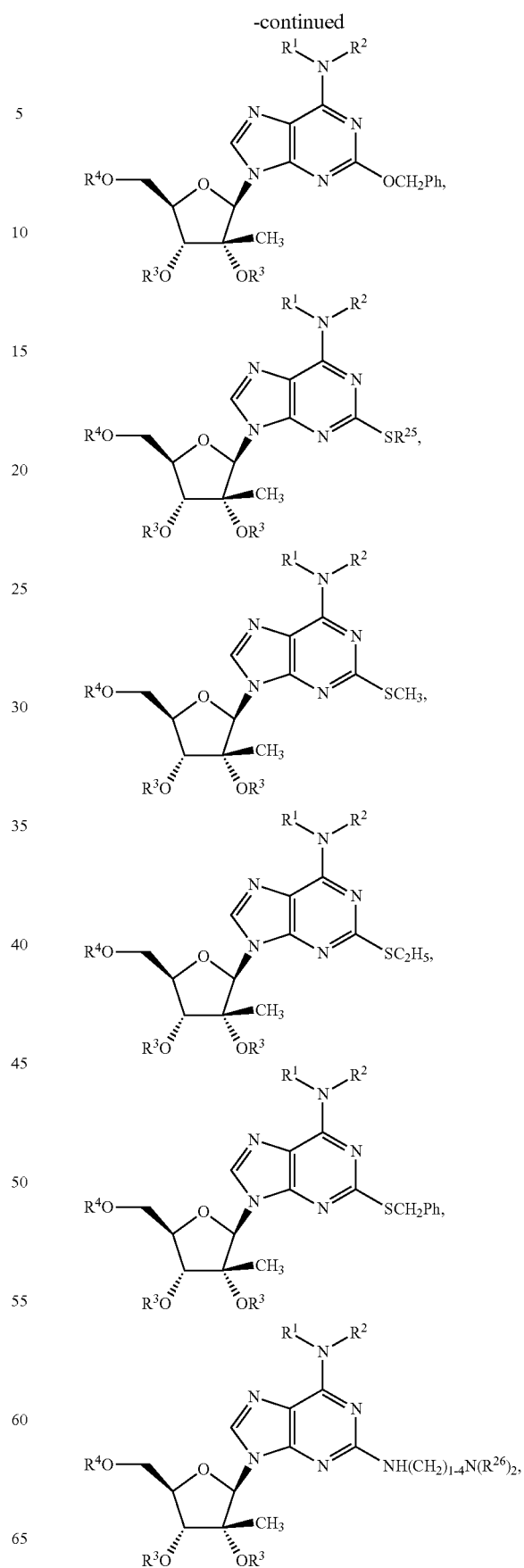

211
-continued
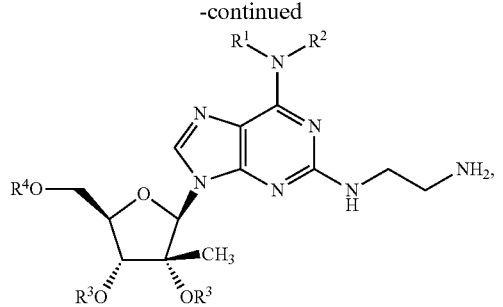
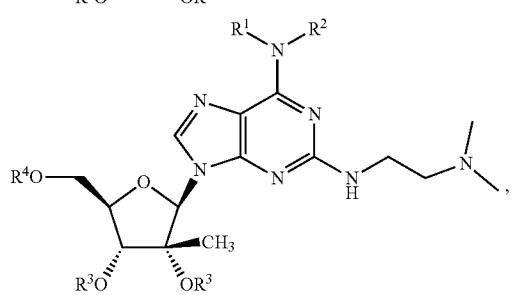
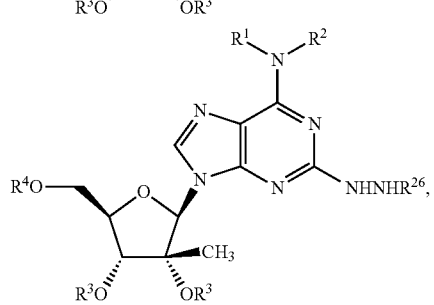
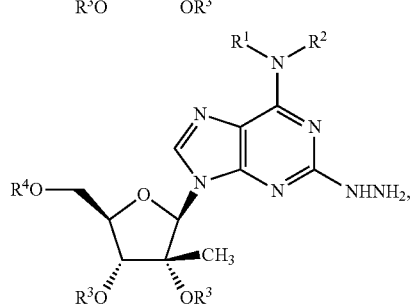
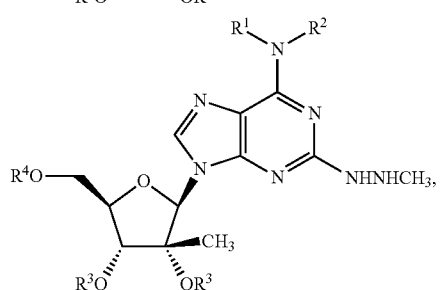
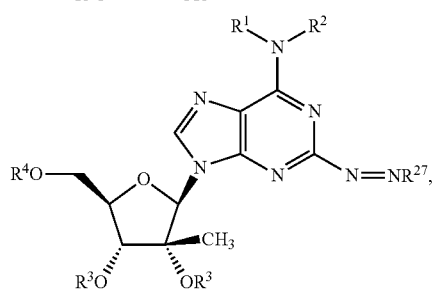
212
-continued
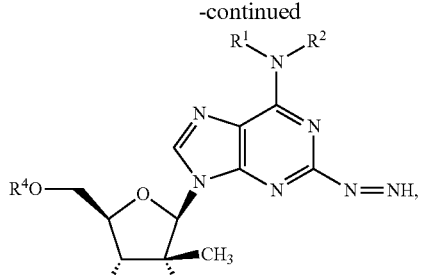
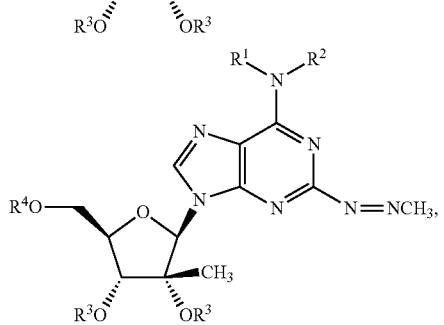
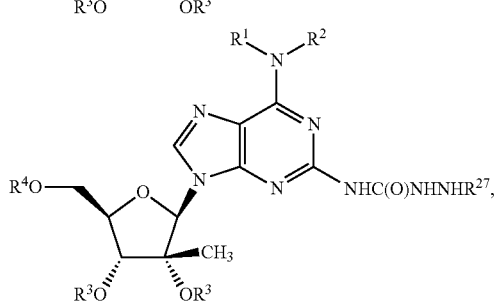
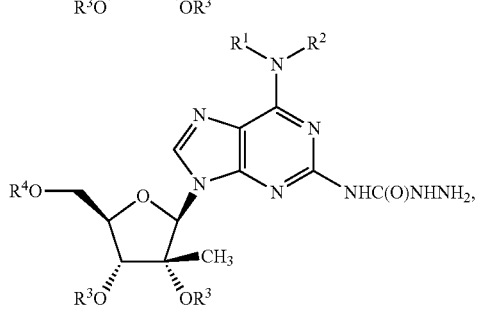
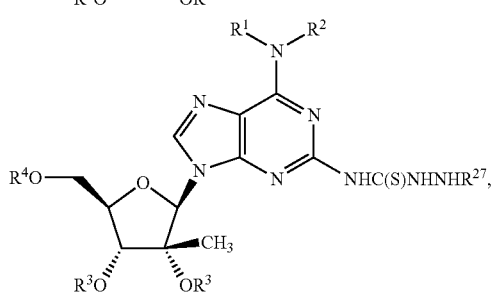
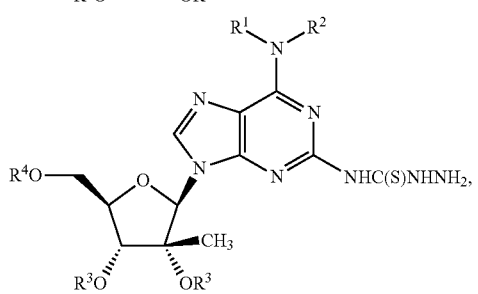

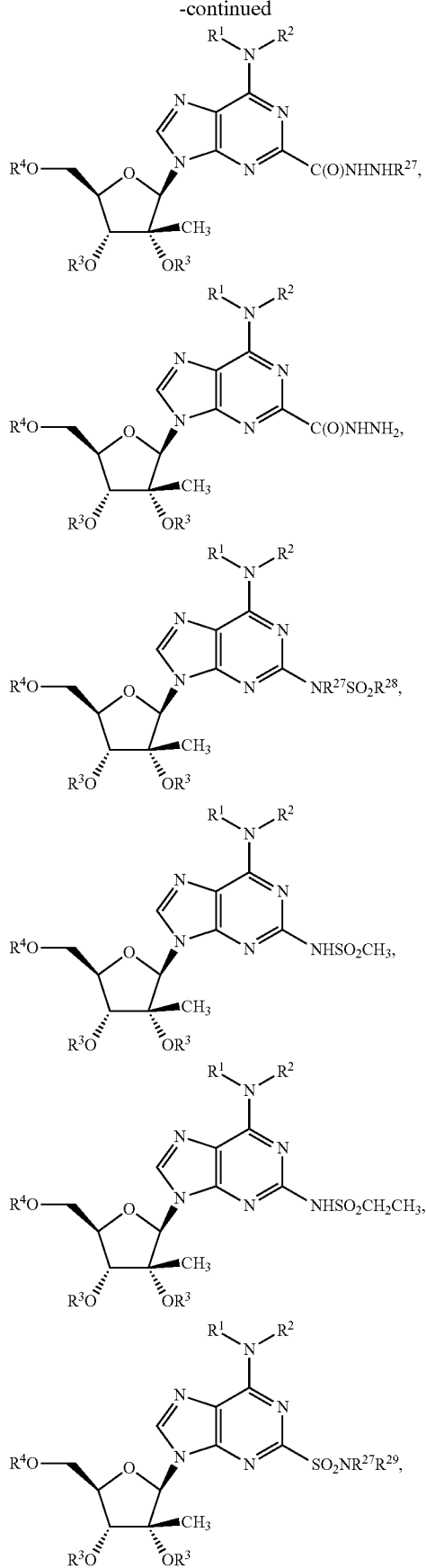
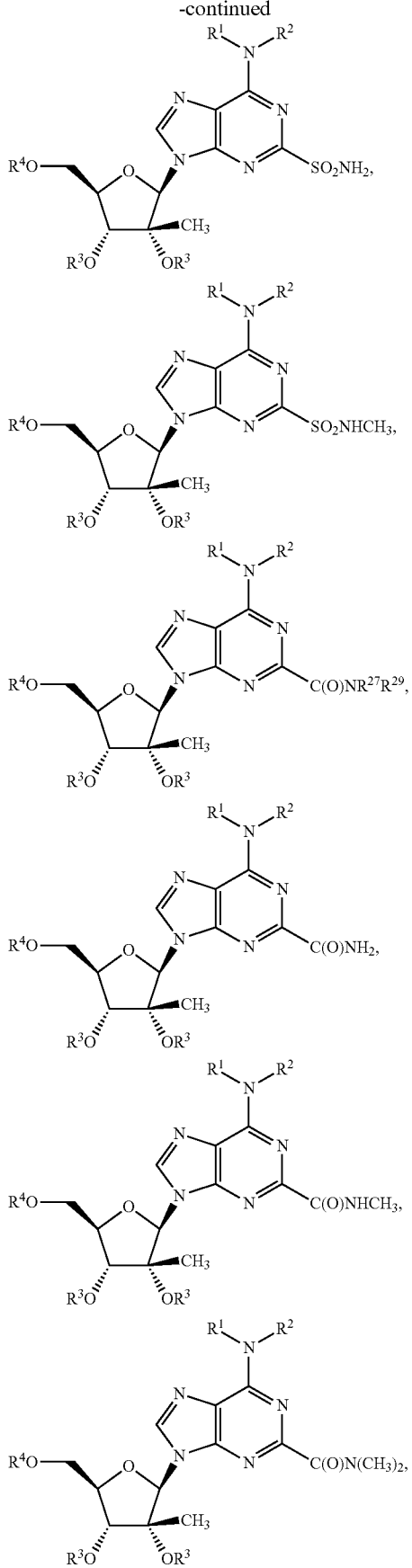

215
-continued
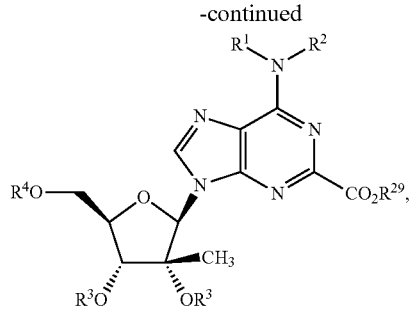
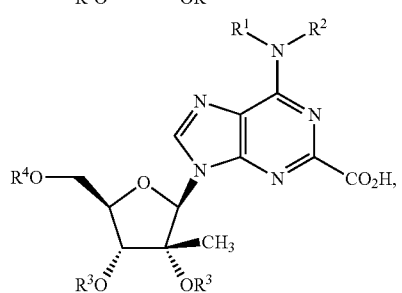
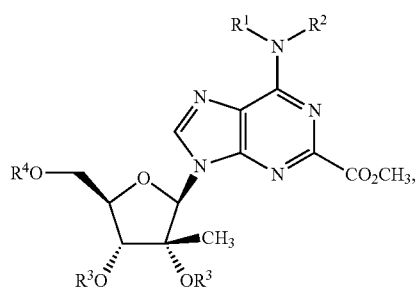
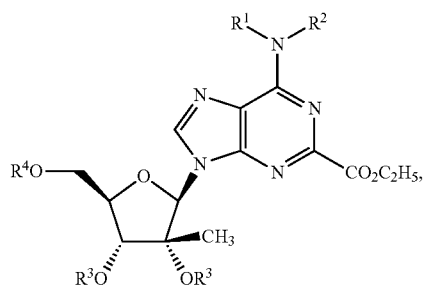
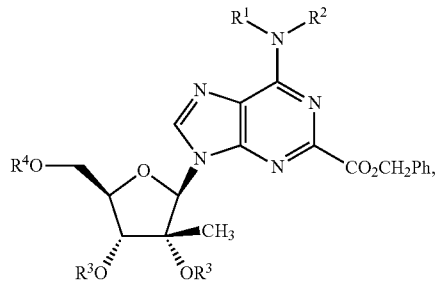
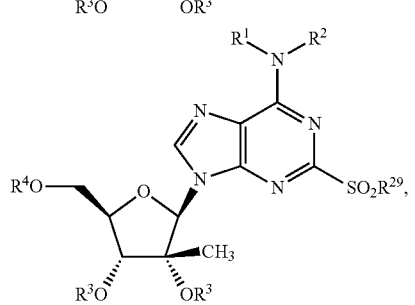
216
-continued
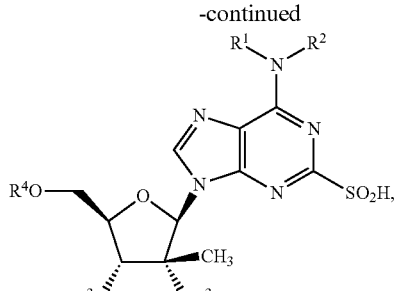
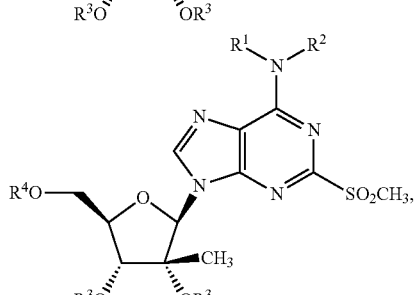
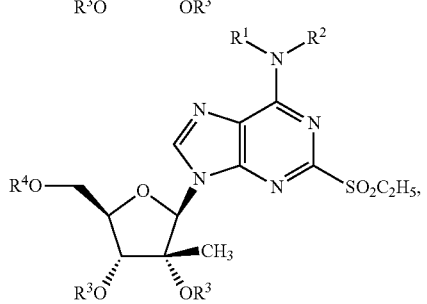
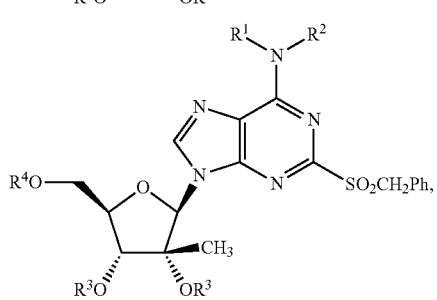
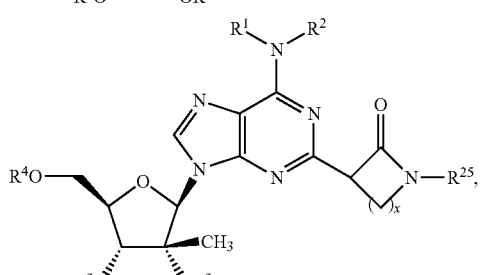
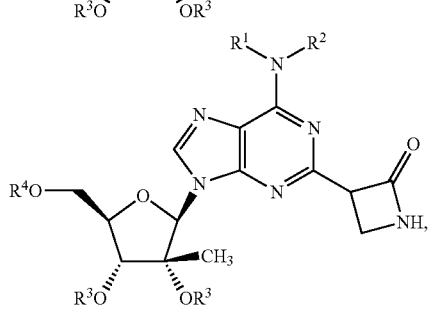

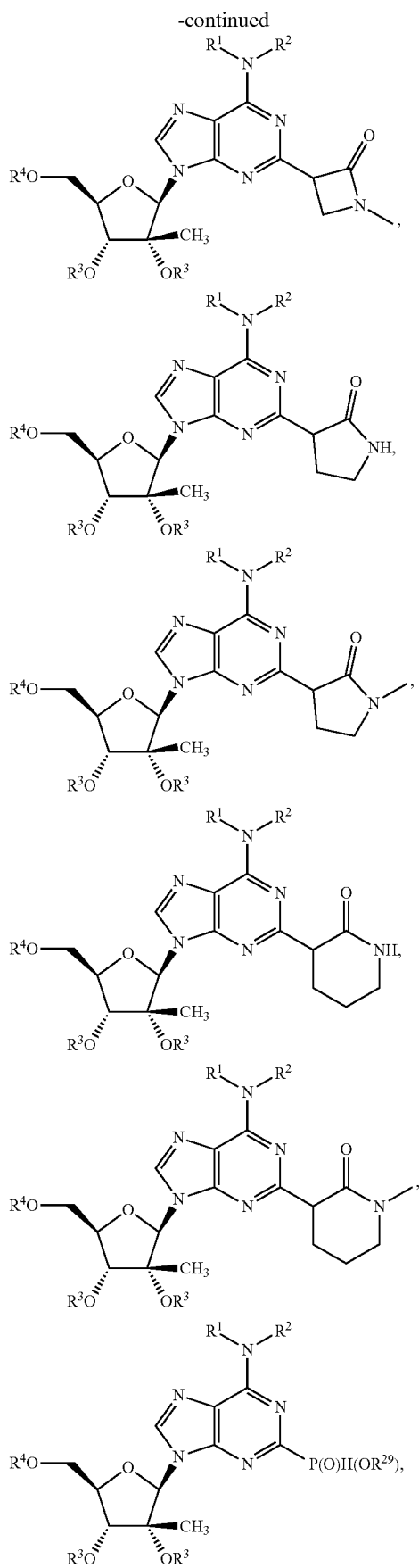
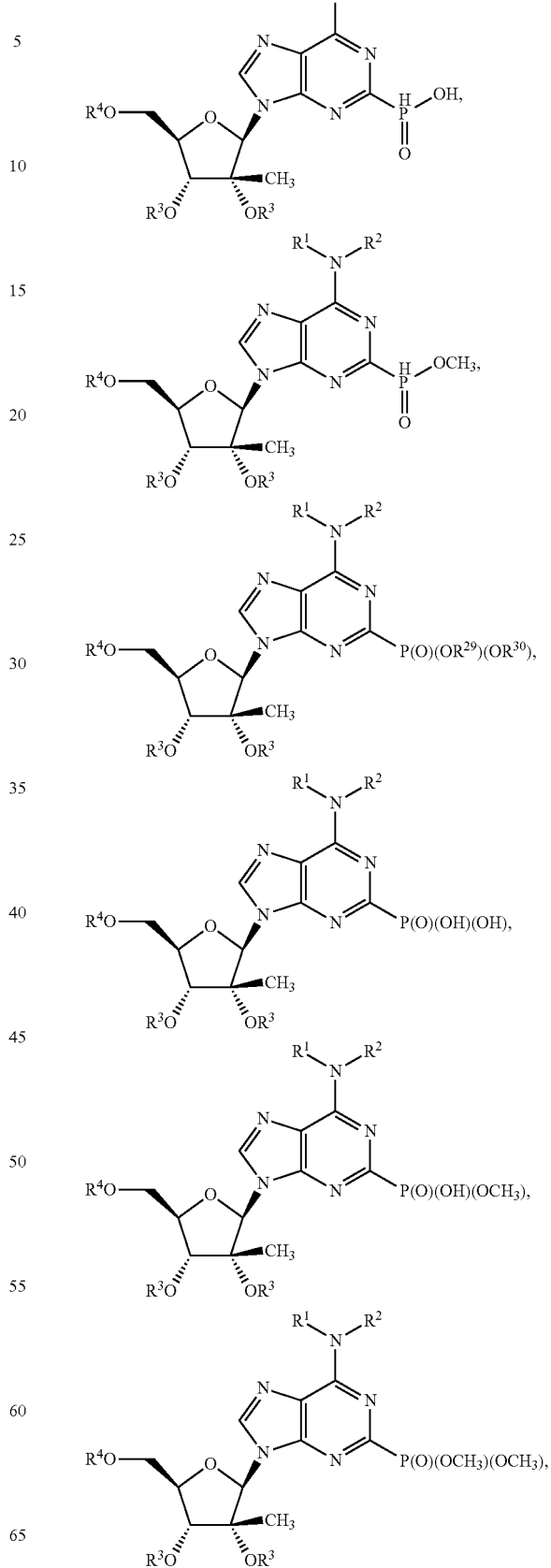

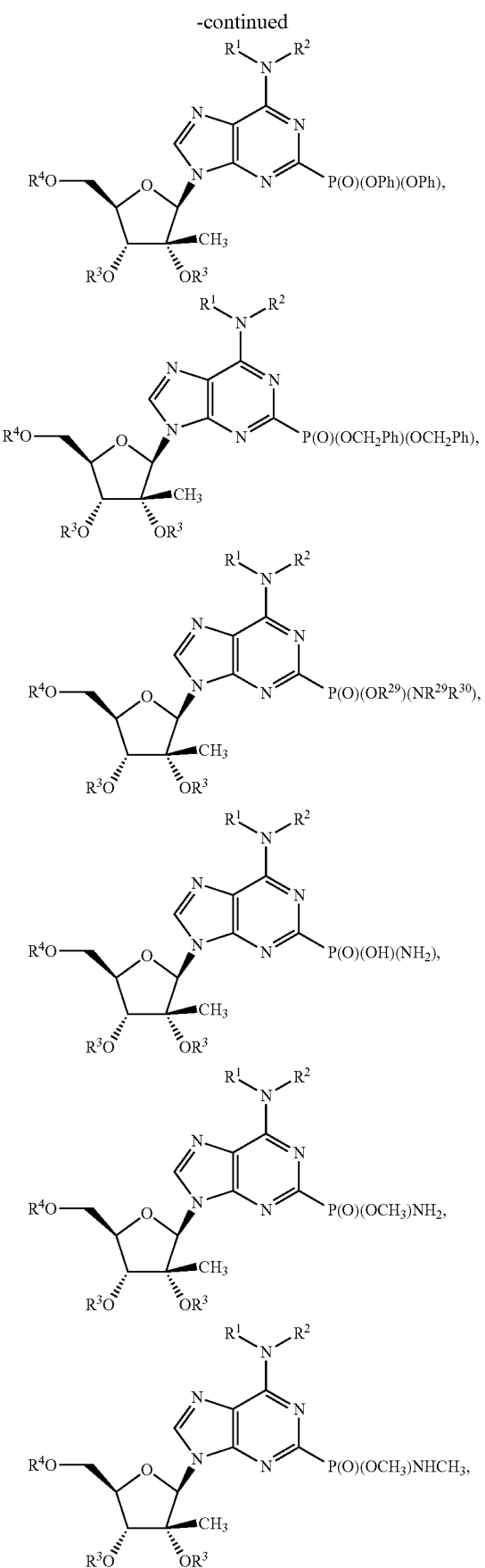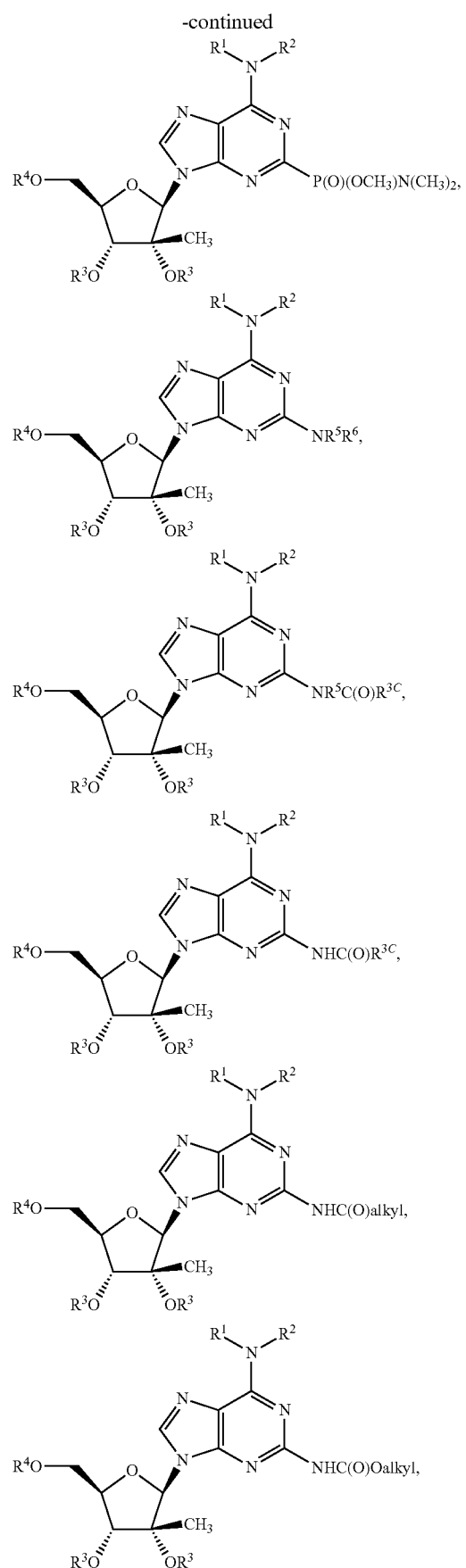

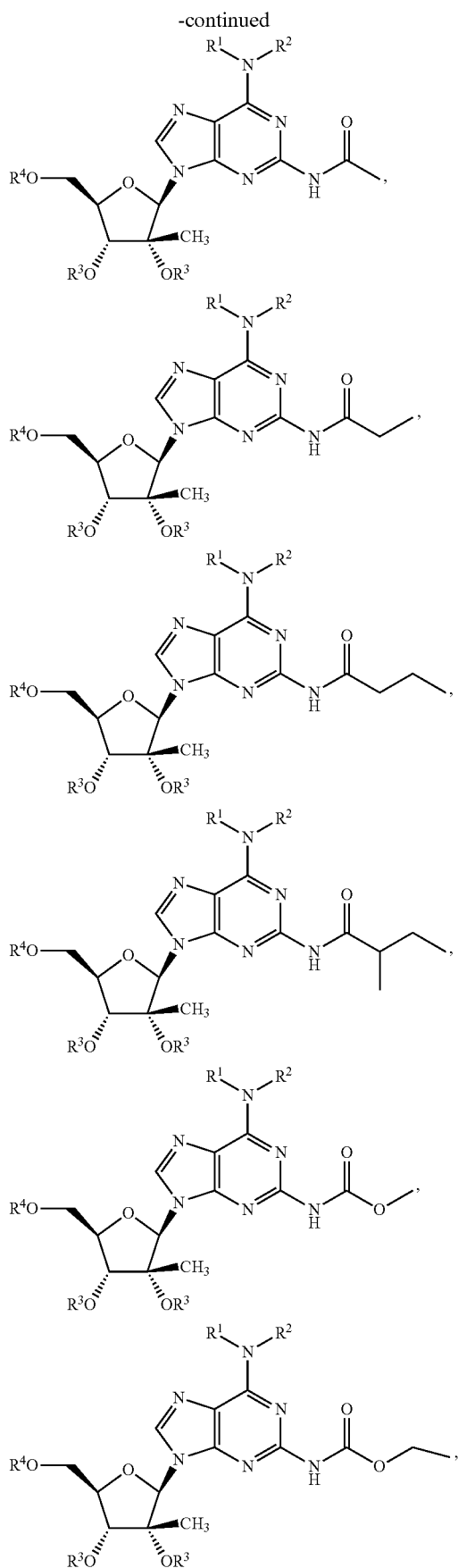
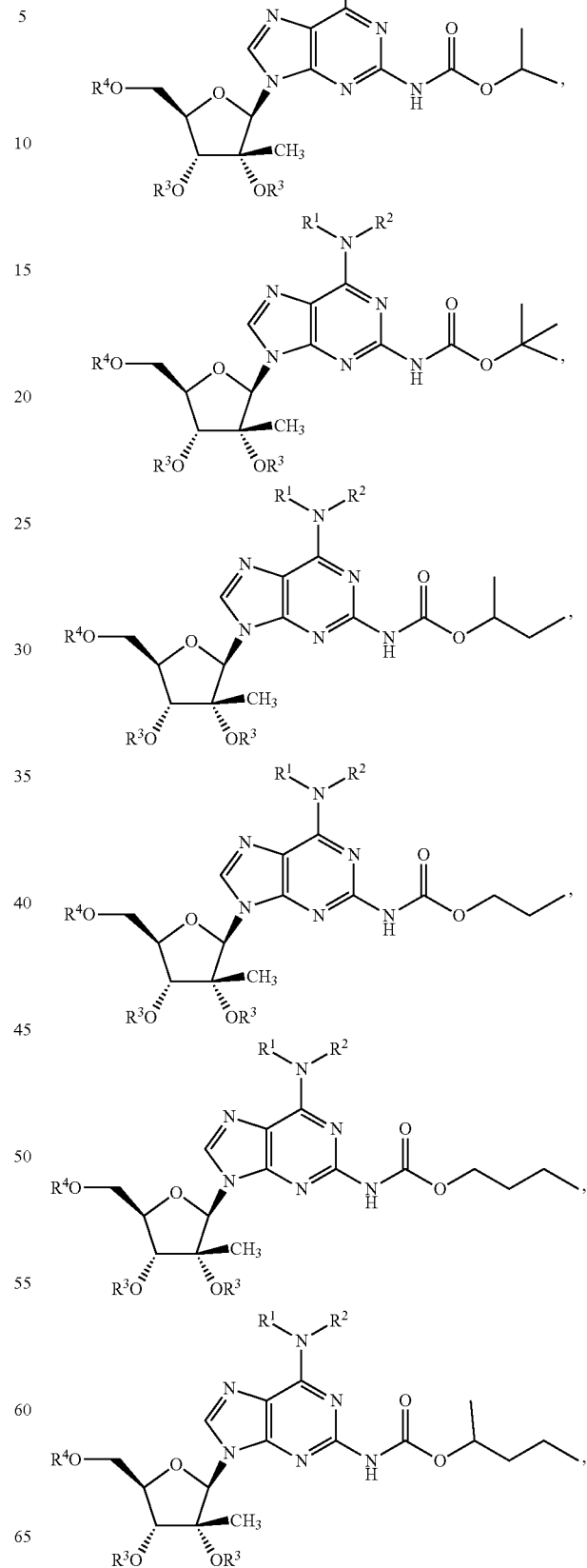

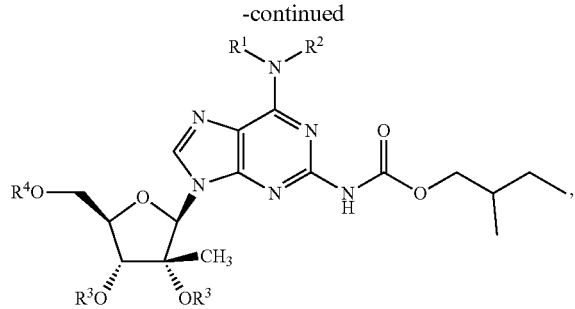
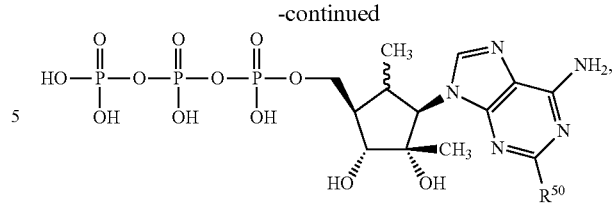
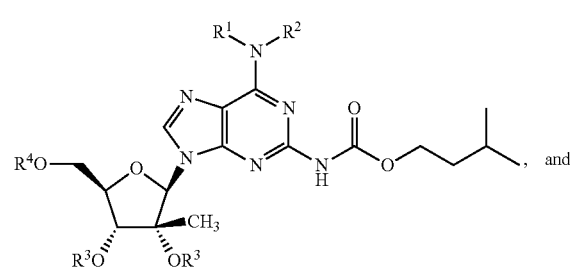
, and
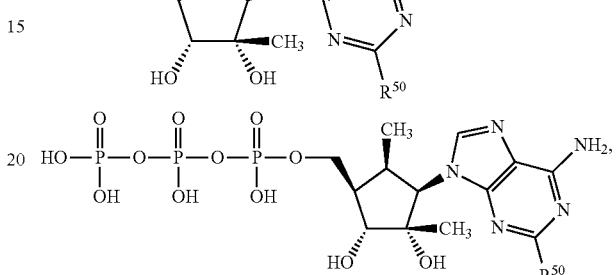
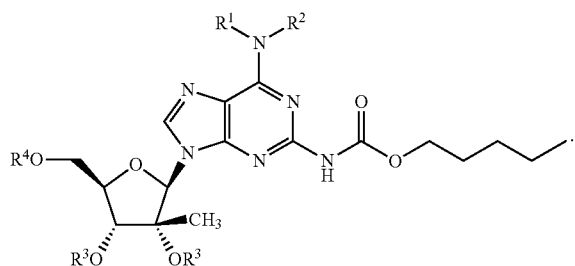
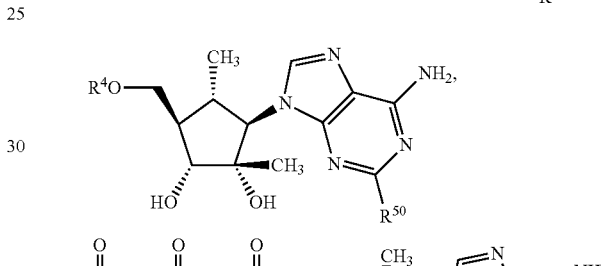
In an alternative embodiment, the use of an effective amount of a compound of Formula V or a pharmaceutically acceptable salt thereof, for the treatment of an infection of an RNA virus in a host, including a human in need thereof is provided. Non-limiting examples of compounds of Formula V include:
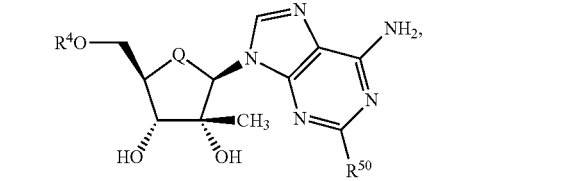
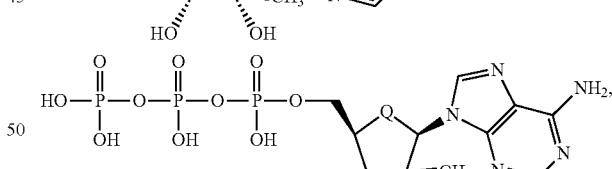
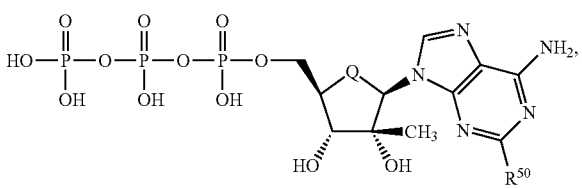
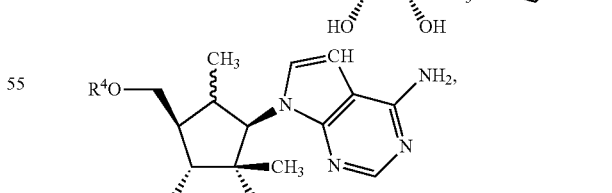
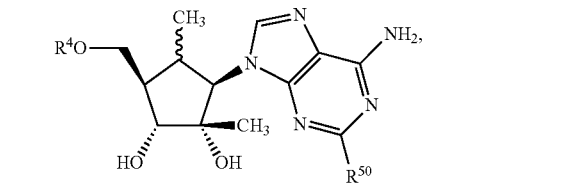
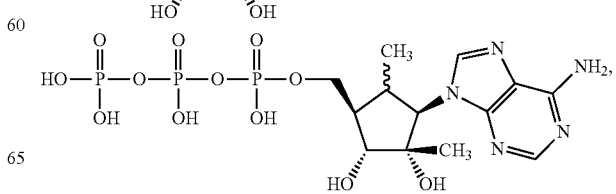

225
-continued
226
-continued
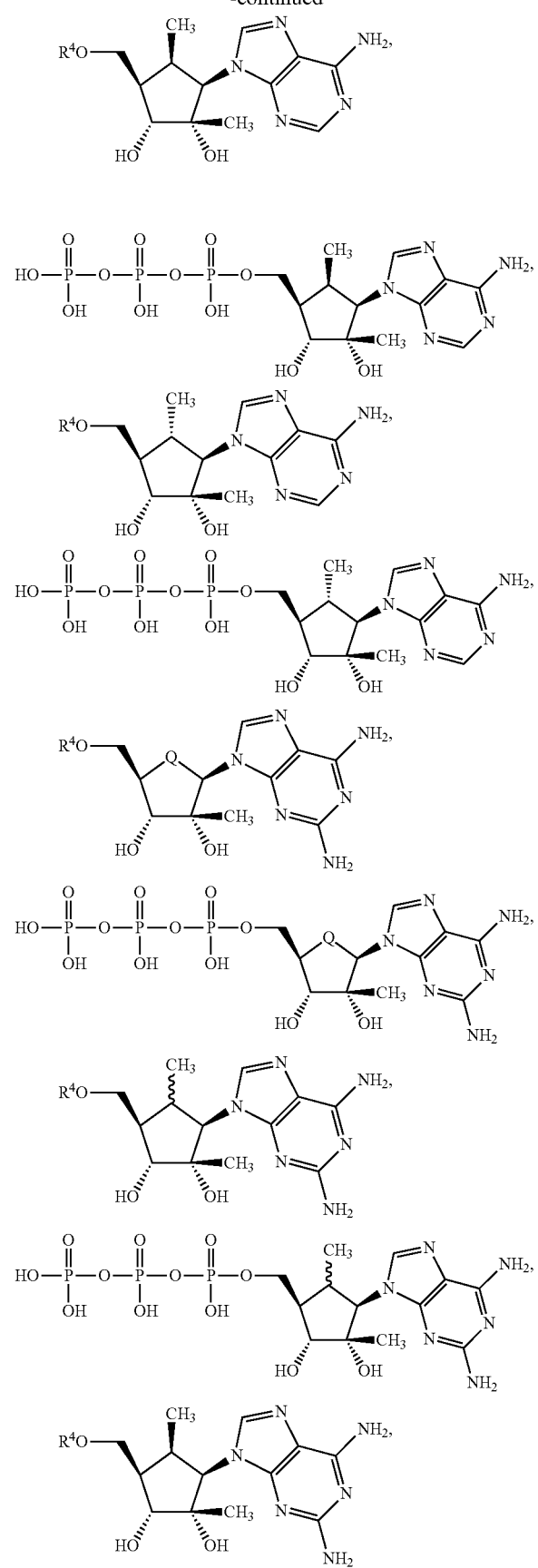
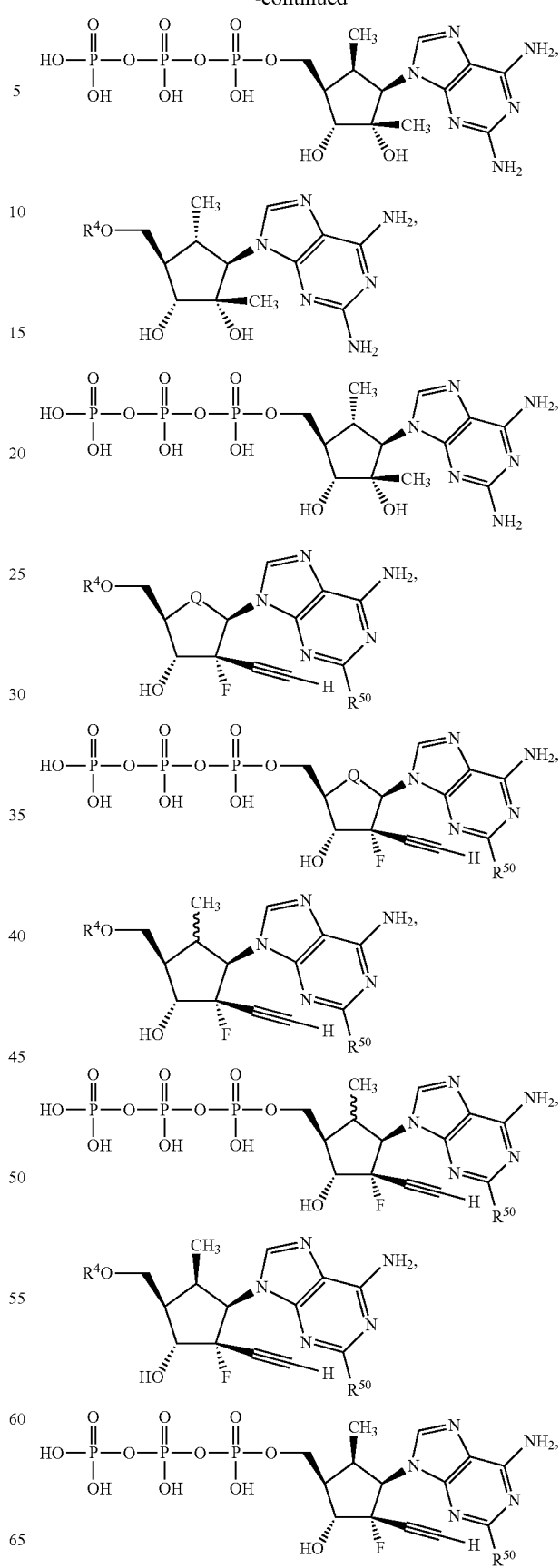

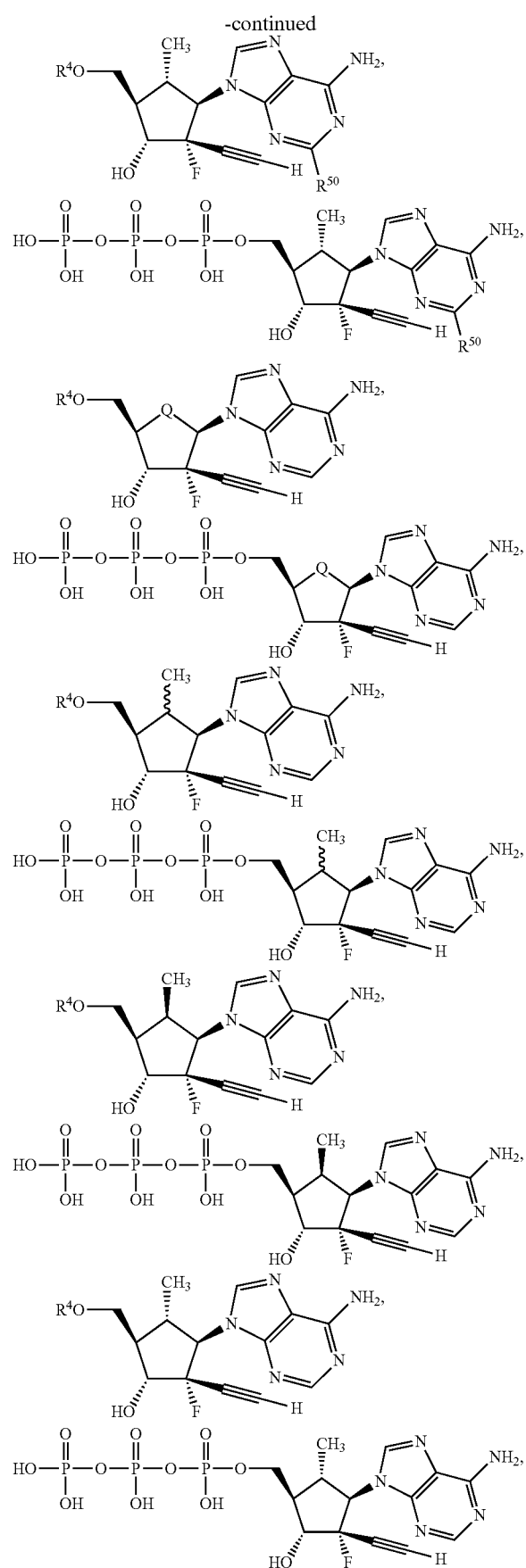
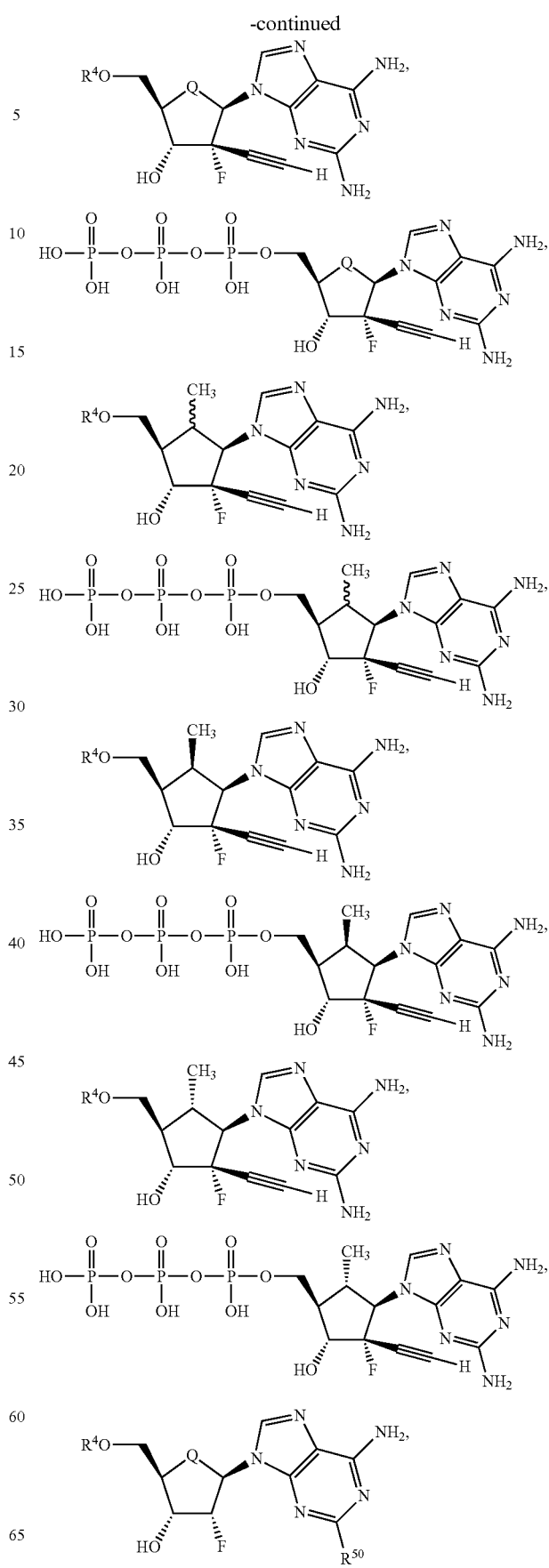

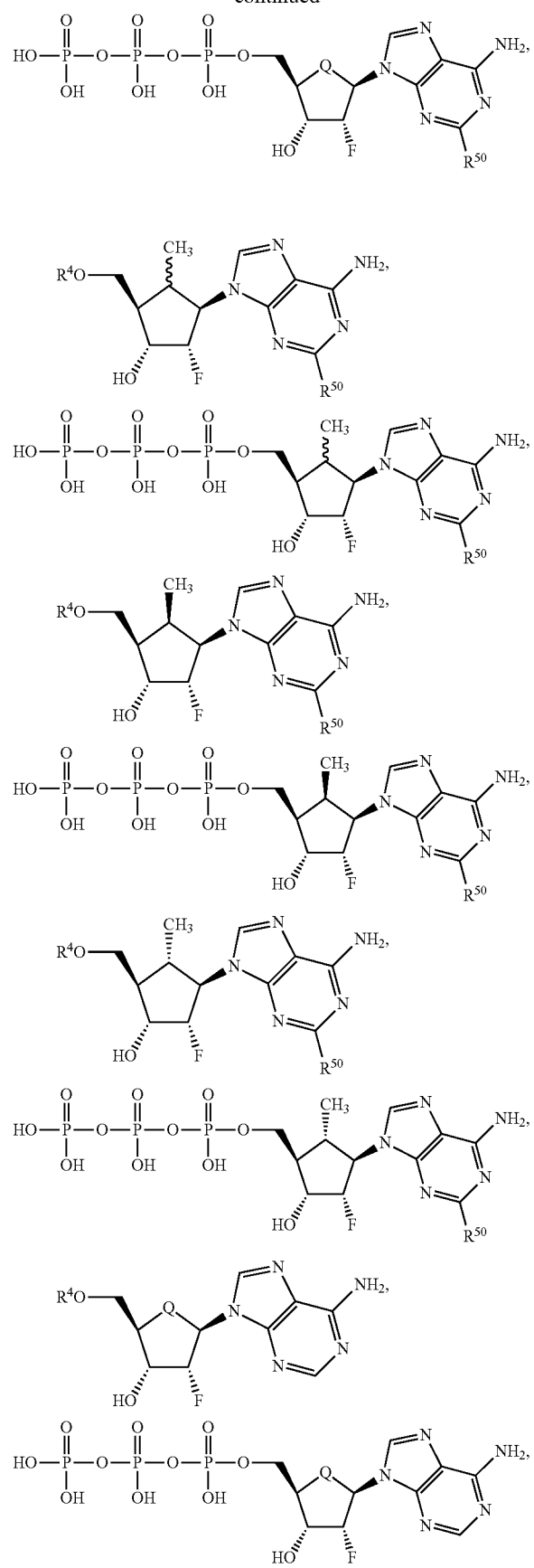
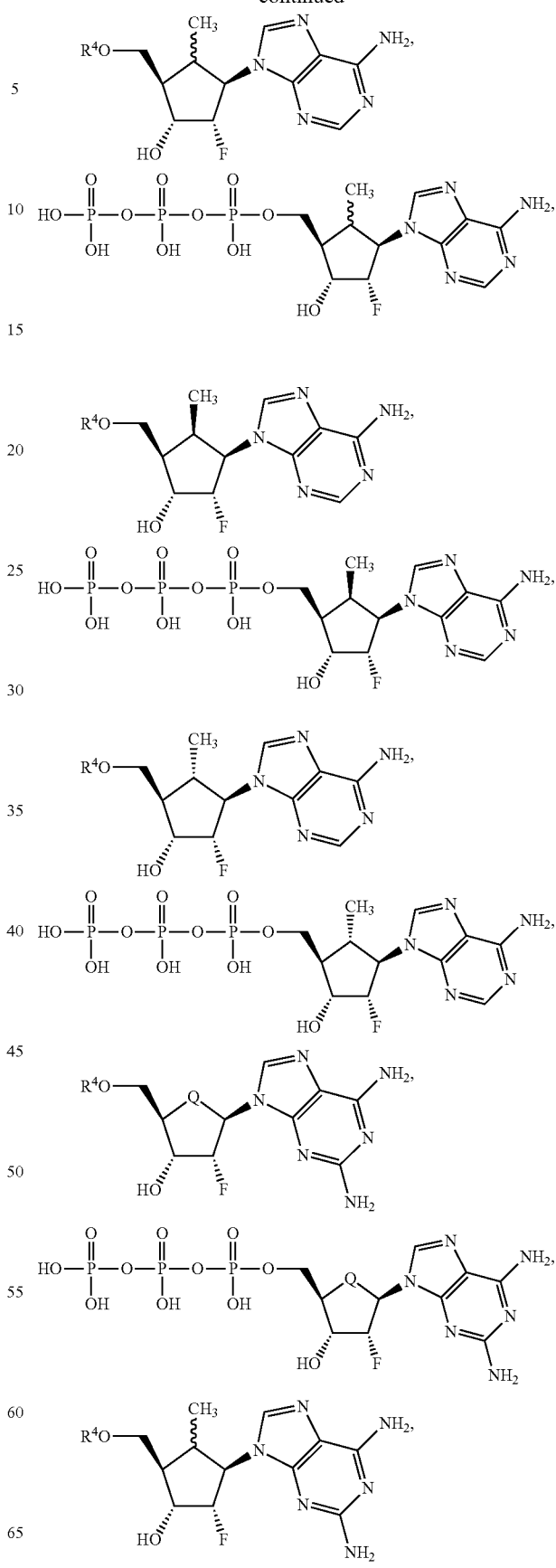

231
-continued
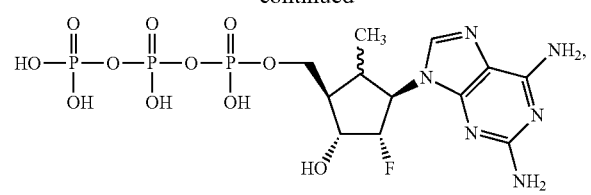
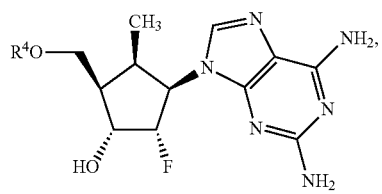
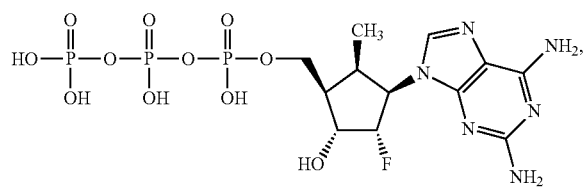
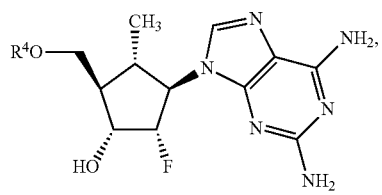
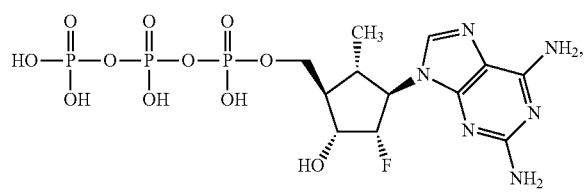
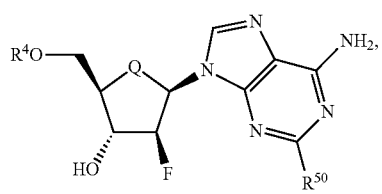
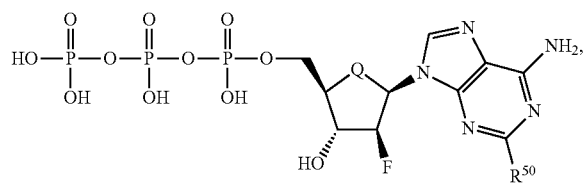
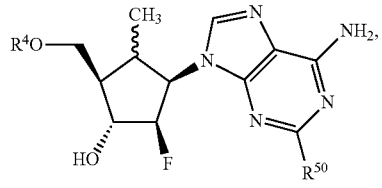
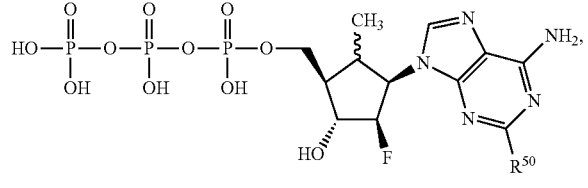
232
-continued
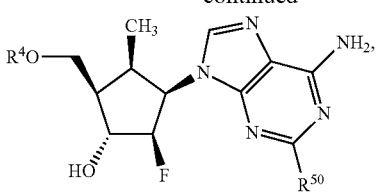
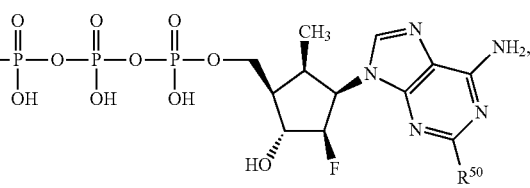
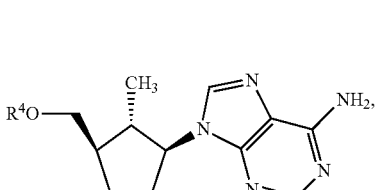
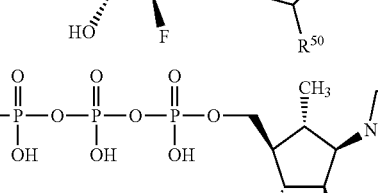
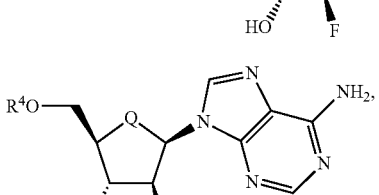
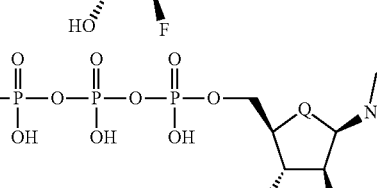
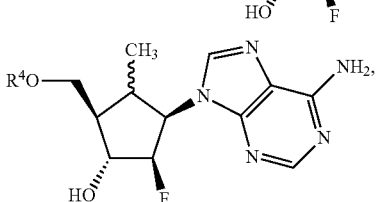
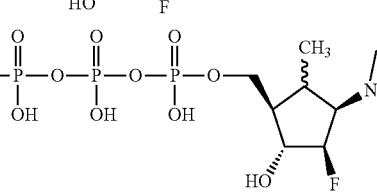
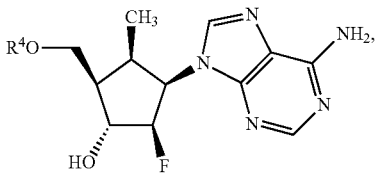

233 234

235
-continued
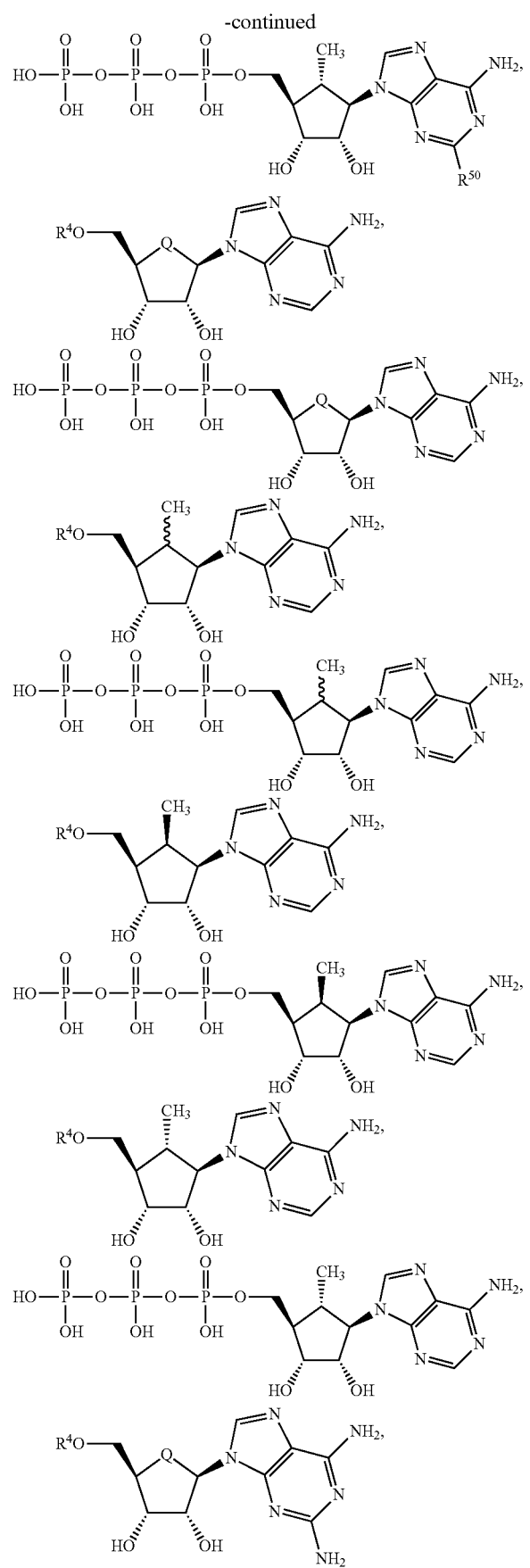
236
-continued
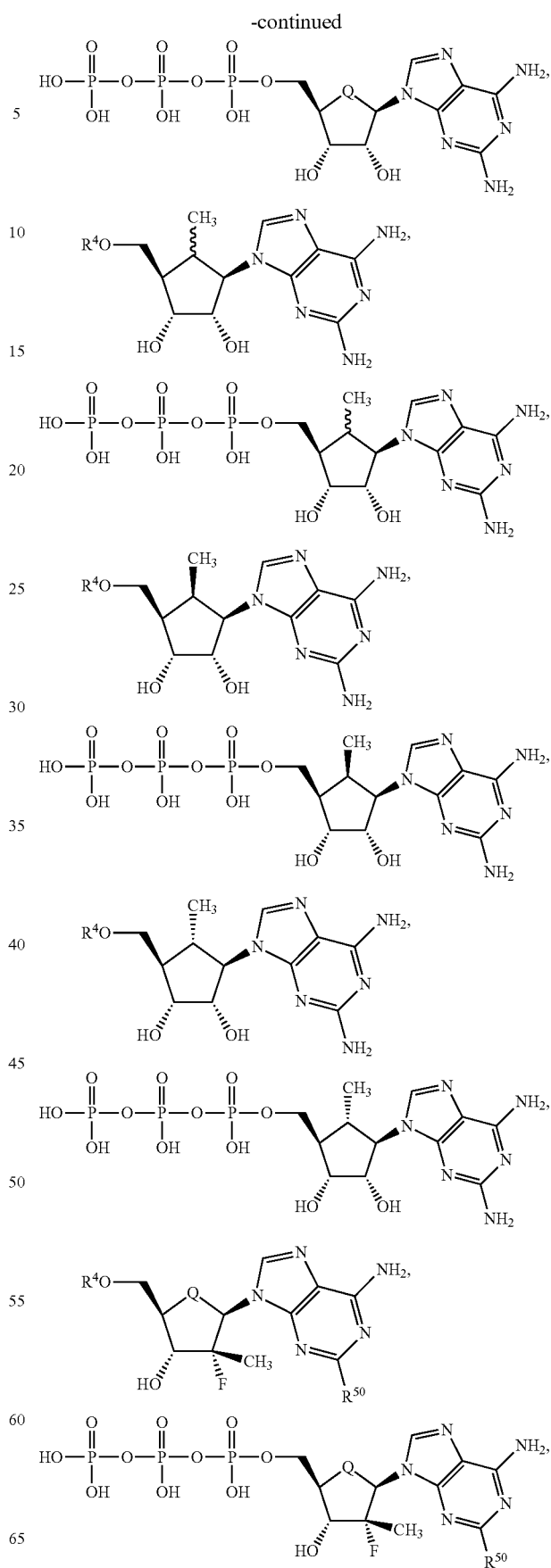

237
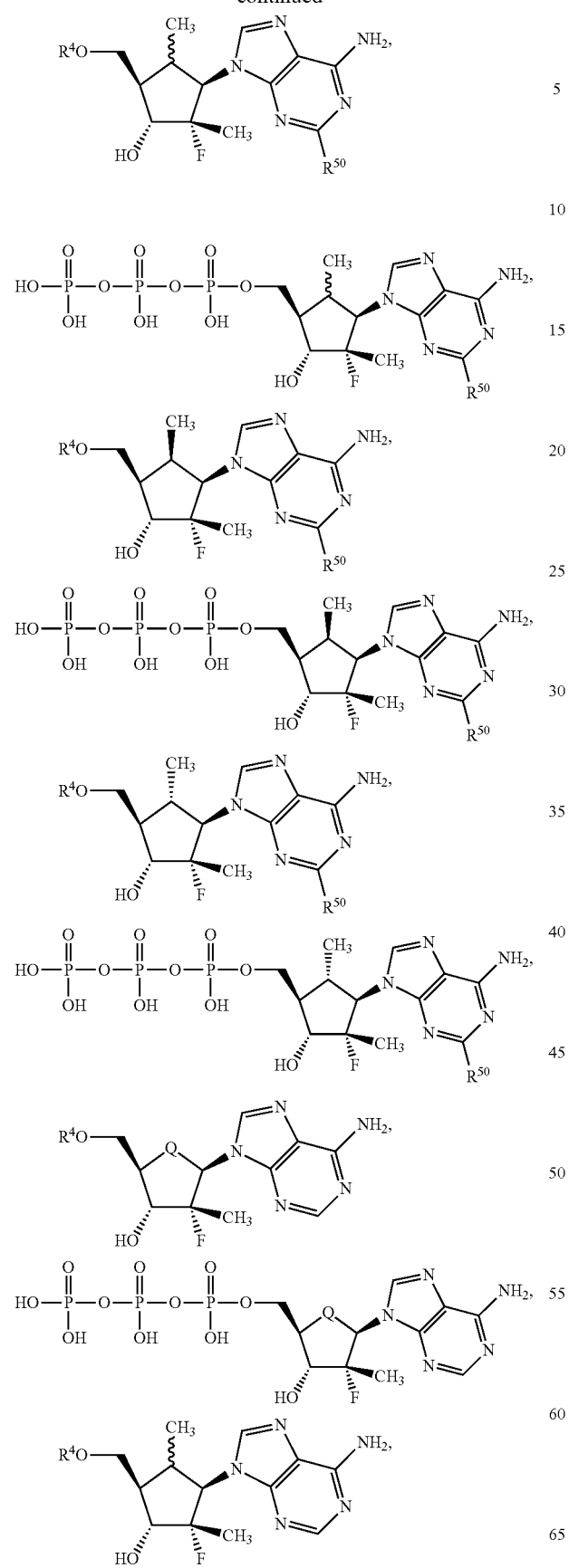
238
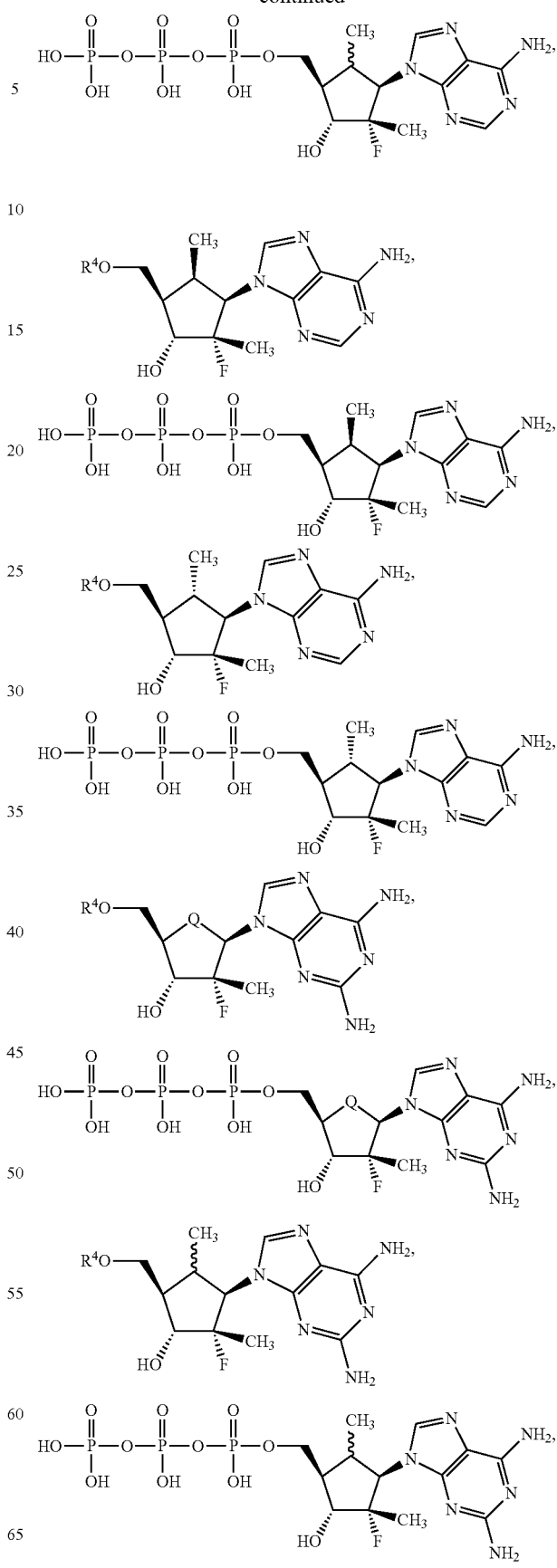

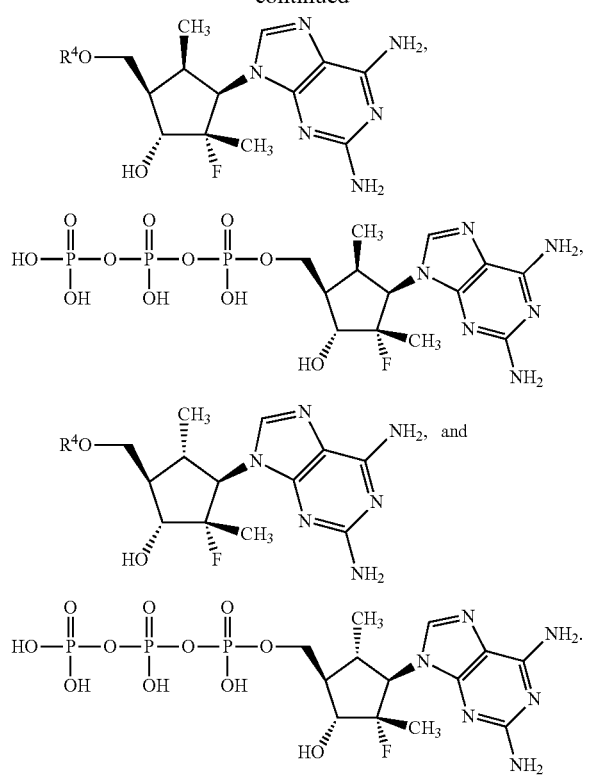
In one embodiment, the use of an effective amount of a compound of Formula VI or a pharmaceutically acceptable salt thereof, for the treatment of an infection of an RNA virus in a host, including a human in need thereof is provided. Non-limiting examples of compounds of Formula VI include:
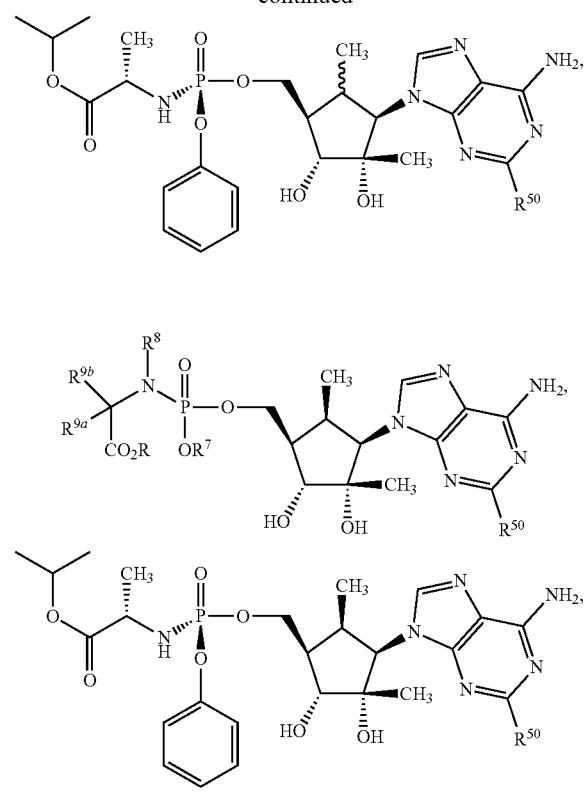
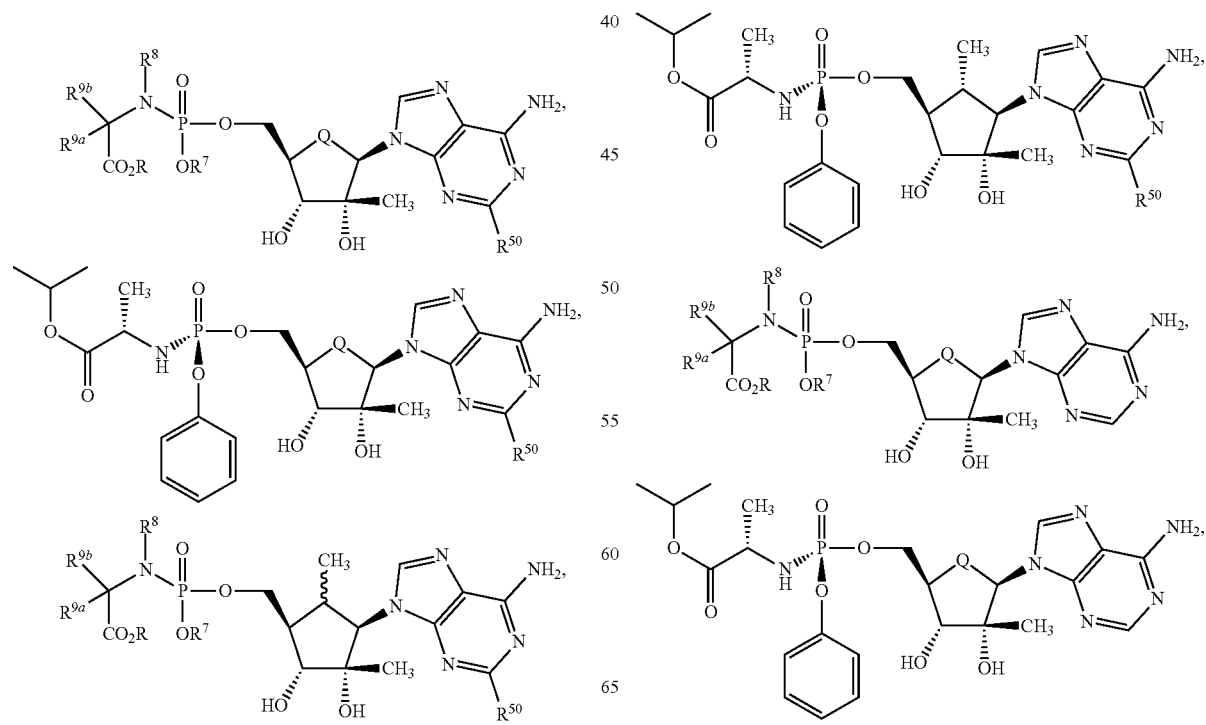

-continued
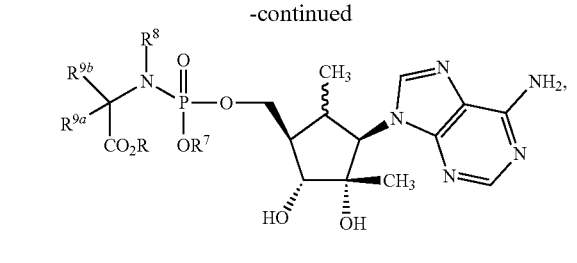
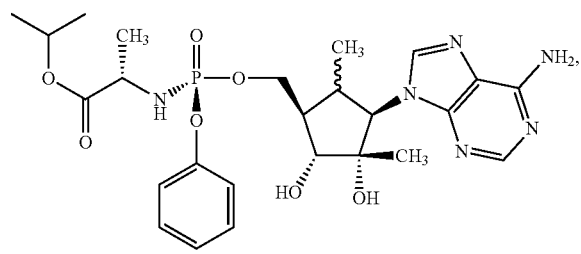
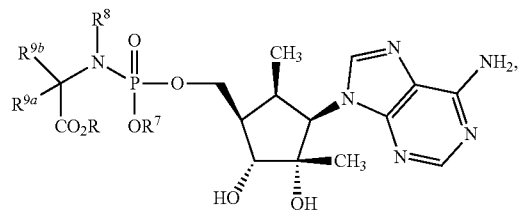
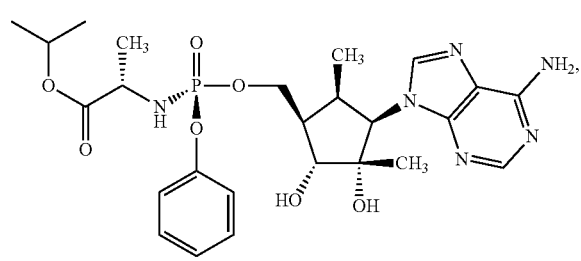
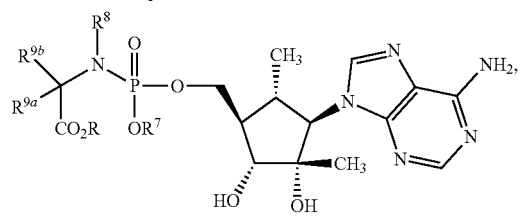
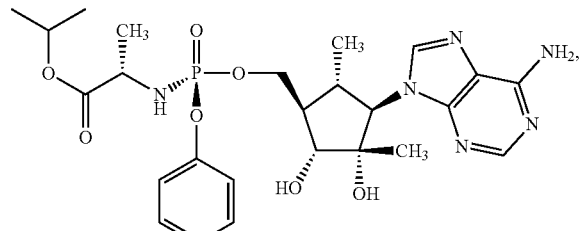
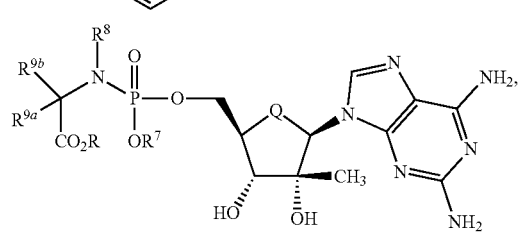
-continued
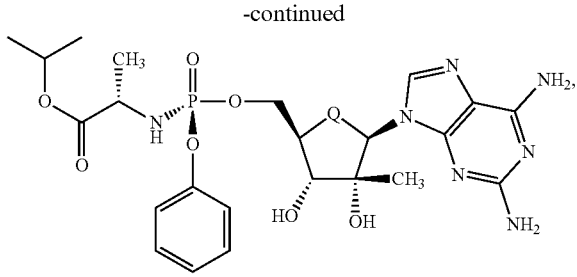
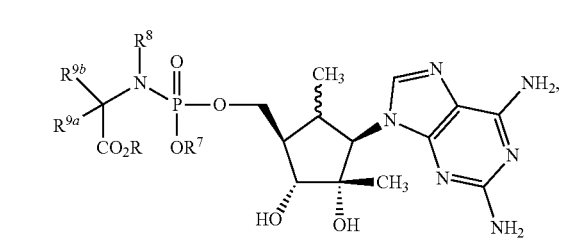
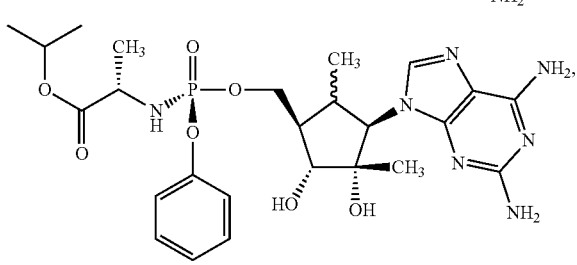
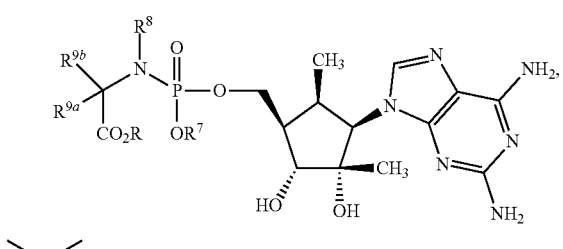
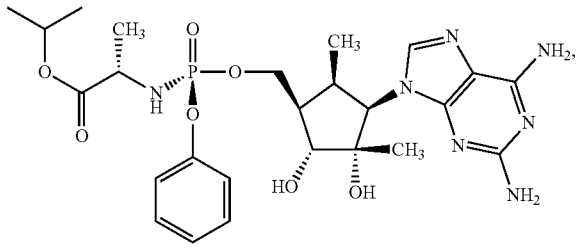
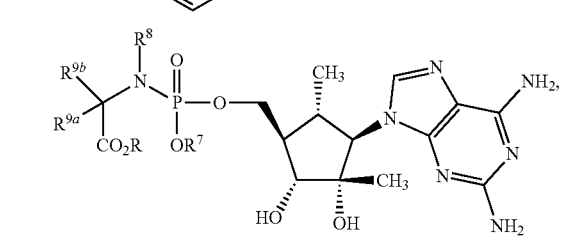
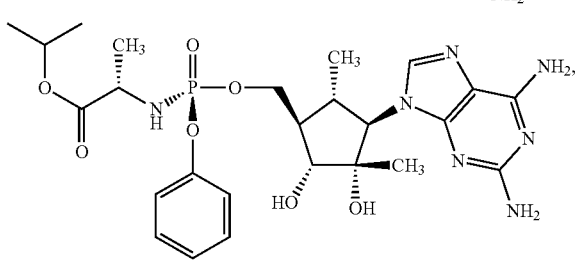

243
-continued
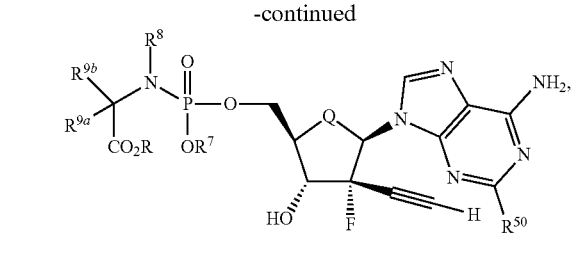
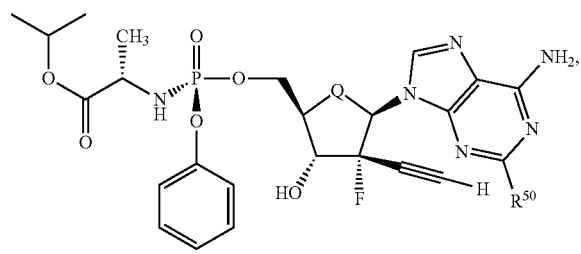
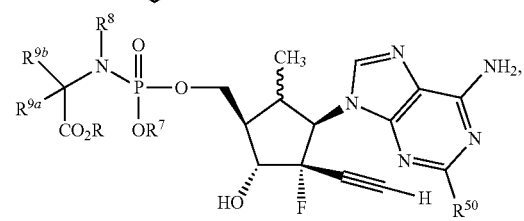
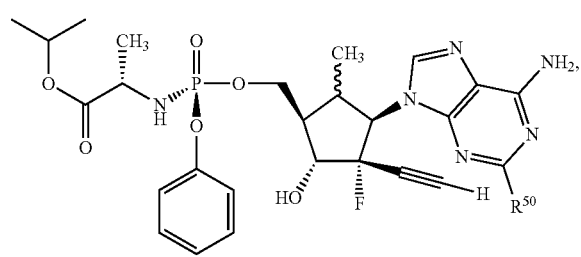
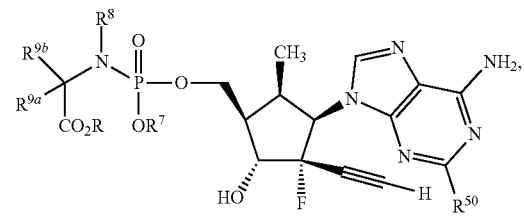
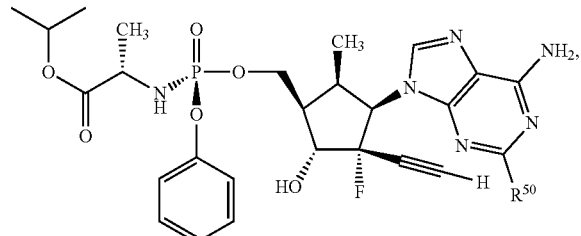
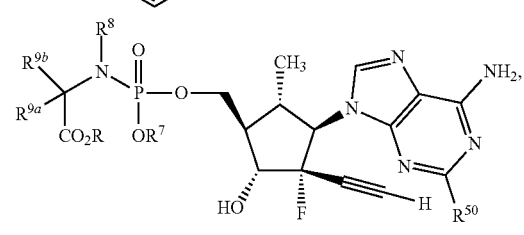
244
-continued
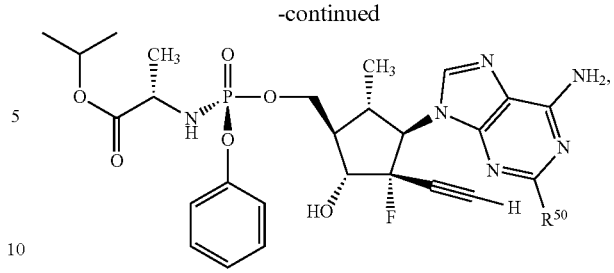
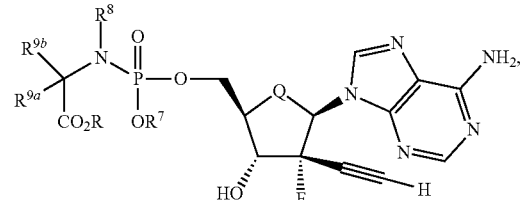
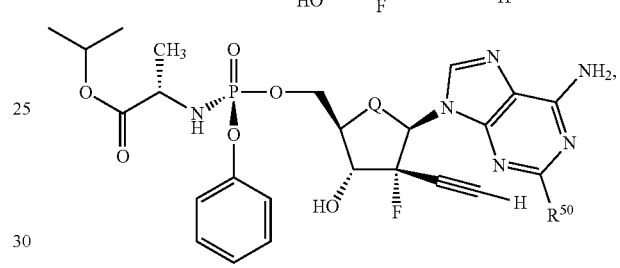
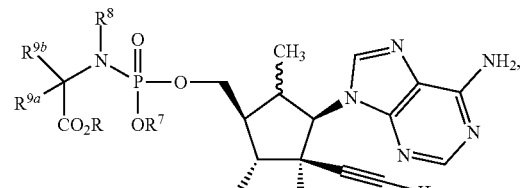
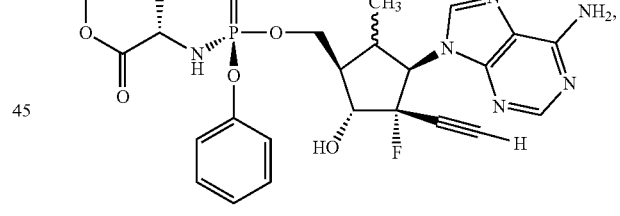
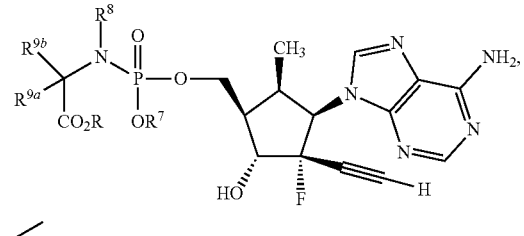
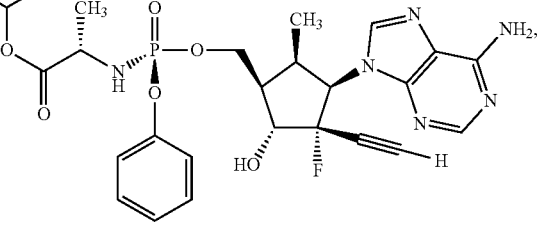

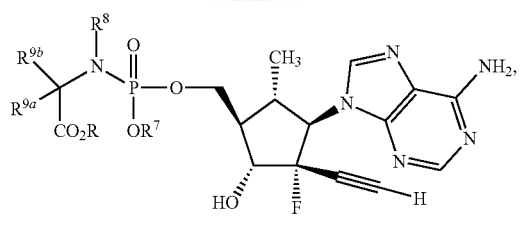
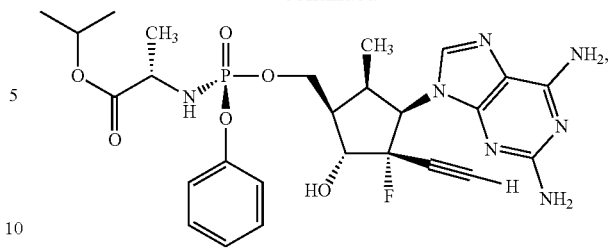
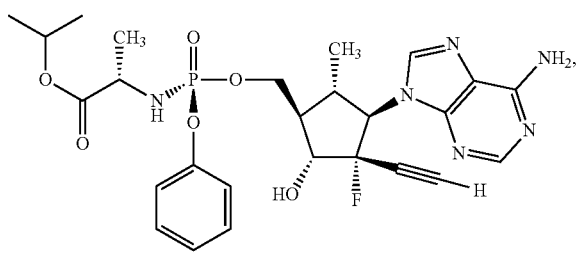
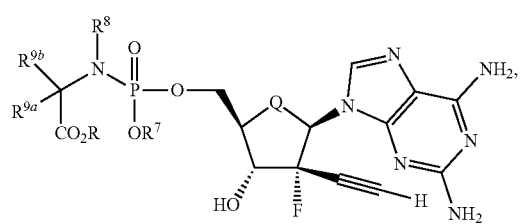
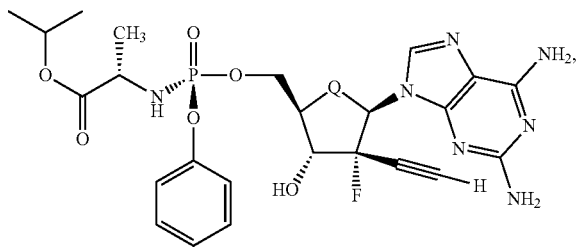
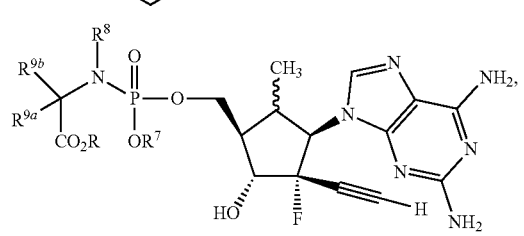
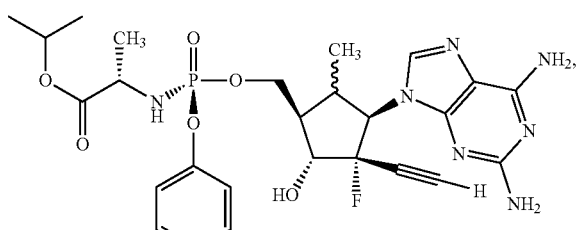
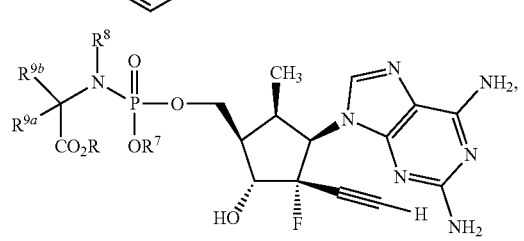

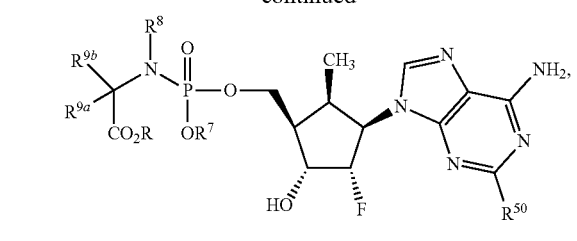
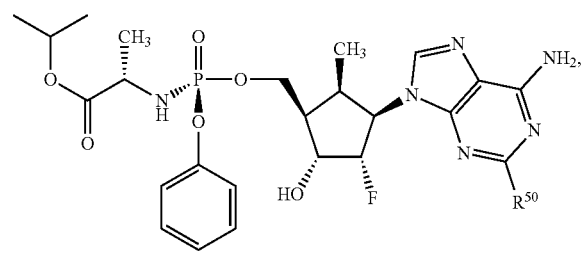
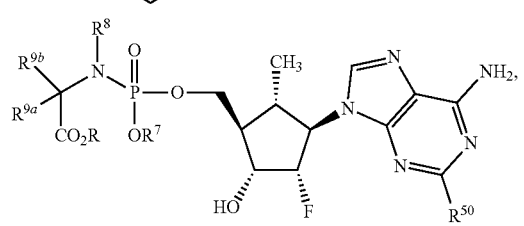
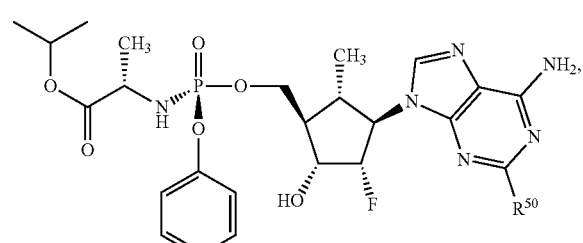
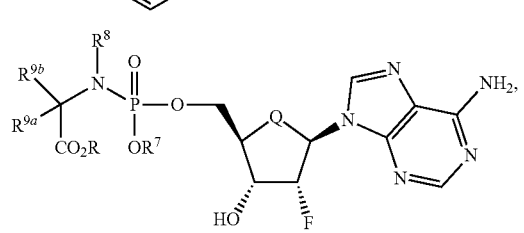
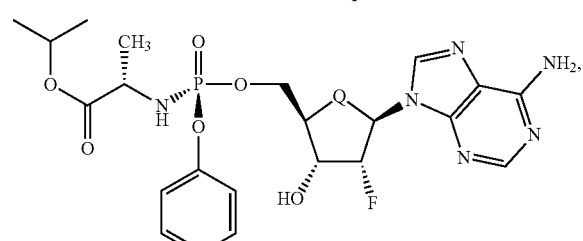
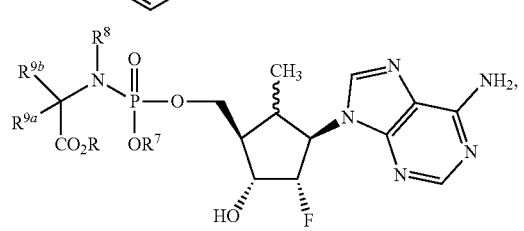
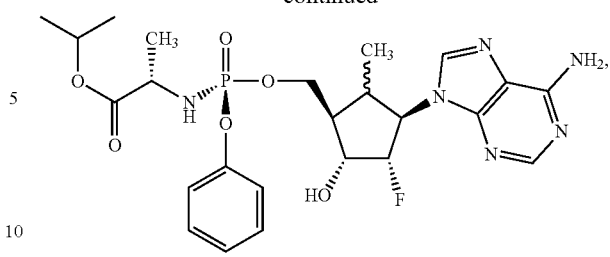
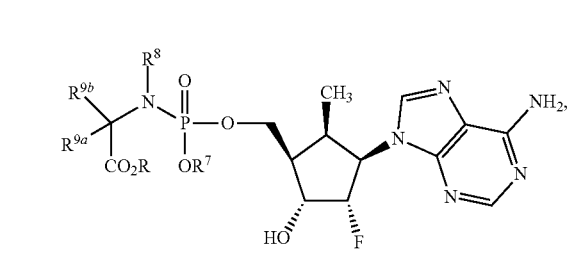
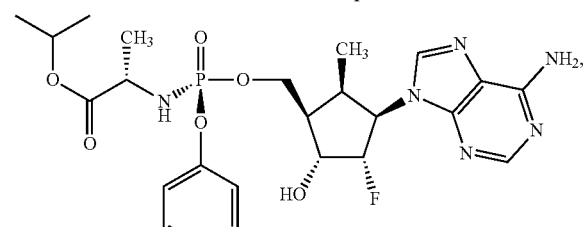
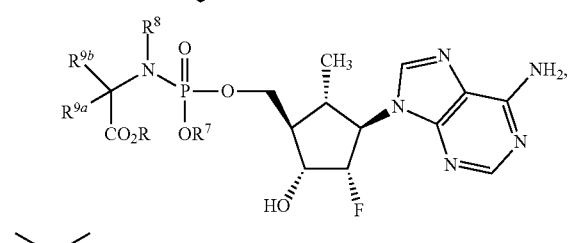
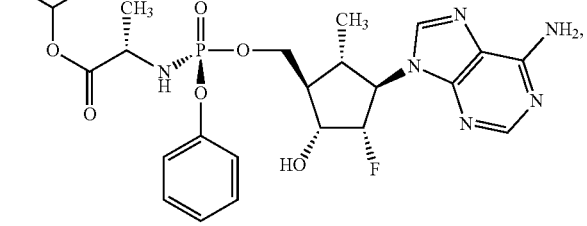
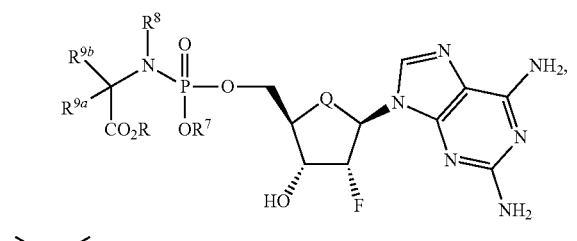
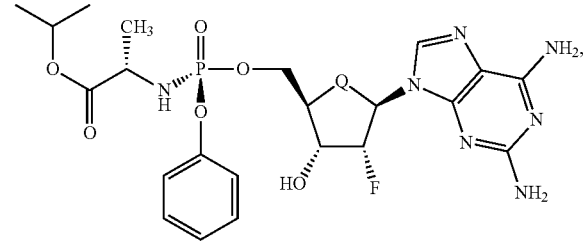

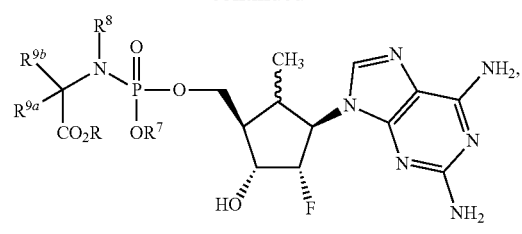
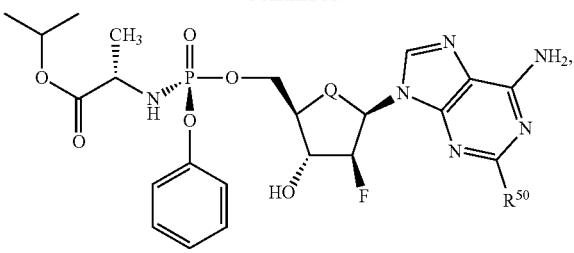
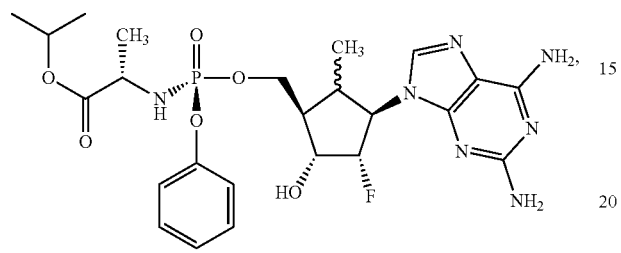
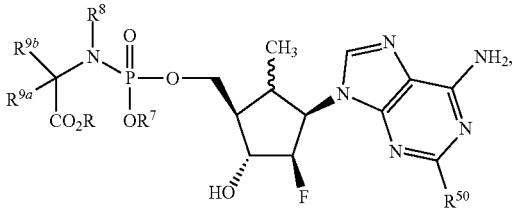
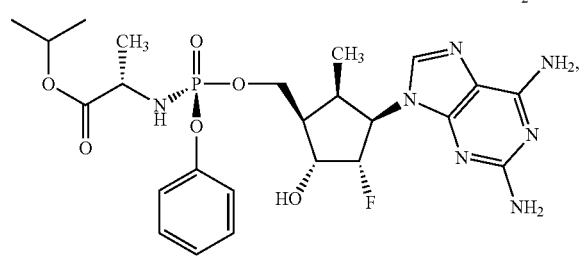
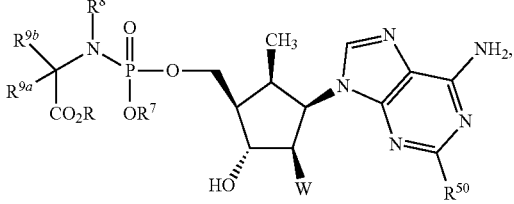
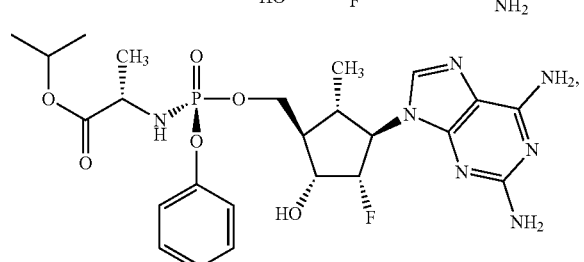
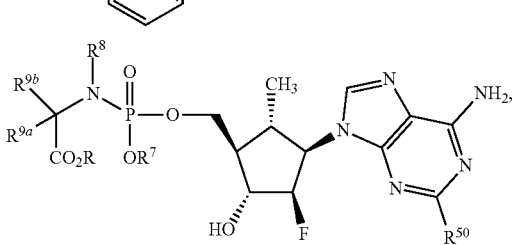
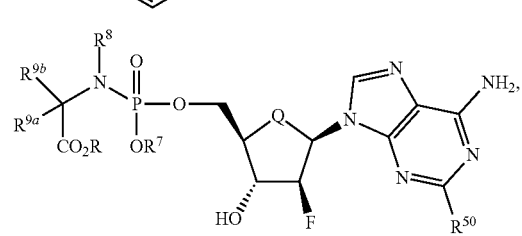
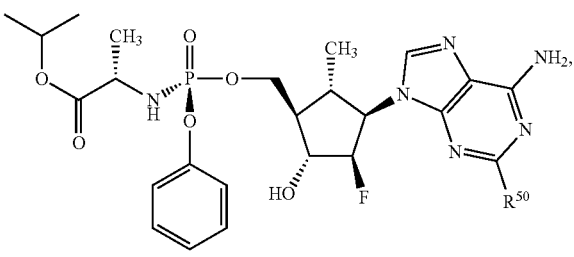

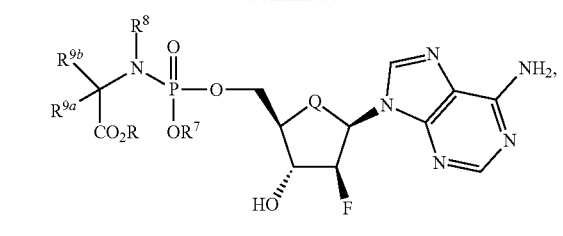
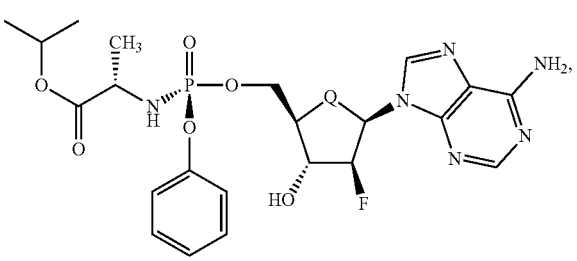
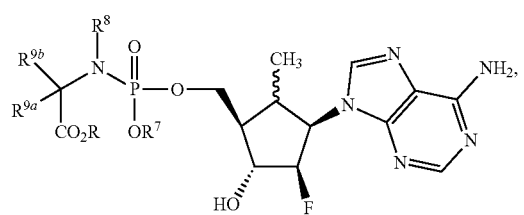
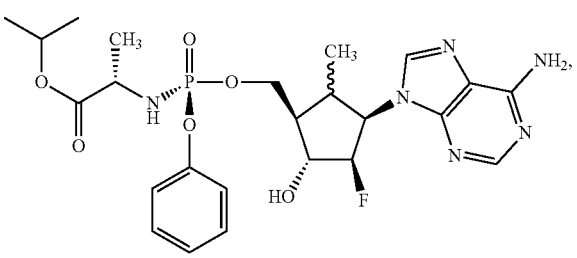
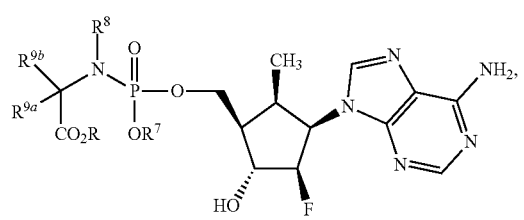
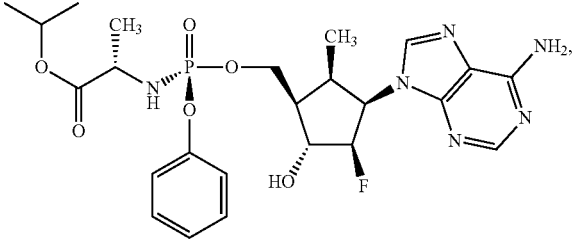
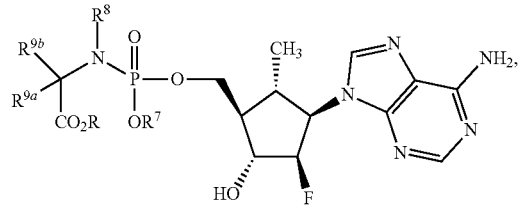
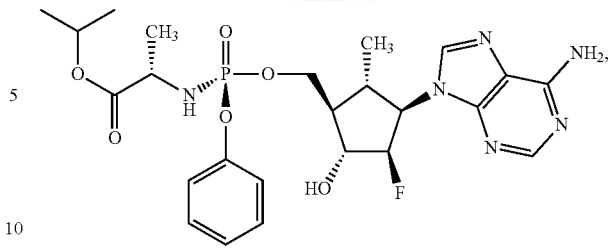
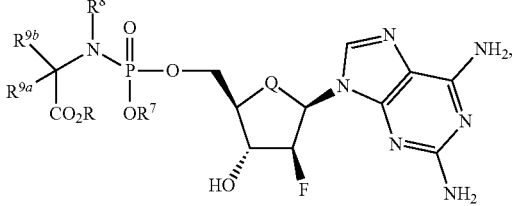
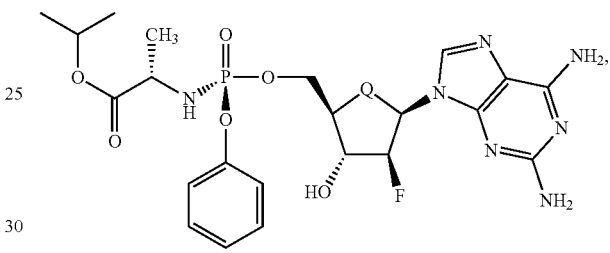
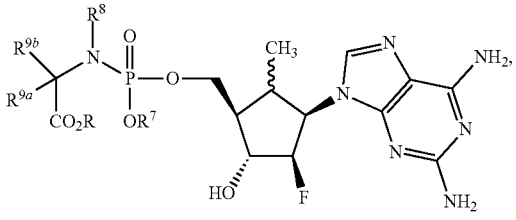
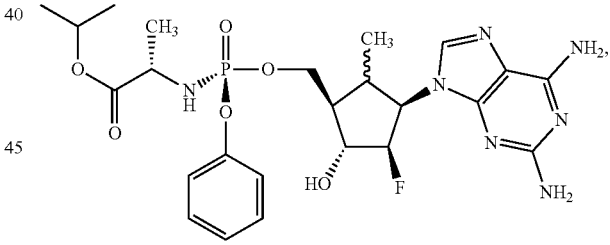
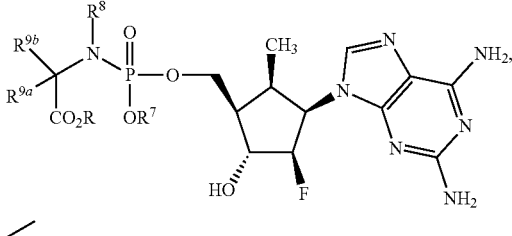
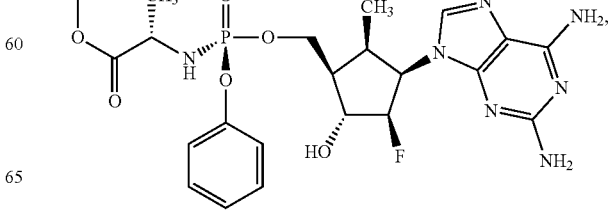

253
-continued
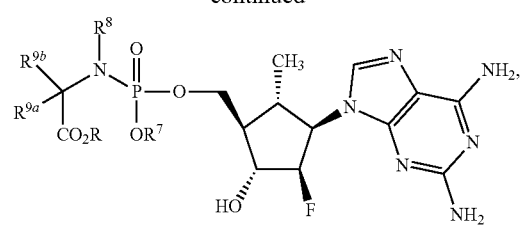
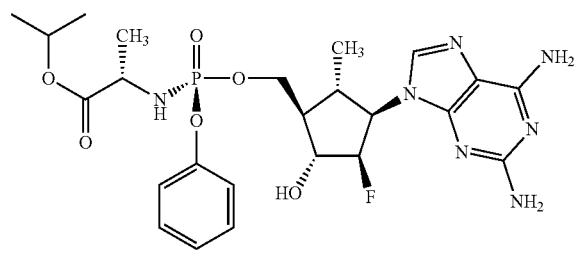
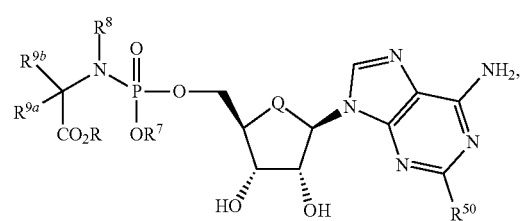
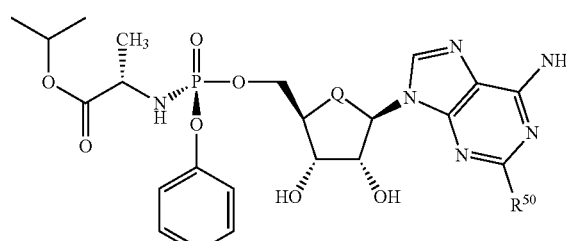
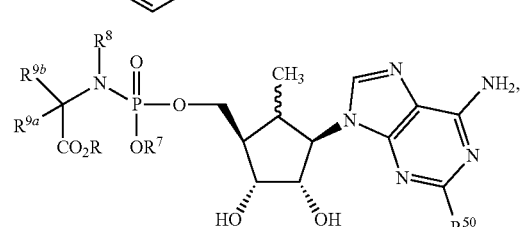
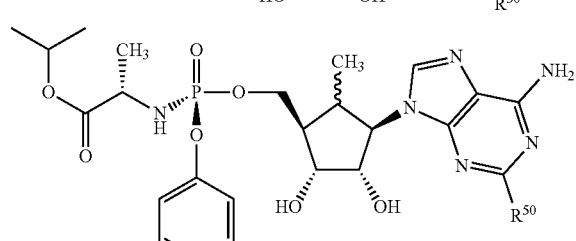
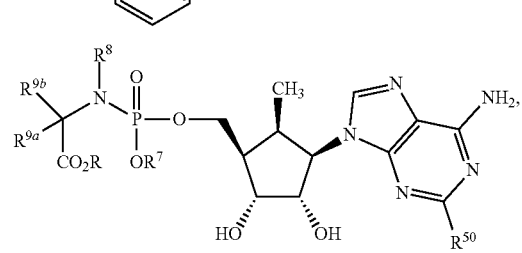
254
-continued
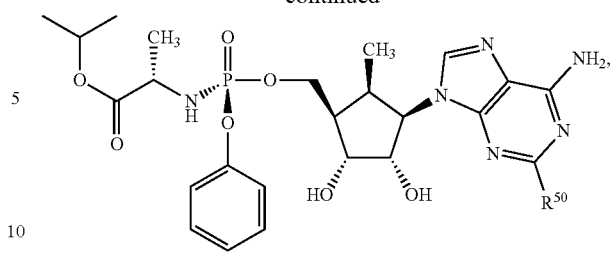
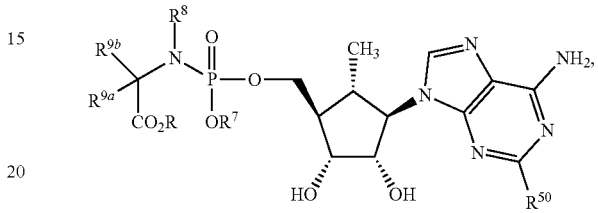
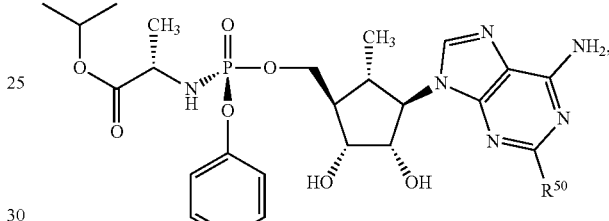
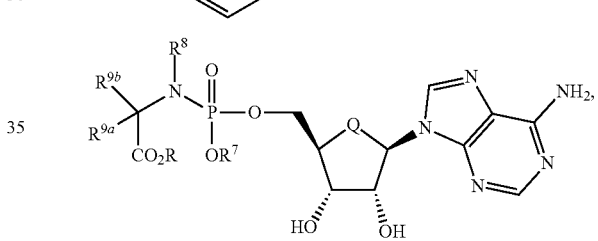
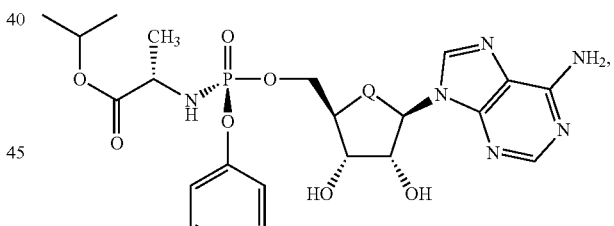
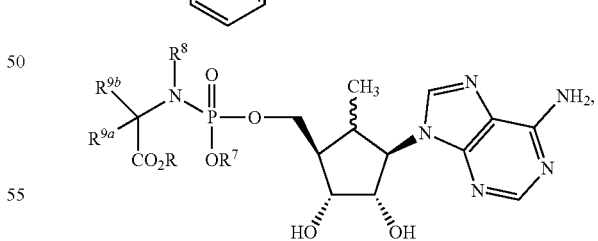
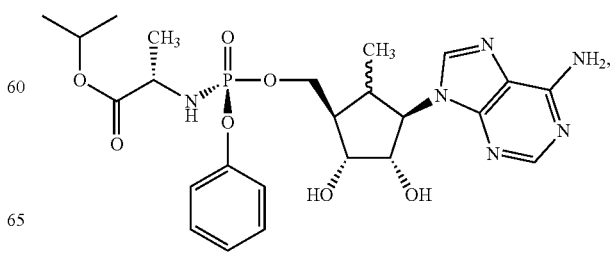

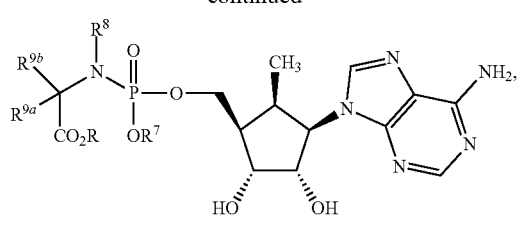
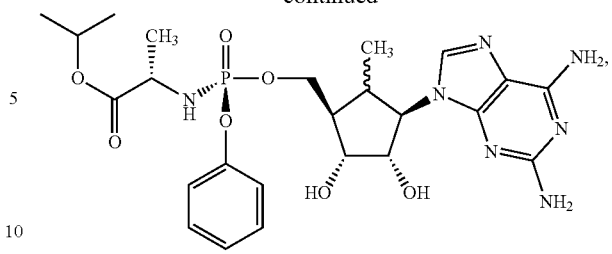
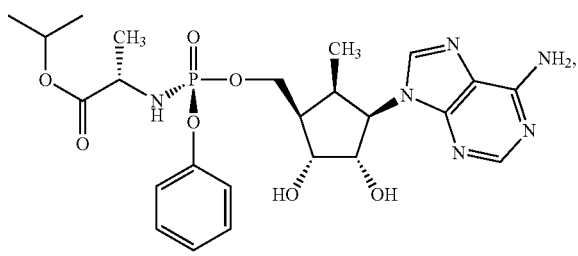
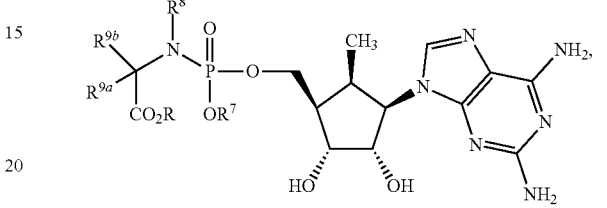
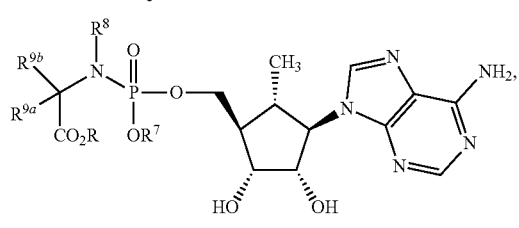
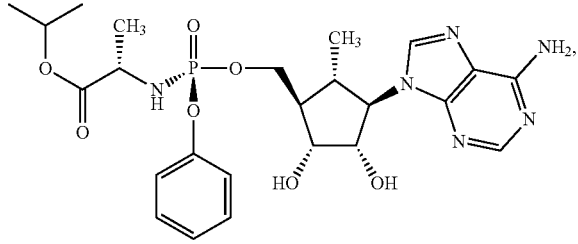
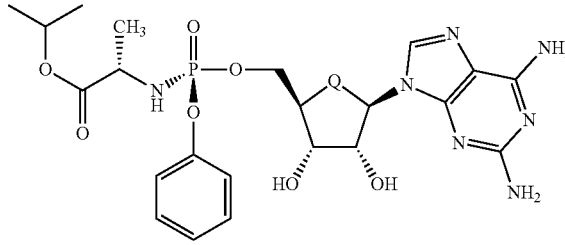
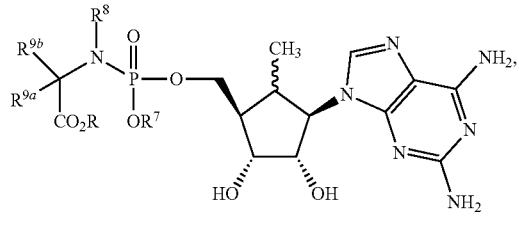
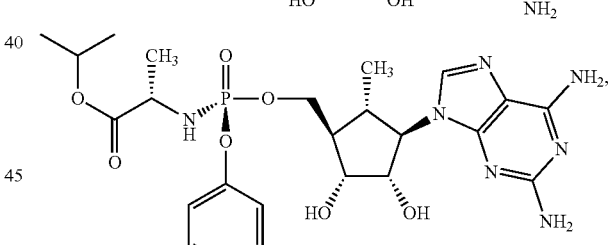
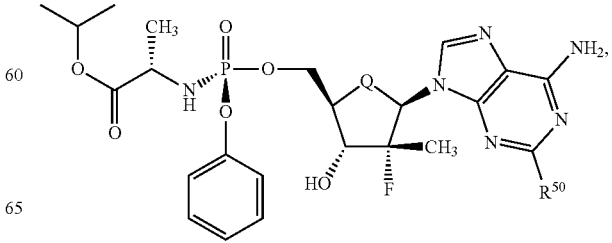

257
-continued
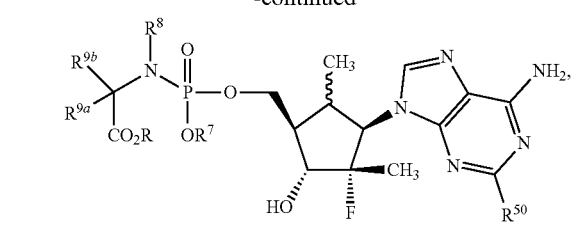
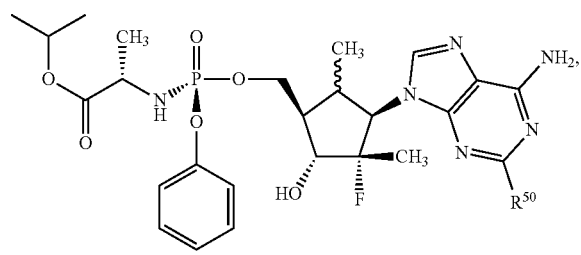
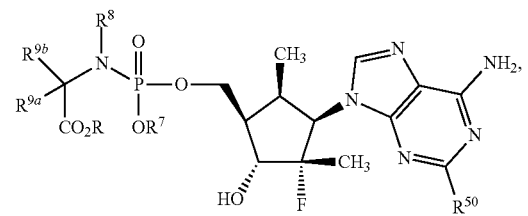
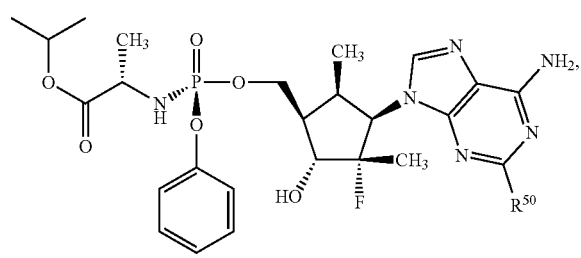
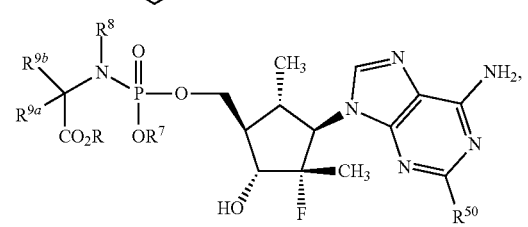
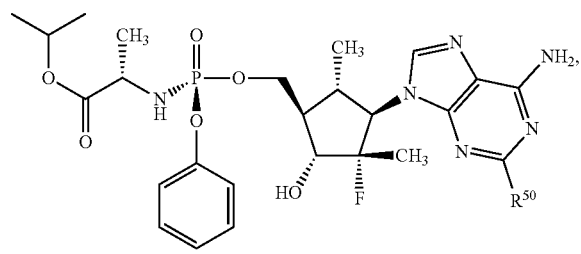
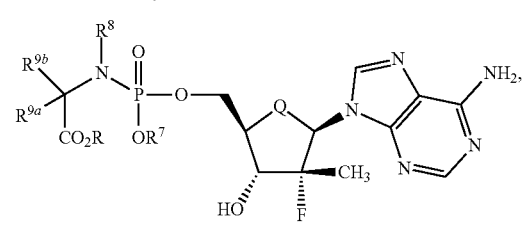
258
-continued
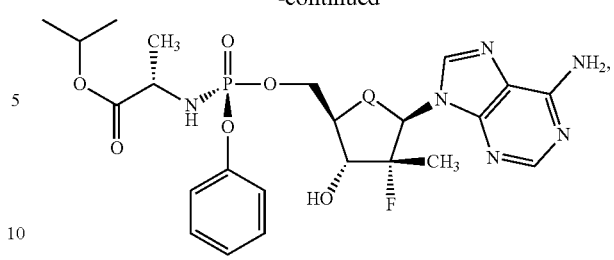
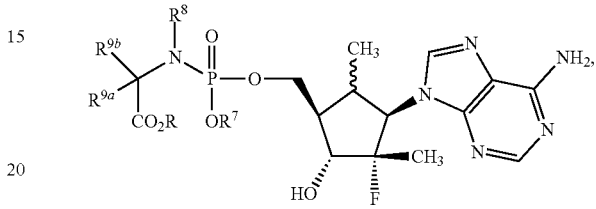
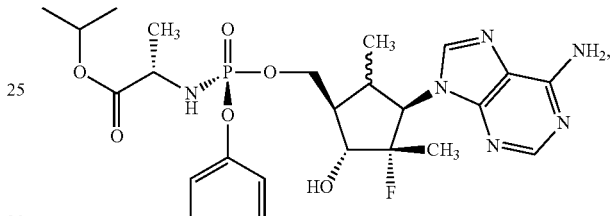
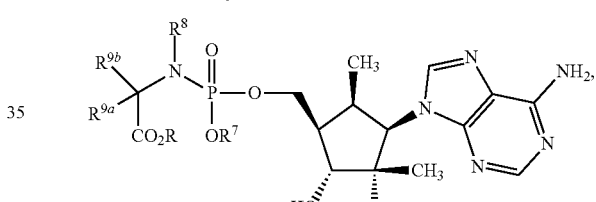
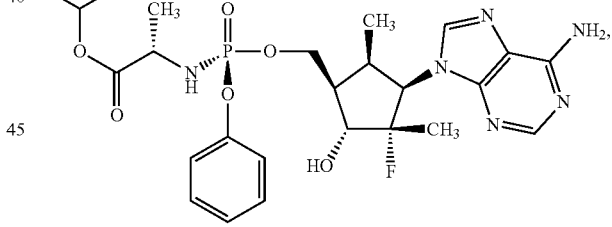
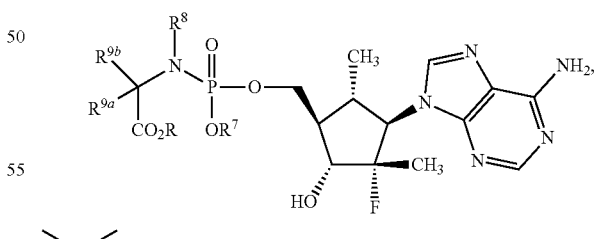
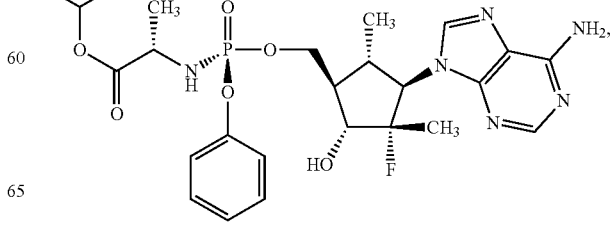

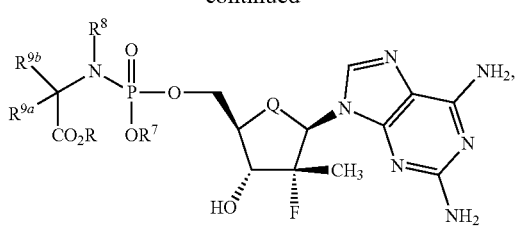
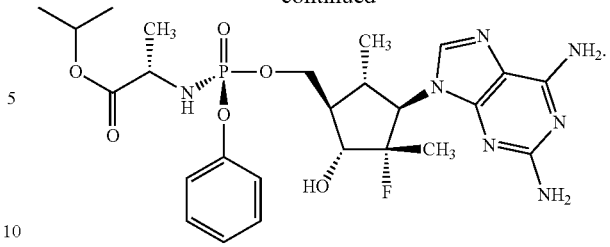
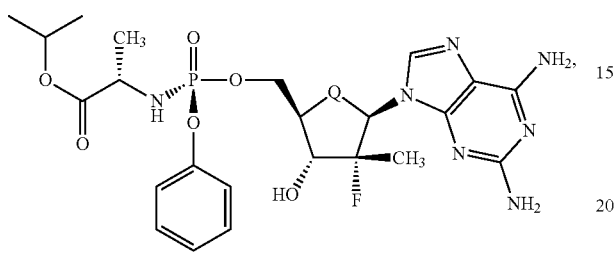
In some embodiments, $R^3$ is H and $R^4$ is
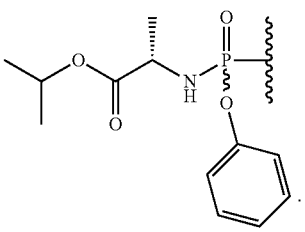 [SMILES: *P(=O)(N[C@@H](C)C(=O)OC(C)C)Oc1ccccc1]
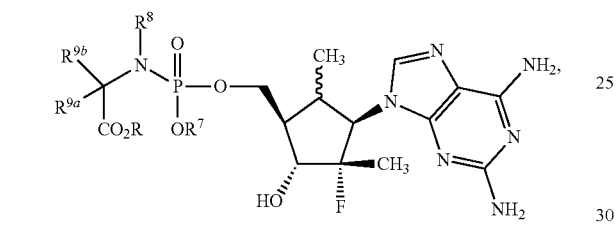
In some embodiments, $R^3$ is H and $R^4$ is
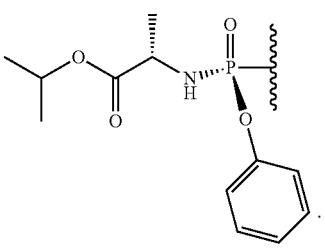 [SMILES: *[P@@](=O)(N[C@@H](C)C(=O)OC(C)C)Oc1ccccc1]
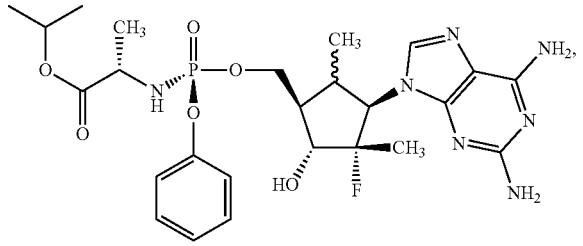
In some embodiments, $R^3$ is H and $R^4$ is
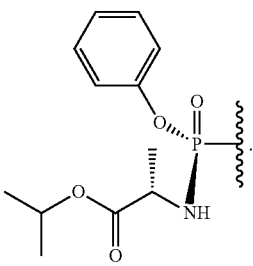 [SMILES: *[P@](=O)(N[C@@H](C)C(=O)OC(C)C)Oc1ccccc1]
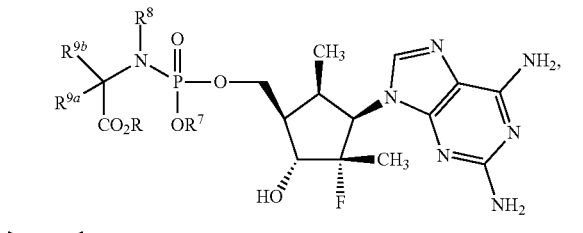
In some embodiments, $R^3$ is H and $R^4$ is
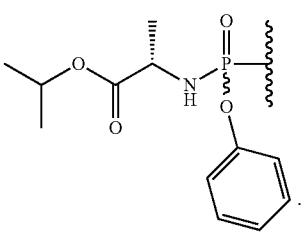 [SMILES: *P(=O)(N[C@@H](C)C(=O)OC(C)C)Oc1ccccc1]
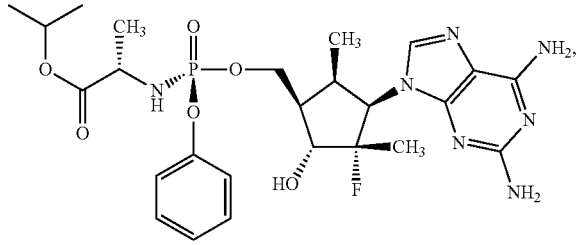
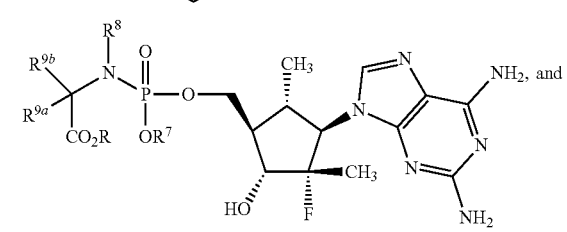

In some embodiments, $R^3$ is H and $R^4$ is

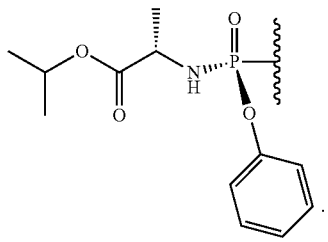 [SMILES: *[P@@](=O)(N[C@@H](C)C(=O)OC(C)C)Oc1ccccc1]

In some embodiments, $R^3$ is H and $R^4$ is

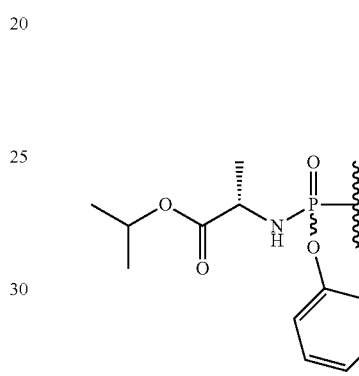

In some embodiments, $R^1$ is $CH_3$, $R^2$ is H, $R^3$ is H and $R^4$ is

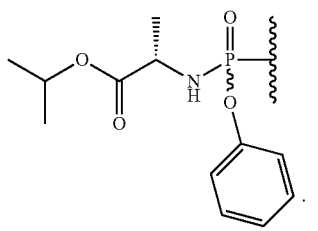 [SMILES: *P(=O)(N[C@@H](C)C(=O)OC(C)C)Oc1ccccc1]

In some embodiments, $R^1$ is $CH_3$, $R^2$ is H, $R^3$ is H and $R^4$ is

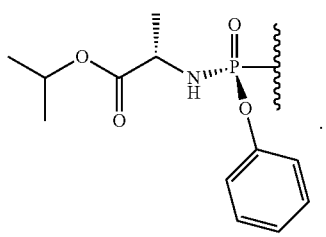 [SMILES: *[P@@](=O)(N[C@@H](C)C(=O)OC(C)C)Oc1ccccc1]

In some embodiments, $R^1$ is $CH_3$, $R^2$ is H, $R^3$ is H and $R^4$ is

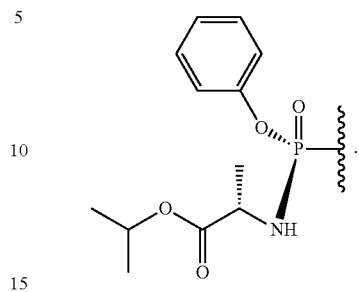

In some embodiments, $R^1$ is $CH_3$, $R^2$ is $CH_3$, $R^3$ is H and $R^4$ is

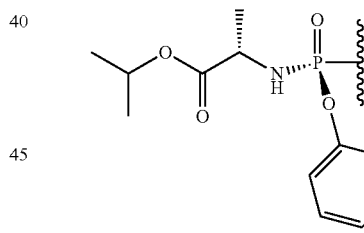

In some embodiments, $R^1$ is $CH_3$, $R^2$ is $CH_3$, $R^3$ is H and $R^4$ is

In some embodiments, $R^1$ is $CH_3$, $R^2$ is $CH_3$, $R^3$ is H and $R^4$ is

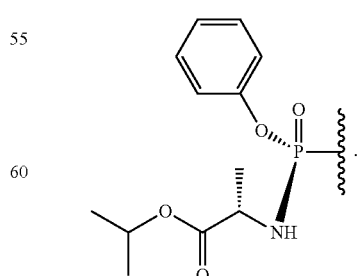

In some embodiments, le is cyclopropyl, $R^2$ is $CH_3$, $R^3$ is H and $R^4$ is

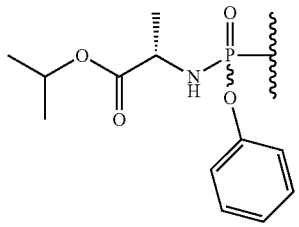

In some embodiments, le is cyclopropyl, $R^2$ is $CH_3$, $R^3$ is H and $R^4$ is

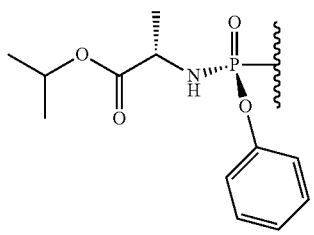

In some embodiments, $R^1$ is cyclopropyl, $R^2$ is $CH_3$, $R^3$ is H and $R^4$ is

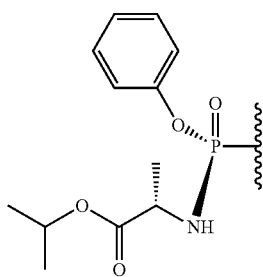

In one embodiment, the use of an effective amount of a compound of Formula III or a pharmaceutically acceptable salt thereof, for the treatment of an infection of an RNA virus in a host, including a human in need thereof is provided. Non-limiting examples of Formula III include but are not limited to:

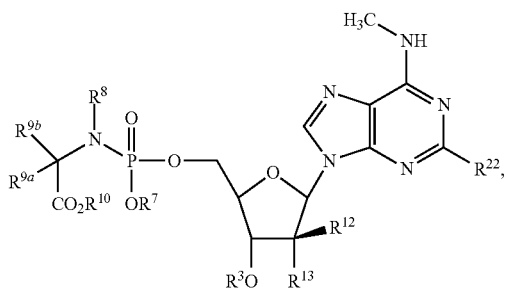

-continued

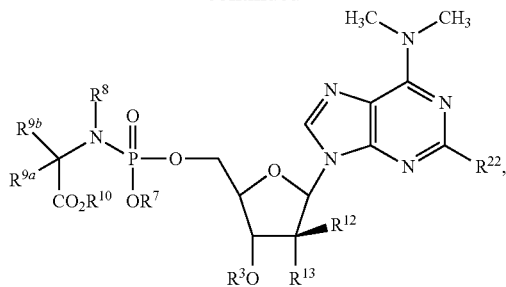

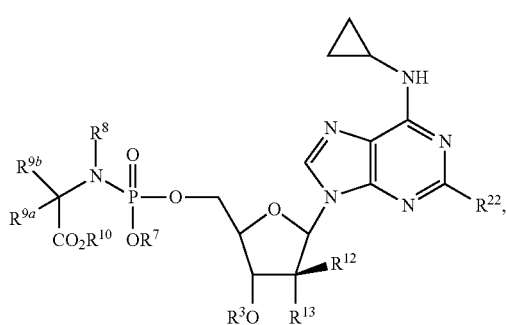

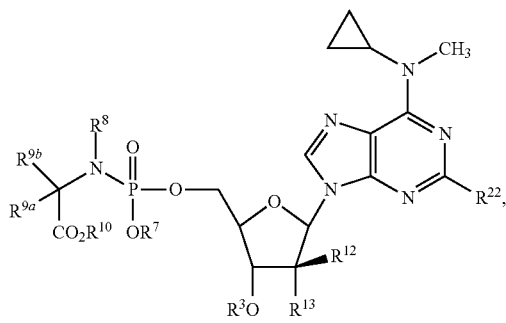

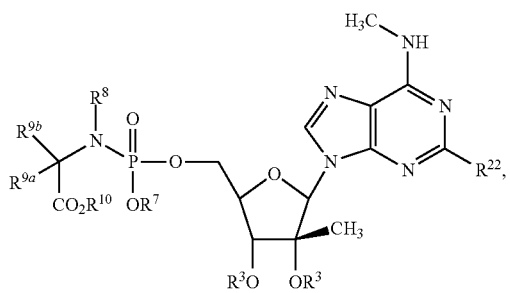

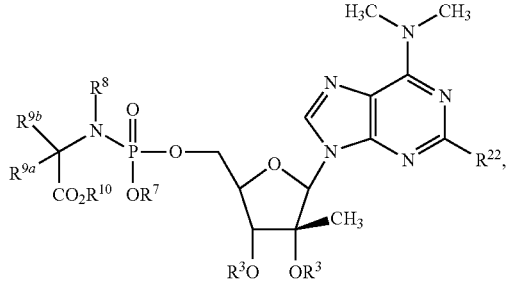

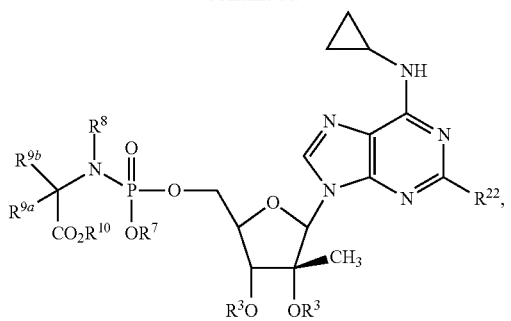
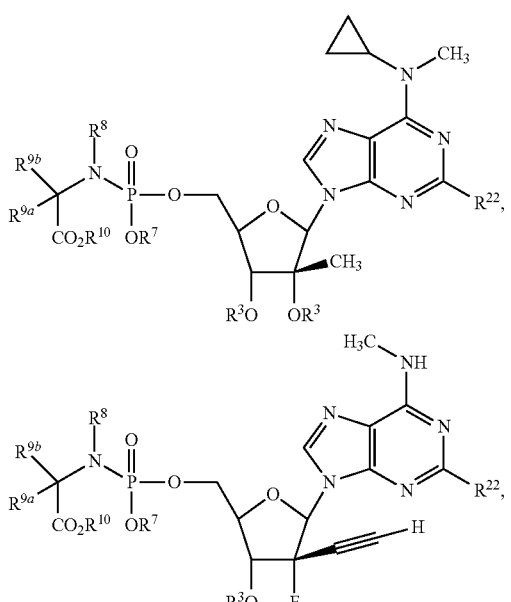
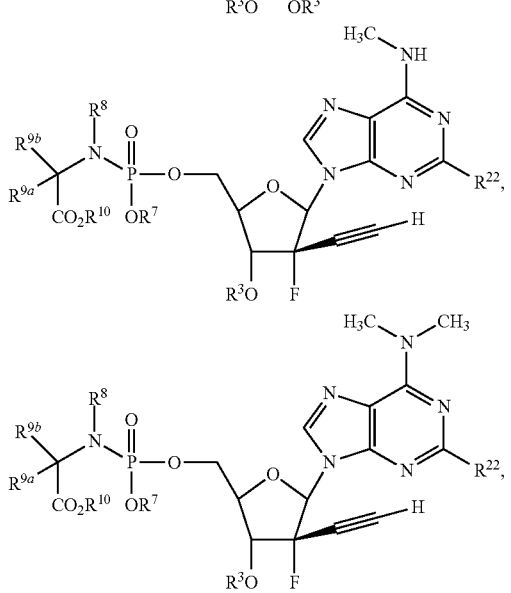
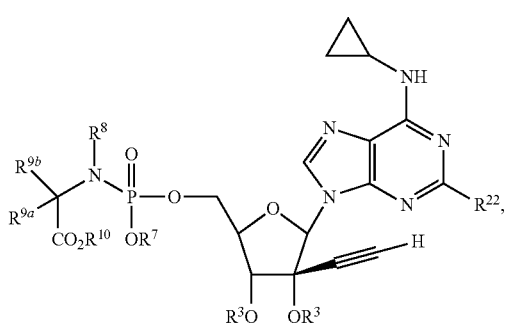
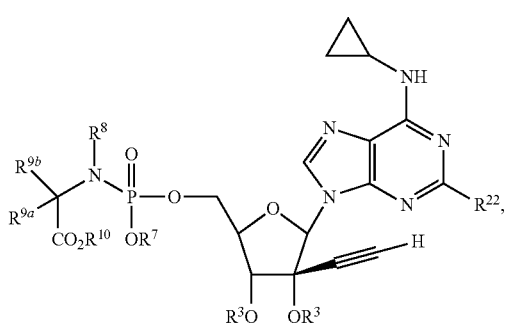
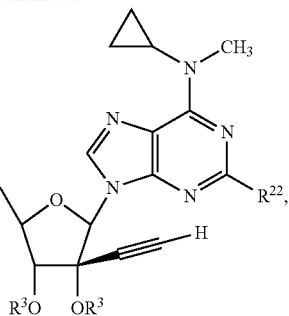
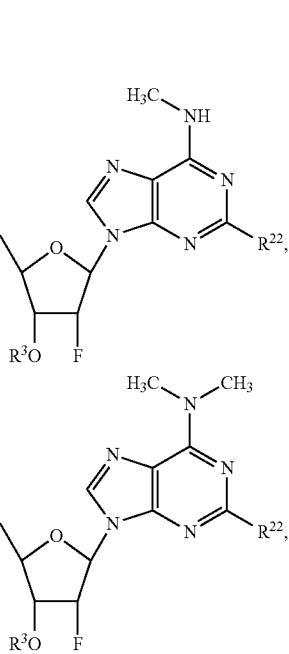
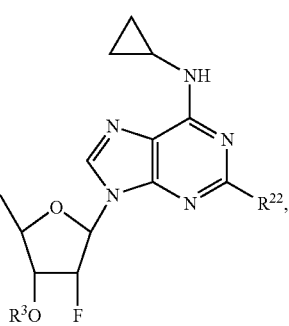
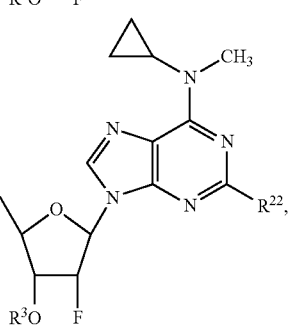
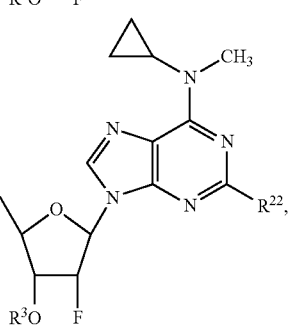

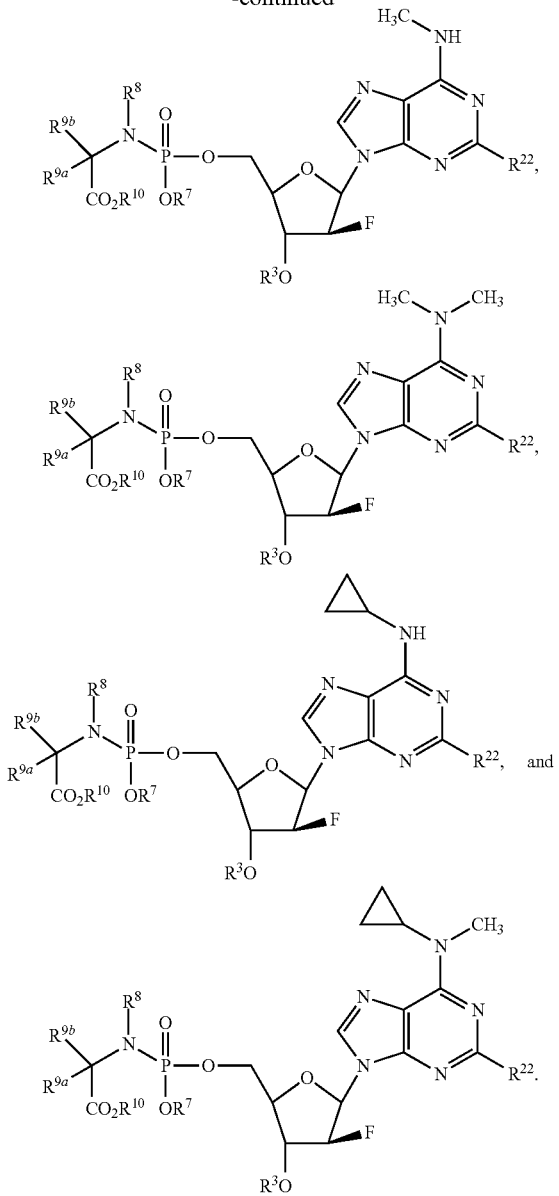

II. Definitions

The following terms are used to describe the present invention. In instances where a term is not specifically defined herein, that term is given an art-recognized meaning by those of ordinary skill applying that term in context to its use in describing the present invention.

The term "alkyl" shall mean within its context, a linear, or branch-chained fully saturated hydrocarbon radical or alkyl group which can be optionally substituted (for example, with halogen, including F). For example, an alkyl group can have 1, 2, 3, 4, 5, 6, 7 or 8 carbon atoms (i.e., $C_1$-$C_8$ alkyl), 1, 2, 3, 4, 5 or 6 carbon atoms (i.e., $C_1$-$C_6$ alkyl) or 1 to 4 carbon atoms (i.e., $C_1$-$C_4$ alkyl). Examples of suitable alkyl groups include, but are not limited to, methyl, ethyl, n-propyl, iso-propyl, n-butyl, isobutyl, sec-butyl, tert-butyl, pentyl, isopentyl, tert-pentyl, neopentyl, hexyl, 2-methylpentyl, 3-methylpentyl, 2,2-dimethylbutyl and 2,3-dimethylbutyl.

The term "alkenyl" refers to a non-aromatic hydrocarbon group which contains at least one double bond between adjacent carbon atoms and a similar structure to an alkyl group as otherwise described herein. For example, an alkenyl group can have 2 to 8 carbon atoms (i.e., $C_2$-$C_8$ alkenyl), or 2 to 4 carbon atoms (i.e., $C_2$-$C_4$ alkenyl). Examples of suitable alkenyl groups include, but are not limited to, ethenyl or vinyl (—CH=$CH_2$), allyl (—$CH_2$CH=$CH_2$), 1-butenyl (—C=CH—$CH_2CH_3$) and 2-butenyl (—$CH_2$CH=$CHCH_2$). The alkenyl group can be optionally substituted as described herein.

The term "alkynyl" refers to a non-aromatic hydrocarbon group containing at least one triple bond between adjacent carbon atoms and a similar structure to an alkyl group as otherwise described herein. For example, an alkynyl group can have 2 to 8 carbon atoms (i.e., $C_2$-$C_8$ alkyne), or 2 to 4 carbon atoms (i.e., $C_2$-$C_4$ alkynyl). Examples of alkynyl groups include, but are not limited to, acetylenic or ethynyl and propargyl. The alkynyl group can be optionally substituted as described herein.

The term "acyl" refers to the moiety —C(O)R in which the carbonyl moiety is bonded to R, for example, —C(O)alkyl. R can be selected from alkoxy, alkyl, cycloalkyl, lower alkyl (i.e., $C_1$-$C_4$); alkoxyalkyl, including methoxymethyl; aralkyl-including benzyl, aryloxyalkyl-such as phenoxymethyl; aryl including phenyl optionally substituted with halogen, $C_1$ to $C_4$ alkyl or $C_1$ to $C_4$ alkoxy. In one embodiment, the term "acyl" refers to a mono, di or triphosphate.

The term "lower acyl" refers to an acyl group in which the carbonyl moiety is lower alkyl (i.e., $C_1$-$C_4$).

The term "alkoxy" refers to the group —OR' where —OR' is —O-alkyl, —O-alkenyl, —O— alkynyl, —O—($C_0$-$C_2$)(cycloalkyl), —O—($C_0$-$C_2$)(heterocyclo), —O—($C_0$-$C_2$)(aryl), or —O—($C_0$-$C_2$)(heteroaryl), each of which can be optionally substituted.

The term "amino" refers to the group —$NH_2$.

The term "amino acid" or "amino acid residue" refers to a D- or L-natural or non-naturally occurring amino acid. Representative amino acids include, but are not limited to, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine, among others.

The term "azido" refers to the group —$N_3$.

The term "aryl" or "aromatic", in context, refers to a substituted (as otherwise described herein) or unsubstituted monovalent aromatic radical having a single ring (e.g., phenyl or benzyl) or condensed rings (e.g., naphthyl, anthracenyl, phenanthrenyl, etc.) and can be bound to the compound according to the present invention at any available stable position on the ring(s) or as otherwise indicated in the chemical structure presented. The aryl group can be optionally substituted as described herein.

"Cycloalkyl", "carbocycle", or "carbocyclyl" refers to a saturated (i.e., cycloalkyl) or partially unsaturated (e.g., cycloakenyl, cycloalkadienyl, etc.) ring having 3 to 7 carbon atoms as a monocycle. Monocyclic carbocycles have 3 to 7 ring atoms, still more typically 5 or 6 ring atoms. Non-limiting examples of cycloalkyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, and 1-cyclo-hex-3-enyl.

The term "cyano" refers to the group —CN.

The term "halogen" or "halo" refers to chloro, bromo, fluoro or iodo.

A heteroaryl ring system is a saturated or unsaturated ring with one or more nitrogen, oxygen, or sulfur atoms in the ring (monocyclic) including but not limited to imidazole, furyl, pyrrole, furanyl, thiene, thiazole, pyridine, pyrimidine, purine, pyrazine, triazole, oxazole, or fused ring systems such as indole, quinoline, etc., among others, which may be optionally substituted as described above. Heteroaryl groups include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazino-pyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising two or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" or "heterocyclo" refers to a cyclic group which contains at least one heteroatom, i.e., O, N, or S, and may be aromatic (heteroaryl) or non-aromatic. Exemplary non-aromatic heterocyclic groups for use in the present invention include, for example, pyrrolidinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethylene urea, 1,3-dioxolane, 1,3-dioxane, 1,4-dioxane, phthalimide, and succinimide, among others, all of which may be optionally substituted.

The term "hydroxyl" refers to the group —OH.

The term "nitro" refers to the group —NO$_2$.

The term "pharmaceutically acceptable salt" or prodrug" is used throughout the specification to describe any pharmaceutically acceptable form (such as an ester, phosphoramidate, thiophosphoramidate, phosphate ester, salt of an ester, or a related group) of a 2'-substituted-N$^6$-substituted purine nucleotide which, upon administration to a patient, provides the desired active compound. Examples of pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example calcium) salts of carboxylic acids can also be made.

"Pharmaceutically acceptable prodrug" refers to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated, thiophoshoramidated, dethiophoshoramidated, phoshoramidated or dephosphoramidated to produce the active compound. The compounds of this invention possess antiviral activity against an RNA virus, or are metabolized to a compound that exhibits such activity. The 2'-substituted-N$^6$-substituted purine nucleoside can also be administered as a 5'-phosphoether lipid, a bisphosphoramidate, a 3',5'-cyclic phosphoramidate, a 3',5'-cyclic thiophosphoramidate, a DTE conjugate, a mixed phosphoramidate-SATE derivative or a "SATE" derivative.

The term "phosphonic acid" refers to the group —P(O)(OH)$_2$.

In one embodiment, the term purine or pyrimidine base includes, but is not limited to, adenine, N$^6$-alkylpurines, N$^6$-acylpurines (wherein acyl is —C(O)alkyl, —C(O)(aryl) C$_0$-C$_4$alkyl, or —C(O)(C$_0$-C$_4$alkyl)aryl), N$^6$-benzylpurine, N$^6$-halopurine, N$^6$-vinylpurine, N$^6$-acetylenic purine, N$^6$-acyl purine, N$^6$-hydroxyalkyl purine, N$^6$-thioalkyl purine, N$^2$-alkylpurines, N$^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-hydroxyalkyl purine, C$^5$-amidopyrimidine, C$^5$-cyanopyrimidine, C$^5$-nitropyrimidine, C$^5$-aminopyrimidine, N$^2$-alkylpurines, N$^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include benzyl, trimethylsilyl, dimethylhexylsilyl, t-butyldimethylsilyl, t-butyldiphenylsilyl, trityl, alkyl groups, and acyl groups such as acetyl and propionyl; methanesulfonyl, and p-toluenesulfonyl. Alternatively, the purine or pyrimidine base can optionally be substituted such that it forms a viable prodrug, which can be cleaved in vivo. Examples of appropriate substituents include an acyl moiety.

The term "substituted" or "optionally substituted" indicates that the moiety can have at least one additional substituent including, but not limited to, halogen (F, Cl, Br, I), OH, phenyl, benzyl, N$_3$, CN, acyl, alkyl, including methyl; alkenyl, alkynyl, alkoxy, haloalkyl; including CHF$_2$, CH$_2$F and CF$_3$; etc. In one embodiment, the term "substituted" or "optionally substituted" indicates that the moiety can have at least one additional substituent including, but not limited to, azido, cyano, halogen (fluoro, chloro, bromo, or iodo), alkyl, alkenyl, alkynyl, cycloalkyl, heterocycle, aryl, heteroaryl, haloalkyl, hydroxyl, alkoxy, amino, —NH(C$_1$-C$_6$ unsubstituted alkyl), —NH(C$_1$-C$_6$ substituted alkyl), —NH—(C$_0$-C$_2$alkyl)(C$_3$-C$_8$cycloalkyl), —NH—(C$_0$-C$_2$alkyl)(C$_3$-C$_8$heterocycle), —NH—(C$_0$-C$_2$alkyl)(aryl), —N(C$_1$-C$_6$ unsubstituted alkyl)$_2$, —N(C$_1$-C$_6$ unsubstituted alkyl)(C$_1$-C$_6$ substituted alkyl), —N(C$_1$-C$_6$ substituted alkyl)$_2$, —NH—(C$_0$-C$_2$alkyl)(C$_3$-C$_8$cycloalkyl), —NH—(C$_0$-C$_2$alkyl)(C$_3$-C$_8$heterocycle), —NH—(C$_0$-C$_2$alkyl)(aryl), acyl, nitro, sulfonic acid, sulfate, phosphonic acid, phosphate, phosphonate, or thiol.

The term "sulfonate esters", represented by the formula, R$^{14}$S(O)$_2$OR$^{15}$, comprise R$^{14}$ wherein R$^{14}$ is alkyl, haloalkyl, aralkyl or aryl. R$^{15}$ is alkyl, aryl or aralkyl.

The term "sulfonic acid" refers to the group —SO$_2$OH.

The term "thiol" refers to the group —SH.

The term "nitrogen-protecting group" as used herein refers to a moiety that is covalently attached to nitrogen and which can be removed, and typically replaced with hydrogen, when appropriate. For example, a nitrogen-protecting group may be a group that is removed in vivo after administration to a host, in vitro by a cell, or it may be removed during a manufacturing process. Suitable nitrogen-protecting groups useful in the present invention are described by Greene and Wuts in Protective Groups in Organic Synthesis (1991) New York, John Wiley and Sons, Inc.

The term "oxygen-protecting group" as used herein refers to a moiety that is covalently attached to oxygen and which can be removed, and typically replaced with hydrogen, when appropriate. For example, an oxygen-protecting group may be a group that is removed in vivo after administration to a host, in vitro by a cell, or it may be removed during a manufacturing process. Suitable oxygen-protecting groups useful in the present invention are described by Greene and Wuts in Protective Groups in Organic Synthesis (1991) New York, John Wiley and Sons, Inc.

"Phosphate" refers to the group —OP(O)(OH)$_2$.

"Phosphate ester" refers to mono, di, and tri phosphates unless otherwise indicated.

The term "phosphoamidate", "phosphoramidate", or "phosphoroamidate" is a moiety that has a phosphorus bound to three oxygen groups and an amine (which may optionally be substituted). Suitable phosphoramidates useful in the present invention are described by Madela, Karolina and McGuigan in 2012, "Progress in the development of anti-hepatitis C virus nucleoside and nucleotide prodrugs", *Future Medicinal Chemistry* 4(5), pages 625-650 10:1021/jm300074y and Dominique, McGuigan and Balzarini in 2004, "Aryloxy Phosphoramidate Triesters as Pro-Tides", *Mini Reviews in Medicinal Chemistry* 4(4), pages 371-381. Additional phosphoramidates useful in the present invention are described in U.S. Pat. Nos. 5,233,031, 7,115,590, 7,547,704, 7,879,815, 7,888,330, 7,902,202, 7,951,789, 7,964,580, 8,071,568; 8,148,349, 8,263,575, 8,324,179, 8,334,270, 8,552,021, 8,563,530, 8,580,765, 8,735,372, 8,759,318; EP 2120565; EP 1143995; U.S. Pat. Nos. 6,455,513; and 8,334,270. Other phosphoramidates are described in the nucleoside patents described in the Background of the Invention.

Phosphoramidate groups for use in the present invention include those of the structures:

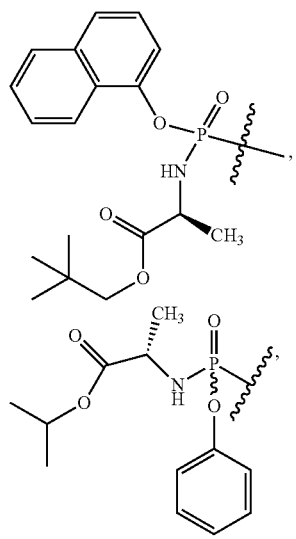

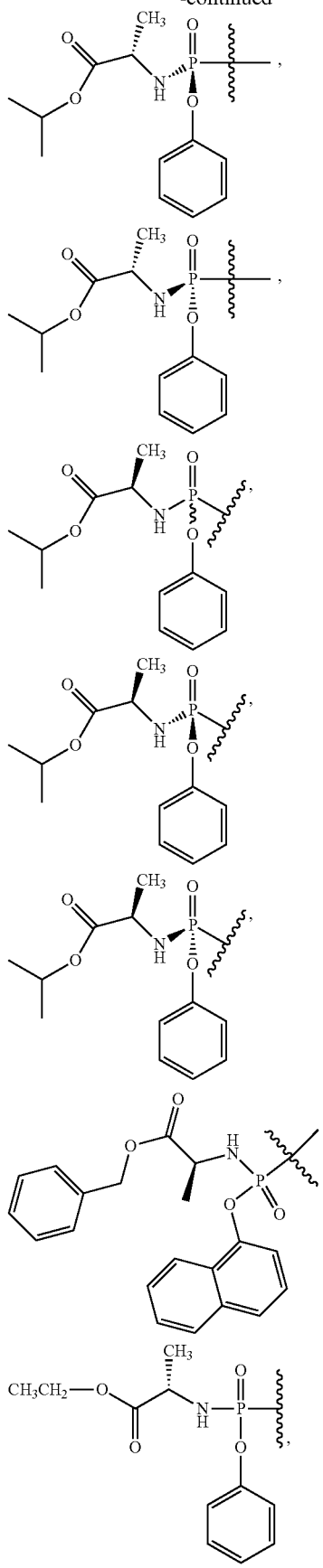

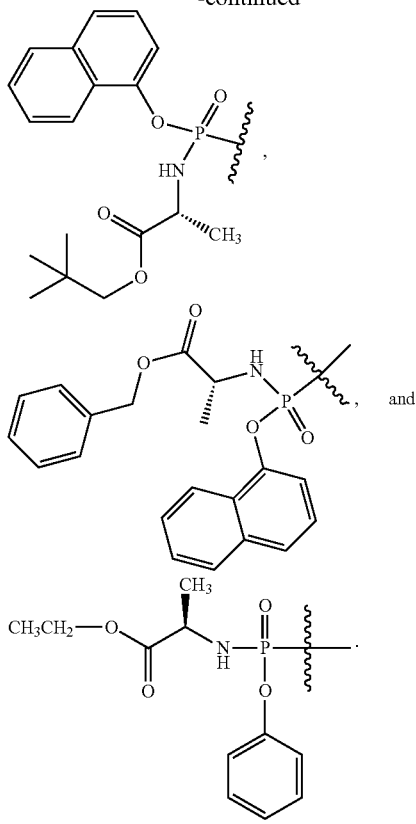

Other phosphoramidates for use in the present invention include those of the structure:

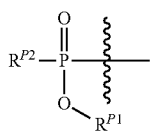

wherein:
$R^{P1}$ is an optionally substituted linear, branched, or cyclic alkyl group, or an optionally substituted aryl, heteroaryl or heterocyclic group or a linked combination thereof, and
$R^{P2}$ is a —$NR^{N1}R^{N2}$ group or a B' group;
wherein:
$R^{N1}$ and $R^{N2}$ are each independently H, $C_{1-8}$alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; which may be optionally substituted; or
$R^{N1}$ and $R^{N2}$ along with the nitrogen atom to which that are attached, join to form a 3 to 7 membered heterocyclic ring;
B' is a

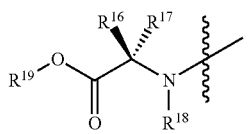

group;
wherein:
$R^{16}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);
$R^{17}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);
$R^{18}$ is hydrogen or $C_1$-$C_3$alkyl; or
$R^{16}$ and $R^{17}$ can form a ($C_3$-$C_7$)cycloalkyl or ($C_3$-$C_7$) heterocyclic group; or
$R^{18}$ and $R^{16}$ or $R^{17}$ can form ($C_3$-$C_6$)heterocyclic group; and
$R^{19}$ is hydrogen, ($C_1$-$C_6$)alkyl, ($C_3$-$C_6$)alkenyl, ($C_3$-$C_6$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-; or
B' is a

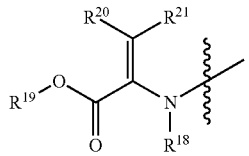

group;
wherein:
$R^{20}$ is hydrogen, ($C_1$-$C_3$)alkyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-;
$R^{21}$ is hydrogen, ($C_1$-$C_3$)alkyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; and
$R^{18}$ and $R^{19}$ are as defined above.

Typical $R^{P1}$ groups include optionally substituted phenyl, naphthyl, and monocyclic heteroaryl groups, especially those groups (particularly lipophilic groups) which enhance bioavailability of the compounds in the cells of the patient and which exhibit reduced toxicity, enhanced therapeutic index and enhanced pharmacokinetics (the compounds are metabolized and excreted more slowly).

The term phosphoramidate is used throughout the specification to describe a group that is found at the 5' or 3' position of the furanose ring of the nucleoside compound and forms a prodrug form of the nucleoside compound. In one embodiment, phosphoramidates can be found at both the 5' and 3' position of the furanose ring of the nucleoside compound and form a prodrug form of the nucleoside compound. In another embodiment, the phosphoramidate found at the 5' position of the furanose ring of the nucleoside can form a cyclic phosphoramidate compound by forming a bond with the 3'-hydroxyl substituent at the 3' position of the furanose ring of the nucleoside compound and form a prodrug form of the nucleoside compound.

The term "thiophosphoamidate", "thiophosphoramidate", or "thiophosphoroamidate" is a moiety that has a phosphorus bound to sulfur, two oxygen groups and an amine (which may optionally be substituted). Thiophosphoramidates useful in the present invention are described in U.S. Pat. No. 8,772,474 and WO 2012/040124.

Thiophosphoramidate groups for use in the present invention include those of the structures:

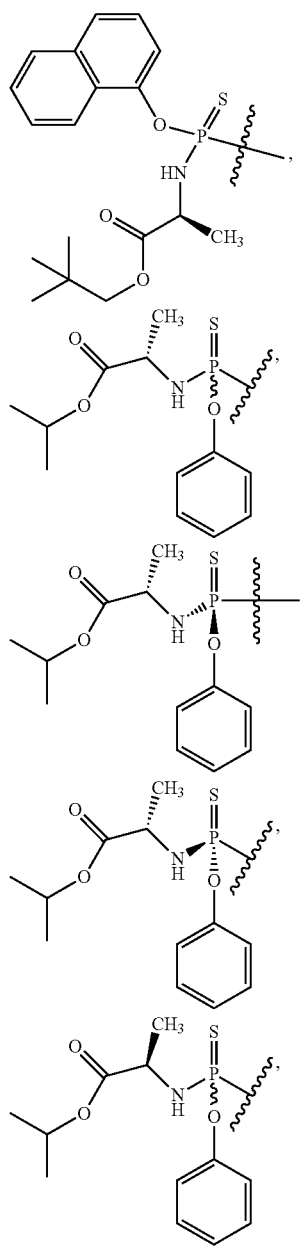

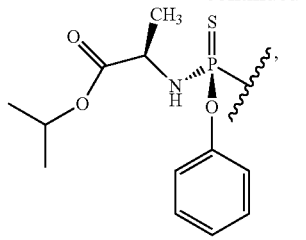

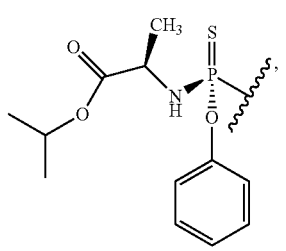

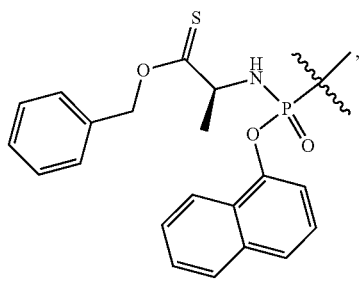

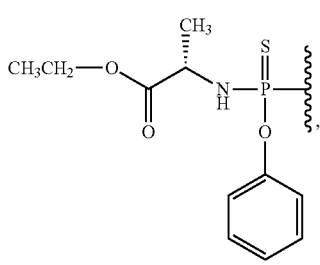

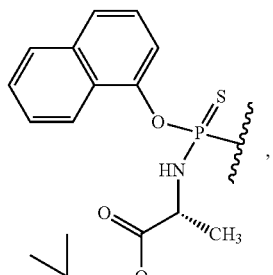

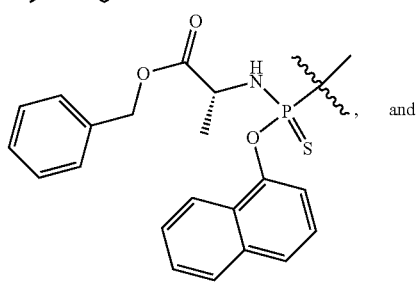

and

-continued

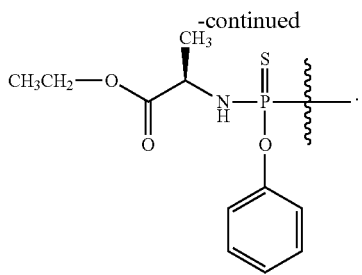

Other thiophosphoramidates include those of the structure:

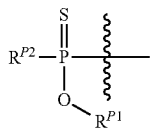

wherein:
$R^{P1}$ is an optionally substituted linear, branched, or cyclic alkyl group, or an optionally substituted aryl, heteroaryl or heterocyclic group or a linked combination thereof, and
$R^{P2}$ is a —$NR^{N1}R^{N2}$ group or a B' group;
wherein:
$R^{N1}$ and $R^{N2}$ are each independently H, $C_1$-$C_8$ alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; or
$R^{N1}$ and $R^{N2}$ along with the nitrogen atom to which that are attached, join to form a 3 to 7 membered heterocyclic ring;
B' is a

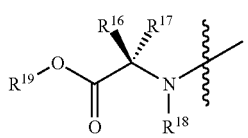

group;
wherein:
$R^{16}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl) $C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);
$R^{17}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl) $C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);
$R^{18}$ is hydrogen or $C_1$-$C_3$alkyl; or
$R^{16}$ and $R^{17}$ can form a ($C_3$-$C_7$)cycloalkyl or ($C_3$-$C_7$) heterocyclic group; or
$R^{18}$ and $R^{16}$ or $R^{17}$ can form ($C_3$-$C_6$) heterocyclic group; and
$R^{19}$ is hydrogen, ($C_1$-$C_6$)alkyl, ($C_3$-$C_6$)alkenyl, ($C_3$-$C_6$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl) $C_0$-$C_4$alky-; or
B' is a

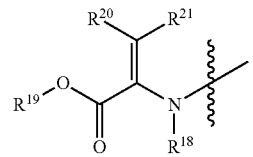

group; and
$R^{18}$, $R^{19}$, $R^{20}$ and $R^2$ are as defined above.
Typical $R^{P1}$ groups include optionally substituted phenyl, naphthyl, and monocyclic heteroaryl groups, especially those groups (particularly lipophilic groups) which enhance bioavailability of the compounds into the cells of the patient and which exhibit reduced toxicity, enhanced therapeutic index and enhanced pharmacokinetics (the compounds are metabolized and excreted more slowly).

The thiophosphoramidate can be at the 5' or 3' position of the furanose ring of the nucleoside compound to form a prodrug form of the nucleoside compound. In one embodiment, thiophosphoramidates can be found at both the 5' and 3' position of the furanose ring of the nucleoside compound and form a prodrug form of the nucleoside compound. In another embodiment, the thiophosphoramidate found at the 5' position of the furanose ring of the nucleoside can form a cyclic thiophosphoramidate compound by forming a bond with the 3'-hydroxyl substituent at the 3' position of the furanose ring of the nucleoside compound and form a prodrug form of the nucleoside compound.

The term "D-configuration" as used in the context of the present invention refers to the principle configuration which mimics the natural configuration of sugar moieties as opposed to the unnatural occurring nucleosides or "L" configuration. The term "β" or "β anomer" is used with reference to nucleoside analogs in which the nucleoside base is configured (disposed) above the plane of the furanose moiety in the nucleoside analog.

The terms "coadminister" and "coadministration" or combination therapy are used to describe the administration of at least one of the 2'-substituted-$N^6$-substituted purine nucleotide compounds according to the present invention in combination with at least one other active agent, for example where appropriate at least one additional anti-RNA virus agent, including other 2'-substituted-$N^6$-substituted purine nucleotide agents which are disclosed herein. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term "host", as used herein, refers to a unicellular or multicellular organism in which an RNA virus can replicate, including cell lines and animals, and typically a human. The term host specifically refers to infected cells, cells transfected with all or part of an RNA virus genome, and animals, in particular, primates (including chimpanzees) and humans. In most animal applications of the present invention, the host is a human patient. Veterinary applications, in certain indications, however, are clearly anticipated by the present invention (such as chimpanzees). The host can be for example, bovine, equine, avian, canine, feline, etc.

Isotopic Substitution

The present invention includes the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in described structures. Alternatively, or in addition, isotopes of carbon, e.g., $^{13}C$ and $^{14}C$, may be used. A typical isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetics or pharmacodynamics, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby an H-isotope, i.e., hydrogen/protium ($^1H$), is substituted by an H-isotope, i.e., deuterium ($^2H$). Deuterium substitution can be partial or complete. Partial deuterium substitution means that at least one hydrogen is substituted by at least one deuterium.

In certain embodiments, the isotope is 90, 95, 96, 97, 98 or 99% or more enriched in an isotope at any location of interest. In some embodiments, it is deuterium that is 90, 95, 96, 97, 98 or 99% enriched at a desired location. Unless indicated to the contrary, the deuteration is at least 80% at the selected location. Deuteration of the nucleoside can occur at any replaceable hydrogen that provides the desired results.

III. Methods of Treatment or Prophylaxis

Treatment, as used herein, refers to the administration of an active compound to a host who is infected with an RNA virus, for example, a human.

The term "prophylactic" or preventative when used refers to the administration of an active compound to prevent or reduce the likelihood of an occurrence of the viral disorder. The present invention includes both treatment and prophylactic or preventative therapies. In one embodiment, the active compound is administered to a host who has been exposed to and thus at risk of infection by an RNA virus infection.

The invention is directed to a method of treatment or prophylaxis of an RNA virus, including drug resistant and multidrug resistant forms of RNA virus and related disease states, conditions, or complications of an RNA virus infection, as well as other conditions that are secondary to an RNA virus infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others. The method comprises administering to a host in need thereof an effective amount of at least one 2'-substituted-$N^6$-substituted purine nucleotide as described herein, optionally in combination with at least one additional bioactive agent, for example, an additional anti-RNA virus agent, further in combination with a pharmaceutically acceptable carrier additive and/or excipient.

In yet another aspect, the present invention is a method for prevention or prophylaxis of an RNA virus infection or a disease state or related or follow-on disease state, condition or complication of an RNA virus infection, including hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular (liver) cancer, among others, said method comprising administering to a patient at risk with an effective amount of at least one compound according to the present invention as described above in combination with a pharmaceutically acceptable carrier, additive, or excipient, optionally in combination with another anti-RNA virus agent.

The 5'-stabilized 2'-substituted-$N^6$-substituted purine nucleotide can be administered if desired as any salt or prodrug that upon administration to the recipient is capable of providing directly or indirectly the parent compound, or that exhibits activity itself. Nonlimiting examples are the pharmaceutically acceptable salts and a compound, which has been modified at a function group, such as a hydroxyl or amine function, to modify the biological activity, pharmacokinetics, half-life, controlled delivery, lipophilicity, absorption kinetics, ease of phosphorylation to the active 5'-triphosphate or efficiency of delivery using a desired route of administration of the compound. Methods to modify the properties of an active compound to achieve target properties are known to those of skill in the art or can easily be assessed by standard methods, for example, acylation, phosphorylation, thiophosphoramidation, phosphoramidation, phosphonation, alkylation, or pegylation.

In one embodiment, an active compound is administered to a host that is infected with a double stranded RNA virus.

In one embodiment, an active compound is administered to a host that is infected with a positive-stranded RNA virus.

In one embodiment, an active compound is administered to a host that is infected with a negative-stranded RNA virus.

In one embodiment, an active compound is administered to a host that is infected with a double stranded RNA virus from the family Amalgaviridae. In one embodiment, an active compound is administered to a host that is infected with a double stranded RNA virus from the family Birnaviridae. In one embodiment, an active compound is administered to a host that is infected with a double stranded RNA virus from the family Chrysoviridae. In one embodiment, an active compound is administered to a host that is infected with a double stranded RNA virus from the family Cystoviridae. In one embodiment, an active compound is administered to a host that is infected with a double stranded RNA virus from the family Endornaviridae. In one embodiment, an active compound is administered to a host that is infected with a double stranded RNA virus from the family Hypoviridae. In one embodiment, an active compound is administered to a host that is infected with a double stranded RNA virus from the family Megabirnaviridae. In one embodiment, an active compound is administered to a host that is infected with a double stranded RNA virus from the family Partitiviridae. In one embodiment, an active compound is administered to a host that is infected with a double stranded RNA virus from the family Picobirnaviridae. In one embodiment, an active compound is administered to a host that is infected with a double stranded RNA virus from the family Quadriviridae. In one embodiment, an active compound is administered to a host that is infected with a double stranded RNA virus from the family Reoviridae. In one embodiment, an active compound is administered to a host that is infected with a double stranded RNA virus from the family Totiviridae.

In one embodiment, an active compound is administered to a host that is infected with a positive-sense RNA virus from the order Nidovirales. In one embodiment, an active compound is administered to a host that is infected with a positive-sense RNA virus from the order Picornavirales. In one embodiment, an active compound is administered to a host that is infected with a positive-sense RNA virus from the order Tymovirales. In one embodiment, an active compound is administered to a host that is infected with a positive-sense RNA virus from the family Arteviridae. In one embodiment, an active compound is administered to a host that is infected with a positive-sense RNA virus from the family Coronaviridae. In one embodiment, an active compound is administered to a host that is infected with a positive-sense RNA virus from the family Mesoniviridae. In one embodiment, an active compound is administered to a host that is infected with a positive-sense RNA virus from the family Roniviridae. In one embodiment, an active compound is administered to a host that is infected with a positive-sense RNA virus from the family Dicistroviridae. In one embodiment, an active compound is administered to a host that is infected with a positive-sense RNA virus from the family Ifaviridae. In one embodiment, an active compound is administered to a host that is infected with a positive-sense RNA virus from the family Marnaviridae. In one embodiment, an active compound is administered to a host that is infected with a positive-sense RNA virus from the family Picornaviridae. In one embodiment, an active compound is administered to a host that is infected with a positive-sense RNA virus from the family Secoviridae. In one embodiment, an active compound is administered to a host that is infected with a positive-sense RNA virus from the family Alphaflexiviridae. In one embodiment, an active compound is administered to a host that is infected with a positive-sense RNA virus from the family Betaflexiviridae. In one embodiment, an active compound is administered to a host that is infected with a positive-sense RNA virus from the family Gammaflexiviridae. In one embodiment, an active compound is administered to a host that is infected with a positive-sense RNA virus from the family Tymoviridae. In one embodiment, an active compound is administered to a host that is infected with a positive-sense RNA virus from the family Alphatetraviridae. In one embodiment, an active compound is administered to a host that is infected with a positive-sense RNA virus from the family Alvernaviridae. In one embodiment, an active compound is administered to a host that is infected with a positive-sense RNA virus from the family Astroviridae. In one embodiment, an active compound is administered to a host that is infected with a positive-sense RNA virus from the family Barnaviridae. In one embodiment, an active compound is administered to a host that is infected with a positive-sense RNA virus from the family Benyviridae. In one embodiment, an active compound is administered to a host that is infected with a positive-sense RNA virus from the family Bromoviridae. In one embodiment, an active compound is administered to a host that is infected with a positive-sense RNA virus from the family Caliciviridae. In one embodiment, an active compound is administered to a host that is infected with a positive-sense RNA virus from the family Carmotetraviridae. In one embodiment, an active compound is administered to a host that is infected with a positive-sense RNA virus from the family Closteroviridae. In one embodiment, an active compound is administered to a host that is infected with a positive-sense RNA virus from the family Fusariviridae. In one embodiment, an active compound is administered to a host that is infected with a positive-sense RNA virus from the family Hepeviridae. In one embodiment, an active compound is administered to a host that is infected with a positive-sense RNA virus from the family Leviviridae. In one embodiment, an active compound is administered to a host that is infected with a positive-sense RNA virus from the family Luteoviridae. In one embodiment, an active compound is administered to a host that is infected with a positive-sense RNA virus from the family Narnaviridae. In one embodiment, an active compound is administered to a host that is infected with a positive-sense RNA virus from the family Nodaviridae. In one embodiment, an active compound is administered to a host that is infected with a positive-sense RNA virus from the family Permutotetraviridae. In one embodiment, an active compound is administered to a host that is infected with a positive-sense RNA virus from the family Potyviridae. In one embodiment, an active compound is administered to a host that is infected with a positive-sense RNA virus from the family Togaviridae. In one embodiment, an active compound is administered to a host that is infected with a positive-sense RNA virus from the family Tombusviridae. In one embodiment, an active compound is administered to a host that is infected with a positive-sense RNA virus from the family Virgaviridae. In one embodiment, an active compound is administered to a host that is infected with a positive-sense RNA virus from the family Flaviviridae genuses Flavivirus and Pestivirus.

In one embodiment, the Flavivirus infection is Dengue fever. In a further embodiment, the Dengue fever is Dengue virus type 1, type 2, type 3, or type 4. In one embodiment, the Flavivirus infection is West Nile fever. In one embodiment, the Flavivirus infection is Yellow fever. In one embodiment, the Flavivirus infection is from the Zika virus. In one embodiment, the Pestivirus infection is BVDV.

In one embodiment, an active compound is administered to a host that is infected with a negative-sense ssRNA virus from the order Mononegavirales. In one embodiment, an active compound is administered to a host that is infected with a negative-sense ssRNA virus from the family Bornaviridae. In one embodiment, an active compound is administered to a host that is infected with a negative-sense ssRNA virus from the family Filoviridae. In one embodiment, an active compound is administered to a host that is infected with a negative-sense ssRNA virus from the family Paramyxoviridae. In one embodiment, an active compound is administered to a host that is infected with a negative-sense ssRNA virus from the family Rhabdoviridae. In one embodiment, an active compound is administered to a host that is infected with a negative-sense ssRNA virus from the family Nyamiviridae. In one embodiment, an active compound is administered to a host that is infected with a negative-sense ssRNA virus from the family Arenaviridae. In one embodiment, an active compound is administered to a host that is infected with a negative-sense ssRNA virus from the family Bunyaviridae. In one embodiment, an active compound is administered to a host that is infected with a negative-sense ssRNA virus from the family Ophioviridae. In one embodiment, an active compound is administered to a host that is infected with a negative-sense ssRNA virus from the family Orthomyxoviridae.

In one embodiment, an active compound is administered to a host that is infected with Borna disease virus. In one embodiment, an active compound is administered to a host that is infected with Ebola virus. In one embodiment, an active compound is administered to a host that is infected with Marburg virus. In one embodiment, an active compound is administered to a host that is infected with Measles virus. In one embodiment, an active compound is administered to a host that is infected with Mumps virus. In one embodiment, an active compound is administered to a host that is infected with Nipah virus. In one embodiment, an active compound is administered to a host that is infected with Hendra virus. In one embodiment, an active compound is administered to a host that is infected with Newcastle disease virus (NDV). In one embodiment, an active compound is administered to a host that is infected with Rhabdoviridae.

In one embodiment, an active compound is administered to a host that is infected with Rabies virus. In one embodiment, an active compound is administered to a host that is infected with Nyamiviridae. In one embodiment, an active compound is administered to a host that is infected with Nyavirus. In one embodiment, an active compound is administered to a host that is infected with Arenaviridae. In one embodiment, an active compound is administered to a host that is infected with Lassa virus.

In one embodiment, an active compound is administered to a host that is infected with Bunyaviridae. In one embodiment, an active compound is administered to a host that is infected with Hantavirus. In one embodiment, an active compound is administered to a host that is infected with Crimean-Congo hemorrhagic fever. In one embodiment, an active compound is administered to a host that is infected with Ophioviridae. In one embodiment, an active compound is administered to a host that is infected with Orthomyxoviridae. In one embodiment, an active compound is administered to a host that is infected with influenza virus. In one embodiment, an active compound is administered to a host that is infected with subtype 5 Coxsackie B virus.

IV. Pharmaceutical Compositions

In an aspect of the invention, pharmaceutical compositions according to the present invention comprise an anti-RNA virus effective amount of at least one of the 5'-stabilized 2'-substituted-$N^6$-substituted purine nucleotide compounds described herein, optionally in combination with a pharmaceutically acceptable carrier, additive, or excipient, further optionally in combination or alternation with at least one other active compound. In certain embodiments, the treated virus is other than a hepacivirus or other than HCV.

In an aspect of the invention, pharmaceutical compositions according to the present invention comprise an anti-RNA virus effective amount of at least one of the active 2'-substituted-$N^6$-substituted purine nucleotide compounds described herein, optionally in combination with a pharmaceutically acceptable carrier, additive, or excipient, further optionally in combination with at least one other antiviral, such as an anti-RNA virus agent.

The invention includes pharmaceutical compositions that include an effective amount to treat an RNA virus infection of one of the 2'-substituted-$N^6$-substituted purine nucleotide compounds of the present invention or its salt or prodrug, in a pharmaceutically acceptable carrier or excipient. In an alternative embodiment, the invention includes pharmaceutical compositions that include an effective amount to prevent an RNA virus infection of one of the 2'-substituted-$N^6$-substituted purine nucleotide compounds of the present invention or its salt or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated, and such therapeutic amount can be determined by the attending physician or specialist. In one embodiment, the patient is a human.

The 5'-stabilized 2'-substituted-$N^6$-substituted purine nucleotide compounds according to the present invention can be formulated in an admixture with a pharmaceutically acceptable carrier. In general, it is typical to administer the pharmaceutical composition in orally administrable form, but certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or other vehicle, for example, this can be easily accomplished by minor modifications (salt formulation, esterification, etc.) which are well within the ordinary skill in the art. It is also well within the routineers' skill to modify the route of administration and dosage regimen of a particular compound in order to manage the pharmacokinetics of the present compounds for maximum beneficial effect in patients.

In certain pharmaceutical dosage forms, the prodrug form of the compounds, especially including acylated (acetylated or other), and ether (alkyl and related) derivatives, phosphate esters, thiophosphoramidates, phosphoramidates, and various salt forms of the present compounds, are typical. One of ordinary skill in the art will recognize how to readily modify the present compounds to prodrug forms to facilitate delivery of active compounds to a targeted site within the host organism or patient. The routineer also will take advantage of favorable pharmacokinetic parameters of the prodrug forms, where applicable, in delivering the present compounds to a targeted site within the host organism or patient to maximize the intended effect of the compound.

The amount of compound included within therapeutically active formulations according to the present invention is an effective amount for treating the RNA virus infection, reducing the likelihood of an RNA virus infection or the inhibition, reduction, and/or abolition of an RNA virus or its secondary effects, including disease states, conditions, and/or complications which occur secondary to an RNA virus infection. In general, a therapeutically effective amount of the present compound in pharmaceutical dosage form usually ranges from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. The active nucleoside compound according to the present invention is often administered in amounts ranging from about 0.1 mg/kg to about 15 mg/kg per day of the patient, depending upon the pharmacokinetics of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of an RNA virus infection, or a secondary disease state, condition or complication of an RNA virus infection, the compositions will be administered in oral dosage form in amounts ranging from about 250 micrograms up to about 500 mg or more at least once a day, for example, at least 25, 50, 100, 150, 250 or 500 milligrams, up to four times a day. The present compounds are often administered orally, but may be administered parenterally, topically, or in suppository form, as well as intranasally, as a nasal spray or as otherwise described herein.

In the case of the co-administration of the present compounds in combination with another anti-RNA virus compound as otherwise described herein, the amount of the compound according to the present invention to be administered ranges from about 0.01 mg/kg of the patient to about 500 mg/kg. or more of the patient or considerably more, depending upon the second agent to be co-administered and its potency against the virus, the condition of the patient and severity of the disease or infection to be treated and the route of administration. The other anti-RNA virus agent may for example be administered in amounts ranging from about 0.01 mg/kg to about 500 mg/kg. In certain embodiments, these compounds may be often administered in an amount ranging from about 0.5 mg/kg to about 50 mg/kg or more (usually up to about 100 mg/kg), generally depending upon the pharmacokinetics of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous intravenous drip to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds for an oral route of administration. The most effective dosage form will depend upon the bioavailability/pharmacokinetics of the particular agent chosen as well as the severity of disease in the patient. Oral dosage forms are particularly typical, because of ease of administration and prospective favorable patient compliance.

To prepare the pharmaceutical compositions according to the present invention, a therapeutically effective amount of one or more of the compounds according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including, but not limited to, water, glycols, oils, alcohols, flavoring agents, preservatives, coloring agents may be used. For solid oral preparations such as powders, tablets, capsules, and for solid preparations such as suppositories, suitable carriers and additives including, but not limited to, starches, sugar carriers, such as dextrose, manifold, lactose, and related carriers, diluents, granulating agents, lubricants, binders, disintegrating agents may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In typical embodiments, according to the present invention, the compounds and compositions are used to treat, prevent or delay an RNA virus infection or a secondary disease state, condition or complication of an RNA virus infection.

V. Combination and Alternation Therapy

It is well recognized that drug-resistant variants of viruses can emerge after prolonged treatment with an antiviral agent. Drug resistance most typically occurs by mutation of a gene that encodes for an enzyme used in viral replication. The efficacy of a drug against an RNA virus infection can be prolonged, augmented, or restored by administering the compound in combination or alternation with another, and perhaps even two or three other, antiviral compounds that induce a different mutation or act through a different pathway, from that of the principle drug. Alternatively, the pharmacokinetics, bio distribution, half-life, or other parameter of the drug can be altered by such combination therapy (which may include alternation therapy if considered concerted). Since the disclosed 2'-substituted-$N^6$-substituted purine nucleotides are polymerase inhibitors, it may be useful to administer the compound to a host in combination with, for example a:
  (1) Protease inhibitor, such as an NS3/4A protease inhibitor;
  (2) NS5A inhibitor;
  (3) Another polymerase inhibitor;
  (4) NS5B non-substrate inhibitor;
  (5) Interferon alfa-2a, which may be pegylated or otherwise modified, and/or ribavirin;
  (6) Non-substrate-based inhibitor;
  (7) Helicase inhibitor;
  (8) Antisense oligodeoxynucleotide (S-ODN);
  (9) Aptamer;
  (10) Nuclease-resistant ribozyme;
  (11) iRNA, including microRNA and SiRNA;
  (12) Antibody, partial antibody or domain antibody to the virus; or
  (13) Viral antigen or partial antigen that induces a host antibody response.

Drugs that are currently approved for influenza are Amantadine, Rimantadine, Oseltamivir and Rapivab®. Any of these drugs can be used in combination or alternation with an active compound provided herein to treat a viral infection susceptible to such. Ribavirin is used to treat measles, Influenza A, influenza B, parainfluenza, severe RSV bronchiolitis and SARS as well as other viral infections, and therefore is particularly useful in combination with the present compound for treatment of the host infected with a single stranded RNA virus.

Currently, there are no approved drugs for West Nile virus. Physicians are recommended to provide intensive support therapy, which may involve hospitalization, intravenous fluids, use of a ventilator to assist breathing, medications to control seizures, brain swelling, nausea and vomiting, and the use of antibiotics to prevent bacterial infections for making the disease even worse. This highlights the importance of the present compounds for viral medical therapy.

In addition, there is no vaccine or specific treatment for the Zika virus. Instead the focus is on relieving symptoms which includes rest, rehydration and acetaminophen for fever and pain.

There is also no vaccine or specific treatment for Dengue fever. Supportive case for those infected include fluid replacement and analgesics, along with acetaminophen, aspirin, and nonsteroidal anti-inflammatory drugs to treat fever and other symptoms.

The Yellow Fever Vaccine (YF-Vax) is manufactured by Sanofi Pasteur, Inc. and is recommended for those aged 9 and older who are traveling to areas of high risk, including South American and Africa. In one embodiment, a compound of Formula I, Formula II, Formula III, Formula IV, Formula V, or Formula VI is administered to a host in combination with the YF-Vax. No treatment exists for Yellow Fever, but an emphasis is placed on easing fever, muscle pain, and dehydration. Due to the risk of internal bleeding, aspirin and nonsteroidal anti-inflammatory drugs are not recommended.

VI. Process of Preparation of
2'-Substituted-2-$N^6$-Substituted Purine Nucleotides
of the Invention General methods for providing the compounds of the present invention are known in the art or described herein. The synthesis of 2'-chloro nucleotides is described in US 20150366888, WO 2014058801; WO 2015/066370 and WO 2015200219.

The following abbreviations are used in the synthetic schemes.
n-BuLi: n-Butyllithium
BSA: N,O-bis(trimethylsilyl)acetamide
$CBr_4$: Carbon tetrabromide
DBU: 1,8-Diazabicyclo[5.4.0]undec-7-ene
DAST: Diethylaminosulfur trifluoride
DCM: Dichloromethane
DIEA: N,N-Diisopropylethylamine
DMF: N,N-dimethylformamide
EA: Ethyl acetate
EtOAc: Ethyl acetate
EtOH: Ethanol
$Et_3N$: Triethylamine
$Na_2SO_4$: Sodium sulphate (anhydrous)
MeCN: Acetonitrile
$MeNH_2$: Methylamine
MeOH: Methanol
NaOH: Sodium hydroxide
$Na_2SO_4$: Sodium sulfate
$Na_2S_2O_3$: Sodium thiosulfate
$NaHCO_3$: Sodium bicarbonate
$NH_4Cl$: Ammonium chloride
$NH_4OH$: Ammonium hydroxide
NLT: Not less than
PE: Petroleum ether
$Ph_3P$: Triphenylphosphine
pTSA $H_2O$: p-Toluenesulfonic acid monohydrate
RT: Room Temperature
Silica gel (230 to 400 mesh, Sorbent)
TBAF: Tetrabutylammonium fluoride
THF: Tetrahydrofuran (THF), anhydrous
TMSCl: Chlorotrimethylsilane
TMSOTf: Trimethylsilyl trifluoromethanesulfonate
$TIPDSiCl_2$: 1,3-Dichloro-1,1,3,3-tetraisopropyldisiloxane
t-BuMgCl: t-Butyl magnesium chloride
t-BuOK: Sodium tert-butoxide
t-BuOH: Tert-butanol

EXAMPLES

General Methods
$^1H$, $^{19}F$ and $^{31}P$ NMR spectra were recorded on a 300 MHz Fourier transform Brücker spectrometer. Spectra were obtained from samples prepared in 5 mm diameter tubes in $CDCl_3$, $CD_3OD$ or DMSO-$d_6$. The spin multiplicities are indicated by the symbols s (singlet), d (doublet), t (triplet), m (multiplet) and br (broad). Coupling constants (J) are reported in Hz. MS spectra were obtained using electrospray ionization (ESI) on an Agilent Technologies 6120 quadrupole MS apparatus. The reactions were generally carried out under a dry nitrogen atmosphere using Sigma-Aldrich anhydrous solvents. All common chemicals were purchased from commercial sources.

Preparation of Stereospecific Phosphorus Enantiomers
Certain of the active compounds described herein have a chiral phosphorus moiety. Any of the active compounds described herein can be provided as an isolated phosphorus enantiomeric form, for example, at least 80%, 90%, 95%, 96%, 97% or 98% of the R or S enantiomer, using methods known to those of skill in the art. For example, there are a number of publications that describe how to obtain such compounds including, but not limited to, column chromatography, for example, as described in U.S. Pat. Nos. 8,859,756; 8,642,756 and 8,333,309 to Ross, et al.

Example 1. Modification of the 2-Amino Moiety in the Active Compounds

One of ordinary skill in the art can add a substituent to the 2-amino purine moiety by methods well known to those skilled in the art. One non-limiting process is provided here, and others can be easily adapted. ((2R,3R,4R,5R)-3-(benzoyloxy)-5-bromo-4-fluoro-4-methyltetrahydrofuran-2-yl)methyl benzoate, is treated with commercially available 2,6-dichloropurine, a base and a mixture of organic solvents at an elevated temperature to generate (2R,3R,4R,5R)-5-(2,6-dichloro-9H-purin-9-yl)-2-(benzoyloxymethyl)-4-fluoro-4-methyl-tetrahydrofuran-3-yl benzoate. In one embodiment, the base is potassium tert-butoxide. In one embodiment, the mixture of organic solvents comprises tert-butanol and acetonitrile. The compound, (2R,3R,4R,5R)-5-(2,6-dichloro-9H-purin-9-yl)-2-(benzoyloxymethyl)-4-fluoro-4-methyltetrahydrofuran-3-yl benzoate is treated with an amine, a base and an organic solvent at ambient temperature to generate 2-chloro-$N^6$-substituted purines. In one embodiment, the amine is methylamine. In one embodiment, the base is triethylamine. In one embodiment, the organic solvent is ethanol. One skilled in the art will also recognize that upon treatment with an amine and base, the benzoate groups on the nucleoside will simultaneously be removed to generate the deprotected furanose moiety. 2-Chloro-$N^6$-substituted purines can then be treated with an amine, and an organic solvent in a sealed tube at an elevated temperature of about 100° C. to generate $N^2,N^6$-disubstituted purine nucleosides of the present invention. In one embodiment, the amine is methylamine. In one embodiment, the organic solvent is ethanol. $N^2,N^6$-Disubstituted purine nucleosides of the present invention can be treated with a base, isopropyl ((R,S)-(pentafluorophenoxy)-phenoxyphosphoryl)-L-alaninate and an organic solvent at a reduced temperature to generate compounds of Formula I-VI. In one embodiment, the base is tert-butyl magnesium chloride. In one embodiment, the organic solvent is tetrahydrofuran.

Example 2. Preparation of PPAL-S

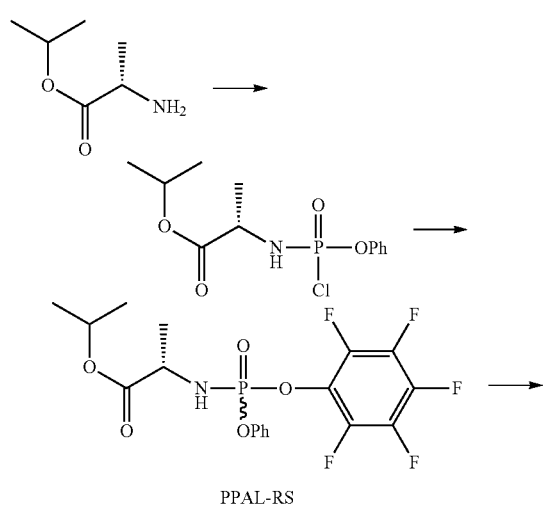

PPAL-RS

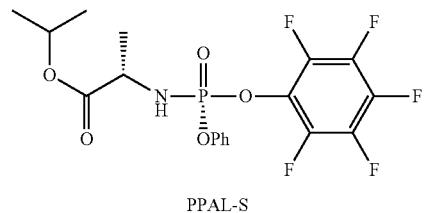

PPAL-S

Step 1. Preparation of Racemic PPAL

To a stirred solution of phenyl dichlorophosphate (250 g) in EtOAc (800 mL) was added isopropyl L-alaninate (200 g) in triethylamine (120 g) at −10° C. The reaction was stirred at −10° C. for 1 h. 2,3,4,5,6-Pentafluorophenol (220 g) in triethylamine (120 g) and EtOAc (400 mL) was added at −5° C. and stirred at −5° C. for 0.5 h. The reaction mixture was allowed to warm to 25° C. and stirred at 25° C. for 2 h. The solution was filtrated, washed with EtOAc (2×200 mL), and the combined organic phases were evaporated under vacuum to afford solid PPAL-RS (racemate).

Step 2. Preparation of PPAL-RS

To a stirred solution of PPAL-RS in EtOAc (200 mL) and n-heptane (1.4 L), was added 2,3,4,5,6-pentafluorophenol (10.1 g) in triethylamine (6 g), and the reaction was stirred for about 4-8 h. After the R-isomer of the solid was less than 0.5% of the reaction mixture, the solid was filtered. The solid was dissolved in EtOAc (4 L), washed with water (2×100 mL), brine (1 L), dried over anhydrous $Na_2SO_4$, and filtered. The solvent was removed under vacuum to afford PPAL-S (350 g).

$^1$H NMR (400 MHz, DMSO-$d_6$) δ=7.42-7.40 (m, 2H), 7.24-7.22 (m, 3H), 6.87 (dd, J=14.1, 9.9 Hz, 1H), 4.90-4.84 (m, 1H), 3.94-3.88 (m, 1H), 1.27 (dd, J=7.1, 1.1 Hz, 3H), 1.15 (dd, J=6.2, 1.2 Hz, 6H) ppm. $^{13}$P NMR (160 MHz, DMSO-$d_6$) δ=0.37 ppm.

Example 3. Preparation of PPAL-R

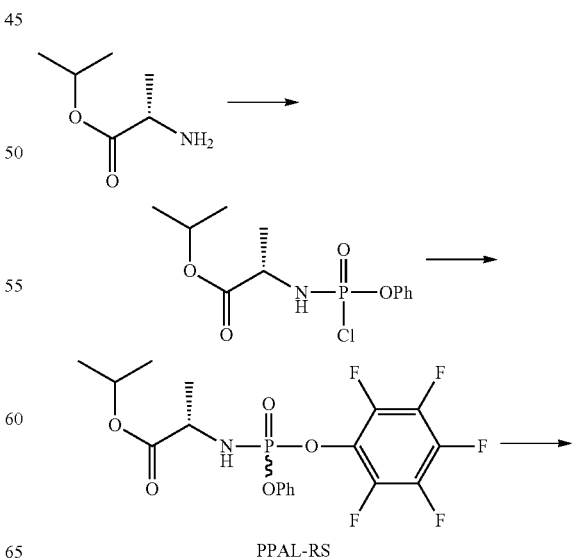

PPAL-RS

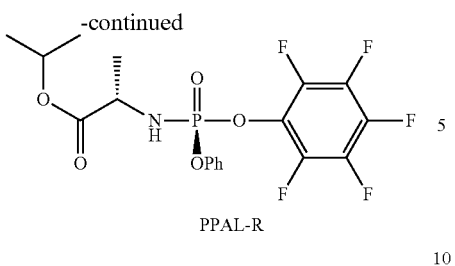

PPAL-R

To a three-necked round bottom flask fitted with a mechanic stirrer were added phenyl dichlorophosphate (189.6 g, 0.90 mol) and anhydrous EtOAc (750 mL). The solution was cooled to −10° C. under a nitrogen atmosphere. Iso-propyl L-alaninate (118 g, 0.90 mmol) and triethylamine (100 g, 1.1 eq) were added to the above solution. A pre-cooled (below 10° C.) mixture of 2,3,4,5,6-pentafluorophenol (165 g, 1 eq) and triethylamine (90.5 g, 1 eq) in EtOAc (300 mL) was added to the mixture via an addition funnel at −5° C. and the resulting mixture was stirred between 20-25° C. for 1 hour. The white precipitate (TEA·HCl) was filtered off and rinsed with EtOAc. The filtrate was concentrated under reduced pressure to yield PPAL-RS (approximately 280 g (S/R=1/1)) as a white solid. PPAL-RS (280 g) was triturated in 300 mL of heptane/EtOAc (20:1) at room temperature for 5 min. The white suspension was filtered and the solid was rinsed with a mixture of heptane/EtOAc (20.1). The filtrate was cooled to 8° C. and the solid was collected by filtration. Crude PPAL-R (10 g) was obtained with 95% chiral purity. The crude product was purified following the above step. PPAL-R (5 g) was obtained in NLT 98% chiral purity.

$^1$H NMR (400 MHz, DMSO-$d_6$) δ=7.43-7.39 (m, 2H), 7.27-7.22 (m, 3H), 6.87 (dd, J=14.1, 9.9 Hz, 1H), 4.89-4.85 (m, 1H), 3.95-3.90 (m, 1H), 1.27 (dd, J=7.1, 1.1 Hz, 3H), 1.14 (dd, J=6.2, 1.2 Hz, 6H). $^{13}$P NMR (160 MHz, DMSO-$d_6$) δ=0.35.

Stereospecific Syntheses of Compounds of Formulas I-IV

Synthesis of β-D-2′-Deoxy-2′-α-fluoro-2′-β-ethynyl-N$^6$-substituted-2,6-diaminopurine Nucleotides

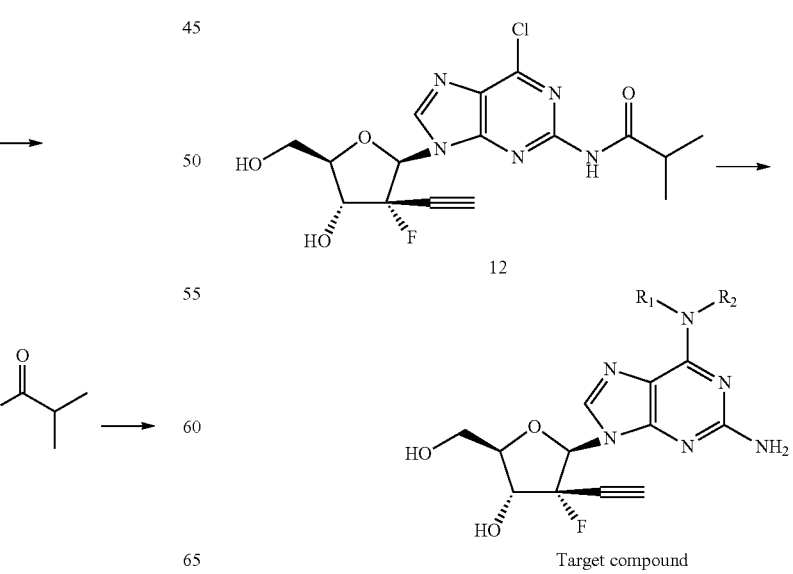

Example 4. General Route to β-D-2'-Deoxy-2'-α-fluoro-2'-β-ethynyl-N⁶-substituted-2,6-diaminopurine Nucleotides

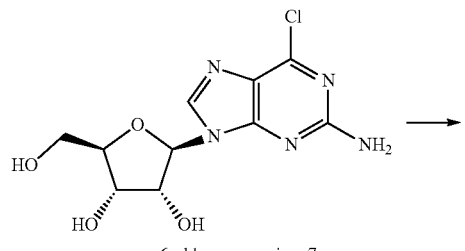

6-chloroguanosine, 7

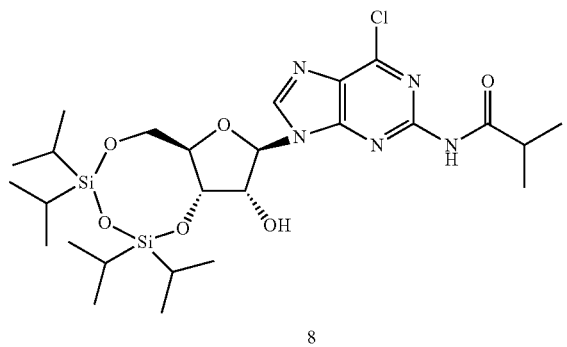

8

Step 1. Preparation of Compound 8.

To a solution of 6-chloroguanosine (100 g, 332 mmol) in pyridine (400 mL) was added TIPDSiCl₂ (110 mL, 1.05 eq.) dropwise at −5~5° C. under a N₂ atmosphere. After stirring at −5~5° C. for 2 h, TLC showed that the starting material was consumed. DCM (600 mL) was added and TMSCl (85 mL, 2 eq.) was added dropwise at 0-5° C. After stirring at 0-5° C. for 2 h, TLC showed that the intermediate was consumed. Isobutyryl chloride was added dropwise at 0-5° C. After stirring at 0-5° C. for 2 h, TLC showed the intermediate was consumed. Water was added and the content was extracted with DCM. The organic phase was washed with 0.5N HCl to remove pyridine. The pH of the content was washed to 5-6, and pTSA·H₂O (9.2 g, 484.5 mmol) was added at 0-5° C. After stirring at 0-5° C. for 1 h, TLC showed the intermediate was consumed. Water was added and the organic phase was washed with water, saturated aqueous NaHCO₃ and brine. The organic layer was dried over Na₂SO₄ and the solvent was removed in vacuo. The residue was purified with column chromatography (PE/EA=100→10/1) to afford a light yellow solid (82 g, 40%).

¹H NMR (400 MHz, DMSO-d₆) δ 10.88 (s, 1H), 8.55 (s, 1H), 5.91 (d, J=1.6 Hz, 1H), 5.53 (d, J=4.6 Hz, 1H), 4.72-4.58 (m, 2H), 4.16 (dd, J=12.4, 4.8 Hz, 1H), 4.00 (ddd, J=7.7, 4.8, 2.6 Hz, 1H), 3.93 (dd, J=12.4, 2.7 Hz, 1H), 2.78 (h, J=6.9 Hz, 1H), 1.26-1.12 (m, 3H), 1.10 (d, J=6.7 Hz, 6H), 1.09-0.88 (m, 24H).

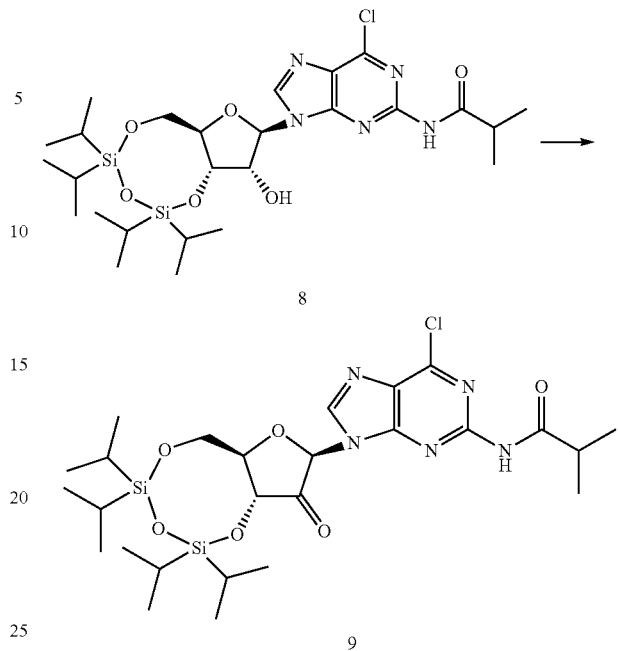

Step 2. Preparation of Compound 9.

To a solution of 8 (10.0 g, 16.3 mmol) in DCM (100 mL) was added Dess-Martin periodinane at RT and the reaction was stirred for 12 h. TLC showed the starting material was consumed. The reaction mixture was then diluted with DCM (200 mL) and washed with saturated aqueous Na₂S₂O₃ and brine. The organic phase was then dried over Na₂SO₄ and concentrated to afford crude 9 as a light yellow solid (12 g). The crude product can be used directly in the next step without purification.

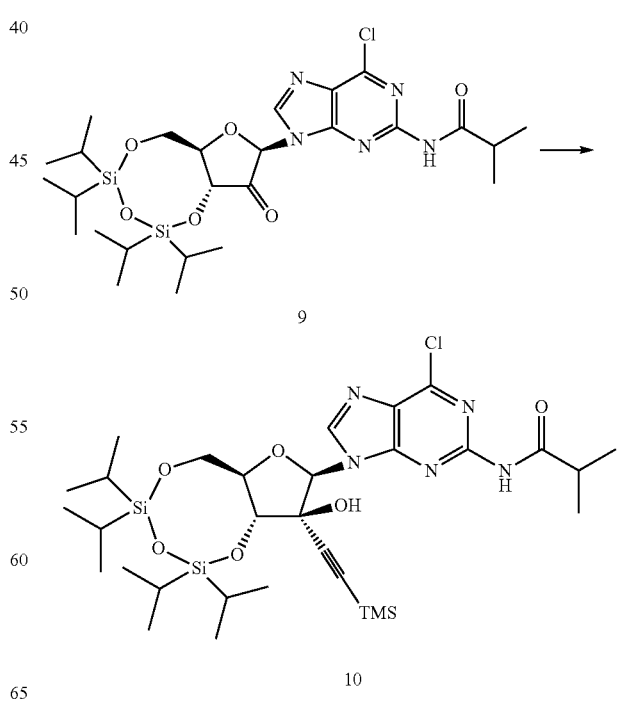

Step 3. Preparation of Compound 10.

To a solution of ethynyltrimethylsilane (18.6 mL, 142.7 mmol) in THF (240 mL) was added n-BuLi (46 mL, 2.5 M, 115.0 mmol) dropwise at −15-20° C. under a $N_2$ atmosphere. After stirring for 30 min, the reaction was cooled to −70° C. and 9 (crude, 16.3 mmol) in THF (60 mL) was added at 15-20° C. The content was then warmed to 0° C. TLC showed the starting material was consumed. Saturated aqueous $NH_4Cl$ was added and the reaction was extracted with EA (100 mL) three times. The organic phase was combined, washed with brine, and further dried over $Na_2SO_4$. After concentration in vacuo, the residue was purified by column chromatography (PE/EA=100→10/1) to afford a light yellow solid (6.0 g, 52%).

$^1$H NMR (300 MHz, $CDCl_3$) δ 8.39 (s, 1H), 8.07 (s, 1H), 6.18 (s, 1H), 4.42 (d, J=7.2 Hz, 1H), 4.21-4.02 (m, 3H), 2.94 (d, J=8.5 Hz, 1H), 1.25 (t, J=8.8 Hz, 3H), 1.12-1.01 (m, 30H), 0.17 (d, J=1.4 Hz, 9H).

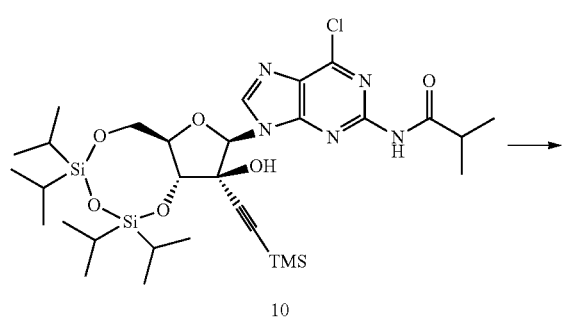

10

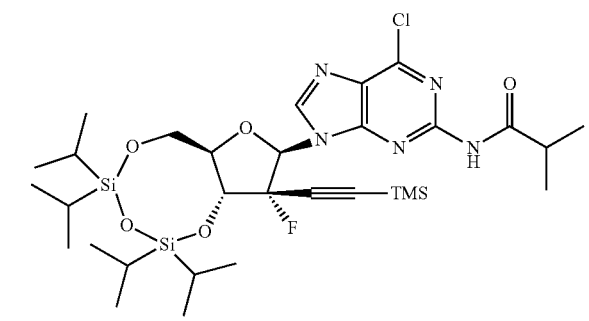

11

Step 4. Preparation of Compound 11.

To a solution of 10 (6.0 g, 8.4 mmol) in DCM (240 mL) was added pyridine (4.2 mL, 52.9 mmol) under a $N_2$ atmosphere. The reaction was cooled to −70° C. and DAST (12 mL, 90.4 mmol) was added. The content was then warmed to −30° C. TLC showed that the starting material was consumed. The reaction was poured into saturated aqueous $NaHCO_3$ and then extracted with DCM (200 mL). The organic phase was washed with brine and dried over $Na_2SO_4$. After being concentrated in vacuo, the residue was purified with column chromatography (PE/EA=100→10/1) to afford a light yellow solid (3.8 g, 63%).

$^1$H NMR (400 MHz, $CDCl_3$) δ 8.57 (s, 1H), 8.37 (s, 1H), 6.24 (s, 1H), 5.98 (s, 2H), 5.32 (s, 1H), 4.44 (d, J=8.0 Hz, 1H), 4.23-4.07 (m, 4H), 2.91 (m, 1H) 1.32-1.27 (m, 10H), 1.13-1.06 (m, 24H), 0.23 (s, 9H).

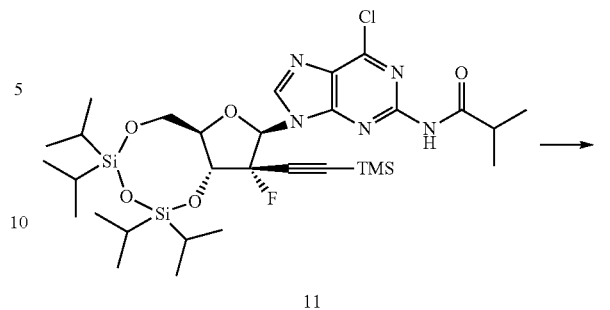

11

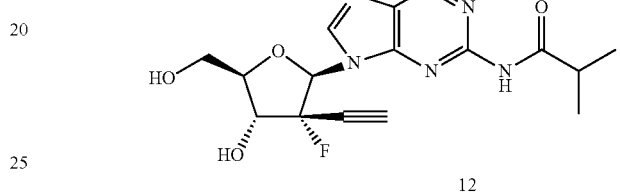

12

Step 5. Preparation of Compound 12.

To a solution of 11 (3.8 g, 5.3 mmol) in THF (120 mL) was added AcOH (1.3 g, 22 mmol) and TBAF (4.2 g, 15.9 mmol) at RT. The reaction was stirred at RT for 30 min. TLC showed the starting material was consumed. After being concentrated in vacuo, the residue was purified with column chromatography (EA) to afford the product as a white solid (2.0 g, 95%).

$^1$H NMR (300 MHz, Methanol-$d_4$) δ 8.75 (s, 1H), 6.57 (d, J=16.4 Hz, 1H), 4.99 (dd, J=21.7, 9.3 Hz, 1H), 4.14-3.95 (m, 2H), 3.91 (dd, J=12.8, 3.8 Hz, 1H), 3.14 (d, J=5.3 Hz, 1H), 2.81 (dt, J=13.7, 6.8 Hz, 1H), 1.22 (dd, J=6.9, 3.1 Hz, 6H).

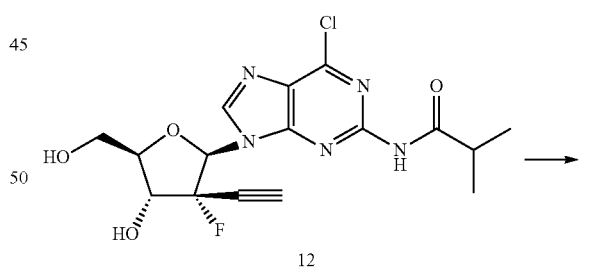

12

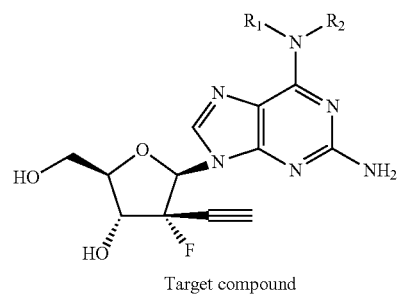

Target compound

General Procedure for Amino Displacement and Deprotection:

To a solution of 12 (350 mg, 0.88 mmol) in dioxane (20 mL) was added a methanol or water solution of the corresponding amine (free base or salt as hydrochloride plus DIEA) at RT. The content was stirred at RT for 1-12 h. TLC showed the starting material was consumed. After concentration in vacuo, the residue was used directly in the next step without purification. The residue was dissolved in methanol (10 mL) and aqueous NaOH (2.5 N, 10 mL) was added. After stirring overnight at RT, TLC showed that starting material was consumed. The pH of the content was adjusted to 7-8 with 1 N HCl. The solution was concentrated and purified with column chromatography (DCM/MeOH=100→20/1) to afford the product as an off-white solid (yield: 40-80% over two steps). Table 1 illustrates the structures of compounds 1, 3, and 5 and the corresponding mass spectra and $^1$H NMR for the respective compounds.

TABLE 1

Characterization of Compounds 1, 3, and 5

| Compound No. | Structure | $^1$H NMR/MS |
|---|---|---|
| 1 | 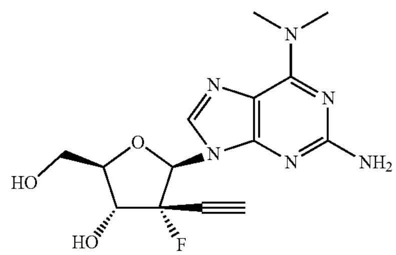 [SMILES: C#C[C@@]1(F)[C@H](O)[C@@H](CO)O[C@H]1n1cnc2c(N(C)C)nc(N)nc21] | $^1$H NMR (400 MHz, Methanol-$d_4$) δ 8.05 (s, 1H), 6.27 (d, J = 16.9 Hz, 1H), 4.75 (dd, J = 21.7, 9.1 Hz, 1H), 4.06 (dd, J = 11.0, 2.4 Hz, 2H), 3.87 (dd, J = 13.1, 3.2 Hz, 1H), 3.42 (s, 6H), 3.37 (s, 2H), 3.18 (d, J = 5.4 Hz, 1H). [M + H]$^+$ = 336.9 |
| 3 | 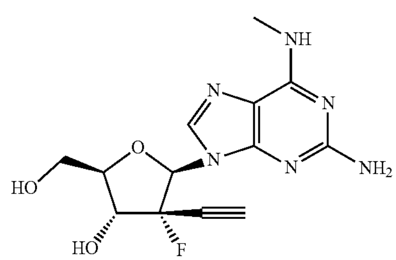 [SMILES: C#C[C@@]1(F)[C@H](O)[C@@H](CO)O[C@H]1n1cnc2c(NC)nc(N)nc21] | $^1$H NMR (400 MHz, DMSO-$d_6$) δ 7.94 (s, 1H), 7.30 (s, 1H), 6.20-6.09 (m, 2H), 5.98 (s, 2H), 5.33 (t, J = 5.3 Hz, 1H), 4.57 (dt, J = 22.1, 8.0 Hz, 1H), 4.12 (q, J = 5.3 Hz, 1H), 3.91 (d, J = 9.3 Hz, 1H), 3.70 (t, J = 8.6 Hz, 1H), 3.36 (s, 1H), 3.18 (d, J = 5.2 Hz, 2H), 2.89 (d, J = 7.0 Hz, 3H). [M + H]$^+$ = 323.0 |
| 5 | 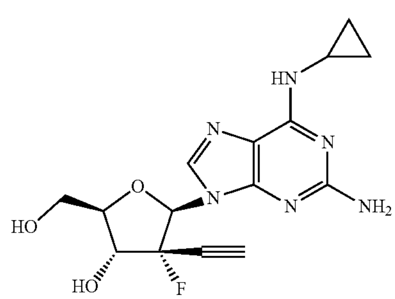 [SMILES: C#C[C@@]1(F)[C@H](O)[C@@H](CO)O[C@H]1n1cnc2c(NC3CC3)nc(N)nc21] | $^1$H NMR (400 MHz, Methanol-$d_4$) δ 8.07 (s, 1H), 6.26 (d, J = 16.9 Hz, 1H), 4.76 (dd, J = 21.8, 9.3 Hz, 1H), 4.11-4.01 (m, 2H), 3.89 (d, J = 3.0 Hz, 1H), 3.89-3.75 (m, 1H), 3.37 (s, 2H), 3.21 (d, J = 5.4 Hz, 1H), 2.97-2.86 (m, 1H), 1.00-0.77 (m, 2H), 0.67-0.46 (m, 2H). [M + H]$^+$ = 348.8 |

Example 5. Synthesis of 6-N-Alkylnucleoside Pronucleotides

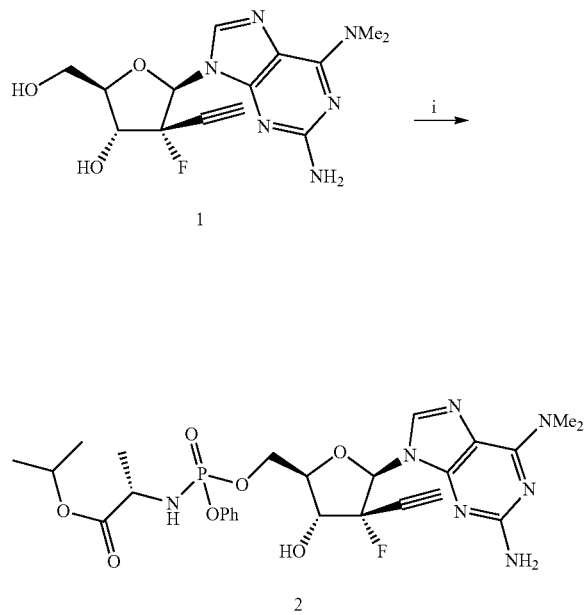

i) Isopropyl ((R,S)-(pentafluorophenoxy)-phenoxy-phosphoryl)-L-alaninate, t-BuMgCl, THF, 0° C.

Preparation of (2S)-Isopropyl 2-(((((2R,3R,4R,5R)-5-(2-amino-6-(dimethylamino)-9H-purin-9-yl)-4-ethynyl-4-fluoro-3-hydroxytetrahydrofuran-2-yl)methoxy)(phenoxy)phosphoryl)amino) Propanoate (2)

To a solution of compound 1 (30 mg, 0.09 mmol) in dry THF (2.0 mL) was added tert-butylmagnesium chloride (1 N in THF) (125 μL, 0.13 mmol) dropwise at 0° C. The solution was stirred for 15 mins at 0° C. and for 45 mins at room temperature (RT). The reaction mixture was cooled down to 0° C. and a solution of isopropyl ((R,S)-(pentafluorophenoxy)-phenoxy-phosphoryl)-L-alaninate (49 mg, 0.11 mmol) in dry THF (1.0 mL) was added dropwise. The resulting solution was slowly warmed to RT and stirred for 15 h. The reaction mixture was then diluted with EtOAc (10 mL) and saturated NH$_4$Cl aq. solution (8 mL). The phases were separated and the aqueous layer was back-extracted with EtOAc (2×5 mL). The combined organics were washed with saturated NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product 2 (12 mg, 22%) was obtained as a white solid.

$^1$H NMR (300 MHz, CD$_3$OD) δ 7.79 (s, 0.5H), 7.77 (s, 0.5H), 7.36-7.14 (m, 5H), 6.28 (d, J=17.4 Hz) and 6.26 (d, J=17.5 Hz, 1H), 5.00-4.44 (m, 5H), 4.23-4.16 (m, 1H), 3.69-3.81 (m, 1H), 3.42 (bs, 3H), 3.40 (bs, 3H), 1.32-1.26 (m, 3H), 1.20-1.15 (m, 6H). $^{31}$P NMR (121 MHz, CD$_3$OD) δ 4.04 (s), 3.98 (s). MS (ESI) m/z calcd. for C$_{26}$H$_{34}$FN$_7$O$_7$P [M+H]$^+$ 606.2; found 606.2.

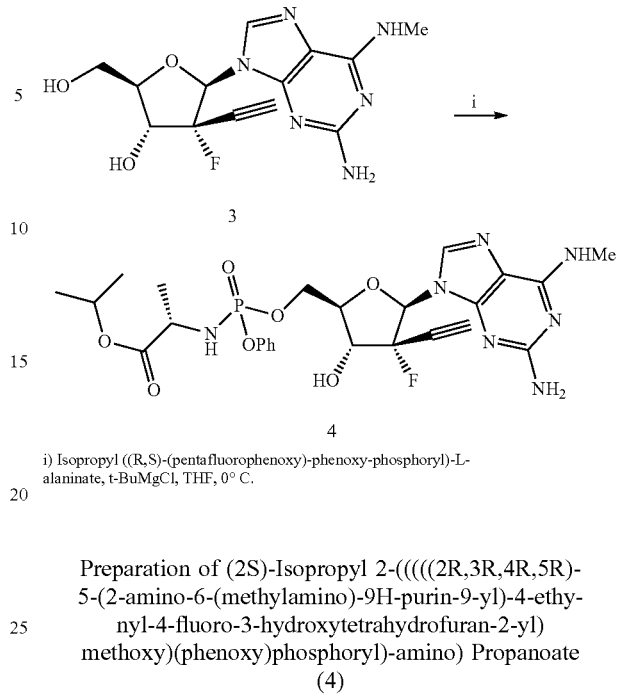

i) Isopropyl ((R,S)-(pentafluorophenoxy)-phenoxy-phosphoryl)-L-alaninate, t-BuMgCl, THF, 0° C.

Preparation of (2S)-Isopropyl 2-(((((2R,3R,4R,5R)-5-(2-amino-6-(methylamino)-9H-purin-9-yl)-4-ethynyl-4-fluoro-3-hydroxytetrahydrofuran-2-yl)methoxy)(phenoxy)phosphoryl)-amino) Propanoate (4)

To a solution of compound 3 (30 mg, 0.09 mmol) in dry THF (2.0 mL) was added tert-butylmagnesium chloride (1 N in THF) (112 μL, 0.11 mmol) dropwise at 0° C. The solution was stirred for 15 mins at 0° C. and for 45 mins at RT. The reaction mixture was cooled down to 0° C. and a solution of isopropyl ((R,S)-(pentafluorophenoxy)-phenoxy-phosphoryl)-L-alaninate (51 mg, 0.11 mmol) in dry THF (1.0 mL) was added dropwise. The resulting solution was slowly warmed to RT and stirred for 15 h. The reaction mixture was then diluted with EtOAc (10 mL) and saturated NH$_4$Cl aq. solution (8 mL). The phases were separated and the aqueous layer was back-extracted with EtOAc (2×5 mL). The combined organics were washed with saturated NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product 4 (9 mg, 16%) was obtained as a white solid.

$^1$H NMR (300 MHz, CD$_3$OD) δ 7.81, 7.79 (s+s, 1H), 7.36-7.14 (m, 5H), 6.26 (d, J=17.4 Hz, 0.1H), 6.24 (d, J=17.4 Hz, 0.9H), 4.93-4.89 (overlapped with H$_2$O, m, 1H), 4.80-4.78 (m, 1H), 4.53-4.49 (m, 2H), 4.21-4.18 (m, 1H), 3.95-3.84 (m, 1H), 3.23-3.20 (m, 1H), 3.04 (bs, 1H), 1.31-1.14 (m, 9H). $^{31}$P NMR (121 MHz, CD$_3$OD) δ 4.06 (s), 3.97 (s). MS (ESI) m/z calcd. for C$_{25}$H$_{32}$FN$_7$O$_7$P [M+H]$^+$ 592.2; found 592.2.

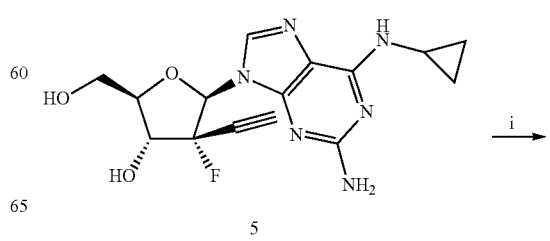

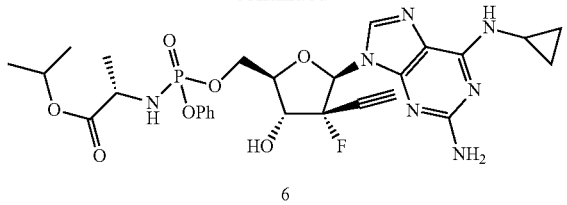

6 i) Isopropyl ((R,S)-(pentafluorophenoxy)-phenoxy-phosphoryl)-L-alaninate, t-BuMgCl, THF, 0° C.

Preparation of (2S)-Isopropyl 2-(((((2R,3R,4R,5R)-5-(2-amino-6-(cyclopropylamino)-9H-purin-9-yl)-4-ethynyl-4-fluoro-3-hydroxytetrahydrofuran-2-yl)methoxy)(phenoxy)phosphoryl)amino) Propanoate (6)

To a solution of compound 5 (30 mg, 0.09 mmol) in dry THF (3.0 mL) was added tert-butylmagnesium chloride (1 N in THF) (120 μL, 0.12 mmol) dropwise at 0° C. The solution was stirred for 15 mins at 0° C. and for 45 mins at RT. The reaction mixture was cooled to 0° C. and a solution of isopropyl ((R,S)-(pentafluorophenoxy)-phenoxy-phosphoryl)-L-alaninate (47 mg, 0.10 mmol) in dry THF (1.0 mL) was added dropwise. The resulting solution was slowly warmed to RT and stirred for 15 h. The reaction mixture was then diluted with EtOAc (10 mL) and saturated NH$_4$Cl aq. solution (8 mL). The phases were separated and the aqueous layer was back-extracted with EtOAc (2×5 mL). The combined organics were washed with saturated NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product 6 (19 mg, 35%) was obtained as a white solid.

$^1$H NMR (300 MHz, CD$_3$OD) δ 7.82, 7.79 (s+s, 1H), 7.44-7.17 (m, 5H), 6.26 (d, J=17.1 Hz), 6.24 (d, J=17.1 Hz, 1H), 4.93-4.89 (overlapped with H$_2$O, m, 1H), 4.79-4.46 (m, 3H), 4.24-4.07 (m, 1H), 3.92-3.83 (m, 1H), 3.25-3.22 (m, 1H), 2.92-2.89 (m, 1H), 1.31-1.14 (m, 9H), 0.85-0.82 (m, 2H), 0.63-0.57 (m, 2H). $^{31}$P NMR (121 MHz, CD$_3$OD) δ 4.03 (s), 3.94 (s). MS (ESI) m/z calcd. for C$_{27}$H$_{34}$FN$_7$O$_7$P [M+H]$^+$ 618.2; found 618.2.

Example 6. Synthesis of β-D-2'-α-Hydroxy-2'-β-methyl-N$^6$-substituted-2,6-diaminopurine Nucleotides

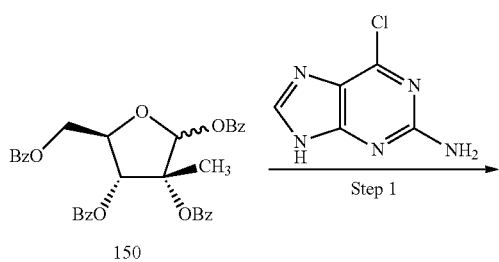

150

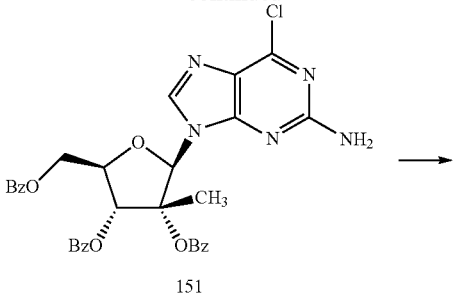

151

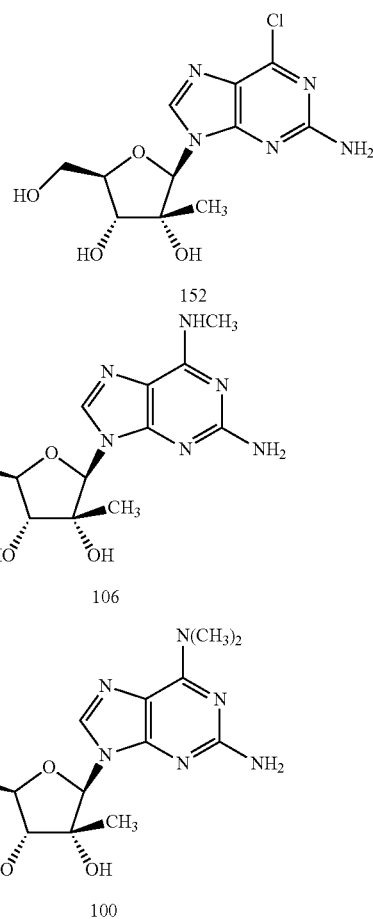

Step 1. Preparation of Compound 151.

To a pre-cooled (0° C.) solution containing 1,2,3,5-tetra-O-benzoyl-2-C-methyl-D-ribofuranose, 150, (2.50 g, 4.3 mmol), 2-amino-6-chloropurine (0.8 g, 4.68 mmol), 1,8-diazabicycl[5.4.0]undec-7-ene (DBU) (1.94 g, 12.75 mmol) and anhydrous acetonitrile (50 mL), trimethylsilyl triflate (3.8 g, 17.2 mmol) was added dropwise. The reaction mixture was heated at 65° C. for 4 h, allowed to cool to room temperature, poured into saturated aqueous sodium (150 mL) and extracted with dichloromethane (3×100 mL). The combined organic fractions were dried over sodium sulfate and concentrated in vacuo. The residue was purified over silica gel using hexane/ethyl acetate (4:1) as the eluent to afford 151 (3.5 g, 73%) as a colorless foam.

$^1$H NMR (400 MHz, DMSO-d$_6$) δ 8.41 (s, 1H), 8.04 (ddt, J=22.8, 6.9, 1.4 Hz, 4H), 7.98-7.83 (m, 3H), 7.74-7.59 (m, 3H), 7.63-7.46 (m, 4H), 7.40 (t, J=7.8 Hz, 2H), 7.22 (s, 2H), 6.64 (s, 1H), 5.97 (d, J=4.5 Hz, 1H), 4.92-4.75 (m, 3H), 2.90 (s, 3H), 2.74 (s, 3H), 1.61 (s, 3H).

Step 2. Preparation of Compound 152.

A solution containing 151 (0.65 g, 1.03 mmol) and saturated methanolic ammonia (15 mL) was stirred in a sealed container for 7 h. The solvent was removed and the residue was purified on silica gel using methanol/DCM (1:40) as the eluent. Fractions containing the product were pooled and concentrated in vacuo to afford 152 (0.30 g, 92%) as a colorless powder.

Step 3. Preparation of Compound 106.

To a solution containing 152 (0.3 g, 1.0 mmol) and 1,4-dioxane (2 mL) was added methylamine solution (1 mL). The reaction was stirred for 2 h and concentrated in vacuo. The residue was purified on silica gel using methanol/DCM (1:40) as the eluent. Fractions containing the product were pooled and concentrated in vacuo to afford 106 (0.150 g, 50%) as a colorless powder.

$^1$H NMR (400 MHz, DMSO-$d_6$) δ 8.01 (s, 1H), 7.24 (s, 1H), 5.89 (s, 2H), 5.79 (s, 1H), 5.20 (dd, J=6.2, 3.2 Hz, 2H), 5.05 (s, 1H), 4.11 (q, J=5.2 Hz, 1H), 4.08-3.97 (m, 1H), 3.89-3.77 (m, 2H), 3.66 (ddd, J=12.2, 5.4, 3.3 Hz, 1H), 3.17 (d, J=5.3 Hz, 3H), 0.79 (s, 3H).

Step 4. Preparation of Compound 107.

column chromatography (C-18 silica, H$_2$O/MeOH 0 to 100%). Product 107 (23 mg, 22%) was obtained as a white solid.

$^1$H NMR (300 MHz, CD$_3$OD) δ 7.84 (s, 1H), 7.38-7.16 (m, 5H), 5.96-5.93 (s+s, 1H), 4.97-4.90 (m, 1H), 4.63-4.42 (m, 2H), 4.26-4.15 (m, 2H), 3.98-3.87 (m, 1H), 3.06 (s, 3H), 1.33-1.29 (m, 3H), 1.22-1.15 (m, 6H), 0.98-0.95 (s+s, 3H). $^{31}$P NMR (121 MHz, CD$_3$OD) δ 4.18 (s), 4.05 (s). MS (ESI) m/z calcd. for C$_{24}$H$_{35}$N$_7$O$_9$P [M+H]$^+$ 580.2; found 580.2.

Step 5. Preparation of Compound 100.

To a solution containing 152 (0.3 g, 1.0 mmol) and 1,4-dioxane (2 mL) was added dimethylamine solution (1 mL). The reaction was stirred for 2 h and concentrated in vacuo. The residue was purified on silica gel using methanol/DCM (1:40) as the eluent. Fractions containing the product were pooled and concentrated in vacuo to afford 100 (0.200 g, 70%) as a colorless powder.

$^1$H NMR (400 MHz, Methanol-$d_4$) δ 8.10 (s, 1H), 5.95 (s, 1H), 4.24 (d, J=8.7 Hz, 1H), 4.08-3.99 (m, 2H), 3.91-3.82 (m, 1H), 3.42 (s, 6H), 3.37 (s, 2H), 0.95 (s, 3H).

Step 6. Preparation of Compound 101.

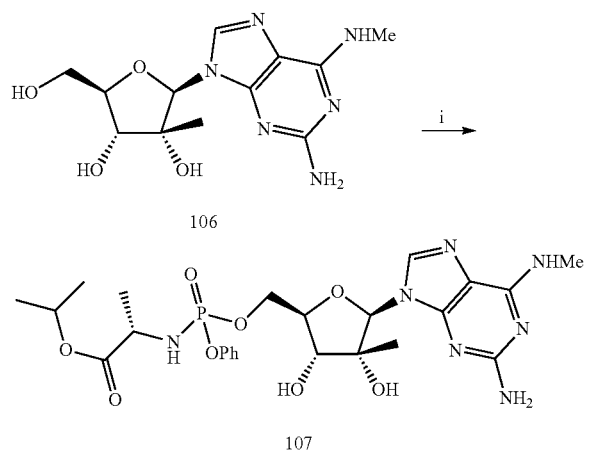

107 i) Isopropyl ((R,S)-(pentafluorophenoxy)-phenoxy-phosphoryl)-L-alaninate, t-BuMgCl, DMF, 0° C.

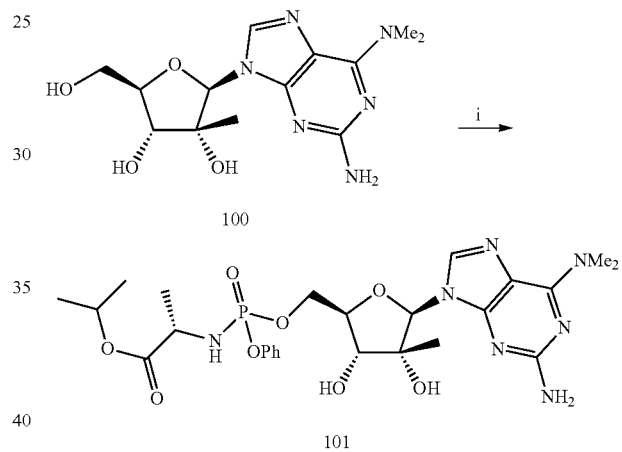

101 i) Isopropyl ((R,S)-(pentafluorophenoxy)-phenoxy-phosphoryl)-L-alaninate, t-BuMgCl, THF, 0° C.

(2S)-Isopropyl 2-(((((2R,3R,4R,5R)-5-(2-amino-6-(methylamino)-9H-purin-9-yl)-3,4-dihydroxy-4-methyltetrahydrofuran-2-yl)methoxy)(phenoxy) phosphoryl)amino) Propanoate (107)

To a solution of compound 106 (55 mg, 0.18 mmol) in dry DMF (4.0 mL) was added tert-butylmagnesium chloride (1 N in THF) (265 μL, 0.27 mmol) dropwise at 0° C. The solution was stirred for 15 mins at 0° C. and for 45 mins at RT. The reaction mixture was cooled down to 0° C. and a solution of isopropyl ((RS)-(pentafluorophenoxy)-phenoxy-phosphoryl)-L-alaninate (105 mg, 0.23 mmol) in dry THF (2.0 mL) was added dropwise. The resulting solution was slowly warmed up to RT and stirred for 15 h. The reaction mixture was then diluted with EtOAc (15 mL) and saturated NH$_4$Cl aq. solution (10 mL). The phases were separated and the aqueous layer was back-extracted with EtOAc (2×10 mL). The combined organics were washed with saturated NH$_4$Cl aq. solution (15 mL) and brine (15 mL), dried over Na$_2$SO$_4$ and concentrated.

The residue was purified by column chromatography (silica gel, DCM/MeOH 0 to 10/a) and by reverse phase (2S)-Isopropyl 2-(((((2R,3R,4R,5R)-5-(2-amino-6-(dimethylamino)-9H-purin-9-yl)-3,4-dihydroxy-4-methyltetrahydrofuran-2-yl)methoxy)(phenoxy) phosphoryl)amino) Propanoate (101)

To a solution of compound 100 (30 mg, 0.09 mmol) in dry THF (2.0 mL) was added tert-butylmagnesium chloride (1 N in THF) (130 μL, 0.13 mmol) dropwise at 0° C. The solution was stirred for 15 mins at 0° C. and for 45 mins at RT. The reaction mixture was cooled down to 0° C. and a solution of isopropyl ((R,S)-(pentafluorophenoxy)-phenoxy-phosphoryl)-L-alaninate (46 mg, 0.11 mmol) in dry THF (1.0 mL) was added dropwise. The resulting solution was slowly warmed up to RT and stirred for 15 h. The reaction mixture was then diluted with EtOAc (10 mL) and saturated NH$_4$Cl aq. solution (8 mL). The phases were separated and the aqueous layer was back-extracted with EtOAc (2×5 mL). The combined organics were washed with saturated NH$_4$Cl aq. solution (10 mL) and brine (10 mL), dried over Na$_2$SO$_4$ and concentrated. The residue was purified by column chromatography (silica gel, DCM/MeOH 0 to 10%) and by reverse phase column chromatography (C-18 silica, H₂O/MeOH 0 to 100%). Product 101 (30 mg, 55%) was obtained as a white solid.

¹H NMR (300 MHz, CD₃OD) δ 7.81, 7.80 (s+s, 1H), 7.37-7.15 (m, 5H), 5.97, 5.95 (s+s, 1H), 4.96-4.88 (overlapped with H₂O, m, 1H), 4.60-4.42 (m, 2H), 4.19-3.90 (m, 3H), 3.41 (Is, 6H), 1.33-1.15 (m, 10H), 0.96, 0.93 (s+s, 3H). ³¹P NMR (121 MHz, CD₃OD) δ 4.16 (s), 4.07 (s). MS (ESI) m/z calcd. for C₂₅H₃₇N₇O₉P [M+H]⁺ 594.2; found 594.2.

Example 7. Synthesis of (2S)-Isopropyl 2-(((((2R,3R,4R,5R)-5-(2-amino-6-(cyclopropyl(methyl)amino)-9H-purin-9-yl)-3,4-dihydroxy-4-methyltetrahydrofuran-2-yl)methoxy)(phenoxy)phosphoryl)amino)propanoate (103)

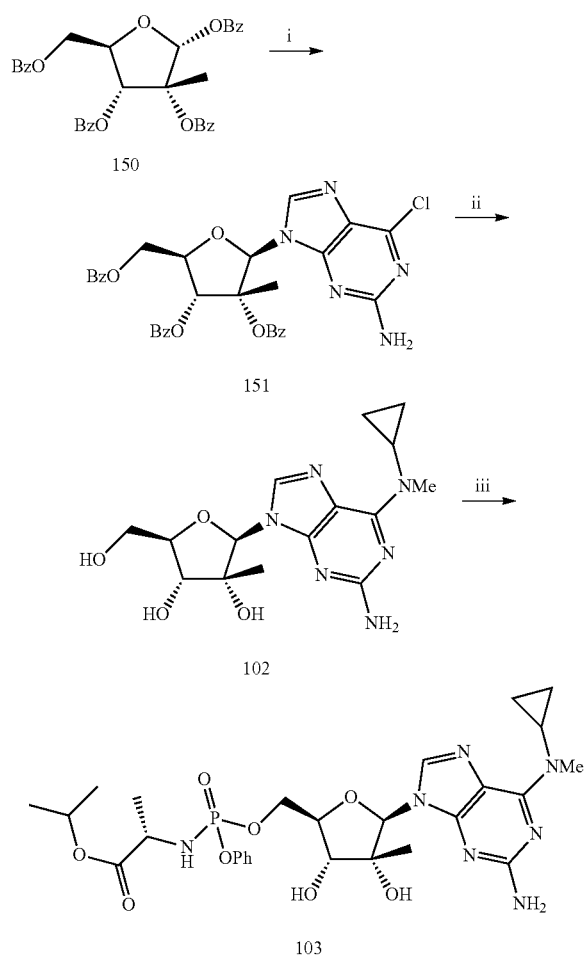

i) 2-Amino-6-chloropurine, BSA, TMSOTf, MeCN, reflux; ii) N-Methyl-cyclopropylamine hydrochloride, Et₃N, MeOH, 100° C.; iii) Isopropyl ((R,S)-(pentafluorophenoxy)-phenoxy-phosphoryl)-L-alaninate, t-BuMgCl, THF, 0° C.

Step 1. Preparation of (2R,3R,4R,5R)-2-(2-Amino-6-chloro-9H-purin-9-yl)-5-((benzoyloxy)methyl)-3-methyltetrahydrofuran-3,4-diyl Dibenzoate (151)

To a suspension of 2-amino-6-chloropurine (1.17 g, 6.90 mmol) in dry acetonitrile (100 mL) was added N,O-bis(trimethylsilyl)acetamide (2.50 mL, 10.20 mmol). The mixture was heated at reflux for 2 h. The resulting solution was cooled down to RT and 150 (2.00 g, 3.45 mmol) was added. The solution was cooled down to 0° C. and TMSOTf (1.87 mL, 10.20 mmol) was added dropwise over 2 mins. The reaction mixture was heated at reflux for 2 h, cooled to RT and concentrated. The residue was partitioned between EtOAc (100 mL) and saturated NaHCO₃ aq. solution (80 mL). The phases were separated and the aqueous layer was back-extracted with EtOAc (2×40 mL). The combined organics were washed with saturated NaHCO₃ aq. solution (100 mL), brine (100 mL), dried over Na₂SO₄ and concentrated. The residue was purified by column chromatography (silica gel, PE/EtOAc 10 to 80%). Product 151 (1.75 g, 81%) was obtained as a white foam.

Step 2. Preparation of (2R,3R,4R,5R)-2-(2-Amino-6-(cyclopropyl(methyl)amino)-9H-purin-9-yl)₅-(hydroxymethyl)-3-methyltetrahydrofuran-3,4-diol (102)

To a suspension of compound 151 (610 mg, 0.97 mmol) in MeOH (30 mL) was added N-methylcyclopropylamine hydrochloride (313 mg, 2.91 mmol) and triethylamine (410 µL, 2.91 mmol). The reaction mixture was heated at 100° C. in a sealed container for 15 h and cooled to RT. Then, 30% NH₄H (5 mL) was added and the mixture was heated at 100° C. in a sealed container for 2 h. The solution was cooled to RT and concentrated. The residue was purified by column chromatography (silica gel, DCM/MeOH 0 to 15%). Product 102 (245 mg, 72%) was obtained as a white solid.

¹H NMR (300 MHz, CD₃OD) δ 8.14 (s, 1H), 5.94 (s, 1H), 4.21 (d, J=8.7 Hz, 1H), 4.02-3.98 (m, 2H), 3.83 (dd, J=3.0, 12.9 Hz, 1H), 3.31 (overlapped with MeOH, s, 3H), 3.16-3.09 (m, 1H), 0.93-0.90 (m, 5H), 0.72-0.69 (m, 2H). MS (ESI) m/z calcd. for C₁₅H₂₃N₆O₄ [M+H]⁺ 351.2; found 351.2.

Step 3. Preparation of (2S)-Isopropyl 2-(((((2R,3R,4R,5R)-5-(2-amino-6-(cyclopropyl(methyl)amino)-9H-purin-9-yl)-3,4-dihydroxy-4-methyltetrahydrofuran-2-yl)methoxy)(phenoxy)phosphoryl) amino) Propanoate (103)

To a solution of compound 102 (60 mg, 0.17 mmol) in dry THF (4.0 mL) was added tert-butylmagnesium chloride (1 N in THF) (240 µL, 0.24 mmol) dropwise at 0° C. The solution was stirred for 15 mins at 0° C. and for 45 mins at RT. The reaction mixture was cooled to 0° C. and a solution of isopropyl ((R,S)-(pentafluorophenoxy)-phenoxy-phosphoryl)-L-alaninate (85 mg, 0.19 mmol) in dry THF (1.5 mL) was added dropwise. The resulting solution was slowly warmed up to RT and stirred for 15 h. The reaction mixture was then diluted with EtOAc (10 mL) and saturated NH₄Cl aq. solution (8 mL). The phases were separated and the aqueous layer was back-extracted with EtOAc (2×5 mL). The combined organics were washed with saturated NH₄Cl aq. solution (10 mL), brine (10 mL), dried over Na₂SO₄ and concentrated. The residue was purified by column chromatography (silica gel, DCM/MeOH 0 to 10%) and by reverse phase column chromatography (C-18 silica, H₂O/MeOH 0 to 100%). Product 103 (51 mg, 48%) was obtained as a white solid.

¹H NMR (300 MHz, CD₃OD) δ 7.84 (s+s, 1H), 7.35-7.15 (m, 5H), 5.98, 5.96 (s+s, 1H), 4.95-4.86 (overlapped with H₂O, m, 1H), 4.60-4.43 (m, 2H), 4.24-4.14 (m, 2H), 3.96-3.87 (m, 1H), 3.35, 3.34 (s+s, 3H), 3.17-3.11 (m, 1H), 1.32-1.27 (m, 3H), 1.20-1.15 (m, 6H), 0.97-0.90 (m, 5H), 0.73-0.69 (m, 2H). $^{31}$P NMR (121 MHz, CD$_3$OD) δ 4.06 (s), 3.97 (s). MS (ESI) m/z calcd. for C$_{27}$H$_{39}$N$_7$O$_8$P [M+H]$^+$ 620.3; found 620.2.

Example 8. Synthesis of (2S)-Isopropyl 2-(((((2R, 3R,4R,5R)-5-(2-amino-6-(cyclopropylamino)-9H-purin-9-yl)-3,4-dihydroxy-4-methyltetrahydrofuran-2-yl)methoxy)(phenoxy)phosphoryl)amino) Propanoate (105)

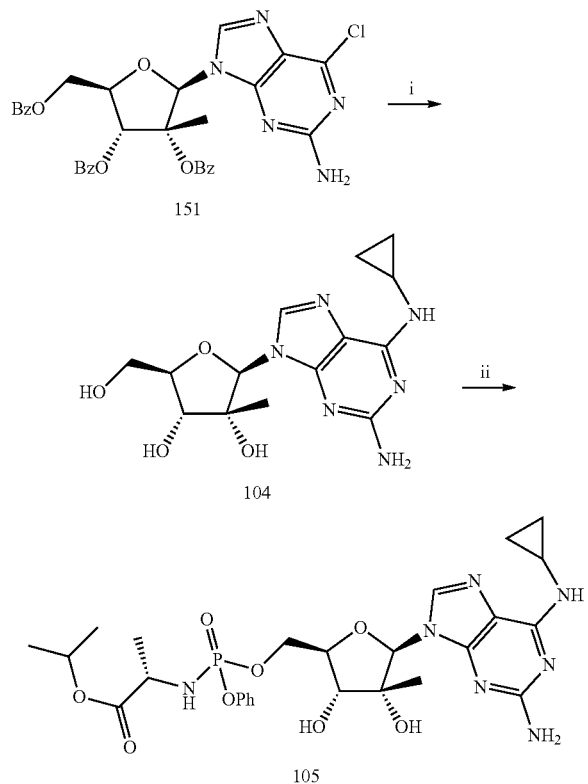

i) Cyclopropylamine, MeOH, 100° C.; ii) Isopropyl ((R,S)-(pentafluorophenoxy)-phenoxy-phosporyl)-L-alaninate, t-BuMgCl, THF, 0° C.

Step 1. Preparation of (2R,3R,4R,5R)-2-(2-Amino-6-(cyclopropylamino)-9H-purin-9-yl)-5-(hydroxymethyl)-3-methyltetrahydrofuran-3,4-diol (104)

To a suspension of compound 151 (1.00 g, 1.59 mmol) in MeOH (40 mL) was added cyclopropylamine (1.45 mL, 20.67 mmol). The reaction mixture was heated at 100° C. in a sealed container for 15 h and cooled to RT. Then, 30% NH$_4$OH (5 mL) was added and the mixture was heated at 100° C. in a sealed container for 3 h. The solution was cooled to RT and concentrated. The residue was purified by column chromatography (silica gel, DCM/MeOH 0 to 20%). Product 104 (438 mg, 82%) was obtained as a white solid.

$^1$H NMR (300 MHz, CD$_3$OD) δ 8.09 (s, 1H), 5.91 (s, 1H), 4.23 (d, J=8.7 Hz, 1H), 4.04-3.99 (m, 1H), 3.87 (dd, J=3.3, 12.6 Hz, 1H), 2.92-2.90 (m, 1H), 0.94 (s, 3H), 0.85-0.82 (m, 2H), 0.62-0.60 (m, 2H). MS (ESI) m/z calcd. for C$_{14}$H$_{21}$N$_6$O$_4$[M+H]$^+$ 337.2; found 337.2.

Step 2. Preparation of (2S)-Isopropyl 2-(((((2R,3R, 4R,5R)-5-(2-amino-6-(cyclopropylamino)-9H-purin-9-yl)-3,4-dihydroxy-4-methyltetrahydrofuran-2-yl) methoxy)(phenoxy)phosphoryl)amino) Propanoate (105)

To a solution of compound 104 (104 mg, 0.31 mmol) in dry THF (6.0 mL) was added tert-butylmagnesium chloride (1 N in THF) (430 μL, 0.43 mmol) dropwise at 0° C. The solution was stirred for 15 mins at 0° C. and for 45 mins at RT. Then, the reaction mixture was cooled to 0° C. and a solution of isopropyl ((R,S)-(pentafluorophenoxy)-phenoxy-phosphoryl)-L-alaninate (154 mg, 0.34 mmol) in dry THF (2.5 mL) was added dropwise. The resulting solution was slowly warmed to RT and stirred for 15 h. The reaction mixture was diluted with EtOAc (20 mL) and saturated NH$_4$Cl aq. solution (15 mL). The phases were separated and the aqueous layer was back-extracted with EtOAc (2×10 mL). The combined organics were washed with saturated NH$_4$Cl aq. solution (20 mL), brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product 105 (75 mg, 40%) was obtained as a white solid.

$^1$H NMR (300 MHz, CD$_3$OD) δ 7.83 (s, 1H), 7.36-7.17 (m, 5H), 5.95-5.92 (s+s, 1H), 4.97-4.84 (overlapped with H$_2$O, m, 1H), 4.60-4.44 (m, 2H), 4.25-4.16 (m, 2H), 3.95-3.86 (m, 1H), 2.94-2.87 (m, 1H), 1.31-1.28 (m, 3H), 1.20-1.14 (m, 6H), 0.97-0.94 (s+s, 3H), 0.86-0.83 (m, 2H), 0.63-0.56 (m, 2H). $^{31}$P NMR (121 MHz, CD$_3$OD) δ 4.00 (s), 3.92 (s). MS (ESI) m/z calcd. for C$_{26}$H$_{37}$N$_7$O$_9$P [M+H]$^+$ 606.2; found 606.2.

Example 9. Synthesis of (S)-Isopropyl 2-(((S)-(((2R,3R,4R,5R)-5-(2-amino-6-(methylamino)-9H-purin-9-yl)-4-fluoro-3-hydroxytetrahydrofuran-2-yl) methoxy)(phenoxy)phosphoryl)-amino) Propanoate (201)

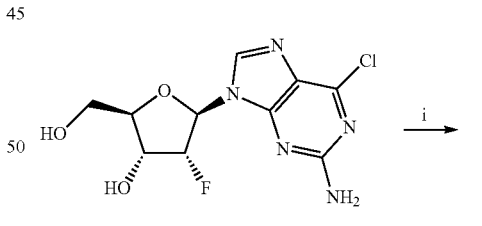

250

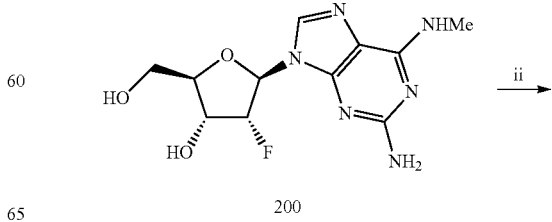

200

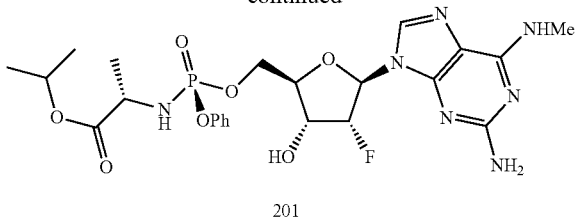

201 i) MeNH₂, EtOH, 85° C.; ii) Isopropyl ((S)-(pentafluorophenoxy)-phenoxy-phosphoryl)-L-alaninate, t-BuMgCl, DMF, -10° C.

Step 1. Preparation of (2R,3R,4R,5R)-5-(2-Amino-6-(methylamino)-9H-purin-9-yl)-4-fluoro-2-(hydroxymethyl) tetrahydrofuran-3-ol (200)

Compound 250 can be prepared according to Tuttle, J. V. et al., "Purine 2'-Deoxy-2'-fluororibosides as Antiinfluenza Virus Agents", J. Med. Chem., 36:119-125 (1992). A solution of compound 250 (5.2 g, 17.3 mmol) in methylamine (33% in EtOH) (150 mL) was heated at 85° C. in a sealed container for 3 h, cooled to RT and concentrated. The residue was purified by column chromatography (silica gel, DCM/MeOH 0 to 15%). The product, 200, (4.9 g, 95%) was obtained as a white solid.

$^1$H NMR (300 MHz, DMSO-D$_6$) δ 7.94 (s, 1H), 7.30 (bs, NH), 6.06 (dd, J=3.3, 16.5 Hz, 1H), 5.93 (bs, NH$_2$), 5.68 (bs, OH), 5.32 (dt, J=53.1, 3.6 Hz, 1H), 5.30 (bs, OH), 4.40 (dt, J=16.8, 4.5 Hz, 1H), 3.96-3.94 (m, 1H), 3.76-3.56 (m, 2H), 2.89 (bs, 3H). MS (ESI) m/z calcd. for C$_{11}$H$_{16}$FN$_6$O$_3$[M+H]$^+$ 299.1; found 299.2.

Step 2. Preparation of (S)-Isopropyl 2-(((S)-(((2R,3R,4R,5R)-5-(2-amino-6-(methylamino)-9H-purin-9-yl)-4-fluoro-3-hydroxytetrahydrofuran-2-yl)methoxy)(phenoxy)phosphoryl)amino) Propanoate (201)

To a solution of compound 200 (70 mg, 0.23 mmol) in dry DMF (3 mL) was added tert-butylmagnesium chloride (1 N in THF) (310 μL, 0.31 mmol) dropwise at 0° C. The solution was stirred for 20 mins at 0° C. and for 40 mins at RT. The reaction mixture was cooled to −10° C. and a solution of isopropyl ((S)-(pentafluorophenoxy)-phenoxy-phosphoryl)-L-alaninate (118 mg, 0.27 mmol) in dry DMF (3 mL) was added dropwise. The resulting solution was slowly warmed to 10° C. and stirred for 15 h at this temperature. The reaction mixture was diluted with EtOAc (20 mL) and saturated NH$_4$Cl aq. solution (15 mL). The phases were separated and the aqueous layer was back-extracted with EtOAc (2×10 mL). The combined organics were washed with saturated NH$_4$Cl aq. solution (20 mL), brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product 201 (22 mg, 17%) was obtained as a white solid.

$^1$H NMR (300 MHz, CD$_3$OD) δ 7.82 (s, 1H), 7.33-7.13 (m, 5H), 6.13 (dd, J=18.6, 1.9 Hz, 1H), 5.39 (ddd, J=52.9, 4.5, 2.0 Hz, 1H), 4.94-4.88 (m, 1H), 4.81-4.68 (m, 1H), 4.46 (ddd, J=11.5, 6.3, 2.6 Hz, 1H), 4.32 (m, 1H), 4.20 (m, 1H), 3.87 (dq, J=9.6, 7.2 Hz, 1H), 3.03 (s, 3H), 1.28 (d, J=7.1 Hz, 3H), 1.18 (d, J=6.2 Hz), 1.16 (d, J=6.2 Hz). $^{31}$P NMR (121 MHz, CD$_3$OD) δ 2.40 (s). MS (ESI) m/z calcd. for C$_{23}$H$_{32}$FN$_7$O$_7$P [M+H]$^+$ 568.2; found 568.2.

Example 10. Synthesis of (S)-Isopropyl 2-(((S)-(((2R,3R,445R)-5-(2-amino-6-(dimethylamino)-9H-purin-9-yl)-4-fluoro-3-hydroxytetrahydrofuran-2-yl)methoxy)(phenoxy)phosphoryl)amino) Propanoate (203)

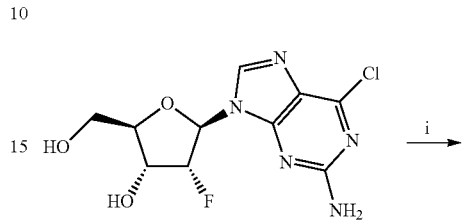

250

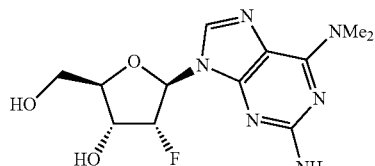

202

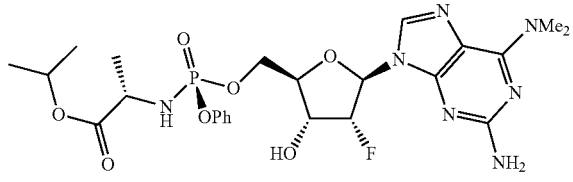

203 i) Me$_2$NH•HCl, Et$_3$N, EtOH, 85° C.; ii) Isopropyl ((S)-(pentafluorophenoxy)-phenoxy-phosphoryl)-L-alaninate, t-BuMgCl, DMF, -10° C.

Step 1. Preparation of (2R,3R,4R,5R)-5-(2-Amino-6-(dimethylamino)-9H-purin-9-yl)-4-fluoro-2-(hydroxymethyl)tetrahydrofuran-3-ol (202)

To a solution of compound 250 (10.5 g, 35 mmol) in EtOH (220 mL) was added dimethylamine hydrochloride (14.0 g, 173 mmol) and triethylamine (24.0 mL, 173 mmol). The reaction mixture was heated at 85° C. in a sealed container for 3 h, cooled to room temperature (RT) and concentrated. The residue was purified by column chromatography (silica gel, DCM/MeOH 0 to 10%). The product, 202, (10.8 g, 99%) was obtained as a white solid.

$^1$H NMR (300 MHz, DMSO-D$_6$) δ 7.97 (s, 1H), 6.07 (dd, J=3.0, 16.5 Hz, 1H), 5.91 (bs, NH$_2$), 5.66 (bs, OH), 5.27 (dt, J=53.1, 3.3 Hz, 1H), 5.25 (t, J=5.4 Hz, OH), 4.44-4.33 (m, 1H), 3.94-3.92 (m, 1H), 3.76-3.54 (m, 2H), 3.34 (s, overlapped with H$_2$O, 6H). MS (ESI) m/z calcd. for C$_{12}$H$_{18}$FN$_6$O$_3$[M+H]$^+$ 313.1; found 313.2.

Step 2. Preparation of (S)-Isopropyl 2-(((S)-(((2R,3R,4R,5R)-5-(2-amino-6-(dimethylamino)-9H-purin-9-yl)-4-fluoro-3-hydroxytetrahydrofuran-2-yl)methoxy)(phenoxy)phosphoryl)amino) Propanoate (203)

To a solution of compound 202 (70 mg, 0.22 mmol) in dry DMF (3 mL) was added tert-butylmagnesium chloride (1 N in THF) (305 μL, 0.31 mmol) dropwise at 0° C. The solution was stirred for 20 mins at 0° C. and for 40 mins at RT. The reaction mixture was cooled to −10° C. and a solution of isopropyl ((S)-(pentafluorophenoxy)-phenoxy-phosphoryl)-L-alaninate (116 mg, 0.27 mmol) in dry DMF (3 mL) was added dropwise. The resulting solution was slowly warmed up to 10° C. and stirred for 15 h at this temperature. The reaction mixture was then diluted with EtOAc (20 mL) and saturated NH$_4$Cl aq. solution (15 mL). The phases were separated and the aqueous layer was back-extracted with EtOAc (2×10 mL). The combined organics were washed with saturated NH$_4$Cl aq. solution (20 mL), brine (20 mL), dried over Na$_2$SO$_4$ and concentrated. The residue was purified by column chromatography (silica gel, DCM/MeOH 0 to 10%) and by reverse phase column chromatography (C-18 silica, H$_2$O/MeOH 0 to 100%). Product 203 (27 mg, 21%) was obtained as a white solid.

$^1$H NMR (300 MHz, CD$_3$OD) δ 7.80 (s, 1H), 7.33-7.13 (m, 5H), 6.14 (dd, J=18.7, 2.0 Hz, 1H), 5.38 (ddd, J=53.0, 4.6, 2.1 Hz, 1H), 4.95-4.89 (m, 1H), 4.72 (ddd, J=19.7, 7.6, 4.7 Hz, 1H), 4.46 (ddd, J=11.5, 6.2, 2.6 Hz, 1H), 4.32 (ddd, J=10.8, 5.9, 4.6 Hz, 1H), 4.20 (m, 1H), 3.88 (dq, J=9.7, 7.0 Hz, 1H), 3.39 (s, 6H), 1.28 (dd, J=7.1, 0.6 Hz, 3H), 1.18 (d, J=6.2 Hz), 1.17 (d, J=6.3 Hz). $^{31}$P NMR (121 MHz, CD$_3$OD) δ 2.41 (s). MS (ESI) m/z calcd. for C$_{24}$H$_{34}$FN$_7$O$_7$P [M+H]$^+$ 582.2; found 582.2.

Example 11. Synthesis of (2S)-Isopropyl 2-(((S)-(((1R,3R,4S,5R)-3-(6-amino-9H-purin-9-yl)-4,5-dihydroxy-2-methylcyclopentyl)methoxy)phenoxy) phosphoryl)amino)propanoate (Compound 204)

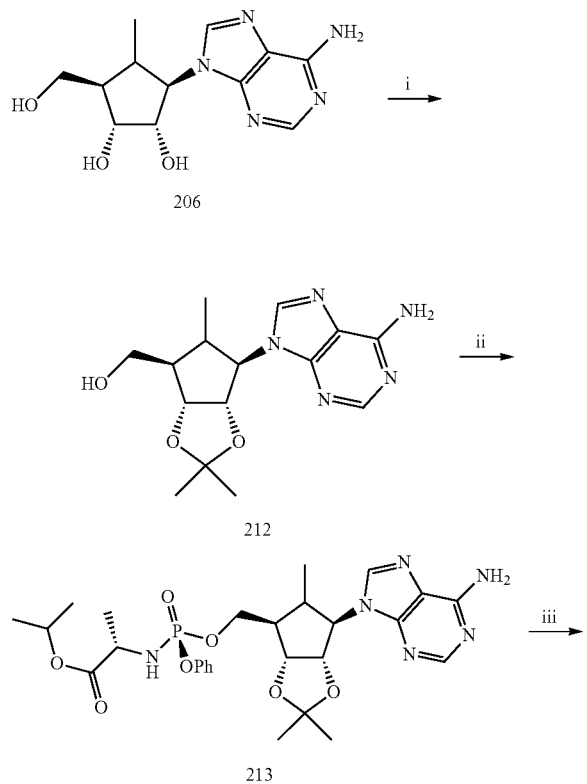

206

212

213

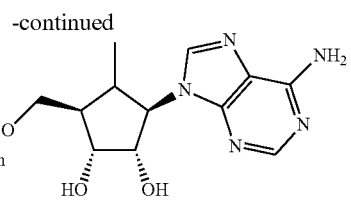

204 i) 2,2-Dimethoxypropane, H$_2$SO$_4$, acetone; ii) Isopropyl ((S)-(pentafluorophenoxy)-phenoxy-phosphoryl)-L-alaninate, t-BuMgCl, THF -10° C.; iii) HCl, 2-propanol Step 1. Preparation of ((3aR,4R,6R,6aS)-6-(6-Amino-9H-purin-9-yl)-2,2,5-trimethyltetrahydro-3aH-cyclopenta [d][1,3]dioxol-4-yl)methanol (212)

To a solution of Compound 206 (32 mg, 0.115 mmol) in acetone (5.0 mL) was added 2,2-dimethoxypropane (300 μL, 2.30 mmol) and concentrated H$_2$SO$_4$ (1 drop). The reaction mixture was stirred at RT. Then, triethylamine (100 μL) was added and the solvent were removed. The residue was purified by column chromatography (silica gel, DCM/MeOH 100:0 to 90:10) to afford Compound 212 (33 mg, 0.102 mmol, 89%) as a white solid.

Step 2. Preparation of (2S)-Isopropyl 2-(((S)-(((3aR,4R,6R,6aS)-6-(6-amino-9H-purin-9-yl)-2,2,5-trimethyltetrahydro-3aH-cyclopenta[d][1,3]dioxol-4-yl)methoxy)(phenoxy)phosphoryl) amino) propanoate (213)

To a solution of Compound 212 (32 mg, 0.10 mmol) in dry THF (2 mL) at 0° C. was added tert-butyl magnesium chloride (1.0 M in THF, 150 μL, 0.15 mmol) dropwise over 10 min. The reaction mixture was stirred for 15 min at 0° C. and then for an additional 15 min at room temperature. The reaction mixture was cooled to 0° C. before a solution of isopropyl ((S)-(pentafluorophenoxy)-phenoxy-phosphoryl)-L-alaninate (61 mg, 0.14 mmol) dissolved in dry THF (1 mL) was added dropwise over 10 min. The reaction mixture was stirred at 0° C. for 30 min and 18 h at room temperature. The reaction was quenched with a saturated aqueous NH$_4$Cl solution (4 mL) and extracted with EtOAc (3×5 mL). The combined organic layers were dried over Na$_2$SO$_4$ and concentrated. The residue was purified by column chromatography (silica gel, DCM/MeOH 100:0 to 90:10) to afford Compound 213 (26 mg, 0.04 mmol, 44%) as a white solid.

Step 3. (2S)-Isopropyl 2-(((S)-(((1R,3R,4S,5R)-3-(6-Amino-9H-purin-9-yl)-4,5-dihydroxy-2-methyl-cyclopentyl)methoxy)(phenoxy)phosphoryl)amino) propanoate (204)

Compound 213 (26 mg, 0.04 mmol) was treated with a solution of HCl (2 N in 2-propanol) (3 mL) for 30 mins at 0° C. and for 2 h at RT. The reaction mixture was concentrated. The residue was purified by column chromatography (silica gel, DCM/MeOH 100:0 to 90:10) and by reverse phase column chromatography (C-18 silica, H$_2$O/MeOH 100:0 to 0:100). Compound 204 (mixture of 2 diastereoisomers, 6 mg, 0.01 mmol, 25% yield) was obtained as a white solid.

$^1$H NMR (300 MHz, CD$_3$OD) δ 8.25-8.09 (m, 2H), 7.42-7.14 (m, 5H), 5.05-4.90 (m, 1H, overlapped with H$_2$O), 4.63-4.20 (m, 4H), 4.11-3.84 (m, 2H), 2.91-1.87 (m, 2H), 1.40-1.18 (m, 9H), 1.00 (d, J=6.7 Hz) and 0.57 (d, J=7.6 Hz, 3H). 31P NMR (121 MHz, CD3OD) δ 2.14 (s), 2.09 (s). MS (ESI) m/z calcd. for C24H34N6O7P [M+H]+ 549.2; found 549.2.

Example 12. Preparation of isopropyl ((((R,S)-(2R,3R,4R,5R)-5-(2-amino-6-(methylamino)-9H-purin-9-yl)-4-fluoro-3-hydroxy-4-methyltetrahydrofuran-2-yl)methoxy)-phenoxy-phosphoryl)-L-alaninate (205)

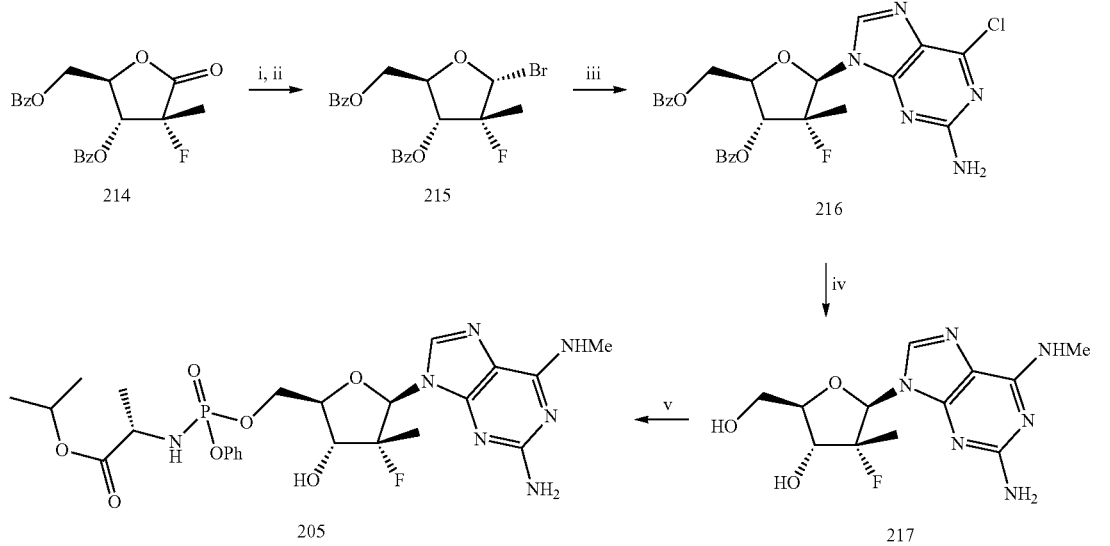

i) Li(OtBu)₃AlH, THF, -30° C.-->-15° C.; ii) PPh₃, CBr₄, DCM, -20° C.-->0° C.; iii) 2-amino-6-chloropurine, tBuOK, tBuOH/MeCN 9:1, 65° C.; iv) MeNH₂ (33%), MeOH, 85° C.; v) Isopropyl ((R,S)-pentafluorophenoxy)-phenoxy-phosphoryl)-L-alaninate, tBuMgCl, THF, 0° C.--> r.t.

Step 1. Preparation of ((2R,3R,4R,5R)-3-(benzoyloxy)-5-bromo-4-fluoro-4-methyltetrahydrofuran-2-yl)methyl Benzoate (215)

To a solution of (2R)-3,5-di-O-benzoyl-2-fluoro-2-C-methyl-D-ribono-γ-lactone (214, 24.8 g, 66.6 mmol) in dry THF (333 mL) under a nitrogen atmosphere and cooled to -30° C., was added lithium tri-tert-butoxyaluminum hydride (1.0 M in THF, 22.6 mL, 22.6 mmol) dropwise. After completion of the addition the reaction mixture was slowly warmed up to -15° C. over 90 minutes. EtOAc was added (300 mL) and the mixture was quenched with a saturated aq. NH₄Cl solution (200 mL). The resulting solution was filtered on Celite® and the filtrate was extracted twice with EtOAc. The combined organics were dried (Na₂SO₄), filtered, and concentrated. The residue was taken up in dry DCM (225 mL) under a nitrogen atmosphere, cooled to -20° C., and PPh₃ (19.1 g, 72.8 mmol) was added. After 10 min of stirring at -20° C., CBr₄ (26.0 g, 78.4 mmol) was added and the reaction mixture was allowed to slowly warm to 0° C. over 2 h. The resulting mixture was poured onto a silica gel column and eluted with PE/EtOAc (gradient 100:0 to 80:20). The fractions containing the α-bromofuranoside were collected and concentrated to afford the product 215 (18.1 g, 41.3 mmol, 62% over two steps) as a thick colorless oil.

¹H NMR (300 MHz, CDCl₃) δ 8.15-8.11 (m, 2H), 8.04-8.01 (m, 2H), 7.64-7.55 (m, 2H), 7.51-7.41 (m, 4H), 6.34 (d, J=1.6 Hz, 1H), 5.29 (dd, J=5.5, 3.1 Hz, 1H), 4.89-4.85 (m, 1H), 4.78 (dd, J=12.5, 3.2 Hz, 1H), 4.63 (dd, J=12.5, 4.5 Hz, 1H), 1.72 (d, J=21.6 Hz, 3H). ¹⁹F NMR (282 MHz, CDCl₃) δ -150.0.

Step 2. Preparation of (2R,3R,4R,5R)-5-(2-amino-6-chloro-9H-purin-9-yl)-2-(benzoyloxymethyl)-4-fluoro-4-methyltetrahydrofuran-3-yl Benzoate (216)

2-Amino-6-chloropurine (2.63 g, 15.5 mmol) was suspended in t-BuOH (54 mL) under a nitrogen atmosphere. The reaction mixture was heated to 30° C. and potassium tert-butoxide (1.69 g, 15.1 mmol) was added. After 45 minutes, a solution of bromofuranoside 2 (2.24 g, 5.12 mmol) dissolved in anhydrous MeCN (6 mL) was added, the reaction mixture was heated to 65° C. for 16 h, and then cooled to room temperature. Saturated aq. NH₄Cl solution (70 mL) was added and the resulting solution was extracted with EtOAc (3×60 mL). The combined organics were dried (Na₂SO₄), filtered, and concentrated. The residue was purified twice by column chromatography (gradient PE/EtOAc 80:20 to 0:100 then 60:40 to 20:80) to afford the product 216 (1.56 g, 2.96 mmol, 57%) as a white solid.

¹H NMR (300 MHz, CDCl₃) δ 8.05-8.02 (m, 2H), 7.95-7.92 (m, 2H), 7.88 (s, 1H), 7.63-7.57 (m, 1H), 7.53-7.41 (m, 3H), 7.35-7.30 (m, 2H), 6.43 (dd, J=22.6, 9.1 Hz, 1H), 6.12 (d, J=18.3 Hz, 1H), 5.34 (br s, 2H), 5.00 (dd, J=11.9, 4.5 Hz, 1H), 4.79-4.73 (m, 1H), 4.60 (dd, J=11.9, 5.3 Hz, 1H), 1.34 (d, J=22.6 Hz, 3H). ¹⁹F NMR (282 MHz, CDCl₃) δ -157.0. MS (ESI) m/z calcd. for C₂₅H₂₂FN₅O₅ [M+H]⁺ 526.9; found 527.0.

Step 3. Preparation of (2R,3R,4R,5R)-5-(2-amino-6-(methylamino)-9H-purin-9-yl)-4-fluoro-2-(hydroxymethyl)-4-methyltetrahydrofuran-3-ol (217)

To a solution of compound 216 (575 mg, 1.09 mmol) in MeOH (9 mL) was added methylamine (33% in absolute EtOH, 1.7 mL, 1.81 mmol). The reaction mixture was heated to 85° C. in a sealed tube for 16 h, cooled to room temperature and concentrated. The residue was purified by column chromatography (gradient DCM/MeOH 100:0 to 85:15) and reverse phase column chromatography (gradient H₂O/MeOH 100:0 to 0:100) to afford the product 217 (286 mg, 0.91 mmol, 84%) as a white solid.

¹H NMR (300 MHz, CD₃OD) δ 8.06 (s, 1H), 6.11 (d, J=18.1 Hz, 1H), 4.41 (dd, J=24.4, 9.1 Hz, 1H), 4.07-4.01 (m, 2H), 3.86 (dd, J=12.9, 3.3 Hz, 1H), 3.04 (br s, 3H), 1.16 (d, J=22.3 Hz, 3H). ¹⁹F NMR (282 MHz, CD₃OD) δ −163.7. MS (ESI) m/z calcd. for C₁₂H₁₉FN₆O₃ [M+H]⁺ 313.1; found 313.2.

Step 4. Preparation of isopropyl ((((R,S)-(2R,3R,4R,5R)-5-(2-amino-6-(methylamino)-9H-purin-9-yl)-4-fluoro-3-hydroxy-4-methyltetrahydrofuran-2-yl)methoxy)-phenoxy-phosphoryl)-L-alaninate (205)

To a solution of compound 217 (114 mg, 365 μmol) in dry THF (4 mL) under a nitrogen atmosphere and cooled to 0° C. was added t-butyl magnesium chloride (1.0 M in THF, 0.66 mL, 660 μmol) dropwise over 10 min. The reaction mixture was stirred for 15 min at 0° C. and then another 15 min at room temperature. The reaction mixture was cooled to 0° C. before a solution of isopropyl ((R,S)-(pentafluorophenoxy)-phenoxy-phosphoryl)-L-alaninate, Ross, B. S., Reddy, P. G., Zhang, H. R., Rachakonda, S., and Sofia, M. J., J. Org, Chem., (2011), (253 mg, 558 μmol) dissolved in dry THF (1 mL) was added dropwise over 10 min. The reaction mixture was stirred at 0° C. for 30 min followed by 18 h at room temperature. The reaction was quenched with a saturated aq. NH₄Cl solution (4 mL) and extracted with EtOAc (3×5 mL). The combined organics were dried, filtered (Na₂SO₄), and concentrated. The residue was purified by column chromatography (gradient DCM/MeOH 100:0 to 90:10) and reverse phase column chromatography (gradient H₂O/MeOH 100:0 to 0:100) to afford product 205 (a mixture of diastereomers, 101 mg, 174 μmol, 48%) as a white solid.

¹H NMR (300 MHz, CD₃OD) δ 7.83 (s, 0.55H), 7.82 (s, 0.45H), 7.38-7.16 (m, 5H), 6.15 (d, J=18.5 Hz, 0.45 H), (d, J=18.8 Hz, 0.55 H), 4.99-4.88 (overlapped with H₂O, m, 1H), 4.65-4.36 (m, 3H), 4.25-4.17 (m, 1H), 3.97-3.85 (m, 1H), 3.05 (br s, 3H), 1.32-1.28 (m, 3H), 1.25-1.15 (m, 9H). ¹⁹F NMR (282 MHz, CD₃OD) δ −162.8 (s), −163.3 (s). ³¹P NMR (121 MHz, CD₃OD) δ 4.10 (s), 3.99 (s). MS (ESI) m/z calcd. for C₂₄H₃₄FN₇O₇P [M+H]⁺ 582.2; found 582.2.

Table 2 illustrates the structures of compounds 207, 208, 209, and 210 along with the corresponding mass spectra and ¹H NMR for the respective compounds. Compounds were synthesized via the general method shown in Example 4.

TABLE 2

Mass Spectra and ¹H NMR of Compounds 207, 208, 209, and 210

| Compd No. | Structure | ¹HNMR and Mass Spectra |
|---|---|---|
| 207 | 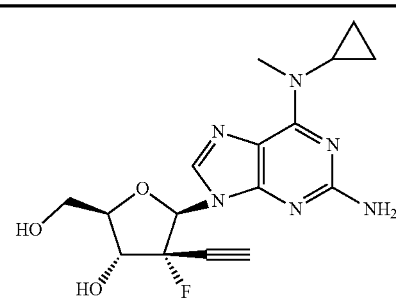 | ¹H NMR (400 MHz, Methanol-d₄) δ 8.11 (s, 1H), 6.29 (d, J = 16.9 Hz, 1H), 4.76 (dd, J = 21.7, 9.0 Hz, 1H), 4.10-4.01 (m, 2H), 3.87 (dd, J = 13.1, 3.1 Hz, 1H), 3.37 (s, 1H), 3.24-3.11 (m, 2H), 1.00-0.87 (m, 2H), 0.74 (td, J = 4.6, 2.8 Hz, 2H). [M + H]+ = 363.0 |
| 208 | 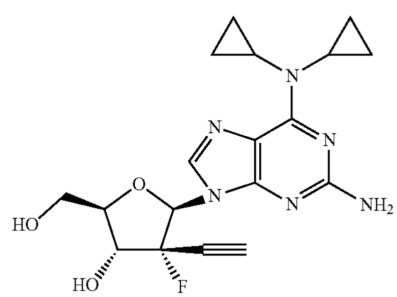 [SMILES: C#C[C@@]1(F)[C@H](O)[C@@H](CO)O[C@H]1n1cnc2c(N(C3CC3)C3CC3)nc(N)nc21] | ¹H NMR (400 MHz, Methanol-d₄) δ 8.16 (s, 1H), 6.30 (d, J = 16.8 Hz, 1H), 4.76 (dd, J = 21.6, 9.1 Hz, 1H), 4.10-4.01 (m, 2H), 3.87 (dd, J = 12.9, 2.9 Hz, 1H), 3.23 (s, 2H), 3.22 (s, 1H), 3.00 (tt, J = 7.0, 3.7 Hz, 2H), 1.21 (s, 4H), 1.03-0.86 (m, 4H), 0.77 (dt, J = 5.5, 3.4 Hz, 4H). [M + H]+ = 389.0 |
| 209 | 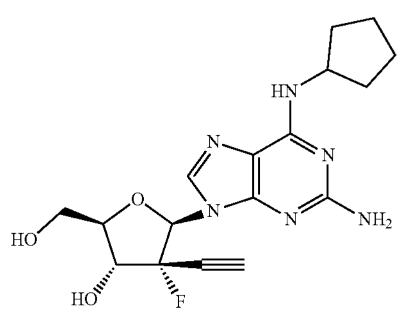 [SMILES: C#C[C@@]1(F)[C@H](O)[C@@H](CO)O[C@H]1n1cnc2c(NC3CCCC3)nc(N)nc21] | ¹H NMR (400 MHz, Methanol-d₄) δ 8.05 (s, 1H), 6.25 (d, J = 16.9 Hz, 1H), 4.77 (dd, J = 21.8, 9.2 Hz, 1H), 4.50 (s, 1H), 4.11-4.01 (m, 2H), 3.87 (dd, J = 13.0, 3.0 Hz, 1H), 3.37 (s, 2H), 3.21 (d, J = 5.4 Hz, 1H), 2.14-2.01 (m, 2H), 1.89-1.70 (m, 2H), 1.75-1.64 (m, 1H), 1.60 (s, 1H), 1.68-1.50 (m, 1H). [M + H]+ = 377.0 |

TABLE 2-continued

Mass Spectra and $^1$H NMR of Compounds 207, 208, 209, and 210

| Compd No. | Structure | $^1$HNMR and Mass Spectra |
|---|---|---|
| 210 | [structure] | $^1$H NMR (400 MHz, Methanol-d$_4$) δ 8.08 (s, 1H), 6.28 (d, J = 16.7 Hz, 1H), 4.76 (dd, J = 21.7, 9.0 Hz, 1H), 4.10-4.01 (m, 2H), 3.99 (s, 2H), 3.87 (dd, J = 13.1, 3.2 Hz, 1H), 3.37 (s, 1H), 3.19 (d, J = 5.4 Hz, 1H), 2.03 (s, 4H). [M + H]+ = 363.1 |

Example 13. Non-limiting Examples of Compounds of the Present Invention

Compounds of the present invention include those in Table 3 and Table 4. Compound number, structure and molecular weight of illustrative compounds of the invention are also shown.

TABLE 3

Compounds of the Present Invention

| Cmpd No. | Structure | MW |
|---|---|---|
| 1 | [structure] | 336.3 |
| 2 | [structure] | 605.6 |
| 3 | [structure] | 322.3 |

TABLE 3-continued

Compounds of the Present Invention

| Cmpd No. | Structure | MW |
|---|---|---|
| 4 | 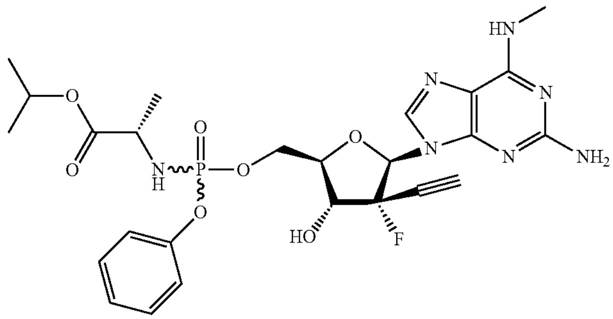 | 591.5 |
| 5 | 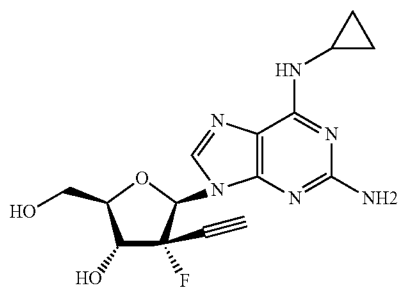 | 348.3 |
| 6 | 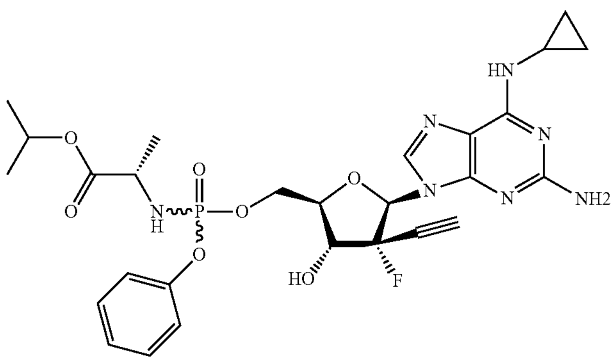 | 617.6 |
| 100 | 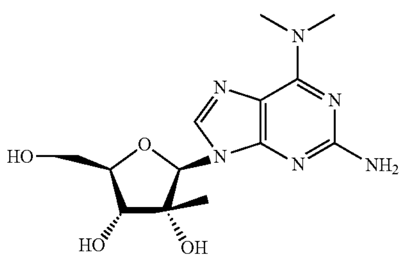 | 324.3 |
| 101 | 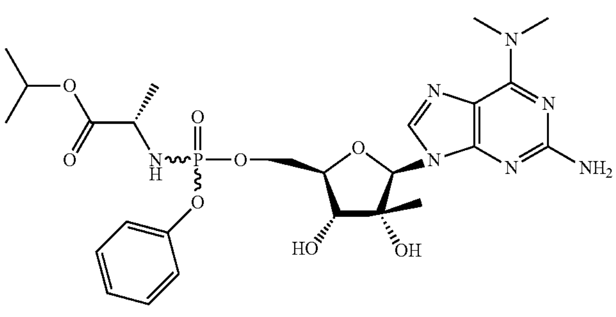 | 593.6 |

TABLE 3-continued

| Cmpd No. | Structure | MW |
|---|---|---|
| 102 | 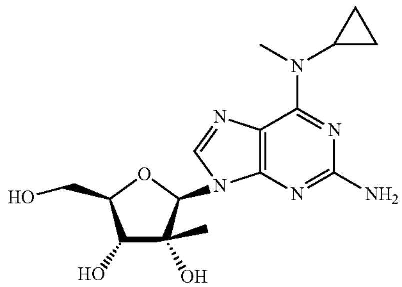 | 350.4 |
| 103 | 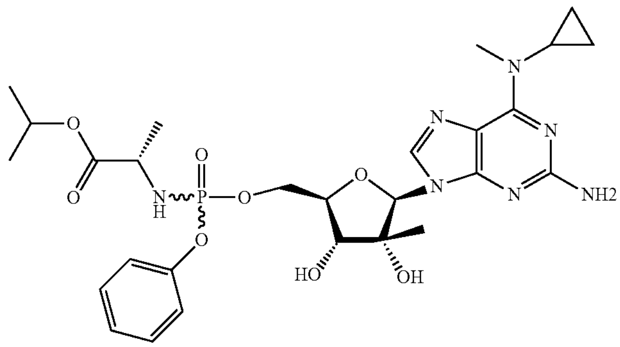 | 619.6 |
| 104 | 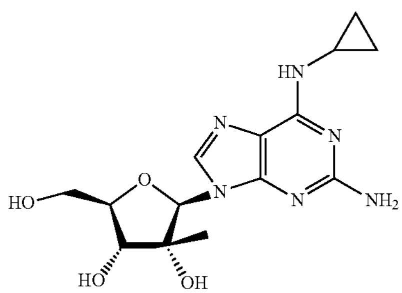 | 336.4 |
| 105 | 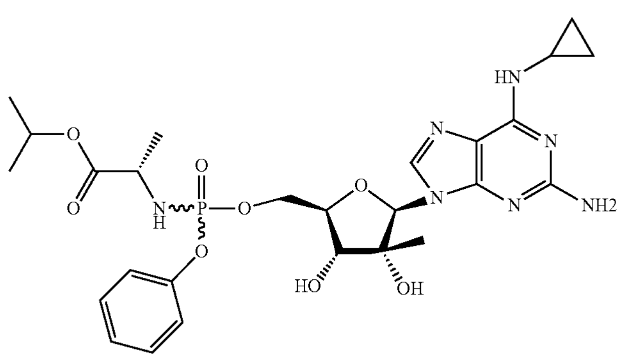 | 605.6 |
| 106 | 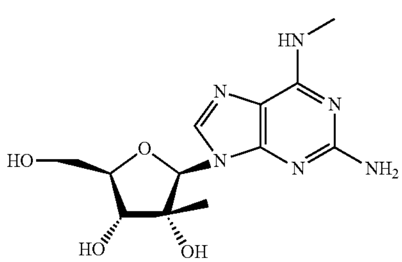 | 310.3 |

TABLE 3-continued
Compounds of the Present Invention
| Cmpd No. | Structure | MW |
|---|---|---|
| 107 | 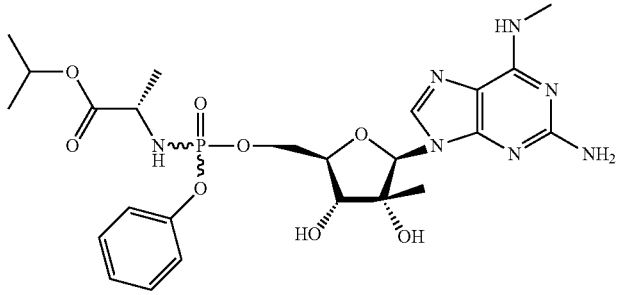 | 579.5 |
| 200 | 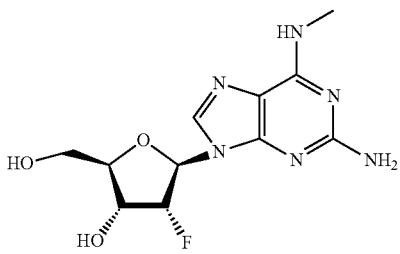 | 298.3 |
| 201 | 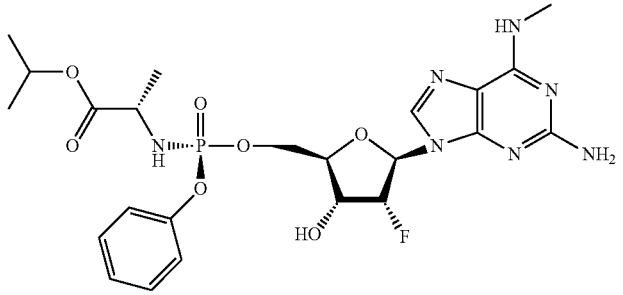 | 567.5 |
| 202 | 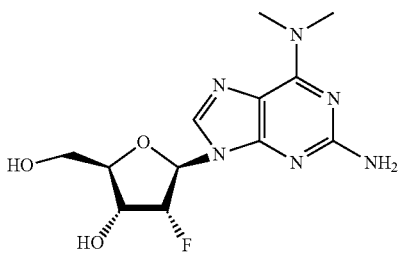 | 312.3 |
| 203 | 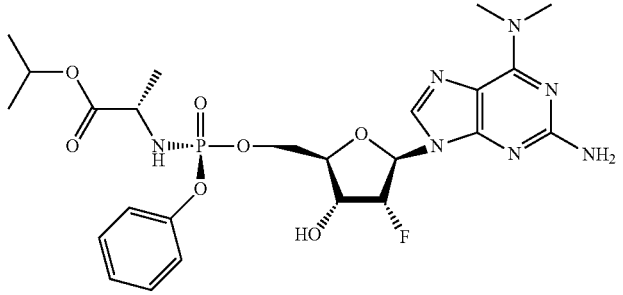 | 581.5 |

TABLE 4
Additional Compounds of the Present Invention
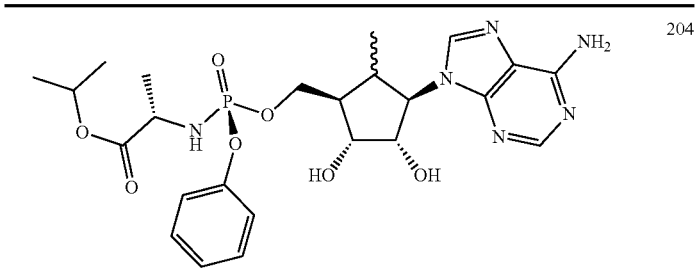
204
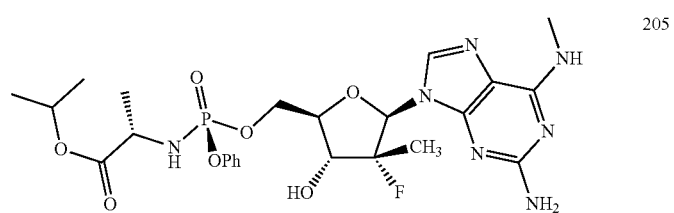
205
206
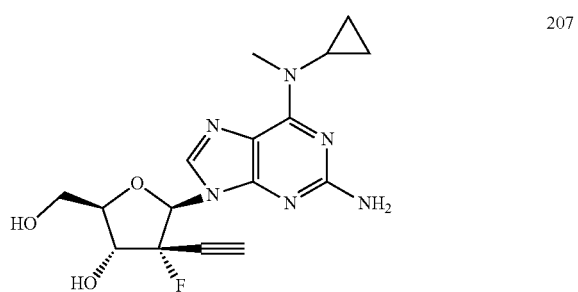
207
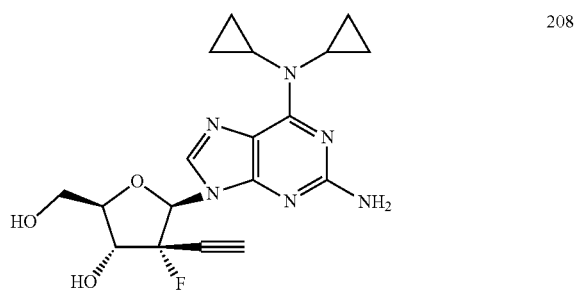
208
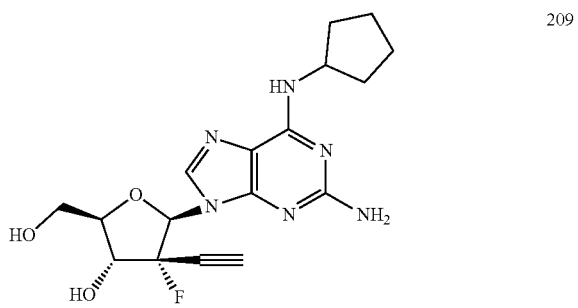
209

TABLE 4-continued

Additional Compounds of the Present Invention

210: [Structure: 9-(2-deoxy-2-fluoro-2-ethynyl-β-D-ribofuranosyl)-2-amino-6-(pyrrolidin-1-yl)purine]

Example 14. Compounds of the Present Invention are Active Against Dengue Virus Type 2 and Yellow Fever Virus Compounds of the present invention were measured for activity against Dengue virus type 2 (DENV-2) and Yellow Fever (YFV). Inhibition of virus-induced cytopathic effects (CPE) and cell viability following YFV replication in BHK21 cells were measured by XTT tetrazolium dye staining. Cells (3×103 cells per well) were seeded in 98-well flat-bottom tissue culture plates and allowed to adhere overnight. Following overnight incubation, diluted test compounds and virus diluted to a pre-determined titer to yield 85 to 95% cell killing at 6 days post-infection were added to the plate. Following incubation at 37° C., 5% $CO_2$ for six days, cell viability was measured by XTT staining. The optical density of the cell culture plate was determined spectrophotometrically at 450 and 650 nm using Softmax Pro 4.6 software. Percent CPE reduction of the virus-infected wells and the percent cell viability of uninfected drug control wells were calculated to determine the $EC_{50}$ values using four parameter curve fit analysis.

Results are presented in Table 5. Compound 205 is the most potent compound with an $EC_{50}$ of 0.8 µM in the DENV-2 assay and an $EC_{50}$ value of 1.2 µM in the YFV assay.

TABLE 5

Activity of Selected Compounds against DENV-2 and YFV

| Compd No. | Structure | DENV-2 $EC_{50}$ (µM) | YFV $EC_{50}$ (µM) |
|---|---|---|---|
| 2 | [Phosphoramidate prodrug structure with N,N-dimethyl adenine base] | 72.5 | 12.6 |
| 4 | [Phosphoramidate prodrug structure with N-methyl adenine base] | 612.0 | 7.0 |
| 6 | [Phosphoramidate prodrug structure with N-cyclopropyl 2-amino adenine base] | 42.0 | 4.4/6 |

TABLE 5-continued

Activity of Selected Compounds against DENV-2 and YFV

| Compd No. | Structure | DENV-2 EC$_{50}$ (μM) | YFV EC$_{50}$ (μM) |
|---|---|---|---|
| 204 | 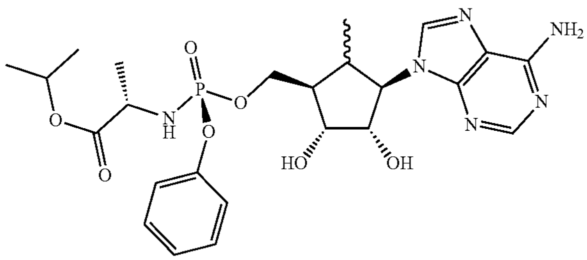 [SMILES: CC(C)OC(=O)[C@H](C)N[P@](=O)(OC[C@H]1C(C)[C@@H](n2cnc3c(N)ncnc32)[C@H](O)[C@@H]1O)Oc1ccccc1] | >2.1 | >2.1 |
| 205 | 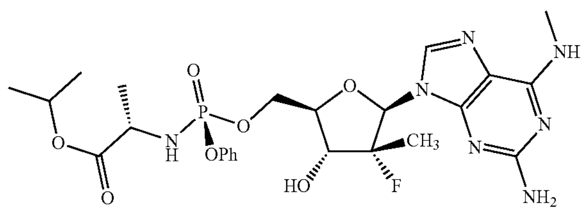 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F] | 0.8 | 1.2 |
| 206 | 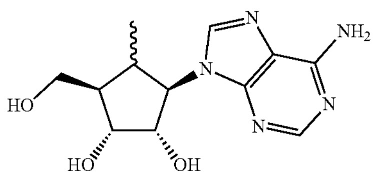 [SMILES: CC1[C@@H](n2cnc3c(N)ncnc32)[C@H](O)[C@H](O)[C@H]1CO] | 1.83 | 2.3 |

This specification has been described with reference to embodiments of the invention. Given the teaching herein, one of ordinary skill in the art will be able to modify the invention for a desired purpose and such variations are considered within the scope of the invention.

We claim:

1. A method of treating a human host in need thereof infected with a virus selected from the group consisting of yellow fever, West Nile, Zika, and Japanese B encephalitis comprising administering an effective amount of a compound Formula IIIe:

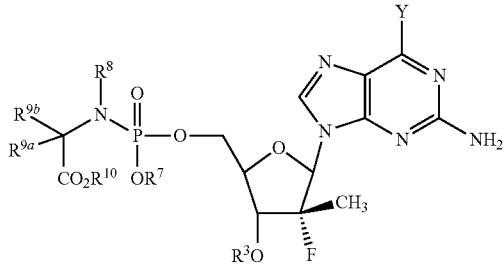

Formula IIIe or a pharmaceutically acceptable salt thereof;
wherein:
Y is NR$^1$R$^2$;
R$^1$ is methyl;
R$^2$ is hydrogen;
R$^3$ is hydrogen
R$^7$ is heteroaryl or aryl;
R$^8$ is hydrogen or C$_{1-6}$alkyl;
R$^{9a}$ and R$^{9b}$ are independently selected from hydrogen, and C$_{1-6}$alkyl,
R$^{10}$ is C$_{1-6}$alkyl.

2. The method of claim 1, wherein:
R$^7$ is aryl;
R$^8$ is hydrogen;
R$^{9a}$ and R$^{9b}$ are independently selected from methyl and hydrogen; and
R$^{10}$ is C$_{1-6}$alkyl.

3. The method of claim 2, wherein:
R$^7$ is phenyl;
R$^8$ is hydrogen;
R$^{9a}$ and R$^{9b}$ are independently selected from methyl and hydrogen; and
R$^{10}$ is isopropyl.

4. The method of claim 1, wherein the compound is:

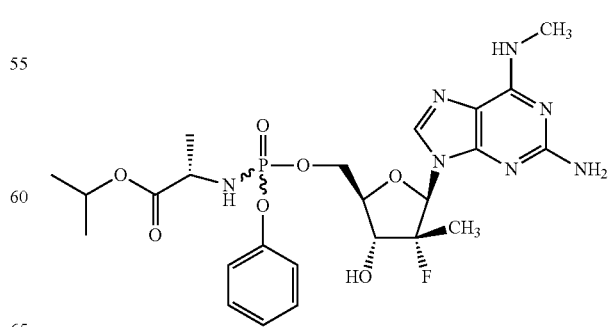

or a pharmaceutically acceptable salt thereof.

5. The method of claim 4, wherein the compound is

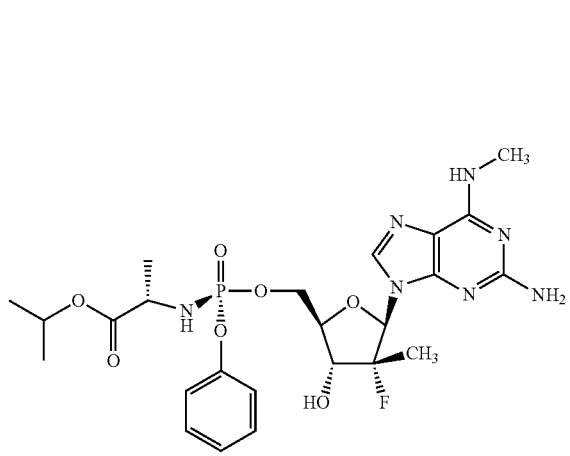 [SMILES: CNc1nc(N)nc2c1ncn2[C@@H]1O[C@H](CO[P@](=O)(N[C@@H](C)C(=O)OC(C)C)Oc2ccccc2)[C@@H](O)[C@@]1(C)F]

or a pharmaceutically acceptable salt thereof.

6. The method of claim 4, wherein the compound is

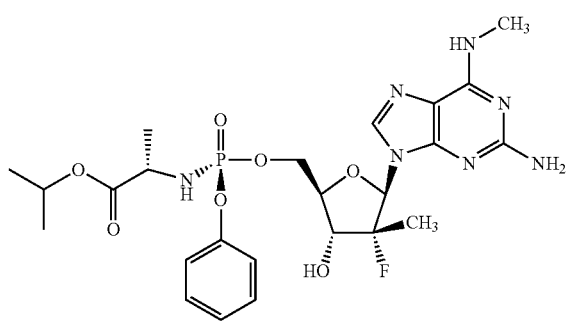 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

or a pharmaceutically acceptable salt thereof.

7. The method of claim 1, wherein the compound is:

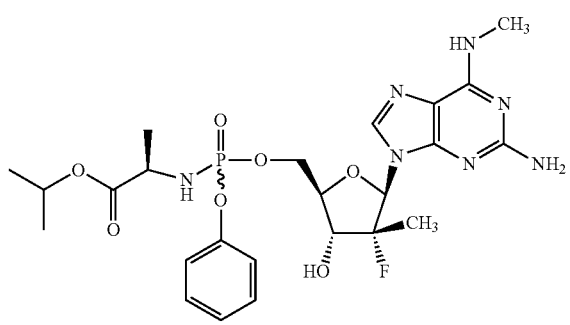 [SMILES: CNc1nc(N)nc2c1ncn2[C@@H]1O[C@H](COP(=O)(N[C@H](C)C(=O)OC(C)C)Oc2ccccc2)[C@@H](O)[C@@]1(C)F]

or a pharmaceutically acceptable salt thereof.

8. The method of claim 7, wherein the compound is:

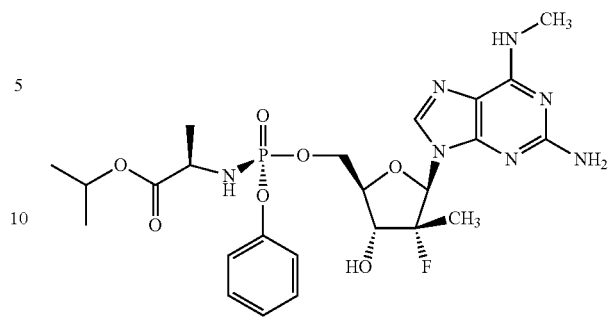

or a pharmaceutically acceptable salt thereof.

9. The method of claim 7, wherein the compound is

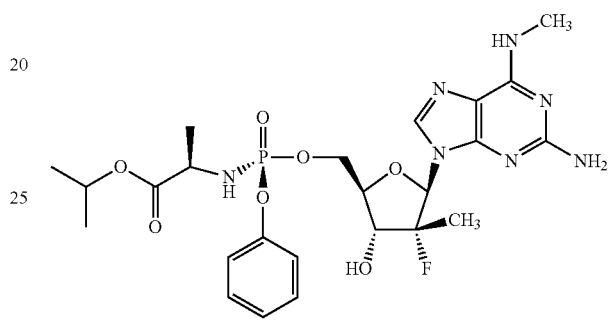

or a pharmaceutically acceptable salt thereof.

10. The method of claim 1, wherein the virus is yellow fever.

11. The method of claim 1, wherein the virus is West Nile fever.

12. The method of claim 1, wherein the virus is Zika virus.

13. The method of claim 1, wherein the virus is Japanese B encephalitis.

14. The method of claim 1, wherein the compound is administered in a dosage form suitable for oral administration.

15. The method of claim 14, wherein the compound is administered in a solid dosage form.

16. The method of claim 15, wherein the solid dosage form is a tablet or capsule.

17. The method of claim 1, wherein the compound is administered in a dosage form suitable for intravenous administration.

18. The method of claim 1, wherein the compound is administered in a dosage form suitable for parental administration.

19. The method of claim 5, wherein the virus is yellow fever.

20. The method of claim 5, wherein the virus is West Nile fever.

21. The method of claim 5, wherein the virus is Zika virus.

22. The method of claim 5, wherein the virus is Japanese B encephalitis.

23. The method of claim 6, wherein the virus is yellow fever.

24. The method of claim 6, wherein the virus is West Nile fever.

25. The method of claim 6, wherein the virus is Zika virus.

26. The method of claim 6, wherein the virus is Japanese B encephalitis.

* * * * *